United States Patent
Gip et al.

(10) Patent No.: US 12,215,163 B2
(45) Date of Patent: Feb. 4, 2025

(54) CD25 ANTIBODIES

(71) Applicant: iBio, Inc., Bryan, TX (US)

(72) Inventors: Phung Tu Gip, San Francisco, CA (US); Bing Li, Foster City, CA (US); Matthew P. Greving, San Carlos, CA (US); Matt Lundberg, San Mateo, CA (US); Mohan Srinivasan, Cupertino, CA (US)

(73) Assignee: iBio, Inc., San Diego, CA (US)

( * ) Notice: Subject to any disclaimer, the term of this patent is extended or adjusted under 35 U.S.C. 154(b) by 499 days.

(21) Appl. No.: 17/320,125

(22) Filed: May 13, 2021

(65) Prior Publication Data

US 2023/0220102 A1     Jul. 13, 2023

Related U.S. Application Data

(63) Continuation of application No. PCT/US2019/061552, filed on Nov. 14, 2019.

(60) Provisional application No. 62/767,405, filed on Nov. 14, 2018.

(51) Int. Cl.
*C07K 16/28* (2006.01)
*A61P 37/06* (2006.01)
*C12N 15/63* (2006.01)

(52) U.S. Cl.
CPC .......... *C07K 16/2896* (2013.01); *A61P 37/06* (2018.01); *C12N 15/63* (2013.01); *C07K 2317/24* (2013.01); *C07K 2317/565* (2013.01); *C07K 2317/92* (2013.01)

(58) Field of Classification Search
CPC ............ C07K 16/2896; C07K 2317/24; C07K 2317/565; C07K 2317/92; C07K 2317/33; C07K 2317/52; C07K 2317/55; C07K 2317/56; C07K 2317/732; C07K 2317/76; C07K 2317/94; C07K 16/2866; A61P 37/06; A61P 35/04; C12N 15/63
See application file for complete search history.

(56) References Cited

U.S. PATENT DOCUMENTS

| | | | |
|---|---|---|---|
| 7,438,907 | B2 | 10/2008 | Schuurman et al. |
| 2012/0276125 | A1 | 11/2012 | Ast et al. |
| 2017/0342112 | A1 | 11/2017 | Altermann et al. |
| 2018/0141999 | A1 | 5/2018 | Chandran et al. |
| 2020/0010554 | A1 | 1/2020 | Goubier et al. |

FOREIGN PATENT DOCUMENTS

| | | | | |
|---|---|---|---|---|
| WO | WO-2011/051327 | A2 | 5/2011 | |
| WO | WO-2011/051327 | A3 | 5/2011 | |
| WO | WO-2014/028776 | A1 | 2/2014 | |
| WO | WO-2014/145907 | A1 | 9/2014 | |
| WO | 2018089829 | A1 | 5/2018 | |
| WO | WO-2018167104 | A1 * | 9/2018 | ....... A61K 39/39533 |
| WO | WO-2018/195226 | A1 | 10/2018 | |
| WO | WO-2020/102603 | A1 | 5/2020 | |

OTHER PUBLICATIONS

Wilkinson, DS et. al. "Partial CD25 Antagonism Enables Dominance of Antigen-Inducible CD25(high) FOXP3+ Regulatory T Cells as a Basis for a regulatory T Cell-Based Adoptive Immunotherapy", 2017, Frontiers in Immunology, 8(1782), 1-21. (Year: 2017).*
European Patent Office, Supplementary Partial European Search Report for EP 19883467 dated Jul. 5, 2022, 13 pp.
International Search Report mailed on Apr. 27, 2020, for PCT Application No. PCT/US2019/061552, filed on Nov. 14, 2019, 5 pages.
International Search Report mailed on Apr. 21, 2020, for PCT Application No. PCT/US2019/061567, filed on Nov. 14, 2019, 5 pages.
Wilkinson, D.S. et al. (2017). "Partial CD25 Antagonism Enables Dominance of Antigen-Inducible CD25$^{high}$ FOXP3$^+$ Regulatory T Cells as a Basis for a Regulatory T Cell-Based Adoptive Immunotherapy," Frontiers in Immunology 8:1-21.
Written Opinion of the International Searching Authority mailed on Apr. 27, 2020, for PCT Application No. PCT/US2019/061552, filed on Nov. 14, 2019, 7 pages.
Written Opinion of the International Searching Authority mailed on Apr. 21, 2020, for PCT Application No. PCT/US2019/061567, filed on Nov. 14, 2019, 7 pages.
U.S. Appl. No. 17/320,118, filed May 13, 2021, by Greving et al.
China Intellectual Property Office, Examination Report for Chinese Patent Appl. No. 100089, dated Nov. 28, 2023, 15 pp. with translation.

* cited by examiner

*Primary Examiner* — Nelson B Moseley, II
*Assistant Examiner* — Alyssa Rae Stonebraker
(74) *Attorney, Agent, or Firm* — Edwin S. Flores; Daniel J. Chalker; Chalker Flores, LLP

(57) ABSTRACT

Provided herein are antibodies that specifically bind to CD25. Also provided herein are methods of making the antibodies described, and methods of use thereof. For example, the CD25 antibodies may be used therapeutically to treat cancer or autoimmune diseases, and in certain aspects: disrupt the trimerization of the beta, gamma, and alpha (CD25) chains of the IL-2 receptor, bind to a different epitope than to which Daclizumab or Baciliximab bind, exhibit a higher affinity of binding to CD25 at a pH lower than 7.4, when compared to the affinity of binding to CD25 at a pH of 7.4, and/or exhibit a higher affinity of binding to CD25 at a pH of about 6.5.

24 Claims, 36 Drawing Sheets
Specification includes a Sequence Listing.

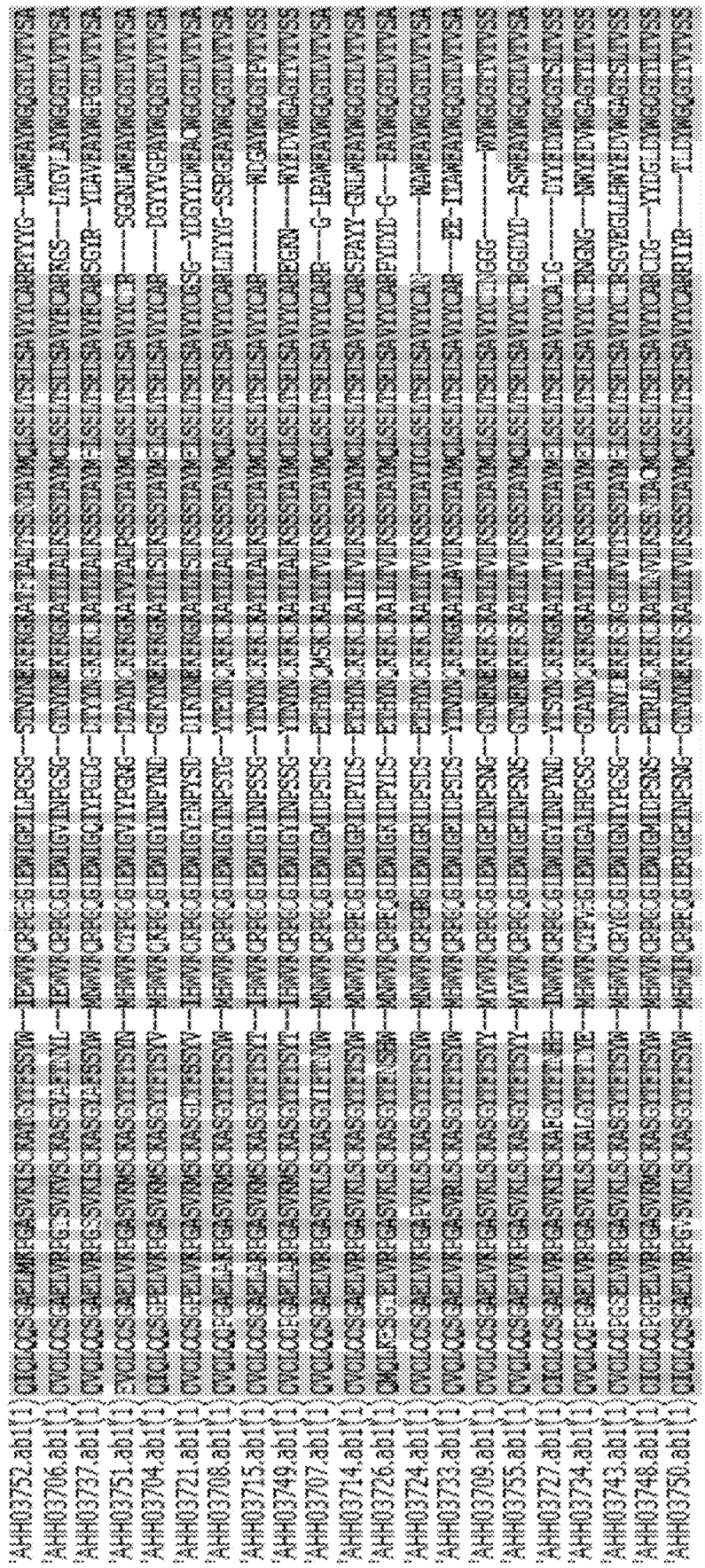
FIG. 3A - Continued

FIG. 3B    CD25 Antibodies - VH Sequences

FIG. 3B - Continued

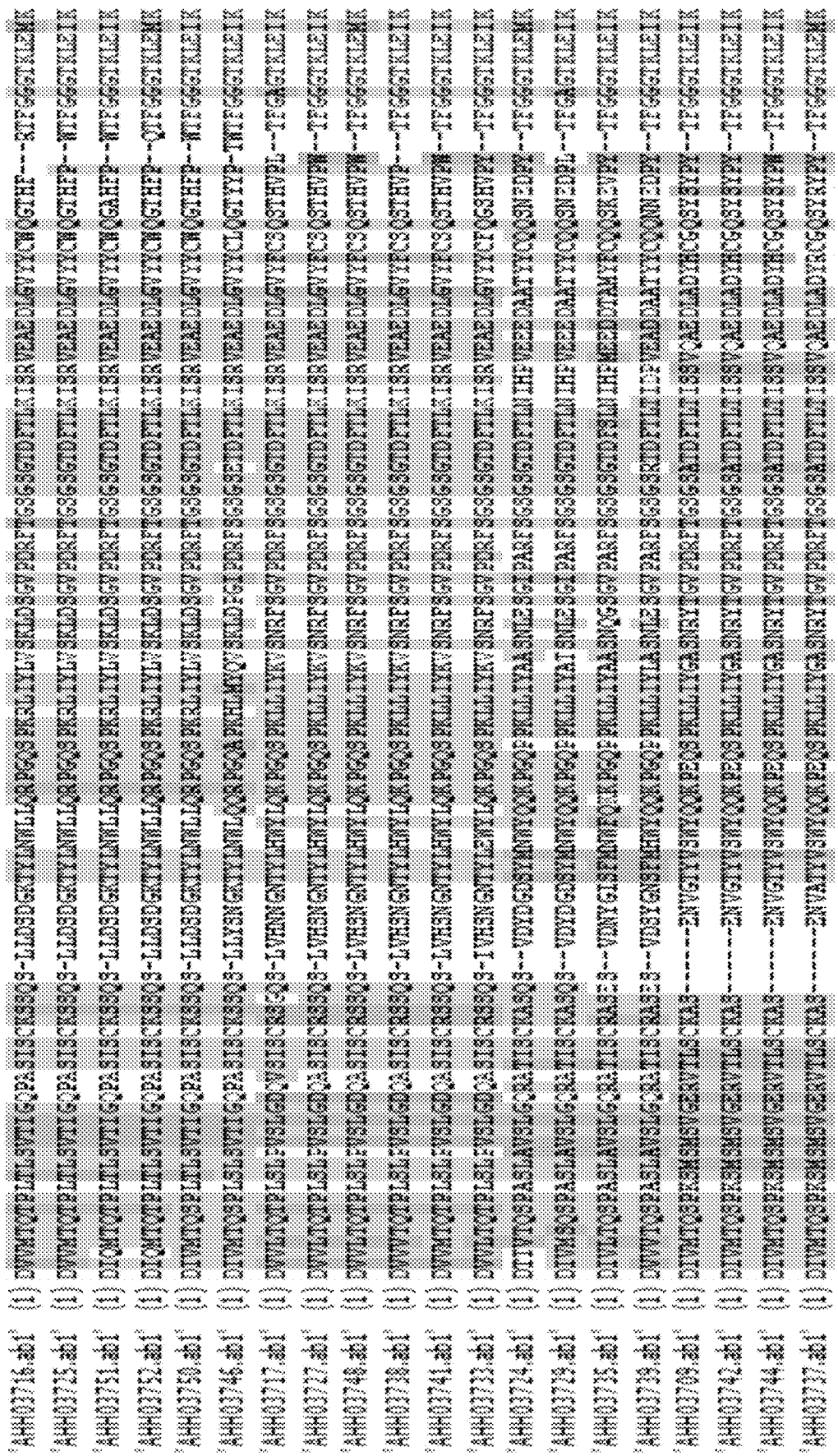
FIG. 4A - Continued

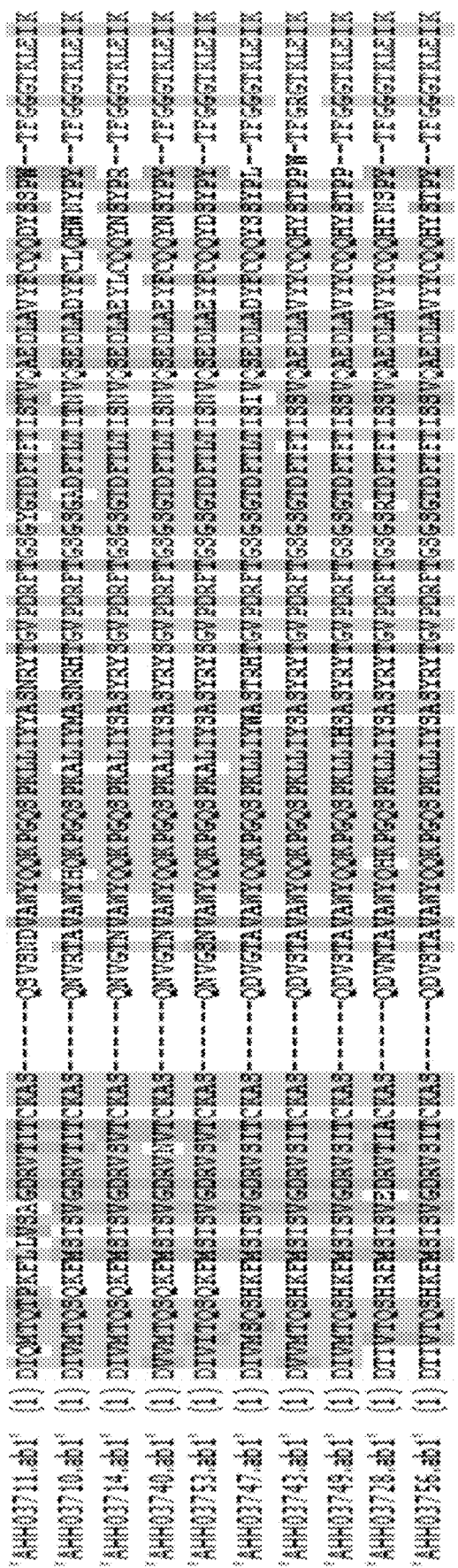
FIG. 4A - Continued

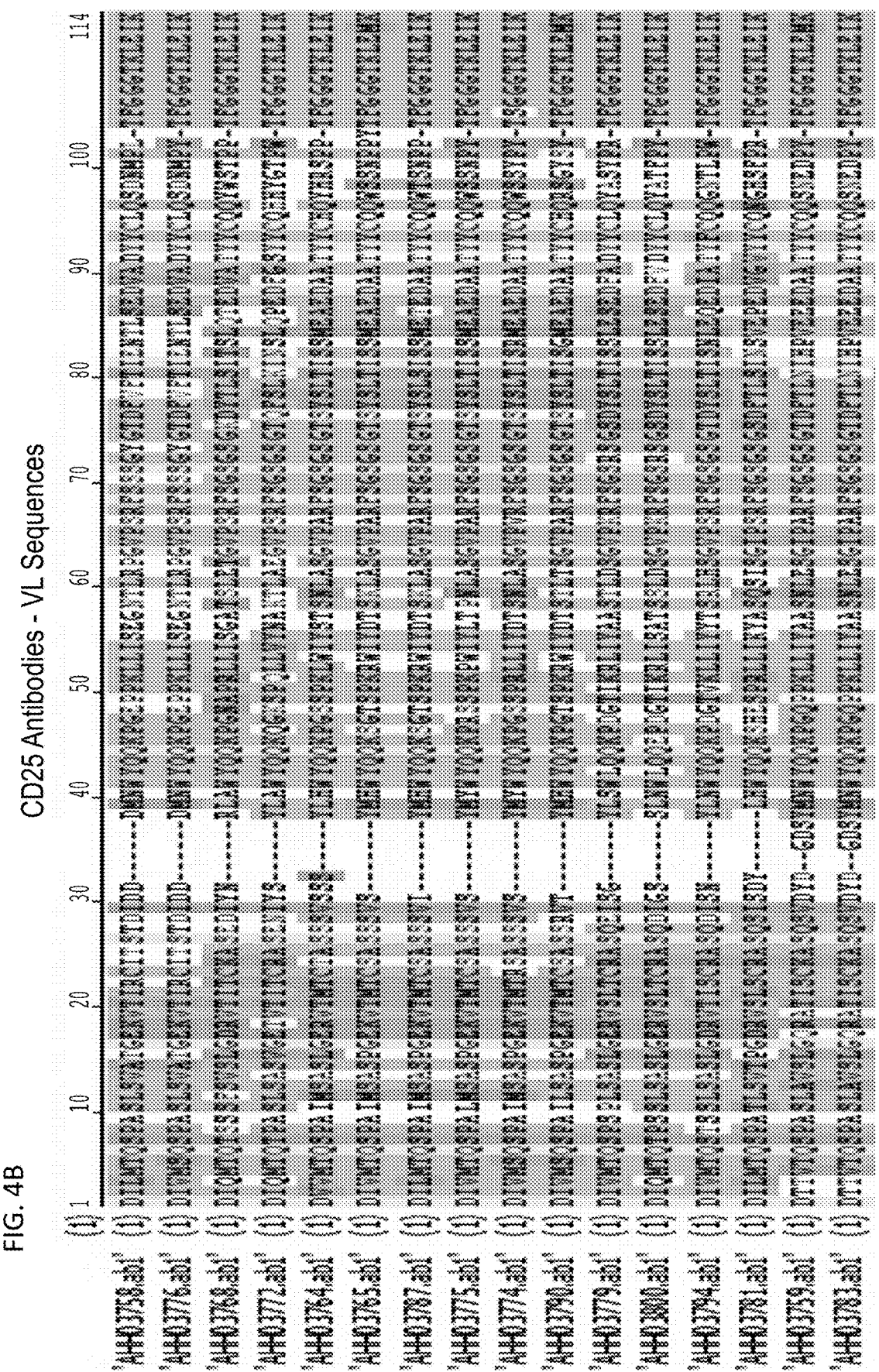

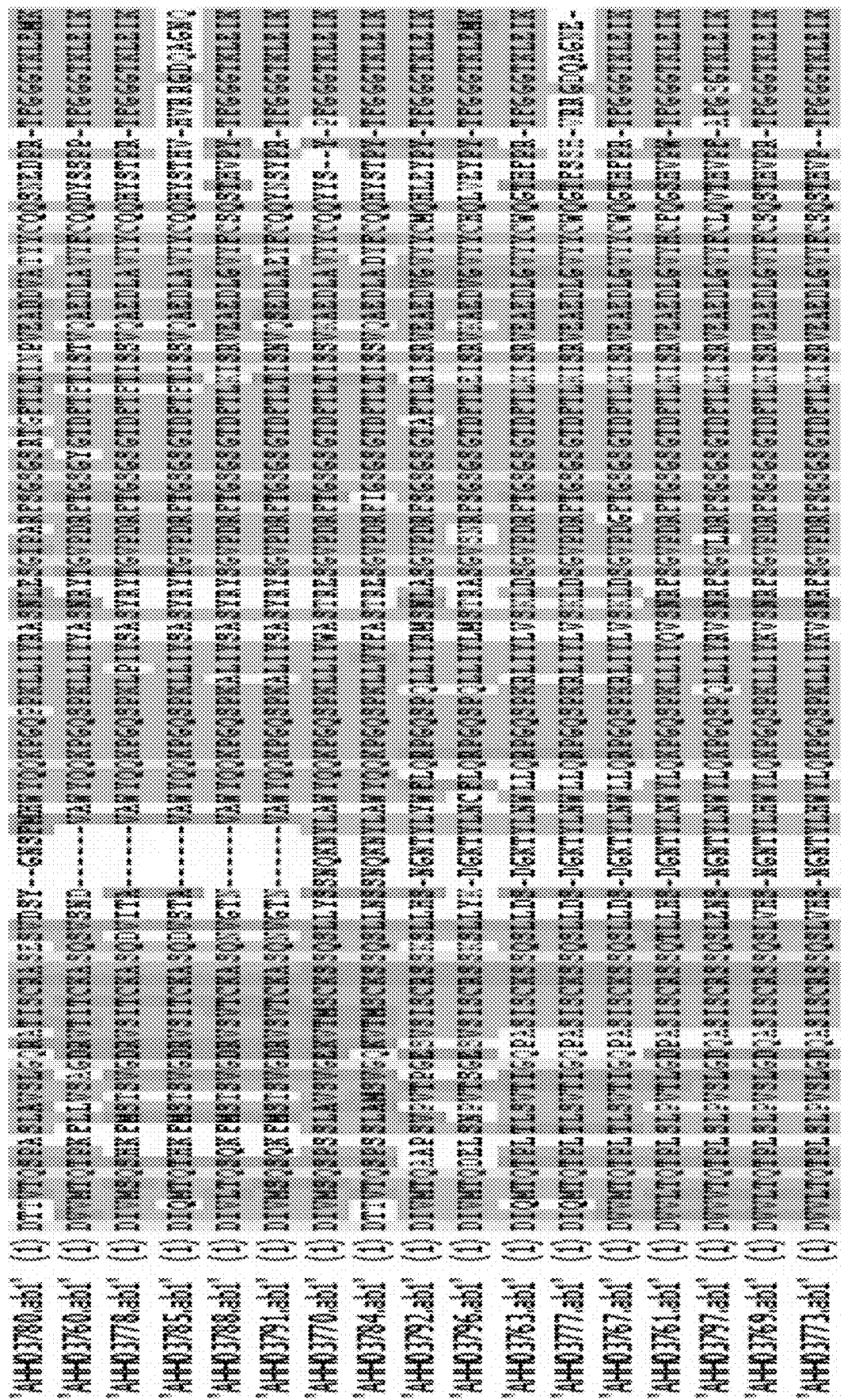
FIG. 4B - Continued

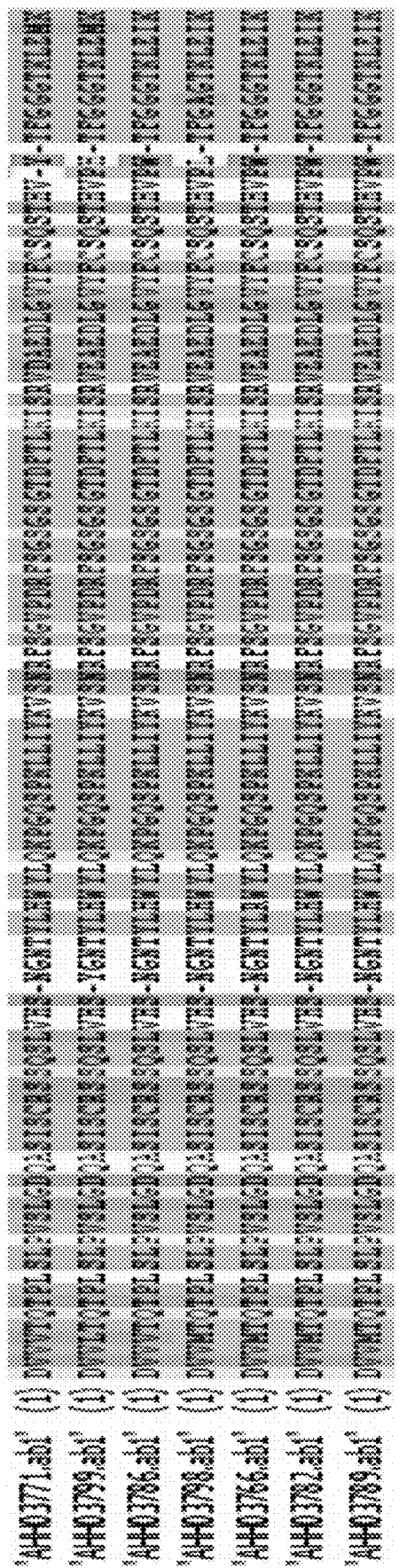
FIG. 4B - Continued

FIG. 5 CD25 Antibodies - VH Sequences

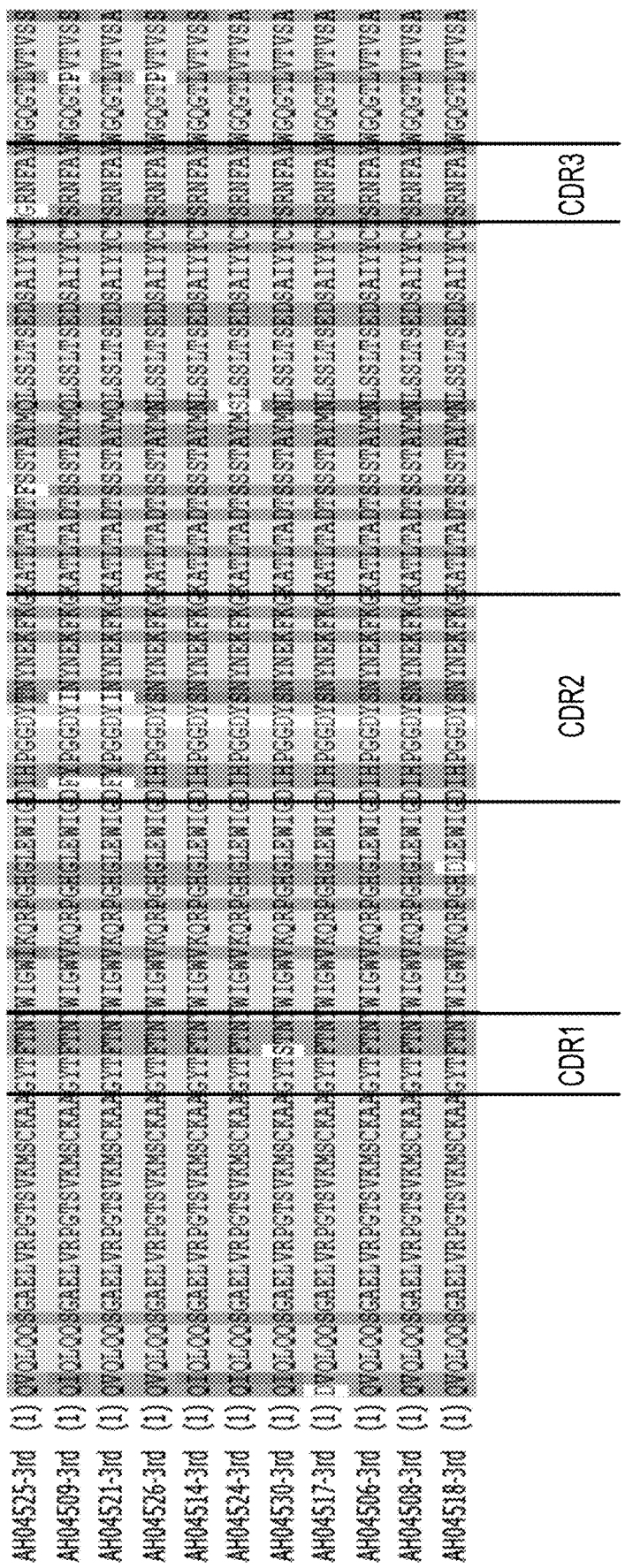
FIG. 5 - Continued

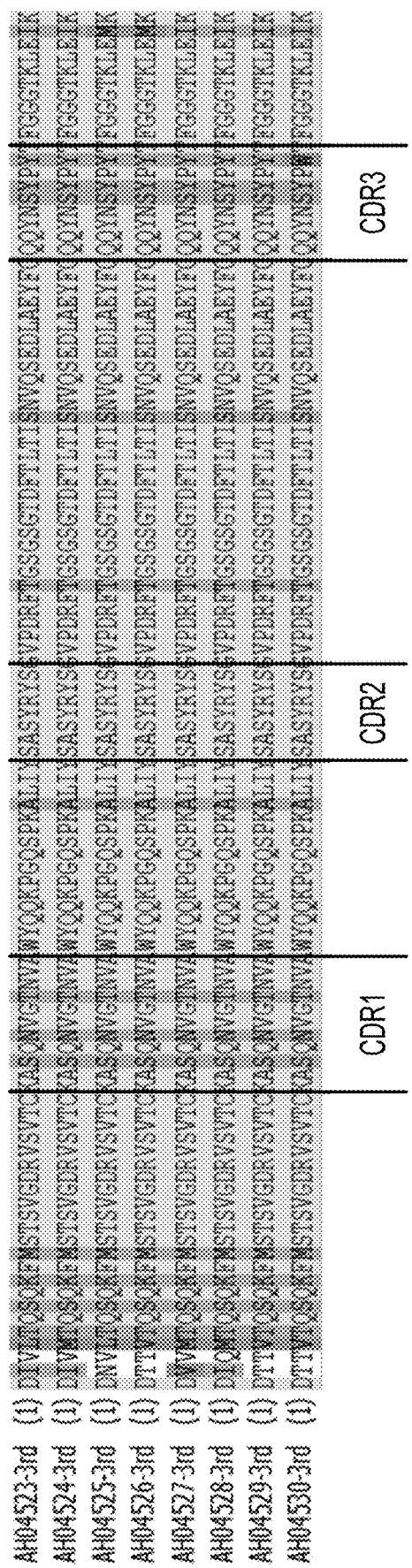
FIG. 6 - Continued

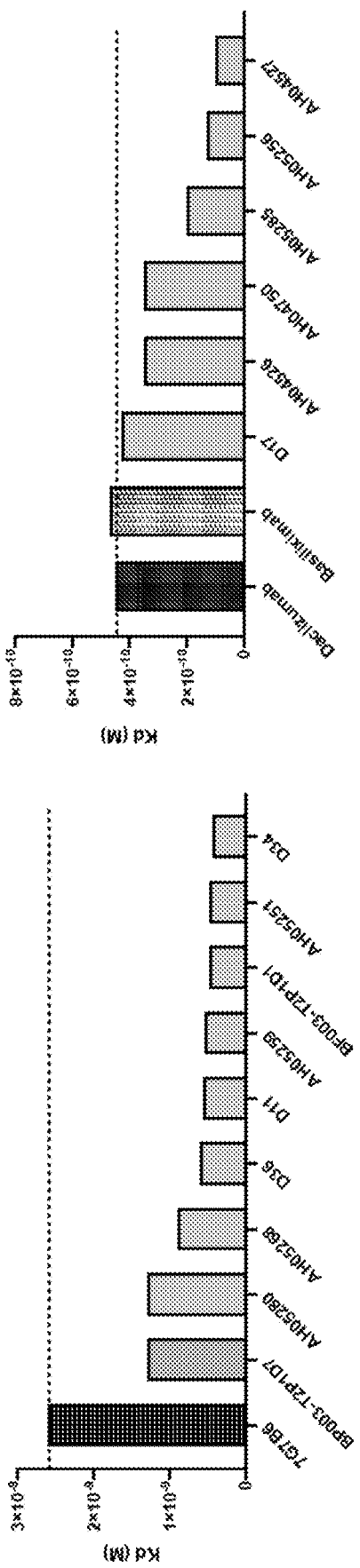
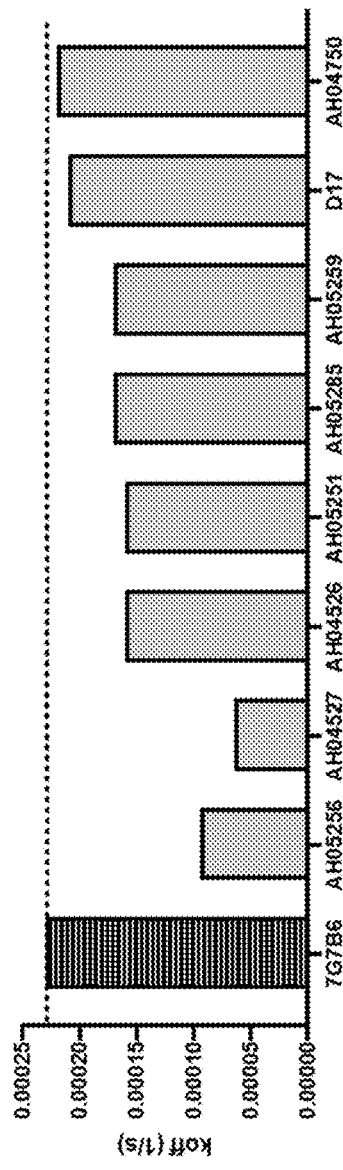
FIG. 13B
FIG. 13C

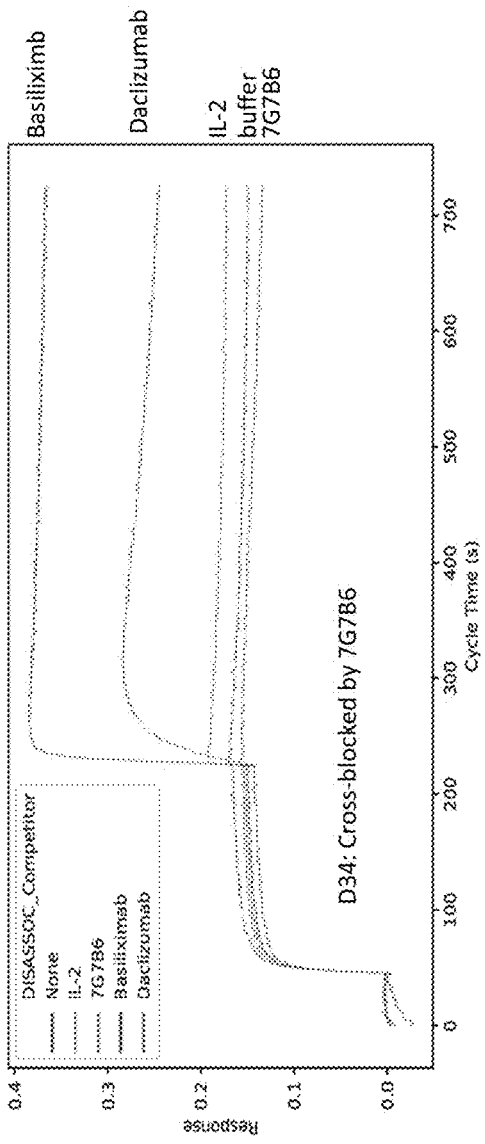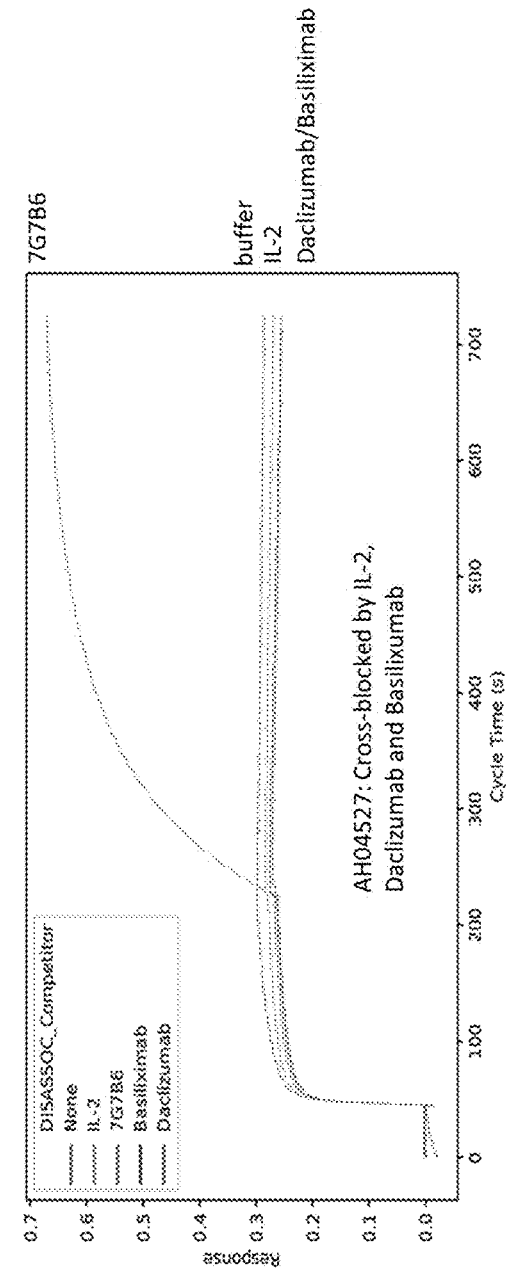
FIG. 14A
FIG. 14B

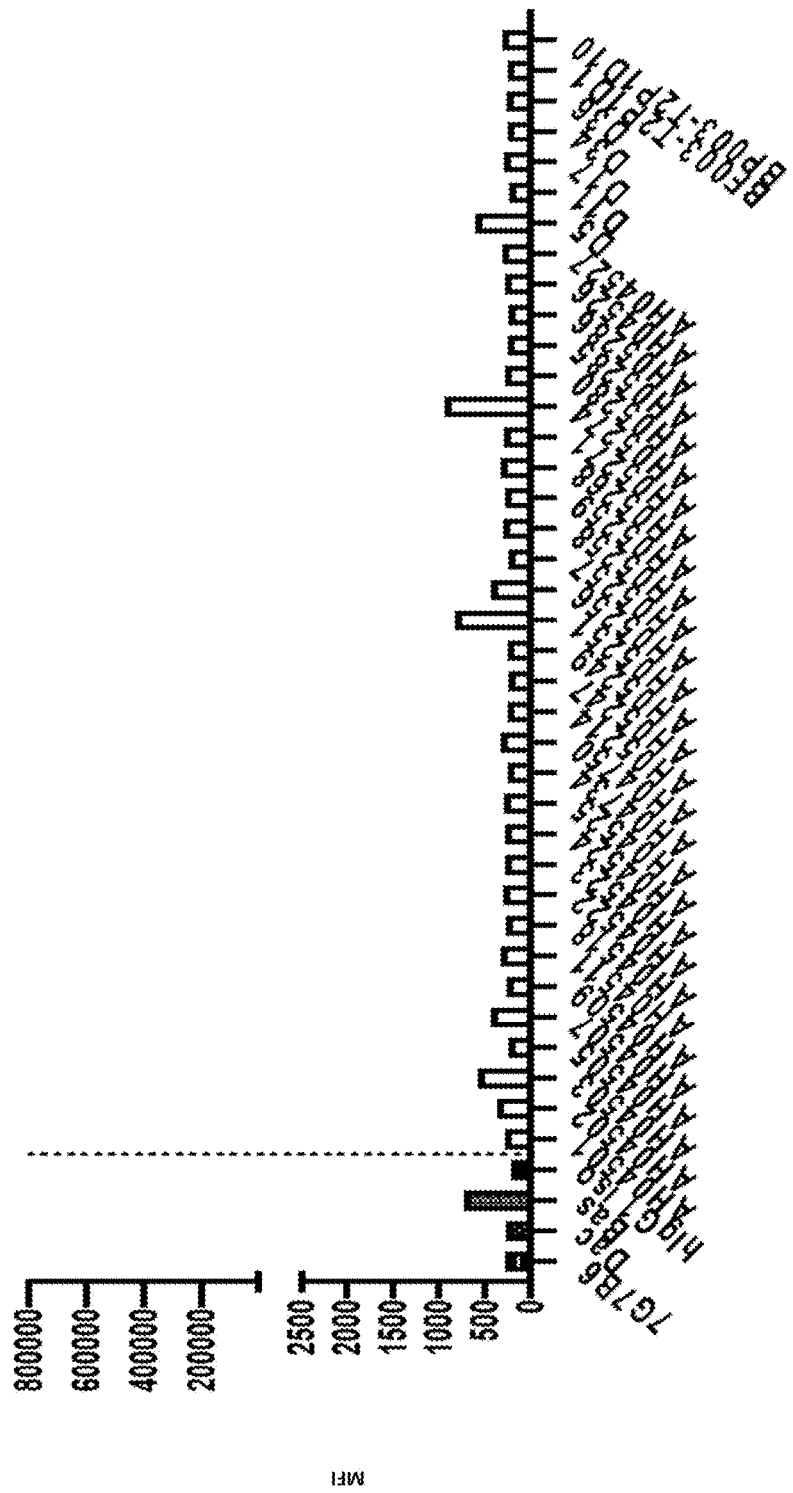

FIG. 18B
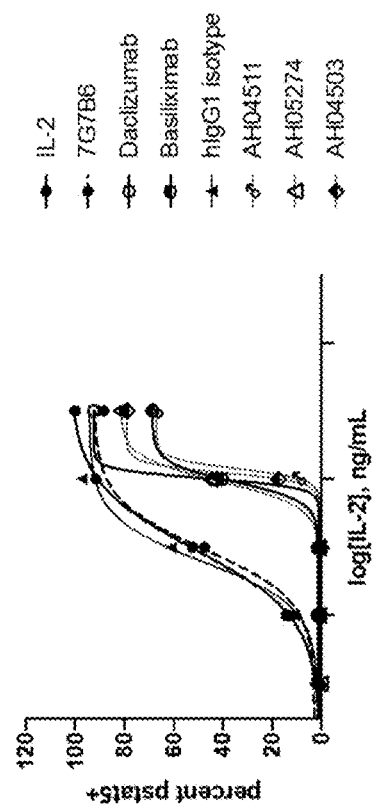
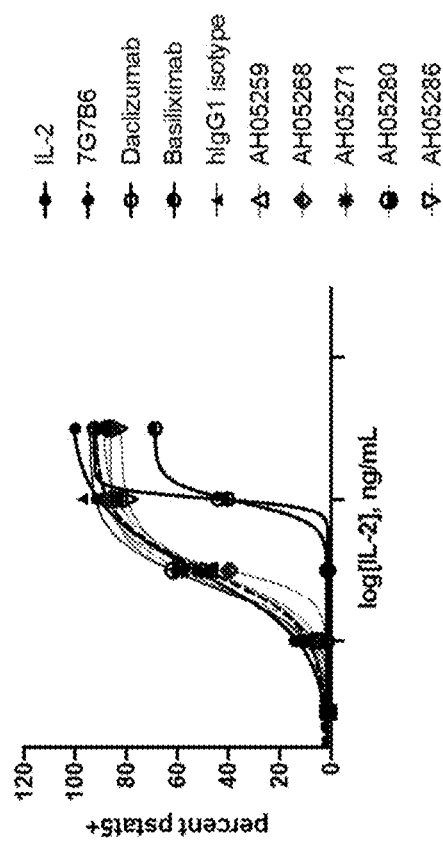

ND25 ANTIBODIES

CROSS-REFERENCE TO RELATED APPLICATIONS

This application is a continuation of International Application No. PCT/US2019/061552, filed Nov. 14, 2019, which claims the priority benefit of U.S. Provisional Application No. 62/767,405, filed on Nov. 14, 2018, the entire contents of which are hereby incorporated by reference in their entirety for all purposes.

INCORPORATION-BY-REFERENCE OF MATERIALS FILED ON COMPACT DISC

The present application includes a Sequence Listing which has been submitted in ASCII format via EFS-Web and is hereby incorporated by reference in its entirety. Said ASCII copy, created on Nov. 18, 2021, is named RBYC_022.01US_SeqList_ST25.txt and is 521,445 bytes in size.

BACKGROUND

The CD25 protein is the alpha chain of interleukin-2 (IL-2) receptor and is a transmembrane protein present on regulatory T cells, and activated T cells. In a normal state, regulatory T cells constitutively express CD25 and act to suppress the expansion of effector cells. Regulatory T cells maintain the healthy state and inhibit effector T cells from reacting against self antigens or over-reacting to foreign antigens. In a normal, protective immune response, effector T cells multiply after contact with foreign antigen and overcome inhibition by regulatory T cells. In case of proliferative diseases, however cancer cells disable the healthy immune response by increasing the amount of regulatory T cells and thereby limiting the generation of effector T cells against them. Additional molecular tools to alter the proliferation of CD25-expressing regulatory T cells are needed, for example to dampen the immune system for use in cancer therapies or to upregulate the immune system for use in autoimmune diseases; provided herein are such tools.

SUMMARY

Provided herein are antibodies that specifically bind to CD25 (anti-CD25 antibodies, interchangeably referred to herein as CD25 antibodies). The antibodies may be human, chimeric or humanized. Also provided herein are methods of use and methods of making the antibodies described. For example, the CD25 antibodies may be used therapeutically to treat cancer, comprising administering to a subject in need thereof an antibody or a pharmaceutical composition thereof. Also provided are methods of producing the CD25 antibodies described herein.

In one aspect, provided herein is a monoclonal CD25 antibody which binds to human CD25, and possesses at least one, at least two, at least three, at least four, at least five, or at lease six of the following characteristics:

a. the antibody does not disrupt the binding of the IL-2 ligand to the alpha chain of the IL-2 receptor (CD25), and binds to a different epitope than to which 7G7B6 binds;

b. the antibody does not disrupt the binding of the IL-2 ligand to the alpha chain of the IL-2 receptor (CD25), but does disrupt the trimerization of the beta, gamma, and alpha (CD25) chains of the IL-2 receptor;

c. the antibody disrupts the binding of the IL-2 ligand to the alpha, beta, and/or gamma chains of the IL-2 receptor, and binds to a different epitope than to which daclizumab or baciliximab bind;

d. the antibody exhibits a higher affinity of binding to CD25 at pH lower than 7.4, when compared to the affinity of binding to CD25 at a pH of 7.4;

e. the antibody comprises the amino acid sequence of any one of the variable heavy chains presented in Tables 1A, 1C, 1E, 1G, 1I, 1K, 2A, 2B, 2C, 4A, and 5A or FIGS. 3A, 3B and 5, humanized versions thereof, or an amino acid sequence comprising at least a 80%, at least a 85%, at least a 90%, or at least a 95% sequence identity thereto;

f. the antibody comprises the amino acid sequence of any one of the variable light chains presented in Tables 1B, 1D, 1F, 1H, 1J, 1L, 3A, 3B, 3C, 4B, and 5B or FIGS. 4A, 4B and 6, humanized versions thereof, or an amino acid sequence comprising at least a 80%, at least a 85%, at least a 90%, or at least a 95% sequence identity thereto;

g. the VH of the antibody comprises any one of the amino acid sequence of CDRH1, CDRH2, and CDRH3 as presented in Tables 1A, 1C, 1E, 1G, 1I, 1K, 2A, 2B, 2C, 4A, 5A, and 6 or contained in the sequences presented in FIGS. 3A, 3B and 5;

h. the VL of the CD25 antibody comprises any one of the amino acid sequence of CDRL1, CDRL2, and CDRL3 as presented in Tables 1B, 1D, 1F, 1H, 1J, 1L, 3A, 3B, 3C, 4B, 5B and 7, or contained in the sequences presented in FIGS. 4A, 4B and 6; and i. the antibody comprises the amino acid sequence of CDRH1, CDRH2, and CDRH3 of any one of the combinations presented in Table 6 and the amino acid sequence of CDRL1, CDRL2, and CDRL3 of any one of the combinations presented in Table 7.

In some embodiments, the VH of the antibody comprises the amino acid sequence of CDRH1, CDRH2, and CDRH3 combinations as presented in Tables 1A, 1C, 1E, 1G, 1I, 1K, 2A, 2B, 2C, 4A, 5A, or 6 or contained in the sequences presented in FIG. 3A, 3B or 5.

In some embodiments, the VL of the CD25 antibody comprises the amino acid sequence of CDRL1, CDRL2, and CDRL3 combinations as presented in Tables 1B, 1D, 1F, 1H, 1J, 1L, 3A, 3B, 3C, 4B, 5B, or 7 or contained in the sequences presented in FIG. 4A, 4B or 6.

In some embodiments, the CD25 antibody comprises the amino acid sequence of CDRH1, CDRH2, and CDRH3 of any one of the combinations presented in Table 6.

In some embodiments, the CD25 antibody comprises the amino acid sequence of CDRL1, CDRL2, and CDRL3 of any one of the combinations presented in Table 7.

In some embodiments the antibody is a human antibody.
In some embodiments the antibody is a humanized antibody.
In some embodiments the antibody is a chimeric antibody.
In some embodiments the antibody is an antibody fragment.
In some embodiments the antibody also binds cynomologous monkey CD25.

In another aspect, provided herein is a method of treating a subject in need thereof comprising administering to the subject a therapeutically effective amount of any one of the antibodies or pharmaceutical compositions described herein. In some embodiments, provided herein is a method of depleting the number of regulatory T cells in a subject comprising administering to the subject a therapeutically effective amount of any one of the antibodies or pharmaceutical compositions described herein. In some embodiments, the subject suffers from cancer; in other embodiments, the subject suffers from an autoimmune-related disease or disorder.

In another aspect, provided herein is a method of depleting the number of regulatory T cells in a sample comprising peripheral blood mononuclear cells comprising contacting the sample with any one of the antibodies described herein.

In related aspects, provided herein are pharmaceutical compositions or kits comprising any one or more of the antibodies described herein, nucleic acid sequences encoding any of the antibodies described herein, vectors comprising the nucleic acid and phage expressing any of the antibodies described herein.

All of the above features described herein (including any accompanying claims, abstract and drawings), and/or all of the steps of any method or process so disclosed, may be combined in any combination, except combinations where at least some of such features and/or steps are mutually exclusive.

DESCRIPTION OF THE DRAWINGS

The present application can be understood by reference to the following description taken in conjunction with the accompanying figures.

FIG. 3A and FIG. 3B depict variable heavy chain (VH) amino acid sequences of exemplary CD25 antibodies (SEQ ID NOs: 61-107, 1501 and 432-460) of the disclosure.

FIG. 4A and FIG. 4B depict variable light chain (VL) amino acid sequences of exemplary CD25 antibodies (SEQ ID NOs: 703, 705, 707, 709, 715, 717, 722, 724, 725, 727, 728, 739, 742, 745, 747, 749-752, 754-756, 759, 762, 765, 767, 769, 776, 780, 781, 783, 785, 787, 789, 791, 794, 797, 799, 801, 803, 804, 806, 809-811, 813, 815, 818, 824, 827, 829, 835, 841, 842, 844, 846, 848, 849, 851, 853, 875-880, 882, 884, 886, 888, 892, 897, 901-903, 905-908, 914, 917, 919-922) of the disclosure.

FIG. 5 depicts VH amino acid sequences of exemplary CD25 antibodies (SEQ ID NOs: 868, 869, 1222, 1229-1238, 1316-1318 and 1327-1335) of the disclosure.

FIGS. 13A-13C depict differences in Kd and Koff rates for several Fab clones that were reformatted to human IgG1 antibodies (FIG. 13A). Several reformatted clones have better affinity and Koff rates than commercially available antibodies 7G7B6, Daclizumab and Basiliximab (FIG. 13B, FIG. 13C).

FIGS. 14A-14D show representative data from epitope bining cross competition assays against IL-2 and commercially available antibodies 7G7B6, Daclizumab and Basiliximab, using Fab clones that were reformatted to human IgG1 antibodies. Antibodies had different cross blocking profiles.

FIGS. 15A-15B depicts specific binding of human IgG1 reformatted Fab on CD25+ cell lines SUDHL-1 and HEK IL-2 reporter cells (FIG. 15A) and no binding on CD25– cell line SUDHL-2 (FIG. 15B).

FIGS. 18A-18B. show differences in pSTAT5 levels across several human IgG1 reformatted Fab clones at 5 ug/ml, compared to IL-2 levels at 0.1 ng/mL (FIG. 18A). FIG. 18B shows pSTAT5 levels with IL-2 dose response curve (starting at 10 ng/mL with 10 fold dilutions) with 5 ug/mL of each antibody. Some clones were shown to be better IL-2 blocker and IL-2 nonblockers than commercially available antibodies, 7G7B6, Daclizumab and Basiliximab at 0.1 ng/mL.

DETAILED DESCRIPTION

Figure 1:
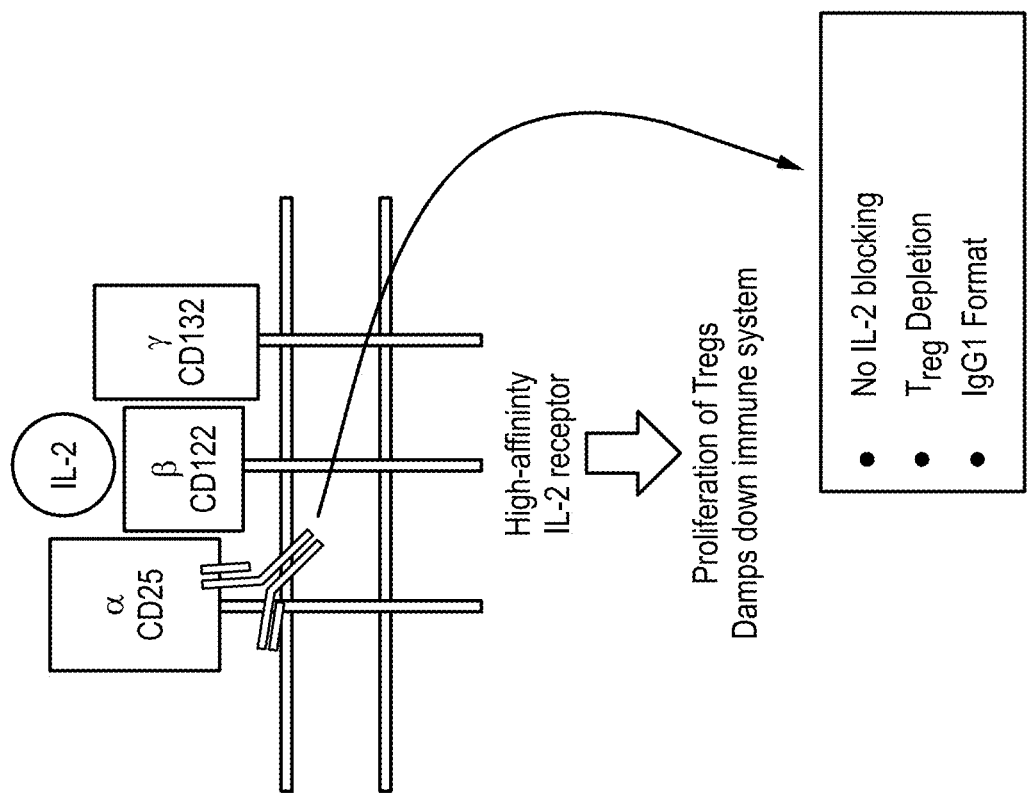
FIG. 1 is an exemplary description of the desired characteristics of one of the class of CD25 antibodies described herein: CD25 antibodies that block the alpha chain of the IL-2 receptor (CD25) only, do not block binding of IL-2, do not disrupt signal transduction mediated by IL-2, and leads to depletion of Tregs. Data are collected with Fab clones, but as provided herein, in some embodiments, the CD25 antibodies are full length antibodies, i.e. human IgG1 antibodies.

Provided herein are antibodies that specifically bind to CD25. The antibodies may be human, chimeric or humanized. Also provided herein are methods of use and methods of making the antibodies described. For example, the CD25 antibodies may be used therapeutically to treat cancer, comprising administering to a subject in need thereof an antibody or a pharmaceutical composition thereof. Also provided are methods of producing the CD25 antibodies described herein.

Definitions

Unless defined otherwise herein, all technical and scientific terms used herein have the same meaning as commonly understood by one of ordinary skill in the art to which this invention belongs. Any methods and materials similar or equivalent to those described herein can be used in the practice or testing of the present invention, exemplary methods and materials are described.

The headings provided herein are not limitations of the various aspects or embodiments of the invention. Accordingly, the terms defined immediately below are more fully defined by reference to the specification as a whole.

Numeric ranges are inclusive of the numbers defining the range.

The term antibody, as used herein, includes but is not limited to a monoclonal antibody, polyclonal antibody, human antibody, humanized antibody, non-human antibody, chimeric antibody, monovalent antibody and antigen-binding fragments of the antibody (e.g Fab fragment, a Fab'2 fragment, or a scFV). Also provided herein are antibody-drug conjugates, bispecific antibodies, and multispecific antibodies that exhibit specificity for CD25. A non-human antibody (e.g. a mouse antibody) may be "humanized" using conventional techniques (e.g. by introducing changes in the framework region, while retaining mouse CDRs).

The terms "polynucleotide" and "nucleic acid" are used interchangeably herein, and refer to a polymeric form of nucleotides of any length, which may be ribonucleotides or deoxyribonucleotides. The terms include, but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms encompass nucleic acids containing known analogues of natural nucleotides and having similar binding properties, and are metabolized in a manner similar to naturally-occurring nucleotides, unless specifically limited or stated otherwise.

When a nucleic acid or amino acid sequence is said to have a certain percent "sequence identity" or "identity" or is a certain percent "identical" to another nucleic acid or amino acid sequence, that percentage of bases or amino acids are the same, and in the same relative position, when the sequences are aligned, when comparing the two sequences.

The terms "individual," "subject," and "patient" are used interchangeably herein and refer to any subject for whom treatment or therapy is desired. The subject may be a mammalian subject. Mammalian subjects include, e. g., humans, non-human primates, rodents, (e.g., rats, mice), lagomorphs (e.g., rabbits), ungulates (e.g., cows, sheep, pigs, horses, goats, and the like), etc. In some embodiments, the subject is a human. In some embodiments, the subject is a non-human primate. In some embodiments, the subject is a companion animal (e.g. cats, dogs).

Antibodies

Provided herein are antibodies that specifically bind to CD25. Such antibodies are capable of binding to the CD25 antigen either alone or associated with other molecules to form high affinity IL-2 receptors which is present on regulatory T cells.

In some embodiments, the CD25 antibody is a humanized antibody that specifically binds to CD25.

In some embodiments, the CD25 antibody is a chimeric antibody that for example a mouse-human chimeric antibody, e.g. an antibody that comprises mouse variable domains, and a human constant region.

A CD25 antibody of the disclosure can be any of a human IgA, IgD, IgE, IgG, or IgM antibody. The IgA antibody can be an IgA1 or an IgA2 antibody. The IgG antibody can be an IgG1, IgG2, IgG2a, IgG2b, IgG3 or IgG4 antibody. A combination of any of these antibodies can also be made and used. In some embodiments, the constant region is of the IgG type, e.g. of the human IgG type. In some embodiments, the constant region is of the IgG1 type, e.g. of the human IgG1 type.

In some embodiments, the CD25 antibody exhibits cross reactivity to more than one species, for example specifically binds to both human CD25 and non-human CD25, for example specifically binds to both human CD25 and cynomolgus monkey CD25.

The KD (affinity constant) of the antibodies provided herein range from about $10^{-5}$ to about $10^{-14}$ nM. In some embodiments the KD of the antibodies provided herein range from about $10^{-8}$ to about $10^{-12}$ nM. In exemplary embodiments, the KD of a CD25 antibody is at least about $10^{-5}$ nM, about $10^{-6}$ nM, about $10^{-7}$ nM nM, about $10^{-8}$ nM, about $10^{-9}$ nM, about $10^{-10}$ nM, about $10^{-11}$ nM, about $10^{-12}$ nM, about $10^{-13}$ nM, or even about $10^{-14}$ nM.

The Kd (off-rate constant) of the antibodies provided herein range from about $10^{-2}$ to about $10^{-6}$ 1/s.

In some embodiments, the CD25 antibody exhibits the same affinity (KD) for the CD25 antigen at both physiological pH (about 7.4) and non-physiological pH. In some embodiments, the CD25 antibody exhibits the same off-rate (Kd) for the CD25 antigen at both physiological pH (about 7.4) and non-physiological pH.

In some embodiments, the CD25 antibody exhibits different affinities (different KD) for the CD25 antigen at physiological pH (about 7.4) and non-physiological pH. In some embodiments, the CD25 antibody exhibits different off-rate constants (different Kd) for the CD25 antigen at physiological pH (about 7.4) and non-physiological pH.

In some embodiments, the CD25 antibody exhibits a lower affinity (higher KD) for the CD25 antigen at physiological pH (about 7.4) than at a pH that is lower than physiological pH, for example when the pH is 7.3, 7.2, 7.1, 7.0, 6.9, 6.8, 6.7, 6.6, 6.5, 6.4, 6.3, 6.2, 6.1, or lower. In exemplary embodiments, the antibody exhibits a higher affinity for the CD25 antigen at a pH of about 6.5, when compared to the affinity at a pH of about 7.4. In some embodiments, such antibodies are useful for retaining activity, or exhibiting enhanced activity in an acidic environment, a hypoxic environment, for example a tumor microenvironment.

In some embodiments, the antibody is a non IL-2-blocking antibody (a non IL-2 blocker)—that is, the binding of the antibody to CD25 does not disrupt or prevent binding of the IL-2 ligand to CD25 (the IL-2 alpha chain), and does not affect IL-2 mediated signal transduction, e.g. signaling through the IL-2/JAK3/STAT-5 signaling pathway. In some embodiments, the antibody does not disrupt the binding of IL-2 ligand to CD25 (IL-2 alpha chain), and binds to a different epitope than where the 7G7B6 antibody binds. In some embodiments, the antibody does not disrupt the binding of the IL-2 ligand to CD25 (IL-2 alpha chain), but does disrupt the trimerization of the beta, gamma, and alpha (CD25) chains of the IL-2 receptor.

In some embodiments, the antibody is an IL-2 blocking antibody (IL-2 blocker), e.g., the antibody disrupts or prevents binding of the IL-2 ligand to the alpha, beta, and/or gamma chains of the receptor, and decreases or inhibits IL-2 mediated signal transduction. In certain embodiments, the antibody disrupts or prevents binding of the IL-2 ligand to CD25. In some embodiments, the antibody disrupts or prevents the binding of the IL-2 ligand to CD25, and binds to a different epitope than to which either daclizumab or baciliximab bind.

In some embodiments, the CD25 antibody is a partially blocking antibody (partial IL-2 blocker), and partially, but not completely, disrupts binding of the IL-2 ligand to the alpha, beta, and/or gamma chains of the IL-2 receptor (CD25), and/or partially, but not completely decreases IL-2 mediated signal transduction.

In some embodiments, the CD25 antibody disrupts or prevents heterotrimerization of the alpha, beta, and gamma IL-2 chains. In some embodiments, the antibody does not block binding of the IL-2 ligand with CD25, but does disrupt or prevent heterotrimerization of the alpha, beta, and gamma IL-2 chains. In certain embodiments, the antibody selectively binds to regulatory T cells. In other embodiments, the antibody selectively binds T effector cells.

In some embodiments, binding of the CD25 antibody leads to the depletion of regulatory T cells (Tregs), while allowing for expansion of effector T cells (Teff).

In some embodiments, the antibody binds to CD25 in the trans orientation. In other embodiments the antibody binds to CD25 in the cis orientation. In still further embodiments, the antibody is capable of binding to CD25 in either the cis or the trans configuration.

In some embodiments, the CD25 antibody exhibits greater binding affinity to CD25, as compared to the binding of 7G7B6 (anti-human CD25 with mouse IgG2a Fc receptor; IL-2 non blocker; BioXcell) to CD25.

Tables 1A-1L, 2A-2C, 3A-3C, 4A-4B, 5A-5B, 6, and 7 and FIGS. 3A, 3B, 4A, 4B, 5, and 6 provide exemplary sequences for the CD25 antibodies described herein. It is noted that the complementarity determining region (CDR) and framework (FR) sequences shown are based on the IMGT convention for antibody annotation. However a skilled artisan can determine other articulations of CDR and framework sequences based on the presented VH and VL sequences, using other algorithms/conventions for antibody annotation, such as Kabat and Chothia. Accordingly the CDRs and FR sequences of the disclosure are not limited to those exemplary CDRs and FR sequences annotated in the below tables, but rather the CDRs as would be understood and determined by a skilled artisan, given the sequence of the variable region.

TABLE 1A

D5 VH Sequences

D5 VH - Nucleic Acid catgtgcaactgcagcagtctggagctgagctggtaaggcctgggacttc
agtgaagatatcctgcaaggcttctggctacaccttcactaactactggc
taggttgggtaaagcagaggcctggacatggacttgagtggattggagat
atttaccctggaggtggttatactaactacaatgagaagttcaagggcaa
ggccacactgactgcagacacatcctccagcactgcctacatgcagctca
gtagcctgacatctgaggactctgctgtctatttctgtgcaagagttact
ccggcttcctggggccaaggcaccagtctcacagtctcctcgg (SEQ
ID NO: 1)

D5 VH - Amino Acid

HVQLQQSGAELVRPGTSVKISCKASGYTFTNYWLGWVKQRPGHGLEWIGD
IYPGGGYTNYNEKFKGKATLTADTSSSTAYMQLSSLTSEDSAVYFCARVT
PASWGQGTSLTVSS (SEQ ID NO: 2)

D5 VH CDR1 - IMGT ggctacaccttcactaactactgg (SEQ ID NO: 3)

GYTFTNYW (SEQ ID NO: 4)

TABLE 1A-continued

D5 VH Sequences

D5 VH CDR2 - IMGT atttaccctggaggtggttatact (SEQ ID NO: 5)

IYPGGGYT (SEQ ID NO: 6)

D5 VH CDR3 - IMGT gcaagagttactccggcttcc (SEQ ID NO: 7)

ARVTPAS (SEQ ID NO: 8)

TABLE 1B

D5 VL Sequences

D5 VL - Nucleic Acid gatattgtgatgacccagtctcaaaaattcatgtccacatcagtaggaga
cagggtcagcgtcacctgcaaggccagtcagaatgtgggtactaatgtag
cctggtatcaacagaaaccagggcaatctcctaaagcactgatttactcg
gcatcctaccggtacagtggagtccctgatcgcttcacaggcagtggatc
tgggacagatttcactctcaccatcagcaatgtgcagtctgaagacttgg
cagagtatttctgtcagcaatataacagctatccgtacacgttcggaggg
gggaccaagctggaaatgaaac (SEQ ID NO: 9)

D5 VL - Amino Acid

DIVMTQSQKFMSTSVGDRVSVTCKASQNVGTNVAWYQQKPGQSPKALIYS
ASYRYSGVPDRFTGSGSGTDFTLTISNVQSEDLAEYFCQQYNSYPYTFGG
GTKLEMK (SEQ ID NO: 10)

D5 VL - CDR1-IMGT cagaatgtgggtactaat (SEQ ID NO: 11)

QNVGTN (SEQ ID NO: 12)

D5 VL - CDR2-IMGT tcggcatcc

SAS (SEQ ID NO: 13)

D5 VL - CDR3-IMGT cagcaatataacagctatccgtacacg (SEQ ID NO: 14)

QQYNSYPYT (SEQ ID NO: 15)

TABLE 1C

D11 VH Sequences

D11 VH-Nucleic Acid cagatccaactgcagcagcctggggctgagctggtgaggcctgggggttc
actgaaaatttcctgcaagggttctggctacacattcactgattatgcta
tgcactgggtgaggcagagtcatgcaaagagtctagagtggattggagtt
attagtacttactctggtgatgctatctacaaccagaagttcaagggcaa
ggccacaatgactgtcgacaaatcctccagcacagcctatctggaacttg
ccagactgacatctgacgattctgccatctattactgtgcaagagggta
acttttgactactggggccaaggcaccactgtcacagtctcctcgg
(SEQ ID NO: 16)

D11 VH - Amino Acid

QIQLQQPGAELVRPGVSLKISCKGSGYTFTDYAMHWVRQSHAKSLEWIGV
ISTYSGDAIYNQKFKGKATMTVDKSSSTAYLELARLTSDDSAIYYCARGV
TFDYWGQGTTVTVSS (SEQ ID NO: 17)

TABLE 1C-continued

D11 VH Sequences

D11 VH - CDR1-IMGT ggctacacattcactgattatgct (SEQ ID NO: 18)

GYTFTDYA (SEQ ID NO: 19)

D11 VH - CDR2-IMGT attagtacttactctggtgatgct (SEQ ID NO: 20)

ISTYSGDA (SEQ ID NO: 21)

D11 VH - CDR3-IMGT gcaagagggtaacttttgactac (SEQ ID NO: 22)

ARGVTFDY (SEQ ID NO: 23)

TABLE 1D

D11 VL Sequences

D11 VL-Nucleic Acid gacatccagatgacacagactacatcctccctgtctgcctctctgggaga
cagagtcaccatcacttgcagggcaagtcaggacattagcaattatttag
aatggtatcagcagaaacagggaaaatctcctcagtcctggtctataat
gcaaaaaccttagcagaaggtgtgccatcaaggttcagtggcagtggatc
aggcacacagttttctctgaagatcaacagcctgcagcctgaagattttg
ggagttattactgtcaacatcattatgatactccgtacacgttcggaggg
gggaccaagctggaaataaaac (SEQ ID NO: 24)

D11 VL - Amino Acid

DIQMTQTTSSLSASLGDRVTITCRASQDISNYLEWYQQKQGKSPQLLVYN
AKTLAEGVPSRFSGSGSGTQFSLKINSLQPEDFGSYYCQHHYDTPYTFGG
GTKLEIK (SEQ ID NO: 25)

D11 VL - CDR1-IMGT caggacattagcaattat (SEQ ID NO: 26)

QDISNY (SEQ ID NO: 27)

D11 VL - CDR2-IMGT aatgcaaaa

NAK (SEQ ID NO: 28)

D11 VL - CDR3-IMGT caacatcattatgatactccgtacacg (SEQ ID NO: 29)

QHHYDTPYT (SEQ ID NO: 30)

TABLE 1E

D16 VH Sequences

D16 VH - Nucleic Acid caggtgcaaatgcagcagtctggagctgagctggtaaggcctgggacttc
agtgaagatatcctgcaaggcttctggctacaccttcactaactactggc
taggttgggtaaagcagaggcctggacatggacttgagtggattggagat
atttaccctggaggtggttatactaactacaatgagaagttcaagggcaa
ggccacactgactgcagacacatcctccagcactgcctacatgcagctca
gtagcctgacatctgaggactctgctgtctatttctgtgcaagagttact
ccggcttcctggggccaaggcaccactctcacagtctcctcgg (SEQ ID NO: 31)

TABLE 1E-continued

D16 VH Sequences

D16 VH - Amino Acid

QVQMQQSGAELVRPGTSVKISCKASGYTFTNYWLGWVKQRPGHGLEWIGD
IYPGGGYTNYNEKPKGKATLTADTSSSTAYMQLSSLTSEDSAVYFCARVT
PASWGQGTTLTVSS (SEQ ID NO: 32)

D16 VH - CDR1-IMGT ggctacaccttcactaactactgg (SEQ ID NO: 3)

GYTFTNYW (SEQ ID NO: 4)

D16 VH - CDR2-IMGT atttaccctggaggtggttatact (SEQ ID NO: 5)

IYPGGGYT (SEQ ID NO: 6)

D16 VH - CDR3-IMGT gcaagagttactccggcttcc (SEQ ID NO: 7)

ARVTPAS (SEQ ID NO: 8)

TABLE 1F

D16 VL Sequences

D16 VL - Nucleic Acid gatatccagatgacccagtctcaaaaattcatgtccacatcagtaggaga
cagggtcagcgtcacctgcaaggccagtcagaatgtgggtactaatgtag
cctggtatcaacagaaaccagggcaatctcctaaagcactgatttactcg
gcatcctaccggtacagtggagtccctgatcgcttcacaggcagtggatc
tgggacagatttcactctcaccatcagcaatgtgcagtctgaagacttgg
cagagtatttctgtcagcaatataacagctatccgtggacgttcggtgga
ggcaccaagctggaaatcaaac (SEQ ID NO: 33)

D16 VL - Amino Acid

DIQMTQSQKFMSTSVGDRVSVTCKASQNVGTNVAWYQQKPGQSPKALIYS
ASYRYSGVPDRFTGSGSGTDFTLTISNVQSEDLAEYFCQQYNSYPWTFGG
GTKLEIK (SEQ ID NO: 34)

D16 VL - CDR1-IMGT cagaatgtgggtactaat (SEQ ID NO: 11)

QNVGTN (SEQ ID NO: 12)

D16 VL - CDR2-IMGT tcggcatcc

SAS (SEQ ID NO: 13)

D16 VL - CDR3-IMGT cagcaatataacagctatccgtggacg (SEQ ID NO: 35)

QQYNSYPWT (SEQ ID NO: 36)

TABLE 1G

D17 VH Sequences

D17 VH - Nucleic Acid Sequence cagatccaactgcagcagtctggagctgagctggtaaggcctgggacttc
agtgaagatatcctgcaaggcttctggctacaccttcactaactactggc
taggttgggtaaagcagaggcctggacatggacttgagtggattggagat
atttaccctggaggtggttatactaactacaatgagaagttcaagggcaa
ggccacactgactgcagacacatcctccagcactgcctacatgcagctca

TABLE 1G-continued

D17 VH Sequences gtagcctgacatctgaggactctgctgtctatttctgtgcaagagttact
ccggcttcctggggccaaggcaccactctcacagtctctgcgg (SEQ
ID NO: 37)

D17 VH - Amino Acid Sequence

QIQLQQSGAELVRPGTSVKISCKASGYTFTNYWLGWVKQRPGHGLEWIGD
IYPGGGYTNYNEKFKGKATLTADTSSSTAYMQLSSLTSEDSAVYFCARVT
PASWGQGTTLTVSA (SEQ ID NO: 38)

D17 VH - CDR1-IMGT ggctacaccttcactaactactgg (SEQ ID NO: 3)

GYTFTNYW (SEQ ID NO: 4)

D17 VH - CDR2-IMGT atttaccctggaggtggttatact (SEQ ID NO: 5)

IYPGGGYT (SEQ ID NO: 6)

D17 VH - CDR3-IMGT gcaagagttactccggcttcc (SEQ ID NO: 7)

ARVTPAS (SEQ ID NO: 8)

TABLE 1H

D17 VL Sequences

D17 VL - Nucleic Acid Sequence gacattctgctgacccagtctcaaaaattcatgtccacatcagtaggaga
cagggtcagcgtcacctgcaaggccagtcagaatgtgggtactaatgtag
cctggtatcaacagaaaccagggcaatctcctaaagcactgatttactcg
gcatcctaccggtacagtggagtccctgatcgcttcacaggcagtggatc
tgggacagatttcactctcaccatcagcaatgtgcagtctgaagacttgg
cagagtatttctgtcagcaatataacagctatcctctcacgttcggaggg
gggaccaagctggaaataaaac (SEQ ID NO: 39)

D17 VL - Amino Acid Sequence

DILLTQSQKFMSTSVGDRVSVTCKASQNVGTNVAWYQQKPGQSPKALIYS
ASYRYSGVPDRFTGSGSGTDFTLTISNVQSEDLAEYFCQQYNSYPLTFGG
GTKLEIK (SEQ ID NO: 40)

D17 VL - CDR1-IMGT cagaatgtgggtactaat (SEQ ID NO: 11)

QNVGTN (SEQ ID NO: 12)

D17 VL - CDR2-IMGT tcggcatcc

SAS (SEQ ID NO: 13)

D17 VL - CDR3-IMGT cagcaatataacagctatcctctcacg (SEQ ID NO: 41)

QQYNSYPLT (SEQ ID NO: 42)

TABLE 1I

D34 VH Sequences

D34 VH - Nucleic Acid Sequence caggtccaactgcagcagtctggggctgagctggtgaggcctggggtctc
agtgaagatttcctgcaaggggttctggctacacattcactgattatgct

TABLE 1I-continued

D34 VH Sequences tgcactgggtgaagcagagtcatgcaaagagtctagagtggattggagtt
attagtacttactctggtgatgttagttacaaccagaagttcaagggcaa
ggccacaatgactgtcgacaaatcctccagcacagcctatatggaacttg
ccagactgacatctgaggattctgccatctattactgtgcaagaggggta
acttttgactcctggggccaaggcaccacggtcaccgtctcctcg (SEQ
ID NO: 43)

D34 VH - Amino Acid Sequence

QVQLQQSGAELVRPGVSVKISCKGSGYTFTDYAMHWVKQSHAKSLEWIGV
ISTYSGDVSYNQKFKGKATMTVDKSSSTAYMELARLTSEDSAIYYCARGV
TFDSWGQGTTVTVSS (SEQ ID NO: 44)

D34 VH - CDR1-IMGT ggctacacattcactgattatgct (SEQ ID NO: 18)

GYTFTDYA (SEQ ID NO: 19)

D34 VH - CDR2-IMGT attagtacttactctggtgatgtt (SEQ ID NO: 45)

ISTYSGDV (SEQ ID NO: 46)

D34 VH - CDR3-IMGT gcaagaggggtaacttttgactcc (SEQ ID NO: 47)

ARGVTFDS (SEQ ID NO: 48)

TABLE 1J

D34 VL Sequences

D34 VL - Nucleic Acid Sequence gacatccagatgacacagtctccagcctccctatctgcatctgtgggaga
aactgtcaccatcacatgtcgagcaagtgagaatagttacagttatttag
aatggtatcagcagaaacagggaaaatctcctcagctcctggtctataat
gcaaaaactttagcagaaggtgtgccatcaaggttcagtggcagtggatc
aggcacacagttttctctgaagatcaacagcctgcagcctgaagattttg
ggcttattactgtcaacatcattatggtactccgtacacgttcggaggg
gggaccaagctggaaataaaac (SEQ ID NO: 49)

D34 VL - Amino Acid Sequence

DIQMTQSPASLSASVGETVTITCRASENSYSYLEWYQQKQGKSPQLLVYN
AKTLAEGVPSRFSGSGSGTQFSLKINSLQPEDFGTYYCQHHYGTPYTFGG
GTKLEIK (SEQ ID NO: 50)

D34 VL - CDR1-IMGT gagaatagttacagttat (SEQ ID NO: 51)

ENSYSY (SEQ ID NO: 52)

D34 VL - CDR2-IMGT aatgcaaaa

NAK (SEQ ID NO: 28)

D34 VL - CDR3-IMGT caacatcattatggtactccgtacacg (SEQ ID NO: 53)

QHHYGTPYT (SEQ ID NO: 54)

TABLE 1K

D36 VH Sequences

D36 VH - Nucleic Acid Sequence caggtccaactgcagcagcctggggctgagctggtgaggcctggggtttc
actgaagatttcctgcaagggttctggctacacattcactgattatgcta
tgcactgggtgaggcagagtcatgcaaagagtctagagtggattggagtt
attagtacttactctggtgatgctctctacaaccagaagttcaagggcaa
ggccacaatgactgtcgacaaatcctccagcacagcctatctggaacttg
ccagactgacatctgaggattctgccatctattactgtgcgcgaggggta
acttttgactactggggccaaggcaccactctcacagtctcctcgg
(SEQ ID NO: 55)

D36 VH - Amino Acid Sequence

QVQLQQPGAELVRPGVSLKISCKGSGYTFTDYAMHWVRQSHAKSLEWIGV
ISTYSGDALYNQKFKGKATMTVDKSSSTAYLELARLTSEDSAIYYCARGV
TFDYWGQGTTLTVSS (SEQ ID NO: 56)

D36 VH - CDR1-IMGT ggctacacattcactgattatgct (SEQ ID NO: 18)

GYTFTDYA (SEQ ID NO: 19)

D36 VH - CDR2-IMGT attagtacttactctggtgatgct (SEQ ID NO: 20)

ISTYSGDA (SEQ ID NO: 21)

D36 VH - CDR3-IMGT gcgcgaggggtaacttttgactac (SEQ ID NO: 57)

ARGVTFDY (SEQ ID NO: 23)

TABLE 1l

D36 VL Sequences

D36 VL - Nucleic Acid Sequence gatgttgtgatgacccagtctccagcctccctatctgcatctgtgggaga
aactgtcaccatcacatgtcgagcaagtgagaatagttacagttatttag
aatggtatcagcagaaacagggaaaatcccctcagctcctggtctataat
gcaaaaactttagcagaaggtgtgccatcaaggttcagtggcagtggatc
aggcacacagttttctctgaagatcaacagcctgcagcctgaagattttg
ggacttattactgtcaacatcattatggtactccgtacacgttcggaggg
gggaccaagctggaaatgaac (SEQ ID NO: 58)

D36 VL Amino Acid Sequence

DVVMTQSPASLSASVGETVTITCRASENSYSYLEWYQQKQGKSPQLLVYN
AKTLAEGVPSRFSGSGSGTQFSLKINSLQPEDFGTYYCQHHYGTPYTFGG
GTKLEMK (SEQ ID NO: 59)

D36 VL - CDR1-IMGT gagaatagttacagttat (SEQ ID NO: 51)

ENSYSY (SEQ ID NO: 52)

D36 VL - CDR2-IMGT aatgcaaaa

NAK (SEQ ID NO: 28)

D36 VL - CDR3-IMGT caacatcattatggtactccgtacacg (SEQ ID NO: 53)

QHHYGTPYT (SEQ ID NO: 54)

TABLE 2A

Exemplary Clones - Heavy Chain Sequences

| ID | V-D-J-REGION | H-FR1 | CDRH1 | H-FR2 | CDRH2 | H-FR3 | CDRH3 | JUNCTION | J-REGION | H-FR4 |
|---|---|---|---|---|---|---|---|---|---|---|
| AHH 03702 | DVKLVESGGGL VKPGGSLKLSC AASGFTFSSYA MSWVRQTPEKR LEWVASISSGG STYYPDSVKGR FTISRDNARNI LYLQMSSLRSE DTAMYYCARGE IWGKAWFAYWG QGTLVTVSA (SEQ ID NO: 60) | DVKL VESG GGLV KPGG SLKL SCAA S (SEQ ID NO: 108) | GFTFS SYA (SEQ ID NO: 151) | MSWV RQTP EKRL EWVA S (SEQ ID NO: 184) | ISSGG ST (SEQ ID NO: 224) | YYPDS VKGRF TISRD NARNI LYLQM SSLRS EDTAM YYC (SEQ ID NO: 259) | ARGEI WGKAW FAY (SEQ ID NO: 297) | CARGE IWGKA WFAYW (SEQ ID NO: 345) | WFAYW GQGTL TVSAV (SEQ ID NO: 392) | WGQG TLVT VSA (SEQ ID NO: 421) |
| AHH 03703 | QVQMKQSGPEL KKPGETVKISC KASGYTLTDYS MHWVKQAPGKG LKWMGWINTET GEPTYADDFKG RFAFSLETSAS TAYLQINNLKN EDTATYFCAWG NHYWGQGTTVT VSS (SEQ ID NO: 61) | QVQM KQSG PELK KPGE TVKI SCKA S (SEQ ID NO: 109) | GYTLT DYS (SEQ ID NO: 152) | MHWV KQAP GKGL KWMG W (SEQ ID NO: 185) | INTET GEP (SEQ ID NO: 225) | TYADD FKGRF AFSLE TSAST AYLQI NNLKN EDTAT YFC (SEQ ID NO: 260) | AWGNH Y (SEQ ID NO: 298) | CAWGN HYW (SEQ ID NO: 346) | YWGQG TTVTV SS (SEQ ID NO: 393) | WGQG TTVT VSS (SEQ ID NO: 422) |
| AHH 03704 | QIQLQQSGPEL VKPGASVKMSC KASGYTFTSYV MHWVKQKPGQG LEWIGYINPYN DGTKYNEKFKG | QIQL QQSG PELV KPGA SVKM SCKA S | GYTFT SYV (SEQ ID NO: 153) | MHWV KQKP GQGL EWIG Y | INPYN DGT (SEQ ID NO: 226) | KYNEK FKGKA TLTSD KSSST AYMEL SSLTS | ARDGY YVGPA Y | CARDG YVGP AYW | AYWGQ GTLVT VSA | WGQG TLVT VSA (SEQ ID NO: |

TABLE 2A-continued

Exemplary Clones - Heavy Chain Sequences

| ID | V-D-J-REGION | H-FR1 | CDRH1 | H-FR2 | CDRH2 | H-FR3 | CDRH3 | JUNCTION | J-REGION | H-FR4 |
|---|---|---|---|---|---|---|---|---|---|---|
| | KATLTSDKSSS TAYMELSSLTS EDSAVYYCARD GYYVGPAYWGQ GTLVTVSA (SEQ ID NO: 62) | S (SEQ ID NO: 110) | | ID NO: 186) | | EDSAV YYC (SEQ ID NO: 261) | 299) | 347) | 394) | 421) |
| AHH 03705 | EVLLVESGGGL VKPGGSLKLSC AASGFAFSSYD MSWVRQTPEKR LEWVAYISSGG GSTYYPDTVKG RFTISRDNAKN TLYLQMSSLKS EDTAMYYCARN YRSWFAYWGQG TLVTVSA (SEQ ID NO: 63) | EVLL VESG GGLV KPGG SLKL SCAA S (SEQ ID NO: 111) | GFAFS SYD (SEQ ID NO: 154) | MSWV RQTP EKRL EWVA Y (SEQ ID NO: 187) | ISSGG GST (SEQ ID NO: 227) | YYPDT VKGRF TISRD NAKNT LYLQM SSLKS EDTAM YYC (SEQ ID NO: 262) | ARNYR SWFAY (SEQ ID NO: 300) | CARNY RSWFA YW (SEQ ID NO: 348) | WFAYW (SEQ ID NO: 392) | WGQG TLVT VSA (SEQ ID NO: 421) |
| AHH 03706 | QVQLQQSGAEL VRPGTSVKVSC KASGYAFTNYL IEWVKQRPGQG LEWIGVINPGS GGTNYNEKFKG KATLTADKSSS TAYMQLSSLTS DDSAVYFCARK GSLTGVLAYWG QGTLVTVSA (SEQ ID NO: 64) | QVQL QQSG AELV RPGT SVKV SCKA S (SEQ ID NO: 112) | GYAFT NYL (SEQ ID NO: 155) | IEWV KQRP GQGL EWIG V (SEQ ID NO: 188) | INPGS GGT (SEQ ID NO: 228) | NYNEK FKGKA TLTAD KSSST AYMQL SSLTS DDSAV YFC (SEQ ID NO: 263) | ARKGS LTGVL AY (SEQ ID NO: 301) | CARKG SLTGV LAYW (SEQ ID NO: 349) | AYWGQ GTLVT VSA (SEQ ID NO: 394) | WGQG TLVT VSA (SEQ ID NO: 421) |
| AHH 03707 | QVQLQQSGAEL VRPGASVKLSC KASGYIFTNYW MNWVKQRPGQG LEWIGMIDPSD SETHYNQMSKD KATLTVDKSSS TAYMQLSSLTS EDSAVYYCARR GLRAWFAYWGQ GTLVTVSA (SEQ ID NO: 65) | QVQL QQSG AELV RPGA SVKL SCKA S (SEQ ID NO: 113) | GYIFT NYW (SEQ ID NO: 156) | MNWV KQRP GQGL EWIG M (SEQ ID NO: 189) | IDPSD SET (SEQ ID NO: 229) | HYNQM SKDKA TLTVD KSSST AYMQL SSLTS EDSAV YYC (SEQ ID NO: 264) | ARRGL RAWFA Y (SEQ ID NO: 302) | CARRG LRAWF AYW (SEQ ID NO: 350) | WFAYW GQGTL VTVSA (SEQ ID NO: 392) | WGQG TLVT VSA (SEQ ID NO: 421) |
| AHH 03708 | QVQLQQPGAEL AKPGASVKMSC KASGYTFTSYW MHWVKQRPGQG LEWIGYINPST GYTEYNQKFKD KATLTADKSSS TAYMQLSSLTS EDSAVYYCARL DYYGSSRGFAY WGQGTLVTVSA (SEQ ID NO: 66) | QVQL QQPG AELA KPGA SVKM SCKA S (SEQ ID NO: 114) | GYTFT SYW (SEQ ID NO: 157) | MHWV KQRP GQGL EWIG Y (SEQ ID NO: 190) | INPST GYT (SEQ ID NO: 230) | EYNQK FKDKA TLTAD KSSST AYMQL SSLTS EDSAV YYC (SEQ ID NO: 265) | ARLDY YGSSR GFAY (SEQ ID NO: 303) | CARLD YYGSS RGFAY W (SEQ ID NO: 351) | FAYWG QGTLV TVSA (SEQ ID NO: 395) | WGQG TLVT VSA (SEQ ID NO: 421) |
| AHH 03709 | QVQLQQSGAEL VKPGASVKLSC KASGYTFTSYY MYWVKQRPGQG LEWIGEINPSN GGTNFNEKFKS KATLTVDKSSS TAYMQLSSLTS EDSAVYYCTNG GGWYWGQGTTV | QVQL QQSG AELV KPGA SVKL SCKA S (SEQ ID NO: | GYTFT SYY (SEQ ID NO: 158) | MYWV KQRP GQGL EWIG E (SEQ ID NO: 191) | INPSN GGT (SEQ ID NO: 231) | NFNEK FKSKA TLTVD KSSST AYMQL SSLTS EDSAV YYC (SEQ ID | TNGGG WY (SEQ ID NO: 304) | CTNGG GWYW (SEQ ID NO: 352) | GGWYW GQGTT VTVSS (SEQ ID NO: 396) | WGQG TTVT VSS (SEQ ID NO: 422) |

TABLE 2A-continued

Exemplary Clones - Heavy Chain Sequences

| ID | V-D-J-REGION | H-FR1 | CDRH1 | H-FR2 | CDRH2 | H-FR3 | CDRH3 | JUNCTION | J-REGION | H-FR4 |
|---|---|---|---|---|---|---|---|---|---|---|
| | TVSS (SEQ ID NO: 67) | 115) | | | | NO: 266) | | | | |
| AHH 03711 | QIQLVQSGPEL KKPGETVKISC KASGYTFTNYG MNWVKQTPGKG LKWMGWINTYT GEPTYADDFKG RFAFSLETSAS TAYLQINNLKN EDTATYFCASY YDSTYVGFAYW GQGTLVTVSA (SEQ ID NO: 68) | QIQL VQSG PELK KPGE TVKI SCKA S (SEQ ID NO: 116) | GYTFT NYG (SEQ ID NO: 159) | MNWV KQTP GKGL KWMG W (SEQ ID NO: 192) | INTYT GEP (SEQ ID NO: 232) | TYADD FKGRF AFSLE TSAST AYLQI NNLKN EDTAT YFC (SEQ ID NO: 260) | ASYYD STYVG FAY (SEQ ID NO: 305) | CASYY DSTYV GFAYW (SEQ ID NO: 353) | FAYWG QGTLV TVSA (SEQ ID NO: 395) | WGQG TLVT VSA (SEQ ID NO: 421) |
| AHH 03712 | EVLLVESGGGL VQPGGSLKLSC ATSGFTFSDYY MYWVRQTPEKR LEWVAYISNGG GSTYYPDTVKG RFTISRDNAKN TLYLQMSRLKS EDTAMYYCASP LGYDGFAYWGQ GTLVTVSA (SEQ ID NO: 69) | EVLL VESG GGLV QPGG SLKL SCAT S (SEQ ID NO: 117) | GFTFS DYY (SEQ ID NO: 160) | MYWV RQTP EKRL EWVA Y (SEQ ID NO: 193) | ISNGG GST (SEQ ID NO: 233) | YYPDT VKGRF TISRD NAKNT LYLQM SRLKS EDTAM YYC (SEQ ID NO: 267) | ASPLG YDGFA Y (SEQ ID NO: 306) | CASPL GYDGF AYW (SEQ ID NO: 354) | FAYWG QGTLV TVSA (SEQ ID NO: 395) | WGQG TLVT VSA (SEQ ID NO: 421) |
| AHH 03713 | QVQMKQSGPGL VAPSQSLSITC TVSGFSLTSYG VHWVRQPPGKG LEWLGVIWAGG STNYNSALMSR LSISKDNSKSQ VFLKMNSLQTD DTAMYYCARGA YFDYWGQGTTV TVSS (SEQ ID NO: 70) | QVQM KQSG PGLV APSQ SLSI TCTV S (SEQ ID NO: 118) | GFSLT SYG (SEQ ID NO: 161) | VHWV RQPP GKGL EWLG V (SEQ ID NO: 194) | IWAGG ST (SEQ ID NO: 234) | NYNSA LMSRL SISKD NSKSQ VFLKM NSLQT DDTAM YYC (SEQ ID NO: 268) | ARGA YFDY (SEQ ID NO: 307) | CARGA YFDYW (SEQ ID NO: 355) | YFDYW GQGTT VTVSS (SEQ ID NO: 397) | WGQG TTVT VSS (SEQ ID NO: 422) |
| AHH 03714 | QVQLQQSGAEL VRPGASVKLSC KASGYTFTSYW MNWVKQRPEQG LEWIGRIDPYD SETHYNQKFKD KAILTVDKSSS TAYMQLSSLTS EDSAVYYCARS PAYYGNLWFAY WGQGTLVTVSA (SEQ ID NO: 71) | QVQL QQSG AELV RPGA SVKL SCKA S (SEQ ID NO: 113) | GYTFT SYW (SEQ ID NO: 157) | MNWV KQRP EQGL EWIG R (SEQ ID NO: 195) | IDPYD SET (SEQ ID NO: 235) | HYNQK FKDKA ILTVD KSSST AYMQL SSLTS EDSAV YYC (SEQ ID NO: 269) | ARSP AYYG NLWF AY (SEQ ID NO: 308) | CARSP AYYGN LWFAY W (SEQ ID NO: 356) | WFAYW GQGTL VTVSA (SEQ ID NO: 392) | WGQG TLVT VSA (SEQ ID NO: 421) |
| AHH 03715 | QVQLQQSGAEL ARPGASVKMSC KASGYTFTSYT IHWVKQRPGQG LEWIGYINPSS GYTNYNQKFKD KATLTADKSSS TAYMQLSSLTS EDSAVYYCARW DGAYWGQGTPV TVSS (SEQ ID NO: 72) | QVQL QQSG AELA RPGA SVKM SCKA S (SEQ ID NO: 119) | GYTFT SYT (SEQ ID NO: 162) | IHWV KQRP GQGL EWIG (SEQ ID NO: 196) | INPSS GYT (SEQ ID NO: 236) | NYNQK FKDKA TLTAD KSSST AYMQL SSLTS EDSAV YYC (SEQ ID NO: 270) | ARWD GAY (SEQ ID NO: 309) | CARW DGAY W (SEQ ID NO: 357) | WGQGT PVTVS S (SEQ ID NO: 398) | WGQG TPVT VSS (SEQ ID NO: 398) |
| AHH 03716 | DVKLVESGGGL VKPGGSLKLSC AASGFTFSSYA MSWVRQFPEKR | DVKL VESG GGLV KPGG | GFTFS SYA (SEQ ID | MSWV RQFP EKRL EWVA | ISSGG SYT (SEQ ID | YYPDT VTGRF TISRD NAKNT | ARGG MITP FAY (SEQ | CARGG MITPF AYW (SEQ | FAYWG QGTLV TVSS (SEQ | WGQG TLVT VSS (SEQ |

TABLE 2A-continued

Exemplary Clones - Heavy Chain Sequences

| ID | V-D-J-REGION | H-FR1 | CDRH1 | H-FR2 | CDRH2 | H-FR3 | CDRH3 | JUNCTION | J-REGION | H-FR4 |
|---|---|---|---|---|---|---|---|---|---|---|
| | LEWVAEISSGG SYTYYPDTVTG RFTISRDNAKN TLYLEMSSLRS EDTAMYYCARG GMITPFAYWGQ GTLVTVSS (SEQ ID NO: 73) | SLKL SCAA S (SEQ ID NO: 108) | NO: 151) | E (SEQ ID NO: 197) | NO: 237) | LYLEM SSLRS EDTAM YYC (SEQ ID NO: 271) | ID NO: 310) | ID NO: 358) | ID NO: 399) | ID NO: 413) |
| AHH 03717 | QVILKESGPGI LQPSQTLSLTC SFSGFSLSTSG MSVGWIRQPSG KGLEWLAHIWW NDDKYYNPALK SRLTISKDTSN NQVFLKIASVV TADTATYYCAR IGGNDGYYWYF DVWGAGTTVTV SS (SEQ ID NO: 74) | QVIL KESG PGIL QPSQ TLSL TCSF S (SEQ ID NO: 120) | GFSLS TSGMS (SEQ ID NO: 163) | VGWI RQPS GKGL EWLA H (SEQ ID NO: 198) | IWWND DK (SEQ ID NO: 238) | YYNPA LKSRL TISKD TSNNQ VFLKI ASVVT ADTAT YYC (SEQ ID NO: 272) | ARIG GNDG YYWY FDV (SEQ ID NO: 311) | CARIG GNDGY YWYFD VW (SEQ ID NO: 359) | YWYFD VWGAG TTVTV SS (SEQ ID NO: 400) | WGAG TTVT VSS (SEQ ID NO: 423) |
| AHH 03718 | EVKIEESGGGL VQPGGSMKLSC AASGFTFSDAW MDWVRQSPEKG LEWVAEIRSKA NNHATYYAESV KGRFTISRDDS KSSVYLQMNSL RAEDTGIYYCT PQFAYWGQGTT VTVSS (SEQ ID NO: 75) | EVKI EESG GGLV QPGG SMKL SCAA S (SEQ ID NO: 121) | GFTFS DAW (SEQ ID NO: 164) | MDWV RQSP EKGL EWVA E (SEQ ID NO: 199) | IRSKA NNHAT (SEQ ID NO: 239) | YYAES VKGRF TISRD DSKSS VYLQM NSLRA EDTG IYYC (SEQ ID NO: 273) | TPQF AY (SEQ ID NO: 312) | CTPQF AYW (SEQ ID NO: 360) | FAYWG QGTTV TVSS (SEQ ID NO: 401) | WGQG TTVT VSS (SEQ ID NO: 422) |
| AHH 03719 | EVMLVESGGGL VQPGGSLKLSC AASGFTFSSYG MSWVRQTPDKR LELVATINSNG GSTYYPDSVKG RFTISRDNAKN TLYLQMSSLKS EDTAMYYCASH YDEGYWGQGTS LTVSS (SEQ ID NO: 76) | EVML VESG GGLV QPGG SLKL SCAA S (SEQ ID NO: 122) | GFTFS SYG (SEQ ID NO: 165) | MSWV RQTP DKRL ELVA T (SEQ ID NO: 200) | INSNG GST (SEQ ID NO: 240) | YYPDS VKGRF TISRD NAKNT LYLQM SSLKS EDTAM YYC (SEQ ID NO: 274) | ASHY DEGY (SEQ ID NO: 313) | CASHY DEGYW (SEQ ID NO: 361) | YWGQG TSLTV SS (SEQ ID NO: 402) | WGQG TSLT VSS (SEQ ID NO: 424) |
| AHH 03720 | EVKLEESGGGL VQPGGSMKLSC VASGFTFSNYW MNWVRQSPEKG LEWVAEIRLKS NNYATHYAESV KGRFTISRDDS KSSVYLQMNNL RAEDTGIYYCT GSDYWQGTTV TVSS (SEQ ID NO: 77) | EVKL EESG GGLV QPGG SMKL SCVA S (SEQ ID NO: 123) | GFTFS NYW (SEQ ID NO: 166) | MNWV RQSP EKGL EWVA E (SEQ ID NO: 201) | IRLKS NNYAT (SEQ ID NO: 241) | HYAES VKGRF TISRD DSKSS VYLQM NNLRA EDTGI YYC (SEQ ID NO: 275) | TGSDY (SEQ ID NO: 314) | CTGSD YW (SEQ ID NO: 362) | DYWGQ GTTVT VSS (SEQ ID NO: 403) | WGQG TTVT VSS (SEQ ID NO: 422) |
| AHH 03721 | QVQLQQSGPEL VKPGASVKMSC KASGDTFSSYV IHWVKQKPGQG LEWIGYFNPYS DDIKYNEKFKG KATLTSDKSSS TAYMELSSLTS EDSAVYYCGSG YDGYYDWFACW GQGTLVTVSA | QVQL QQSG PELV KPGA SVKM SCKA S (SEQ ID NO: 124) | GDTFS SYV (SEQ ID NO: 167) | IHWV KQKP GQGL EWIG (SEQ ID NO: 202) | FNPYS DDI (SEQ ID NO: 242) | KYNEK FKGKA TLTSD KSSST AYMEL SSLTS EDSAV YYC | GSGYD GYYDW FAC (SEQ ID NO: 315) | CGSGY DGYYD WFACW (SEQ ID NO: 363) | WFACW GQGTL VTVSA (SEQ ID NO: 404) | WGQG TLVT VSA (SEQ ID NO: 421) |

TABLE 2A-continued

Exemplary Clones - Heavy Chain Sequences

| ID | V-D-J-REGION | H-FR1 | CDRH1 | H-FR2 | CDRH2 | H-FR3 | CDRH3 | JUNCTION | J-REGION | H-FR4 |
|---|---|---|---|---|---|---|---|---|---|---|
| | (SEQ ID NO: 78) | | | | | (SEQ ID NO: 261) | | | | |
| AHH 03722 | QIQLAQSGPEL KKPGETVKISC KASGYSFTKNG MNWVKQAPKG LKWMGWINTYT GEPTYADDFKG RFAFSLETSAS TAYLQINNLKN EDTATYFCARE PKTLDYWGQGT TVTVSS (SEQ ID NO: 79) | QIQL AQSG PELK KPGE TVKI SCKA S (SEQ ID NO: 125) | GYSFT KNG (SEQ ID NO: 168) | MNWV KQAP GKGL KWMG W (SEQ ID NO: 203) | INTYT GEP (SEQ ID NO: 232) | TYADD FKGRF AFSLE TSAST AYLQI NNLKN EDTAT YFC (SEQ ID NO: 260) | AREPK TLDY (SEQ ID NO: 316) | CAREP KTLDY W (SEQ ID NO: 364) | DYWGQ GTTVT VSS (SEQ ID NO: 403) | WGQG TTVT VSS (SEQ ID NO: 422) |
| AHH 03724 | QVQLQQSGAEL VKPGAPVKLSC KASGYTFTSYW MNWVKQRPGRG LEWIGRIDPSD SETHYNQKFKD KATLTVDKSSS TAYIQLSSLTS EDSAVYYCANW AWFAYWGQGTL VTVSA (SEQ ID NO: 80) | QVQL QQSG AELV KPGA PVKL SCKA S (SEQ ID NO: 126) | GYTFT SYW (SEQ ID NO: 157) | MNWV KQRP GRGL EWIG R (SEQ ID NO: 204) | IDPSD SET (SEQ ID NO: 229) | HYNQK FKDKA TLTVD KSSST AYIQL SSLTS EDSAV YYC (SEQ ID NO: 276) | ANWA WFAY (SEQ ID NO: 317) | CANWA WFAYW (SEQ ID NO: 365) | WFAYW GQGTL VTVSA (SEQ ID NO: 392) | WGQG TLVT VSA (SEQ ID NO: 421) |
| AHH 03726 | QMQLKESGTEL VRPGASVKLSC KASGYTFNSHW MNWVKQRPEQG LEWIGKIDPYD SETHYNQKFKD KAILTVDKSSS TAYMQLSSLTS EDSAVYYCARP YDYDGFAYWGQ GTLVTVSA (SEQ ID NO: 81) | QMQL KESG TELV RPGA SVKL SCKA S (SEQ ID NO: 127) | GYTFN SHW (SEQ ID NO: 169) | MNWV KQRP EQGL EWIG K (SEQ ID NO: 205) | IDPYD SET (SEQ ID NO: 235) | HYNQK FKDKA ILTVD KSSST AYMQL SSLTS EDSAV YYC (SEQ ID NO: 269) | ARPY DYDG FAY (SEQ ID NO: 318) | CARPY DYDGF AYW (SEQ ID NO: 366) | FAYWG QGTLV TVSA (SEQ ID NO: 395) | WGQG TLVT VSA (SEQ ID NO: 421) |
| AHH 03727 | QIQLQQSGAEL VRPGASVKISC KAFGYTFTNHH INWVKQRPGQG LDWIGYINPYN DYTSYNQKFKG KATLTVDKSSS TAYMELSSLTS EDSAVYYCADG DYYFDYWGQGT SLTVSS (SEQ ID NO: 82) | QIQL QQSG AELV RPGA SVKI SCKA F (SEQ ID NO: 128) | GYTF TNHH (SEQ ID NO: 170) | INWV KQRP GQGL DWIG (SEQ ID NO: 206) | INPYN DYT (SEQ ID NO: 243) | SYNQK FKGKA TLTVD KSSST AYMEL SSLTS EDSAV YYC (SEQ ID NO: 277) | ADGD YYFD Y (SEQ ID NO: 319) | CADGD YYFDY W (SEQ ID NO: 367) | YFDYW GQGTS LTVSS (SEQ ID NO: 405) | WGQG TSLT VSS (SEQ ID NO: 424) |
| AHH 03728 | DVLLVESGGDL VKPGGSLKLSC VVSGLTFSSYG MSWVRQTPDKR LEWVATISSGG SYIYYVDSVKG RFTISRDNAKN TLYLQMSSLKS EDTAIYYCARQ DDGYYRIFDYW GQGTTLTVSS (SEQ ID NO: 83) | DVLL VESG GDLV KPGG SLKL SCVV S (SEQ ID NO: 129) | GLTF SSYG (SEQ ID NO: 171) | MSWV RQTP DKRL EWVA T (SEQ ID NO: 207) | ISSGG SYI (SEQ ID NO: 244) | YYVDS VKGRF TISRD NAKNT LYLQM SSLKS EDTAI YYC (SEQ ID NO: 278) | ARQD DGYY RIFD Y (SEQ ID NO: 320) | CARQD DGYYR IFDYW (SEQ ID NO: 368) | FDYWG QGTTL TVSS (SEQ ID NO: 406) | WGQG TTLT VSS (SEQ ID NO: 425) |
| AHH 03729 | EVKIEESGGGL VQPGGSMKLSC AASGFTFNDAW MDWVRQSPEKG LEWVAEIRSKA | EVKI EESG GGLV QPGG SMKL | GFTF NDAW (SEQ ID NO: | MDWV RQSP EKGL EWVA E | IRSKA NNHAT (SEQ ID NO: | YYAES VKGRF TISRD DSQSS VYLQM (SEQ ID | TNYG SNPL DY (SEQ ID | CTNYG SNPLD YW (SEQ ID | DYWGQ GTTLT IPS (SEQ ID | WGQG TTLT IPS (SEQ ID |

TABLE 2A-continued

Exemplary Clones - Heavy Chain Sequences

| ID | V-D-J-REGION | H-FR1 | CDRH1 | H-FR2 | CDRH2 | H-FR3 | CDRH3 | JUNCTION | J-REGION | H-FR4 |
|---|---|---|---|---|---|---|---|---|---|---|
| | NNHATYYAESV KGRFTISRDDS QSSVYLQMNSL RTENTGIYYCT NYGSNPLDYWG QGTTLTIPS (SEQ ID NO: 84) | SCAA S (SEQ ID NO: 121) | (SEQ ID NO: 172) | (SEQ ID NO: 199) | (SEQ ID NO: 239) | NSLRT ENTGI YYC (SEQ ID NO: 279) | NO: 321) | NO: 369) | NO: 407) | NO: 426) |
| AHH 03730 | QVTLKESGPGL VAPSQSLSITC TVSGFSLTSYG VHWVRQPPGKG LEWLGVIWAGG STNYNSALMSR LGISKDNSKSQ VFLKMNSLQTD ESAFYYCAREG TGPWFAYWGQG TTAPSP (SEQ ID NO: 85) | QVTL KESG PGLV APSQ SLSI TCTV S (SEQ ID NO: 130) | GFSL TSYG (SEQ ID NO: 161) | VHWV RQPP GKGL EWLG V (SEQ ID NO: 194) | IWAGG ST (SEQ ID NO: 234) | NYNSA LMSRL GISKD NSKSQ VFLKM NSLQT DESAF YYC (SEQ ID NO: 280) | AREG TGPW FAY (SEQ ID NO: 322) | CAREG TGPWF AYW (SEQ ID NO: 370) | WFAYW GQGTT APSP (SEQ ID NO: 408) | WGQG TTAP SP (SEQ ID NO: 427) |
| AHH 03731 | DVQLQQSGPDL VKPSQSLSLTC TVTGYSITSGY SWHWIRQPPGN KLEWMGYIHYS GSTNYNPSLKS RISITRDTSKN QFFLQLNSVTT EGTATYYCARD PPFAYWGQGTL VTVSA (SEQ ID NO: 86) | DVQL QQSG PDLV KPSQ SLSL TCTV T (SEQ ID NO: 131) | GYSI TSGY S (SEQ ID NO: 173) | WHWI RQFP GNKL EWMG Y (SEQ ID NO: 208) | IHYSG ST (SEQ ID NO: 245) | NYNPS LKSRI SITRD TSKNQ FFLQL NSVTT EGTAT YYC (SEQ ID NO: 281) | ARDP PFAY (SEQ ID NO: 323) | CARDP PFAYW (SEQ ID NO: 371) | FAYWG QGTL VTVSA (SEQ ID NO: 395) | WGQG TLVT VSA (SEQ ID NO: 421) |
| AHH 03733 | QVQLQQSGAEL VKPGASVRLSC KASGYTFTSYW MHWVKQRPGQG LEWIGEIDPSD SYTNYNQKFKG KATLAVDKSSS TAYMQLSSLTS EDSAVYYCARE EITAWFAYWGQ GTLVTVSA (SEQ ID NO: 87) | QVQL QQSG AELV KPGA SVRL SCKA S (SEQ ID NO: 132) | GYTF TSYW (SEQ ID NO: 157) | MHWV KQRP GQGL EWIG E (SEQ ID NO: 209) | IDPSD SYT (SEQ ID NO: 246) | NYNQK FKGKA TLAVD KSSST AYMQL SSLTS EDSAV YYC (SEQ ID NO: 282) | AREE ITAW FAY (SEQ ID NO: 324) | CAREE ITAWF AYW (SEQ ID NO: 372) | WFAYW GQGTL VTVSA (SEQ ID NO: 392) | WGQG TLVT VSA (SEQ ID NO: 421) |
| AHH 03734 | QVQLQQPGAEL VRPGASVKLSC KALGYTFTDYE MHWVKQTPVHG LEWIGAIHPGS GGTAYNQKFKG KATLTADKSSS TAYMELSSLTS EDSAVYYCTRN GNGNWYFDVWG AGTTLTVSS (SEQ ID NO: 88) | QVQL QQPG AELV RPGA SVKL SCKA L (SEQ ID NO: 133) | GYTFT DYE (SEQ ID NO: 174) | MHWV KQTP VHGL EWIG A (SEQ ID NO: 210) | IHPGS GGT (SEQ ID NO: 247) | AYNQK FKGKA TLTAD KSSST AYMEL SSLTS EDSAV YYC (SEQ ID NO: 283) | TRNG NGNW YFDV (SEQ ID NO: 325) | CTRNG NGNWY FDVW (SEQ ID NO: 373) | WYFDV WGAGT TLTVS S (SEQ ID NO: 409) | WGAG TTLT VSS (SEQ ID NO: 428) |
| AHH 03737 | QVQLQQSGAEL VRPGSSVKISC KASGYAFSSYW MNWVKQRPGQG LEWIGQIYPGD GDTYYNGKFKD KATLTADKSSS TAYMHLSSLTS EDSAVYFCARS GYRDAVFAYW GPGTLVTVSA (SEQ ID NO: 134) | QVQL QQSG AELV RPGS SVKI SCKA S (SEQ ID NO: 134) | GYAF SSYW (SEQ ID NO: 175) | MNWV KQRP GQGL EWIG Q (SEQ ID NO: 211) | IYPGD GDT (SEQ ID NO: 248) | YYNGK FKDKA TLTAD KSSST AYMHL SSLTS EDSAV YFC (SEQ ID NO: ) | ARSG YRD AVFA Y (SEQ ID NO: 326) | CARSG YRDA VFAYW (SEQ ID NO: 374) | FAYWG PGTLV TVSA (SEQ ID NO: 410) | WGPG TLVT VSA (SEQ ID NO: 429) |

TABLE 2A-continued

Exemplary Clones - Heavy Chain Sequences

| ID | V-D-J-REGION | H-FR1 | CDRH1 | H-FR2 | CDRH2 | H-FR3 | CDRH3 | JUNCTION | J-REGION | H-FR4 |
|---|---|---|---|---|---|---|---|---|---|---|
| | (SEQ ID NO: 89) | | | | | 284) | | | | |
| AHH 03738 | EVQLLESGGGL VQPGGSLKLSC AASGFTFSSYG MSWVRQTPDKR LELVATINSNG GSTYYPDSVKG RFTISRDNAKN TLYLQMSSLKS EDTAMYYCARG GNPYLGQGTLV TVSA (SEQ ID NO: 90) | EVQL LESG GGLV QPGG SLKL SCAA S (SEQ ID NO: 135) | GFTF SSYG (SEQ ID NO: 165) | MSWV RQTP DKRL ELVA T (SEQ ID NO: 200) | INSNG GST (SEQ ID NO: 240) | YYPDS VKGRF TISRD NAKNT LYLQM SSLKS EDTAM YYC (SEQ ID NO: 274) | ARGG NPY (SEQ ID NO: 327) | CARGG NPYL (SEQ ID NO: 375) | YLGQG TLVTV SA (SEQ ID NO: 411) | LGQG TLVT VSA (SEQ ID NO: 430) |
| AHH 03739 | EVQLVETGGGL VQPGGSRGLSC EGSGFTFSGFW MSWVRQTPGKT LEWIGDINSDG SAINYAPSIKD RFTIFRDNDKS TLYLQMSNVRS EDTATYFCMRY GSSYWYFD (SEQ ID NO: 91) | EVQL VETG GGLV QPGG SRGL SCEG S (SEQ ID NO: 136) | GFTFS GFW (SEQ ID NO: 176) | MSWV RQTP GKTL EWIG D (SEQ ID NO: 212) | INSDG SAI (SEQ ID NO: 249) | NYAPS IKDRF TIFRD NDKST LYLQM SNVRS EDTAT YFC (SEQ ID NO: 285) | MRYG SSYW YFD (SEQ ID NO: 328) | | LLVLR C (SEQ ID NO: 412) | |
| AHH 03740 | EVKIEESGGGL VQPGGSMKLSC VASGFTFSSYW MSWVRQSPEKG LEWVAEIRLKS DNYATHYAESV KGKFTISRDDS KSRLYLQMNSL RAEDTGIYYCT RYYYGESWGQG TLVTVSS (SEQ ID NO: 92) | EVKI EESG GGLV QPGG SMKL SCVA S (SEQ ID NO: 137) | GFTFS SYW (SEQ ID NO: 177) | MSWV RQSP EKGL EWVA E (SEQ ID NO: 213) | IRLKS DNYAT (SEQ ID NO: 250) | HYAES VKGKF TISRD DSKSR LYLQM NSLRA EDTGI YYC (SEQ ID NO: 286) | TRYY YGES (SEQ ID NO: 329) | CTRYY YGESW (SEQ ID NO: 376) | WGQGT LVTVS S (SEQ ID NO: 413) | WGQG TLVT VSS (SEQ ID NO: 413) |
| AHH 03742 | EVMLVESGGDL VKPGGSLKLSC AASGFTFSSYG MSWVRQTPDKR LEWVATISSGG SYTYYPDSVKG RFTISRDNAKN TLYLQMSSLKS EDTAMYYCARH YYDYDYWYFDV WGAGTTVTSS (SEQ ID NO: 93) | EVML VESG GDLV KPGG SLKL SCAA S (SEQ ID NO: 138) | GFTFS SYG (SEQ ID NO: 165) | MSWV RQTP DKRL EWVA T (SEQ ID NO: 207) | ISSGG SYT (SEQ ID NO: 237) | YYPDS VKGRF TISRD NAKNT LYLQM SSLKS EDTAM YYC (SEQ ID NO: 274) | ARHY YDYD YWYF DV (SEQ ID NO: 330) | CARHY YDYDY WYFDV W (SEQ ID NO: 377) | YWYFD VWGAG TTVTV SS (SEQ ID NO: 400) | WGAG TTVT VSS (SEQ ID NO: 423) |
| AHH 03743 | QVQLQQPGSEL VRPGASVKLSC KASGYTFTSYW MHWVKQRYGQG LEWIGNIYPGS GSTNYDEKFKS KGTLTVDTSSS TAYMHLSSLTS EDSAVYYCTRS GVEGLLHWYFD VWGAGTSLTVS S (SEQ ID NO: 94) | QVQL QQPG SELV RPGA SVKL SCKA S (SEQ ID NO: 139) | GYTFT SYW (SEQ ID NO: 157) | MHWV KQRY GQGL EWIG N (SEQ ID NO: 214) | IYPGS GST (SEQ ID NO: 251) | NYDEK FKSKG TLTVD TSSST AYMHL SSLTS EDSAV YYC (SEQ ID NO: 287) | TRSG VEGL LHWY FDV (SEQ ID NO: 331) | CTRSG VEGLL HWYFD VW (SEQ ID NO: 378) | WYFDV WGAGT SLTVS S (SEQ ID NO: 414) | WGAG TSLT VSS (SEQ ID NO: 431) |
| AHH 03746 | EVKIEESGGGL VQPGGSMKLSC VASGFTFSSYW MSWVRQSPEKG | EVKI EESG GGLV QPGG | GFTFS SYW (SEQ ID | MSWV RQSP EKGL EWVA | IRLKS DNYAT (SEQ ID | HYAES VKGKF TISRD DSKSR | TCDY DGGA WFAY (SEQ | CTCDY DGGAW FAYW (SEQ | WFAYW GQGTL VTVSA (SEQ | WGQG TLVT VSA (SEQ |

TABLE 2A-continued

Exemplary Clones - Heavy Chain Sequences

| ID | V-D-J-REGION | H-FR1 | CDRH1 | H-FR2 | CDRH2 | H-FR3 | CDRH3 | JUNCTION | J-REGION | H-FR4 |
|---|---|---|---|---|---|---|---|---|---|---|
| | LEWVAEIRLKS DNYATHYAESV KGKFTISRDDS KSRLYLQMNSL RAEDTGIYYCT CDYDGGAWFAY WGQGTLVTVSA (SEQ ID NO: 95) | SMKL SCVA S (SEQ ID NO: 137) | NO: 177) | E (SEQ ID NO: 213) | NO: 250) | LYLQM NSLRA EDTGI YYC (SEQ ID NO: 286) | ID NO: 332) | ID NO: 379) | ID NO: 392) | ID NO: 421) |
| AHH 03748 | QIQLQQPGPEL VRPGASVKMSC KASGYTFTSYW MHWVKQRPGQG LEWIGMIDPSN SETRLNQKFKD KATLNVDKSSN TACMQLSSLTS EDSAVYYCARC DGYYDGLDYWG QGTTLTVSS (SEQ ID NO: 96) | QIQL QQPG PELV RPGA SVKM SCKA S (SEQ ID NO: 140) | GYTFT SYW (SEQ ID NO: 157) | MHW VKQR PGQG LEWI GM (SEQ IDNO: 215) | IDPSN SET (SEQ ID NO: 252) | RLNQK FKDKA TLNVD KSSNT ACMQL SSLTS EDSAV YYC (SEQ ID NO: 288) | ARCD GYYD GLDY (SEQ ID NO: 333) | CARCD GYYDG LDYW (SEQ ID NO: 380) | GLDYW (SEQ ID NO: 415) | WGQG TTLT VSS (SEQ ID NO: 425) |
| AHH 03749 | QVQLQQPGAEL ARPGASVKMSC KASGYTFTSYT IHWVKQRPGQG LEWIGYINPSS GYTNYNQKFKD KATLTADKSSS TAYMQLSSLTS EDSAVYYCARE GKNWYFDVWGA GTTVTVSS (SEQ ID NO: 97) | QVQL QQPG AELA RPGA SVKM SCKA S (SEQ ID NO: 141) | GYTFT SYT (SEQ ID NO: 162) | IHWV KQRP GQGL EWIG (SEQ ID NO: 196) | INPSS GYT (SEQ ID NO: 236) | NYNQK FKDKA TLTAD KSSST AYMQL SSLTS EDSAV YYC (SEQ ID NO: 270) | AREG KNWY FDV (SEQ ID NO: 334) | CAREG KNWYF DVW (SEQ ID NO: 381) | WYFDV WGAGT TVTVS S (SEQ ID NO: 416) | WGAG TTVT VSS (SEQ ID NO: 423) |
| AHH 03750 | QIQLQQSGAEL VRPGVSVKLSC KASGYTFTSYW MHWIKQRPEQG LERIGEINPSN GGTNYNEKFKS KATLTVDKSSS TAYMQLSSLTS EDSAVYYCARR IYRTLDYWGQG TTVTVSS (SEQ ID NO: 98) | QIQL QQSG AELV RPGV SVKL SCKA S (SEQ ID NO: 142) | GYTFT SYW (SEQ ID NO: 157) | MHWI KQRP EQGL ERIG E (SEQ ID NO: 216) | INPSN GGT (SEQ ID NO: 231) | NYNEK FKSA TLTVD KSSST AYMQL SSLTS EDSAV YYC (SEQ ID NO: 289) | ARRI YRTL DY (SEQ ID NO: 335) | CARRI YRTLD YW (SEQ ID NO: 382) | TLDYW GQGTT VTVSS (SEQ ID NO: 417) | WGQG TTVT VSS (SEQ ID NO: 422) |
| AHH 03751 | EVQLQQSGAEL VKPGASVKMSC KASGYTFTSYN MHWVKQTPGQG LEWIGVIYPGN GDTAYNQKFKG KATVTADRSSS TAYMQLSSLTS EDSAVYYCTRS GGNLWFAYWGQ GTLVTVSA (SEQ ID NO: 99) | EVQL QQSG AELV KPGA SVKM SCKA S (SEQ ID NO: 143) | GYTFT SYN (SEQ ID NO: 178) | MHWV KQTP GQGL EWIG V (SEQ ID NO: 217) | IYPGN GDT (SEQ ID NO: 253) | AYNQ KFKGK ATVTA DRSSS TAYMQ LSSLT SEDSA VYYC (SEQ ID NO: 290) | TRSG GNLW FAY (SEQ ID NO: 336) | CTRSG GNLWF AYW (SEQ ID NO: 383) | WFAYW GQGTL VTVSA (SEQ ID NO: 392) | WGQG TLVT VSA (SEQ ID NO: 421) |
| AHH 03752 | QIQLQQSGAEL MKPGASVKISC KATGYTFSSYW IEWVKQRPGHG LEWIGEILPGS GSTNYNEKFKG KATFTADTSSN TAYMQLSSLTS EDSAVYYCARR YYGNAWFAYWG QGTLVTVSA (SEQ ID NO: ) | QIQL QQSG AELM KPGA SVKI SCKA T (SEQ ID ) | GYTFS SYW (SEQ ID NO: 179) | IEWV KQRP GHGL EWIG (SEQ ID NO: 218) | ILPGS GST (SEQ ID NO: 254) | NYNEK FKGKA TFTAD TSSNT AYMQL SSLTS EDSAV YYC (SEQ ID NO: 337) | ARRT YYGN AWFA Y (SEQ ID NO: ) | CARRT YYGNA WFAYW (SEQ ID NO: 384) | WFAYW GQGTL VTVSA (SEQ ID NO: 392) | WGQG TLVT VSA (SEQ ID NO: 421) |

TABLE 2A-continued

Exemplary Clones - Heavy Chain Sequences

| ID | V-D-J-REGION | H-FR1 | CDRH1 | H-FR2 | CDRH2 | H-FR3 | CDRH3 | JUNCTION | J-REGION | H-FR4 |
|---|---|---|---|---|---|---|---|---|---|---|
| | TYYGNAWFAYW GQGTLVTVSA (SEQ ID NO: 100) | | | | | NO: 144) | | | NO: 291) | |
| AHH 03753 | QVKLVESGGGL VQPGGSLRLSC ATSGFTFTDYY MSWVRQPPGKA LEWLGFIRNKA NGYTTEYSASV KGRFTISRDNS QSILYLQMNTL RAEDSATYYCA RDKRITTVEAW FAYWGQGTLVT VSA (SEQ ID NO: 101) | QVKL VESG GGLV QPGG SLRL SCAT S (SEQ ID NO: 145) | GFTFT DYY (SEQ ID NO: 180) | MSWV RQPP GKAL EWLG F (SEQ ID NO: 219) | IRNKA NGYTT (SEQ ID NO: 255) | EYSAS VKGRF TISRD NSQSI LYLQM NTLRA EDSAT YYC (SEQ ID NO: 292) | ARDK RITT VEAW FAY (SEQ ID NO: 338) | CARDK RITTV EAWFA YW (SEQ ID NO: 385) | WFAYW GQGTL VTVSA (SEQ ID NO: 392) | WGQG TLVT VSA (SEQ ID NO: 421) |
| AHH 03754 | EVKLVETGGGL VKPGGSLKLSC AASGFTFSSYA MSWVRQTPEKR LEWVASISSGG STYYPDSVKGR FTISRDNARNI LYLQMSSLRSE DTAMYYCARGY GSSFAYWGQGT PVTVSS (SEQ ID NO: 102) | EVKL VETG GGLV KPGG SLKL SCAA S (SEQ ID NO: 146) | GFTFS SYA (SEQ ID NO: 151) | MSWV RQTP EKRL EWVA S (SEQ ID NO: 184) | ISSGG ST (SEQ ID NO: 224) | YYPDS VKGRF TISRD NARNI LYLQM SSLRS EDTAM YYC (SEQ ID NO: 259) | ARGY GSSF AY (SEQ ID NO: 339) | CARGY GSSFA YW (SEQ ID NO: 386) | SFAYW GQGTP VTVSS (SEQ ID NO: 418) | WGQG TPVT VSS (SEQ ID NO: 398) |
| AHH 03755 | QVQLQQSGAEL VKPGASVKLSC KASGYTFTSYY MYWVKQRPGQG LEWIGEINPSN SGTNFNEKFKS KATLTVDKSSS TAYMQLSSLTS EDSAVYYCTRG GDYDASWFAYW GQGTLVTVSA (SEQ ID NO: 103) | QVQL QQSG AELV KPGA SVKL SCKA S (SEQ ID NO: 158) | GYTFT SYY (SEQ ID NO: 191) | MYWV KQRP GQGL EWIG E (SEQ ID NO: 256) | INPSN SGT (SEQ ID NO: 256) | NFNEK FKSKA TLTVD KSSST AYMQL SSLTS EDSAV YYC (SEQ ID NO: 266) | TRGG DYDA SWFA Y (SEQ ID NO: 340) | CTRGG DYDAS WFAYW (SEQ ID NO: 387) | WFAYW GQGTL VTVSA (SEQ ID NO: 392) | WGQG TLVT VSA (SEQ ID NO: 421) |
| AHH 03756 | QVQMKESGPEP VKPGASVKMSC RASGYTLTDYV VSWVKQRLGQG LEWIGEIYPGS GSTYYNEKFKD KVTLTADTSSN TVHIQLSSLTS EDSAVYFCARR TARAFDYWGQG TTVTVSS (SEQ ID NO: 104) | QVQM KESG PEPV KPGA SVKM SCRA S (SEQ ID NO: 147) | GYTLT DYV (SEQ ID NO: 181) | VSWV KQRL GQGL EWIG E (SEQ ID NO: 220) | IYPGS GST (SEQ ID NO: 251) | YYNEK FKDKV TLTAD TSSNT VHIQL SSLTS EDSAV YFC (SEQ ID NO: 293) | ARRT ARAF DY (SEQ ID NO: 341) | CARRT ARAFD YW (SEQ ID NO: 388) | FDYWG QGTTV TVSS (SEQ ID NO: 419) | WGQG TTVT VSS (SEQ ID NO: 422) |
| AHH 03757 | EVKLVESGGGL VKPGGSLKLSC AASGFTFSSYA MSWVRQTPEKR LEWVATISSGG SYTYYPDSVKG RFTISRDNAKN TLYLQMSSLRS EDTAMYYCARR IGYDGGGSWFA YWGQGTLVTVS A (SEQ ID NO: 105) | EVKL VESG GGLV KPGG SLKL SCAA S (SEQ ID NO: 148) | GFTFS SYA (SEQ ID NO: 151) | MSWV RQTP EKRL EWVA T (SEQ ID NO: 221) | ISSGG SYT (SEQ ID NO: 237) | YYPDS VKGRF TISRD NAKNT LYLQM SSLRS EDTAM YYC (SEQ ID NO: 294) | ARRI GYDG GGSW FAY (SEQ ID NO: 342) | CARRI GYDGG GSWFA YW (SEQ ID NO: 389) | WFAYW GQGTL VTVSA (SEQ ID NO: 392) | WGQG TLVT VSA (SEQ ID NO: 421) |

TABLE 2A-continued

Exemplary Clones - Heavy Chain Sequences

| ID | V-D-J-REGION | H-FR1 | CDRH1 | H-FR2 | CDRH2 | H-FR3 | CDRH3 | JUNCTION | J-REGION | H-FR4 |
|---|---|---|---|---|---|---|---|---|---|---|
| AHH03758 | EVKIVESGGGLVQPKGSLKLSCAASGFTFNTYAMNWVRQAPEKGLEWVARIRSKSNNYVTYYADSLKDRFTISRDDSQSMLYLQMNNLKTEDTCHVLLCERVRRCVLGPRDSGHCLC (SEQ ID NO: 106) | EVKIVESGGGLVQPKGSLKLSCAAS (SEQ ID NO: 149) | GFTFNTYA (SEQ ID NO: 182) | MNWVRQAPEKGLEWVAR (SEQ ID NO: 222) | IRSKSNNYVT (SEQ ID NO: 257) | YYADSLKDRFTISRDDSQSMLYLQMNNLKTEDTCHVLL (SEQ ID NO: 295) | CERVRRCV (SEQ ID NO: 343) | LCERVRRCVL (SEQ ID NO: 390) | CVLGPRDSGHCLC (SEQ ID NO: 420) | WGQGTLVTVSA (SEQ ID NO: 421) |
| AHH03759 | QVQLVETGGGLVRPGNSLKLSCVTSGFTFSNYRMHWLRQPPGKRLEWIAVITVKSDNYGANYAESVKGRFTISRDDSKSSVYLQMNRLREEDTATYYCSRWFAYWGQGTLVTVSA (SEQ ID NO: 107) | QVQLVETGGGLVRPGNSLKLSCVTS (SEQ ID NO: 150) | GFTFSNYR (SEQ ID NO: 183) | MHWLRQPPGKRLEWIAV (SEQ ID NO: 223) | ITVKSDNYGA (SEQ ID NO: 258) | NYAESVKGRFTISRDSKSSVYLQMNRLREEDTATYYC (SEQ ID NO: 296) | SRWFAY (SEQ ID NO: 344) | CSRWFAYW (SEQ ID NO: 391) | WFAYWGQGTLVTVSA (SEQ ID NO: 392) | WGQGTLVTVSA (SEQ ID NO: 421) |

TABLE 2B

Exemplary Clones-Heavy Chain Sequences

| ID | V-D-J-REGION | H-FR1 | CDRH1 | H-FR2 | CDRH2 | H-FR3 | CDRH3 | JUNCTION | J-REGION | H-FR4 |
|---|---|---|---|---|---|---|---|---|---|---|
| AHH03760 | QVQLQQSGAELVRPGASVKLSCKALGYTFTDYEMHWVKQTPVHGLGWIGAIHPGSGGTAYNQKFKGKATLTADKSSSTAYMELSSLTSEDSAVYYCTRSDYGSSYEFAYWGQGTLVTVSS (SEQ ID NO: 432) | QVQLQQSGAELVRPGASVKLSCKAL (SEQ ID NO: 461) | GYTFTDYE (SEQ ID NO: 174) | MHWVKQTPVHGLGWIGA (SEQ ID NO: 493) | IHPGSGGT (SEQ ID NO: 247) | AYNQKFKGKATLTADKSSSTAYMELSSLTSEDSAVYYC (SEQ ID NO: 283) | TRSDYGSSYEFAY (SEQ ID NO: 531) | CTRSDYGSSYEFAYW (SEQ ID NO: 558) | FAYWGQGTLVTVSS (SEQ ID NO: 399) | WGQGTLVTVSS (SEQ ID NO: 413) |
| AHH03765 | QIQLKESGPGLVKPSQSLSLTCTVTGYSITSDYAWNWIRQFPGNKLEWMGYISYSGSTSYNPSLKSRISITRDTSKNQFFLQLNSVTTEDTATYYCARSRGNYFDYWGQGTTVTVSS (SEQ ID NO: 433) | QIQLKESGPGLVKPSQSLSLTCTVT (SEQ ID NO: 462) | GYSITSDYA (SEQ ID NO: 482) | WNWIRQFPGNKLEWMGY (SEQ ID NO: 494) | ISYSGST (SEQ ID NO: 506) | SYNPSLKSRISITRDTSKNQFFLQLNSVTTEDTATYYC (SEQ ID NO: 516) | ARSRGNYFDY (SEQ ID NO: 532) | CARSRGNYFDYW (SEQ ID NO: 559) | YFDYWGQGTTVTVSS (SEQ ID NO: 397) | WGQGTTVTVSS (SEQ ID NO: 422) |
| AHH03767 | QIQLQQSGAELARPGASVRMSCKASGYTFTSYTIHWVKQRPGQGLEWIGYINPSSGYTNYNQKFKDKATLTADKSSSTAYMQ | QIQLQQSGAELARPGASVRMSCKAS (SEQ ID NO: ) | GYTFTSYT (SEQ ID NO: 162) | IHWVKQRPGQGLEWIG (SEQ ID NO: 196) | INPSSGYT (SEQ ID NO: 236) | NYNQKFKDKATLTADKSSSTAYMQLSSLTSEDSA | ARSGLRQAWFAY (SEQ ID NO: 533) | CARSGLRQAWFAYW (SEQ ID NO: 560) | WFAYWGQGTLVTVSA (SEQ ID NO: 392) | WGQGTLVTVSA (SEQ ID NO: 421) |

TABLE 2B-continued

Exemplary Clones-Heavy Chain Sequences

| ID | V-D-J-REGION | H-FR1 | CDRH1 | H-FR2 | CDRH2 | H-FR3 | CDRH3 | JUNC-TION | J-REGION | H-FR4 |
|---|---|---|---|---|---|---|---|---|---|---|
| | LSSLTSEDSAV YYCARSGLRQ AWFAYWGQG TLVTVSA (SEQ ID NO: 434) | 463) | | | | VYYC (SEQ ID NO: 270) | | | | |
| AHH 03768 | QVQLVETGGG LVRPGNSLKLS CVTSGFTFSNY RMHWLRQPLG KRLEWIAVITV KSDNYGANYA ESVKGRFTISR DDSKSSVYLQ MNRLREEDTA TYYCSRLFAY WGQGTLVTVS A (SEQ ID NO: 435) | QVQL VETG GGLV RPGNS LKLSC VTS (SEQ ID NO: 150) | GFTFSN YR (SEQ ID NO: 183) | MHW LRQP LGKR LEWI AV (SEQ ID NO: 495) | ITVKS DNYG A (SEQ ID NO: 258) | NYAE SVKG RFTIS RODS KSSV YLQM NRLR EEDT ATYY C (SEQ ID NO: 296) | SRLFA Y (SEQ ID NO: 534) | CSRLF AYW (SEQ ID NO: 561) | FAYWGQ GTLVTV SA (SEQ ID NO: 395) | WGQG TLVT VSA (SEQ ID NO: 421) |
| AHH 03770 | QVQLQQPGAE LVKPGASVKL SCKASGYTFTS YWMHWVKLR PGQGFEWIGEI NPSNGGTNYN EKFKRKATLT VDKSSSTAYM QLSSLTSEDSA VYYCTITGFDV WGAGTTVTVS S (SEQ ID NO: 436) | QVQL QQPG AELV KPGAS VKLSC KAS (SEQ ID NO: 464) | GYTFTS YW (SEQ ID NO: 157) | MHW VKLR PGQG FEWI GE (SEQ ID NO: 496) | INPSN GGT (SEQ ID NO: 231) | NYNE KFKR KATL TVDK SSSTA YMQL SSLTS EDSA VYYC (SEQ ID NO: 517) | TITGFD V (SEQ ID NO: 535) | CTITGF DVW (SEQ ID NO: 562) | FDVWGA GTTVTV SS (SEQ ID NO: 585) | WGAG TTVT VSS (SEQ ID NO: 423) |
| AHH 03771 | QIQLQQSGAEL VKPGASVKLS CKTSGYTFTTY WIQWVKQRPG QGLGWIGEIFP GTGTTYYNEK FKGKATLTIDT SSSTAYMQLSS LTSEDSAVYFC ARGGYYNSSP FAYWGQGTLV TVSA (SEQ ID NO: 437) | QIQLQ QSGAE LVKPG ASVKL SCKTS (SEQ ID NO: 465) | GYTFT TYW (SEQ ID NO: 483) | IQWV KQRP GQGL GWIG E (SEQ ID NO: 497) | IFPGTG TT (SEQ ID NO: 507) | YYNE KFKG KATL TIDTS SSTA YMQL SSLTS EDSA VYFC (SEQ ID NO: 518) | ARGGY YNSSP FAY (SEQ ID NO: 536) | CARGG YYNSS PFAYW (SEQ ID NO: 563) | FAYWGQ GTLVTV SA (SEQ ID NO: 395) | WGQG TLVT VSA (SEQ ID NO: 421) |
| AHH 03772 | DVQLVESGGG LVQPGGSLRLS CATSGFTFTDY YMSWVRQPPG KALEWLGFIR NKANGYTTEY SASVKGRFTIS RDNSQSILYLQ MNTLRAEDSA TYYCARDGEV RRALAYWGQ GTLVTVSA (SEQ ID NO: 438) | DVQL VESGG GLVQP GGSLR LSCAT S (SEQ ID NO: 466) | GFTFTD YY (SEQ ID NO: 180) | MSWV RQPP GKAL EWLG F (SEQ ID NO: 219) | IRNKA NGYTT (SEQ ID NO: 255) | EYSA SVKG RFTIS RDNS QSILY LQMN TLRA EDSA TYYC (SEQ ID NO: 292) | ARDGE VRRAL AY (SEQ ID NO: 537) | CARDG EVRRA LAYW (SEQ ID NO: 564) | AYWGQ GTLVTV SA (SEQ ID NO: 394) | WGQG TLVT VSA (SEQ ID NO: 421) |
| AHH 03773 | QVQLQQPAAE LARPGASVKM SCKASGYTFTS STMHWVKQRP GQGLEWIGYIN PSSGYTEYNQ KFKDKTTLTA DKSSSTAYMQ LSSLTSEDSAV YYCVRHYYFD YWGQGTTVTV | QVQL QQPA AELAR PGASV KMSC KAS (SEQ ID NO: 467) | GYTFTS ST (SEQ ID NO: 484) | MHW VKQR PGQG LEWI GY (SEQ ID NO: 190) | INPSSG YT (SEQ ID NO: 236) | EYNQ KFKD KTTL TADK SSSTA YMQL SSLTS EDSA VYYC (SEQ ID NO: | VRHYY FDY (SEQ ID NO: 538) | CVRHY YFDY W (SEQ ID NO: 565) | YFDYWG QGTTVT VSS (SEQ ID NO: 397) | WGQG TTVT VSS (SEQ ID NO: 422) |

TABLE 2B-continued

Exemplary Clones-Heavy Chain Sequences

| ID | V-D-J-REGION | H-FR1 | CDRH1 | H-FR2 | CDRH2 | H-FR3 | CDRH3 | JUNCTION | J-REGION | H-FR4 |
|---|---|---|---|---|---|---|---|---|---|---|
| | SS (SEQ ID NO: 439) | | | | | 519) | | | | |
| AHH 03774 | EVMLVESGGG LVKPGGSLKIS CAASGFTFSSY TMSWVRQNPE KRLEWVATISS GGGYTYYLDS VKGRFTPSRD NGKNTLNLQM SSLKSEDTAM YYCTRVSAKY FDVWGAGTTL TVSS (SEQ ID NO: 440) | EVML VESGG GLVKP GGSLK ISCAA S (SEQ ID NO: 468) | GFTFSS YT (SEQ ID NO: 485) | MSWV RQNP EKRL EWVA T(SEQ ID NO: 498) | ISSGG GYT (SEQ ID NO: 508) | YYLD SVKG RFTPS RDNG KNTL NLQM SSLKS EDTA MYYC (SEQ ID NO: 519) | TRVSA KYFDV (SEQ ID NO: 539) | CTRVS AKYFD VW (SEQ ID NO: 566) | YFDVWG AGTTLT VSS (SEQ ID NO: 586) | WGAG TTLT VSS (SEQ ID NO: 428) |
| AHH 03776 | QVQLQQSGAE LVKPGASVKL SCKASGYTFT NFYLYWVKQR PGQGLEWIGGI NPSNGGTNFN EKFKSKATLT VDKSSSTAYM QLSSLTSEDSA VYYCTRSYYD YDWYFDVWG AGTTVTVSS (SEQ ID NO: 441) | QVQL QQSG AELV KPGAS VKLSC KAS (SEQ ID NO: 115) | GYTFT NFY (SEQ ID NO: 486) | LYWV KQRP GQGL EWIG G (SEQ ID NO: 499) | INPSN GGT (SEQ ID NO: 231) | NFNE KFKS KATL TVDK SSSTA YMQL SSLTS EDSA VYYC (SEQ ID NO: 266) | TRSYY DYDW YFD (SEQ ID NO: 540) | CTRSY YD YD WYFD VW (SEQ ID NO: 567) | DWYFDV WGAGTT VTVSS (SEQ ID NO: 587) | WGAG TTVT VSS (SEQ ID NO: 423) |
| AHH 03777 | QVQLQQSGAE LVRPGASVKL SCKASGYTFTS YWINWVKQRP GQGLEWIGNIY PSDSYTNYNQ KFKDKATLTV DKSSSTAYMQ LSSPTSEDSAV YYCTRQNYYG SSHWYFDVW GAGTTLTVSS (SEQ ID NO: 442) | QVQL QQSG AELVR PGASV KLSCK AS (SEQ ID NO: 113) | GYTFTS YW (SEQ ID NO: 157) | INWV KQRP GQGL EWIG N (SEQ ID NO: 500) | IYPSDS YT (SEQ ID NO: 509) | NYNQ KFKD KATL TVDK SSSTA YMQL SSPTS EDSA VYYC (SEQ ID NO: 521) | TRQNY YGSSH WYFD V (SEQ ID NO: 541) | CTRQN YYGSS HWYF DVW (SEQ ID NO: 568) | WYFDV WGAGTT LTVSS (SEQ ID NO: 409) | WGAG TTLT VSS (SEQ ID NO: 428) |
| AHH 03778 | QVQLQQPGAE LVKPGAPVKL SCKASGYTFTS YWMNWVKQR PGRGLEWIGRI DPSDSETHYN QKFKDKATLT VDKSSSTAYIQ LSSLTSEDSAV YYCANWAWF AYWGQGTLVT VSS (SEQ ID NO: 443) | QVQL QQPG AELV KPGAP VKLSC KAS (SEQ ID NO: 469) | GYTFTS YW (SEQ ID NO: 157) | MNW VKQR PGRG LEWI GR (SEQ ID NO: 204) | IDPSDS ET (SEQ ID NO: 229) | HYNQ KFKD KATL TVDK SSSTA YIQLS SLTSE DSAV YYC (SEQ ID NO: 276) | ANWA WFAY (SEQ ID NO: 317) | CANW AWFA YW (SEQ ID NO: 365) | WFAYW GQGTLV TVSS (SEQ ID NO: 588) | WGQG TLVT VSS (SEQ ID NO: 413) |
| AHH 03779 | QIQFAQSGPEL KKPGETVKISC KAFGYTFTDY SMHWVKQAP GKGLKWMGW INTETGEPTYA DDFKGRFAFSL ETSASTAYLQI NNLKNEDTAT YFCASFYYGN FAYYFDYRGQ GTTLTVSS (SEQ ID NO: 444) | QIQFA QSGPE LKKPG ETVKI SCKAF (SEQ ID NO: 470) | GYTFT DYS (SEQ ID NO: 487) | MHW VKQA PGKG LKW MGW (SEQ ID NO: 185) | INTET GEP (SEQ ID NO: 225) | TYAD DFKG RFAFS LETSA STAY LQINN LKNE DTAT YFC (SEQ ID NO: 260) | ASFYY GNFAY YFDY (SEQ ID NO: 542) | CASFY YGNFA YYFDY R(SEQ ID NO: 569) | YFDYRG QGTTLT VSS (SEQ ID NO: 589) | RGQG TTLT VSS (SEQ ID NO: 597) |

TABLE 2B-continued

Exemplary Clones-Heavy Chain Sequences

| ID | V-D-J-REGION | H-FR1 | CDRH1 | H-FR2 | CDRH2 | H-FR3 | CDRH3 | JUNCTION | J-REGION | H-FR4 |
|---|---|---|---|---|---|---|---|---|---|---|
| AHH 03780 | EVKIEESGGGLVQPGGAMKLSCVASGFTFSNYWMNWVRQSPEKGLEWVAEIRLKSNNYATYYAESVKGRFTISRDDSQSSVYLQMNDLRTEDTGIYYCTRIYDSGSSYTWYFDVWGAGTTVTVSS (SEQ ID NO: 445) | EVKIEESGGGLVQPGGAMKLSCVAS (SEQ ID NO: 471) | GFTFSNYW (SEQ ID NO: 166) | MNWVRQSPEKGLEWVAE (SEQ ID NO: 201) | IRLKSNNYAT (SEQ ID NO: 241) | YYAESVKGRFTISRDDSQSSVYLQMNDLRTEDTGIYYC (SEQ ID NO: 522) | TRIYDSGSSYTWYFDV (SEQ ID NO: 543) | CTRIYDSGSSYTWYFDVW (SEQ ID NO: 570) | WYFDVWGAGTTVTVSS (SEQ ID NO: 416) | WGAGTTVTVSS (SEQ ID NO: 423) |
| AHH 03782 | QVILKESGPGILQPSQTLSLTCSFSGFSLSTSGMSVGWIRQPSGKGLEWLAHIWWNDDKYYNPALKSRLTISKDTPNNQVFLKIASWTADTATYYCARIGGNDGYYWYFDVWGAGTSLTVSS (SEQ ID NO: 446) | QVILKESGPGILQPSQTLSLTCSFS (SEQ ID NO: 120) | GFSLSTSGMS (SEQ ID NO: 163) | VGWIRQPSGKGLEWLAH (SEQ ID NO: 198) | IWWNDDK (SEQ ID NO: 238) | YYNPALKSRLTISKDTPNNQVFLKIASWTADTATYYC (SEQ ID NO: 523) | ARIGGNDGYYWYFDV (SEQ ID NO: 311) | CARIGGNDGYYWYFDVW (SEQ ID NO: 359) | YWYFDVWGAGTSLTVSS (SEQ ID NO: 590) | WGAGTSLTVSS (SEQ ID NO: 431) |
| AHH 03783 | QIQLQQSGAELVKPGASVKLSCKASGYTFTSYWMHWVKQRPGQGLEWIGEINPSNGRTNYNEKFKSKATLTVDKSSSTAYMQLSSLTSEDSAVYYCARDSSGYGAYWGQGTLVTVSS (SEQ ID NO: 447) | QIQLQQSGAELVKPGASVKLSCKAS (SEQ ID NO: 472) | GYTFTSYW (SEQ ID NO: 157) | MHWVKQRPGQGLEWIGE (SEQ ID NO: 209) | INPSNGRT (SEQ ID NO: 510) | NYNEKFKSKATLTVDKSSSTAYMQLSSLTSEDSAVYYC (SEQ ID NO: 289) | ARDSSGYGAY (SEQ ID NO: 544) | CARDSSGYGAYW (SEQ ID NO: 571) | YGAYWGQGTLVTVSS (SEQ ID NO: 591) | WGQGTLVTVSS (SEQ ID NO: 413) |
| AHH 03784 | QVQLQQSGAELAKPGASVKMSCKASGYTFTSYWMHWVKQRPGQGLEWIGYINPSTGYTEYNQKFKDKATLTADKSSSTAYMQLSSLTSEDSAVYYCARYDGYYYFDYWGQGTTLTVSS (SEQ ID NO: 448) | QVQLQQSGAELAKPGASVKMSCKAS (SEQ ID NO: 473) | GYTFTSYW (SEQ ID NO: 157) | MHWVKQRPGQGLEWIGY (SEQ ID NO: 190) | INPSTGYT (SEQ ID NO: 230) | EYNQKFKDKATLTADKSSSTAYMQLSSLTSEDSAVYYC (SEQ ID NO: 265) | ARYDGYYYFDY (SEQ ID NO: 545) | CARYDGYYYFDYW (SEQ ID NO: 572) | YFDYWGQGTTLTVSS (SEQ ID NO: 592) | WGQGTTLTVSS (SEQ ID NO: 425) |
| AHH 03785 | QVQLQQSGAELVRPGASVKLSCKASGYTFTSYWINWVKQRPGQGLEWIGNIYPSDSYTNYQKFKDKATLTVDKSSSTAYMQLSSPTSEDSAVYYCTSHYYGRAWFAYWGQGTLVTVL (SEQ ID NO: 449) | QVQLQQSGAELVRPGASVKLSCKAS (SEQ ID NO: 113) | GYTFTSYW (SEQ ID NO: 157) | INWVKQRPGQGLEWIGN (SEQ ID NO: 500) | IYPSDSYT (SEQ ID NO: 509) | NYNQKFKDKATLTVDKSSSTAYMQLSSPTSEDSAVYYC (SEQ ID NO: 521) | TSHYYGRAWFAY (SEQ ID NO: 546) | CTSHYYGRAWFAYW (SEQ ID NO: 573) | WFAYWGQGTLVTVL (SEQ ID NO: 593) | WGQGTLVTVL (SEQ ID NO: 598) |
| AHH 03786 | QIQLQQPGAELVKPGASVKLS | QIQLQQPGAE | GYTFTRYY | MYWVKQR | INPSNGGT | NFNEKFKS | TKGGFYDFFA | CTKGGYDFFA | FFAYWGQGTLVT | WGQGTLVT |

TABLE 2B-continued

Exemplary Clones-Heavy Chain Sequences

| ID | V-D-J-REGION | H-FR1 | CDRH1 | H-FR2 | CDRH2 | H-FR3 | CDRH3 | JUNCTION | J-REGION | H-FR4 |
|---|---|---|---|---|---|---|---|---|---|---|
|  | CKASGYTFTR YYMYWVKQR PGQGLEWIGEI NPSNGGTNFN EKFKSKATLT VDKSSTAYM QLNSLTSDDSA VYYCTKGGFY DFFAYWGQGT LVTVSA (SEQ ID NO: 450) | LVKPG ASVKL SCKAS (SEQ ID NO: 474) | (SEQ ID NO: 488) | PGQG LEWI GE (SEQ ID NO: 191) | (SEQ ID NO: 231) | KATL TVDK SSSTA YMQL NSLTS DDSA VYYC (SEQ ID NO: 524) | Y (SEQ ID NO: 547) | AYW (SEQ ID NO: 574) | VSA (SEQ ID NO: 594) | VSA (SEQ ID NO: 421) |
| AHH 03787 | EVMLVESGGG LVQPGGSLKLS CAASGFTFSSY GMSWVRQTPD KRLELVATINS NGGSTYYPDS VKGRFTISRDN AKNTLYLQMS SLKSEDTAMY YCASLAYWGQ GTLVTVSA (SEQ ID NO: 451) | EVML VESGG GLVQP GGSLK LSCAA S (SEQ ID NO: 122) | GFTFSS YG (SEQ ID NO: 165) | MSWV RQTP DKRL ELVA T(SEQ ID NO: 200) | INSNG GST (SEQ ID NO: 240) | YYPD SVKG RFTIS RDNA KNTL YLQM SSLKS EDTA MYYC (SEQ ID NO: 274) | ASLAY (SEQ ID NO: 548) | CASLA YW (SEQ ID NO: 575) | AYWGQ GTLVTV SA (SEQ ID NO: 394) | WGQG TLVTV VSA (SEQ ID NO: 421) |
| AHH 03788 | QIQLQQSGPDL VKPGASVKISC KASGYTFTDY YINWMKQKPG QGLEWIGWIY PGSGNTKYNE KFKGKATLTV DTSSSTAYMQ LSSLTSEDTAV YFCARVYSGF DVWGAGTTVT VSS (SEQ ID NO: 452) | QIQLQ QSGPD LVKPG ASVKI SCKAS (SEQ ID NO: 475) | GYTFT DYY (SEQ ID NO: 489) | INWM KQKP GQGL EWIG W (SEQ ID NO: 501) | IYPGS GNT (SEQ ID NO: 511) | KYNE KFKG KATL TVDT SSSTA YMQL SSLTS EDTA VYFC (SEQ ID NO: 525) | ARVYS GFDV (SEQ ID NO: 549) | CARVY SGFDV W (SEQ ID NO: 576) | FDVWGA GTTVTV SS (SEQ ID NO: 585) | WGAG TTVT VSS (SEQ ID NO: 423) |
| AHH 03790 | QIQLQQSGPEL VKPGASVKMS CKAPGYTFTS YYIHWVKQRP GQGLEWIGWI YPGDGSTKYN EKFKGKTTLT ADKSSSTAYM LLSSLTSEDSAI YFCARGDYF AWFAYWGQG TLVTVSA (SEQ ID NO: 453) | QIQLQ QSGPE LVKPG ASVK MSCK AP (SEQ ID NO: 476) | GYTFTS YY (SEQ ID NO: 158) | IHWV KQRP GQGL EWIG W (SEQ ID NO: 502) | IYPGD GST (SEQ ID NO: 512) | KYNE KFKG KTTL TADK SSSTA YMLL SSLTS EDSAI YFC (SEQ ID NO: 526) | ARGDG YFAWF AY (SEQ ID NO: 550) | CARGD GYFA WFAY W (SEQ ID NO: 577) | WFAYW GQGTLV TVSA (SEQ ID NO: 392) | WGQG TLVT VSA (SEQ ID NO: 421) |
| AHH 03791 | QIQLQQSGAEL MKPGASVKIS CKATGYTFSS YWIEWVKQRP GHGLEWIGEIL PGSGSTKYNE KFKGKATFTA DTSSNTAYMQ LSSLTSEDSAV YYCARSAHRY DAWFAYWGQ GTLVTVL (SEQ ID NO: 454) | QIQLQ QSGAE LMKP GASV KISCK AT (SEQ ID NO: 144) | GYTFSS YW (SEQ ID NO: 179) | IEWV KQRP GHGL EWIG SEQ ID NO: 218) | ILPGSG ST (SEQ ID NO: 254) | KYNE KFKG KATF TADT SSNT AYMQ LSSLT SEDS AVYY C (SEQ ID NO: 527) | ARSAH RYDA WFAY (SEQ ID NO: 551) | CARSA HRYDA WFAY W (SEQ ID NO: 578) | WFAYW GQGTLV TVL (SEQ ID NO: 593) | WGQG TLVT VL (SEQ ID NO: 598) |
| AHH 03792 | QIQLQQPGAEL VKPGASVKLS CKASGYTFTN YYMYWVNQR PGQGLEWIGGI NPTNGGTNFN AKFKNKATLT | QIQLQ QPGAE LVKPG ASVKL SCKAS (SEQ ID | GYTFT NYY (SEQ ID NO: 490) | MYW VNQR PGQG LEWI GG (SEQ ID | INPTN GGT (SEQ ID NO: 513) | NFNA KFKN KATL TVDK SSNT AYMQ LSSLT | TRGM AYRYD GAGW FAY (SEQ ID NO: 552) | CTRGM AYRYD GAGW FAYW (SEQ ID NO: 579) | WFAYW GQGTPV TVSS (SEQ ID NO: 595) | WGQG TPVT VSS (SEQ ID NO: 398) |

TABLE 2B-continued

Exemplary Clones-Heavy Chain Sequences

| ID | V-D-J-REGION | H-FR1 | CDRH1 | H-FR2 | CDRH2 | H-FR3 | CDRH3 | JUNC-TION | J-REGION | H-FR4 |
|---|---|---|---|---|---|---|---|---|---|---|
| | VDKSSNTAYM QLSSLTSEDSA VYYCTRGMA YRYDGAGWF AYWGQGTPVT VSS (SEQ ID NO: 455) | 474) | | 503) | | SEDS AVYY C (SEQ ID NO: 528) | | | | |
| AHH 03793 | QVQLQQPGAE LVRPGASVKL SCKASGYTFTS YWMNWVKQR PEQGLEWIGRI DPYDSETHYN QKFKDKAILT VDKSSSTAYM QLSSLTSEDSA VYYCARGGRG TWFAYWGQG TLVTVSA (SEQ ID NO: 456) | QVQL QQPG AELVR PGASV KLSCK AS (SEQ ID NO: 477) | GYTFTS YW (SEQ ID NO: 157) | MNW VKQR PEQG LEWI GR (SEQ ID NO: 195) | IDPYD SET (SEQ ID NO: 235) | HYNQ KFKD KAILT VDKS SSTA YMQL SSLTS EDSA VYYC (SEQ ID NO: 269) | ARGGR GTWFA Y (SEQ ID NO: 553) | CARGG RGTWF AYW (SEQ ID NO: 580) | WFAYW GQGTLV TVSA (SEQ ID NO: 392) | WGQG TLVT VSA (SEQ ID NO: 421) |
| AHH 03794 | DVMLVESGGG LVQPGGSLRLS CATSGFTFTDY YMSWVRQPPG KALEWLGFIR NKANGYTTEY SASVKGRFTIS RDNSQSILYLQ MNTLRAEDSA TYYCARGWG NWFAYWGQG TLVTVSA (SEQ ID NO: 457) | DVML VESGG GLVQP GGSLR LSCAT S (SEQ ID NO: 478) | GFTFTD YY (SEQ ID NO: 180) | MSWV RQPP GKAL EWLG F (SEQ ID NO: 219) | IRNKA NGYTT EY (SEQ ID NO: 255) | EYSA SVKG RFTIS RDNS QSILY LQMN TLRA EDSA TYYC (SEQ ID NO: 292) | ARGW GNWF AY (SEQ ID NO: 554) | CARG WGNW FAYW (SEQ ID NO: 581) | WFAYW GQGTLV TVSA (SEQ ID NO: 392) | WGQG TLVT VSA (SEQ ID NO: 421) |
| AHH 03795 | EVMLVESGGG LVQPGGSRKL SCAASGFTFSS FGIHWVRQAP EKGLEWVAYI SGGGGTISYAD TVKGRFTISRD NPKNTLFLQM TSLRSEDTAIY YCARWGGYF DYWGQGTSLT VSS (SEQ ID NO: 458) | EVML VESGG GLVQP GGSR KLSCA AS (SEQ ID NO: 479) | GFTFSS FG (SEQ ID NO: 491) | IHWV RQAP EKGL EWVA (SEQ ID NO: 504) | ISGGG GTI (SEQ ID NO: 514) | SYAD TVKG RFTIS RDNP KNTL FLQM TSLRS EDTAI YYC (SEQ ID NO: 529) | ARWR GGYFD Y (SEQ ID NO: 555) | CARW RGGYF DYW (SEQ ID NO: 582) | YFDYWG QGTSLT VSS (SEQ ID NO: 405) | WGQG TSLTV SS (SEQ ID NO: 424) |
| AHH 03797 | QIQLQQSGAEL VRPGASVKLS CKASGYTFTS YWINWVKQRP GQGLEWIGNIY PSDSYTNYNQ KFKDKATLTV DKSSSTAYMQ LSSPTSEDSAV YYCTRTGGST MTPWFAYWG QGTLVTVSS (SEQ ID NO: 459) | QIQLQ QSGAE LVRPG ASVKL SCKAS (SEQ ID NO: 480) | GYTFTS YW (SEQ ID NO: 157) | INWV KQRP GQGL EWIG N (SEQ ID NO: 500) | IYPSDS YT (SEQ ID NO: 509) | NYNQ KFKD KATL TVDK SSSTA YMQL SSPTS EDSA VYYC (SEQ ID NO: 521) | TRTGG STMTP WFAY (SEQ ID NO: 556) | CTRTG GSTMT PWFAY W (SEQ ID NO: 583) | WFAYW GQGTLV TVSS (SEQ ID NO: 588) | WGQG TLVT VSS (SEQ ID NO: 413) |
| AHH 03799 | QVTLKESGPGI LQPSQTLSLTC SFSGFSLSTSG MGVSWIRQPS GKGLEWLAHI YWDDDKRYN PSLKSRLTISK DTSRNQVFLKI TSVDTTDTAT YYCARRAGDY | QVTL KESGP GILQP SQTLS LTCSF S (SEQ ID NO: 481) | GFSLST SGMG (SEQ ID NO: 492) | VSWI RQPS GKGL EWLA H (SEQ ID NO: 505) | IYWDD DK (SEQ ID NO: 515) | RYNP SLKSR LTISK DTSR NQVF LKITS VDTT DTAT YYC (SEQ ID | ARRAG DYGNP FPY (SEQ ID NO: 557) | CARRA GDYG NPPPY W (SEQ ID NO: 584) | FPYWGQ GTLVTV SA (SEQ ID NO: 596) | WGQG TLVT VSA (SEQ ID NO: 421) |

TABLE 2B-continued

Exemplary Clones-Heavy Chain Sequences

| ID | V-D-J-REGION | H-FR1 | CDRH1 | H-FR2 | CDRH2 | H-FR3 | CDRH3 | JUNC-TION | J-REGION | H-FR4 |
|---|---|---|---|---|---|---|---|---|---|---|
| | GNPFPYWGQG TLVTVSA (SEQ ID NO: 460) | | | | | | | ID NO: 530) | | |

TABLE 2C

Exemplary Clones-Heavy Chain Sequences

| ID | V-D-J-REGION | H-FR1 | CDRH1 | H-FR2 | CDRH2 | H-FR3 | CDRH3 | JUNC-TION |
|---|---|---|---|---|---|---|---|---|
| >AH04501-VH | QVQLQQPGAELVR PGTSVKMSCKAAG YTFTNYWIGWVKQ RPGHGLEWIGDIHP GGDYSNYNEKFKG KATLTADTSSSTAY MNLSSLTSEDSAIY YCTSRNFAYWGQG TLVTVSA (SEQ ID NO: 1318) | QVQLQ QPGAEL VRPGTS VKMSC KAA (SEQ ID NO: 1315) | GYTFT NY (SEQ ID NO: 990) | WIGW VKQR PGHGL EWIG (SEQ ID NO: 1458) | DIHPG GDYSN YNEKF KG (SEQ ID NO: 692) | KATLTA DTSSST AYMNLS SLTSEDS AIYYCT (SEQ ID NO: 1044) | SRNFAY (SEQ ID NO: 1379) | WGQGT LVTVSA (SEQ ID NO: 421) |
| >AH04515-VH | QVQLQQPGAELVR PGTSVKMSCKAAG YTFTNYWIGWVKQ RPGHGLEWIGDIHP GGDYSNYNEKFKG KATLTADTSSSTAY MNLSSLTSEDSAIY YCTSRNFAYWGQG TLVTVSA (SEQ ID NO: 1318) | QVQLQ QPGAEL VRPGTS VKMSC KAA (SEQ ID NO: 1315) | GYTFT NY (SEQ ID NO: 990) | WIGW VKQR PGHGL EWIG (SEQ ID NO: 1458) | DIHPG GDYSN YNEKF KG (SEQ ID NO: 692) | KATLTA DTSSST AYMNLS SLTSEDS AIYYCT (SEQ ID NO: 1044) | SRNFAY (SEQ ID NO: 1379) | WGQGT LVTVSA (SEQ ID NO: 421) |
| >AH04502-VH | QIQLQQSGAELVRP GTSVKMSCKAAGY TFTNYWIGWVKQR PGHGLEWIGDIHPG GGYTNYNEKFKGK ATLTADTSSSTAD MQLSSLTSEDSAIY YCTSRNFAYWGQG TLVTVSA (SEQ ID NO: 1234) | QIQLQQ SGAELV RPGTSV KMSCK AA (SEQ ID NO: 1228) | GYTFT NY (SEQ ID NO: 990) | WIGW VKQR PGHGL EWIG (SEQ ID NO: 1458) | DIHPG GGYT NYNE KFKG (SEQ ID NO: 696) | KATLTA DTSSST ADMQLS SLTSEDS AIYYCT (SEQ ID NO: 1043) | SRNFAY (SEQ ID NO: 1379) | WGQGT LVTVSA (SEQ ID NO: 421) |
| >AH04512-VH | QIQLQQSGAELVRP GTSVKMSCKAAGY TFTNYWIGWVKQR PGHGLEWIGDIHPG GGYTNYNEKFKGK ATLTADTSSSTAY MQLSSLTSEDSAIY YCTSRNFAYWGQG TLVTVSA (SEQ ID NO: 1235) | QIQLQQ SGAELV RPGTSV KMSCK AA (SEQ ID NO: 1228) | GYTFT NY (SEQ ID NO: 990) | WIGW VKQR PGHGL EWIG (SEQ ID NO: 1458) | DIHPG GGYT NYNE KFKG (SEQ ID NO: 696) | KATLTA DTSSST AYMQLS SLTSEDS AIYYCT (SEQ ID NO: 1045) | SRNFAY (SEQ ID NO: 1379) | WGQGT LVTVSA (SEQ ID NO: 421) |
| >AH04522-VH | QIQLQQSGAELVRP GTSVKMSCKAAGY TFTNYWIGWVKQR PGHGLEWIGDIHPG GGYTNYNEKFKGK ATLTADTSSSTAY MQLSSLTSEDSAIY YCTSRNFAYWGQG TLVTVSA (SEQ ID NO: 1235) | QIQLQQ SGAELV RPGTSV KMSCK AA (SEQ ID NO: 1228) | GYTFT NY (SEQ ID NO: 990) | WIGW VKQR PGHGL EWIG (SEQ ID NO: 1458) | DIHPG GGYT NYNE KFKG (SEQ ID NO: 696) | KATLTA DTSSST AYMQLS SLTSEDS AIYYCT (SEQ ID NO: 1045) | SRNFAY (SEQ ID NO: 1379) | WGQGT LVTVSA (SEQ ID NO: 421) |
| >AH04513-VH | QIQLQQSGAELVRP GTSVKMSCKAAGY TFTNYWIGWVKQR PGHGLEWIGDIHPG GGYTNYNEKFKGK ATLTADTSSSTAY | QIQLQQ SGAELV RPGTSV KMSCK AA (SEQ ID | GYTFT NY (SEQ ID NO: 990) | WIGW VKQR PGHGL EWIG (SEQ ID | DIHPG GGYT NYNE KFKG (SEQ ID | KATLTA DTSSST AYMQLS SLTSEDS AIYYCT (SEQ ID | SRNFAY (SEQ ID NO: 1379) | WGQGT P VTVSS (SEQ ID NO: 398) |

TABLE 2C-continued

Exemplary Clones-Heavy Chain Sequences

| ID | V-D-J-REGION | H-FR1 | CDRH1 | H-FR2 | CDRH2 | H-FR3 | CDRH3 | JUNC-TION |
|---|---|---|---|---|---|---|---|---|
| | MQLSSLTSEDSAIY YCTSRNFAYWGQG TPVTVSS (SEQ ID NO: 1236) | | 1228) | | 1458) | 696) | NO: 1045) | |
| >AH04523-VH | QIQLQQSGAELVRP GTSVKMSCKAAGY TFTNYWIGWVKQR PGHGLEWIGDIHPG GSYTNYNENFKGK ATFTADTSSSTTYM QLSSLTSEDSAIYFC TSRNFAKWGQGTP VTVSS (SEQ ID NO: 1237) | QIQLQQ SGAELV RPGTSV KMSCK AA (SEQ ID NO: 1228) | GYTFT NY (SEQ ID NO: 990) | WIGW VKQR PGHGL EWIG (SEQ ID NO: 1458) | DIHPG GSYTN YNENF KG (SEQ ID NO: 697) | KATFTA DTSSSTT YMQLSS LTSEDS AIYFCT (SEQ ID NO: 1041) | SRNFAK (SEQ ID NO: 1377) | WGQGT PVTVSS (SEQ ID NO: 398) |
| >AH04503-VH | QVQLQQPGAELVR PGTSVKMSCKAAG YTFSNYWIGWVKQ RPGHGLEWIGDIHP GGGYINYNEKFTG KATLTADTSSSTAY MQLSSLTSEDSAIY YCVSRNFANWGQG TLVTVSA (SEQ ID NO: 1316) | QVQLQ QPGAEL VRPGTS VKMSC KAA (SEQ ID NO: 1315) | GYTFS NY (SEQ ID NO: 985) | WIGW VKQR PGHGL EWIG (SEQ ID NO: 1458) | DIHPG GGYIN YNEKF TG (SEQ ID NO: 695) | KATLTA DTSSST AYMQLS SLTSEDS AIYYCV (SEQ ID NO: 1046) | SRNFAN (SEQ ID NO: 1378) | WGQGT LVTVSA (SEQ ID NO: 421) |
| >AH04529-VH | QVQLQQPGAELVR PGTSVKMSCKAAG YTFSNYWIGWVKQ RPGHGLEWIGDIHP GGGYINYNEKFTG KATLTADTSSSTAY MQLSSLTSEDSAIY YCVSRNFANWGQG TPVTVSS (SEQ ID NO: 1317) | QVQLQ QPGAEL VRPGTS VKMSC KAA (SEQ ID NO: 1315) | GYTFS NY (SEQ ID NO: 985) | WIGW VKQR PGHGL EWIG (SEQ ID NO: 1458) | DIHPG GGYIN YNEKF TG (SEQ ID NO: 695) | KATLTA DTSSST AYMQLS SLTSEDS AIYYCV (SEQ ID NO: 1046) | SRNFAN (SEQ ID NO: 1378) | WGQGT PVTVSS (SEQ ID NO: 398) |
| >AH04510-VH | QVQLQQSGAELVR PGTSVKMSCKAAG YTFSNYWIGWVKQ RPGHGLEWIGDIHP GGGYINYNEKFTG KATLTADTSSSTAY MQLSSLTSEDSAIY YCVSRNFANWGQG TLVTVSA (SEQ ID NO: 1327) | QVQLQ QSGAEL VRPGTS VKMSC KAA (SEQ ID NO: 1326) | GYTFS NY (SEQ ID NO: 985) | WIGW VKQR PGHGL EWIG (SEQ ID NO: 1458) | DIHPG GGYIN YNEKF TG (SEQ ID NO: 695) | KATLTA DTSSST AYMQLS SLTSEDS AIYYCV (SEQ ID NO: 1046) | SRNFAN (SEQ ID NO: 1378) | WGQGT LVTVSA (SEQ ID NO: 421) |
| >AH04528-VH | QVQLQQSGAELVR PGTSVKMSCKAAG YTFSNYWIGWVKQ RPGRGLEWIGDIHP GGGYINYNEKFTG KATLTADTSSSTAY MQLSSLTSGDSAIY YCVSRNFANWGQG TLVTVSA (SEQ ID NO: 1328) | QVQLQ QSGAEL VRPGTS VKMSC KAA (SEQ ID NO: 1326) | GYTFS NY (SEQ ID NO: 985) | WIGW VKQR PGRGL EWIG (SEQ ID NO: 1459) | DIHPG GGYIN YNEKF TG (SEQ ID NO: 695) | KATLTA DTSSST AYMQLS SLTSGD SAIYYC V (SEQ ID NO: 1048) | SRNFAN (SEQ ID NO: 1378) | WGQGT LVTVSA (SEQ ID NO: 421) |
| >AH04511-VH | QIQLQQSGAELVRP GTSVKMSCKAAGY TFSNYWIGWVKQR PGHGLEWIGDIHPG GGYINYNEKFTGK ATLTADTSSSTAY MQLSSLTSEDSAIY YCVSRNFANWGQG TLVTVSA (SEQ ID NO: 1229) | QIQLQQ SGAELV RPGTSV KMSCK AA (SEQ ID NO: 1228) | GYTFS NY (SEQ ID NO: 985) | WIGW VKQR PGHGL EWIG (SEQ ID NO: 1458) | DIHPG GGYIN YNEKF TG (SEQ ID NO: 695) | KATLTA DTSSST AYMQLS SLTSEDS AIYYCV (SEQ ID NO: 1046) | SRNFAN (SEQ ID NO: 1378) | WGQGT LVTVSA (SEQ ID NO: 421) |
| >AH04504-VH | QIQLQQSGAELVRP GTSVKMSCKAAGY TFTKYWIGWVKQR SGHGLEWIGDIHPG | QIQLQQ SGAELV RPGTSV KMSCK | GYTFT KY (SEQ ID NO: | WIGW VKQR SGHGL EWIG | DIHPG GGYIN YNEKF TG | KATLTA DTSSST AYMQLS SLTSEDS | SRNFAN (SEQ ID NO: 1378) | WGQGT LVTVSA (SEQ ID NO: 421) |

TABLE 2C-continued

Exemplary Clones-Heavy Chain Sequences

| ID | V-D-J-REGION | H-FR1 | CDRH1 | H-FR2 | CDRH2 | H-FR3 | CDRH3 | JUNCTION |
|---|---|---|---|---|---|---|---|---|
| | GGYINYNEKFTGK ATLTADTSSSTAY MQLSSLTSEDSAIY YCVSRNFANWGQG TLVTVSA (SEQ ID NO: 1230) | AA (SEQ ID NO: 1228) | (SEQ ID NO: 989) | (SEQ ID NO: 1460) | (SEQ ID NO: 695) | AIYYCV (SEQ ID NO: 1046) | | |
| >AH04520-VH | QIQLQQPGAELVRP GTSVKMSCKAAGY TFTKYWIGWVKQR PGHGLEWIGDIHPG GGYINYNEKFTGK ATLTAGTSSSTAY MQLSSLTSEDSAIY YCVSRNFANWGQG TLVTVSA (SEQ ID NO: 1222) | QIQLQQ PGAELV RPGTSV KMSCK AA (SEQ ID NO: 1221) | GYTFT KY (SEQ ID NO: 989) | WIGW VKQR PGHGL EWIG (SEQ ID NO: 1458) | DIHPG GGYIN YNEKF TG (SEQ ID NO: 695) | KATLTA GTSSST AYMQLS SLTSEDS AIYYCV (SEQ ID NO: 1050) | SRNFAN (SEQ ID NO: 1378) | WGQGT LVTVSA (SEQ ID NO: 421) |
| >AH04507-VH | QVQLQQSGAELVR PGTSVKMSCKAAG YTFTNYWIGWVKQ RPGHGLEWIGDIHP GGGYIDYNEKFTG KATLTADTSSSTAY MQLSSLTSEDSAIY YCVSRNFAKWGQG TLVTVSA (SEQ ID NO: 1334) | QVQLQ QSGAEL VRPGTS VKMSC KAA (SEQ ID NO: 1326) | GYTFT NY (SEQ ID NO: 990) | WIGW VKQR PGHGL EWIG (SEQ ID NO: 1458) | DIHPG GGYID YNEKF TG (SEQ ID NO: 694) | KATLTA DTSSST AYMQLS SLTSEDS AIYYCV (SEQ ID NO: 1046) | SRNFAK (SEQ ID NO: 1377) | WGQGT LVTVSA (SEQ ID NO: 421) |
| >AH04527-VH | QVQLQQSGAELVR PGTSVKMSCKAAG YTFTNYWIGWVKQ RPGHGLEWIGDIHP GGGYIDYNEKFTG KATLTADTSSSTAY MQLSSLTSEDSAIY YCVSRNFAKWGQG TLVTVSA (SEQ ID NO: 1334) | QVQLQ QSGAEL VRPGTS VKMSC KAA (SEQ ID NO: 1326) | GYTFT NY (SEQ ID NO: 990) | WIGW VKQR PGHGL EWIG (SEQ ID NO: 1458) | DIHPG GGYID YNEKF TG (SEQ ID NO: 694) | KATLTA DTSSST AYMQLS SLTSEDS AIYYCV (SEQ ID NO: 1046) | SRNFAK (SEQ ID NO: 1377) | WGQGT LVTVSA (SEQ ID NO: 421) |
| >AH04505-VH | DVQLQQSGAELVR PGTSVKMSCKAAG YTFTNYWIGWVKQ RPGHGLEWIGDIHP GGGYTNYNEKFKG KATLTADTSSSTAY MQLSSLTSEGSAIY YCTSRNFAYWGQG TLVTVSA (SEQ ID NO: 869) | DVQLQ QSGAEL VRPGTS VKMSC KAA (SEQ ID NO: 867) | GYTFT NY (SEQ ID NO: 990) | WIGW VKQR PGHGL EWIG (SEQ ID NO: 1458) | DIHPG GGYT NYNE KFKG (SEQ ID NO: 696) | KATLTA DTSSST AYMQLS SLTSEGS AIYYCT (SEQ ID NO: 1047) | SRNFAY (SEQ ID NO: 1379) | WGQGT LVTVSA (SEQ ID NO: 421) |
| >AH04516-VH | QVQLQQSGAELVR PGTSVKMSCKAAG YTFTNYWIGWVKQ RPGHGLEWIGDIHP GGGYTNYNEKFKG KATLTADTSSSTAY MQLSSLTSEDSAIY YCTSRNFAYWGQG TLVTVSA (SEQ ID NO: 1335) | QVQLQ QSGAEL VRPGTS VKMSC KAA (SEQ ID NO: 1326) | GYTFT NY (SEQ ID NO: 990) | WIGW VKQR PGHGL EWIG (SEQ ID NO: 1458) | DIHPG GGYT NYNE KFKG (SEQ ID NO: 696) | KATLTA DTSSST AYMQLS SLTSEDS AIYYCT (SEQ ID NO: 1045) | SRNFAY (SEQ ID NO: 1379) | WGQGT LVTVSA (SEQ ID NO: 421) |
| >AH04525-VH | QVQLQQSGAELVR PGTSVKMSCKAAG YTFTNYWIGWIKQ RPGHGLEWIGDIHP GGDYTNYNEKFKG KATLTADTFSSTAY MQLSSLTSEDSAIY YCTGRNFAYWGQ GTLVTVSS (SEQ ID NO: 1329) | QVQLQ QSGAEL VRPGTS VKMSC KAA (SEQ ID NO: 1326) | GYTFT NY (SEQ ID NO: 990) | WIGWI KQRP GHGL EWIG (SEQ ID NO: 1456) | DIHPG GDYT NYNE KFKG (SEQ ID NO: 693) | KATLTA DTFSST AYMQLS SLTSEDS AIYYCT (SEQ ID NO: 1042) | GRNFAY (SEQ ID NO: 982) | WGQGT LVTVSS (SEQ ID NO: 413) |
| >AH04509-VH | QIQLQQSGAELVRP GTSVKMSCKAAGY | QIQLQQ SGAELV | GYTFT NY | WIGW VKQR | DFYPG GDYIN | KATLTA DTSSST | SRNFAY (SEQ ID | WGQGT PVTVSS |

TABLE 2C-continued

Exemplary Clones-Heavy Chain Sequences

| ID | V-D-J-REGION | H-FR1 | CDRH1 | H-FR2 | CDRH2 | H-FR3 | CDRH3 | JUNC-TION |
|---|---|---|---|---|---|---|---|---|
| | TFTNYWIGWVKQR PGHGLEWIGDFYP GGDYINYNEKFKG KATLTADTSSSTAY MQLSSLTSEDSAIY YCTSRNFAYWGQG TPVTVSS (SEQ ID NO: 1231) | RPGTSV KMSCK AA (SEQ ID NO: 1228) | (SEQ ID NO: 990) | PGHGL EWIG (SEQ ID NO: 1458) | YNEKF KG (SEQ ID NO: 691) | AYMQLS SLTSEDS AIYYCT (SEQ ID NO: 1045) | NO: 1379 | (SEQ ID NO: 398) |
| >AH04521-VH | QVQLQQSGAELVR PGTSVKMSCKAAG YTFTNYWIGWVKQ RPGHGLEWIGDFYP GGDYINYNEKFKG KATLTADTSSSTAY MQLSSLTSEDSAIY YCTSRNFAYWGQG TLVTVSA (SEQ ID NO: 1331) | QVQLQ QSGAEL VRPGTS VKMSC KAA (SEQ ID NO: 1326) | GYTFT NY (SEQ ID NO: 990) | WIGW VKQR PGHGL EWIG (SEQ ID NO: 1458) | DFYPG GDYIN YNEKF KG (SEQ ID NO: 691) | KATLTA DTSSST AYMQLS SLTSEDS AIYYCT (SEQ ID NO: 1045) | SRNFAY (SEQ ID NO: 1379) | WGQGT LVTVSA (SEQ ID NO: 421) |
| >AH04526-VH | QVQLQQSGAELVR PGTSVKMSCKAAG YTFTNYWIGWVKQ RPGHGLEWIGDIHP GGDYSNYNEKFKG KATLTADTSSSTAY MNLSSLTSEDSAIY YCTSRNFAYWGQG TPVTVSS (SEQ ID NO: 1332) | QVQLQ QSGAEL VRPGTS VKMSC KAA (SEQ ID NO: 1326) | GYTFT NY (SEQ ID NO: 990) | WIGW VKQR PGHGL EWIG (SEQ ID NO: 1458) | DIHPG GDYSN YNEKF KG (SEQ ID NO: 692) | KATLTA DTSSST AYMNLS SLTSEDS AIYYCT (SEQ ID NO: 1044) | SRNFAY (SEQ ID NO: 1379) | WGQGT PVTVSS (SEQ ID NO: 398) |
| >AH04514-VH | QIQLQQSGAELVRP GTSVKMSCKAAGY TFTNYWIGWVKQR PGHGLEWIGDIHPG GDYSNYNEKFKGK ATLTADTSSSTAY MNLSSLTSEDSAIY YCTSRNFAYWGQG TLVTVSS (SEQ ID NO: 1232) | QIQLQQ SGAELV RPGTSV KMSCK AA (SEQ ID NO: 1228) | GYTFT NY (SEQ ID NO: 990) | WIGW VKQR PGHGL EWIG (SEQ ID NO: 1458) | DIHPG GDYSN YNEKF KG (SEQ ID NO: 692) | KATLTA DTSSST AYMNLS SLTSEDS AIYYCT (SEQ ID NO: 1044) | SRNFAY (SEQ ID NO: 1379) | WGQGT LVTVSS (SEQ ID NO: 413) |
| >AH04524-VH | QIQLQQSGAELVRP GTSVKMSCKAAGY TFTNYWIGWVKQR PGHGLEWIGDIHPG GDYSNYNEKFKGK ATLTADTSSSTAY MSLSSLTSEDSAIY YCTSRNFAYWGQG TLVTVSA (SEQ ID NO: 1233) | QIQLQQ SGAELV RPGTSV KMSCK AA (SEQ ID NO: 1228) | GYTFT NY (SEQ ID NO: 990) | WIGW VKQR PGHGL EWIG (SEQ ID NO: 1458) | DIHPG GDYSN YNEKF KG (SEQ ID NO: 692) | KATLTA DTSSST AYMSLS SLTSEDS AIYYCT (SEQ ID NO: 1049) | SRNFAY (SEQ ID NO: 1379) | WGQGT LVTVSA (SEQ ID NO: 421) |
| >AH04530-VH | QIQLQQSGAELVRP GTSVKMSCKAAGY TSTNYWIGWVKQR PGHGLEWIGDIHPG GDYSNYNEKFKGK ATLTADTSSSTAY MNLSSLTSEDSAIY YCTSRNFAYWGQG TLVTVSA (SEQ ID NO: 1238) | QIQLQQ SGAELV RPGTSV KMSCK AA (SEQ ID NO: 1228) | GYTST NY (SEQ ID NO: 996) | WIGW VKQR PGHGL EWIG (SEQ ID NO: 1458) | DIHPG GDYSN YNEKF KG (SEQ ID NO: 692) | KATLTA DTSSST AYMNLS SLTSEDS AIYYCT (SEQ ID NO: 1044) | SRNFAY (SEQ ID NO: 1379) | WGQGT LVTVSA (SEQ ID NO: 421) |
| >AH04517-VH | DVQLQQSGAELVR PGTSVKMSCKAAG YTFTNYWIGWVKQ RPGHGLEWIGDIHP GGDYSNYNEKFKG KATLTADTSSSTAY MNLSSLTSEDSAIY YCTSRNFAYWGQG TLVTVSA (SEQ ID NO: 868) | DVQLQ QSGAEL VRPGTS VKMSC KAA (SEQ ID NO: 867) | GYTFT NY (SEQ ID NO: 990) | WIGW VKQR PGHGL EWIG (SEQ ID NO: 1458) | DIHPG GDYSN YNEKF KG (SEQ ID NO: 692) | KATLTA DTSSST AYMNLS SLTSEDS AIYYCT (SEQ ID NO: 1044) | SRNFAY (SEQ ID NO: 1379) | WGQGT LVTVSA (SEQ ID NO: 421) |

TABLE 2C-continued

Exemplary Clones-Heavy Chain Sequences

| ID | V-D-J-REGION | H-FR1 | CDRH1 | H-FR2 | CDRH2 | H-FR3 | CDRH3 | JUNCTION |
|---|---|---|---|---|---|---|---|---|
| >AH04506-VH | QVQLQQSGAELVRPGTSVKMSCKAAGYTFTNYWIGWVKQRPGHGLEWIGDIHPGGDYSNYNEKFKGKATLTADTSSSTAYMNLSSLTSEDSAIYYCTSRNFAYWGQGTLVTVSA (SEQ ID NO: 1333) | QVQLQQSGAELVRPGTSVKMSCKAA (SEQ ID NO: 1326) | GYTFTNY (SEQ ID NO: 990) | WIGWVKQRPGHGLEWIG (SEQ ID NO: 1458) | DIHPGGDYSNYNEKFKG (SEQ ID NO: 692) | KATLTADTSSSTAYMNLSSLTSEDSAIYYCT (SEQ ID NO: 1044) | SRNFAY (SEQ ID NO: 1379) | WGQGTLVTVSA (SEQ ID NO: 421) |
| >AH04508-VH | QVQLQQSGAELVRPGTSVKMSCKAAGYTFTNYWIGWVKQRPGHGLEWIGDIHPGGDYSNYNEKFKGKATLTADTSSSTAYMNLSSLTSEDSAIYYCTSRNFAYWGQGTLVTVSA (SEQ ID NO: 1333) | QVQLQQSGAELVRPGTSVKMSCKAA (SEQ ID NO: 1326) | GYTFTNY (SEQ ID NO: 990) | WIGWVKQRPGHGLEWIG (SEQ ID NO: 1458) | DIHPGGDYSNYNEKFKG (SEQ ID NO: 692) | KATLTADTSSSTAYMNLSSLTSEDSAIYYCT (SEQ ID NO: 1044) | SRNFAY (SEQ ID NO: 1379) | WGQGTLVTVSA (SEQ ID NO: 421) |
| >AH04518-VH | QVQLQQSGAELVRPGTSVKMSCKAAGYTFTNYWIGWVKQRPGHDLEWIGDIHPGGDYSNYNEKFKGKATLTADTSSSTAYMNLSSLTSEDSAIYYCTSRNFAYWGQGTLVTVSA (SEQ ID NO: 1330) | QVQLQQSGAELVRPGTSVKMSCKAA (SEQ ID NO: 1326) | GYTFTNY (SEQ ID NO: 990) | WIGWVKQRPGHDLEWIG (SEQ ID NO: 1457) | DIHPGGDYSNYNEKFKG (SEQ ID NO: 692) | KATLTADTSSSTAYMNLSSLTSEDSAIYYCT (SEQ ID NO: 1044) | SRNFAY (SEQ ID NO: 1379) | WGQGTLVTVSA (SEQ ID NO: 421) |

TABLE 3A

Exemplary Clones-Light Chain Sequences

| ID | V-J-REGION | L-FR1 | CDRL1 | L-FR2 | CDRL2 | L-FR3 | CDRL3 | JUNCTION | J-REGION | L-FR4 |
|---|---|---|---|---|---|---|---|---|---|---|
| AHH03703 | DTTVTQSHKFMSTSVGDRVSITCKASQDVSTAVAWYQQKPGQSPKLLIYSASYRYTGVPDRFTGSGSGTDFTFTISSVQAEDLAVYYCQQHYSTPWTFGGGTKLEIK (SEQ ID NO: 841) | DTTVTQSHKFMSTSVGDRVSITCKAS (SEQ ID NO: 840) | QDVSTA (SEQ ID NO: 1209) | VAWYQQKPGQSPKLLIY (SEQ ID NO: 1427) | SAS (SEQ ID NO: 13) | YRYTGVPDRFTGSGSGTDFTFTISSVQAEDLAVYYC (SEQ ID NO: 1491) | QQHYSTPWT (SEQ ID NO: 1264) | CQQHYSTPWTF (SEQ ID NO: 656) | WTFGGGTKLEIK (SEQ ID NO: 1467) | FGGGTKLEIK (SEQ ID NO: 959) |
| AHH03704 | DILMTQSPSSLAVSVGEKVTMSCKSSQSLLYSSNQKNYLAWYQQKPGQSPKLLIYWASTRESGVPDRFTGSGSGTDFTLTISSVKAEDLAVYYCQQYYSYPWTFGGGTKLEMK (SEQ ID NO: 709) | DILMTQSPSSLAVSVGEKVTMSCKSS (SEQ ID NO: 708) | QSLLYSSNQKNY (SEQ ID NO: 1304) | LAWYQQKPGQSPKLLIY (SEQ ID NO: 1066) | WAS (SEQ ID NO: 1450) | TRESGVPDRFTGSGSGTDFTLTISSVKAEDLAVYYC (SEQ ID NO: 1411) | QQYYSYPWT (SEQ ID NO: 1294) | CQQYYSYPWTF (SEQ ID NO: 676) | WTFGGGTKLEMK (SEQ ID NO: 1468) | FGGGTKLEMK (SEQ ID NO: 961) |
| AHH03706 | DIQMTQTTSSLSASLGDRVTISCSASQGISNYLNWYQQKPDGTVKLLIYYTSS... | DIQMTQTTSSLSASLGDRVTISC (SEQ ID NO: 1211) | QGISNY (SEQ ID NO: 1211) | LNWYQQKPDGTVKLLIY (SEQ ID NO: 1495) | YTS (SEQ ID NO: 1289) | SLHSGVPSRFSGSGSGTDYSL... | QQYSKLPWT (SEQ ID NO: 1289) | CQQYSKLPWTF (SEQ ID NO: 672) | WTFGGGTKLEMK (SEQ ID NO: 1468) | FGGGTKLEMK (SEQ ID NO: ...) |

TABLE 3A-continued

Exemplary Clones-Light Chain Sequences

| ID | V-J-REGION | L-FR1 | CDRL1 | L-FR2 | CDRL2 | L-FR3 | CDRL3 | JUNCTION | J-REGION | L-FR4 |
|---|---|---|---|---|---|---|---|---|---|---|
| | LHSGVPSRFSG SGSGTDYSLTI SNLEPEDIATY YCQQYSKLPW TFGGGTKLEM K (SEQ ID NO: 762) | SAS (SEQ ID NO: 761) | | ID NO: 1088) | | TISNL EPEDI ATYY C (SEQ ID NO: 1368) | | | | 961) |
| AHH 03707 | DIQMNQSPSY LAASPGETITI NCRASKSISKY LAWYQEKPG KTNKLLIYSGS TLQSGIPSRFS GSGSGTDFTL TISSLEPEDFA MYYCQQHNE YPWTFGGGTK LEIK (SEQ ID NO: 717) | DIQM NQSPS YLAA SPGET ITINC RAS (SEQ ID NO: 716) | KSISK Y (SEQ ID NO: 1059) | LAWY QEKP GKTN KLLIY (SEQ ID NO: 1064) | SGS (SEQ ID NO: 1365) | TLQS GIPSR FSGSG SGTD FTLTI SSLEP EDFA MYYC (SEQ ID NO: 1405) | QQHNE YPWT (SEQ ID NO: 1257) | CQQHN EYPWT F (SEQ ID NO: 651) | TFGGGT KLEIK (SEQ ID NO: 1393) | FGGG TKLEI K (SEQ ID NO: 959) |
| AHH 03708 | DVVMTQTPLT LSVTIGQPASI SCKSSQSLLDS DGKTYLNWL LQRPGQSPKR LIYLVSKLDSG VPDRFTGSGS GTDFTLKINR VEAEDLGVYY CWQGTHFPRT FGGGTKLEIK (SEQ ID NO: 905) | DWM TQTPL TLSVT IGQPA SISCK SS (SEQ ID NO: 904) | QSLLD SDGKT Y (SEQ ID NO: 1301) | LNWL LQRP GQSP KRLIY (SEQ ID NO: 1083) | LVS (SEQ ID NO: 1116) | KLDS GVPD RFTGS GSGT DFTL KINR VEAE DLGV YYC (SEQ ID NO: 1055) | WQGT HFPRT (SEQ ID NO: 1464) | CWQG THFPR TF (SEQ ID NO: 688) | TFGGGT KLEIK (SEQ ID NO: 1393) | FGGG TKLEI K (SEQ ID NO: 959) |
| AHH 03709 | DIVMTQSPKS MSMSVGERVT LSCKASENVG TYVSWYQQK PEQSPKLLIYG ASNRYTGVPD RFTGSGSATD FTLTISSVQAE DLADYHCGQS YSYPYTFGGG TKLEIK (SEQ ID NO: 810) | DIVM TQSP KSMS MSVG ERVT LSCK AS (SEQ ID NO: 808) | ENVGT Y (SEQ ID NO: 933) | VSWY QQKP EQSP KLLIY (SEQ ID NO: 1446) | GAS (SEQ ID NO: 975) | NRYT GVPD RFTGS GSAT DFTLT ISSVQ AEDL ADYH C (SEQ ID NO: 1162) | GQSYS YPYT (SEQ ID NO: 981) | CGQSY SYPYT F (SEQ ID NO: 624) | YTFGGG TKLEIK (SEQ ID NO: 1493) | FGGG TKLEI K (SEQ ID NO: 959) |
| AHH 03710 | DIVMTQSQKF MSTSVGDRVT ITCKASQNVR TAVAWYHQK PGQSPKALIY MASNRHTGVP DRFTGSGSGA DFTLTITNVQS EDLADYFCLQ HWNYPYTFG GGTKLEIK (SEQ ID NO: 827) | DIVM TQSQ KFMS TSVG DRVTI TCKA S (SEQ ID NO: 826) | QNVRT A (SEQ ID NO: 1247) | VAWY HQKP GQSP KALIY (SEQ ID NO: 1421) | MAS (SEQ ID NO: 1122) | NRHT GVPD RFTGS GSGA DFTLT ITNVQ SEDL ADYF C (SEQ ID NO: 1161) | LQHW NYPYT (SEQ ID NO: 1093) | CLQH WNYP YTF (SEQ ID NO: 630) | YTFGGG TKLEIK (SEQ ID NO: 1493) | FGGG TKLEI K (SEQ ID NO: 959) |
| AHH 03711 | DIQMTQTPKF LLVSAGDRVT ITCKASQSVSN DVAWYQQKP GQSPKLLIYY ASNRYTGVPD RFTGSGYGTD FTFISTVQAE DLAVYFCQQD YSSPWTFGGG TKLEIK (SEQ ID NO: 747) | DIQM TQTP KFLL VSAG DRVTI TCKA S (SEQ ID NO: 746) | QSVSN D (SEQ ID NO: 1310) | VAWY QQKP GQSP KLLIY (SEQ ID NO: 1427) | YAS (SEQ ID NO: 1476) | NRYT GVPD RFTGS GYGT DFTFT ISTVQ AEDL AVYF C (SEQ ID NO: 1164) | QQDYS SPWT (SEQ ID NO: 1251) | CQQDY SSPWT F (SEQ ID NO: 647) | WTFGGG TKLEIK (SEQ ID NO: 1467) | FGGG TKLEI K (SEQ ID NO: 959) |

TABLE 3A-continued

Exemplary Clones-Light Chain Sequences

| ID | V-J-REGION | L-FR1 | CDRL1 | L-FR2 | CDRL2 | L-FR3 | CDRL3 | JUNCTION | J-REGION | L-FR4 |
|---|---|---|---|---|---|---|---|---|---|---|
| AHH 03713 | DIQMTQTPSSL SASLGERVSLT CRASQEISYL SWLQQKPDGT IKRLIYAASTL DSGVPKRFSG SRSGSDYSLTI SSLESEDFADY YCLQYISYPRT FGGGTKLEIK (SEQ ID NO: 756) | DIQM TQTPS SLSAS LGER VSLT CRAS (SEQ ID NO: 753) | QEISG Y (SEQ ID NO: 1210) | LSWL QQKP DGTIK RLIY (SEQ ID NO: 1111) | AAS (SEQ ID NO: 599) | TLDS GVPK RFSGS RSGS DYSL TISSL ESEDF ADYY C (SEQ ID NO: 1402) | LQYIS YPRT (SEQ ID NO: 1107) | CLQYI SYPRT F (SEQ ID NO: 640) | TFGGGT KLEIK (SEQ ID NO: 1393) | FGGG TKLEI K (SEQ ID NO: 959) |
| AHH 03714 | DIVMTQSQKF MSTSVGDRVS VTCKASQNVG TNVAWYQQK PGQSPKALIYS ASYRYSGVPD RFTGSGSGTD FTLTISNVQSE DLAEYLCQQY NSYPRTFGGG TKLEIK (SEQ ID NO: 824) | DIVM TQSQ KFMS TSVG DRVS VTCK AS (SEQ ID NO: 821) | QNVGT N (SEQ ID NO: 12) | VAWY QQKP GQSP KALIY (SEQ ID NO: 1425) | SAS (SEQ ID NO: 13) | YRYS GVPD RFTGS GSGT DFTLT ISNVQ SEDL AEYL C (SEQ ID NO: 1485) | QQYNS YPRT (SEQ ID NO: 1286) | CQQYN SYPRT F (SEQ ID NO: 670) | TFGGGT KLEIK (SEQ ID NO: 1393) | FGGG TKLEI K (SEQ ID NO: 959) |
| AHH 03715 | DIQMTQSPAS LSVSVGETVI TCRASENIYSN LAWYQQKQG KSPQLLVYAA TNLADGVPSR FSGSGSGTQY SLKINSLQSED FGSYYCQHFW GTPPTFGGGT KLEIK (SEQ ID NO: 724) | DIQM TQSP ASLS VSVG ETVTI TCRA S (SEQ ID NO: 723) | ENIYS N (SEQ ID NO: 929) | LAWY QQKQ GKSP QLLV (SEQ ID NO: 1069) | AAT (SEQ ID NO: 600) | NLAD GVPS RFSGS GSGT QYSL KINSL QSED FGSY YC (SEQ ID NO: 1143) | QHFW GTPPT (SEQ ID NO: 1212) | CQHF WGTPP TF (SEQ ID NO: 642) | TFGGGT KLEIK (SEQ ID NO: 1393) | FGGG TKLEI K (SEQ ID NO: 959) |
| AHH 03716 | DVVMTQTPLT LSVTIGQPASI SCKSSQSLLDS DGKTYLNWL LQRPGQSPKR LIYLVSKLDSG VPDRFTGSGS GTDFTLKISRV EAEDLGVYYC WQGTHFRTFG GGTKLEMK (SEQ ID NO: 906) | DWM TQTPL TLSVT IGQPA SISCK SS (SEQ ID NO: 904) | QSLLD SDGKT Y (SEQ ID NO: 1301) | LNWL LQRP GQSP KRLIY (SEQ ID NO: 1083) | LVS (SEQ ID NO: 1116) | KLDS GVPD RFTGS GSGT DFTL KISRV EAED LGVY YC (SEQ ID NO: 1056) | WQGT HFRT (SEQ ID NO: 1466) | CWQG THFRT F (SEQ ID NO: 690) | TFGGGT KLEMK (SEQ ID NO: 1394) | FGGG TKLE MK (SEQ ID NO: 961) |
| AHH 03717 | DVVLTQTPLS LPVSLGDQVSI SCRSGQSLVH NNGNTYLHW YLQKPGQSPK LLIYKVSNRFS GVPDRFSGSG SGTDFTLKISR VEAEDLGVYF CSQSTHVPLTF GAGTKLEIK (SEQ ID NO: 882) | DWL TQTPL SLPVS LGDQ VSISC RSG (SEQ ID NO: 881) | QSLVH NNGNT Y (SEQ ID NO: 1305) | LHWY LQKP GQSP KLLIY (SEQ ID NO: 1076) | KVS (SEQ ID NO: 1062) | NRFS GVPD RFSGS GSGT DFTL KISRV EAED LGVY FC (SEQ ID NO: 1157) | SQSTH VPLT (SEQ ID NO: 1370) | CSQST HVPLT F (SEQ ID NO: 679) | LTFGAG TKLEIK (SEQ ID NO: 1114) | FGAG TKLEI K (SEQ ID NO: 958) |
| AHH 03718 | DIQMTQSTSSL SASLGDRVTIS CRASQDISNY LNWYQQKPD GTVKLLIYFTS RLYSGVPSRFS GSGSGADYSL TISNLEQEDIA | DIQM TQSTS SLSAS LGDR VTISC RAS ID NO: | QDISN Y (SEQ ID NO: 27) | LNWY QQKP DGTV KLLIY (SEQ ID NO: 1088) | FTS (SEQ ID NO: 972) | RLYS GVPS RFSGS GSGA DYSL TISNL EQEDI ATYF | QQGNT LPRT (SEQ ID NO: 1254) | CQQGN TLPRT F (SEQ ID NO: 648) | TFGGGT KLEIK (SEQ ID NO: 1393) | FGGG TKLEI K (SEQ ID NO: 959) |

TABLE 3A-continued

Exemplary Clones-Light Chain Sequences

| ID | V-J-REGION | L-FR1 | CDRL1 | L-FR2 | CDRL2 | L-FR3 | CDRL3 | JUNCTION | J-REGION | L-FR4 |
|---|---|---|---|---|---|---|---|---|---|---|
| | TYFCQQGNTLPRTFGGGTKLEIK (SEQ ID NO: 739) | 738) | | | | C (SEQ ID NO: 1358) | | | | |
| AHH 03719 | DIQMNQSPSSLSASLGERVSLTCRASQDIGSSLNWLQQEPDGTIKRLIYATSSLDSGVPKRFSGSRSGSDYSLTISSLESEDFVDYYCLQYASSPYTFGGGTKLEIK (SEQ ID NO: 715) | DIQMNQSPSSLSASLGERVSLTCRAS (SEQ ID NO: 714) | QDIGSS (SEQ ID NO: 1199) | LNWLQQEPDGTIKRLIY (SEQ ID NO: 1085) | ATS (SEQ ID NO: 618) | SLDSGVPKRFSGSRSGSDYSLTISSLESEDFVDYYC (SEQ ID NO: 1366) | LQYASSPYT (SEQ ID NO: 1101) | CLQYASSPYTF (SEQ ID NO: 637) | YTFGGGTKLEIK (SEQ ID NO: 1493) | FGGGTKLEIK (SEQ ID NO: 959) |
| AHH 03720 | DVVMTQTTSSLSASLGDRVTISCRASQDISNYLNWYQQRPDGTVKLLIYYTSRLHSGVPSRFSGSGSGTDFSLTISNLEQEDIATYFCQQVYTLPWTFGGGTKLEIK (SEQ ID NO: 914) | DVVMTQTTSSLSASLGDRVTISCRAS (SEQ ID NO: 913) | QDISNY (SEQ ID NO: 27) | LNWYQQRPDGTVKLLIY (SEQ ID NO: 1090) | YTS (SEQ ID NO: 1495) | RLHSGVPSRFSGSGSGTDFSLTISNLEQEDIATYFC (SEQ ID NO: 1351) | QQVYTLPWT (SEQ ID NO: 1273) | CQQVYTLPWTF (SEQ ID NO: 663) | WTFGGGTKLEIK (SEQ ID NO: 1467) | FGGGTKLEIK (SEQ ID NO: 959) |
| AHH 03721 | DIQMTQSPSSLSASLGERVSLTCRASQEISGYLSWLQQKPDGTIKRLIYAASTLDSGVPKRFSGSRSGSDYSLTISSLESEDFADYYCLQYASYPRTFGGGTKLEIK (SEQ ID NO: 728) | DIQMTQSPSSLSASLGERVSLTCRAS (SEQ ID NO: 726) | QEISGY (SEQ ID NO: 1210) | LSWLQQKPDGTIKRLIY (SEQ ID NO: 1111) | AAS (SEQ ID NO: 599) | TLDSGVPKRFSGSRSGSDYSLTISSLESEDFADYYC (SEQ ID NO: 1402) | LQYASYPRT (SEQ ID NO: 1102) | CLQYASYPRTF (SEQ ID NO: 638) | TFGGGTKLEIK (SEQ ID NO: 1393) | FGGGTKLEIK (SEQ ID NO: 959) |
| AHH 03724 | DTTVTQSPASLAVSLGQRATISCKASQSVDYDGDSYMNWYQQKPGQPPKLLIYAASNLESGIPARFSGSGSGTDFTLNIHPVEEEDAATYYCQQSNEDPYTFGGGTKLEMK (SEQ ID NO: 848) | DTTVTQSPASLAVSLGQRATISCKAS (SEQ ID NO: 847) | QSVDYDGDSY (SEQ ID NO: 1308) | MNWYQQKPGQPPKLLIY (SEQ ID NO: 1135) | AAS (SEQ ID NO: 599) | NLESGIPARFSGSGSGTDFTLNIHPVEEEDAATYYC (SEQ ID NO: 1148) | QQSNEDPYT (SEQ ID NO: 1270) | CQQSNEDPYTF (SEQ ID NO: 662) | YTFGGGTKLEMK (SEQ ID NO: 1494) | FGGGTKLEMK (SEQ ID NO: 961) |
| AHH 03725 | DVVMTQTPLTLSVTIGQPASISCKSSQSLLDSDGKTYLNWLQRPGQSPKRLIYLVSKLDSGVPDRFTGSGSGTDFTLKISRVEAEDLGVYYCWQGTHFPWTFGGGTKLEIK (SEQ ID NO: 907) | DWMTQTPLTLSVTIGQPASISCKSS (SEQ ID NO: 904) | QSLLDSDGKTY (SEQ ID NO: 1301) | LNWLQRPGQSPKRLIY (SEQ ID NO: 1083) | LVS (SEQ ID NO: 1116) | KLDSGVPDRFTGSGSGTDFTLKISRVEAEDLGVYYC (SEQ ID NO: 1056) | WQGTHFPWT (SEQ ID NO: 1465) | CWQGTHFPWTF (SEQ ID NO: 689) | WTFGGGTKLEIK (SEQ ID NO: 1467) | FGGGTKLEIK (SEQ ID NO: 959) |
| AHH 03727 | DVVLTQTPLSLPVSLGDQASISCRSSQSLVHS | DWLTQTPLSLPVS | QSLVHSNGNTY (SEQ ID NO: | LHWYLQKPGQSP | KVS (SEQ ID NO: | NRFSGVPDRFSGS | SQSTHVPWT (SEQ ID NO: 1465) | CSQSTHVPWTF (SEQ | WTFGGGTKLEIK (SEQ ID | FGGGTKLEIK |

TABLE 3A-continued

Exemplary Clones-Light Chain Sequences

| ID | V-J-REGION | L-FR1 | CDRL1 | L-FR2 | CDRL2 | L-FR3 | CDRL3 | JUNCTION | J-REGION | L-FR4 |
|---|---|---|---|---|---|---|---|---|---|---|
| | NGNTYLHWY LQKPGQSPKL LIYKVSNRFSG VPDRFSGSGS GTDFTLKISRV EAEDLGVYFC SQSTHVPWTF GGGTKLEIK (SEQ ID NO: 876) | LGDQ ASISC RSS (SEQ ID NO: 874) | ID NO: 1306) | KLLIY (SEQ ID NO: 1076) | 1062) | GSGT DFTL KISRV EAED LGVY FC (SEQ ID NO: 1157) | NO: 1374) | ID NO: 682) | NO: 1467) | (SEQ ID NO: 959) |
| AHH 03728 | DTTVTQSHRF MSTSVEDRVT IACKASQDVN TAVAWYQHK PGQSPKLLIYS ASYRYTGVPD RFTGSGSRTDF TFTISSVQAED LAVYYCQQHF NSPYTFGGGT KLEIK (SEQ ID NO: 844) | DTTV TQSH RFMS TSVE DRVTI ACKA S (SEQ ID NO: 843) | QDVNT A (SEQ ID NO: 1206) | VAWY QHKP GQSP KLLIY (SEQ ID NO: 1422) | SAS (SEQ ID NO: 13) | YRYT GVPD RFTGS GSRT DFTFT ISSVQ AEDL AVYY C (SEQ ID NO: 1492) | QQHFN SPYT (SEQ ID NO: 1256) | CQQHF NSPYT F (SEQ ID NO: 650) | YTFGGG TKLEIK (SEQ ID NO: 1493) | FGGG TKLEI K (SEQ ID NO: 959) |
| AHH 03729 | DIVMSQSPASL AVSLGQRATIS CKASQSVDYD GDSYMNWYQ QKPGQPPKLLI YATSNLESGIP ARFSGSGSGT DFTLNIHPVEE EDAATYYCQQ SNEDPLTFGA GTKLEIK (SEQ ID NO: 787) | DIVM SQSPA SLAV SLGQ RATIS CKAS (SEQ ID NO: 786) | QSVDY DGDSY MN (SEQ ID NO: 1308) | WYQQK PGQPP KLLIY (SEQ ID NO: 1135) | ATS (SEQ ID NO: 618) | NLES GIPAR FSGSG SGTD FTLNI HPVE EEDA ATYY C (SEQ ID NO: 1148) | QQSNE DPLT (SEQ ID NO: 1268) | CQQSN EDPLT F (SEQ ID NO: 660) | LTFGAG TKLEIK (SEQ ID NO: 1114) | FGAG TKLEI K (SEQ ID NO: 958) |
| AHH 03730 | DIQMTRSPSSL SASLGERVSLT CRASQDIGSSL NWLQQEPDGT IKRLIYATSSL DSGVPKRFSG SRSGSDYSLTI SSLESEDFVDY YCLQYASSPW TFGGGTKLEIK (SEQ ID NO: 765) | DIQM TRSPS SLSAS LGER VSLT CRAS (SEQ ID NO: 764) | QDIGS S (SEQ ID NO: 1199) | LNWL QQEP DGTIK RLIY (SEQ ID NO: 1085) | ATS (SEQ ID NO: 618) | SLDS GVPK RFSGS RSGS DYSL TISSL ESEDF VDYY C (SEQ ID NO: 1366) | LQYAS SPWT (SEQ ID NO: 1100) | CLQYA SSPWT F (SEQ ID NO: 636) | WTFGGG TKLEIK (SEQ ID NO: 1467) | FGGG TKLEI K (SEQ ID NO: 959) |
| AHH 03731 | DIVMTQSPAI MSASPGEKVT MTCSASSSVS YMHWYQQKS GTSPKRWIYD TSKLASGVPA RFSGSGSGTSY SLTISSMEAED AATYYCQQW SSNPPTFGGGT KLEIK (SEQ ID NO: 803) | DIVM TQSP AIMS ASPG EKVT MTCS AS (SEQ ID NO: 802) | SSVSY (SEQ ID NO: 1385) | MHW YQQK SGTSP KRWI (SEQ ID NO: 1131) | DTS (SEQ ID NO: 839) | KLAS GVPA RFSGS GSGT SYSLT ISSME AEDA ATYY C (SEQ ID NO: 1052) | QQWSS NPPT (SEQ ID NO: 1274) | CQQW SSNPPT F (SEQ ID NO: 664) | FGGGTK LEIK (SEQ ID NO: 959) | FGGG TKLEI K (SEQ ID NO: 959) |
| AHH 03732 | DTTVTQSPAI MSASPGEKVT MTCSASSSIGY MHWYQQKPG TSPKRWIYDT SKLASGVPAR FSGSGSGTSYS LTISSMEAEDA ATYYCHQRGS YPWTFGGGTK LEIK (SEQ ID NO: 846) | DTTV TQSP AIMS ASPG EKVT MTCS AS (SEQ ID NO: 846) | SSIGY (SEQ ID NO: 1381) | MHW YQQK PGTSP KRWI (SEQ ID NO: 1130) | DTS (SEQ ID NO: 839) | KLAS GVPA RFSGS GSGT SYSLT ISSME AEDA ATYY C (SEQ ID NO: 1052) | HQRGS YPWT (SEQ ID NO: 999) | CHQRG SYPWT F (SEQ ID NO: 626) | WTFGGG TKLEIK (SEQ ID NO: 1467) | FGGG TKLEI K (SEQ ID NO: 959) |

TABLE 3A-continued

Exemplary Clones-Light Chain Sequences

| ID | V-J-REGION | L-FR1 | CDRL1 | L-FR2 | CDRL2 | L-FR3 | CDRL3 | JUNCTION | J-REGION | L-FR4 |
|---|---|---|---|---|---|---|---|---|---|---|
| AHH 03733 | DVVLTQTPLS LPVSLGDQASI SCRSSQSIVHS NGNTYLEWY LQKPGQSPKL LIYKVSNRFSG VPDRFSGSGS GTDFTLKISRV EAEDLGVYYC FQGSHVPYTF GGGTKLEIK (SEQ ID NO: 875) | DWL TQTPL SLPVS LGDQ ASISC RSS (SEQ ID NO: 874) | QSIVH SNGNT Y (SEQ ID NO: 1299) | LEWY LQKP GQSP KLLIY (SEQ ID NO: 1071) | KVS (SEQ ID NO: 1062) | NRFS GVPD RFSGS GSGT DFTL KISRV EAED LGVY YC (SEQ ID NO: 1158) | FQGSH VPYT (SEQ ID NO: 970) | CFQGS HVPYT F (SEQ ID NO: 621) | YTFGGG TKLEIK (SEQ ID NO: 1493) | FGGG TKLEI K (SEQ ID NO: 959) |
| AHH 03734 | DTTVTQSHKF MSTSVGDRVS ITCKASQDVST AVAWYQQKP GQSPKLLIYSA SYRYTGVPDR FTGSGSGTDFT FTISSVQAEDL AVYYCQQHY STPWTFGGGT KLEIK (SEQ ID NO: 841) | DTTV TQSH KPMS TSVG DRVSI TCKA S (SEQ ID NO: 840) | QDVST A (SEQ ID NO: 1209) | VAWY QQKP GQSP KLLIY (SEQ ID NO: 1427) | SAS (SEQ ID NO: 13) | YRYT GVPD RFTGS GSGT DFTFT ISSVQ AEDL AVYY C (SEQ ID NO: 1491) | QQHYS TPWT (SEQ ID NO: 1264) | CQQHY STPWT F (SEQ ID NO: 656) | WTFGGG TKLEIK (SEQ ID NO: 1467) | FGGG TKLEI K (SEQ ID NO: 959) |
| AHH 03735 | DIVLTQSPASL AVSLGQRATIS CRASESVDNY GISFMNWFQK KPGQPPKLLIY AASNQGSGVP ARFSGSGSGT DFSLNIHPMEE DDTAMYFCQ QSKEVPYTFG GGTKLEIK (SEQ ID NO: 769) | DIVLT QSPAS LAVS LGQR ATISC RAS (SEQ ID NO: 768) | ESVDN YGISF (SEQ ID NO: 934) | MNWF QKKP GQPP KLLIY (SEQ ID NO: 1133) | AAS (SEQ ID NO: 599) | NQGS GVPA RFSGS GSGT DFSL NIHP MEED DTAM YFC (SEQ ID NO: 1152) | QQSKE VPYT (SEQ ID NO: 1267) | CQQSK EVPYT F (SEQ ID NO: 659) | YTFGGG TKLEIK (SEQ ID NO: 1493) | FGGG TKLEI K (SEQ ID NO: 959) |
| AHH 03736 | DNVLTQSPSSL AVSVGEKVT MSCKSSQSLL YSSNQKNYLA WYQQKPGQSP KLLIYWASTR ESGVPDRFTG SGSGTDFTLTI SSVKAEDLAV YYCQQYYSYR TFGGGTKLEIK (SEQ ID NO: 835) | DNVL TQSPS SLAV SVGE KVTM SCKSS (SEQ ID NO: 834) | QSLLY SSNQK NY (SEQ ID NO: 1304) | LAWY QQKP GQSP KLLIY (SEQ ID NO: 1066) | WAS (SEQ ID NO: 1450) | TRES GVPD RFTGS GSGT DFTLT ISSVK AEDL AVYY C (SEQ ID NO: 1411) | QQYYS YRT (SEQ ID NO: 1295) | CQQYY SYRTF (SEQ ID NO: 677) | TFGGGT KLEIK (SEQ ID NO: 1393) | FGGG TKLEI K (SEQ ID NO: 959) |
| AHH 03737 | DIVMTQSPKS MSMSVGERVT LSCKASENVA TYVSWYQQK PEQSPKLLIYG ASNRYTGVPD RFTGSGSATD FTLTISSVQAE DLADYRCGQS YRYPYTFGGG TKLEMK (SEQ ID NO: 809) | DIVM TQSP KSMS MSVG ERVT LSCK AS (SEQ ID NO: 808) | ENVAT Y (SEQ ID NO: 932) | VSWY QQKP EQSP KLLIY (SEQ ID NO: 1446) | GAS (SEQ ID NO: 975) | NRYT GVPD RFTGS GSATD FTLT ISSVQ AEDL ADYR C (SEQ ID NO: 1163) | GQSYR YPYT (SEQ ID NO: 979) | CGQSY RYPYT F (SEQ ID NO: 622) | YTFGGG TKLEMK (SEQ ID NO: 1494) | FGGG TKLE MK (SEQ ID NO: 961) |
| AHH 03738 | DVVVTQTPLS LPVSLGDQASI SCRSSQSLVHS NGNTYLHWY LQKPGQSPKL LIYKVSNRFSG | DVW TQTPL SLPVS LGDQ ASISC RSS | QSLVH SNGNT Y (SEQ ID NO: 1306) | LHWY LQKP GQSP KLLIY (SEQ ID NO: 1062) | KVS (SEQ ID NO: | NRFS GVPD RFSGS GSGT DFTL KISRV | SQSTH VPT (SEQ ID NO: 1373) | CSQST HVPTF (SEQ ID NO: 681) | TFGGGT KLEIK (SEQ ID NO: 1393) | FGGG TKLEI K (SEQ ID NO: 959) |

TABLE 3A-continued

Exemplary Clones-Light Chain Sequences

| ID | V-J-REGION | L-FR1 | CDRL1 | L-FR2 | CDRL2 | L-FR3 | CDRL3 | JUNCTION | J-REGION | L-FR4 |
|---|---|---|---|---|---|---|---|---|---|---|
| | VPDRFSGSGS GTDFTLKISRV EAEDLGVYFC SQSTHVPTFG GGTKLEIK (SEQ ID NO: 920) | (SEQ ID NO: 918) | | 1076) | | EAED LGVY FC (SEQ ID NO: 1157) | | | | |
| AHH 03739 | DVVVTQSPAS LAVSLGQRAT ISCRASESVDS YGNSFMHWY QQKPGQPPKL LIYLASNLESG VPARFSGSGS RTDFTLTIDPV EADDAATYYC QQNNEDPYTF GGGTKLEIK (SEQ ID NO: 917) | DVW TQSP ASLA VSLG QRATI SCRA S (SEQ ID NO: 916) | ESVDS YGNSF (SEQ ID NO: 935) | MHW YQQK PGQPP KLLIY (SEQ ID NO: 1129) | LAS (SEQ ID NO: 1063) | NLES GVPA RFSGS GSRT DFTLT IDPVE ADDA ATYY C (SEQ ID NO: 1150) | QQNNE DPYT (SEQ ID NO: 1266) | CQQNN EDPYT F (SEQ ID NO: 658) | YTFGGG TKLEIK (SEQ ID NO: 1493) | FGGG TKLEI K (SEQ ID NO: 959) |
| AHH 03740 | DVVMTQSQKF MSTSVGDRVN VTCKASQNVG TNVAWYQQK PGQSPKALIYS ASYRYSGVPD RFTGSGSGTD FTLTISNVQSE DLAEYFCQQY NSYPYTFGGG TKLEIK (SEQ ID NO: 892) | DWM TQSQ KFMS TSVG DRVN VTCK AS (SEQ ID NO: 891) | QNVGT N (SEQ ID NO: 12) | VAWY QQKP GQSP KALIY (SEQ ID NO: 1425) | SAS (SEQ ID NO: 13) | YRYS GVPD RFTGS GSGT DFTLT ISNVQ SEDL AEYF C (SEQ ID NO: 1483) | QQYNS YPYT (SEQ ID NO: 15) | CQQYN SYPYT F (SEQ ID NO: 671) | YTFGGG TKLEIK (SEQ ID NO: 1493) | FGGG TKLEI K (SEQ ID NO: 959) |
| AHH 03741 | DVVMTQTPLS LPVSLGDQASI SCRSSQSLVHS NGNTYLHWY LQKPGQSPKL LIYKVSNRFSG VPDRFSGSGS GTDFTLKISRV EAEDLGVYFC SQSTHVPWTF GGGTKLEIK (SEQ ID NO: 901) | DWM TQTPL SLPVS LGDQ ASISC RSS (SEQ ID NO: 900) | QSLVH SNGNT Y (SEQ ID NO: 1306) | LHWY LQKP GQSP KLLIY (SEQ ID NO: 1076) | KVS (SEQ ID NO: 1062) | NRFS GVPD RFSGS GSGT DFTL KISRV EAED LGVY FC (SEQ ID NO: 1157) | SQSTH VPWT (SEQ ID NO: 1374) | CSQST HVPWT F (SEQ ID NO: 682) | WTFGGG TKLEIK (SEQ ID NO: 1467) | FGGG TKLEI K (SEQ ID NO: 959) |
| AHH 03742 | DIVMTQSPKS MSMSVGERVT LSCKASENVG TYVSWYQQK PEQSPKLLIYG ASNRYTGVPD RFTGSGSATD FTLTISSVQAE DLADYHCGQS YSYPYTFGGG TKLEIK (SEQ ID NO: 810) | DIVM TQSP KSMS MSVG ERVT LSCK AS (SEQ ID NO: 808) | ENVGT Y (SEQ ID NO: 933) | VSWY QQKP EQSP KLLIY (SEQ ID NO: 1446) | GAS (SEQ ID NO: 975) | NRYT GVPD RFTGS GSAT DFTLT ISSVQ AEDL ADYH C (SEQ ID NO: 1162) | GQSYS YPYT (SEQ ID NO: 981) | CGQSY SYPYT F (SEQ ID NO: 624) | YTFGGG TKLEIK (SEQ ID NO: 1493) | FGGG TKLEI K (SEQ ID NO: 959) |
| AHH 03743 | DVVMTQSHKF MSTSVGDRVS ITCKASQDVST AVAWYQQKP GQSPKLLIYSA SYRYTGVPDR FTGSGSGTDFT FTISSVQAEDL AVYYCQQHY STPPWTFGRG TKLEIK (SEQ ID NO: 886) | DWM TQSH KFMS TSVG DRVSI TCKA S (SEQ ID NO: 885) | QDVST A (SEQ ID NO: 1209) | VAWY QQKP GQSP KLLIY (SEQ ID NO: 1427) | SAS (SEQ ID NO: 13) | YRYT GVPD RFTGS GSGT DFTFT ISSVQ AEDL AVYY C (SEQ ID NO: 1491) | QQHYS TPPWT (SEQ ID NO: 1262) | CQQHY STPPW TF (SEQ ID NO: 654) | WTFGRG TKLEIK (SEQ ID NO: 1469) | FGRG TKLEI K (SEQ ID NO: 964) |

TABLE 3A-continued

Exemplary Clones-Light Chain Sequences

| ID | V-J-REGION | L-FR1 | CDRL1 | L-FR2 | CDRL2 | L-FR3 | CDRL3 | JUNCTION | J-REGION | L-FR4 |
|---|---|---|---|---|---|---|---|---|---|---|
| AHH03744 | DIVMTQSPKS MSMSVGERVT LSCKASENVG TYVSWYQQK PEQSPKLLIYG ASNRYTGVPD RFTGSGSATD FTLTISSVQAE DLADYHCGQS YSYPWTFGGG TKLEIK (SEQ ID NO: 811) | DIVM TQSP KSMS MSVG ERVT LSCK AS (SEQ ID NO: 808) | ENVGT Y (SEQ ID NO: 933) | VSWY QQKP EQSP KLLIY (SEQ ID NO: 1446) | GAS (SEQ ID NO: 975) | NRYT GVPD RFTGS GSAT DFTLT ISSVQ AEDL ADYH C (SEQ ID NO: 1162) | GQSYS YPWT (SEQ ID NO: 980) | CGQSY SYPWT F (SEQ ID NO: 623) | WTFGGG TKLEIK (SEQ ID NO: 1467) | FGGG TKLEI K (SEQ ID NO: 959) |
| AHH03745 | DIQMTQTPSSL SASLGERVSLT CRASQDIGSSL NWLQQEPDGT IKRLIYATSSL DSGVPKRFSG SRSGSDYSLTI SSLESEDFVDY YCLQYASSPR TFGGGTKLEIK (SEQ ID NO: 755) | DIQM TQTPS SLSAS LGER VSLT CRAS (SEQ ID NO: 753) | QDIGS S (SEQ ID NO: 1199) | LNWL QQEP DGTIK RLIY (SEQ ID NO: 1085) | ATS (SEQ ID NO: 618) | SLDS GVPK RFSGS RSGS DYSL TISSL ESEDF VDYY C (SEQ ID NO: 1366) | LQYAS SPRT (SEQ ID NO: 1099) | CLQYA SSPRTF (SEQ ID NO: 635) | TFGGGT KLEIK (SEQ ID NO: 1393) | FGGG TKLEI K (SEQ ID NO: 959) |
| AHH03746 | DIVMTQSPLSL SVTIGQPASIS CKSSQSLLYS NGKTYLNWL QQRPGQAPKH LMYQVSKLDP GIPDRFSGSGS ETDFTLKISRV EAEDLGVYYC LQGTYYPTWT FGGGTKLEIK (SEQ ID NO: 813) | DIVM TQSPL SLSVT IGQPA SISCK SS (SEQ ID NO: 812) | QSLLY SNGKT Y (SEQ ID NO: 1303) | LNWL QQRP GQAP KHLM (SEQ ID NO: 1086) | QVS (SEQ ID NO: 1344) | KLDP GIPDR FSGSG SETDF TLKIS RVEA EDLG VYYC (SEQ ID NO: 1053) | LQGTY YPTWT (SEQ ID NO: 1092) | CLQGT YYPTW TF (SEQ ID NO: 629) | WTFGGG TKLEIK (SEQ ID NO: 1467) | FGGG TKLEI K (SEQ ID NO: 959) |
| AHH03747 | DIVMSQSHKF MSTSVGDRVS ITCKASQDVG TAVAWYQQK PGQSPKLLIY WASTRHTGVP DRFTGSGSGT DFTLTISIVQSE DLADYFCQQY SSYPLTFGGGT KLEIK (SEQ ID NO: 780) | DIVM SQSH KFMS TSVG DRVSI TCKA S (SEQ ID NO: 779) | QDVGT A (SEQ ID NO: 1204) | VAWY QQKP GQSP KLLIY (SEQ ID NO: 1427) | WAS (SEQ ID NO: 1450) | TRHT GVPD RFTGS GSGT DFTLT ISIVQ SEDL ADYF C (SEQ ID NO: 1412) | QQYSS YPLT (SEQ ID NO: 1291) | CQQYS YPLT F (SEQ ID NO: 673) | TFGGGT KLEIK (SEQ ID NO: 1393) | FGGG TKLEI K (SEQ ID NO: 959) |
| AHH03748 | DVVLTQTPLS LPVSLGDQASI SCRSSQSLVHS NGNTYLHWY LQKPGQSPKL LIYKVSNRFSG VPDRFSGSGS GTDFTLKISRV EAEDLGVYFC SQSTHVPWTF GGGTKLEMK (SEQ ID NO: 877) | DVVL TQTPL SLPVS LGDQ ASISC RSS (SEQ ID NO: 874) | QSLVH SNGNT Y (SEQ ID NO: 1306) | LHWY LQKP GQSP KLLIY (SEQ ID NO: 1076) | KVS (SEQ ID NO: 1062) | NRFS GVPD RFSGS GSGT DFTL KISRV EAED LGVY FC (SEQ ID NO: 1157) | SQSTH VPWT (SEQ ID NO: 1374) | CSQST HVPWT F (SEQ ID NO: 682) | WTFGGG TKLEMK (SEQ ID NO: 1468) | FGGG TKLE MK (SEQ ID NO: 961) |
| AHH03749 | DIVMTQSHKF MSTSVGDRVS ITCKASQDVST AVAWYQQKP GQSPKLLIHSA SYRYTGVPDR FTGSGSGTDFT FTISSVQAEDL | DIVM TQSH KFMS TSVG DRVSI TCKA S (SEQ ID NO: | QDVST A (SEQ ID NO: 1209) | VAWY QQKP GQSP KLLIH (SEQ ID NO: 1426) | SAS (SEQ ID NO: 13) | YRYT GVPD RFTGS GSGT DFTFT ISSVQ AEDL AVYY | QQHYS TPPT (SEQ ID NO: 1261) | CQQHY STPPTF (SEQ ID NO: 653) | TFGGGT KLEIK (SEQ ID NO: 1393) | FGGG TKLEI K (SEQ ID NO: 959) |

TABLE 3A-continued

Exemplary Clones-Light Chain Sequences

| ID | V-J-REGION | L-FR1 | CDRL1 | L-FR2 | CDRL2 | L-FR3 | CDRL3 | JUNCTION | J-REGION | L-FR4 |
|---|---|---|---|---|---|---|---|---|---|---|
| | AVYYCQQHYSTPPTFGGGTKLEIK (SEQ ID NO: 801) | 800) | | | | C (SEQ ID NO: 1491) | | | | |
| AHH 03750 | DIVMTQSPLTLSVTIGQPASISCKSSQSLLDSDGKTYLNWLLQRPGQSPKRLIYLVSKLDSGVPDRFTGSGSGTDFTLKISRVEAEDLGVYYCWQGTHFPWTFGGGTKLEIK (SEQ ID NO: 815) | DIVMTQSPLTLSVTIGQPASISCK SS (SEQ ID NO: 814) | QSLLDSDGKTY (SEQ ID NO: 1301) | LNWLLQRPGQSPKRLIY (SEQ ID NO: 1083) | LVS (SEQ ID NO: 1116) | KLDSGVPDRFTGSGSGTDFTLKISRVEAEDLGVYYC (SEQ ID NO: 1056) | WQGTHFPWT (SEQ ID NO: 1465) | CWQGTHFPWTF (SEQ ID NO: 689) | WTFGGGTKLEIK (SEQ ID NO: 1467) | FGGGTKLEIK (SEQ ID NO: 959) |
| AHH 03751 | DIQMTQTPLTLSVTIGQPASISCKSSQSLLDSDGKTYLNWLLQRPGQSPKRLIYLVSKLDSGVPDRFTGSGSGTDFTLKISRVEAEDLGVYYCWQGAHFPWTFGGGTKLEIK (SEQ ID NO: 749) | DIQMTQTPLTLSVTIGQPASISCK SS (SEQ ID NO: 748) | QSLLDSDGKTY (SEQ ID NO: 1301) | LNWLLQRPGQSPKRLIY (SEQ ID NO: 1083) | LVS (SEQ ID NO: 1116) | KLDSGVPDRFTGSGSGTDFTLKISRVEAEDLGVYYC (SEQ ID NO: 1056) | WQGAHFPWT (SEQ ID NO: 1461) | CWQGAHFPWTF (SEQ ID NO: 685) | WTFGGGTKLEIK (SEQ ID NO: 1467) | FGGGTKLEIK (SEQ ID NO: 959) |
| AHH 03752 | DIQMTQTPLTLSVTIGQPASISCKSSQSLLDSDGKTYLNWLLQRPGQSPKRLIYLVSKLDSGVPDRFTGSGSGTDFTLKISRVEAEDLGVYYCWQGTHFPQTFGGGTKLEMK (SEQ ID NO: 750) | DIQMTQTPLTLSVTIGQPASISCK SS (SEQ ID NO: 748) | QSLLDSDGKTY (SEQ ID NO: 1301) | LNWLLQRPGQSPKRLIY (SEQ ID NO: 1083) | LVS (SEQ ID NO: 1116) | KLDSGVPDRFTGSGSGTDFTLKISRVEAEDLGVYYC (SEQ ID NO: 1056) | WQGTHFPQT (SEQ ID NO: 1463) | CWQGTHFPQTF (SEQ ID NO: 687) | TFGGGTKLEMK (SEQ ID NO: 1394) | FGGGTKLEMK (SEQ ID NO: 961) |
| AHH 03753 | DIVITQSQKFMSTSVGDRVSVTCKASQNVGSNVAWYQQKPGQSPKALIYSASYRYSGVPDRFTGSGSGTDFTLTISNVQSEDLAEYFCQQYDYPYTFGGGTKLEIK (SEQ ID NO: 767) | DIVITQSQKFMSTSVGDRVSVTCKAS (SEQ ID NO: 766) | QNVGSN (SEQ ID NO: 1244) | VAWYQQKPGQSPKALIY (SEQ ID NO: 1425) | SAS (SEQ ID NO: 13) | YRYSGVPDRFTGSGSGTDFTLTISNVQSEDLAEYFC (SEQ ID NO: 1483) | QQYDYPYT (SEQ ID NO: 1280) | CQQYDYPYTF (SEQ ID NO: 669) | YTFGGGTKLEIK (SEQ ID NO: 1493) | FGGGTKLEIK (SEQ ID NO: 959) |
| AHH 03754 | DIQMTQSPSSLSASLGERVSLTCRASQDIGSSLNWLQQEPDGTIKRLIYATSSLDSGVPKRFSGSRSGSDYSLTISSLESEDFVDYYCLQYASSPHTFGGGTKLEIK (SEQ ID NO: 727) | DIQMTQSPSSLSASLGERVSLTCRAS (SEQ ID NO: 726) | QDIGSS (SEQ ID NO: 1199) | LNWLQQEPDGTIKRLIY (SEQ ID NO: 1085) | ATS (SEQ ID NO: 618) | SLDSGVPKRFSGSRSGSDYSLTISSLESEDFVDYYC (SEQ ID NO: 1366) | LQYASSPHT (SEQ ID NO: 1098) | CLQYASSPHTF (SEQ ID NO: 634) | TFGGGTKLEIK (SEQ ID NO: 1393) | FGGGTKLEIK (SEQ ID NO: 959) |
| AHH 03755 | DIQMTQSPASLSVSVGETVTI | DIQMTQSP | ENIYSN (SEQ | LAWYQQKQ | AAT (SEQ ID | NLADGVPS | QHFWGTPWT | CQHFWGTP | WTFGGGTKLEMK | FGGGTKLE |

TABLE 3A-continued

Exemplary Clones-Light Chain Sequences

| ID | V-J-REGION | L-FR1 | CDRL1 | L-FR2 | CDRL2 | L-FR3 | CDRL3 | JUNC-TION | J-REGION | L-FR4 |
|---|---|---|---|---|---|---|---|---|---|---|
| | TCRASENIYSN LAWYQQKG KSPQLLVYAA TNLADGVPSR FSGSGSGTQY SLKINSLQSED FGSYYCQHFW GTPWTFGGGT KLEMK (SEQ ID NO: 725) | ASLS VSVG ETVTI TCRA S (SEQ ID NO: 723) | ID NO: 929) | GKSP QLLV (SEQ ID NO: 1069) | NO: 600) | RFSGS GSGT QYSL KINSL QSED FGSY YC (SEQ ID NO: 1143) | (SEQ ID NO: 1213) | WTF (SEQ ID NO: 1468) | (SEQ ID NO: 643) | MK (SEQ ID NO: 961) |
| AHH 03756 | DTTVTQSHKF MSTSVGDRVS ITCKASQDVST AVAWYQQKP GQSPKLLIYSA SYRYTGVPDR FTGSGSGTDFT FTISSVQAEDL AVYYCQQHY STPYTFGGGT KLEIK (SEQ ID NO: 842) | DTTV TQSH KFMS TSVG DRVSI TCKA S (SEQ ID NO: 840) | QDVST A (SEQ ID NO: 1209) | VAWY QQKP GQSP KLLIY (SEQ ID NO: 1427) | SAS (SEQ ID NO: 13) | YRYT GVPD RFTGS GSGT DFTFT ISSVQ AEDL AVYY C (SEQ ID NO: 1491) | QQHYS TPYT (SEQ ID NO: 1265) | CQQHY STPYT F (SEQ ID NO: 657) | YTFGGG TKLEIK (SEQ ID NO: 1493) | FGGG TKLEI K (SEQ ID NO: 959) |
| AHH 03757 | DIQMTQSPAS LSVSVGETVAI TCRASENIYSN LAWYQQKG KSPQLLVYAA TNLADGVPSR FSGSGSGTQY SLKINSLQSED FGSYYCQHFW GTPWTFGGGT KLEMK (SEQ ID NO: 722) | DIQM TQSP ASLS VSVG ETVAI TCRA S (SEQ ID NO: 721) | ENIYS N (SEQ ID NO: 929) | LAWY QQKQ GKSP QLLV (SEQ ID NO: 1069) | AAT (SEQ ID NO: 600) | NLAD GVPS RFSGS GSGT QYSL KINSL QSED FGSY YC (SEQ ID NO: 1143) | QHFW GTPWT (SEQ ID NO: 1213) | CQHF WGTP WTF (SEQ ID NO: 1468) | WTFGGG TKLEMK (SEQ ID NO: 643) | FGGG TKLE MK (SEQ ID NO: 961) |

TABLE 3B

Exemplary Clones-Light Chain Sequences

| ID | V-J-REGION | L-FR1 | CDRL1 | L-FR2 | CDRL2 | L-FR3 | CDRL3 | JUNC-TION | J-REGION | L-FR4 |
|---|---|---|---|---|---|---|---|---|---|---|
| AHH 03758 | DILMTQSPASL SVATGEKVTI RCITSTDIDDD MNWYQQKPG EPPKLLISEGN TLRPGVPSRFS SSGYGTDFVF TIENTLSEDVA DYYCLQSDN MPLTFGGGTK LEIK (SEQ ID NO: 705) | DILM TQSP ASLS VATG EKVTI RCITS (SEQ ID NO: 704) | TDIDD D (SEQ ID NO: 1391) | MNWY QQKPG EPPKL LIS (SEQ ID NO: 1134) | EGN (SEQ ID NO: 925) | TLRP GVPS RFSSS GYGT DFVF TIENT LSED VADY YC (SEQ ID NO: 1406) | LQSDN MPLT (SEQ ID NO: 1094) | CLQS DNMP LTF (SEQ ID NO: 631) | TFGGGT KLEIK (SEQ ID NO: 1393) | FGGG TKLEI K (SEQ ID NO: 959) |
| AHH 03759 | DTTVTQSPAS LAVSLGQRAT ISCKASQSVD YDGDSYMNW YQQKPGQPPK LLIYAASNLES GIPARFSGSGS GTDFTLNIHPV EEEDAATYYC QQSNEDPYTF GGGTKLEMK (SEQ ID NO: 848) | DTTV TQSP ASLA VSLG QRATI SCKA S (SEQ ID NO: 847) | QSVDY DGDSY (SEQ ID NO: 1308) | MNWY QQKPG QPPKL LIY (SEQ ID NO: 1135) | AAS (SEQ ID NO: 599) | NLES GIPAR FSGSG SGTD FTLNI HPVE EEDA ATYY C (SEQ ID NO: 1148) | QQSNE DPYT (SEQ ID NO: 1270) | CQQS NEDP YTF (SEQ ID NO: 662) | YTFGGG TKLEMK (SEQ ID NO: 1494) | FGGG TKLE MK (SEQ ID NO: 961) |

TABLE 3B-continued

Exemplary Clones-Light Chain Sequences

| ID | V-J-REGION | L-FR1 | CDRL1 | L-FR2 | CDRL2 | L-FR3 | CDRL3 | JUNCTION | J-REGION | L-FR4 |
|---|---|---|---|---|---|---|---|---|---|---|
| AHH 03760 | DVVMTQTPKF LLVSAGDRVT ITCKASQSVSN DVAWYQQKP GQSPKLLIYY ASNRYTGVPD RFTGSGYGTD FTFTISTVQAE DLAVYFCQQD YSSPPTFGGGT KLEIK (SEQ ID NO: 897) | DVVM TQTP KFLL VSAG DRVTI TCKA S (SEQ ID NO: 896) | QSVSN D (SEQ ID NO: 1310) | VAWY QQKPG QSPKL LIY (SEQ ID NO: 1427) | YAS (SEQ ID NO: 1476) | NRYT GVPD RFTGS GYGT dftft ISTVQ AEDL AVYF C (SEQ ID NO: 1164) | QQDY SSPPT (SEQ ID NO: 1250) | CQQD YSSPP TF (SEQ ID NO: 646) | TFGGGT KLEIK (SEQ ID NO: 1393) | FGGG TKLEI K (SEQ ID NO: 959) |
| AHH 03761 | DVVLTQTPLS LPVTLGDPASI SCRSSQTLLHS DGNTYLKWY LQKPGQSPKL LIYQVSNRFSG VPDRFTGSGS GTDPTLKISRV EAEDLGVYHC FQGSHVPWTF GGGTKLEIK (SEQ ID NO: 884) | DVVL TQTPL SLPVT LGDP ASISC RSS (SEQ ID NO: 883) | QTLLH SDGNT Y (SEQ ID NO: 1311) | LKWY LQKPG QSPKL LIY (SEQ ID NO: 1080) | QVS (SEQ ID NO: 1344) | NRFS GVPD RFTGS GSGT DFTL KISRV EAED LGVY HC (SEQ ID NO: 1160) | FQGSH VPWT (SEQ ID NO: 969) | CFQG SHVP WTF (SEQ ID NO: 620) | WTFGGG TKLEIK (SEQ ID NO: 1467) | FGGG TKLEI K (SEQ ID NO: 959) |
| AHH 03763 | DIQMTQTPLT LSVTIGQPASI SCKSSQSLLDS DGKTYLNWL LQRPGQSPKR LIYLVSKLDSG VPDRFTGSGS GTDPTLKISRV EAEDLGVYYC WQGTHFPRTF GGGTKLEIK (SEQ ID NO: 751) | DIQM TQTPL TLSVT IGQPA SISCK SS (SEQ ID NO: 748) | QSLLD SDGKT Y (SEQ ID NO: 1301) | LNWLL QRPGQ SPKRLI Y (SEQ ID NO: 1083) | LVS (SEQ ID NO: 1116) | KLDS GVPD RFTGS GSGT DFTL KISRV EAED LGVY YC (SEQ ID NO: 1056) | WQGT HFPRT (SEQ ID NO: 1464) | CWQG THFPR TF (SEQ ID NO: 688) | TFGGGT KLEIK (SEQ ID NO: 1393) | FGGG TKLEI K (SEQ ID NO: 959) |
| AHH 03764 | DVVMTQSPAI MSASLGERVT MTCTASSSVS SSYLHWYQQ KPGSSPKLWI YSTSNLASGV PARFSGSGSGT SYSLTISSMEA EDAATYYCHQ YHRSPPTFGG GTKLEIK (SEQ ID NO: 888) | DVVM TQSP AIMS ASLG ERVT MTCT AS (SEQ ID NO: 887) | ssvsss Y (SEQ ID NO: 1384) | LHWY QQKPG SSPKL WIY (SEQ ID NO: 1077) | STS (SEQ ID NO: 1386) | NLAS GVPA RFSGS GSGT SYSLT ISSME AEDA ATYY C (SEQ ID NO: 1144) | HQYH RSPPT (SEQ ID NO: 1001) | CHQY HRSPP TF (SEQ ID NO: 628) | FGGGTK LEIK (SEQ ID NO: 959) | FGGG TKLEI K (SEQ ID NO: 959) |
| AHH 03765 | DIVMTQSPAI MSASPGEKVT MTCSASSSVS YMHWYQQKS GTSPKRWIYD TSKLASGVPA RFSGSGSGTSY SLTISSMEAED AATYYCQQW SSNPPYTFGG GTKLEMK (SEQ ID NO: 804) | DIVM TQSP AIMS ASPG EKVT MTCS AS (SEQ ID NO: 802) | SSVSY (SEQ ID NO: 1385) | MHWY QQKSG TSPKR WIY (SEQ ID NO: 1131) | DTS (SEQ ID NO: 839) | KLAS GVPA RFSGS GSGT SYSLT ISSME AEDA ATYY C (SEQ ID NO: 1052) | QQWS SNPPY T (SEQ ID NO: 1275) | CQQW SSNPP YTF (SEQ ID NO: 665) | YTFGGG TKLEMK (SEQ ID NO: 1494) | FGGG TKLE MK (SEQ ID NO: 961) |
| AHH 03766 | DVVMTQTPLS LPVSLGDQASI SCRSSQSLVHS NGNTYLRWY LQKPGQSPKL LIYKVSNRFSG | DVVM TQTPL SLPVS LGDQ ASISC RSS | QSLVH SNGNT Y (SEQ ID NO: 1306) | LRWYL QKPGQ SPKLLI Y (SEQ ID NO: 1108) | KVS (SEQ ID NO: 1062) | NRFS GVPD RFSGS GSGT DFTL KISRV | SQSTH VPWT (SEQ ID NO: 1374) | CSQST HVPW TF (SEQ ID NO: 682) | WTFGGG TKLEIK (SEQ ID NO: 1467) | FGGG TKLEI K (SEQ ID NO: 959) |

TABLE 3B-continued

Exemplary Clones-Light Chain Sequences

| ID | V-J-REGION | L-FR1 | CDRL1 | L-FR2 | CDRL2 | L-FR3 | CDRL3 | JUNCTION | J-REGION | L-FR4 |
|---|---|---|---|---|---|---|---|---|---|---|
| | VPDRFSGSGS GTDFTLKISRV EAEDLGVYFC SQSTHVPWTF GGGTKLEIK (SEQ ID NO: 903) | (SEQ ID NO: 900) | | | | EAED LGVY FC (SEQ ID NO: 1157) | | | | |
| AHH 03767 | DVVMTQTPLT LSVTIGQPASI SCKSSQSLLDS DGKTYLNWL LQRPGQSPKR LIYLVSKLDSG VPDGFTGSGS GTDFTLKISRV EAEDLGVYYC WQGTHFPRTF GGGTKLEIK (SEQ ID NO: 908) | DVVM TQTPL TLSVT IGQPA SISCK SS (SEQ ID NO: 904) | QSLLD SDGKT Y (SEQ ID NO: 1301) | LNWLL QRPGQ SPKRLI Y (SEQ ID NO: 1083) | LVS (SEQ ID NO: 1116) | KLDS GVPD GFTG SGSG TDFTL KISRV EAED LGVY YC (SEQ ID NO: 1054) | WQGT HFPRT TF (SEQ ID NO: 1464) | CWQG THFPR TF (SEQ ID NO: 688) | TFGGGT KLEIK (SEQ ID NO: 1393) | FGGG TKLEI K (SEQ ID NO: 959) |
| AHH 03768 | DIQMTQTSSSF SVSLGDRVTIT CKASEDIYNR LAWYQQKPG NAPRLLISGAT SLETGVPSRFS GSGSGKDYTL SITSLQTEDVA TYYCQQYWS TPPTFGGGTK LEIK (SEQ ID NO: 759) | DIQM TQTSS SFSVS LGDR VTITC KAS (SEQ ID NO: 758) | EDIYN R (SEQ ID NO: 924) | LAWY QQKPG NAPRL LIS (SEQ ID NO: 1065) | GAT (SEQ ID NO: 976) | SLETG VPSRF SGSGS GKDY TLSIT SLQTE DVAT YYC (SEQ ID NO: 1367) | QQYW STPPT (SEQ ID NO: 1292) | CQQY WSTP PTF (SEQ ID NO: 674) | TFGGGT KLEIK (SEQ ID NO: 1393) | FGGG TKLEI K (SEQ ID NO: 959) |
| AHH 03769 | DVVLTQTPLS LPVSLGDQASI SCRSSQSLVHS NGNTYLHWY LQKPGQSPKL LIYKVSNRFSG VPDRFSGSGS GTDFTLKISRV EAEDLGVYFC SQSTHVPRTF GGGTKLEIK (SEQ ID NO: 878) | DVVL TQTPL SLPVS LGDQ ASISC RSS (SEQ ID NO: 874) | QSLVH SNGNT Y (SEQ ID NO: 1306) | LHWY LQKPG QSPKL LIY (SEQ ID NO: 1076) | KVS (SEQ ID NO: 1062) | NRFS GVPD RFSGS GSGT DFTL KISRV EAED LGVY FC (SEQ ID NO: 1372) | SQSTH VPRT (SEQ ID NO: 1372) | CSQST HVPR TF (SEQ ID NO: 680) | TFGGGT KLEIK (SEQ ID NO: 1393) | FGGG TKLEI K (SEQ ID NO: 959) |
| AHH 03770 | DIVMSQSPSSL AVSVGEKVT MSCKSSQSLL YSSNQKNYLA WYQQKPGQSP KLLIYWASTR ESGVPDRFTG SGSGTDFTLTI SSVKAEDLAV YYCQQYYSYP FGGGTKLEIK (SEQ ID NO: 791) | DIVM SQSPS SLAV SVGE KVTM SCKSS (SEQ ID NO: 790) | QSLLY SSNQK NY (SEQ ID NO: 1304) | LAWY QQKPG QSPKL LIY (SEQ ID NO: 1066) | WAS (SEQ ID NO: 1450) | TRES GVPD RFTGS GSGT DFTLT ISSVK AEDL AVYY C (SEQ ID NO: 1411) | QQYY SYP (SEQ ID NO: 1293) | CQQY YSYPF (SEQ ID NO: 675) | FGGGTK LEIK (SEQ ID NO: 959) | FGGG TKLEI K (SEQ ID NO: 959) |
| AHH 03771 | DVVVTQTPLS LPVSLGDQASI SCRSSQSLVHS NGNTYLHWY LQKPGQSPKL LIYKVSNRFSG VPDRFSGSGS GTDFTLKISRV DAEDLGVYFC SQSTHVYTFG GGTKLEMK | DVV TQTPL SLPVS LGDQ ASISC RSS (SEQ ID NO: 918) | QSLVH SNGNT Y (SEQ ID NO: 1306) | LHWY LQKPG QSPKL LIY (SEQ ID NO: 1076) | KVS (SEQ ID NO: 1062) | NRFS GVPD RFSGS GSGT DFTL KISRV DAED LGVY FC (SEQ ID NO: | SQSTH VYT (SEQ ID NO: 1376) | CSQST HVYT F (SEQ ID NO: 684) | YTFGGG TKLEMK (SEQ ID NO: 1494) | FGGG TKLE MK (SEQ ID NO: 961) |

TABLE 3B-continued

Exemplary Clones-Light Chain Sequences

| ID | V-J-REGION | L-FR1 | CDRL1 | L-FR2 | CDRL2 | L-FR3 | CDRL3 | JUNCTION | J-REGION | L-FR4 |
|---|---|---|---|---|---|---|---|---|---|---|
| | (SEQ ID NO: 921) | | | | | 1155) | | | | |
| AHH 03772 | DIQMTQTPAS LSASVGETVTI TCRASENIYSY LAWYQQKQG KSPQLLVYNA KTLAEGVPSR FSGSGSGTQFS LKINSLQPEDF GSYYCQHHY GTPWTFGGGT KLEIK (SEQ ID NO: 745) | DIQM TQTP ASLS ASVG ETVTI TCRA S (SEQ ID NO: 744) | ENIYS Y (SEQ ID NO: 930) | LAWY QQKQ GKSPQ LLVY (SEQ ID NO: 1069) | NAK (SEQ ID NO: 28) | TLAE GVPS RFSGS GSGT QFSL KINSL QPED FGSY YC (SEQ ID NO: 1398) | QHHY GTPW T (SEQ ID NO: 1217) | CQHH YGTP WTF (SEQ ID NO: 644) | WTFGGG TKLEIK (SEQ ID NO: 1467) | FGGG TKLEI K (SEQ ID NO: 959) |
| AHH 03773 | DVVLTQTPLS LPVSLGDQASI SCRSSQSLVHS NGNTYLHWY LQKPGQSPKL LIYKVSNRFSG VPDRFSGSGS GTDFTLKISRV EAEDLGVYFC SQSTHVPTFG GGTKLEIK (SEQ ID NO: 879) | DVVL TQTPL SLPVS LGDQ ASISC RSS (SEQ ID NO: 874) | QSLVH SNGNT Y (SEQ ID NO: 1306) | LHWY LQKPG QSPKL LIY (SEQ ID NO: 1076) | KVS (SEQ ID NO: 1062) | NRFS GVPD RFSGS GSGT DFTL KISRV EAED LGVY FC (SEQ ID NO: 1157) | SQSTH VPT (SEQ ID NO: 1373) | CSQST HVPT F (SEQ ID NO: 681) | TFGGGT KLEIK (SEQ ID NO: 1393) | FGGG TKLEI K (SEQ ID NO: 959) |
| AHH 03774 | DIVMSQSPAI MSASPGEKVT MTRSASSSVS YMYWYQQKP GSSPRLLIYDT SNLASGVPVR FSGSGSGTSYS LTISRMEAED AATYYCQQW SSYPYTSGGG TKLEIK (SEQ ID NO: 785) | DIVM SQSPA IMSAS PGEK VTMT RSAS (SEQ ID NO: 784) | SSVSY (SEQ ID NO: 1385) | MYWY QQKPG SSPRLL IY (SEQ ID NO: 1140) | DTS (SEQ ID NO: 839) | NLAS GVPV RFSGS GSGT SYSLT ISRME AEDA ATYY C (SEQ ID NO: 1146) | QQWS SYPYT (SEQ ID NO: 1278) | CQQW SSYPY TS (SEQ ID NO: 667) | SGGGTK LEIK (SEQ ID NO: 1364) | SGGG TKLEI K (SEQ ID NO: 1364) |
| AHH 03775 | DIVMTQSPAL MSASPGEKVT MTCSASSSVS YMYWYQQKP RSSPKPWIYLT PNLASGVPAR FSGSGSGTSYS LTISSMEADA ATYYCQQWSS NPYTFGGGTK LEIK (SEQ ID NO: 806) | DIVM TQSP ALMS ASPG EKVT MTCS AS (SEQ ID NO: 805) | SSVSY (SEQ ID NO: 1385) | MYWY QQKPR SSPKP WIY (SEQ ID NO: 1141) | LTP (SEQ ID NO: 1115) | NLAS GVPA RFSGS GSGT SYSLT ISSME AEDA ATYY C (SEQ ID NO: 1144) | QQWS SNPYT (SEQ ID NO: 1276) | CQQW SSNPY TF (SEQ ID NO: 666) | FGGGTK LEIK (SEQ ID NO: 959) | FGGG TKLEI K (SEQ ID NO: 959) |
| AHH 03776 | DIVMSQSPASL SVATGEKVTI RCITSTDIDDD MNWYQQKPG EPPKLLISEGN TLRPGVPSRFS SSGYGTDFVF TIENTLSEDVA DYYCLQSDN MPYTFGGGTK LEIK (SEQ ID NO: 789) | DIVM SQSPA SLSV ATGE KVTIR CITS (SEQ ID NO: 788) | TDIDD D (SEQ ID NO: 1391) | MNWY QQKPG EPPKL LIS (SEQ ID NO: 1134) | EGN (SEQ ID NO: 925) | TLRP GVPS RFSSS GYGT DFVF TIENT LSED VADY YC (SEQ ID NO: 1406) | LQSDN MPYT (SEQ ID NO: 1095) | CLQS DNMP YTF (SEQ ID NO: 632) | YTFGGG TKLEIK (SEQ ID NO: 1493) | FGGG TKLEI K (SEQ ID NO: 959) |
| AHH 03777 | DIQMTQTPLT LSVTIGQPASI SCKSSQSLLDS DGKTYLNWL LQRPGQSPKR | DIQM TQTPL TLSVT IGQPA SISCK | QSLLD SDGKT Y (SEQ ID NO: 1301) | LNWLL QRPGQ SPKRLI Y | LVS (SEQ ID NO: 1116) | KLDS GVPD RFTGS GSGT DFTL | WQGT FSSH (SEQ ID NO: 1462) | CWQG TFSSH V | VRRGDQ AGNE V (SEQ ID NO: 1441) | FGGG TKLE MK (SEQ ID |

TABLE 3B-continued

Exemplary Clones-Light Chain Sequences

| ID | V-J-REGION | L-FR1 | CDRL1 | L-FR2 | CDRL2 | L-FR3 | CDRL3 | JUNCTION | J-REGION | L-FR4 |
|---|---|---|---|---|---|---|---|---|---|---|
| | LIYLVSKLDSG VPDRFTGSGS GTDFTLKISRV EAEDLGVYYC WQGTFSSHVR RGDQAGNE (SEQ ID NO: 752) | SS (SEQ ID NO: 748) | | 1083) | | KISRV EAED LGVY YC (SEQ ID NO: 1056) | | 686) | | 961) |
| AHH 03778 | DIVMSQHKF MSTSVGDRVS ITCKASQDVIT AVAWYQQKP GQSPKLPIYSA SYRYTGVPDR FTGSGSGTDFT FTISSVQAEDL AVYYCQQHY STPRTFGGGT KLEIK (SEQ ID NO: 781) | DIVM SQSH KFMS TSVG DRVSI TCKA S (SEQ ID NO: 779) | QDVIT A (SEQ ID NO: 1205) | VAWY QQKPG QSPKL PIY (SEQ ID NO: 1428) | SAS (SEQ ID NO: 13) | YRYT GVPD RFTGS GSGT dftft ISSVQ AEDL AVYY C (SEQ ID NO: 1491) | QQHY STPRT (SEQ ID NO: 1263) | CQQH YSTPR TF (SEQ ID NO: 655) | TFGGGT KLEIK (SEQ ID NO: 1393) | FGGG TKLEI K (SEQ ID NO: 959) |
| AHH 03779 | DIVMTQSPSPL SASLGERVSLT CRASQEISGYL SWLQQKPDGT IKRLIYAASTL DSGVPKRFSG SRSGSDYSLTI SSLESEDFADY YCLQYASYPR TFGGGTKLEIK (SEQ ID NO: 818) | DIVM TQSPS PLSAS LGER VSLT CRAS (SEQ ID NO: 817) | QEISG Y (SEQ ID NO: 1210) | LSWLQ QKPDG TIKRLI Y (SEQ ID NO: 1111) | AAS (SEQ ID NO: 599) | TLDS GVPK RFSGS RSGS DYSL TISSL ESEDF ADYY C (SEQ ID NO: 1402) | LQYAS YPRT (SEQ ID NO: 1102) | CLQY ASYP RTF (SEQ ID NO: 638) | TFGGGT KLEIK (SEQ ID NO: 1393) | FGGG TKLEI K (SEQ ID NO: 959) |
| AHH 03780 | DTTVTQSPAS LAVSLGQRAT ISCRASESVDS YGNSFMHWY QQKPGQPPKL LIYRASNLESG IPARFSGSGSR TGFTLTINPVE ADDVATYYC QQSNEDPRTF GGGTKLEMK (SEQ ID NO: 851) | DTTV TQSP ASLA VSLG QRATI SCRA S (SEQ ID NO: 850) | ESVDS YGNSF (SEQ ID NO: 935) | MHWY QQKPG QPPKL LIY (SEQ ID NO: 1129) | RAS (SEQ ID NO: 1346) | NLES GIPAR FSGSG SRTGF TLTIN PVEA DDVA TYYC (SEQ ID NO: 1149) | QQSNE DPRT (SEQ ID NO: 1269) | CQQS NEDP RTF (SEQ ID NO: 661) | TFGGGT KLEMK (SEQ ID NO: 1394) | FGGG TKLE MK (SEQ ID NO: 961) |
| AHH 03781 | DILMTQSPATL SVTPGDRVSL SCRASQSISDY LHWYQQKSH ESPRLLIKYAS QSISGIPSRFSG SGSGSDFTLSI NSVEPEDVGV YYCQNGHSFP RTFGGGTKLEI K (SEQ ID NO: 707) | DILM TQSP ATLS VTPG DRVS LSCR AS (SEQ ID NO: 706) | QSISD Y (SEQ ID NO: 1296) | LHWY QQKSH ESPRL LIK (SEQ ID NO: 1079) | YAS (SEQ ID NO: 1476) | QSISG IPSRF SGSGS GSDF TLSIN SVEPE DVGV YYC (SEQ ID NO: 1297) | QNGH SFPRT (SEQ ID NO: 1242) | CQNG HSFPR TF (SEQ ID NO: 645) | TFGGGT KLEIK (SEQ ID NO: 1393) | FGGG TKLEI K (SEQ ID NO: 959) |
| AHH 03782 | DVVMTQTPLS LPVSLGDQASI SCRSSQSLVHS NGNTYLHWY LQKPGQSPKL LIYKVSNRFSG VPDRFSGSGS GTDFTLKISRV EAEDLGVYFC SQSTHVPWTF GGGTKLEIK | DVVM TQTPL SLPVS LGDQ ASISC RSS (SEQ ID NO: 900) | QSLVH SNGNT Y (SEQ ID NO: 1306) | LHWY LQKPG QSPKL LIY (SEQ ID NO: 1076) | KVS (SEQ ID NO: 1062) | NRFS GVPD RFSGS GSGT DFTL KISRV EAED LGVY FC (SEQ ID NO: | SQSTH VPWT (SEQ ID NO: 1374) | CSQST HVPW TF (SEQ ID NO: 682) | WTFGGG TKLEIK (SEQ ID NO: 1467) | FGGG TKLEI K (SEQ ID NO: 959) |

TABLE 3B-continued

Exemplary Clones-Light Chain Sequences

| ID | V-J-REGION | L-FR1 | CDRL1 | L-FR2 | CDRL2 | L-FR3 | CDRL3 | JUNC-TION | J-REGION | L-FR4 |
|---|---|---|---|---|---|---|---|---|---|---|
| | (SEQ ID NO: 901) | | | | | 1157) | | | | |
| AHH 03783 | DTTVTQSPAS LAVSLGQRAT ISCKASQSVD YDGDSYMNW YQQKPGQPPK LLIYAASNLES GIPARFSGSGS GTDFTLNIHPV EEEDAATYYC QQSNEDPYTF GGGTKLEIK (SEQ ID NO: 849) | DTTV TQSP ASLA VSLG QRATI SCKA S (SEQ ID NO: 847) | QSVDY DGDSY MNW (SEQ ID NO: 1308) | MNWY QQKPG QPPKL LIY (SEQ ID NO: 1135) | AAS (SEQ ID NO: 599) | NLES GIPAR FSGSG SGTD FTLNI HPVE EEDA ATYY C (SEQ ID NO: 1148) | QQSNE DPYT (SEQ ID NO: 1270) | CQQS NEDP YTF (SEQ ID NO: 662) | YTFGGG TKLEIK (SEQ ID NO: 1493) | FGGG TKLEI K (SEQ ID NO: 959) |
| AHH 03784 | DTTVTQSPSSL AMSVGQKVT MSCKSSQSLL NSSNQKNYLA WYQQKPGQSP KLLVYFASTR ESGVPDRFIGS GSGTDFTLTIS SVQAEDLADY FCQQHYSTPY TFGGGTKLEIK (SEQ ID NO: 853) | DTTV TQSPS SLAM SVGQ KVTM SCKSS (SEQ ID NO: 852) | QSLLN SSNQK NY (SEQ ID NO: 1302) | LAWY QQKPG QSPKL LVY (SEQ ID NO: 1067) | FAS (SEQ ID NO: 957) | TRES GVPD RFIGS GSGT DFTLT ISSVQ AEDL ADYF C (SEQ ID NO: 1410) | QQHY STPYT (SEQ ID NO: 1265) | CQQH YSTP YTF (SEQ ID NO: 657) | YTFGGG TKLEIK (SEQ ID NO: 1493) | FGGG TKLEI K (SEQ ID NO: 959) |
| AHH 03785 | DIQMTQTHKF MSTSVGDRVS ITCKASQDVST AVAWYQQKP GQSPKLLIYSA SYRYTGVPDR FTGSGSGTDFT FTISSVQAEDL AVYYCQQHY STHVHVRRGD QAGNQ (SEQ ID NO: 742) | DIQM TQTH KFMS TSVG DRVSI TCKA S (SEQ ID NO: 741) | QDVST A (SEQ ID NO: 1209) | VAWY QQKPG QSPKL LIY (SEQ ID NO: 1427) | SAS (SEQ ID NO: 13) | YRYT GVPD RFTGS GSGT dftft ISSVQ AEDL AVYY C (SEQ ID NO: 1491) | QQHY STHVH (SEQ ID NO: 1259) | CQQH YSTH VHV (SEQ ID NO: 652) | VHVRRG DQAGNQ (SEQ ID NO: 1434) | FGGG TKLEI K (SEQ ID NO: 959) |
| AHH 03786 | DVVVTQTPLS LPVSLGDQASI SCRSSQSLVHS NGNTYLHWY LQKPGQSPKL LIYKVSNRFSG VPDRFSGSGS GTDFTLKISRV EAEDLGVYFC SQSTHVPWTF GGGTKLEIK (SEQ ID NO: 922) | DVW TQTPL SLPVS LGDQ ASISC RSS (SEQ ID NO: 918) | QSLVH SNGNT Y (SEQ ID NO: 1306) | LHWY LQKPG QSPKL LIY (SEQ ID NO: 1076) | KVS (SEQ ID NO: 1062) | NRFS GVPD RFSGS GSGT DFTL KISRV EAED LGVY FC (SEQ ID NO: 1157) | SQSTH VPWT (SEQ ID NO: 1374) | CSQST HVPW TF (SEQ ID NO: 682) | WTFGGG TKLEIK (SEQ ID NO: 1467) | FGGG TKLEI K (SEQ ID NO: 959) |
| AHH 03787 | DILMTQSPAIM SASPGEKVTM TCSASSSVIYM HWYQQKSGT SPKRWIYDTS KLASGVPARF SGSGSGTSYSL SISSMETEDAA TYYCQQWTS NPPTFGGGTK LEIK (SEQ ID NO: 703) | DILM TQSP AIMS ASPG EKVT MTCS AS (SEQ ID NO: 702) | SSVIY (SEQ ID NO: 1383) | MHWY QQKSG TSPKR WIY (SEQ ID NO: 1131) | DTS (SEQ ID NO: 839) | KLAS GVPA RFSGS GSGT SYSLS ISSME TEDA ATYY C (SEQ ID NO: 1051) | QQWT SNPPT (SEQ ID NO: 1279) | CQQW TSNPP TF (SEQ ID NO: 668) | FGGGTK LEIK (SEQ ID NO: 959) | FGGG TKLEI K (SEQ ID NO: 959) |
| AHH 03788 | DIVLTQSQKF MSTSVGDRVS VTCKASQNVG | DIVLT QSQK FMST | QNVGT N (SEQ ID NO: | VAWY QQKPG QSPKA | SAS (SEQ ID NO: 13) | YRYS GVPD RFTGS | SQSTH VPYT (SEQ | CSQST HVPY TF | YTFGGG TKLEIK (SEQ ID | FGGG TKLEI K |

TABLE 3B-continued

Exemplary Clones-Light Chain Sequences

| ID | V-J-REGION | L-FR1 | CDRL1 | L-FR2 | CDRL2 | L-FR3 | CDRL3 | JUNCTION | J-REGION | L-FR4 |
|---|---|---|---|---|---|---|---|---|---|---|
| | TNVAWYQQK PGQSPKALIYS ASYRYSGVPD RFTGSGSGTD FTLKISRVEAE DLGVYFCSQS THVPYTFGGG TKLEIK (SEQ ID NO: 776) | SVGD RVSV TCKA S (SEQ ID NO: 773) | 12) | LIY (SEQ ID NO: 1425) | | GSGT DFTL KISRV EAED LGVY FC (SEQ ID NO: 1479) | ID NO: 1375) | (SEQ ID NO: 683) | NO: 1493) | (SEQ ID NO: 959) |
| AHH 03789 | DVVMTQTPLS LPVSLGDQASI SCRSSQSLVHS NGNTYLHWY LQKPGQSPKL LIYKVSNRFSG VPDRFSGSGS GTDFTLKISRV EAEDLGVYFC SQSTHVPWTF GGGTKLEIK (SEQ ID NO: 901) | DVVM TQTPL SLPVS LGDQ ASISC RSS (SEQ ID NO: 900) | QSLVH SNGNT Y (SEQ ID NO: 1306) | LHWY LQKPG QSPKL LIY (SEQ ID NO: 1076) | KVS (SEQ ID NO: 1062) | NRFS GVPD RFSGS GSGT DFTL KISRV EAED LGVY FC (SEQ ID NO: 1157) | SQSTH VPWT (SEQ ID NO: 1374) | CSQST HVPW TF (SEQ ID NO: 682) | WTFGGG TKLEIK (SEQ ID NO: 1467) | FGGG TKLEI K (SEQ ID NO: 959) |
| AHH 03790 | DIVMSQSPAIL SASPGEKVTM TCSASSRVTY MHWYQQKPG TSPKRWIYDT STLTSGVPARF SGSGSGTSYSL TISGMEAEDA ATYYCHQRSG YSYTFGGGTK LEMK (SEQ ID NO: 783) | DIVM SQSPA ILSAS PGEK VTMT CSAS (SEQ ID NO: 782) | SRVTY (SEQ ID NO: 1380) | MHWY QQKPG TSPKR WIY (SEQ ID NO: 1130) | DTS (SEQ ID NO: 839) | TLTSG VP AR FSGSG SGTS YSLTI SGME AEDA ATYY C (SEQ ID NO: 1407) | HQRS GYSYT (SEQ ID NO: 1000) | CHQR SGYS YTF (SEQ ID NO: 627) | YTFGGG TKLEMK (SEQ ID NO: 1494) | FGGG TKLE MK (SEQ ID NO: 961) |
| AHH 03791 | DIVMSQSQKF MSTSVGDRVS VTCKASQNVG TNVAWYQQK PGQSPKALIYS ASYRYSGVPD RFTGSGSGTD FTLTISNVQSE DLAEYFCQQY NSYPRTFGGG TKLEIK (SEQ ID NO: 794) | DIVM SQSQ KFMS TSVG DRVS VTCK AS (SEQ ID NO: 793) | QNVGT N (SEQ ID NO: 12) | VAWY QQKPG QSPKA LIY (SEQ ID NO: 1425) | SAS (SEQ ID NO: 13) | YRYS GVPD RFTGS GSGT DFTLT ISNVQ SEDL AEYF C (SEQ ID NO: 1483) | QQYN SYPRT (SEQ ID NO: 1286) | CQQY NSYP RTF (SEQ ID NO: 670) | TFGGGT KLEIK (SEQ ID NO: 1393) | FGGG TKLEI K (SEQ ID NO: 959) |
| AHH 03792 | DIVMTQAAPS VPVTPGESVSI SCRSSKSLLHS NGNTYLYWFL QRPGQSPQLLI YRMSNLASGV PDRFSGSGSGT AFTLRISRVEA EDVGVYYCM QHLEYPYTFG GGTKLEIK (SEQ ID NO: 797) | DIVM TQAA PSVPV TPGES VSISC RSS (SEQ ID NO: 796) | KSLLH SNGNT YLYWFL (SEQ ID NO: 1060) | LYWFL QRPGQ SPQLLI Y (SEQ ID NO: 1121) | RMS (SEQ ID NO: 1360) | NLAS GVPD RFSGS GSGT AFTL RISRV EAED VGVY YC (SEQ ID NO: 1145) | MQHL EYPYT (SEQ ID NO: 1136) | CMQH LEYP YTF (SEQ ID NO: 641) | TFGGGT KLEIK (SEQ ID NO: 1393) | FGGG TKLEI K (SEQ ID NO: 959) |
| AHH 03794 | DIVMTQSTSSL SASLGDRVTIS CRASQDISNY LNWYQQKPD GTVKLLIYYTS RLHSGVPSRFS GSGSGTDYSL TISNLEQEDIA TYFCQQGNTL PWTFGGGTKL | DIVM TQSTS SLSAS LGDR VTISC RAS (SEQ ID NO: 828) | QDISN Y (SEQ ID NO: 27) | LNWY QQKPD GTVKL LIY (SEQ ID NO: 1088) | YTS (SEQ ID NO: 1495) | RLHS GVPS RFSGS GSGT DYSL TISNL EQEDI ATYF C (SEQ | QQGN TLPWT (SEQ ID NO: 1255) | CQQG NTLP WTF (SEQ ID NO: 649) | WTFGGG TKLEIK (SEQ ID NO: 1467) | FGGG TKLEI K (SEQ ID NO: 959) |

TABLE 3B-continued

Exemplary Clones-Light Chain Sequences

| ID | V-J-REGION | L-FR1 | CDRL1 | L-FR2 | CDRL2 | L-FR3 | CDRL3 | JUNCTION | J-REGION | L-FR4 |
|---|---|---|---|---|---|---|---|---|---|---|
| | EIK (SEQ ID NO: 829) | | | | | ID NO: 1353) | | | | |
| AHH 03796 | DIVMTQDELS NPVTSGESVSI SCRSSKSLLYK DGKTYLNCFL QRPGQSPQLLI YLMSTRASGV SNRFSGSGSGT DFTLEISRVKA EDVGVYYCH QLVEYPYTFG GGTKLEMK (SEQ ID NO: 799) | DIVM TQDE LSNP VTSG ESVSI SCRSS (SEQ ID NO: 798) | KSLLY KDGKT Y (SEQ ID NO: 1061) | LNCFL QRPGQ SPQLLI Y (SEQ ID NO: 1082) | LMS (SEQ ID NO: 1081) | TRAS GVSN RFSGS GSGT DFTLE ISRVK AEDV GVYY C (SEQ ID NO: 1409) | HQLV EYPYT (SEQ ID NO: 998) | CHQL VEYP YTF (SEQ ID NO: 625) | YTFGGG TKLEMK (SEQ ID NO: 1494) | FGGG TKLE MK (SEQ ID NO: 961) |
| AHH 03797 | DVVVTQTPLS LPVSLGDQASI SCRSSQSLENS NGNTYLNWY LQKPGQSPQL LIYRVSNRFSG VLDRFSGSGS GTDFTLKISRV EAEDLGVYFC LQVTHVPFAF GSGTKLEIK (SEQ ID NO: 919) | DVV TQTPL SLPVS LGDQ ASISC RSS (SEQ ID NO: 918) | QSLEN SNGNT LQKPG QSPQL LIY (SEQ ID NO: 1300) | LNWY (SEQ ID NO: 1087) | RVS (SEQ ID NO: 1361) | NRFS GVLD RFSGS GSGT DFTL KISRV EAED LGVY FC (SEQ ID NO: 1153) | LQVT HVPFA (SEQ ID NO: 1096) | CLQV THVP FAF (SEQ ID NO: 633) | FAFGSGT KLEIK (SEQ ID NO: 956) | FGSG TKLEI K (SEQ ID NO: 965) |
| AHH 03798 | DVVMTQTPLS LPVSLGDQASI SCRSSQSLVHS NGNTYLHWY LQKPGQSPKL LIYKVSNRFSG VPDRFSGSGS GTDFTLKISRV EAEDLGVYFC SQSTHVPLTFG AGTKLEIK (SEQ ID NO: 902) | DVVM TQTPL SLPVS LGDQ ASISC RSS (SEQ ID NO: 900) | QSLVH SNGNT Y (SEQ ID NO: 1306) | LHWY LQKPG QSPKL LIY (SEQ ID NO: 1076) | KVS (SEQ ID NO: 1062) | NRFS GVPD RFSGS GSGT DFTL KISRV EAED LGVY FC (SEQ ID NO: 1157) | SQSTH VPLT (SEQ ID NO: 1370) | CSQST HVPL TF (SEQ ID NO: 679) | LTFGAG TKLEIK (SEQ ID NO: 1114) | FGAG TKLEI K (SEQ ID NO: 958) |
| AHH 03799 | DVVLTQTPLS LPVSLGDQASI SCRSSQSLVHS YGNTYLHWY LQKPGQSPKL LIYKVSNRFSG VPDRFSGSGS GTDFTLKISRV EAEDLGVYFC SQSTHVPHTF GGGTKLEMK (SEQ ID NO: 880) | DVVL TQTPL SLPVS LGDQ ASISC RSS (SEQ ID NO: 874) | QSLVH SYGNT Y (SEQ ID NO: 1307) | LHWY LQKPG QSPKL LIY (SEQ ID NO: 1076) | KVS (SEQ ID NO: 1062) | NRFS GVPD RFSGS GSGT DFTL KISRV EAED LGVY FC (SEQ ID NO: 1157) | SQSTH VPHT (SEQ ID NO: 1369) | CSQST HVPH TF (SEQ ID NO: 678) | TFGGGT KLEMK (SEQ ID NO: 1394) | FGGG TKLE MK (SEQ ID NO: 961) |
| AHH 03800 | DIQMTQTPSSL SASLGERVSLT CRASQDIGSSL NWLQQEPDGT IKRLISATSSL DSGVPKRFSG SRSGSDYSLTI SSLESEDFVDY YCLQYATFPY TFGGGTKLEIK (SEQ ID NO: 754) | DIQM TQTPS SLSAS LGER VSLT CRAS (SEQ ID NO: 753) | QDIGS S (SEQ ID NO: 1199) | LNWL QQEPD GTIKR LIS (SEQ ID NO: 1084) | ATS (SEQ ID NO: 618) | SLDS GVPK RFSGS RSGS DYSL TISSL ESEDF VDYY C (SEQ ID NO: 1366) | LQYA TFPYT (SEQ ID NO: 1104) | CLQY ATPP YTF (SEQ ID NO: 639) | YTFGGG TKLEIK (SEQ ID NO: 1493) | FGGG TKLEI K (SEQ ID NO: 959) |

TABLE 3C

Exemplary Clones-Light Chain Sequences

| ID | V-J-REGION | L-FR1 | CDRL1 | L-FR2 | CDRL2 | L-FR3 | CDRL3 | JUNCTION |
|---|---|---|---|---|---|---|---|---|
| >AH04501-VL | DVVMTQTQKFTSTSVG DRVSVTCKASQNVGTN VAWYQQKPGQSPKALI YSASYRYSGVPDRFTGS GSGTDFTLTISNVQSEDL AEYFCQQYNSYPYTFGG GTKLEIK (SEQ ID NO: 912) | DVVMT QTQKFT STSVGD RVSVTC (SEQ ID NO: 910) | KASQN VGTNV A (SEQ ID NO: 1038) | WYQQ KPGQS PKALI Y (SEQ ID NO: 1471) | SASYR YSG (SEQ ID NO: 1362) | VPDRF TGSGS GTDFT LTISN VQSED LAEYF C (SEQ ID NO: 1439) | QQYN SYPYT (SEQ ID NO: 15) | FGGGT KLEIK (SEQ ID NO: 959) |
| >AH04502-VL | DIVMTQSQKFMSTSVGD RVSVTCKASQNVGINVA WYQQKPGQSPKALIYSA SYRYSGVPDRFTGSGSG TDFTLTISNVQSEDLAEY FCQQYNSYPYTFGGGTK LEIK (SEQ ID NO: 822) | DIVMTQ SQKFMS TSVGDR VSVTC (SEQ ID NO: 819) | KASQN VGINV A (SEQ ID NO: 1037) | WYQQ KPGQS PKALI Y (SEQ ID NO: 1471) | SASYR YSG (SEQ ID NO: 1362) | VPDRF TGSGS GTDFT LTISN VQSED LAEYF C (SEQ ID NO: 1439) | QQYN SYPYT (SEQ ID NO: 15) | FGGGT KLEIK (SEQ ID NO: 959) |
| >AH04503-VL | DIQMTQSQKFMSTSVGD RVSVTCKASQNVGTNV AWYQQKPGQSPKALIYS ASYRYSGVPDRFTGSGS GTDFTLTISNVQSEDLAE YFCQQYNSYPWTFGGG TKLEIK (SEQ ID NO: 34) | DIQMTQ SQKFMS TSVGDR VSVTC (SEQ ID NO: 733) | KASQN VGTNV A (SEQ ID NO: 1038) | WYQQ KPGQS PKALI Y (SEQ ID NO: 1471) | SASYR YSG (SEQ ID NO: 1362) | VPDRF TGSGS GTDFT LTISN VQSED LAEYF C (SEQ ID NO: 1439) | QQYN SYPW T (SEQ ID NO: 36) | FGGGT KLEIK (SEQ ID NO: 959) |
| >AH04504-VL | DTTVTQSQKFMSTSVGD RVSVTCKASQNVGTNV AWYQQKPGQSPKALIYS ASYRYSGVPDRFTGSGS GTDFTLTISNVQSEDLAE YFCQQYNSYPYTFGGGT KLEIK (SEQ ID NO: 859) | DTTVTQ SQKFMS TSVGDR VSVTC (SEQ ID NO: 855) | KASQN VGTNV A (SEQ ID NO: 1038) | WYQQ KPGQS PKALI Y (SEQ ID NO: 1471) | SASYR YSG (SEQ ID NO: 1362) | VPDRF TGSGS GTDFT LTISN VQSED LAEYF C (SEQ ID NO: 1439) | QQYN SYPYT (SEQ ID NO: 15) | FGGGT KLEIK (SEQ ID NO: 959) |
| >AH04505-VL | DTTVTQSQKFMSTSVGD RVSVTCKASQNVGTNV AWYQQKPGQSPKALIYS ASYRYSGVPDRFTGSGS GTDFTLTISNVQSEDLAE YFCQQYNSYPYTFGGGT KLEMK (SEQ ID NO: 860) | DTTVTQ SQKFMS TSVGDR VSVTC (SEQ ID NO: 855) | KASQN VGTNV A (SEQ ID NO: 1038) | WYQQ KPGQS PKALI Y (SEQ ID NO: 1471) | SASYR YSG (SEQ ID NO: 1362) | VPDRF TGSGS GTDFT LTISN VQSED LAEYF C (SEQ ID NO: 1439) | QQYN SYPYT (SEQ ID NO: 15) | FGGGT KLEM K (SEQ ID NO: 961) |
| >AH04506-VL | DIQMTQSQKFMSTSVGD RVSVTCKASQNVGTNV AWYQQKPGQSPKALIYS ASYRYSGVPDRFTGSGS GTDFTLTISNVQSEDLAE YFCQQYNSYPWTFGGG TKLEIK (SEQ ID NO: 34) | DIQMTQ SQKFMS TSVGDR VSVTC (SEQ ID NO: 733) | KASQN VGTNV A (SEQ ID NO: 1038) | WYQQ KPGQS PKALI Y (SEQ ID NO: 1471) | SASYR YSG (SEQ ID NO: 1362) | VPDRF TGSGS GTDFT LTISN VQSED LAEYF C (SEQ ID NO: 1439) | QQYN SYPW T (SEQ ID NO: 36) | FGGGT KLEIK (SEQ ID NO: 959) |
| >AH04507-VL | DTTVTQSQKFMSTSVGD RVSVTCKASQNVGTNV AWYQQKPGQSPKALIYS ASYRYSGVPDRFTGSGS GTDFTLTISNVQSEDLAE YFCQQYNSYPYTFGGGT KLEIK (SEQ ID NO: 859) | DTTVTQ SQKFMS TSVGDR VSVTC (SEQ ID NO: 855) | KASQN VGTNV A (SEQ ID NO: 1038) | WYQQ KPGQS PKALI Y (SEQ ID NO: 1471) | SASYR YSG (SEQ ID NO: 1362) | VPDRF TGSGS GTDFT LTISN VQSED LAEYF C (SEQ ID NO: 1439) | QQYN SYPYT (SEQ ID NO: 15) | FGGGT KLEIK (SEQ ID NO: 959) |
| >AH04508-VL | DIVLTQSQKFMSTSVGD RVSVTCKASQNVGTNV AWYQQKPGQSPKALIYS ASYRYSGVPDRFAGSGS | DIVLTQ SQKFMS TSVGDR VSVTC | KASQN VGTNV A (SEQ ID NO: | WYQQ KPGQS PKALI Y (SEQ | SASYR YSG (SEQ ID NO: | VPDRF AGSGS GTDFT LTISN | QQYN SYPYT (SEQ ID NO: | FGGGT KLEIK (SEQ ID NO: |

TABLE 3C-continued

Exemplary Clones-Light Chain Sequences

| ID | V-J-REGION | L-FR1 | CDRL1 | L-FR2 | CDRL2 | L-FR3 | CDRL3 | JUNCTION |
|---|---|---|---|---|---|---|---|---|
| | GTDFTLTISNVQSEDLAE YFCQQYNSYPYTFGGGT KLEIK (SEQ ID NO: 775) | (SEQ ID NO: 772) | 1038) | ID NO: 1471) | 1362) | VQSED LAEYF C (SEQ ID NO: 1437) | 15) | 959) |
| >AH04509-VL | DTTVTQSQRFMSTSVGD RVSVTCKASQNVGTNV AWYQQKPGQSPKPLIYS ASYRYSGVPDRFTGSGS GTDFTLTINNVQSEDLA EYFCQQYNNSPLTFGGG TKLEIK (SEQ ID NO: 864) | DTTVTQ SQRFMS TSVGDR VSVTC (SEQ ID NO: 862) | KASQN VGTNV A (SEQ ID NO: 1038) | WYQQ KPGQS PKPLI Y (SEQ ID NO: 1473) | SASYR YSG (SEQ ID NO: 1362) | VPDRF TGSGS GTDFT LTINN VQSED LAEYF C (SEQ ID NO: 1438) | QQYN NSPLT (SEQ ID NO: 1282) | FGGGT KLEIK (SEQ ID NO: 959) |
| >AH04510-VL | DIVMTQSQKFMSTSVGD RVSVTCKASQNVGTNV AWYQQKPGQSPKALIYS ASYRYSGVPDRFTGSGS GTDFTLTISNVQSEDLAE YFCQQYNSYPYTFGGGT KLEIK (SEQ ID NO: 823) | DIVMTQ SQKFMS TSVGDR VSVTC (SEQ ID NO: 819) | KASQN VGTNV A (SEQ ID NO: 1038) | WYQQ KPGQS PKALI Y (SEQ ID NO: 1471) | SASYR YSG (SEQ ID NO: 1362) | VPDRF TGSGS GTDFT LTISN VQSED LAEYF C (SEQ ID NO: 1439) | QQYN SYPYT (SEQ ID NO: 15) | FGGGT KLEIK (SEQ ID NO: 959) |
| >AH04511-VL | DIVMSQSQKFMSTSVGD RVSVTCKASQNVGTNV AWYQQKPGQSPKALIYS ASYRYSGVPDRFTGSGS GTDFTLTISNVQSEDLAE YFCQQYNSYPYTFGGGT KLEIK (SEQ ID NO: 795) | DIVMSQ SQKFMS TSVGDR VSVTC (SEQ ID NO: 792) | KASQN VGTNV A (SEQ ID NO: 1038) | WYQQ KPGQS PKALI Y (SEQ ID NO: 1471) | SASYR YSG (SEQ ID NO: 1362) | VPDRF TGSGS GTDFT LTISN VQSED LAEYF C (SEQ ID NO: 1439) | QQYN SYPYT (SEQ ID NO: 15) | FGGGT KLEIK (SEQ ID NO: 959) |
| >AH04512-VL | DIQMTQSQKFMSTSVGD RVSVTCKASQNVGTNV AWYQQKPGQSPKALIYS ASYRYSGVPDRFTGSGS GTDFTLTISNVQSEDLAE YFCQQYNSYPYTFGGGT KLEMK (SEQ ID NO: 735) | DIQMTQ SQKFMS TSVGDR VSVTC (SEQ ID NO: 733) | KASQN VGTNV A (SEQ ID NO: 1038) | WYQQ KPALI Y (SEQ ID NO: 1471) | SASYR YSG (SEQ ID NO: 1362) | VPDRF TGSGS GTDFT LTISN VQSED LAEYF C (SEQ ID NO: 1439) | QQYN SYPYT (SEQ ID NO: 15) | FGGGT KLEM K (SEQ ID NO: 961) |
| >AH04513-VL | DILMTQSQKFMSTSVGD RVSVTCKASQNVGTNV AWYQQKPGQSPKALIYS ASYRYSGVPDRFTGSGS GTDFTLTISNVQSEDLAE YFCQQYNSYPYTFGGGT KLEIK (SEQ ID NO: 712) | DILMTQ SQKFMS TSVGDR VSVTC (SEQ ID NO: 710) | KASQN VGTNV A (SEQ ID NO: 1038) | WYQQ KPGQS PKALI Y (SEQ ID NO: 1471) | SASYR YSG (SEQ ID NO: 1362) | VPDRF TGSGS GTDFT LTISN VQSED LAEYF C (SEQ ID NO: 1439) | QQYN SYPYT (SEQ ID NO: 15) | FGGGT KLEIK (SEQ ID NO: 959) |
| >AH04514-VL | DIQMTQSQKFMSTSVGD RVSVTCKASQNVGTNV AWYQQKPGQSPKALIYS ASYRYSGVPDRFTGSGS GTDFTLTISNVQSEDLAE YFCQQYNSYPYTFGGGT KLEIK (SEQ ID NO: 736) | DIQMTQ SQKFMS TSVGDR VSVTC (SEQ ID NO: 733) | KASQN VGTNV A (SEQ ID NO: 1038) | WYQQ KPGQS PKALI Y (SEQ ID NO: 1471) | SASYR YSG (SEQ ID NO: 1362) | VPDRF TGSGS GTDFT LTISN VQSED LAEYF C (SEQ ID NO: 1439) | QQYN SYPYT (SEQ ID NO: 15) | FGGGT KLEIK (SEQ ID NO: 959) |
| >AH04515-VL | DIVLTQSQKFMSTSVGD RVSVTCKASQNVGTNV AWYQQKPGQSPKALIYS ASYRYSGVPDRFTGSGS GTDFTLTISNVQSEDLAE | DIVLTQ SQKFMS TSVGDR VSVTC (SEQ ID NO: 1038) | KASQN VGTNV A (SEQ ID NO: 1038) | WYQQ KPGQS PKALI Y (SEQ ID NO: 1471) | SASYR YSG (SEQ ID NO: 1362) | VPDRF TGSGS GTDFT LTISN VQSED | QQYN SYPYT (SEQ ID NO: 15) | FGGGT KLEM K (SEQ ID NO: 961) |

TABLE 3C-continued

Exemplary Clones-Light Chain Sequences

| ID | V-J-REGION | L-FR1 | CDRL1 | L-FR2 | CDRL2 | L-FR3 | CDRL3 | JUNCTION |
|---|---|---|---|---|---|---|---|---|
| | YFCQQYNSYPYTFGGGT KLEMK (SEQ ID NO: 777) | NO: 772) | | 1471) | | LAEYF C (SEQ ID NO: 1439) | | |
| >AH04516-VL | DTTVTQSQKFMSTVGD RVSVTCKASQNVGTNV AWYQQKPGQSPKALIYS ASYRYSGVPDRFTGSGS GTDFTLTISNVQSEDLAE YFCQQYNSYPWTFGGG TKLEIK (SEQ ID NO: 861) | DTTVTQ SQKFMS TSVGDR VSVTC (SEQ ID NO: 855) | KASQN VGTNV A (SEQ ID NO: 1038) | WYQQ KPGQS PKALI Y (SEQ ID NO: 1471) | SASYR YSG (SEQ ID NO: 1362) | VPDRF TGSGS GTDFT LTISN VQSED LAEYF C (SEQ ID NO: 1439) | QQYN SYPW T (SEQ ID NO: 36) | FGGGT KLEIK (SEQ ID NO: 959) |
| >AH04517-VL | DIQMTQSQKFMSTVGD RVSVTCKASQSVGTNVA WYQQKPGQSPKALIYSA SYRYSGVPDRFTGSGSG TDFTLTISNVQSEDLAEY FCQQYNNYPWTFGGGT KLEIK (SEQ ID NO: 737) | DIQMTQ SQKFMS TSVGDR VSVTC (SEQ ID NO: 733) | KASQS VGTNV A (SEQ ID NO: 1040) | WYQQ KPGQS PKALI Y (SEQ ID NO: 1471) | SASYR YSG (SEQ ID NO: 1362) | VPDRF TGSGS GTDFT LTISN VQSED LAEYF C (SEQ ID NO: 1439) | QQYN NYPW T (SEQ ID NO: 1284) | FGGGT KLEIK (SEQ ID NO: 959) |
| >AH04518-VL | DILLTQSQKFMSTVGD RVSVTCKASQNVGTNV AWYQQKPGQSPKALIYS ASYRYSGVPDRFTGSGS GTDFTLTISNVQSEDLAE YFCQQYNSYPYTFGGGT KLEIK (SEQ ID NO: 701) | DILLTQ SQKFMS TSVGDR VSVTC (SEQ ID NO: 699) | KASQN VGTNV A (SEQ ID NO: 1038) | WYQQ KPGQS PKALI Y (SEQ ID NO: 1471) | SASYR YSG (SEQ ID NO: 1362) | VPDRF TGSGS GTDFT LTISN VQSED LAEYF C (SEQ ID NO: 1439) | QQYN SYPYT (SEQ ID NO: 15) | FGGGT KLEIK (SEQ ID NO: 959) |
| >AH04520-VL | DIQMTQSQKFMSTVGD RVSVTCKASQNVGTNV AWYQQKPGQSPKALIYS ASYRYSGVPDRFTGSGS GTDFTLTISNVQSEDLAE YFCQQYNSYPYTFGGGT KLEMK (SEQ ID NO: 735) | DIQMTQ SQKFMS TSVGDR VSVTC (SEQ ID NO: 733) | KASQN VGTNV A (SEQ ID NO: 1038) | WYQQ KPGQS PKALI Y (SEQ ID NO: 1471) | SASYR YSG (SEQ ID NO: 1362) | VPDRF TGSGS GTDFT LTISN VQSED LAEYF C (SEQ ID NO: 1439) | QQYN SYPYT (SEQ ID NO: 15) | FGGGT KLEM K (SEQ ID NO: 961) |
| >AH04521-VL | DTTVTQSQKFMSTVGD RVSVTCKASQNVGTNV AWYQQKPGQSPKALIYS ASYRYSGVPDRFTGSGS GTDFTLTISNVQSEDLAE YFCQQYNSYPYTFGGGT KLEIK (SEQ ID NO: 859) | DTTVTQ SQKFMS TSVGDR VSVTC (SEQ ID NO: 855) | KASQN VGTNV A (SEQ ID NO: 1038) | WYQQ KPGQS PKALI Y (SEQ ID NO: 1471) | SASYR YSG (SEQ ID NO: 1362) | VPDRF TGSGS GTDFT LTISN VQSED LAEYF C (SEQ ID NO: 1439) | QQYN SYPYT (SEQ ID NO: 15) | FGGGT KLEIK (SEQ ID NO: 959) |
| >AH04522-VL | DTTVTQSQKFMSTVGD RVSVTCKAGQNVGTNV AWYQQKPGQSPKALIYS ASYRYSGVPDRFTGSGS GTDFTLTISNVQSEDLAE YFCQQYNSYPYTFGGGT KLEIK (SEQ ID NO: 857) | DTTVTQ SQKFMS TSVGDR VSVTC (SEQ ID NO: 855) | KAGQ NVGTN VA (SEQ ID NO: 1036) | WYQQ KPGQS PKALI Y (SEQ ID NO: 1471) | SASYR YSG (SEQ ID NO: 1362) | VPDRF TGSGS GTDFT LTISN VQSED LAEYF C (SEQ ID NO: 1439) | QQYN SYPYT (SEQ ID NO: 15) | FGGGT KLEIK (SEQ ID NO: 959) |
| >AH04523-VL | DIVLTQSQKFMSTVGD RVSVTCKASQNVGTNV AWYQQKPGQSPKALIYS ASYRYSGVPDRFTGSGS GTDFTLTISNVQSEDLAE YFCQQYNSYPYTFGGGT KLEIK (SEQ ID NO: 778) | DIVLTQ SQKFMS TSVGDR VSVTC (SEQ ID NO: 772) | KASQN VGTNV A (SEQ ID NO: 1038) | WYQQ KPGQS PKALI Y (SEQ ID NO: 1471) | SASYR YSG (SEQ ID NO: 1362) | VPDRF TGSGS GTDFT LTISN VQSED LAEYF C (SEQ ID NO: 1439) | QQYN SYPYT (SEQ ID NO: 15) | FGGGT KLEIK (SEQ ID NO: 959) |

TABLE 3C-continued

Exemplary Clones-Light Chain Sequences

| ID | V-J-REGION | L-FR1 | CDRL1 | L-FR2 | CDRL2 | L-FR3 | CDRL3 | JUNCTION |
|---|---|---|---|---|---|---|---|---|
| >AH04524-VL | DIVMTQSQKFMSTVGD RVSVTCKASQNVGTNV AWYQQKPGQSPKALIYS ASYRYSGVPDRFTGSGS GTDFTLTISNVQSEDLAE YFCQQYNSYPYTFGGGT KLEIK (SEQ ID NO: 825) | DIVMTQ SQKFMS TSVGDR VSVTC (SEQ ID NO: 819) | KASQN VGTNV A (SEQ ID NO: 1038) | WYQQ KPGQS PKALI Y (SEQ ID NO: 1471) | SASYR YSG (SEQ ID NO: 1362) | VPDRF TGSGS GTDFT LTISN VQSED LAEYF C (SEQ ID NO: 1439) | QQYN SYPYT (SEQ ID NO: 15) | FGGGT KLEIK (SEQ ID NO: 959) |
| >AH04525-VL | DNVLTQSQKFMSTVGD RVSVTCKASQNVGTNV AWYQQKPGQSPKALIYS ASYRYSGVPDRFTGSGS GTDFTLTISNVQSEDLAE YFCQQYNSYPYTFGGGT KLEMK (SEQ ID NO: 838) | DNVLT QSQKF MSTSV GDRVS VTC (SEQ ID NO: 836) | KASQN VGTNV A (SEQ ID NO: 1038) | WYQQ KPGQS PKALI Y (SEQ ID NO: 1471) | SASYR YSG (SEQ ID NO: 1362) | VPDRF TGSGS GTDFT LTISN VQSED LAEYF C (SEQ ID NO: 1439) | QQYN SYPYT (SEQ ID NO: 15) | FGGGT KLEM K (SEQ ID NO: 961) |
| >AH04526-VL | DTTVTQSQKFMSTVGD RVSVTCKASQNVGTNV AWYQQKPGQSPKALIYS ASYRYSGVPDRFTGSGS GTDFTLTISNVQSEDLAE YFCQQYNSYPYTFGGGT KLEMK (SEQ ID NO: 860) | DTTVTQ SQKFMS TSVGDR VSVTC (SEQ ID NO: 855) | KASQN VGTNV A (SEQ ID NO: 1038) | WYQQ KPGQS PKALI Y (SEQ ID NO: 1471) | SASYR YSG (SEQ ID NO: 1362) | VPDRF TGSGS GTDFT LTISN VQSED LAEYF C (SEQ ID NO: 1439) | QQYN SYPYT (SEQ ID NO: 15) | FGGGT KLEM K (SEQ ID NO: 961) |
| >AH04527-VL | DVVMTQSQKFMSTVG DRVSVTCKASQNVGTN VAWYQQKPGQSPKALI YSASYRYSGVPDRFTGS GSGTDFTLTISNVQSEDL AEYFCQQYNSYPYTFGG GTKLEIK (SEQ ID NO: 895) | DVVMT QSQKF MSTSV GDRVS VTC (SEQ ID NO: 893) | KASQN VGTNV A (SEQ ID NO: 1038) | WYQQ KPGQS PKALI Y (SEQ ID NO: 1471) | SASYR YSG (SEQ ID NO: 1362) | VPDRF TGSGS GTDFT LTISN VQSED LAEYF C (SEQ ID NO: 1439) | QQYN SYPYT (SEQ ID NO: 15) | FGGGT KLEIK (SEQ ID NO: 959) |
| >AH04528-VL | DIQMTQSQKFMSTVGD RVSVTCKASQNVGTNV AWYQQKPGQSPKALIYS ASYRYSGVPDRFTGSGS GTDFTLTISNVQSEDLAE YFCQQYNSYPYTFGGGT KLEIK (SEQ ID NO: 736) | DIQMTQ SQKFMS TSVGDR VSVTC (SEQ ID NO: 733) | KASQN VGTNV A (SEQ ID NO: 1038) | WYQQ KPGQS PKALI Y (SEQ ID NO: 1471) | SASYR YSG (SEQ ID NO: 1362) | VPDRF TGSGS GTDFT LTISN VQSED LAEYF C (SEQ ID NO: 1439) | QQYN SYPYT (SEQ ID NO: 15) | FGGGT KLEIK (SEQ ID NO: 959) |
| >AH04529-VL | DTTVTQSQKFMSTVGD RVSVTCKASQNVGTNV AWYQQKPGQSPKALIYS ASYRYSGVPDRFTGSGS GTDFTLTISNVQSEDLAE YFCQQYNSYPYTFGGGT KLEIK (SEQ ID NO: 859) | DTTVTQ SQKFMS TSVGDR VSVTC (SEQ ID NO: 855) | KASQN VGTNV A (SEQ ID NO: 1038) | WYQQ KPGQS PKALI Y (SEQ ID NO: 1471) | SASYR YSG (SEQ ID NO: 1362) | VPDRF TGSGS GTDFT LTISN VQSED LAEYF C (SEQ ID NO: 1439) | QQYN SYPYT (SEQ ID NO: 15) | FGGGT KLEIK (SEQ ID NO: 959) |
| >AH04530-VL | DTTVTQSQKFMSTVGD RVSVTCKASQNVGTNV AWYQQKPGQSPKALIYS ASYRYSGVPDRFTGSGS GTDFTLTISNVQSEDLAE YFCQQYNSYPWTFGGG TKLEIK (SEQ ID NO: 861) | DTTVTQ SQKFMS TSVGDR VSVTC (SEQ ID NO: 855) | KASQN VGTNV A (SEQ ID NO: 1038) | WYQQ KPGQS PKALI Y (SEQ ID NO: 1471) | SASYR YSG (SEQ ID NO: 1362) | VPDRF TGSGS GTDFT LTISN VQSED LAEYF C (SEQ ID NO: 1439) | QQYN SYPW T (SEQ ID NO: 36) | FGGGT KLEIK (SEQ ID NO: 959) |

TABLE 4A

Exemplary Clones-Heavy Chain Sequences

| ID | HFR1 | CDRH1 | HFR2 | CDRH2 | HFR3 | CDRH3 | HFR4 |
|---|---|---|---|---|---|---|---|
| BL_592989-2015_G2_P8_G02 | QVQLQQSGAELVRPGTSLKMSCKAA (SEQ ID NO: 1324) | GYTFTNYW (SEQ ID NO: 4) | IGWVKQRPGHGLEWIGD (SEQ ID NO: 1010) | IHPGGGYT (SEQ ID NO: 1015) | NYNEKFKGKATLTADTSSSTTYMQLSSLTSEDSAIYYC (SEQ ID NO: 1181) | TSRNFAY (SEQ ID NO: 1419) | WGQGTPVTVSS (SEQ ID NO: 398) |
| BL_592989-2016_H2_P8_H02 | PGPTQQPGSELVRPGASVKLSCKAS (SEQ ID NO: 1191) | GYTFTSYW (SEQ ID NO: 157) | MHWVKQRHGQGLEWIGN (SEQ ID NO: 1123) | IYPGSGST (SEQ ID NO: 251) | NYDEKFKSKGTLTVDTSSSTAYMHLSSLASEDSAVYYC (SEQ ID NO: 1166) | TRSGVEGLLHWYFD (SEQ ID NO: 1416) | VWGAGTTVTVSS (SEQ ID NO: 1448) |
| BL_592989-2017_A3_P8_A03 | QVQLQQSGSELVRPGASVKLSCKAS (SEQ ID NO: 1342) | GYTFTSYW (SEQ ID NO: 157) | MHWVKQRHGQGLEWIGN (SEQ ID NO: 1123) | IYPGSGST (SEQ ID NO: 251) | NYDEKFKSKGTLTVDTSSSTAYMHLSSLTSEDSAVYCC (SEQ ID NO: 1167) | TRWITTDHYFDY (SEQ ID NO: 1417) | WGRGTTLTVSS (SEQ ID NO: 1455) |
| BL_592989-2018_B3_P8_B03 | QIQLQQPGAELVRPTSVKISCKAS (SEQ ID NO: 1220) | GYTFTNYW (SEQ ID NO: 4) | LGWVKQRPGHGLEWIGD (SEQ ID NO: 1075) | IYPGGGYT (SEQ ID NO: 6) | NYNEKFKGKATLTADTSSSTAYMQLNSLTSEDSAVYFC (SEQ ID NO: 1176) | ARVSPAS (SEQ ID NO: 615) | WGQGTTLTVSS (SEQ ID NO: 425) |
| BL_592989-2019_C3_P8_C03 | QVQLQQPGAELVRPGTSVKISCKAS (SEQ ID NO: 1314) | GYTFTNYW (SEQ ID NO: 4) | LGWVKQRPGHGLEWIGD (SEQ ID NO: 1075) | IYPGGGYT (SEQ ID NO: 6) | NYNEKFKGKATLTADTSSSTAYMQLSSLTSEDSAVYFC (SEQ ID NO: 1178) | ARVTPAS (SEQ ID NO: 8) | WGQGTTLTVSS (SEQ ID NO: 425) |
| BL_592989-2021_E3_P8_E03 | QIQLQQSGAELVRPGTSVKMSCKAA (SEQ ID NO: 1228) | GYTFTNYW (SEQ ID NO: 4) | IGWVKQRPGHGLEWIGD (SEQ ID NO: 1010) | IHPGGGYT (SEQ ID NO: 1015) | NYNEKFKGKATLTADTSSSTAYMQLSSLTSEDSAIYYC (SEQ ID NO: 1177) | TSRNFAY (SEQ ID NO: 1419) | WGQGTPVTVSS (SEQ ID NO: 398) |
| BL_592989-2022_F3_P8_F03 | QVQLQQSGAELVRPGTSVKMSCKAA (SEQ ID NO: 1326) | GYTFTNYW (SEQ ID NO: 4) | IGWVKQRPGHGLEWIGD (SEQ ID NO: 1010) | IHPGGGYT (SEQ ID NO: 1015) | NYNEKFKGKATLTADTSSSTAYMQLSSLTSEGSAIYYC (SEQ ID NO: 1179) | TSRNFAY (SEQ ID NO: 1419) | WGQGTLVTVSA (SEQ ID NO: 421) |
| BL_592989-2023_G3_P8_G03 | PGPTQQPGSELVRPGASVKLSCKAS (SEQ ID NO: 1191) | GYTFTSYW (SEQ ID NO: 157) | MHWVKQRHGQGLEWIGN (SEQ ID NO: 1123) | IYPGSGST (SEQ ID NO: 251) | NYDEKFKSKGTLTVDTSSSTAYMHLSSLASEDSAVYYC (SEQ ID NO: 1166) | TRSGVEGLLHWYFD (SEQ ID NO: 1416) | VWGAGTTVTVSS (SEQ ID NO: 1448) |
| BL_592989-2024_H3_P8_H03 | QVQLQQSGAEVAKPGASVKMSCKAS (SEQ ID NO: 1340) | GYTSTGYW (SEQ ID NO: 995) | MHWVKQRPGQGLEWIGY (SEQ ID NO: 190) | INPSTGYT (SEQ ID NO: 230) | EYNQKFEDKATLTADKSSNTAYMQLSSLTSEDSAVYYC (SEQ ID NO: 954) | ARGGYFDY (SEQ ID NO: 606) | WGQGTSLTVSS (SEQ ID NO: 424) |
| BL_592989-2025_A4_P8_A04 | QVQLQQSGAELVRPGTSVKISCKAS (SEQ | GYTFTNYW | LGWIKQRPGH | IYPGGGYT | NYNEKFKGKATLTADTS | ARVTPAS | WGQGTSL |

TABLE 4A-continued

Exemplary Clones-Heavy Chain Sequences

| ID | HFR1 | CDRH1 | HFR2 | CDRH2 | HFR3 | CDRH3 | HFR4 |
|---|---|---|---|---|---|---|---|
| | ID NO: 1325) | (SEQ ID NO: 4) | GLEWI GD (SEQ ID NO: 1074) | (SEQ ID NO: 6) | SSTAYMQLS SLTSEDSAV YFC (SEQ ID NO: 1178) | (SEQ ID NO: 8) | TVSS (SEQ ID NO: 424) |
| BL_592989-2026_B4_P8_B04 | QAYLQQSGAELVRP GVSVKISCKGS (SEQ ID NO: 1196) | GYTFT DYA (SEQ ID NO: 19) | MHWV KQSHA KSLEW IGV (SEQ ID NO: 1126) | ISTYSG DV (SEQ ID NO: 46) | SYNQKFKG KATMTVDK SSSTAYMEL ARLTPEDSAI YC (SEQ ID NO: 1388) | ARGVT FDS (SEQ ID NO: 48) | WGQ GTTL TVSS (SEQ ID NO: 425) |
| BL_592989-2027_C4_P8_C04 | QVQLQQSGAELVRP GTSVKISCKAS (SEQ ID NO: 1325) | GYTFT NYW (SEQ ID NO: 4) | LGWV KQRPG HGLEW IGD (SEQ ID NO: 1075) | IYPGG GYT (SEQ ID NO: 6) | NYNEKFKG KATLTADTS SSTAYMQLS SLTSEDSAV YFC (SEQ ID NO: 1178) | ARVTP AS (SEQ ID NO: 8) | WGQ GTTV TVSS (SEQ ID NO: 422) |
| BL_592989-2029_E4_P8_E04 | QVQLQQSGAELVRP GTSVKMSCKAA (SEQ ID NO: 1326) | GYTFT NYW (SEQ ID NO: 4) | IGWIK QRPGH GLEWI GD (SEQ ID NO: 1007) | IHPGG DYT (SEQ ID NO: 1013) | NYNEKFKG KATLTADTF SSTAYMQLS SLTSEDSAIY YC (SEQ ID NO: 1171) | TGRNF AY (SEQ ID NO: 1395) | WGQ GTLV TVSS (SEQ ID NO: 413) |
| BL_592989-2030_F4_P8_F04 | QVQLQQPGAELVRP GTSVKMSCKAA (SEQ ID NO: 1315) | GYTFT NYW (SEQ ID NO: 4) | IGWVK QRPGH GLEWI GD (SEQ ID NO: 1010) | IHPGG GYT (SEQ ID NO: 1015) | NYNEKFKG KATLTADTS SSTAYMQLS SLTSEDSAIY YC (SEQ ID NO: 1177) | TSRNF AY (SEQ ID NO: 1419) | WGQ GTLV TVSA (SEQ ID NO: 421) |
| BL_592989-2031_G4_P8_G04 | QIQLQQSGAELVRPG TSLKMSCKAA (SEQ ID NO: 1226) | GYTFT NYW (SEQ ID NO: 4) | IGWVK QRPGH GLEWI GD (SEQ ID NO: 1010) | IHPGG GYT (SEQ ID NO: 1015) | NYNEKFKG KATLTADTS SSTTYMQLS SLTSEDSAIY YC (SEQ ID NO: 1181) | TSRNF AY (SEQ ID NO: 1419) | WGQ GTLV TVSA (SEQ ID NO: 421) |
| BL_592989-2032_H4_P8_H04 | QVQLQQSGAELVRP GTSVKMSCKAA (SEQ ID NO: 1326) | GYTFS NYW (SEQ ID NO: 986) | IGWVK QRPGH GLEWI GD (SEQ ID NO: 1010) | IHPGG GYI (SEQ ID NO: 1014) | NYNEKFTGK ATLTADTSS STAYMQLSS LTSEDSAIY YC (SEQ ID NO: 1184) | VSRNF AN (SEQ ID NO: 1445) | WGQ GTLV TVSA (SEQ ID NO: 421) |
| BL_592989-2033_A5_P8_A05 | QVQLQQSGAELVRP GVSVKISCKGS (SEQ ID NO: 1338) | GYTFT DYA (SEQ ID NO: 19) | MHWV KQSHA KSLEW IGV (SEQ ID NO: 1126) | ISTYSG DV (SEQ ID NO: 46) | SYNQKFKG KATMTVDK SSSTAYMEL ARLTSEDSAI YYC (SEQ ID NO: 1389) | ARGVT FDS (SEQ ID NO: 48) | WGQ GTTL TVSS (SEQ ID NO: 425) |
| BL_592989-2034_B5_P8_B05 | QVQLQQSGAELVRP GTSVKISCKAS (SEQ ID NO: 1325) | GYTFT NYW (SEQ ID NO: 4) | LGWIK QRPGH GLEWI GD (SEQ ID NO: 1074) | IYPGG GYT (SEQ ID NO: 6) | NYNEKFKG KATLTADTS SSTAYMQLS SLTSEDSAV YFC (SEQ ID NO: 1178) | ARVTP AS (SEQ ID NO: 8) | WGQ GTSL TVSS (SEQ ID NO: 424) |
| BL_592989-2035_C5_P8_C05 | QVQLQQPGAELVRP GTSVKISCKAS (SEQ ID NO: 1314) | GYTFT NYW (SEQ ID NO: 4) | LGWV KQRPG HGLEW IGD | IYPGG GYT (SEQ ID NO: 6) | NYNEKFKG KATLTADTS SSTAYMQLS SLTSEDSAV | ARVTP AS (SEQ ID NO: 8) | WGQ GTSL TVSS (SEQ |

TABLE 4A-continued

Exemplary Clones-Heavy Chain Sequences

| ID | HFR1 | CDRH1 | HFR2 | CDRH2 | HFR3 | CDRH3 | HFR4 |
|---|---|---|---|---|---|---|---|
| | | | (SEQ ID NO: 1075) | | YFC (SEQ ID NO: 1178) | | ID NO: 424) |
| BL_592989-2037_E5_P8_E05 | QIQLQQSGAELVRPGTSVKMSCKAA (SEQ ID NO: 1228) | GYTFT NYW (SEQ ID NO: 4) | IGWVK QRPGH GLEWI GD (SEQ ID NO: 1010) | IHPGG DYS (SEQ ID NO: 1012) | NYNEKFKG KATLTADTS SSTAYMNLS SLTSEDSAIY YC (SEQ ID NO: 1174) | TSRNF AY (SEQ ID NO: 1419) | WGQ GTLV TVSA (SEQ ID NO: 421) |
| BL_592989-2038_F5_P8_F05 | QVQLQQPGAELVRP GTSVKMSCKAA (SEQ ID NO: 1315) | GYTFT NYW (SEQ ID NO: 4) | IGWVK QRPGH GLEWI GD (SEQ ID NO: 1010) | IHPGG GYI (SEQ ID NO: 1014) | NYNEKFTGK ATLTADTSS STAYMQLSS LTSEDSAIY YC (SEQ ID NO: 1184) | VSRNF AN (SEQ ID NO: 1445) | WGQ GTLV TVSA (SEQ ID NO: 421) |
| BL_592989-2039_G5_P8_G05 | QIQLQQSGAELVRPG TSVKMSCKAA (SEQ ID NO: 1228) | GYTFT NYW (SEQ ID NO: 4) | IGWVK QRPGH GLEWI GD (SEQ ID NO: 1010) | IHPGG GYT (SEQ ID NO: 1015) | NYNEKFKG KATLTADTS SSTAYMQLS SLTSEDSAIY YC (SEQ ID NO: 1177) | TSRNF AY (SEQ ID NO: 1419) | WGQ GTLV TVSA (SEQ ID NO: 421) |
| BL_592989-2040_H5_P8_H05 | QIQLQQSGAELVRPG TSVKMSCKAA (SEQ ID NO: 1228) | GYTFT NYW (SEQ ID NO: 4) | IGWVK QRPGH GLEWV GD (SEQ ID NO: 1011) | IHPGG GYT (SEQ ID NO: 1015) | NYNEKFKG KATLTADTS SSTAYMQLS SLTSEDSAIY YC (SEQ ID NO: 1177) | TSRNF AY (SEQ ID NO: 1419) | WGQ GTLV TVSA (SEQ ID NO: 421) |
| BL_592989-2041_A6_P8_A06 | QVQLQQSGAELVRP GVSLKISCKGS (SEQ ID NO: 1337) | GYTFT DYA (SEQ ID NO: 19) | MHWV RQSHA KSLEW IGV (SEQ ID NO: 1128) | ISTYSG DA (SEQ ID NO: 21) | IYNQKFKGK ATMTVDKSS STAYLELAR LTSDDSAIY YC (SEQ ID NO: 1033) | ARGVT FDY (SEQ ID NO: 23) | WGQ GTTV TVSS (SEQ ID NO: 422) |
| BL_592989-2042_B6_P8_B06 | QIQLQQSGAEMVRP GVSVKISCKGS (SEQ ID NO: 1241) | GYTFT DYA (SEQ ID NO: 19) | MHWV RQSHA KSLEW IGV (SEQ ID NO: 1128) | ISTYSG DV (SEQ ID NO: 46) | SYNQKFKG KATMTVDK SSSTAYMEL ARLTSEDSAI YYC (SEQ ID NO: 1389) | ARGVT FDS (SEQ ID NO: 48) | WGQ GTTL TVSS (SEQ ID NO: 425) |
| BL_592989-2043_C6_P8_C06 | QIQLQQSGAEMVRP GVSVKISCKGS (SEQ ID NO: 1241) | GYTFT DYA (SEQ ID NO: 19) | MHWV RQSHA KSLEW IGV (SEQ ID NO: 1128) | ISTYSG DV (SEQ ID NO: 46) | SYNQKFKG KATMTVDK SSSTAYMEL ARLTSEDSAI YYC (SEQ ID NO: 1389) | ARGVT FDS (SEQ ID NO: 48) | WGQ GTTL TVSS (SEQ ID NO: 425) |
| BL_592989-2044_D6_P8_D06 | QVQLQQSGAELVRP GTSVKISCKAS (SEQ ID NO: 1325) | GYTFT NYW (SEQ ID NO: 4) | LGWV KQRPG HGLEW IGD (SEQ ID NO: 1075) | IYPGG GYT (SEQ ID NO: 6) | NYNEKFKG KATLTADTS SLTSEDSAV YFC (SEQ ID NO: 1178) | ARVTP AS (SEQ ID NO: 8) | WGQ GTTL TVSS (SEQ ID NO: 425) |
| BL_592989-2045_E6_P8_E06 | QIQLQQSGAELVRPG TSVKMSCKAA (SEQ ID NO: 1228) | GYTFT NYW (SEQ ID NO: 4) | IGWVK QRPGH GLEWI GD (SEQ ID NO: 1010) | IHPGG DYS (SEQ ID NO: 1012) | NYNEKFKG KATLTADTS SSTAYMNLS SLTSEDSAIY YC (SEQ ID NO: 1174) | TSRNF AY (SEQ ID NO: 1419) | WGQ GTLV TVSA (SEQ ID NO: 421) |

TABLE 4A-continued

Exemplary Clones-Heavy Chain Sequences

| ID | HFR1 | CDRH1 | HFR2 | CDRH2 | HFR3 | CDRH3 | HFR4 |
|---|---|---|---|---|---|---|---|
| BL_592989-2046_F6_P8_F06 | QIQLQQSGAELVRPG TSVKMSCKAA (SEQ ID NO: 1228) | GYTFT NYW (SEQ ID NO: 4) | IGWVK QRPGH GLEWI GD (SEQ ID NO: 1010) | IHPGG DYS (SEQ ID NO: 1012) | NYNEKFKG KATLTADTS SSTAYMNLS SLTSEDSAIY YC (SEQ ID NO: 1174) | TSRNF AY (SEQ ID NO: 1419) | WGQ GTLV TVSA (SEQ ID NO: 421) |
| BL_592989-2047_G6_P8_G06 | QIQLQQSGAELVRPG TSVKMSCKAA (SEQ ID NO: 1228) | GYTFT NYW (SEQ ID NO: 4) | IGWVK QRPGH GLEWI GD (SEQ ID NO: 1010) | IHPGG GYT (SEQ ID NO: 1015) | NYNEKFKG KATLTADTS SSTAYMQLS SLTSEDSAIY YC (SEQ ID NO: 1177) | TSRNF AY (SEQ ID NO: 1419) | WGQ GTLV TVSA (SEQ ID NO: 421) |
| BL_592989-2048_H6_P8_H06 | QIQLQQSGAELVRPG TSVKMSCKAA (SEQ ID NO: 1228) | GYTFT NYW (SEQ ID NO: 4) | IGWVK QRPGH GLEWI GD (SEQ ID NO: 1010) | IHPGG DYS (SEQ ID NO: 1012) | NYNEKFKG KATLTADTS SSTAYMNLS SLTSEDSAIY YC (SEQ ID NO: 1174) | TSRNF AY (SEQ ID NO: 1419) | WGQ GTLV TVSA (SEQ ID NO: 421) |
| BL_592989-2049_A7_P8_A07 | QIQLQQSGAEMVRP GVSVKISCKGS (SEQ ID NO: 1241) | GYTFT DYA (SEQ ID NO: 19) | MHWV RQSHA KSLEW IGV (SEQ ID NO: 1128) | ISTYSG DV (SEQ ID NO: 46) | SYNQKFKG KATMTVDK SSSTAYMEL ARLTSEDSAI YYC (SEQ ID NO: 1389) | ARGVT FDS (SEQ ID NO: 48) | WGQ GTTL TVSS (SEQ ID NO: 425) |
| BL_592989-2051_C7_P8_C07 | QVQLQQSGAELVRP GTSVKISCKAS (SEQ ID NO: 1325) | GYTFT NYW (SEQ ID NO: 4) | LGWIK QRPGH GLEWI GD (SEQ ID NO: 1074) | IYPGG GYT (SEQ ID NO: 6) | NYNEKFKG KATLTADTS SSTAYMQLS SLTSEDSAV YFC (SEQ ID NO: 1178) | ARVTP AS (SEQ ID NO: 8) | WGQ GTSL TVSS (SEQ ID NO: 424) |
| BL_592989-2052_D7_P8_D07 | QAYLQQSGAELVRS GASVKLSCTAS (SEQ ID NO: 1197) | GFNIK DYY (SEQ ID NO: 977) | IHWVK QRPEQ GLEWI GW (SEQ ID NO: 1017) | IDPDN GET (SEQ ID NO: 1003) | EYAPKFQGK ATMTADTSS NTAHLQLSS LTSEDTAVY YC (SEQ ID NO: 946) | TVFWY GNNYA GFAY (SEQ ID NO: 1420) | WGQ GTLV TVSA (SEQ ID NO: 421) |
| BL_592989-2054_F7_P8_F07 | QVQLQQSGAELVRP GTSVKMSCKAA (SEQ ID NO: 1326) | GYTFT NYW (SEQ ID NO: 4) | IGWVK QRPGH GLEWI GD (SEQ ID NO: 1010) | IHPGG DYS (SEQ ID NO: 1012) | NYNEKFKG KATLTADTS SSTAYMNLS SLTSEDSAIY YC (SEQ ID NO: 1174) | TSRNF AY (SEQ ID NO: 1419) | WGQ GTLV TVSA (SEQ ID NO: 421) |
| BL_592989-2055_G7_P8_G07 | QIQLQQSGAELVRPG TSVKMSCKAA (SEQ ID NO: 1228) | GYTFT NYW (SEQ ID NO: 4) | IGWVK LRPGH GLEWI GD (SEQ ID NO: 1008) | INPGG GYT (SEQ ID NO: 1023) | NYNEKFEGK ATLTADTSS STAYMQLSS LTSEDSAIY YC (SEQ ID NO: 1168) | TSRNF AY (SEQ ID NO: 1419) | WGQ GTLV TVSA (SEQ ID NO: 421) |
| BL_592989-2059_C8_P8_C08 | QIQLQQSGAELVRPG TSVKISCKAS (SEQ ID NO: 1227) | GYTFT NYW (SEQ ID NO: 4) | LGWV KQRPG HGLEW IGD (SEQ ID NO: 1075) | IYPGG GYT (SEQ ID NO: 6) | NYNEKFKG KATLTADTS PSTAYMQLS SLTSEDSAV YFC (SEQ ID NO: 1172) | VRVTP AS (SEQ ID NO: 1443) | WGQ GTTV TVSS (SEQ ID NO: 422) |
| BL_592989-2060_D8_P8_D08 | QIQLQQSGAELVRPG VSLKISCKGS (SEQ ID NO: 1239) | GYTFT DYA (SEQ ID NO: 19) | MQWV RQSHA KSLEW IGV | ISTYSG DA (SEQ ID NO: 21) | IYNQKFKGK ATMTVDKSS STAYLELAR LTSEDSAIY | ARGVT FDY (SEQ ID NO: 23) | WGQ GTTL TVSS (SEQ |

TABLE 4A-continued

Exemplary Clones-Heavy Chain Sequences

| ID | HFR1 | CDRH1 | HFR2 | CDRH2 | HFR3 | CDRH3 | HFR4 |
|---|---|---|---|---|---|---|---|
| | | | (SEQ ID NO: 1137) | | YC (SEQ ID NO: 1034) | | ID NO: 425) |
| BL_592989-2061_E8_P8_E08 | QVQLQQSGAELVRPGTSVKMSCKAA (SEQ ID NO: 1326) | GYTFTNYW (SEQ ID NO: 4) | IGWVKQRPGHGLEWIGD (SEQ ID NO: 1010) | IHPGGGYI (SEQ ID NO: 1014) | NYNEKFTGKATLTADTSSSTAYMQLSSLTSEDSAIYYC (SEQ ID NO: 1184) | VSRNFAN (SEQ ID NO: 1445) | WGQGTPVTVSS (SEQ ID NO: 398) |
| BL_592989-2062_F8_P8_F08 | QVQLQQSGAELVRPGVSLKISCKGS (SEQ ID NO: 1337) | GYTFTDYA (SEQ ID NO: 19) | MHWVRQSHAKNLEWIGV (SEQ ID NO: 1127) | IITYSGDA (SEQ ID NO: 1020) | LYNQKFKGKATMTVDKSSSTAYLELARLTSDDSAIYYC (SEQ ID NO: 1119) | AXGVTFDY (SEQ ID NO: 619) | WGQGTSLTVSS (SEQ ID NO: 424) |
| BL_592989-2063_G8_P8_G08 | PIQLQQSGAELVRPGASVKLSCKAS (SEQ ID NO: 1192) | GYTFTSYW (SEQ ID NO: 157) | MNWVKQRPEQGLEWIGR (SEQ ID NO: 195) | IDPYDSET (SEQ ID NO: 235) | HYNQKFKDKAILTVDKSSSTAYMQLSSLTSEDSAVYYC (SEQ ID NO: 269) | AREASYYYGNAWFA (SEQ ID NO: 601) | YWGQGTLVTALS (SEQ ID NO: 1496) |
| BL_592989-2064_H8_P8_H08 | QIQLQQSGAELVRPGTSVKMSCKAA (SEQ ID NO: 1228) | GYTSTNYW (SEQ ID NO: 997) | IGWVKQRPGHGLEWIGD (SEQ ID NO: 1010) | IHPGGDYS (SEQ ID NO: 1012) | NYNEKFKGKATLTADTSSSTAYMNLSSLTSEDSAIYYC (SEQ ID NO: 1174) | TSRNFAY (SEQ ID NO: 1419) | WGQGTLVTVSA (SEQ ID NO: 421) |
| BL_592989-2065_A9_P8_A09 | QVQLQQSGAELVRPGVSLKISCKGS (SEQ ID NO: 1337) | gytftDYA (SEQ ID NO: 19) | MHWVRQSHAKSLEWIGV (SEQ ID NO: 1128) | ISTYSGDA (SEQ ID NO: 21) | LYNQKFKGKATMTVDKSSSTAYLELARLTSDDSAIYYC (SEQ ID NO: 1119) | ARGVTFDY (SEQ ID NO: 23) | WGQGTSLTVSS (SEQ ID NO: 424) |
| BL_592989-2067_C9_P8_C09 | QIQLQQPGAELVRPGTSVKISCKAS (SEQ ID NO: 1220) | GYAFTNYW (SEQ ID NO: 984) | LGWVKQRPGHGLEWIGD (SEQ ID NO: 1075) | IYPGGGYT (SEQ ID NO: 6) | NYNEKFKGKATLTADTSSSTAYMQLSSLTSEDSAVYFC (SEQ ID NO: 1178) | ARVTPAS (SEQ ID NO: 8) | WGQGTTVTVSS (SEQ ID NO: 422) |
| BL_592989-2068_D9_P8_D09 | QVQLQQSGAELVRPGVSLKISCKGS (SEQ ID NO: 1337) | GYTFTDYA (SEQ ID NO: 19) | MHWVRQSHAKSLEWIGV (SEQ ID NO: 1128) | ISTYSGDA (SEQ ID NO: 21) | IYNQKFKGKATMTVDKSSSTAYLELARLTSDDSAIYYC (SEQ ID NO: 1033) | ARGVTFDY (SEQ ID NO: 23) | WGQGTTVTVSS (SEQ ID NO: 422) |
| BL_592989-2069_E9_P8_E09 | QAYLQQSGAELVRPGTSVKMSCKAA (SEQ ID NO: 1194) | GYTFTNYW (SEQ ID NO: 4) | IGWVKQRPGHGLEWIGD (SEQ ID NO: 1010) | IHPGGDYS (SEQ ID NO: 1012) | NYNEKFKGKATLTADTSSSTAYMNLSSLTSEDSAIYYC (SEQ ID NO: 1174) | TSRNFAY (SEQ ID NO: 1419) | WGQGTLVTVSA (SEQ ID NO: 421) |
| BL_592989-2070_F9_P8_F09 | QIQLQQSGAELVRPGVSVKISCKGS (SEQ ID NO: 1240) | GYTFTDYA (SEQ ID NO: 19) | MHWVKQSHAKSLEWIGV (SEQ ID NO: 1126) | ISTYSGDV (SEQ ID NO: 46) | SYNQKFKGKATMTVDKSSSTAYMELARLTSEDSAIYYC (SEQ ID NO: 1389) | ARGVTFDS (SEQ ID NO: 48) | WGQGTSLTVSS (SEQ ID NO: 424) |

TABLE 4A-continued

Exemplary Clones-Heavy Chain Sequences

| ID | HFR1 | CDRH1 | HFR2 | CDRH2 | HFR3 | CDRH3 | HFR4 |
|---|---|---|---|---|---|---|---|
| BL_592989-2071_G9_P8_G09 | QVQLQQSGAELVRPGTSVRMSCKAA (SEQ ID NO: 1336) | GYTFTNYW (SEQ ID NO: 4) | IGWVKQRPGHGLEWIGD (SEQ ID NO: 1010) | IHPGGGYT (SEQ ID NO: 1015) | NYNEKFKGKATLTADTSSSTAYMQLSSLTSEDSAIYYC (SEQ ID NO: 1177) | TSRNFAY (SEQ ID NO: 1419) | WGQGTLVTVSA (SEQ ID NO: 421) |
| BL_592989-207_4B_10P_8B10 | QVQLQQSGAELVRPGTSVKISCKAS (SEQ ID NO: 1325) | GYTFTNYW (SEQ ID NO: 4) | LGWVKQRPGHGLEWIGD (SEQ ID NO: 1075) | IYPGGGYT (SEQ ID NO: 6) | NYNEKFKGKATLTADTSSSTAYMQLSSLTSEDSAVYFC (SEQ ID NO: 1178) | ARVTPAS (SEQ ID NO: 8) | WGQGTTLTVSS (SEQ ID NO: 425) |
| BL_592989-2076_D10_P8_D10 | QIQLQQPGAELVRPGTSVKISCKAS (SEQ ID NO: 1220) | GYTFTNYW (SEQ ID NO: 4) | LGWVKQRPGHGLEWIGD (SEQ ID NO: 1075) | IYPGGGYT (SEQ ID NO: 6) | NYNEKFKGKATLTADTSSSTAYMQLSSLTSEDSAVYFC (SEQ ID NO: 1178) | ARVTPAS (SEQ ID NO: 8) | WGQGTSLTVSS (SEQ ID NO: 424) |
| BL_592989-2077_E10_P8_E10 | QVQLQQPGAELVRPGTSVKMSCKAA (SEQ ID NO: 1315) | GYTFTNYW (SEQ ID NO: 4) | IGWVKQRPGHGLEWIGD (SEQ ID NO: 1010) | IHPGGGYT (SEQ ID NO: 1015) | NYNEKFEGKATLTADTSSSTAYMQLSSLTSEGSAIYYC (SEQ ID NO: 1169) | TSRNFAY (SEQ ID NO: 1419) | WGQGTLVTVSA (SEQ ID NO: 421) |
| BL_592989-2078_F10_P8_F10 | QIQLQQSGAELVRPGTSVKMSCKAA (SEQ ID NO: 1228) | GYTFTNYW (SEQ ID NO: 4) | IGWVKQRPGHGLEWIGD (SEQ ID NO: 1010) | IHPGGDYS (SEQ ID NO: 1012) | NYNEKFKGKATLTADTSSSTAYMNLSSLTSGDSAIYYC (SEQ ID NO: 1175) | TSRNFAY (SEQ ID NO: 1419) | WGQGTLVTVSA (SEQ ID NO: 421) |
| BL_592989-2079_G10_P8_G10 | QVQLQQSGAELVRPGTSVKMSCKAA (SEQ ID NO: 1326) | GYTFTNYW (SEQ ID NO: 4) | IGWVKQRPGHGLEWIGD (SEQ ID NO: 1010) | FYPGGDYI (SEQ ID NO: 973) | NYNEKFKGKATLTADTSSSTAYMQLSSLTSEDSAIYYC (SEQ ID NO: 1177) | TSRNFAY (SEQ ID NO: 1419) | WGQGTLVTVSA (SEQ ID NO: 421) |
| BL_592989-2080_H10_P8_H10 | QIQLQQSGAELAKPGASVKMSCKAS (SEQ ID NO: 1225) | GYTFTRYW (SEQ ID NO: 992) | MHWVKQRPGQGLEWIGY (SEQ ID NO: 190) | INPSTGYT (SEQ ID NO: 230) | EYNEKFEDKATLTADKSSSTAYMQLSSLTSEDSAVYC (SEQ ID NO: 950) | ARWGNFDY (SEQ ID NO: 617) | WGQGTSLTVSS (SEQ ID NO: 424) |
| BP003-T2P1A7 | QIQLQQSGAEMVRPGVSVKISCKGS (SEQ ID NO: 1241) | GYTFTDYA (SEQ ID NO: 19) | MHWVRQSHAKSLEWIGV (SEQ ID NO: 1128) | ISTYSGDV (SEQ ID NO: 46) | SYNQKFKGKATMTVDKSSSTAYMELARLTSEDSAIYYC (SEQ ID NO: 1389) | ARGVTFDS (SEQ ID NO: 48) | WGQGTTLTVSS (SEQ ID NO: 425) |
| BP003-T2P1C8 | QIQLQQSGAELVRPGTSVKISCKAS (SEQ ID NO: 1227) | GYTFTNYW (SEQ ID NO: 4) | LGWVKQRPGHGLEWIGD (SEQ ID NO: 1075) | IYPGGGYT (SEQ ID NO: 6) | NYNEKFKGKATLTADTSPSTAYMQLSSLTSEDSAVYFC (SEQ ID NO: 1172) | VRVTPAS (SEQ ID NO: 1443) | WGQGTTVTVSS (SEQ ID NO: 422) |
| BP003-T2P1F4 | QVQLQQPGAELVRPGTSVKMSCKAA (SEQ ID NO: 1315) | GYTFTNYW (SEQ ID NO: 4) | IGWVKQRPGHGLEWI | IHPGGGYT (SEQ ID | NYNEKFKGKATLTADTSSSTAYMQLS | TSRNFAY (SEQ ID | WGQGTLVTVSA |

TABLE 4A-continued

Exemplary Clones-Heavy Chain Sequences

| ID | HFR1 | CDRH1 | HFR2 | CDRH2 | HFR3 | CDRH3 | HFR4 |
|---|---|---|---|---|---|---|---|
| | | NO: 4) | GD (SEQ ID NO: 1010) | NO: 1015) | SLTSEDSAIY YC (SEQ ID NO: 1177) | NO: 1419) | (SEQ ID NO: 421) |
| BP003-T2P1G2 | QVQLQQSGAELVRP GTSLKMSCKAA (SEQ ID NO: 1324) | GYTFT NYW (SEQ ID NO: 4) | IGWVK QRPGH GLEWI GD (SEQ ID NO: 1010) | IHPGG GYT (SEQ ID NO: 1015) | NYNEKFKG KATLTADTS SSTTYMQLS SLTSEDSAIY YC (SEQ ID NO: 1181) | TSRNF AY (SEQ ID NO: 1419) | WGQ GTPV TVSS (SEQ ID NO: 398) |
| BP003-T2P1G4 | QIQLQQSGAELVRPG TSLKMSCKAA (SEQ ID NO: 1226) | GYTFT NYW (SEQ ID NO: 4) | IGWVK QRPGH GLEWI GD (SEQ ID NO: 1010) | IHPGG GYT (SEQ ID NO: 1015) | NYNEKFKG KATLTADTS SSTTYMQLS SLTSEDSAIY YC (SEQ ID NO: 1181) | TSRNF AY (SEQ ID NO: 1419) | WGQ GTLV TVSA (SEQ ID NO: 421) |
| BP003-T2P1G7 | QIQLQQSGAELVRPG TSVKMSCKAA (SEQ ID NO: 1228) | GYTFT NYW (SEQ ID NO: 4) | IGWVK LRPGH GLEWI GD (SEQ ID NO: 1008) | INPGG GYT (SEQ ID NO: 1023) | NYNEKFEGK ATLTADTSS STAYMQLSS LTSEDSAIY YC (SEQ ID NO: 1168) | TSRNF AY (SEQ ID NO: 1419) | WGQ GTLV TVSA (SEQ ID NO: 421) |
| BP003-T2P1H5 | QIQLQQSGAELVRPG TSVKMSCKAA (SEQ ID NO: 1228) | GYTFT NYW (SEQ ID NO: 4) | IGWVK QRPGH GLEWV GD (SEQ ID NO: 1011) | IHPGG GYT (SEQ ID NO: 1015) | NYNEKFKG KATLTADTS SSTAYMQLS SLTSEDSAIY YC (SEQ ID NO: 1177) | TSRNF AY (SEQ ID NO: 1419) | WGQ GTLV TVSA (SEQ ID NO: 421) |
| BP003T3P2-1 | QVQLQQSGAELVRP GVSLKISCKGS (SEQ ID NO: 1337) | GYTFT DYA (SEQ ID NO: 19) | MHWV RQSHA KSLEW IGV (SEQ ID NO: 1128) | ISTYSG DA (SEQ ID NO: 21) | IYNQKFKGK ATMTVDKSS STAYLELAR LTSDDSAIY YC (SEQ ID NO: 1033) | ARGVT FDY (SEQ ID NO: 23) | WGQ GTTV TVSS (SEQ ID NO: 422) |
| BP003T3P2-10 | QVQLQQSGAELVRP GVSLKISCKGS (SEQ ID NO: 1337) | GYTFT DYA (SEQ ID NO: 19) | MHWV RQSHA KSLEW IGV (SEQ ID NO: 1128) | ISTYSG DA (SEQ ID NO: 21) | LYNQKFKG KATMTVDK SSSTAYLEL ARLTSDDSA IYYC (SEQ ID NO: 1119) | ARGVT FDY (SEQ ID NO: 23) | WGQ GTTL TVSS (SEQ ID NO: 425) |
| BP003T3P2-11 | QVQLQQSGAELVRP GVSLKISCKGS (SEQ ID NO: 1337) | GYTFT DYA (SEQ ID NO: 19) | MHWV RQSHA KSLEW IGV (SEQ ID NO: 1128) | ISTYSG DA (SEQ ID NO: 21) | LYNQKFKG KATMTVDK SSSTAYLEL ARLTSDDSA IYYC (SEQ ID NO: 1119) | ARGVT FDY (SEQ ID NO: 23) | WGQ GTTL TVSS (SEQ ID NO: 425) |
| BP003T3P2-12 | QAYLQQSGAELVRP GVSLKISCKGS (SEQ ID NO: 1195) | GYTFT DYA (SEQ ID NO: 19) | MHWV RQSHA KSLEW IGV (SEQ ID NO: 1128) | ISTYSG DA (SEQ ID NO: 21) | LYNQKFGK ATMTVDKSS STAYLELAR LTSDDSAIY YC (SEQ ID NO: 1118) | ARGVT FDY (SEQ ID NO: 23) | WGQ GTTL TVSS (SEQ ID NO: 425) |
| BP003T3P2-13 | QVQLQQSGAELVRP GVSLKISCKGS (SEQ ID NO: 1337) | GYTFT DYA (SEQ ID NO: 19) | MHWV RQSHA KSLEW IGV (SEQ ID NO: 1128) | ISTYSG DA (SEQ ID NO: 21) | IYNQKFGKA TMTVDKSSS TAYLELARL TSDDSAIYY C (SEQ ID NO: 1031) | ARGVT FDY (SEQ ID NO: 23) | WGQ GTTV TVSS (SEQ ID NO: 422) |

TABLE 4A-continued

Exemplary Clones-Heavy Chain Sequences

| ID | HFR1 | CDRH1 | HFR2 | CDRH2 | HFR3 | CDRH3 | HFR4 |
|---|---|---|---|---|---|---|---|
| BP003T3P2-14 | QIQLQQPGAELVRPGVSLKISCKGS (SEQ ID NO: 1223) | GYTFTDYA (SEQ ID NO: 19) | MHWVRQSHAKSLEWIGV (SEQ ID NO: 1128) | ISTYSGDA (SEQ ID NO: 21) | IYNQKFGKATMTVDKSSSTAYLELARLTSDDSAIYYC (SEQ ID NO: 1031) | ARGVTFDY (SEQ ID NO: 23) | WGQGTTVTVSS (SEQ ID NO: 422) |
| BP003T3P2-15 | QVQLQQSGAELVRPGVSLKISCKGS (SEQ ID NO: 1337) | GYTFTDYA (SEQ ID NO: 19) | MHWVRQSHAKSLEWIGV (SEQ ID NO: 1128) | ISTYSGDA (SEQ ID NO: 21) | IYNQKFGKATMTVDKSSSTAYLELARLTSDDSAIYYC (SEQ ID NO: 1031) | ARGVTFDY (SEQ ID NO: 23) | WGQGTTVTVSS (SEQ ID NO: 422) |
| BP003T3P2-16 | EVQLQQSGAELVRPGVSLKISCKGS (SEQ ID NO: 940) | GYTFTDYA (SEQ ID NO: 19) | MHWVRQSHAKSLEWIGV (SEQ ID NO: 1128) | ISTYSGDA (SEQ ID NO: 21) | IYNQKFGKATMTVDKSSSTAYLELARLTSDDSAIYYC (SEQ ID NO: 1031) | ARGVTFDY (SEQ ID NO: 23) | WGQGTTLTVSS (SEQ ID NO: 425) |
| BP003T3P2-17 | QIQLQQSGAELVRPGVSLKISCKGS (SEQ ID NO: 1239) | GYTFTDYA (SEQ ID NO: 19) | MHWVRQSHAKSLEWIGV (SEQ ID NO: 1128) | ISTYSGDA (SEQ ID NO: 21) | IYNQKFGKATMTVDKSSSTAYLELARLTSDDSAIYYC (SEQ ID NO: 1031) | ARGVTFDY (SEQ ID NO: 23) | WGQGTSLTVSS (SEQ ID NO: 424) |
| BP003T3P2-18 | QVQLQQSGAELVRPGVSLKISCKGS (SEQ ID NO: 1337) | GYTFTDYA (SEQ ID NO: 19) | MHWVRQSHAKSLEWIGV (SEQ ID NO: 1128) | ISTYSGDA (SEQ ID NO: 21) | IYNQKFGKATMTVDKSSSTAYLELARLTSDDSAIYYC (SEQ ID NO: 1031) | ARGVTFDY (SEQ ID NO: 23) | WGQGTTLTVSS (SEQ ID NO: 425) |
| BP003T3P2-19 | QVQLQQSGAELVRPGVSLKISCKGS (SEQ ID NO: 1337) | GYTFTDYA (SEQ ID NO: 19) | MHWVRQSHAKSLEWIGV (SEQ ID NO: 1128) | ISTYSGDA (SEQ ID NO: 21) | IYNQKFGKATMTVDKSSSTAYLELARLTSEDSAIYYC (SEQ ID NO: 1032) | ARGVTFDY (SEQ ID NO: 23) | WGQGTTLTVSS (SEQ ID NO: 425) |
| BP003T3P2-2 | QVQLQQSGAELVRPGVSLKISCKGS (SEQ ID NO: 1337) | GYTFTDYA (SEQ ID NO: 19) | MHWVRQSHAKSLEWIGV (SEQ ID NO: 1128) | ISTYSGDA (SEQ ID NO: 21) | IYNQKFGKATMTVDKSSTAYLELARLTSDDSAIYYC (SEQ ID NO: 1033) | ARGVTFDY (SEQ ID NO: 23) | WGQGTTVTVSS (SEQ ID NO: 422) |
| BP003T3P2-20 | QVQLQQSGAGLVRPGVSLKISCKGS (SEQ ID NO: 1341) | GYTFTDYA (SEQ ID NO: 19) | MHWVRQSHAKSLEWIGV (SEQ ID NO: 1128) | ISTYSGDA (SEQ ID NO: 21) | IYNQKFGKATMTVDKSSSTAYLELARLTSEDSAIYYC (SEQ ID NO: 1032) | ARGVTFDY (SEQ ID NO: 23) | WGQGTTLTVSS (SEQ ID NO: 425) |
| BP003T3P2-21 | QVQLQQSGAELVRPGVSLKISCKGS (SEQ ID NO: 1337) | GYTFTDYA (SEQ ID NO: 19) | MQWVRQSHAKSLEWIGV (SEQ ID NO: 1137) | ISTYSGDA (SEQ ID NO: 21) | IYNQKFGKATMTVDKSSSTAYLELARLTSEDSAIYYC (SEQ ID NO: 1032) | ARGVTFDY (SEQ ID NO: 23) | WGQGTSLTVSS (SEQ ID NO: 424) |
| BP003T3P2-22 | QVQLQQSGAELVRPGVSLKISCKGS (SEQ ID NO: 1337) | GYTFTDYA (SEQ ID NO: 19) | MHWVRQSHAKSLEW (SEQ ID | ISTYSGDA | IYNQKFDKATMTVDKSSSTAYLELARL | ARGVTFDY (SEQ ID | WGQGTTLTVSS |

TABLE 4A-continued

Exemplary Clones-Heavy Chain Sequences

| ID | HFR1 | CDRH1 | HFR2 | CDRH2 | HFR3 | CDRH3 | HFR4 |
|---|---|---|---|---|---|---|---|
| | | GYTFT DYA (SEQ ID NO: 19) | MHWV KQSHA KSLEW IGV (SEQ ID NO: 1128) | ISTYSG DV (SEQ ID NO: 21) | TSEDSAIYY C (SEQ ID NO: 1030) | (SEQ ID NO: 23) | (SEQ ID NO: 425) |
| BP003T3P2-23 | QVQLQQSGAELVRP GVSVKISCKGS (SEQ ID NO: 1338) | GYTFT DYA (SEQ ID NO: 19) | MHWV KQSHA KSLEW IGV (SEQ ID NO: 1126) | ISTYSG DV (SEQ ID NO: 46) | SYNQKFKG KATMTVDK SSSTAYMEL ARLTSEDSAI YYC (SEQ ID NO: 1389) | ARGVT FDS (SEQ ID NO: 48) | WGQ GTTL TVSS (SEQ ID NO: 425) |
| BP003T3P2-24 | QVQLQQSGAELVRP GVSVKISCKGS (SEQ ID NO: 1338) | GYTFT DYA (SEQ ID NO: 19) | MHWV KQSHA KSLEW IGV (SEQ ID NO: 1126) | ISTYSG DV (SEQ ID NO: 46) | SYNQKFKG KATMTVDK SSSTAYMEL ARLTSEDSAI YYC (SEQ ID NO: 1389) | ARGVT FDS (SEQ ID NO: 48) | WGQ GTTL TVSS (SEQ ID NO: 425) |
| BP003T3P2-25 | QIQLQQSGAELVRPG VSVKISCKGS (SEQ ID NO: 1240) | GYTFT DYA (SEQ ID NO: 19) | MHWV KQSHA KSLEW IGV (SEQ ID NO: 1126) | ISTYSG DV (SEQ ID NO: 46) | SYNQKFKG KATMTVDK SSSTAYMEL ARLTSEDSAI YYC (SEQ ID NO: 1389) | ARGVT FDS (SEQ ID NO: 48) | WGQ GTSL TVSS (SEQ ID NO: 424) |
| BP003T3P2-26 | QVQLQQSGAELVRP GISVKISCKGS (SEQ ID NO: 1323) | GYTFT DYA (SEQ ID NO: 19) | MRWV KQSHA KSLEW IGV (SEQ ID NO: 1138) | IXTYSG DV (SEQ ID NO: 1029) | SYNQKFGK ATMTVDKSS STAYMELAR LTSEDSAIY YC (SEQ ID NO: 1387) | ARGVT FDS (SEQ ID NO: 48) | WGR GTSL TVSS (SEQ ID NO: 1454) |
| BP003T3P2-27 | QVQLQQSGAELVRP GISVKISCKGS (SEQ ID NO: 1323) | GYTFT DYG (SEQ ID NO: 987) | MRWV KQSPA XSLEW IGV (SEQ ID NO: 1139) | ISTYSG DV (SEQ ID NO: 46) | NYNQKFGK ATMTVDKSS STAYMELAR LTSEDSAIY YC (SEQ ID NO: 1190) | ARGVT FDS (SEQ ID NO: 48) | XGR GTXL TVSS (SEQ ID NO: 1474) |
| BP003T3P2-28 | QVQLQQSGAELAKP GASVKMSCKAS (SEQ ID NO: 473) | GYTFT RYW (SEQ ID NO: 992) | IHWVK QRPGQ DLEWI GY (SEQ ID NO: 1018) | INPRTD YT (SEQ ID NO: 1025) | EYNQKFKD KATLTADKS SSTAYMQLS SLTSDDSAV YYC (SEQ ID NO: 955) | ARHGY FDY (SEQ ID NO: 611) | WGQ GTTL TVSS (SEQ ID NO: 425) |
| BP003T3P2-29 | QVQLQQPGAELAKP GASVKMSCKAS (SEQ ID NO: 114) | GYTFT RYW (SEQ ID NO: 992) | IHWVK QRPGQ DLEWI GY (SEQ ID NO: 1018) | INPRTD YT (SEQ ID NO: 1025) | EYNQKFKD KATLTADKS SSTAYMQLS SLTSDDSAV YYC (SEQ ID NO: 955) | ARHGY FDY (SEQ ID NO: 611) | WGQ GTTL TVSS (SEQ ID NO: 425) |
| BP003T3P2-3 | QVQLQQSGAELVRP GVSLKISCKGS (SEQ ID NO: 1337) | GYTFT DYA (SEQ ID NO: 19) | MHWV RQSHA KSLEW IGV (SEQ ID NO: 1128) | ISTYSG DA (SEQ ID NO: 21) | IYNQKFKGK ATMTVDKSS STAYLELAR LTSDDSAIY C (SEQ ID NO: 1033) | ARGVT FDY (SEQ ID NO: 23) | WGQ GTTV TVSS (SEQ ID NO: 422) |
| BP003T3P2-30 | QVQLQQPGAELAKP GASVKMSCKAS (SEQ ID NO: 114) | GYTFT RYW (SEQ ID NO: 992) | IHWVK QRPGQ DLEWI GY (SEQ ID NO: 1018) | INPRTD YT (SEQ ID NO: 1025) | EYNQKFKD KATLTADKS SSTAYMQLS SLTSDDSAV YYC (SEQ ID NO: 955) | ARHGY FDY (SEQ ID NO: 611) | WGQ GTTL TVSS (SEQ ID NO: 425) |

TABLE 4A-continued

Exemplary Clones-Heavy Chain Sequences

| ID | HFR1 | CDRH1 | HFR2 | CDRH2 | HFR3 | CDRH3 | HFR4 |
|---|---|---|---|---|---|---|---|
| BP003T3P2-31 | QVQLQQPGAELAKP GASVKMSCKAS (SEQ ID NO: 114) | GYTFT RYW (SEQ ID NO: 992) | IHWVK QRPGQ DLEWI GY (SEQ ID NO: 1018) | INPRTD YT (SEQ ID NO: 1025) | EYNQKFKD KATLTADKS SSTAYMQLS SLTSDDSAV YYC (SEQ ID NO: 955) | ARHGY FDY (SEQ ID NO: 611) | WGQ GTTL TVSS (SEQ ID NO: 425) |
| BP003T3P2-32 | QVQLQQSGAELAKP GASVKMSCKAS (SEQ ID NO: 473) | GYTFT RYW (SEQ ID NO: 992) | IHWVK QRPGQ DLEWI GY (SEQ ID NO: 1018) | INPRTD YT (SEQ ID NO: 1025) | EYNQKFDK ATLTADKSS STAYMQLXS LTSDDSAVY YC (SEQ ID NO: 952) | ARHGY FDY (SEQ ID NO: 611) | WGQ GTTL TVSS (SEQ ID NO: 425) |
| BP003T3P2-33 | QVQLQQPGAELAKP GASVKMSCKAS (SEQ ID NO: 114) | GYTFT RYW (SEQ ID NO: 992) | IHWVK QRPGQ DLEWI GY (SEQ ID NO: 1018) | INPRTD YT (SEQ ID NO: 1025) | EYNQKFDK ATLTADKSS STAYMQLSS LTSDDSAVY YC (SEQ ID NO: 951) | ARHGY FDY (SEQ ID NO: 611) | WGQ GTTL TVSS (SEQ ID NO: 425) |
| BP003T3P2-34 | QVQLQQPGAELAKP GASVKMSCKAS (SEQ ID NO: 114) | GYTFT RYW (SEQ ID NO: 992) | IHWVK QRPGQ DLEWI GY (SEQ ID NO: 1018) | INPRTD YT (SEQ ID NO: 1025) | EYNQKFDK ATLTADKSS STAYMQLSS LTSDDSAVY YC (SEQ ID NO: 951) | ARHGY FDY (SEQ ID NO: 611) | WGQ GTTL TVSS (SEQ ID NO: 425) |
| BP003T3P2-35 | QVQLQQSGAELAKP GASVKMSCKAS (SEQ ID NO: 473) | GYTFT RYW (SEQ ID NO: 992) | IHWVK QRPGQ DLEWI GY (SEQ ID NO: 1018) | INPRTD YT (SEQ ID NO: 1025) | EYNQKFDK ATLTADKSS STAYMQLSS LTSDDSAVY YC (SEQ ID NO: 951) | ARHGY FDY (SEQ ID NO: 611) | WGQ GTTL TVSS (SEQ ID NO: 425) |
| BP003T3P2-36 | QVQLQQSGAELAKP GASVKMSCKAS (SEQ ID NO: 473) | GYTFT RYW (SEQ ID NO: 992) | MHWV KQRPG QDLEW IGY (SEQ ID NO: 1125) | INPRTD YT (SEQ ID NO: 1025) | EYNQKFDK ATLTADKSS STAYMQLSS LTSDDSAVY YC (SEQ ID NO: 951) | ARHGY FDY (SEQ ID NO: 611) | WGQ GTTL TVSS (SEQ ID NO: 425) |
| BP003T3P2-37 | QIQLQQPGAELAKPG ASVKMSCKAS (SEQ ID NO: 1218) | GYTFT RYW (SEQ ID NO: 992) | MHWV KQRPG QDLEW IGY (SEQ ID NO: 1125) | INPRTD YT (SEQ ID NO: 1025) | EYNQKFDK ATLTADKSS STAYMQLSS LTSDDSAVY YC (SEQ ID NO: 951) | ARHGY FDY (SEQ ID NO: 611) | WGQ GTTV TVSS (SEQ ID NO: 422) |
| BP003T3P2-38 | QVQMKQSGAELAKP GASVKMSCKAS (SEQ ID NO: 1343) | GYTFT RYW (SEQ ID NO: 992) | MHWV KQRPG QGLEW IGY (SEQ ID NO: 190) | INPSSD YT (SEQ ID NO: 1026) | EYNQKFKD KATLTADKS SSTAYMQLS SLTSEDSAV YYC (SEQ ID NO: 265) | ARGTV WDY (SEQ ID NO: 608) | WGQ GTTV TVSS (SEQ ID NO: 422) |
| BP003T3P2-39 | QIQLQQSGAELAKPG ASVKMSCKAS (SEQ ID NO: 1225) | GYTFT RYW (SEQ ID NO: 992) | MHWV KQRPG QGLEW IGY (SEQ ID NO: 190) | INPSTD YT (SEQ ID NO: 1027) | EYNEKFDKA TLTADKSSS TAYMQLSSL TSEDSAVYF C (SEQ ID NO: 949) | VRSPIL DY (SEQ ID NO: 1442) | WGQ GTSL TVSS (SEQ ID NO: 424) |
| BP003T3P2-4 | QVQLQQSGAELVRP GVSLKISCKGS (SEQ ID NO: 1337) | GYTFT DYA (SEQ ID NO: | MHWV RQSHA KSLEW (SEQ ID | ISTYSG DA | IYNQKFKGK ATMTVDKSS STAYLELAR | ARGVT FDY (SEQ ID | WGQ GTTV TVSS |

TABLE 4A-continued

Exemplary Clones-Heavy Chain Sequences

| ID | HFR1 | CDRH1 | HFR2 | CDRH2 | HFR3 | CDRH3 | HFR4 |
|---|---|---|---|---|---|---|---|
| | | NO: 19) | IGV (SEQ ID NO: 1128) | NO: 21) | LTSDDSAIY YC (SEQ ID NO: 1033) | NO: 23) | (SEQ ID NO: 422) |
| BP003T3P2-40 | QVQLQQSGAELVRP GTSVKISCKAS (SEQ ID NO: 1325) | GYTFT NYW (SEQ ID NO: 4) | LGWV KQRPG HGLEW IGD (SEQ ID NO: 1075) | IYPGG GYT (SEQ ID NO: 6) | NYNEKFKG KATLTADTS SSTAYMQLS SLTSEDSAV YFC (SEQ ID NO: 1178) | ARVTP AS (SEQ ID NO: 8) | WGQ GTSL TVSS (SEQ ID NO: 424) |
| BP003T3P2-41 | QAYLQQSGAELVRP GTSVKISCKAS (SEQ ID NO: 1193) | GYTFT NYW (SEQ ID NO: 4) | LGWV KQRPG HGLEW IGD (SEQ ID NO: 1075) | IYPGG GYT (SEQ ID NO: 6) | NYNEKFKG KATLTADTS SSTAYMQLS SLTSEDSAV YFC (SEQ ID NO: 1178) | ARVTP AS (SEQ ID NO: 8) | WGQ GTSL TVSS (SEQ ID NO: 424) |
| BP003T3P2-42 | QVQLQQPGAELVRP GTSVKISCKAS (SEQ ID NO: 1314) | GYTFT NYW (SEQ ID NO: 4) | LGWV KQRPG HGLEW IGD (SEQ ID NO: 1075) | IYPGG GYT (SEQ ID NO: 6) | NYNEKFKG KATLTADTS SSTAYMQLS SLTSEDSAV YFC (SEQ ID NO: 1178) | ARVTP AS (SEQ ID NO: 8) | WGQ GTTL TVSS (SEQ ID NO: 425) |
| BP003T3P2-43 | QVQLQQSGAELVRP GTSVKISCKAS (SEQ ID NO: 1325) | GYTFT NYW (SEQ ID NO: 4) | LGWV KQRPG HGLEW IGD (SEQ ID NO: 1075) | IYPGG GYT (SEQ ID NO: 6) | NYNEKFKG KATLTADTS SSTAYMQLS SLTSEDSAV YFC (SEQ ID NO: 1178) | ARVTP AS (SEQ ID NO: 8) | WGQ GTTV TVSS (SEQ ID NO: 422) |
| BP003T3P2-44 | QVQLQPGAELVRPG TSVKISCKAS (SEQ ID NO: 1313) | GYTFT NYW (SEQ ID NO: 4) | LGWV KQRPG HGLEW IGD (SEQ ID NO: 1075) | IYPGG GYT (SEQ ID NO: 6) | NYNEKFKG KATLTADTS SSTAYMQLS SLTSEDSAV YFC (SEQ ID NO: 1178) | ARVTP AS (SEQ ID NO: 8) | WGQ GTTV TVSS (SEQ ID NO: 422) |
| BP003T3P2-45 | QVQLQQSGAELVRP GTSVKISCKAS (SEQ ID NO: 1325) | GYTFT NYW (SEQ ID NO: 4) | LGWV KQRPG HGLEW IGD (SEQ ID NO: 1075) | IYPGG GYT (SEQ ID NO: 6) | NYNEKFKG KATLTADTS SSTAYMQLS SLTSEDSAV YFC (SEQ ID NO: 1178) | ARVTP AS (SEQ ID NO: 8) | WGQ GTTL TVSS (SEQ ID NO: 425) |
| BP003T3P2-46 | QVQLQQSGAELVRP GTSVKISCKAS (SEQ ID NO: 1325) | GYTFT NYW (SEQ ID NO: 4) | LGWV KQRPG HGLEW IGD (SEQ ID NO: 1075) | IYPGG GYT (SEQ ID NO: 6) | NYNEKFGK ATLTADTSS STAYMQLSS LTSEDSAVY FC (SEQ ID NO: 1170) | ARVTP AS (SEQ ID NO: 8) | WGQ GTTV TVSS (SEQ ID NO: 422) |
| BP003T3P2-47 | QVQLQQSGAELVRP GASVKISCKAS (SEQ ID NO: 1322) | GYTFT NYW (SEQ ID NO: 4) | LGWV KQRPG HGLEW IGD (SEQ ID NO: 1075) | IYPGG GYT (SEQ ID NO: 6) | NYNEKFGK ATLTADTSS STAYMQLSS LTSEDSAVY FC (SEQ ID NO: 1170) | ARVTP AS (SEQ ID NO: 8) | WGQ GTTL TVSS (SEQ ID NO: 425) |
| BP003T3P2-48 | QVQLQQSGAELVRP GTSVKISCKAS (SEQ ID NO: 1325) | GYTFT NYW (SEQ ID NO: 4) | LGWIK QRPGH GLEWI GD (SEQ ID NO: 1074) | IYPGG GYT (SEQ ID NO: 6) | NYNEKFGK ATLTADTSS STAYMQLSS LTSEDSAVY FC (SEQ ID NO: 1170) | ARVTP AS (SEQ ID NO: 8) | WGQ GTSL TVSS (SEQ ID NO: 424) |

TABLE 4A-continued

Exemplary Clones-Heavy Chain Sequences

| ID | HFR1 | CDRH1 | HFR2 | CDRH2 | HFR3 | CDRH3 | HFR4 |
|---|---|---|---|---|---|---|---|
| BP003T3P2-49 | QVQLQQSGAELVRP GTSVKISCKAS (SEQ ID NO: 1325) | GYTFT NYW (SEQ ID NO: 4) | LGWV KQRPG HGLEW IGD (SEQ ID NO: 1075) | IYPGG GYT (SEQ ID NO: 6) | NYNEKFGK ATLTADTSS STAYMQLSS LTSEDSAVY FC (SEQ ID NO: 1170) | ARVTP AS (SEQ ID NO: 8) | WGQ GTTV TVSS (SEQ ID NO: 422) |
| BP003T3P2-5 | QIQLQQSGAELVRPG VSLKISCKGS (SEQ ID NO: 1239) | GYTFT DYA (SEQ ID NO: 19) | MHWV RQSHA KSLEW IGV (SEQ ID NO: 1128) | ISTYSG DA (SEQ ID NO: 21) | IYNQKFKGK ATMTVDKSS STAYLELAR LTSDDSAIY YC (SEQ ID NO: 1033) | ARGVT FDY (SEQ ID NO: 23) | WGQ GTSL TVSS (SEQ ID NO: 424) |
| BP003T3P2-50 | QVQLQQSGAELVRP GTSVKISCKAS (SEQ ID NO: 1325) | GYTFT NYW (SEQ ID NO: 4) | LGWV KQRPG HGLEW IGD (SEQ ID NO: 1075) | IYPGG GYT (SEQ ID NO: 6) | NYNEKFGK ATLTADTSS STAYMQLSS LTSEDSAVY FC (SEQ ID NO: 1170) | ARVTP AS (SEQ ID NO: 8) | WGQ GTTL TVSS (SEQ ID NO: 425) |
| BP003T3P2-51 | QVQLQQSGAELVRP GTSVKISCKAS (SEQ ID NO: 1325) | GYTFT NYW (SEQ ID NO: 4) | LGWV KQRPG HGLEW IGD (SEQ ID NO: 1075) | IYPGG GYT (SEQ ID NO: 6) | NYNEKFGK ATLTADTSS STAYMQLSS LTSEDSAVY FC (SEQ ID NO: 1170) | ARVTP AS (SEQ ID NO: 8) | WGQ GTTV TVSS (SEQ ID NO: 422) |
| BP003T3P2-52 | QVQLQQSGAELVRP GTSVKISCKAS (SEQ ID NO: 1325) | GYTFT NYW (SEQ ID NO: 4) | LGWV KQRPG HGLEW IGD (SEQ ID NO: 1075) | IYPGG GYT (SEQ ID NO: 6) | NYNEKFGK ATLTADTSS STAYMQLSS LTSEDSAVY FC (SEQ ID NO: 1170) | ARVTP AS (SEQ ID NO: 8) | WGQ GTTV TVSS (SEQ ID NO: 422) |
| BP003T3P2-53 | QVQLQQSGAELVRP GTSVKISCKAS (SEQ ID NO: 1325) | GYTFT NYW (SEQ ID NO: 4) | LGWV KQRPG HGLEW IGD (SEQ ID NO: 1075) | IYPGG GYT (SEQ ID NO: 6) | NYNEKFGK ATLTADTSS STAYMQLSS LTSEDSAVY FC (SEQ ID NO: 1170) | ARVTP AS (SEQ ID NO: 8) | WGQ GTTL TVSS (SEQ ID NO: 425) |
| BP003T3P2-54 | QVQLQQSGAELVRP GTSVKISCKAS (SEQ ID NO: 1325) | GYTFT NYW (SEQ ID NO: 4) | LGWV KQRPG HGLEW IGD (SEQ ID NO: 1075) | IYPGG GYA (SEQ ID NO: 1035) | NYNEKFGK ATLTADTSS STAYMQLSS LTSEDSAVY FC (SEQ ID NO: 1170) | ARVTP AS (SEQ ID NO: 8) | WGQ GTTL TVSS (SEQ ID NO: 425) |
| BP003T3P2-55 | QIQLQQSGAELVRPG TSVKISCKAS (SEQ ID NO: 1227) | GYTFT NYW (SEQ ID NO: 4) | LGWV KQRPG HGLEW IGD (SEQ ID NO: 1075) | IYPGG GYT (SEQ ID NO: 6) | NYNEKFGK ATLTADTSS STAYMQLSS LTSEDSAVY FC (SEQ ID NO: 1170) | ARVTP AS (SEQ ID NO: 8) | WGQ GTTL TVSS (SEQ ID NO: 425) |
| BP003T3P2-56 | QIQLQQSGAELVRPG TSVKISCKAS (SEQ ID NO: 1227) | GYTFT NYW (SEQ ID NO: 4) | LGWV KQRPG HGLEW IGD (SEQ ID NO: 1075) | IYPGG GYT (SEQ ID NO: 6) | NYNEKFGK ATLTADTSS STAYMQLSS LTSEDSAVY FC (SEQ ID NO: 1170) | ARVTP AS (SEQ ID NO: 8) | WGQ GTSL TVSS (SEQ ID NO: 424) |
| BP003T3P2-57 | QIQLQQSGAELVRPG TSVKISCKAS (SEQ ID NO: 1227) | GYTFT NYW (SEQ ID NO: 4) | LGWV KQRPG HGLEW | IYPGG GYT (SEQ | NYNEKFGK ATLTADTSS STAYMQLSS | ARVTP AS (SEQ ID | WGQ GTTL TVSS |

TABLE 4A-continued

Exemplary Clones-Heavy Chain Sequences

| ID | HFR1 | CDRH1 | HFR2 | CDRH2 | HFR3 | CDRH3 | HFR4 |
|---|---|---|---|---|---|---|---|
| | | NO: 4) | IGD (SEQ ID NO: 1075) | NO: 6) | LTSEDSAVY FC (SEQ ID NO: 1170) | NO: 8) | (SEQ ID NO: 425) |
| BP003T3P2-58 | QIQLQQSGAELVRPG TSVKISCKAS (SEQ ID NO: 1227) | GYTFT NYW (SEQ ID NO: 4) | LGWV KQRPG HGLEW IGD (SEQ ID NO: 1075) | IYPGG GYT (SEQ ID NO: 6) | NYNEKFGK ATLTADTSS STAYMQLSS LTSEDSAVY FC (SEQ ID NO: 1170) | ARVTP AS (SEQ ID NO: 8) | WGQ GTTL TVSS (SEQ ID NO: 424) |
| BP003T3P2-59 | QIQLQQSGAELVRPG TSVKISCKAS (SEQ ID NO: 1227) | GYTFT NYW (SEQ ID NO: 4) | LGWV KQRPG HGLEW IGD (SEQ ID NO: 1075) | IYPGG GYT (SEQ ID NO: 6) | NYNEKFKK ATLTADTSS VTAYMQLSS LTSEDSAVY FC (SEQ ID NO: 1183) | ARVTP AS (SEQ ID NO: 8) | WGQ GTTV TVSS (SEQ ID NO: 422) |
| BP003T3P2-6 | EVQLQQSGAELVRP GVSLKISCKGS (SEQ ID NO: 940) | GYTFT DYA (SEQ ID NO: 19) | MHWV RQSHA KSLEW IGV (SEQ ID NO: 1128) | ISTYSG DA (SEQ ID NO: 21) | IYNQKFKGK ATMTVDKSS STAYLELAR LTSDDSAIY YC (SEQ ID NO: 1033) | ARGVT PDY (SEQ ID NO: 23) | WGQ GTTL TVSS (SEQ ID NO: 425) |
| BP003T3P2-60 | QVQLQQSGAELVRP GTSVKISCKAS (SEQ ID NO: 1325) | GYTFT NYW (SEQ ID NO: 4) | LGWV KQRPG HGLEW IGD (SEQ ID NO: 1075) | IYPGG GYT (SEQ ID NO: 6) | NYNEKFKK ATLTADTSS STAYMQLSS LTSEDSAVY FC (SEQ ID NO: 1182) | ARVTP AS (SEQ ID NO: 8) | WGQ GTTL TVSS (SEQ ID NO: 425) |
| BP003T3P2-61 | QVQLQQSGAELVRP GTSVKISCKAS (SEQ ID NO: 1325) | GYTFT NYW (SEQ ID NO: 4) | LGWV KQRPG HGLEW IGD (SEQ ID NO: 1075) | IYPGG GYT (SEQ ID NO: 6) | NYNEKFKK ATLTADTSS STAYMQLSS LTSEDSAVY FC (SEQ ID NO: 1182) | ARVTP AS (SEQ ID NO: 8) | WGQ GTSL TVSS (SEQ ID NO: 424) |
| BP003T3P2-62 | EVQLQESGADLMKP GASVKISCKAS (SEQ ID NO: 939) | GYTFS NYW (SEQ ID NO: 986) | IEWIKQ RPGHG LEWVG E (SEQ ID NO: 1006) | ILPGSG FT (SEQ ID NO: 1021) | NYNENFGK ATFTADTSS NTTYMQLSS LTSEDSAVY YC (SEQ ID NO: 1185) | ARGGT SVVHF DY (SEQ ID NO: 605) | WGQ GTTL TVSS (SEQ ID NO: 425) |
| BP003T3P2-63 | QVQLQQSGADLMKP GASVKMSCRAS (SEQ ID NO: 1321) | GYTFS NYW (SEQ ID NO: 986) | IEWIKQ RPGHG LEWIG E (SEQ ID NO: 1005) | ILPGSG FT (SEQ ID NO: 1021) | NYNENFKG KATFTADTS SNTTYMLLS SLSSEDSAV YYC (SEQ ID NO: 1187) | ARGGT SVVHF DS (SEQ ID NO: 604) | WGQ GTSL TVSS (SEQ ID NO: 424) |
| BP003T3P2-64 | QIQLQQSGADLMKP GASVKISCKAS (SEQ ID NO: 1224) | GYTFS NYW (SEQ ID NO: 986) | IEWIKQ RPGHG LEWVG E (SEQ ID NO: 1006) | ILPGSG FT (SEQ ID NO: 1021) | NYNENFKG KATFTADTS SNTTYMQLS SLTSEDSAV YYC (SEQ ID NO: 1188) | ARGGT SVVHF DY (SEQ ID NO: 605) | WGQ GTTL TVSS (SEQ ID NO: 425) |
| BP003T3P2-65 | EVLLQQSGADLMKP GASVKISCKAS (SEQ ID NO: 938) | GYTFS NYW (SEQ ID NO: 986) | IEWIKQ RPGHG LEWIG E (SEQ ID NO: 1005) | ILPGSG FT (SEQ ID NO: 1021) | NYNENFKG KATFTADTS SNTTYMQLS SLTSEDSAV YYC (SEQ ID NO: 1188) | ARGGT SVVHF DFDY (SEQ ID NO: 603) | WGQ GTTV TVSS (SEQ ID NO: 422) |

TABLE 4A-continued

Exemplary Clones-Heavy Chain Sequences

| ID | HFR1 | CDRH1 | HFR2 | CDRH2 | HFR3 | CDRH3 | HFR4 |
|---|---|---|---|---|---|---|---|
| BP003T3P2-66 | EVRLQQSGAELVRSGASVKLSCTAS (SEQ ID NO: 943) | GFNIKDYY (SEQ ID NO: 977) | MHWVKQRPEQGLEWIGW (SEQ ID NO: 1124) | IDPENGDT (SEQ ID NO: 1004) | EYAPKFQGKATMTADTSSNTAYLQLSSLTSEDTAVYYC (SEQ ID NO: 947) | NVITTATTWFAY (SEQ ID NO: 1165) | WGQGTLVTVSS (SEQ ID NO: 413) |
| BP003T3P2-67 | EVLLQQFGAELVRSGASVKLSCTAS (SEQ ID NO: 937) | GFNIKDYY (SEQ ID NO: 977) | IHWVKQRPEQGLEWIGW (SEQ ID NO: 1017) | IDPDNGET (SEQ ID NO: 1003) | EYAPKFQGKATMTTDTSSNTAHLQLSSLTSEDTAVYYC (SEQ ID NO: 948) | TVFWYGNNYAGFAY (SEQ ID NO: 1420) | WGQGTLVTVSS (SEQ ID NO: 413) |
| BP003T3P2-68 | EVHLQQSGAELVRSGASVKLSCTAS (SEQ ID NO: 936) | GFNIKDYY (SEQ ID NO: 977) | IHWVKQRPEQGLEWIGW (SEQ ID NO: 1017) | IDPDNGET (SEQ ID NO: 1003) | EYAPKFQGKATMTADTSSNTAHLQLSSLTSEDTAVYYC (SEQ ID NO: 946) | TVFWYGNNYAGFAY (SEQ ID NO: 1420) | WGAGTSLTVSS (SEQ ID NO: 431) |
| BP003T3P2-69 | EVRLQQSGAELVRSGASVKLSCTAS (SEQ ID NO: 943) | GFNIKDYY (SEQ ID NO: 977) | IHWVKQRPEQGLEWIGW (SEQ ID NO: 1017) | IDPDNGET (SEQ ID NO: 1003) | EYAPKFQGKATMTADTSSNTAHLQLSSLTSEDTAVYYC (SEQ ID NO: 946) | TVFWYGNNYAGFAY (SEQ ID NO: 1420) | WGQGTLVTVSA (SEQ ID NO: 421) |
| BP003T3P2-7 | EVQLQQSGAELVRPGVSLKISCKGS (SEQ ID NO: 940) | GYTFTDYA (SEQ ID NO: 19) | MHWVRQSHAKSLEWIGV (SEQ ID NO: 1128) | ISTYSGDA (SEQ ID NO: 21) | IYNQKFKGKATMTVDKSSSTAYLELARLTSDDSAIYYC (SEQ ID NO: 1033) | ARGVTFDY (SEQ ID NO: 23) | WGQGTTLTVSS (SEQ ID NO: 425) |
| BP003T3P2-70 | QAYLQQSGAELVRSGASVKLSCTAS (SEQ ID NO: 1197) | GFNIKDYY (SEQ ID NO: 977) | IHWVKQRPEQGLEWIGW (SEQ ID NO: 1017) | IDPDNGET (SEQ ID NO: 1003) | EYAPKFGKATMTADTSSNTAHLQLSSLTSEDTAVYYC (SEQ ID NO: 945) | TVFWYGNNYAGFAY (SEQ ID NO: 1420) | WGQGTTVSA (SEQ ID NO: 1453) |
| BP003T3P2-71 | QAYLQQSGAELVRSGASVKLSCTAS (SEQ ID NO: 1197) | GFNIKDYY (SEQ ID NO: 977) | IHWVKQRPEQGLEWIGW (SEQ ID NO: 1017) | IDPDNGET (SEQ ID NO: 1003) | EYAPKFGKATMTADTSSNTAHLQLSSLTSEDTAVYYC (SEQ ID NO: 945) | TVFWYGNNYAGFAY (SEQ ID NO: 1420) | WGQGTTVSA (SEQ ID NO: 1453) |
| BP003T3P2-72 | QVQLQQSGAELVRSGASVKLSCTAS (SEQ ID NO: 1339) | GFNIKDYY (SEQ ID NO: 977) | IHWVKQRPEQGLEWIGW (SEQ ID NO: 1017) | IDPDNGET (SEQ ID NO: 1003) | EYAPKFGKATMTADTSSNTAHLQLSSLTSEDTAVYYC (SEQ ID NO: 945) | TVFWYGNNYAGFAY (SEQ ID NO: 1420) | WGQGTTVSA (SEQ ID NO: 1453) |
| BP003T3P2-73 | EVRLQQSGAELVRSGASVKLPCTAS (SEQ ID NO: 942) | GFNIKDYY (SEQ ID NO: 977) | IHWVKQRPEQGLEWIGW (SEQ ID NO: 1017) | IDPDNGET (SEQ ID NO: 1003) | EYAPKFGKATMTADTSSNTAHLQLSSLTSEDTAVYYC (SEQ ID NO: 945) | TVFWYGNNYAGFAY (SEQ ID NO: 1420) | WGQGTTVSA (SEQ ID NO: 1453) |
| BP003T3P2-74 | EVLLQQFGAELVRSGASVKLSCTAS (SEQ ID NO: 937) | GFNIKDYY (SEQ ID GLEWI | IHWVK QRPEQ | IDPDN (SEQ ID GET | EYAPKFGKATMTADTSSNTAHLQLSSL | TVFWYGNNYAGFAY | WGQGTTVSA |

TABLE 4A-continued

Exemplary Clones-Heavy Chain Sequences

| ID | HFR1 | CDRH1 | HFR2 | CDRH2 | HFR3 | CDRH3 | HFR4 |
|---|---|---|---|---|---|---|---|
| | | NO: 977) | GW (SEQ ID NO: 1017) | NO: 1003) | TSEDTAVYY C (SEQ ID NO: 945) | (SEQ ID NO: 1420) | (SEQ ID NO: 1453) |
| BP003T3P2-75 | QIQLQQSGAELVRPG VSVKISCKGS (SEQ ID NO: 1240) | GYTFT DYA (SEQ ID NO: 19) | MHWV KQSHA KSLEW IGV (SEQ ID NO: 1126) | ISTYSG DV (SEQ ID NO: 46) | SYNQKFKG KATMTVDK SSSTAYMEL ARLTSEDSAI YYC (SEQ ID NO: 1389) | ARGVT FDS (SEQ ID NO: 48) | WGQ GTTV TVSS (SEQ ID NO: 422) |
| BP003T3P2-8 | EVQLQQSGAELVRP GVSLKISCKGS (SEQ ID NO: 940) | GYTFT DYA (SEQ ID NO: 19) | MHWV RQSHA KSLEW IGV (SEQ ID NO: 1128) | ISTYSG DA (SEQ ID NO: 21) | IYNQKFKGK ATMTVDKSS STAYLELAR LTSDDSAIY YC (SEQ ID NO: 1033) | ARGVT FDY (SEQ ID NO: 23) | WGQ GTTL TVSS (SEQ ID NO: 425) |
| BP003T3P2-9 | QIQLQQSGAELVRPG VSLKISCKGS (SEQ ID NO: 1239) | GYTFT DYA (SEQ ID NO: 19) | MHWV RQSHA KSLEW IGV (SEQ ID NO: 1128) | ISTYSG DA (SEQ ID NO: 21) | IYNQKFKGK ATMTVDKSS STAYLELAR LTSDDSAIY YC (SEQ ID NO: 1033) | ARGVT FDY (SEQ ID NO: 23) | WGQ GTTL TVSS (SEQ ID NO: 425) |

TABLE 4B

Exemplary Clones-Light Chain Sequences

| ID | LFR1 | CDRL1 | LFR2 | CDRL2 | LFR3 | CDRL3 | LFR4 |
|---|---|---|---|---|---|---|---|
| BL_592989-2015_G2_P8_G02 | DIQMTQSQKFMSTS VGDRVSVTCKAS (SEQ ID NO: 734) | QNVGT N (SEQ ID NO: 12) | VAWY QQKPG QSPKA LIY (SEQ ID NO: 1425) | SAS (SEQ ID NO: 13) | YRYSGVPD RFTGSGSG TDFTLTISN VQSEDLAE YFC (SEQ ID NO: 1483) | QQYN SYPYT (SEQ ID NO: 15) | FGGGT KLEMK (SEQ ID NO: 961) |
| BL_592989-2016_H2_P8_H02 | DVVMTQTPLSLPVS LGDQASISCRSS (SEQ ID NO: 900) | QSLVH SNGNT Y (SEQ ID NO: 1306) | LHWYL QKPGQ SPKLLI Y (SEQ ID NO: 1076) | EVS (SEQ ID NO: 944) | NRFSGVPD RFSGSGSGT DFTLKISRV EAEDLGVY FC (SEQ ID NO: 1157) | SQSTH VPYT (SEQ ID NO: 1375) | FGGGT KLEIK (SEQ ID NO: 959) |
| BL_592989-2017_A3_P8_A03 | DIVMTQSPPTLSLSP GERVTLSCKAS (SEQ ID NO: 816) | QDVNT AVA (SEQ ID NO: 1207) | WYQQ KPGQA PRLLIY (SEQ ID NO: 1470) | WAS (SEQ ID NO: 1450) | TRHTGVPS RFSGSGSGT DFTLTISSL QPEDFATY YC (SEQ ID NO: 1414) | QQHY SSPWT (SEQ ID NO: 1258) | FGGGT KLEIK (SEQ ID NO: 959) |
| BL_592989-2018_B3_P8_B03 | DVVMTQSQKFMST SVGDRVSVTCKAS (SEQ ID NO: 894) | QNVGT N (SEQ ID NO: 12) | VAYQQ KPGQS PKALIY (SEQ ID NO: 1430) | SAS (SEQ ID NO: 13) | YRYSGVPD RFTGSGSG TDFTLTISN VQSEDLAE YFC (SEQ ID NO: 1483) | QQYN SYPYT (SEQ ID NO: 15) | FGGGT KLEIK (SEQ ID NO: 959) |
| BL_592989-2019_C3_P8_C03 | DVVMTQSQKFMST SVGDRVSVTCKAS (SEQ ID NO: 894) | QNVGT N (SEQ ID NO: 12) | VAYQQ KPGQS PKALIY (SEQ ID NO: 1430) | SAS (SEQ ID NO: 13) | YRYSGVPD RFTGSGSG TDFTLTISN VQSEDLAE YFC (SEQ ID NO: 1483) | QQYN SYPYT (SEQ ID NO: 15) | FGGGT KLEIK (SEQ ID NO: 959) |

TABLE 4B-continued

Exemplary Clones-Light Chain Sequences

| ID | LFR1 | CDRL1 | LFR2 | CDRL2 | LFR3 | CDRL3 | LFR4 |
|---|---|---|---|---|---|---|---|
| BL_592989-2021_E3_P8_E03 | DIVLTQSQKFMSTSVGDRVSVTCKAS (SEQ ID NO: 773) | QNVGTN (SEQ ID NO: 12) | VAWYQQKPGQSPKALIY (SEQ ID NO: 1425) | SAS (SEQ ID NO: 13) | YRYSGVPDRFTGSGSGTDFTLTISNVQSEDLAEYFC (SEQ ID NO: 1483) | QQYNSYPYT (SEQ ID NO: 15) | FGGGTKLEIK (SEQ ID NO: 959) |
| BL_592989-2022_F3_P8_F03 | DVVMTQTQKFMSTSVGDRVSVTCKAS (SEQ ID NO: 909) | QNVGTN (SEQ ID NO: 12) | VAWYQQKPGQSPKALIY (SEQ ID NO: 1425) | SAS (SEQ ID NO: 13) | YRYSGVPDRFTGSGSGTDFTLTISNVQSEDLAEYFC (SEQ ID NO: 1483) | QQYNSYPYT (SEQ ID NO: 15) | FGGGTKLEIK (SEQ ID NO: 959) |
| BL_592989-2023_G3_P8_G03 | DVVMTQTPLSLPVSLGDQASISCRSS (SEQ ID NO: 900) | QSLVHSNGNTY (SEQ ID NO: 1306) | LHWYLQKPGQSPKLLIY (SEQ ID NO: 1076) | EVS (SEQ ID NO: 944) | NRFSGVPDRFSGSGSGTDFTLKISRVEAEDLGVYFC (SEQ ID NO: 1157) | SQSTHVPYT (SEQ ID NO: 1375) | FGGGTKLEIK (SEQ ID NO: 959) |
| BL_592989-2024_H3_P8_H03 | DIVMTQTTSSLSASLGDRVTISCRAS (SEQ ID NO: 831) | QDIRNY (SEQ ID NO: 1202) | LNYQQKPDGTVKLLIY (SEQ ID NO: 1091) | YTS (SEQ ID NO: 1495) | RLYSGVPSRFSGSGSGTDYSLTISNLEQEDIATYFC (SEQ ID NO: 1359) | QQGNTLPPT (SEQ ID NO: 1253) | FGGGTKLEIK (SEQ ID NO: 959) |
| BL_592989-2025_A4_P8_A04 | DIQMTQSQKFMSTSVGDRVSVTCKAS (SEQ ID NO: 734) | QNVGTN (SEQ ID NO: 12) | VAYQQKPGQSPKALIY (SEQ ID NO: 1430) | SAS (SEQ ID NO: 13) | YRYSGVPDRFTGSGSGTDFTLTISNVQSEDLAEYFC (SEQ ID NO: 1483) | QQYNSYPYT (SEQ ID NO: 15) | FGGGTKLEIK (SEQ ID NO: 959) |
| BL_592989-2026_B4_P8_B04 | DIQMTQSPASLSASVGESVTITCRAS (SEQ ID NO: 718) | ENIYSY (SEQ ID NO: 930) | LEWYQKQGKSPQLLVY (SEQ ID NO: 1072) | NAK (SEQ ID NO: 28) | TLAEGVPSRFSGSGSGTQFSLRINSLQPEDFGTYYC (SEQ ID NO: 1400) | QHHYGSPYT (SEQ ID NO: 1216) | FGGGTKLEIK (SEQ ID NO: 959) |
| BL_592989-2027_C4_P8_C04 | DIQMTQSQKFMSASVGDRVSVTCKAS (SEQ ID NO: 729) | QNVGTN (SEQ ID NO: 12) | VAYQQKPGQSPKALIY (SEQ ID NO: 1430) | SAS (SEQ ID NO: 13) | YRYSGVPDRFTGSGSGTDFTLTISNVQSEDLAEYFC (SEQ ID NO: 1483) | QQYNSYPYT (SEQ ID NO: 15) | FGGGTKLEMK (SEQ ID NO: 961) |
| BL_592989-2029_E4_P8_E04 | DNVLTQSQKFMSTSVGDRVSVTCKAS (SEQ ID NO: 837) | QNVGTN (SEQ ID NO: 12) | VAWYQQKPGQSPKALIY (SEQ ID NO: 1425) | SAS (SEQ ID NO: 13) | YRYSGVPDRFTGSGSGTDFTLTISNVQSEDLAEYFC (SEQ ID NO: 1483) | QQYNSYPYT (SEQ ID NO: 15) | FGGGTKLEMK (SEQ ID NO: 961) |
| BL_592989-2030_F4_P8_F04 | DIVLTQSQKFMSTSVGDRVSVTCKAS (SEQ ID NO: 773) | QNVGTN (SEQ ID NO: 12) | VAWYQQKPGQSPKALIY (SEQ ID NO: 1425) | SAS (SEQ ID NO: 13) | YRYSGVPDRFTGSGSGTDFTLTISNVQSEDLAEYFC (SEQ ID NO: 1483) | QQYNSYPWT (SEQ ID NO: 36) | FGGGTKLEIK (SEQ ID NO: 959) |
| BL_592989-2031_G4_P8_G04 | DIQMTQSQKFMSTSVGDRVSVTCKAS (SEQ ID NO: 734) | QNVGTN (SEQ ID NO: | VAWYQQKPGQSPKA | SAS (SEQ ID NO: 13) | YRYSGVPDRFTGSGSGTDFTLTISN | QQYNSYPYT (SEQ | FGGGTKLEMK (SEQ ID |

TABLE 4B-continued

Exemplary Clones-Light Chain Sequences

| ID | LFR1 | CDRL1 | LFR2 | CDRL2 | LFR3 | CDRL3 | LFR4 |
|---|---|---|---|---|---|---|---|
| | | 12) | LIY (SEQ ID NO: 1425) | | VQSEDLAE YFC (SEQ ID NO: 1483) | ID NO: 15) | NO: 961) |
| BL_592989-2032_H4_P8_H04 | DVVMTQSQKFMST SVGDRVSVTCKAS (SEQ ID NO: 894) | QNVGT N (SEQ ID NO: 12) | VAWY QQKPG QSPKA LIY (SEQ ID NO: 1425) | SAS (SEQ ID NO: 13) | YRYSGVPG RFTGSGSG TDFTLTISN VQSEDLAE YFC (SEQ ID NO: 1490) | QQYN SYPYT (SEQ ID NO: 15) | FGGGT KLEIK (SEQ ID NO: 959) |
| BL_592989-2033_A5_P8_A05 | DIQMTQTPASLSAS VGETVTITCRAS (SEQ ID NO: 744) | ENIYSY (SEQ ID NO: 930) | LEWFQ QKQGK SPQLL VY (SEQ ID NO: 1070) | NAK (SEQ ID NO: 28) | TLAEGVPS RFSVSGSGT QFSLKINSL QPEDFGSY YC (SEQ ID NO: 1401) | QHHY GIPYT (SEQ ID NO: 1214) | FGGGT KLEIK (SEQ ID NO: 959) |
| BL_592989-2034_B5_P8_B05 | DIQMTQSQKFMSTS VGDRVSVTCKAS (SEQ ID NO: 734) | QNVGT N (SEQ ID NO: 12) | VAYQQ KPGQS PKALIY (SEQ ID NO: 1430) | SAS (SEQ ID NO: 13) | YRYSGVPD RFTGSGSG TDFTLTISN VQSEDLAE YFC (SEQ ID NO: 1483) | QQYN SYPYT (SEQ ID NO: 15) | FGGGT KLEIK (SEQ ID NO: 959) |
| BL_592989-2035_C5_P8_C05 | DIVMTQSQKFMSTS VGDRVSVTCKAS (SEQ ID NO: 821) | QNVGT N (SEQ ID NO: 12) | VAYQQ KPGQS PKALIY (SEQ ID NO: 1430) | SAS (SEQ ID NO: 13) | YRYSGVPD RFTGSGSG TDFTLTISN VQSEDLAE YFC (SEQ ID NO: 1483) | QQYN SYPYT (SEQ ID NO: 15) | FGGGT KLEIK (SEQ ID NO: 959) |
| BL_592989-2037_E5_P8_E05 | DIVMSQSQKFMSTS VGDRVSVTCKAS (SEQ ID NO: 793) | QNVGT N (SEQ ID NO: 12) | VAWY QQKPG QSPKA LIY (SEQ ID NO: 1425) | SAS (SEQ ID NO: 13) | YRYSGVPD RFTGSGSG TDFTLTISN VQSEDLAE YFC (SEQ ID NO: 1483) | QQYN SYPYT (SEQ ID NO: 15) | FGGGT KLEIK (SEQ ID NO: 959) |
| BL_592989-2038_F5_P8_F05 | DIVMTQSQKFMSTS VGDRVSVTCKAS (SEQ ID NO: 821) | QNVGT N (SEQ ID NO: 12) | VAWY QQKPG QSPKA LIY (SEQ ID NO: 1425) | SAS (SEQ ID NO: 13) | YRYSGVPD RFTGSGSG TDFTLTISN VQSEDLAE YFC (SEQ ID NO: 1483) | QQYN SYPYT (SEQ ID NO: 15) | FGGGT KLEMK (SEQ ID NO: 961) |
| BL_592989-2039_G5_P8_G05 | DIVMSQSQKFMSTS VGDRVSVTCKAS (SEQ ID NO: 793) | QNVGT N (SEQ ID NO: 12) | VAWY QQKPG QSPKA LIY (SEQ ID NO: 1425) | SAS (SEQ ID NO: 13) | YRYSGVPD RFTGSGSG TDFTLTISN VQSEDLAE YFC (SEQ ID NO: 1483) | QQYN NYPW T (SEQ ID NO: 1284) | FGGGT KLEIK (SEQ ID NO: 959) |
| BL_592989-2040_H5_P8_H05 | DIQMTQSQKFMSTS VGDRVSVTCKAS (SEQ ID NO: 734) | QNVGT N (SEQ ID NO: 12) | VAWY QQKPG QSPKA LIY (SEQ ID NO: 1425) | SAS (SEQ ID NO: 13) | YRYSGVPD RFTGSGSG TDFTLTISN VQSEDLAE YFC (SEQ ID NO: 1483) | QQYN SYPYT (SEQ ID NO: 15) | FGGGT KLEIK (SEQ ID NO: 959) |
| BL_592989-2041_A6_P8_A06 | DVVMTQSPASLSAS VGETVTITCRAS (SEQ ID NO: 890) | ENSY Y (SEQ ID NO: 52) | LEWYQ QKQGK SPQLL VY (SEQ ID NO: 1072) | NAK (SEQ ID NO: 28) | TLAEGVPS RFSGSGSGT QFSLKINSL QPEDFGTY YC (SEQ ID NO: 1399) | QHHY GTPYT (SEQ ID NO: 54) | FGGGT KLEIK (SEQ ID NO: 959) |

TABLE 4B-continued

Exemplary Clones-Light Chain Sequences

| ID | LFR1 | CDRL1 | LFR2 | CDRL2 | LFR3 | CDRL3 | LFR4 |
|---|---|---|---|---|---|---|---|
| BL_592989-2042_B6_P8_B06 | DIQMTQSPASLSAS VGETVTITCRAS (SEQ ID NO: 720) | ENSYS Y (SEQ ID NO: 52) | LEWYQ QKQGK SPQLL VY (SEQ ID NO: 1072) | NAK (SEQ ID NO: 28) | TLAEGVPS RFSGSGSGT QFSLKINSL QPEDFGTY YC (SEQ ID NO: 1399) | QHHY GTPYT (SEQ ID NO: 54) | FGGGT KLEIK (SEQ ID NO: 959) |
| BL_592989-2043_C6_P8_C06 | DIQMTQSPASLSAS VGETVTITCRAS (SEQ ID NO: 720) | ENIYSY (SEQ ID NO: 930) | LEWYQ QKQGK SPQLL VY (SEQ ID NO: 1072) | NAK (SEQ ID NO: 28) | TLAEGVPS RFSGSGSGT QFSLKINSL QPEDFGSY YC (SEQ ID NO: 1398) | QHHY GTPYT (SEQ ID NO: 54) | FGGGT KLEIK (SEQ ID NO: 959) |
| BL_592989-2044_D6_P8_D06 | DIVLTQSQKFMSTS VGDRVSVTCKAS (SEQ ID NO: 773) | QNVGT N (SEQ ID NO: 12) | VAYQQ KPGQS PKALIY (SEQ ID NO: 1430) | SAS (SEQ ID NO: 13) | YRYSGVPD RFTGSGSG TDFTLTISN VQSEDLAE YFC (SEQ ID NO: 1483) | QQYN TYPYT (SEQ ID NO: 1287) | FGGGT KLEMK (SEQ ID NO: 961) |
| BL_592989-2045_E6_P8_E06 | DIVMSQSQKFMSTS VGDRVSVTCKAS (SEQ ID NO: 793) | QNVGT N (SEQ ID NO: 12) | VAWY QQKPG QSPKA LIY (SEQ ID NO: 1425) | SAS (SEQ ID NO: 13) | YRYSGVPD RFTGSGSG TDFTLTISN VQSEDLAE YFC (SEQ ID NO: 1483) | QQYN SYPYT (SEQ ID NO: 15) | FGGGT KLEIK (SEQ ID NO: 959) |
| BL_592989-2046_F6_P8_F06 | DIQMTQSQKFMSTS VGDRVSVTCKAS (SEQ ID NO: 734) | QNVGT N (SEQ ID NO: 12) | VAWY QQKPG QSPKA LIY (SEQ ID NO: 1425) | SAS (SEQ ID NO: 13) | YRYSGVPD RFTGSGSG TGFTLTISN VQSEDLAE YFC (SEQ ID NO: 1487) | QQYN SYPYT (SEQ ID NO: 15) | FGGGT KLEIK (SEQ ID NO: 959) |
| BL_592989-2047_G6_P8_G06 | DIVMSQSQKFMSTS VGDRVSVTCKAS (SEQ ID NO: 793) | QNVGT N (SEQ ID NO: 12) | VAWY QQKPG QSPKA LIY (SEQ ID NO: 1425) | SAS (SEQ ID NO: 13) | YRYSGVPD RFTGSGSG TDFTLTISN VQSEDLAE YFC (SEQ ID NO: 1483) | QQYN NYPW T (SEQ ID NO: 1284) | FGGGT KLEIK (SEQ ID NO: 959) |
| BL_592989-2048_H6_P8_H06 | DIVMSQSQKFMSTS VGDRVSVTCKAS (SEQ ID NO: 793) | QNVGT N (SEQ ID NO: 12) | VAWY QQKPG QSPKA LIY (SEQ ID NO: 1425) | SAS (SEQ ID NO: 13) | YRYSGVPD RFTGSGSG TDFTLTISN VQSEDLAE YFC (SEQ ID NO: 1483) | QQYN SYPYT (SEQ ID NO: 15) | FGGGT KLEIK (SEQ ID NO: 959) |
| BL_592989-2049_A7_P8_A07 | DIQMTQSPASLSAS VGETVTITCRAS (SEQ ID NO: 720) | ENIYSY (SEQ ID NO: 930) | LEWYQ QKQGK SPQLL VY (SEQ ID NO: 1072) | NAK (SEQ ID NO: 28) | TLAEGVPS RFSGSGSGT QFSLKINSL QPEDFGSY YC (SEQ ID NO: 1398) | QHHY GTPYT (SEQ ID NO: 54) | FGGGT KLEIK (SEQ ID NO: 959) |
| BL_592989-2051_C7_P8_C07 | DIQMTQSQKFMSTS VGDRVSVTCKAS (SEQ ID NO: 734) | QNVGT N (SEQ ID NO: 12) | VAYQQ KPGQS PKALIY (SEQ ID NO: 1430) | SAS (SEQ ID NO: 13) | YRYSGVPD RFTGSGSG TDFTLTISN VQSEDLAE YFC (SEQ ID NO: 1483) | QQYN SYPYT (SEQ ID NO: 15) | FGGGT KLEIK (SEQ ID NO: 959) |
| BL_592989-2052_D7_P8_D07 | DVVLTQTPLSLPVSL GDQASISCRSS (SEQ ID NO: 874) | QSIVHS NGNTY (SEQ ID SPKLLI | LEWYL QKPGQ | KVS (SEQ ID NO: | NRFSGVPD RFSGSGSGT DFTLKISKV | FQGSH VPPT (SEQ | FGGGT KLEIK (SEQ ID |

TABLE 4B-continued

Exemplary Clones-Light Chain Sequences

| ID | LFR1 | CDRL1 | LFR2 | CDRL2 | LFR3 | CDRL3 | LFR4 |
|---|---|---|---|---|---|---|---|
| | | NO: 1299) | Y (SEQ ID NO: 1071) | (SEQ ID NO: 1062) | EAEDLGVY YC (SEQ ID NO: 1154) | ID NO: 966) | NO: 959) |
| BL_592989-2054_F7_P8_F07 | DTTVTQSQKFMSTS VGDRVSVTCKAS (SEQ ID NO: 858) | QNVGT N (SEQ ID NO: 12) | VAWY QQKPG QSPKPL IY (SEQ ID NO: 1429) | SAS (SEQ ID NO: 13) | YRYSGVPD RFTGSGSG TDFTLTISN VQSEDLAE YFC (SEQ ID NO: 1483) | QQYN NHPYT (SEQ ID NO: 1281) | FGGGT KLEIK (SEQ ID NO: 959) |
| BL_592989-2055_G7_P8_G07 | DIQMTQSQKFMSTS VGDRASVTCKAS (SEQ ID NO: 731) | QNVGT N (SEQ ID NO: 12) | VAWY QQKPG QSPKA LIY (SEQ ID NO: 1425) | SAS (SEQ ID NO: 13) | YRYSGVPD RFTGSGSG TDFTLTISN VQSEDLAE YFC (SEQ ID NO: 1483) | QQYN SYPW T (SEQ ID NO: 36) | FGGGT KLEIK (SEQ ID NO: 959) |
| BL_592989-2059_C8_P8_C08 | DIVMTQSQKFMSTS VGDRVSVTCKAS (SEQ ID NO: 821) | QNVGT N (SEQ ID NO: 12) | VAYQQ KPGQS PKALIY (SEQ ID NO: 1430) | SAS (SEQ ID NO: 13) | YRYSGVPD RFTGSGSG TDFTLTISN VQSEDLAD YFC (SEQ ID NO: 1482) | QQYN TYPYT (SEQ ID NO: 1287) | FGGGT KLEIK (SEQ ID NO: 959) |
| BL_592989-2060_D8_P8_D08 | DIQMTQSPASLSAS VGESVTITCRAS (SEQ ID NO: 718) | ENIYSY (SEQ ID NO: 930) | LEWYQ QKGK SPQLL VY (SEQ ID NO: 1072) | NAK (SEQ ID NO: 28) | TLAEGVPS RFSGSGSGT QFSLRINSL QPEDFGTY YC (SEQ ID NO: 1400) | QHHY GSPYT (SEQ ID NO: 1216) | FGGGT KLEMK (SEQ ID NO: 961) |
| BL_592989-2061_E8_P8_E08 | DTTVTQSQKFMSTS VGDRVSVTCKAS (SEQ ID NO: 858) | QNVGT N (SEQ ID NO: 12) | VAWY QQKPG QSPKA LIY (SEQ ID NO: 1425) | SAS (SEQ ID NO: 13) | YRYGGVPD RFTGSGSG TDFTLTISN VQSEDLAE YFC (SEQ ID NO: 1477) | QQYN SYPYT (SEQ ID NO: 15) | FGGGT KLEIK (SEQ ID NO: 959) |
| BL_592989-2062_F8_P8_F08 | DIVMTQSPASLSAS VGETVTITCRAS (SEQ ID NO: 807) | ENIYSF (SEQ ID NO: 928) | LVWYQ SPHLL VY (SEQ ID NO: 1117) | NAK (SEQ ID NO: 28) | TLAEGVPS RFSGIGSGT QFSLKINSL QPEDFGTY YC (SEQ ID NO: 1396) | QHHY GTPYT (SEQ ID NO: 54) | FGGGT KLEIK (SEQ ID NO: 959) |
| BL_592989-2063_G8_P8_G08 | DIQMTQSQKFMSTS VGDRVGVTCKAS (SEQ ID NO: 732) | QNVGT NVA (SEQ ID NO: 1246) | WYQQ KPGQS PKALIY (SEQ ID NO: 1471) | SAS (SEQ ID NO: 13) | YRYSGVPD RFTGSGSG TDFTLTISN VQSEDLAE YFC (SEQ ID NO: 1483) | QQYN SYPYT (SEQ ID NO: 15) | FGGGT KLEMK (SEQ ID NO: 961) |
| BL_592989-2064_H8_P8_H08 | DTTVTQSQKFMSTS VGDRVSVTCKAS (SEQ ID NO: 858) | QNVGT N (SEQ ID NO: 12) | VAWY QQKPG QSPKA LIY (SEQ ID NO: 1425) | SAS (SEQ ID NO: 13) | YRYSGVPD RFTGSGSG TDFTLTISN VQSEDLAE YFC (SEQ ID NO: 1483) | QQYN SYPW T (SEQ ID NO: 36) | FGGGT KLEIK (SEQ ID NO: 959) |
| BL_592989-2065_A9_P8_A09 | DIVMTQSPASLSAS VGETVTITCRAS (SEQ ID NO: 807) | ENIYSF (SEQ ID NO: 928) | LVWYQ QKGK SPHLL VY (SEQ ID NO: 1117) | NAK (SEQ ID NO: 28) | TLAEGVPS RFSGIGSGT QFSLKINSL QPEDFGTY YC (SEQ ID NO: 1396) | QHHY GTPYT (SEQ ID NO: 54) | FGGGT KLEIK (SEQ ID NO: 959) |

TABLE 4B-continued

Exemplary Clones-Light Chain Sequences

| ID | LFR1 | CDRL1 | LFR2 | CDRL2 | LFR3 | CDRL3 | LFR4 |
|---|---|---|---|---|---|---|---|
| BL_592989-2067_C9_P8_C09 | DILMTQSQKFMSTSVGDRVSVTCKAS (SEQ ID NO: 711) | QNVGTN (SEQ ID NO: 12) | VAYQQKPGQSPKPLIY (SEQ ID NO: 1432) | SAS (SEQ ID NO: 13) | YRYSGVPDRFTGSGSGTDFTLTISNVQSEDLAEYFC (SEQ ID NO: 1483) | QQYNNYPLT (SEQ ID NO: 1283) | FGGGTKLEIK (SEQ ID NO: 959) |
| BL_592989-2068_D9_P8_D09 | DIQMTQSPASLSASVGETVTITCRAS (SEQ ID NO: 720) | ENIYSY (SEQ ID NO: 930) | LEWYQQKQGKSPQLLVY (SEQ ID NO: 1072) | NAK (SEQ ID NO: 28) | TLVEGVPSRFSGSGSGTQFSLKINSLQPEDFGSYYC (SEQ ID NO: 1408) | QHHYDTPYT (SEQ ID NO: 30) | FGGGTKLEIK (SEQ ID NO: 959) |
| BL_592989-2069_E9_P8_E09 | DTTVTQSQKFMSTSVGDRVSVTCKAS (SEQ ID NO: 858) | QNVGTN (SEQ ID NO: 12) | VAWYQQKPGQSPKALIY (SEQ ID NO: 1425) | SAS (SEQ ID NO: 13) | YRYSGVPDRFTGSGSGTDFTLTISNVQSEDLAEYFC (SEQ ID NO: 1483) | QQYNSYPYT (SEQ ID NO: 15) | FGGGTKLEIK (SEQ ID NO: 959) |
| BL_592989-2070_F9_P8_F09 | DVVMTQSPASLSASVGESVTITCRAS (SEQ ID NO: 889) | ENIYSY (SEQ ID NO: 930) | LEWYQQKQGKSPQLLVY (SEQ ID NO: 1072) | NAK (SEQ ID NO: 28) | TLAEGVPSRFSGSGSGTQFSLRINSLQPEDFGTYYC (SEQ ID NO: 1400) | QHHYGSPYT (SEQ ID NO: 1216) | FGGGTKLEIK (SEQ ID NO: 959) |
| BL_592989-2071_G9_P8_G09 | DTTVTQSQKFMSTSVGDRVSVACKAS (SEQ ID NO: 854) | QNVGTN (SEQ ID NO: 12) | VAWYQQKPGQSPKALIY (SEQ ID NO: 1425) | SAS (SEQ ID NO: 13) | YRYSGVPDRFTGSGSGTDFTLTISNVQSEDLAEYFC (SEQ ID NO: 1483) | QQYNSYPYT (SEQ ID NO: 15) | FGGGTKLEIK (SEQ ID NO: 959) |
| BL_592989-2074_B10_P8_B10 | DTTVTQSQKFMSTSVGDRVSVTCKAS (SEQ ID NO: 858) | QNVGTN (SEQ ID NO: 12) | VAYQQKPGQSPKALIY (SEQ ID NO: 1430) | SAS (SEQ ID NO: 13) | YRYSGVPDRFTGSGSGTDFTLTISNVQSEDLAEYFC (SEQ ID NO: 1483) | QQYNSYPYT (SEQ ID NO: 15) | FGGGTKLEMK (SEQ ID NO: 961) |
| BL_592989-2076_D10_P8_D10 | DIVITQSQKFMSTSVGDRVSVTCKAS (SEQ ID NO: 766) | QNVGTN (SEQ ID NO: 12) | VAYQQKPGQSPKALIY (SEQ ID NO: 1430) | SAS (SEQ ID NO: 13) | YRYSGVPDRLTGSGSGTDFTLTISNVQSEDLAEYFC (SEQ ID NO: 1489) | QQYNRYPYT (SEQ ID NO: 1285) | FGGGTKLEIK (SEQ ID NO: 959) |
| BL_592989-2077_E10_P8_E10 | DIQMTQTQKFMSTSVGDRVSVTCKAS (SEQ ID NO: 757) | QNVGTN (SEQ ID NO: 12) | VAWYQQKPGQSPKALIY (SEQ ID NO: 1425) | SAS (SEQ ID NO: 13) | YRYSGVPDRFTGSGSGTDFTLTISNVQSEDLTEYFC (SEQ ID NO: 1486) | QQYNSYPWT (SEQ ID NO: 36) | FGGGTKLEIK (SEQ ID NO: 959) |
| BL_592989-2078_F10_P8_F10 | DTTVTQSQKFMSTSVGDRVSVTCKAS (SEQ ID NO: 858) | QNVGTN (SEQ ID NO: 12) | VAWYQQKPGQSPKALIY (SEQ ID NO: 1425) | SAS (SEQ ID NO: 13) | YRYSGVPDRFTGSGSGTDFTLTISNVQSEDLAEYFC (SEQ ID NO: 1483) | QQYNSYPYT (SEQ ID NO: 15) | FGGGTKLEMK (SEQ ID NO: 961) |
| BL_592989-2079_G10_P8_G10 | DIQMTQSQKFMSTSVGDRVSVTCKAS (SEQ ID NO: 734) | QNVGTN (SEQ ID NO: 12) | VAWYQQKPGQSPKALIY | SAS (SEQ ID NO: 13) | YRYSGVPDRFTGSGSGTDFTLTISNVQSEDLAE | QQYNSYPWT (SEQ ID NO: | FGGGTKLEMK (SEQ ID NO: |

TABLE 4B-continued

Exemplary Clones-Light Chain Sequences

| ID | LFR1 | CDRL1 | LFR2 | CDRL2 | LFR3 | CDRL3 | LFR4 |
|---|---|---|---|---|---|---|---|
| | | | | | YFC (SEQ ID NO: 1425) | 36) | 961) |
| BL_592989-2080_H10_P8_H10 | DIQMTQSTSSLSASLGDRVTISCRAS (SEQ ID NO: 738) | QDIRNY (SEQ ID NO: 1202) | LNYQQKPDGTVKLLIY (SEQ ID NO: 1091) | YTS (SEQ ID NO: 1495) | RLHSGVPSRFSGSGSGTDYSLTISNLEQEDIATYFC (SEQ ID NO: 1353) | QQGNTLPPT (SEQ ID NO: 1253) | FGGGTKLEIK (SEQ ID NO: 959) |
| BP003-T2P1A7 | DIQMTQSPASLSASVGETVTITCRAS (SEQ ID NO: 720) | ENIYSY (SEQ ID NO: 930) | LEWYQKQGKSPQLLVY (SEQ ID NO: 1072) | NAK (SEQ ID NO: 28) | TLAEGVPSRFSGSGSGTQFSLKINSLQPEDFGSYYC (SEQ ID NO: 1398) | QHHYGTPYT (SEQ ID NO: 54) | FGGGTKLEIK (SEQ ID NO: 959) |
| BP003-T2P1C8 | DIVMTQSQKFMSTSVGDRVSVTCKAS (SEQ ID NO: 821) | QNVGTN (SEQ ID NO: 12) | VAWYQQKPGQSPKALIY (SEQ ID NO: 1425) | SAS (SEQ ID NO: 13) | YRYSGVPDRFTGSGSGTDFTLTISNVQSEDLADYFC (SEQ ID NO: 1482) | QQYNTYPYT (SEQ ID NO: 1287) | FGGGTKLEIK (SEQ ID NO: 959) |
| BP003-T2P1F4 | DIVLTQSQKFMSTSVGDRVSVTCKAS (SEQ ID NO: 773) | QNVGTN (SEQ ID NO: 12) | VAWYQQKPGQSPKALIY (SEQ ID NO: 1425) | SAS (SEQ ID NO: 13) | YRYSGVPDRFTGSGSGTDFTLTISNVQSEDLAEYFC (SEQ ID NO: 1483) | QQYNSYPWT (SEQ ID NO: 36) | FGGGTKLEIK (SEQ ID NO: 959) |
| BP003-T2P1G2 | DIQMTQSQKFMSTSVGDRVSVTCKAS (SEQ ID NO: 734) | QNVGTN (SEQ ID NO: 12) | VAWYQQKPGQSPKALIY (SEQ ID NO: 1425) | SAS (SEQ ID NO: 13) | YRYSGVPDRFTGSGSGTDFTLTISNVQSEDLAEYFC (SEQ ID NO: 1483) | QQYNSYPYT (SEQ ID NO: 15) | FGGGTKLEMK (SEQ ID NO: 961) |
| BP003-T2P1G4 | DIQMTQSQKFMSTSVGDRVSVTCKAS (SEQ ID NO: 734) | QNVGTN (SEQ ID NO: 12) | VAWYQQKPGQSPKALIY (SEQ ID NO: 1425) | SAS (SEQ ID NO: 13) | YRYSGVPDRFTGSGSGTDFTLTISNVQSEDLAEYFC (SEQ ID NO: 1483) | QQYNSYPYT (SEQ ID NO: 15) | FGGGTKLEMK (SEQ ID NO: 961) |
| BP003-T2P1G7 | DIQMTQSQKFMSTSVGDRASVTCKAS (SEQ ID NO: 731) | QNVGTN (SEQ ID NO: 12) | VAWYQQKPGQSPKALIY (SEQ ID NO: 1425) | SAS (SEQ ID NO: 13) | YRYSGVPDRFTGSGSGTDFTLTISNVQSEDLAEYFC (SEQ ID NO: 1483) | QQYNSYPWT (SEQ ID NO: 36) | FGGGTKLEIK (SEQ ID NO: 959) |
| BP003-T2P1H5 | DIQMTQSQKFMSTSVGDRVSVTCKAS (SEQ ID NO: 734) | QNVGTN (SEQ ID NO: 12) | VAWYQQKPGQSPKALIY (SEQ ID NO: 1425) | SAS (SEQ ID NO: 13) | YRYSGVPDRFTGSGSGTDFTLTISNVQSEDLAEYFC (SEQ ID NO: 1483) | QQYNSYPYT (SEQ ID NO: 15) | FGGGTKLEIK (SEQ ID NO: 959) |
| BP003T3P2-1 | DIQMTQSPASLSASVGETVTITCRAS (SEQ ID NO: 720) | ENIYSY (SEQ ID NO: 930) | LEWYQKQGKSPQLLVY (SEQ ID NO: 1072) | NAK (SEQ ID NO: 28) | TLVEGVPSRFSGSGSGTQFSLKINSLQPEDFGSYYC (SEQ ID NO: 1408) | QHHYDTPYT (SEQ ID NO: 30) | FGGGTKLEIK (SEQ ID NO: 959) |

TABLE 4B-continued

Exemplary Clones-Light Chain Sequences

| ID | LFR1 | CDRL1 | LFR2 | CDRL2 | LFR3 | CDRL3 | LFR4 |
|---|---|---|---|---|---|---|---|
| BP003T3P2-10 | DVQMTQSPSSMYAS LGERVTFTCKAS (SEQ ID NO: 872) | QDINR Y (SEQ ID NO: 1201) | LSWFQ QKPGK SPKTLI Y (SEQ ID NO: 1109) | RAN (SEQ ID NO: 1345) | RLVDGVPS RFSGSGSG QNYSLTISS LEYEDMGI YYC (SEQ ID NO: 1357) | LQYD EFPYT (SEQ ID NO: 1106) | FGGGT KLEIK (SEQ ID NO: 959) |
| BP003T3P2-11 | DVQMTQSPSSMYAS LGERVTFTCKAS (SEQ ID NO: 872) | QDINR Y (SEQ ID NO: 1201) | LSWFQ QKPGK SPKTLI Y (SEQ ID NO: 1109) | RAN (SEQ ID NO: 1345) | RLVDGVPS RFSGSGSG QNYSLTISS LEYEDMGI YYC (SEQ ID NO: 1357) | LQYD EFPYT (SEQ ID NO: 1106) | FGGGT KLEIK (SEQ ID NO: 959) |
| BP003T3P2-12 | DVQMNQSPSSMYA SLGERVTITCKAS (SEQ ID NO: 870) | QDINNF (SEQ ID NO: 1200) | LSWFQ QKPGK SPQTLI Y (SEQ ID NO: 1110) | RAN (SEQ ID NO: 1345) | RLVDGVPS RFSGSGSG QHYSLTISG LEYEDLGIY YC (SEQ ID NO: 1356) | LQYD EFPWT (SEQ ID NO: 1105) | FGGGT KLEIK (SEQ ID NO: 959) |
| BP003T3P2-13 | DIQMTQSPASLSAS VGESVTITCRAS (SEQ ID NO: 718) | ENIYSY (SEQ ID NO: 930) | LEWYQ QKQGK SPQLL VY (SEQ ID NO: 1072) | NAK (SEQ ID NO: 28) | TLAEGVPS RFSGSGSGT QFSLKINSL QPEDFGSY YC (SEQ ID NO: 1398) | QHHY GSPYT (SEQ ID NO: 1216) | FGGGT KLEIK (SEQ ID NO: 959) |
| BP003T3P2-14 | DIQMTQSPASLSAS VGETVTITCRAS (SEQ ID NO: 720) | ENIYSY (SEQ ID NO: 930) | LEWYQ QKQGK SPQLL VY (SEQ ID NO: 1072) | NAK (SEQ ID NO: 28) | TLAEGVPS RFSGSGSGT QFSLKINSL QPEDFGSY YC (SEQ ID NO: 1398) | QHHY DTPYT (SEQ ID NO: 30) | FGGGT KLEIK (SEQ ID NO: 959) |
| BP003T3P2-15 | DVVMTQSPASLSAS VGETVTITCRAS (SEQ ID NO: 890) | ENSYS Y (SEQ ID NO: 52) | LEWYQ QKQGK SPQLL VY (SEQ ID NO: 1072) | NAK (SEQ ID NO: 28) | TLAEGVPS RFSGSGSGT QFSLKINSL QPEDFGTY YC (SEQ ID NO: 1399) | QHHY GTPYT (SEQ ID NO: 54) | FGGGT KLEIK (SEQ ID NO: 959) |
| BP003T3P2-16 | DIQMTQSPASLSAS VGETVTITCRAS (SEQ ID NO: 720) | ENIYSY (SEQ ID NO: 930) | LEWYQ QKQGK SPQLL VY (SEQ ID NO: 1072) | NAK (SEQ ID NO: 28) | TLAEGVPS RFSGSGSGT QFSLKINSL QPEDFGSY YC (SEQ ID NO: 1398) | QHHY DTPYT (SEQ ID NO: 30) | FGGGT KLEIK (SEQ ID NO: 959) |
| BP003T3P2-17 | DVQMTQSPASLSAS VGETVTITCRAS (SEQ ID NO: 871) | ENIYSY (SEQ ID NO: 930) | LEWYQ QKQGK SPQLL VY (SEQ ID NO: 1072) | NAK (SEQ ID NO: 28) | TLAEGVPS RFSGSGSGT QFSLKINSL QPEDFGSY YC (SEQ ID NO: 1398) | QHHY DTPYT (SEQ ID NO: 30) | FGGGT KLEIK (SEQ ID NO: 959) |
| BP003T3P2-18 | DIQMTQSPASLSAS VGESVTITCRAS (SEQ ID NO: 718) | ENIYSY (SEQ ID NO: 930) | LEWYQ QKQGK SPQLL VY (SEQ ID NO: 1072) | NAK (SEQ ID NO: 28) | TLAEGVPS RFSGSGSGT QFSLKINSL QPEDFGSY YC (SEQ ID NO: 1398) | QHHY GSPYT (SEQ ID NO: 1216) | FGGGT KLEMK (SEQ ID NO: 961) |
| BP003T3P2-19 | DIQMTQSPASLSAS VGETVTITCRAS (SEQ ID NO: 720) | ENIYSY (SEQ ID NO: 930) | LEWYQ QKQGK SPQLL VY | NAK (SEQ ID NO: 28) | TLAEGVPS RFSGSGSGT QFSLKINSL QPEDFGSY | QHHY DTPYT (SEQ ID NO: | FGGGT KLEIK (SEQ ID NO: |

TABLE 4B-continued

Exemplary Clones-Light Chain Sequences

| ID | LFR1 | CDRL1 | LFR2 | CDRL2 | LFR3 | CDRL3 | LFR4 |
|---|---|---|---|---|---|---|---|
| | | | | | YC (SEQ ID NO: 1398) | 30) | 959) |
| BP003T3P2-2 | DIQMTQSPASLSAS VGETVTITCRAS (SEQ ID NO: 720) | ENIYSY (SEQ ID NO: 930) | LEWYQ QKQGK SPQLL VY (SEQ ID NO: 1072) | NAK (SEQ ID NO: 28) | TLVEGVPS RFSGSGSGT QFSLKINSL QPEDFGSY YC (SEQ ID NO: 1408) | QHHY DTPYT (SEQ ID NO: 30) | FGGGT KLEIK (SEQ ID NO: 959) |
| BP003T3P2-20 | DIVMTQSPASLSAS VGETVTITCRAS (SEQ ID NO: 807) | KNSYS Y (SEQ ID NO: 1057) | LEWYQ QKQGK SPQLL VY (SEQ ID NO: 1072) | NAK (SEQ ID NO: 28) | TLAEGVPS RFSGSGSGT QFSLKINSL QPEDFGTY YC (SEQ ID NO: 1399) | QHHY GTPYT (SEQ ID NO: 54) | FGGGT KLEIK (SEQ ID NO: 959) |
| BP003T3P2-21 | DIQMTQSPASLSAS VGETVTITCRAS (SEQ ID NO: 720) | ENIYSY (SEQ ID NO: 930) | LEWYQ QKQGK SPQLL VY (SEQ ID NO: 1072) | NAK (SEQ ID NO: 28) | TLAEGVPS RFSGSGSGT QFSLKINSL QPEDFGSY YC (SEQ ID NO: 1398) | QHHY GTPYT (SEQ ID NO: 54) | FGGGT KLEMK (SEQ ID NO: 961) |
| BP003T3P2-22 | DIQMTQSPASLSAS VGETVTITCRAS (SEQ ID NO: 720) | ENSYS Y (SEQ ID NO: 52) | LEWYQ QKQGK SPQLL VY (SEQ ID NO: 1072) | NAK (SEQ ID NO: 28) | TLAEGVPS RFSGSGSGT QFSLKINSL QPEDFGTY YC (SEQ ID NO: 1399) | QHHY GTPYT (SEQ ID NO: 54) | FGGGT KLEIK (SEQ ID NO: 959) |
| BP003T3P2-23 | DIQMTQSPASLSAS VGESVTITCRAS (SEQ ID NO: 718) | ENSYS Y (SEQ ID NO: 52) | LEWYQ QKQGK SPQLL VY (SEQ ID NO: 1072) | NAK (SEQ ID NO: 28) | TLAEGVPS RFSGSGSGT QFSLRINSL QPEDFGTY YC (SEQ ID NO: 1400) | QHHY GSPYT (SEQ ID NO: 1216) | FGGGT KLEIK (SEQ ID NO: 959) |
| BP003T3P2-24 | DIQMTQSPASLSAS VGESVTITCRAS (SEQ ID NO: 718) | ENSYS Y (SEQ ID NO: 52) | LEWYQ QKQGK SPQLL VY (SEQ ID NO: 1072) | NAK (SEQ ID NO: 28) | TLAEGVPS RFSGSGSGT QFSLRINSL QPEDFGTY YC (SEQ ID NO: 1400) | QHHY GSPYT (SEQ ID NO: 1216) | FGGGT KLEIK (SEQ ID NO: 959) |
| BP003T3P2-25 | DIQMTQSPASLSAS VGESVTITCRTS (SEQ ID NO: 719) | ENSYS Y (SEQ ID NO: 52) | LEWYQ QKQGK SPQLL VY (SEQ ID NO: 1072) | NAK (SEQ ID NO: 28) | TLAEGVPS RFSGSGSGT QFSLRINSL QPEDFGTY YC (SEQ ID NO: 1400) | QHHY GSPYT (SEQ ID NO: 1216) | FGGGT KLEMK (SEQ ID NO: 961) |
| BP003T3P2-26 | DIVLTQSPASLSASV GESVTITCRAS (SEQ ID NO: 770) | ENIYSY (SEQ ID NO: 930) | VEWYQ QKQGK SPQLL VY (SEQ ID NO: 1433) | NAK (SEQ ID NO: 28) | TLAEGVPS RFSGSGSGT HFSLKINSL QPEDFGNY YC (SEQ ID NO: 1397) | QHHY GSPYT (SEQ ID NO: 1216) | FGGGT KLEMK (SEQ ID NO: 961) |
| BP003T3P2-27 | DIXMTQSTSSLSASL GDRXTITCRAS (SEQ ID NO: 832) | QDISNY (SEQ ID NO: 27) | VNWY QQKPD GTVKL LIY (SEQ ID NO: 1436) | YAS (SEQ ID NO: 1476) | RLHSGVPS RFSGSGSGT DYSLTISNL EQEDFANY FC (SEQ ID NO: 1352) | QQGN TLPWT (SEQ ID NO: 1255) | FGGGT KLEIK (SEQ ID NO: 959) |

TABLE 4B-continued

Exemplary Clones-Light Chain Sequences

| ID | LFR1 | CDRL1 | LFR2 | CDRL2 | LFR3 | CDRL3 | LFR4 |
|---|---|---|---|---|---|---|---|
| BP003T3P2-28 | DIQMTQTTSSLSASL GDRVTISCRAS (SEQ ID NO: 760) | QDISNY (SEQ ID NO: 27) | LNWYQ QKPDG TVKLLI Y (SEQ ID NO: 1088) | HTS (SEQ ID NO: 1002) | NLQSGVPS RFTGSGSG TDYSLTISN LEQEDIATY FC (SEQ ID NO: 1151) | QQSNT LPPT (SEQ ID NO: 1272) | FGGGT KLEIK (SEQ ID NO: 959) |
| BP003T3P2-29 | DIQMTQTTSSLSASL GDRVTISCRAS (SEQ ID NO: 760) | QDISNY (SEQ ID NO: 27) | LNWYQ QKPDG TVKLLI Y (SEQ ID NO: 1088) | HTS (SEQ ID NO: 1002) | RLQSGVPS RFTGSGSG TDYSLTISN LEQEDIATY FC (SEQ ID NO: 1355) | QQSNS LPPT (SEQ ID NO: 1271) | FGGGT KLEIK (SEQ ID NO: 959) |
| BP003T3P2-3 | DIQMTQSPASLSAS VGETVTITCRAS (SEQ ID NO: 720) | ENIYSY (SEQ ID NO: 930) | LEWYQ QKQGK SPQLL VY (SEQ ID NO: 1072) | NAK (SEQ ID NO: 28) | TLVEGVPS RFSGSGSGT QFSLKINSL QPEDFGSY YC (SEQ ID NO: 1408) | QHHY DTPYT (SEQ ID NO: 30) | FGGGT KLEIK (SEQ ID NO: 959) |
| BP003T3P2-30 | DIQMTQTTSSLSASL GDRVTISCRAS (SEQ ID NO: 760) | QDISNY (SEQ ID NO: 27) | LNWYQ QKPDG TVKLLI Y (SEQ ID NO: 1088) | HTS (SEQ ID NO: 1002) | RLQSGVPS RFTGSGSG TDYSLTISN LEQEDIATY FC (SEQ ID NO: 1355) | QQSNS LPPT (SEQ ID NO: 1271) | FGGGT KLEIK (SEQ ID NO: 959) |
| BP003T3P2-31 | DIQMTQTTSSLSASL GDRVTISCRAS (SEQ ID NO: 760) | QDISNY (SEQ ID NO: 27) | LNWYQ QKPDG TVKLLI Y (SEQ ID NO: 1088) | HTS (SEQ ID NO: 1002) | RLQSGVPS RFTGSGSG TDYSLTISN LEQEDIATY FC (SEQ ID NO: 1355) | QQSNS LPPT (SEQ ID NO: 1271) | FGGGT KLEIK (SEQ ID NO: 959) |
| BP003T3P2-32 | DIQMTQSTSSLSASL GDRVTISCRAS (SEQ ID NO: 738) | QDISNY (SEQ ID NO: 27) | LNWYQ QKPDG TVKLLI Y (SEQ ID NO: 1088) | YTS (SEQ ID NO: 1495) | RLHSGVPS RFSGSGSGT DYSLTISNL EQEDIATYF C (SEQ ID NO: 1353) | QQGN TLPPT (SEQ ID NO: 1253) | FGGGT KLEIK (SEQ ID NO: 959) |
| BP003T3P2-33 | DIQMTQTTSSLSASL GDRVTISCRAS (SEQ ID NO: 760) | QDISNY (SEQ ID NO: 27) | LNWYQ QKPDG TVKLLI Y (SEQ ID NO: 1088) | HTS (SEQ ID NO: 1002) | RLQSGVPS RFTGSGSG TDYSLTISN LEQEDIATY FC (SEQ ID NO: 1355) | QQSNS LPPT (SEQ ID NO: 1271) | FGGGT KLEIK (SEQ ID NO: 959) |
| BP003T3P2-34 | DIQMTQTTSSLSASL GDRVTISCRAS (SEQ ID NO: 760) | QDISNY (SEQ ID NO: 27) | LNWYQ QKPDG TVKLLI Y (SEQ ID NO: 1088) | HTS (SEQ ID NO: 1002) | RLQSGVPS RFTGSGSG TDYSLTISN LEQEDIATY FC (SEQ ID NO: 1355) | QQSNS LPPT (SEQ ID NO: 1271) | FGGGT KLEIK (SEQ ID NO: 959) |
| BP003T3P2-35 | DIQMTQTTSSLSASL GDRVTISCRAS (SEQ ID NO: 760) | QDISNY (SEQ ID NO: 27) | LNWYQ QKPDG TVKLLI Y (SEQ ID NO: 1088) | HTS (SEQ ID NO: 1002) | NLQSGVPS RFTGSGSG TDYSLTISN LEQEDIATY FC (SEQ ID NO: 1151) | QQSNT LPPT (SEQ ID NO: 1272) | FGGGT KLEIK (SEQ ID NO: 959) |
| BP003T3P2-36 | DIQMTQSTSSLSASL GDRVTITCRAS (SEQ ID NO: 740) | QDISNY (SEQ ID NO: 27) | LNWYQ QKPDG TVKLLI Y (SEQ ID NO: 1088) | HTS (SEQ ID NO: 1002) | RLHSGVPS RFSGSESGT DYSLTISNL EQEDIATYF C (SEQ ID NO: 1350) | QQSNT LPPT (SEQ ID NO: 1272) | FGGGT KLEIK (SEQ ID NO: 959) |
| BP003T3P2-37 | DVVMTQTTSSLSAS LGDRVTITCRAS (SEQ ID NO: 915) | QDISNY (SEQ ID NO: 27) | LNWYQ QKPDG TVKLLI Y (SEQ ID NO: 1002) | HTS | RLHSGVPS RFSGSESGT DYSLTISNL EQEDIATYF | QQGN TLPPT (SEQ | FGGGT KLEIK (SEQ ID NO: |

TABLE 4B-continued

Exemplary Clones-Light Chain Sequences

| ID | LFR1 | CDRL1 | LFR2 | CDRL2 | LFR3 | CDRL3 | LFR4 |
|---|---|---|---|---|---|---|---|
| | | | ID NO: 1088) | | C (SEQ ID NO: 1350) | 1253) | 959) |
| BP003T3P2-38 | DIQMTQSTSSLSASL GDRVTISCRAS (SEQ ID NO: 738) | QDISNY (SEQ ID NO: 27) | LNWYQ QKPDG TVKLLI Y (SEQ ID NO: 1088) | YTS (SEQ ID NO: 1495) | RLHSGVPS RFSGSGSGT DYSLTISNL EQEDIATYF C (SEQ ID NO: 1353) | QQGN TLPPT (SEQ ID NO: 1253) | FGGGT KLEIK (SEQ ID NO: 959) |
| BP003T3P2-39 | DIVMTQSTSSLSASL GDRVTISCRAS (SEQ ID NO: 828) | QDISNY (SEQ ID NO: 27) | LNWYQ QKPDG TVKLLI Y (SEQ ID NO: 1088) | HTS (SEQ ID NO: 1002) | RLHSGVPS RFSGSESGT DYSLTISNL EQEDIATYF C (SEQ ID NO: 1350) | QQGN TLPPT (SEQ ID NO: 1253) | FGGGT KLEIK (SEQ ID NO: 959) |
| BP003T3P2-4 | DIQMTQSPASLSAS VGETVTITCRAS (SEQ ID NO: 720) | ENIYSY (SEQ ID NO: 930) | LEWYQ QKQGK SPQLL VY (SEQ ID NO: 1072) | NAK (SEQ ID NO: 28) | TLVEGVPS RFSGSGSGT QFSLKINSL QPEDFGSY YC (SEQ ID NO: 1408) | QHHY DTPYT (SEQ ID NO: 30) | FGGGT KLEIK (SEQ ID NO: 959) |
| BP003T3P2-40 | DIVMTQSQKFMSTS VGDRVSVTCKAS (SEQ ID NO: 821) | QNVGT N (SEQ ID NO: 12) | VAWY QQKPG QSPKA LIY (SEQ ID NO: 1425) | SAS (SEQ ID NO: 13) | YRYSGVPD RFTGSGSG TDFTLTISN VQSEDLAE YFC (SEQ ID NO: 1483) | QQYN SYPYT (SEQ ID NO: 15) | FGGGT KLEIK (SEQ ID NO: 959) |
| BP003T3P2-41 | DIVITQSQKFMSTSV GDRVSVTCKAS (SEQ ID NO: 766) | QNVGT N (SEQ ID NO: 12) | VAWY QQKPG QSPKA LIY (SEQ ID NO: 1425) | SAS (SEQ ID NO: 13) | YRYSGVPD RFTGSGSG TDFTLTISN VQSEDLAE YFC (SEQ ID NO: 1483) | QQYN SYPYT (SEQ ID NO: 15) | FGGGT KLEIK (SEQ ID NO: 959) |
| BP003T3P2-42 | DIQMTQSQKFMSTS VGDRVSVTCKAS (SEQ ID NO: 734) | QNVGT N (SEQ ID NO: 12) | VAWY QQKPG QSPKA LIY (SEQ ID NO: 1425) | SAS (SEQ ID NO: 13) | YRYSGVPD RFTGSGSG TDFTLTISN VQSEDLAE YFC (SEQ ID NO: 1483) | QQYN SYPYT (SEQ ID NO: 15) | FGGGT KLEIK (SEQ ID NO: 959) |
| BP003T3P2-43 | DIVLTQSQKFMSTS VGDRVSVTCKAS (SEQ ID NO: 773) | QNVGT N (SEQ ID NO: 12) | VAWY QQKPG QSPKA LIY (SEQ ID NO: 1425) | SAS (SEQ ID NO: 13) | YRYSGVPD RITGRGSGT DFTLTISNV QSEDLADY FC (SEQ ID NO: 1488) | QQYN TYPYT (SEQ ID NO: 1287) | FGGGT KLEIK (SEQ ID NO: 959) |
| BP003T3P2-44 | DIQMTQSQKFMSTS AGDRVSVTCKAS (SEQ ID NO: 730) | QNVGT N (SEQ ID NO: 12) | VAWY QQKPG QSPKA LIY (SEQ ID NO: 1425) | SAS (SEQ ID NO: 13) | YRYSGVPD RFTGSGSG TDFTLTISN VQSEDLAE YFC (SEQ ID NO: 1483) | QQYN SYPYT (SEQ ID NO: 15) | FGGGT KLEIK (SEQ ID NO: 959) |
| BP003T3P2-45 | DIVLTQSQKFMSTS VGDRVSVTCKAS (SEQ ID NO: 773) | QNVGT N (SEQ ID NO: 12) | VAWY QQKPG QSPKA LIY (SEQ ID NO: 1425) | SAS (SEQ ID NO: 13) | YRYSGVPD RFTGSGSG TDFTLTISN VQSEDLAE YFC (SEQ ID NO: 1483) | QQYN TYPYT (SEQ ID NO: 1287) | FGGGT KLEMK (SEQ ID NO: 961) |
| BP003T3P2-46 | RCPDDPSPSSLSASL GERVSLTCRAS (SEQ ID NO: 1347) | QDIGLN (SEQ ID NO: | LNWLQ QEPDG TIKRLI | ATS (SEQ ID NO: | SLDSGVPK RFSGSRSGS DYSLTISSL | LQYAS SPFT (SEQ | FGAGT KLEIK (SEQ ID |

TABLE 4B-continued

Exemplary Clones-Light Chain Sequences

| ID | LFR1 | CDRL1 | LFR2 | CDRL2 | LFR3 | CDRL3 | LFR4 |
|---|---|---|---|---|---|---|---|
| | | Y (SEQ ID NO: 1198) | | 618) | ESEDFVDY YC (SEQ ID NO: 1366) | ID NO: 1085) | NO: 1097) | NO: 958) |
| BP003T3P2-47 | DIVLTQSQKFMSTS VGDRVSVTCKAS (SEQ ID NO: 773) | QNVGT N (SEQ ID NO: 12) | VAWY QQKPG QSPKA LIY (SEQ ID NO: 1425) | SAS (SEQ ID NO: 13) | YRYSGVPD RITGRGSGT DFTLTISNV QSEDLADY FC (SEQ ID NO: 1488) | QQYN TYPYT (SEQ ID NO: 1287) | FGGGT KLEIK (SEQ ID NO: 959) |
| BP003T3P2-48 | DIQMTQSQKFMSTS VGDRVSVTCKAS (SEQ ID NO: 734) | QNVGT N (SEQ ID NO: 12) | VAWY QQKPG QSPKA LIY (SEQ ID NO: 1425) | SAS (SEQ ID NO: 13) | YRYSGVPD RFTGSGSG TDFTLTISN VQSEDLAE YFC (SEQ ID NO: 1483) | QQYN SYPYT (SEQ ID NO: 15) | FGGGT KLEIK (SEQ ID NO: 959) |
| BP003T3P2-49 | DTTVTQSQKFMSTS VGDRVSVTCKAS (SEQ ID NO: 858) | QNVGT N (SEQ ID NO: 12) | VAWY QQKPG QSPKA LIY (SEQ ID NO: 1425) | SAS (SEQ ID NO: 13) | YRYSGVPD RFTGSGSG TDFTLTISN VQSEDLAE YFC (SEQ ID NO: 1483) | QQYN SYPYT (SEQ ID NO: 15) | FGGGT KLEMK (SEQ ID NO: 961) |
| BP003T3P2-5 | DIQMTQSPASLSAS VGETVTITCRAS (SEQ ID NO: 720) | ENIYSY (SEQ ID NO: 930) | LEWYQ QKQGK SPQLL VY (SEQ ID NO: 1072) | NAK (SEQ ID NO: 28) | TLAEGVPS RFSGSGSGT QFSLKINSL QPEDFGSY YC (SEQ ID NO: 1398) | QHHY DTPYT (SEQ ID NO: 30) | FGGGT KLEIK (SEQ ID NO: 959) |
| BP003T3P2-50 | DIVMTQSQKFMSTS VGDRVSVTCKAS (SEQ ID NO: 821) | QNVGT N (SEQ ID NO: 12) | VAWY QQKPG QSPKA LIY (SEQ ID NO: 1425) | SAS (SEQ ID NO: 13) | YRYSGVPD RFTGSGSG TDFTLTISN VQSEDLAE YFC (SEQ ID NO: 1483) | QQYN SYPYT (SEQ ID NO: 15) | FGGGT KLEIK (SEQ ID NO: 959) |
| BP003T3P2-51 | MLVMTQTPLSLPVS LGDQASISCRSS (SEQ ID NO: 1132) | QSLVH SNGNT Y (SEQ ID NO: 1306) | LHWYL QKPGQ SPKLLI Y (SEQ ID NO: 1076) | KVS (SEQ ID NO: 1062) | NRFSGVPD RFSVSGSGT DFTLKISRV EAEDLGVY FC (SEQ ID NO: 1159) | SQSTH VPPT (SEQ ID NO: 1371) | FGGGT KLEIK (SEQ ID NO: 959) |
| BP003T3P2-52 | DTTVTQSQKFMSTS VGDRVSVTCKAS (SEQ ID NO: 858) | QNVGT N (SEQ ID NO: 12) | VAWY QQKPG QSPKA LIY (SEQ ID NO: 1425) | SAS (SEQ ID NO: 13) | YRYSGVPD RFTGSGSG TDFTLTISN VQSEDLAE YFC (SEQ ID NO: 1483) | QQYN SYPYT (SEQ ID NO: 15) | FGGGT KLEMK (SEQ ID NO: 961) |
| BP003T3P2-53 | DVQMTQSQKFMST SVGDRVSVTCKAS (SEQ ID NO: 873) | QNVGT N (SEQ ID NO: 12) | VAWY QQKPG QSPKA LIY (SEQ ID NO: 1425) | SAS (SEQ ID NO: 13) | YRYSGVPD RFTGSGSG TDFTLTISN VQSEDLAE YFC (SEQ ID NO: 1483) | QQYN SYPYT (SEQ ID NO: 15) | FGGGT KLEIK (SEQ ID NO: 959) |
| BP003T3P2-54 | DIQMTQSQKFMSTS VGDRVSVTCKAS (SEQ ID NO: 734) | QNVGT N (SEQ ID NO: 12) | VAWY QQKPG QSPKA LIY (SEQ ID NO: 1425) | SAS (SEQ ID NO: 13) | YRYSGVPD RFTGSGSG TDFTLTISN VQSEDLAE YFC (SEQ ID NO: 1483) | QQYN SYPYT (SEQ ID NO: 15) | FGGGT KLEIK (SEQ ID NO: 959) |

TABLE 4B-continued

Exemplary Clones-Light Chain Sequences

| ID | LFR1 | CDRL1 | LFR2 | CDRL2 | LFR3 | CDRL3 | LFR4 |
|---|---|---|---|---|---|---|---|
| BP003T3P2-55 | DILLTQSQKFMSTSV GDRVSVTCKAS (SEQ ID NO: 700) | QNVGT N (SEQ ID NO: 12) | VAWY QQKPG QSPKA LIY (SEQ ID NO: 1425) | SAS (SEQ ID NO: 13) | YRYSGVPD RFTGSGSG TDFTLTISN VQSEDLAE YFC (SEQ ID NO: 1483) | QQYN SYPYT (SEQ ID NO: 15) | FGGGT KLEMK (SEQ ID NO: 961) |
| BP003T3P2-56 | DIVLTQSQKFMSTS VGDRVSVTCKAS (SEQ ID NO: 773) | QNVGT N (SEQ ID NO: 12) | VAWY QQEPG QSPKA LIY (SEQ ID NO: 1423) | SAS (SEQ ID NO: 13) | YRYSGVPD RFTGSGSG TDFTLTISN VQSEDLAE YFC (SEQ ID NO: 1483) | QQYN SYPYT (SEQ ID NO: 15) | FGGGT KLEIK (SEQ ID NO: 959) |
| BP003T3P2-57 | DILLTQSQKFMSTSV GDRVSVTCKAS (SEQ ID NO: 700) | QNVGT N (SEQ ID NO: 12) | VAWY QQKPG QSPKA LIY (SEQ ID NO: 1425) | SAS (SEQ ID NO: 13) | YRYSGVPD RFTGSGSG TDFTLTISN VQSEDLAE YFC (SEQ ID NO: 1483) | QQYN SYPYT (SEQ ID NO: 15) | FGGGT KLEMK (SEQ ID NO: 961) |
| BP003T3P2-58 | DVVMTQSQKFMST SVGDRVSVTCKAS (SEQ ID NO: 894) | QNVGT N (SEQ ID NO: 12) | VAWY QQKPG QSPKA LIY (SEQ ID NO: 1425) | SAS (SEQ ID NO: 13) | YRYSGVPD RFTGSGSG TDFTLTISN VQSEDLAE YFC (SEQ ID NO: 1483) | QQYN SYPYT (SEQ ID NO: 15) | FGGGT KLEMK (SEQ ID NO: 961) |
| BP003T3P2-59 | RHCESQSHKFMSTSI GDRVSITCKAS (SEQ ID NO: 1349) | QDVRT A (SEQ ID NO: 1208) | VAWY QQKPG QSPKL LIY (SEQ ID NO: 1427) | STS (SEQ ID NO: 1386) | YRYSGVPD RFTGSGSG TDFTLTINS VQSEDLAD YFC (SEQ ID NO: 1481) | QQYS NYLTF (SEQ ID NO: 1290) | GAGTK LEIK (SEQ ID NO: 974) |
| BP003T3P2-6 | DIQMTQSPASLSAS VGETVTITCRAS (SEQ ID NO: 720) | ENIYSY (SEQ ID NO: 930) | LEWYQ QKQGK SPQLL VY (SEQ ID NO: 1072) | NAK (SEQ ID NO: 28) | TLAEGVPS RFSGSGSGT QFSLKINSL QPEDFGSY YC (SEQ ID NO: 1398) | QHHY DTPYT (SEQ ID NO: 30) | FGGGT KLEIK (SEQ ID NO: 959) |
| BP003T3P2-60 | DIVLTQSQKFMSTS VGDRVSVTCKAS (SEQ ID NO: 773) | QNVGT N (SEQ ID NO: 12) | VAWY QQKPG QSPKA LIY (SEQ ID NO: 1425) | SAS (SEQ ID NO: 13) | YRYSGVPD RITGRGSGT DFTLTISNV QSEDLADY FC (SEQ ID NO: 1488) | QQYN TYPYT (SEQ ID NO: 1287) | FGGGT KLEIK (SEQ ID NO: 959) |
| BP003T3P2-61 | DVHMNQSQKFMST SVGNRVSVTCKGS (SEQ ID NO: 865) | QNVGT N (SEQ ID NO: 12) | VXWY QQKPG QSPKA LIY (SEQ ID NO: 1449) | SAS (SEQ ID NO: 13) | YRYNGVPD RFTGSGSG TDFTLTISN VQSEDLAE YFC (SEQ ID NO: 1478) | XQYN SYPYT (SEQ ID NO: 1475) | FGGGT XLEIK (SEQ ID NO: 963) |
| BP003T3P2-62 | DIVMTQTPKFLLVS AGDRVTITCKAS (SEQ ID NO: 830) | QSVNN D (SEQ ID NO: 1309) | WWY QQKPG QSPKL LIY (SEQ ID NO: 1447) | YAS (SEQ ID NO: 1476) | NRYTGVPD RFTGSGYG TDFTFTIST VQAEDLAV YFC (SEQ ID NO: 1164) | QQAY WSPY T (SEQ ID NO: 1248) | FGGGT KLEIK (SEQ ID NO: 959) |
| BP003T3P2-63 | DIVMTQSPPTLSLSP GERVTLSCKAS (SEQ ID NO: 816) | QDVNT A (SEQ ID NO: 1206) | VAWY QQKPG QAPRL LIY (SEQ ID NO: 1450) | WAS (SEQ ID NO:) | TRHTGVPS RFSGSGSGT DFTLTISSL QPEDFATY | QQHY SSPWT (SEQ ID NO:) | FGGGT KLEIK (SEQ ID NO:) |

TABLE 4B-continued

Exemplary Clones-Light Chain Sequences

| ID | LFR1 | CDRL1 | LFR2 | CDRL2 | LFR3 | CDRL3 | LFR4 |
|---|---|---|---|---|---|---|---|
| | | | (SEQ ID NO: 1424) | | YC (SEQ ID NO: 1414) | 1258) | 959) |
| BP003T3P2-64 | EIVMTQSPPTLSLSP GERVTLSCKAS (SEQ ID NO: 926) | QDVNTA (SEQ ID NO: 1206) | VAWY QQKPG QAPRL LIY (SEQ ID NO: 1424) | WAS (SEQ ID NO: 1450) | TRHTGVPS RFSGSGSGT DFTLTISSL QPEDFATY YC (SEQ ID NO: 1414) | QQHY SSPWT (SEQ ID NO: 1258) | FGGGT KLEIK (SEQ ID NO: 959) |
| BP003T3P2-65 | DIVMTQSPPTLSLSP GERVTLSCKAS (SEQ ID NO: 816) | QDVNTA (SEQ ID NO: 1206) | VAWY QQKPG QAPRL LIY (SEQ ID NO: 1424) | WAS (SEQ ID NO: 1450) | TRHTGVPS GFSGSGSG TDFTLTISS LQPEDFAT YYC (SEQ ID NO: 1413) | QQHY SSPWT (SEQ ID NO: 1258) | FGGGT KLEIK (SEQ ID NO: 959) |
| BP003T3P2-66 | RCQMNQSPSSLSAS LGERVSLTCRAS (SEQ ID NO: 1348) | QEISGY (SEQ ID NO: 1210) | LSWLQ QKPDG TIKRLT Y (SEQ ID NO: 1112) | AAS (SEQ ID NO: 599) | TLDSGVPK RFSGSRSGS DYSLTISSL ESEDFADY YC (SEQ ID NO: 1402) | LQYAS YPYT (SEQ ID NO: 1103) | FGGGT KLEMK (SEQ ID NO: 961) |
| BP003T3P2-67 | DVVLTQTPLSLPVSL GDQASISCRSS (SEQ ID NO: 874) | QSIVHS NGNTY (SEQ ID NO: 1299) | LEWYL QKPGQ SPKLLI Y (SEQ ID NO: 1071) | KVS (SEQ ID NO: 1062) | NRFSGVPD RFSGSGSGT DFTLKISRV EAEDLGVY YC (SEQ ID NO: 1158) | FQGSH VPPT (SEQ ID NO: 966) | FGGGT KLEMK (SEQ ID NO: 961) |
| BP003T3P2-68 | DVVVTQTPLSLPVS LGDQASISCRSS (SEQ ID NO: 918) | QSIVHS NGNTY (SEQ ID NO: 1299) | LEWYL QKPGQ SPKLLI Y (SEQ ID NO: 1071) | KVS (SEQ ID NO: 1062) | NRFSGVPD RFSGSGSGT DFTLKISRV EAEDLGVY YC (SEQ ID NO: 1158) | FQGSH VPRT (SEQ ID NO: 967) | FGGGT KLEIK (SEQ ID NO: 959) |
| BP003T3P2-69 | DVVMTQTPLSLPVS LGDQASISCRSN (SEQ ID NO: 899) | QSIVHN NGNTY (SEQ ID NO: 1298) | LEWYL QKPGQ SPKLLI Y (SEQ ID NO: 1071) | KVS (SEQ ID NO: 1062) | NRFSGVPD RFSGSGSGT DFTLKISRV EAEDLGVY YC (SEQ ID NO: 1158) | FQGSY VPRT (SEQ ID NO: 971) | FGGGT KLEIK (SEQ ID NO: 959) |
| BP003T3P2-7 | DIQMTQSPASLSAS VGETVTITCRAS (SEQ ID NO: 720) | ENIYSY (SEQ ID NO: 930) | LEWYQ QKQGK SPQLL VY (SEQ ID NO: 1072) | NAK (SEQ ID NO: 28) | TLAEGVPS RFSGSGSGT QFSLKINSL QPEDFGSY YC (SEQ ID NO: 1398) | QHHY DTPYT (SEQ ID NO: 30) | FGGGT KLEIK (SEQ ID NO: 959) |
| BP003T3P2-70 | DVVMTQTPLSLPVS LGDQASISCRSS (SEQ ID NO: 900) | QSIVHS NGNTY (SEQ ID NO: 1299) | LEWYL QKPGQ SPKLLI Y (SEQ ID NO: 1071) | KVS (SEQ ID NO: 1062) | NRFSGVPD RFSGSGSGT DFTLKISRV EAEDLGVY YC (SEQ ID NO: 1158) | FQGSH VPPT (SEQ ID NO: 966) | FGGGT KLEIK (SEQ ID NO: 959) |
| BP003T3P2-71 | DVVLTQTPLSLPVSL GDQASISCRSS (SEQ ID NO: 874) | QSIVHS NGNTY (SEQ ID NO: 1299) | LEWYL QKPGQ SPKLLI Y (SEQ ID NO: 1071) | KVS (SEQ ID NO: 1062) | NRFSGVPD RFSGSGSGT DFTLKISRV EAEDLGVY YC (SEQ ID NO: 1158) | FQGSH VPPT (SEQ ID NO: 966) | FGGGT KLEIK (SEQ ID NO: 959) |
| BP003T3P2-72 | DVVMTQTPLSLPVS LGDQASISCRSS (SEQ ID NO: 900) | QSIVHS NGNTY (SEQ ID NO: 1299) | LEWYL QKPGQ SPKLLI Y (SEQ ID NO: 1071) | KVS (SEQ ID NO: 1062) | NRFSGVPD RFSGSGSGT DFTLKISRV EAEDLGVY YC (SEQ ID NO: 1158) | FQGSH VPTF (SEQ ID NO: 968) | GGGTK KLEIK (SEQ ID NO: 978) |

TABLE 4B-continued

Exemplary Clones-Light Chain Sequences

| ID | LFR1 | CDRL1 | LFR2 | CDRL2 | LFR3 | CDRL3 | LFR4 |
|---|---|---|---|---|---|---|---|
| BP003T3P2-73 | DVVVTQTPLSLPVS LGDQASISCRSS (SEQ ID NO: 918) | QSIVHS NGNTY (SEQ ID NO: 1299) | LEWYL QKPGQ SPKLLI Y (SEQ ID NO: 1071) | KVS (SEQ ID NO: 1062) | NRFSGVPD RFSGSGSGT DFTLKISRV EAEDLGVY YC (SEQ ID NO: 1158) | FQGSH VPPT (SEQ ID NO: 966) | FGGGT KLEIK (SEQ ID NO: 959) |
| BP003T3P2-74 | DVVLTQTPLSLPVSL GDQASISCRSS (SEQ ID NO: 874) | QSIVHS NGNTY (SEQ ID NO: 1299) | LEWYL QKPGQ SPKLLI Y (SEQ ID NO: 1071) | KVS (SEQ ID NO: 1062) | NRFSGVPD RFSGSGSGT DFTLKISRV EAEDLGVY YC (SEQ ID NO: 1158) | FQGSH VPPT (SEQ ID NO: 966) | FGGGT KLEIK (SEQ ID NO: 959) |
| BP003T3P2-75 | DIQMNQSHKFMSTS VGDRVSITCKAS (SEQ ID NO: 713) | QDVST A (SEQ ID NO: 1209) | VAWY QQKPG QSPKL LIY (SEQ ID NO: 1427) | SAS (SEQ ID NO: 13) | YRYTGVPD RFTGSGSG TDFTFTISS VQAEDLAV YYC (SEQ ID NO: 1491) | QQHY STPYT (SEQ ID NO: 1265) | FGGGT KLEIK (SEQ ID NO: 959) |
| BP003T3P2-8 | DIQMTQSPASLSAS VGETVTITCRAS (SEQ ID NO: 720) | ENIYSY (SEQ ID NO: 930) | LEWYQ QKQGK SPQLL VY (SEQ ID NO: 1072) | NAK (SEQ ID NO: 28) | TLAEGVPS RFSGSGSGT QFSLKINSL QPEDFGSY YC (SEQ ID NO: 1398) | QHHY DTPYT (SEQ ID NO: 30) | FGGGT KLEIK (SEQ ID NO: 959) |
| BP003T3P2-9 | DIVMTQSPASLSAS VGETVTITCRAS (SEQ ID NO: 807) | DNIYN Y (SEQ ID NO: 833) | LEWYQ QKQGK SPQLL VY (SEQ ID NO: 1072) | NAK (SEQ ID NO: 28) | TLGEGVPS RFSGSGSGT QFYLKINSL QPEDFGSY YC (SEQ ID NO: 1404) | QHHY GSPW T (SEQ ID NO: 1215) | FGGGT KLEIK (SEQ ID NO: 959) |

TABLE 5A

Exemplary Clones-Heavy Chain Sequences

| ID | HFR1 | CDRH1 | HFR2 | CDRH2 | HFR3 | CDRH3 | HFR4 |
|---|---|---|---|---|---|---|---|
| AH04507 | QVQLQQSGAELVRPG TSVKMSCKAA (SEQ ID NO: 1326) | GYTFTNYW (SEQ ID NO: 4) | IGWVK QRPGH GLEWI GD (SEQ ID NO: 1010) | IHPGGG YI (SEQ ID NO: 1014) | DYNEKFT GKATLTA DTSSSTA YMQLSSL TSEDSAIY YC (SEQ ID NO: 923) | VSRNFA K (SEQ ID NO: 1444) | WGQGT LVTVSA (SEQ ID NO: 421) |
| AH04522 | QIQLQQSGAELVRPGT SVKMSCKAA (SEQ ID NO: 1228) | GYTFTNYW (SEQ ID NO: 4) | IGWVK QRPGH GLEWI GD (SEQ ID NO: 1010) | IHPGGG YT (SEQ ID NO: 1015) | NYNEKFK GKATLTA DTSSSTA YMQLSSL TSEDSAIY YC (SEQ ID NO: 1177) | TSRNFAY (SEQ ID NO: 1419) | WGQGT LVTVSA (SEQ ID NO: 421) |
| AH04526 | QVQLQQSGAELVRPG TSVKMSCKAA (SEQ ID NO: 1326) | GYTFTNYW (SEQ ID NO: 4) | IGWVK QRPGH GLEWI GD (SEQ ID NO: 1010) | IHPGGD YS (SEQ ID NO: 1012) | NYNEKFK GKATLTA DTSSSTA YMNLSSL TSEDSAIY YC (SEQ ID NO: 1174) | TSRNFAY (SEQ ID NO: 1419) | WGQGT PVTVSS (SEQ ID NO: 398) |

TABLE 5A-continued

Exemplary Clones-Heavy Chain Sequences

| ID | HFR1 | CDRH1 | HFR2 | CDRH2 | HFR3 | CDRH3 | HFR4 |
|---|---|---|---|---|---|---|---|
| AH04527 | QVQLQQSGAELVRPG TSVKMSCKAA (SEQ ID NO: 1326) | GYTFTNYW (SEQ ID NO: 4) | IGWVK QRPGH GLEWI GD (SEQ ID NO: 1010) | IHPGGG YI (SEQ ID NO: 1014) | DYNEKFT GKATLTA DTSSSTA YMQLSD TSEDSAIY YC (SEQ ID NO: 923) | VSRNFA K (SEQ ID NO: 1444) | WGQGT LVTVSA (SEQ ID NO: 421) |
| AH04734 | QVQLQQPAAELARPG ASVKMSCKAS (SEQ ID NO: 467) | GYTFTTST (SEQ ID NO: 993) | MHWV KQRPG QGLEW IGY (SEQ ID NO: 190) | INPRSG YT (SEQ ID NO: 1024) | EYNQKFK DKTTLTA DKSSSTA YMQLSSL TSEDSAV YYC (SEQ ID NO: 519) | ARHYYF DY (SEQ ID NO: 612) | WGQGT TVTVSS (SEQ ID NO: 422) |
| AH04750 | QVQLQQPGAEMAKP GASVKMSCKAS (SEQ ID NO: 1320) | GYTSTAYW (SEQ ID NO: 994) | IHWVK QRPGQ GLEWI GY (SEQ ID NO: 196) | ITPSTGY T (SEQ ID NO: 1028) | EYNQKFE DKATLTA DKSSNTA YMQLNSL TSEDSAV YYC (SEQ ID NO: 953) | ARGGYF DY (SEQ ID NO: 606) | WGQGT TVTVSS (SEQ ID NO: 422) |
| AH05214 | QIQLQQPGAELVKPG ASVKLPCKAS (SEQ ID NO: 1219) | GYTFTSYW (SEQ ID NO: 157) | MHWV KQRPG QGLEW IGE (SEQ ID NO: 209) | INPSNG RT (SEQ ID NO: 510) | NYNEKFK SKATLTV DKSSSTA YMQLSSL TSEDSAV YYC (SEQ ID NO: 289) | ARQLAA Y (SEQ ID NO: 614) | WGQGT TVTVSS (SEQ ID NO: 422) |
| AH05247 | QVQLQQSGADLMKP GASVKMSCRAS (SEQ ID NO: 1321) | GYTFSNYW (SEQ ID NO: 986) | IEWIKQ RPGHG LEWIG E (SEQ ID NO: 1005) | ILPGSGF T (SEQ ID NO: 1021) | NYNENFK GKATFTA DTSSNTT YMLLSSL SSEDSAV YYC (SEQ ID NO: 1187) | ARGGTS WHFDS (SEQ ID NO: 604) | WGQGT TLTVSS (SEQ ID NO: 425) |
| AH05249 | QVQLQQSGADLMKP GASVKMSCRAS (SEQ ID NO: 1321) | GYTFSNYW (SEQ ID NO: 986) | IEWIKQ RPGHG LEWIG E (SEQ ID NO: 1005) | ILPGSGF T (SEQ ID NO: 1021) | NYNENFK GKATFTA DTSSNTT YMLLSSL SSEDSAV YYC (SEQ ID NO: 1187) | ARGGTS WHFDS (SEQ ID NO: 604) | WGQGT TLTVSS (SEQ ID NO: 425) |
| AH05251 | EVRLQQSGAELVRSG ASVKLSCTAS (SEQ ID NO: 943) | GFNIKDYY (SEQ ID NO: 977) | IHWVK QRPEQ GLEWI GW (SEQ ID NO: 1017) | IDPDNG ET (SEQ ID NO: 1003) | EYAPKFQ GKATMT ADTSSNT AHLQLSS LTSEDTA VYYC (SEQ ID NO: 946) | TVFWYG NNYAGF AY (SEQ ID NO: 1420) | WGQGT LVTVSS (SEQ ID NO: 413) |
| AH05256 | QVQLQQPGAELAKPG ASVKMSCKAS (SEQ ID NO: 114) | GYTFTRYW (SEQ ID NO: 992) | IHWVK QRPGQ DLEWI GY (SEQ ID NO: 1018) | INPRTD YT (SEQ ID NO: 1025) | EYNQKFK DKATLTA DKSSSTA YMQLSSL TSDDSAV YYC (SEQ ID NO: 955) | ARHGYF DY (SEQ ID NO: 611) | WGQGT TLTVSS (SEQ ID NO: 425) |
| AH05257 | QVQLQQSGAELVRPG VSLKISCKGS (SEQ ID NO: 1337) | GYTFTDYA (SEQ ID NO: 19) | MHWV RQSHA KSLEW IGV (SEQ ID NO: 21) | ISTYSG DA (SEQ ID NO: 21) | IYNQKFK GKATMT VDKSSST AYLELAR | ARGVTF DY (SEQ ID NO: 23) | WGQGT TLTVSA (SEQ ID NO: |

TABLE 5A-continued

Exemplary Clones-Heavy Chain Sequences

| ID | HFR1 | CDRH1 | HFR2 | CDRH2 | HFR3 | CDRH3 | HFR4 |
|---|---|---|---|---|---|---|---|
| | | | (SEQ ID NO: 1128) | | LTSEDSAI YYC (SEQ ID NO: 1034) | | 1452) |
| AH05258 | QIQLQQSGAELVRPG VSVKISCKGS (SEQ ID NO: 1240) | GYTFTDYA (SEQ ID NO: 19) | MHWV KQSHA KSLEW IGV (SEQ ID NO: 1126) | ISTYSG DV (SEQ ID NO: 46) | SYNQKFK GKATMT VDKSSST AYMELA RLTSEDS AIYYC (SEQ ID NO: 1389) | ARGVTF DS (SEQ ID NO: 48) | WGQGT TLTVSS (SEQ ID NO: 425) |
| AH05259 | QVQLQQSGAELVRPG VSVKISCKGS (SEQ ID NO: 1338) | GYTFTDYA (SEQ ID NO: 19) | MHWV KQSHA KSLEW IGV (SEQ ID NO: 1126) | ISTYSG DV (SEQ ID NO: 46) | SYNQKFK GKATMT VDKSSST AYMELA RLTSEDS AIYYC (SEQ ID NO: 1389) | ARGVTF DS (SEQ ID NO: 48) | WGQGT SLTVSS (SEQ ID NO: 424) |
| AH05268 | QVQLQQSGAELVRPG VSLKISCKGS (SEQ ID NO: 1337) | GYTFTDYA (SEQ ID NO: 19) | MHWV RQSHA KSLEW IGV (SEQ ID NO: 1128) | ISTYSG DA (SEQ ID NO: 21) | LYNQKFK GKATMT VDKSSST AYLELAR LTSDDSAI YYC (SEQ ID NO: 1119) | ARGVTF DY (SEQ ID NO: 23) | WGQGT TLTVSS (SEQ ID NO: 425) |
| AH05271 | QVQLQQSGAELVRPG VSVKISCKGS (SEQ ID NO: 1338) | GYTFTDYA (SEQ ID NO: 19) | MHWV KQSHA KSLEW IGV (SEQ ID NO: 1126) | ISTYSG DV (SEQ ID NO: 46) | SYNQKFK GKATMT VDKSSST AYMELA RLTSEDS ATYYC (SEQ ID NO: 1390) | ARGVTF DS (SEQ ID NO: 48) | WGQGT TLTVSS (SEQ ID NO: 425) |
| AH05274 | QVQLQQSGAELVRPG TSVKISCKAS (SEQ ID NO: 1325) | GYTFTNYW (SEQ ID NO: 4) | LGWIK QRPGH GLEWI GD (SEQ ID NO: 1074) | IYPGGG YT (SEQ ID NO: 6) | NYNEKFK GKATLTA DTSSSTA YMQLSSL TSEDSAV YFC (SEQ ID NO: 1178) | ARVTPAS (SEQ ID NO: 8) | WGQGT SLTVSS (SEQ ID NO: 424) |
| AH05280 | EVRLQQSGADLMKPG ASVKISCKTS (SEQ ID NO: 941) | GYTFSNYW (SEQ ID NO: 986) | TEWIK QRPGH GLEWI GE (SEQ ID NO: 1392) | ILPGSGF T (SEQ ID NO: 1021) | NYNENFK GKATFTA DTSSNTT YMQLSSL TSEDSAV YYC (SEQ ID NO: 1188) | ARGGTS WHFDY (SEQ ID NO: 605) | WGQGT SLTVSS (SEQ ID NO: 424) |
| AH05285 | DVQLQESGAELAKPG ASVKMSCKAS (SEQ ID NO: 866) | GYTFTRFW (SEQ ID NO: 991) | MHWV KQRPG QGLEW IGY (SEQ ID NO: 190) | INPSTD YT (SEQ ID NO: 1027) | EYNQKFK DKATLTA DKSSSTA YMQLSSL TSEDSAV YYC (SEQ ID NO: 265) | ARGTW DY (SEQ ID NO: 607) | WGQGA TVTVSS (SEQ ID NO: 1451) |
| AH05286 | QVQLKQSGADLMKP GASVKISCKAS (SEQ ID NO: 1312) | GYTFSNYW (SEQ ID NO: 986) | IEWIKQ RPGHG LEWIG E (SEQ ID NO: 1005) | ILPGSG YT (SEQ ID NO: 1022) | NYNENFK GKATFTA DTSSNTT YIQLSSLS SEDSAVY YC (SEQ ID NO: 1186) | ARGGTSF VHFDY (SEQ ID NO: 602) | WGQGT TLTVSS (SEQ ID NO: 425) |

TABLE 5A-continued

Exemplary Clones-Heavy Chain Sequences

| ID | HFR1 | CDRH1 | HFR2 | CDRH2 | HFR3 | CDRH3 | HFR4 |
|---|---|---|---|---|---|---|---|
| AH4501 | QVQLQQPGAELVRPGTSVKMSCKAA (SEQ ID NO: 1315) | GYTFTNYW (SEQ ID NO: 4) | IGWVKQRPGHGLEWIGD (SEQ ID NO: 1010) | IHPGGDYS (SEQ ID NO: 1012) | NYNEKFKGKATLTADTSSSTAYMNLSSLTSEDSAIYYC (SEQ ID NO: 1174) | TSRNFAY (SEQ ID NO: 1419) | WGQGTLVTVSA (SEQ ID NO: 421) |
| AH4502 | QIQLQQSGAELVRPGTSVKMSCKAA (SEQ ID NO: 1228) | GYTFTNYW (SEQ ID NO: 4) | IGWVKQRPGHGLEWIGD (SEQ ID NO: 1010) | IHPGGGYT (SEQ ID NO: 1015) | NYNEKFKGKATLTADTSSSTADMQLSSLTSEDSAIYYC (SEQ ID NO: 1173) | TSRNFAY (SEQ ID NO: 1419) | WGQGTLVTVSA (SEQ ID NO: 421) |
| AH4503 | QVQLQQPGAELVRPGTSVKMSCKAA (SEQ ID NO: 1315) | GYTFSNYW (SEQ ID NO: 986) | IGWVKQRPGHGLEWIGD (SEQ ID NO: 1010) | IHPGGGYI (SEQ ID NO: 1014) | NYNEKFTGKATLTADTSSSTAYMQLSSLTSEDSAIYYC (SEQ ID NO: 1184) | VSRNFAN (SEQ ID NO: 1445) | WGQGTLVTVSA (SEQ ID NO: 421) |
| AH4505 | DVQLQQSGAELVRPGTSVKMSCKAA (SEQ ID NO: 867) | GYTFTNYW (SEQ ID NO: 4) | IGWVKQRPGHGLEWIGD (SEQ ID NO: 1010) | IHPGGGYT (SEQ ID NO: 1015) | NYNEKFKGKATLTADTSSSTAYMQLSSLTSEGSAIYYC (SEQ ID NO: 1179) | TSRNFAY (SEQ ID NO: 1419) | WGQGTLVTVSA (SEQ ID NO: 421) |
| AH4509 | QIQLQQSGAELVRPGTSVKMSCKAA (SEQ ID NO: 1228) | GYTFTNYW (SEQ ID NO: 4) | IGWVKQRPGHGLEWIGD (SEQ ID NO: 1010) | FYPGGDYI (SEQ ID NO: 973) | NYNEKFKGKATLTADTSSSTAYMQLSSLTSEDSAIYYC (SEQ ID NO: 1177) | TSRNFAY (SEQ ID NO: 1419) | WGQGTPVTVSS (SEQ ID NO: 398) |
| AH4511 | QIQLQQSGAELVRPGTSVKMSCKAA (SEQ ID NO: 1228) | GYTFSNYW (SEQ ID NO: 986) | IGWVKQRPGHGLEWIGD (SEQ ID NO: 1010) | IHPGGGYI (SEQ ID NO: 1014) | NYNEKFTGKATLTADTSSSTAYMQLSSLTSEDSAIYYC (SEQ ID NO: 1184) | VSRNFAN (SEQ ID NO: 1445) | WGQGTLVTVSA (SEQ ID NO: 421) |
| AH4518 | QVQLQQSGAELVRPGTSVKMSCKAA (SEQ ID NO: 1326) | GYTFTNYW (SEQ ID NO: 4) | IGWVKQRPGHDLEWIGD (SEQ ID NO: 1009) | IHPGGDYS (SEQ ID NO: 1012) | NYNEKFKGKATLTADTSSSTAYMNLSSLTSEDSAIYYC (SEQ ID NO: 1174) | TSRNFAY (SEQ ID NO: 1419) | WGQGTLVTVSA (SEQ ID NO: 421) |
| AH4523 | QIQLQQSGAELVRPGTSVKMSCKAA (SEQ ID NO: 1228) | GYTFTNYW (SEQ ID NO: 4) | IGWVKQRPGHGLEWIGD (SEQ ID NO: 1010) | IHPGGSYT (SEQ ID NO: 1016) | NYNENFKGKATFTADTSSSTTYMQLSSLTSEDSAIYFC (SEQ ID NO: 1189) | TSRNFAK (SEQ ID NO: 1418) | WGQGTPVTVSS (SEQ ID NO: 398) |
| AH4524 | QIQLQQSGAELVRPGTSVKMSCKAA (SEQ ID NO: 1228) | GYTFTNYW (SEQ ID NO: 4) | IGWVKQRPGHGLEWI | IHPGGDYS (SEQ ID NO: | NYNEKFKGKATLTADTSSSTA | TSRNFAY (SEQ ID NO: 1419) | WGQGTLVTVSA (SEQ ID |

TABLE 5A-continued

Exemplary Clones-Heavy Chain Sequences

| ID | HFR1 | CDRH1 | HFR2 | CDRH2 | HFR3 | CDRH3 | HFR4 |
|---|---|---|---|---|---|---|---|
| | | | GD (SEQ ID NO: 1010) | 1012) | YMSLSSL TSEDSAIY YC (SEQ ID NO: 1180) | | NO: 421) |
| AH4525 | QVQLQQSGAELVRPG TSVKMSCKAA (SEQ ID NO: 1326) | GYTFTNYW (SEQ ID NO: 4) | IGWIK QRPGH GLEWI GD (SEQ ID NO: 1007) | IHPGGD YT (SEQ ID NO: 1013) | NYNEKFK GKATLTA DTFSSTA YMQLSSL TSEDSAIY YC (SEQ ID NO: 1171) | TGRNFA Y (SEQ ID NO: 1395) | WGQGT LVTVSS (SEQ ID NO: 413) |
| D11 | QIQLQQPGAELVRPG VSLKISCKGS (SEQ ID NO: 1223) | GYTFTDYA (SEQ ID NO: 19) | MHWV RQSHA KSLEW IGV (SEQ ID NO: 1128) | ISTYSG DA (SEQ ID NO: 21) | IYNQKFK GKATMT VDKSSST AYLELAR LTSDDSAI YYC (SEQ ID NO: 1033) | ARGVTF DY (SEQ ID NO: 23) | WGQGT TVTVSS (SEQ ID NO: 422) |
| D17 | QIQLQQSGAELVRPGT SVKISCKAS (SEQ ID NO: 1227) | GYTFTNYW (SEQ ID NO: 4) | LGWV KQRPG HGLEW IGD (SEQ ID NO: 1075) | IYPGGG YT (SEQ ID NO: 6) | NYNEKFK GKATLTA DTSSSTA YMQLSSL TSEDSAV YFC (SEQ ID NO: 1178) | ARVTPAS (SEQ ID NO: 8) | WGQGT TLTVSA (SEQ ID NO: 1452) |
| D34 | QVQLQQSGAELVRPG VSVKISCKGS (SEQ ID NO: 1338) | GYTFTDYA (SEQ ID NO: 19) | MHWV KQSHA KSLEW IGV (SEQ ID NO: 1126) | ISTYSG DV (SEQ ID NO: 46) | SYNQKFK GKATMT VDKSSST AYMELA RLTSEDS AIYYC (SEQ ID NO: 1389) | ARGVTF DS (SEQ ID NO: 48) | WGQGT TVTVSS (SEQ ID NO: 422) |
| D36 | QVQLQQPGAELVRPG VSLKISCKGS (SEQ ID NO: 1319) | GYTFTDYA (SEQ ID NO: 19) | MHWV RQSHA KSLEW IGV (SEQ ID NO: 1128) | ISTYSG DA (SEQ ID NO: 21) | LYNQKFK GKATMT VDKSSST AYLELAR LTSEDSAI YYC (SEQ ID NO: 1120) | ARGVTF DY (SEQ ID NO: 23) | WGQGT TLTVSS (SEQ ID NO: 425) |
| D5 | QVQLQQSGAELVRPG TSVKISCKAS (SEQ ID NO: 1325) | GYTFTNYW (SEQ ID NO: 4) | LGWV KQRPG HGLEW IGD (SEQ ID NO: 1075) | IYPGGG YT (SEQ ID NO: 6) | NYNEKFK GKATLTA DTSSSTA YMQLSSL TSEDSAV YFC (SEQ ID NO: 1178) | ARVTPAS (SEQ ID NO: 8) | WGQGT SLTVSS (SEQ ID NO: 424) |
| BP003-T2P1C4 | QVQLQQSGAELVRPG TSVKISCKAS (SEQ ID NO: 1325) | GYTFTNYW (SEQ ID NO: 4) | LGWV KQRPG HGLEW IGD (SEQ ID NO: 1075) | IYPGGG YT (SEQ ID NO: 6) | NYNEKFK GKATLTA DTSSSTA YMQLSSL TSEDSAV YFC (SEQ ID NO: 1178) | ARVTPAS (SEQ ID NO: 8) | WGQGT TVTVSS (SEQ ID NO: 422) |
| BP003-T2P1D10 | QIQLQQPGAELVRPGT SVKISCKAS (SEQ ID NO: 1220) | GYTFTNYW (SEQ ID NO: 4) | LGWV KQRPG HGLEW IGD (SEQ ID NO: | IYPGGG YT (SEQ ID NO: 6) | NYNEKFK GKATLTA DTSSSTA YMQLSSL TSEDSAV YFC (SEQ | ARVTPAS (SEQ ID NO: 8) | WGQGT SLTVSS (SEQ ID NO: 424) |

TABLE 5A-continued

Exemplary Clones-Heavy Chain Sequences

| ID | HFR1 | CDRH1 | HFR2 | CDRH2 | HFR3 | CDRH3 | HFR4 |
|---|---|---|---|---|---|---|---|
| | | | | 1075) | ID NO: 1178) | | |
| BP003-T2P1D7 | QAYLQQSGAELVRSGASVKLSCTAS (SEQ ID NO: 1197) | GFNIKDYY (SEQ ID NO: 977) | IHWVKQRPEQGLEWIGW (SEQ ID NO: 1017) | IDPDNGET (SEQ ID NO: 1003) | EYAPKFQGKATMTADTSSNTAHLQLSSLTSEDTAVYYC (SEQ ID NO: 946) | TVFWYGNNYAGFAY (SEQ ID NO: 1420) | WGQGTLVTVSA (SEQ ID NO: 421) |
| BP003-T2P1E3 | QIQLQQSGAELVRPGTSVKMSCKAA (SEQ ID NO: 1228) | GYTFTNYW (SEQ ID NO: 4) | IGWVKQRPGHGLEWIGD (SEQ ID NO: 1010) | IHPGGGYT (SEQ ID NO: 1015) | NYNEKFKGKATLTADTSSSTAYMQLSSLTSEDSAIYYC (SEQ ID NO: 1177) | TSRNFAY (SEQ ID NO: 1419) | WGQGTPVTVSS (SEQ ID NO: 398) |
| BP003-T2P1D1 | QVQLQQSGAELVRPGVSLKISCKGS (SEQ ID NO: 1337) | GYTFTDYA (SEQ ID NO: 19) | MHWVRQSHAKSLEWIGV (SEQ ID NO: 1128) | ISTYSGDA (SEQ ID NO: 21) | IYNQKFKGKATMTVDKSSSTAYLELARLTSDDSAIYYC (SEQ ID NO: 1033) | ARGVTFDY (SEQ ID NO: 23) | WGQGTTVTVSS (SEQ ID NO: 422) |

TABLE 5B

Exemplary Clones-Light Chain Sequences

| ID | LFR1 | CDRL1 | LFR2 | CDRL2 | LFR3 | CDRL3 | LFR4 |
|---|---|---|---|---|---|---|---|
| AH04507 | DTTVTQSQKFMSTSVGDRVSVTCKAS (SEQ ID NO: 858) | QNVGTN (SEQ ID NO: 12) | VAWYQQKPGQSPKALIY (SEQ ID NO: 1425) | SAS (SEQ ID NO: 13) | YRYSGVPDRFTGSGSGTDFTLTISNVQSEDLAEYFC (SEQ ID NO: 1483) | QQYNSYPYT (SEQ ID NO: 15) | FGGGTKLEIK (SEQ ID NO: 959) |
| AH04522 | DTTVTQSQKFMSTSVGDRVSVTCKAG (SEQ ID NO: 856) | QNVGTN (SEQ ID NO: 12) | VAWYQQKPGQSPKALIY (SEQ ID NO: 1425) | SAS (SEQ ID NO: 13) | YRYSGVPDRFTGSGSGTDFTLTISNVQSEDLAEYFC (SEQ ID NO: 1483) | QQYNSYPYT (SEQ ID NO: 15) | FGGGTKLEIK (SEQ ID NO: 959) |
| AH04526 | DTTVTQSQKFMSTSVGDRVSVTCKAS (SEQ ID NO: 858) | QNVGTN (SEQ ID NO: 12) | VAWYQQKPGQSPKALIY (SEQ ID NO: 1425) | SAS (SEQ ID NO: 13) | YRYSGVPDRFTGSGSGTDFTLTISNVQSEDLAEYFC (SEQ ID NO: 1483) | QQYNSYPYT (SEQ ID NO: 15) | FGGGTKLEMK (SEQ ID NO: 961) |
| AH04527 | DVVMTQSQKFMSTSVGDRVSVTCKAS (SEQ ID NO: 894) | QNVGTN (SEQ ID NO: 12) | VAWYQQKPGQSPKALIY (SEQ ID NO: 1425) | SAS (SEQ ID NO: 13) | YRYSGVPDRFTGSGSGTDFTLTISNVQSEDLAEYFC (SEQ ID NO: 1483) | QQYNSYPYT (SEQ ID NO: 15) | FGGGTKLEIK (SEQ ID NO: 959) |
| AH04734 | DIQMTQSTSSLSASLGDRVTISCRAS (SEQ ID NO: 738) | QDIRNY (SEQ ID NO: 1202) | LNWYQQKPDGTVKLLIY (SEQ ID NO: 1088) | YTS (SEQ ID NO: 1495) | RLHSGVPSRFSGSGSGTDYSLTISNLEQEDIATYFC (SEQ ID NO: 1353) | QQGNTLPPT (SEQ ID NO: 1253) | SGGGTKLEIK (SEQ ID NO: 1364) |
| AH04750 | DIQMTQTTSSLSASLGDRVTISCRAS (SEQ ID NO: 760) | QDISNY (SEQ ID NO: 27) | LNWYQQKPDGTVKLLIY (SEQ ID NO: 1088) | YTS (SEQ ID NO: 1495) | RLHSGVPSRFSGSGSGTDYSLTISNLEQEDIATYFC (SEQ ID NO: 1353) | QQGNTLPPT (SEQ ID NO: 1253) | FGGGTKLEMK (SEQ ID NO: 961) |

TABLE 5B-continued

Exemplary Clones-Light Chain Sequences

| ID | LFR1 | CDRL1 | LFR2 | CDRL2 | LFR3 | CDRL3 | LFR4 |
|---|---|---|---|---|---|---|---|
| AH05214 | DILLTQSPALMAA SPGEKVTITCSVS (SEQ ID NO: 698) | SSISSSN (SEQ ID NO: 1382) | LHWYQQK SETSPKPW IY (SEQ ID NO: 1078) | GTS (SEQ ID NO: 983) | NLASGVPVRF SGSGSGTSYSL TISSMEAEDA ATYYC (SEQ ID NO: 1147) | QQWSS YPLT (SEQ ID NO: 1277) | FGGGT KLEIK (SEQ ID NO: 959) |
| AH05247 | DIVMTQSQKFMST SVGDRVSVTCKAS (SEQ ID NO: 821) | QNVGTN (SEQ ID NO: 12) | VAWYQQK PGQSPKAL IY (SEQ ID NO: 1425) | SAS (SEQ ID NO: 13) | YRYSGVPDRF TGSGSGTDFT LTISNVQSEDL AEYFC (SEQ ID NO: 1483) | QQYNS YPLT (SEQ ID NO: 42) | FGGGT KLEIK (SEQ ID NO: 959) |
| AH05249 | DIVMTQTPKFLLV SAGDRVTITCKAS (SEQ ID NO: 830) | QSVNND (SEQ ID NO: 1309) | VVWYQQK PGQSPKLL IY (SEQ ID NO: 1447) | YAS (SEQ ID NO: 1476) | NRYTGVPDRF TGSGYGTDFT FTISTVQAEDL AVYFC (SEQ ID NO: 1164) | QQDYR SPYT (SEQ ID NO: 1249) | FGGGT KLEIK (SEQ ID NO: 959) |
| AH05251 | DVVMTQTPLSLPV NLGDQASISCRSS (SEQ ID NO: 898) | QSIVHSN GNTY (SEQ ID NO: 1299) | LEWYLQK PGQSPKLL IY (SEQ ID NO: 1071) | KVS (SEQ ID NO: 1062) | NRFSGVPDRF SGSGSGTDFTL KISRVEAEDL GIYYC (SEQ ID NO: 1156) | FQGSH VPPT (SEQ ID NO: 966) | FGGGT KLEIK (SEQ ID NO: 959) |
| AH05256 | DIQMTQTTSSLSA SLGDRVTISCRAS (SEQ ID NO: 760) | QDISNY (SEQ ID NO: 27) | LNWYQQK PDGTVKLL IY (SEQ ID NO: 1088) | HTS (SEQ ID NO: 1002) | RLQSGVPSRFT GSGSGTDYSL TISNLEQEDIA TYFC (SEQ ID NO: 1355) | QQSNS LPPT (SEQ ID NO: 1271) | FGGGT KLEIK (SEQ ID NO: 959) |
| AH05257 | DIVMTQSTSSLSAS LGDRVTISCRAS (SEQ ID NO: 828) | QDISNY (SEQ ID NO: 27) | LSWYQQK PDGTIKLLI Y (SEQ ID NO: 1113) | YTS (SEQ ID NO: 1495) | RLHSGVSSRFS GSGSGTDYSL TISNLEQEDFA TYFC (SEQ ID NO: 1354) | QQGHT LPPT (SEQ ID NO: 1252) | FGGGT KLEIK (SEQ ID NO: 959) |
| AH05258 | DIVMTQSHKFMST SVGDRVSITCKAS (SEQ ID NO: 800) | QDVSTA (SEQ ID NO: 1209) | VAWYQQK PGQSPKLL IY (SEQ ID NO: 1427) | SAS (SEQ ID NO: 13) | YRYTGVPDRF TGSGSGTDFTF TISSVQAEDLA VYYC (SEQ ID NO: 1491) | QQHYS TPFT (SEQ ID NO: 1260) | FGSGT KLEIK (SEQ ID NO: 965) |
| AH05259 | DIQMTQTPASLSA SVGETVTITCRAS (SEQ ID NO: 744) | ENIYSF (SEQ ID NO: 928) | LEWFQQK QGKSPQLL VY (SEQ ID NO: 1070) | NAK (SEQ ID NO: 28) | TLAEGVPSRFS VSGSGTQFSL KINSLQPEDFG SYYC (SEQ ID NO: 1401) | QHHYG IPYT (SEQ ID NO: 1214) | FGGGT KLEIK (SEQ ID NO: 959) |
| AH05268 | DVQMTQSPSSMY ASLGERVTFTCKA S (SEQ ID NO: 872) | QDINRY (SEQ ID NO: 1201) | LSWFQQK PGKSPKTL IY (SEQ ID NO: 1109) | RAN (SEQ ID NO: 1345) | RLVDGVPSRF SGSGSGQNYS LTISSLEYEDM GIYYC (SEQ ID NO: 1357) | LQYDE FPYT (SEQ ID NO: 1106) | FGGGT KLEIK (SEQ ID NO: 959) |
| AH05271 | DIQMTQTPASLAA SVGETVTITCRAS (SEQ ID NO: 743) | ENIYFS (SEQ ID NO: 927) | LAWYQQK QGKSPQLL IY (SEQ ID NO: 1068) | NAN (SEQ ID NO: 1142) | TLEDGVPSRFS GSGSGTQFSM KINNMQPEDT ATYFC (SEQ ID NO: 1403) | KQAYD VPWT (SEQ ID NO: 1058) | FGGGT KLEIK (SEQ ID NO: 959) |
| AH05274 | DIQMTQSQKFMST SVGDRVSVTCKAS (SEQ ID NO: 734) | QNVGTN (SEQ ID NO: 12) | VAWYQQK PGQSPKAL IY (SEQ ID NO: 1425) | SAS (SEQ ID NO: 13) | YRYSGVPDRF TGSGSGTDFT LTISNVQSEDL AEYFC (SEQ ID NO: 1483) | QQYNS YPYT (SEQ ID NO: 15) | FGGGT KLEIK (SEQ ID NO: 959) |
| AH05280 | DIVMTQTPKFLLV SAGDRVTITCKAS (SEQ ID NO: 830) | QSVNND (SEQ ID NO: 1309) | VLWYQQK PGQSPKLL IY (SEQ ID NO: 1435) | YAS (SEQ ID NO: 1476) | NRYTGVPDRF TGSGYGTDFT FTISTVQAEDL AVYFC (SEQ ID NO: 1164) | QQAY WSPYT (SEQ ID NO: 1248) | FGGGT KLEIK (SEQ ID NO: 959) |
| AH05285 | DIQMTQTTSSLSA SLGDRVTISCRAS (SEQ ID NO: 760) | QDISNY (SEQ ID NO: 27) | LNWYQQK SDGTVKLL IY (SEQ ID | YTS (SEQ ID NO: | RLHSGVPSRFS GSGSGTDYSL TISNLEQEDIA | QQGNT LPPT (SEQ ID | FGGGT KLEMK (SEQ ID |

TABLE 5B-continued

Exemplary Clones-Light Chain Sequences

| ID | LFR1 | CDRL1 | LFR2 | CDRL2 | LFR3 | CDRL3 | LFR4 |
|---|---|---|---|---|---|---|---|
| | | | NO: 1089) | 1495) | TYFC (SEQ ID NO: 1353) | NO: 1253) | NO: 961) |
| AH05286 | DIVLTQSPPTLSLS PGERVTLSCKAS (SEQ ID NO: 771) | QDVNTA (SEQ ID NO: 1206) | VAWYQQK PGQAPRLL IY (SEQ ID NO: 1424) | WAS (SEQ ID NO: 1450) | TRHTGVPSRFS GSGSGTDFTL TISSLQPEDFA TYYC (SEQ ID NO: 1414) | QQHYS SPWT (SEQ ID NO: 1258) | FGGGT KLEIK (SEQ ID NO: 959) |
| AH4501 | DVVMTQTQKFTS TSVGDRVSVTCKA S (SEQ ID NO: 911) | QNVGTN (SEQ ID NO: 12) | VAWYQQK PGQSPKAL IY (SEQ ID NO: 1425) | SAS (SEQ ID NO: 13) | YRYSGVPDRF TGSGSGTDFT LTISNVQSEDL AEYFC (SEQ ID NO: 1483) | QQYNS YPYT (SEQ ID NO: 15) | FGGGT KLEIK (SEQ ID NO: 959) |
| AH4502 | DIVMTQSQKFMST SVGDRVSVTCKAS (SEQ ID NO: 821) | QNVGIN (SEQ ID NO: 1243) | VAWYQQK PGQSPKAL IY (SEQ ID NO: 1425) | SAS (SEQ ID NO: 13) | YRYSGVPDRF TGSGSGTDFT LTISNVQSEDL AEYFC (SEQ ID NO: 1483) | QQYNS YPYT (SEQ ID NO: 15) | FGGGT KLEIK (SEQ ID NO: 959) |
| AH4503 | DIQMTQSQKFMST SVGDRVSVTCKAS (SEQ ID NO: 734) | QNVGTN (SEQ ID NO: 12) | VAWYQQK PGQSPKAL IY (SEQ ID NO: 1425) | SAS (SEQ ID NO: 13) | YRYSGVPDRF TGSGSGTDFT LTISNVQSEDL AEYFC (SEQ ID NO: 1483) | QQYNS YPWT (SEQ ID NO: 36) | FGGGT KLEIK (SEQ ID NO: 959) |
| AH4505 | DTTVTQSQKFMST SVGDRVSVTCKAS (SEQ ID NO: 858) | QNVGTN (SEQ ID NO: 12) | VAWYQQK PGQSPKAL IY (SEQ ID NO: 1425) | SAS (SEQ ID NO: 13) | YRYSGVPDRF TGSGSGTDFT LTISNVQSEDL AEYFC (SEQ ID NO: 1483) | QQYNS YPYT (SEQ ID NO: 15) | FGGGT KLEMK (SEQ ID NO: 961) |
| AH4509 | DTTVTQSQRFMST SVGDRVSVTCKAS (SEQ ID NO: 863) | QNVGTN (SEQ ID NO: 12) | VAWYQQK PGQSPKPLI Y (SEQ ID NO: 1429) | SAS (SEQ ID NO: 13) | YRYSGVPDRF TGSGSGTDFT LTINNVQSEDL AEYFC (SEQ ID NO: 1480) | QQYNN SPLT (SEQ ID NO: 1282) | FGGGT KLEIK (SEQ ID NO: 959) |
| AH4511 | DIVMSQSQKFMST SVGDRVSVTCKAS (SEQ ID NO: 793) | QNVGTN (SEQ ID NO: 12) | VAWYQQK PGQSPKAL IY (SEQ ID NO: 1425) | SAS (SEQ ID NO: 13) | YRYSGVPDRF TGSGSGTDFT LTISNVQSEDL AEYFC (SEQ ID NO: 1483) | QQYNS YPYT (SEQ ID NO: 15) | FGGGT KLEIK (SEQ ID NO: 959) |
| AH4518 | DILLTQSQKFMST SVGDRVSVTCKAS (SEQ ID NO: 700) | QNVGTN (SEQ ID NO: 12) | VAWYQQK PGQSPKAL IY (SEQ ID NO: 1425) | SAS (SEQ ID NO: 13) | YRYSGVPDRF TGSGSGTDFT LTISNVQSEDL AEYFC (SEQ ID NO: 1483) | QQYNS YPYT (SEQ ID NO: 15) | FGGGT KLEIK (SEQ ID NO: 959) |
| AH4523 | DIVLTQSQKFMST SVGDRVSVTCKAS (SEQ ID NO: 773) | QNVGTN (SEQ ID NO: 12) | VAWYQQK PGQSPKAL IY (SEQ ID NO: 1425) | SAS (SEQ ID NO: 13) | YRYSGVPDRF TGSGSGTDFT LTISNVQSEDL AEYFC (SEQ ID NO: 1483) | QQYNS YPYT (SEQ ID NO: 15) | FGGGT KLEIK (SEQ ID NO: 959) |
| AH4524 | DIVMTQSQKFMST SVGDRVSVTCKAS (SEQIDNO: 821) | QNVGTN (SEQ ID NO: 12) | VAWYQQK PGQSPKAL IY (SEQ ID NO: 1425) | SAS (SEQ ID NO: 13) | YRYSGVPDRF TGSGSGTDFT LTISNVQSEDL AEYFC (SEQ ID NO: 1483) | QQYNS YPYT (SEQ ID NO: 15) | FGGGT KLEIK (SEQ ID NO: 959) |
| AH4525 | DNVLTQSQKFMST SVGDRVSVTCKAS (SEQ ID NO: 837) | QNVGTN (SEQ ID NO: 12) | VAWYQQK PGQSPKAL IY (SEQ ID NO: 1425) | SAS (SEQ ID NO: 13) | YRYSGVPDRF TGSGSGTDFT LTISNVQSEDL AEYFC (SEQ ID NO: 1483) | QQYNS YPYT (SEQ ID NO: 15) | FGGGT KLEMK (SEQ ID NO: 961) |
| D11 | DIQMTQTTSSLSA SLGDRVTITCRAS (SEQ ID NO: 763) | QDISNY (SEQ ID NO: 27) | LEWYQQK QGKSPQLL VY (SEQ ID NO: 1072) | NAK (SEQ ID NO: 28) | TLAEGVPSRFS GSGSGTQFSL KINSLQPEDFG SYYC (SEQ ID NO: 1398) | QHHYD TPYT (SEQ ID NO: 30) | FGGGT KLEIK (SEQ ID NO: 959) |

TABLE 5B-continued

Exemplary Clones-Light Chain Sequences

| ID | LFR1 | CDRL1 | LFR2 | CDRL2 | LFR3 | CDRL3 | LFR4 |
|---|---|---|---|---|---|---|---|
| D17 | DILLTQSQKFMST SVGDRVSVTCKAS (SEQ ID NO: 700) | QNVGTN (SEQ ID NO: 12) | VAWYQQK PGQSPKAL IY (SEQ ID NO: 1425) | SAS (SEQ ID NO: 13) | YRYSGVPDRF TGSGSGTDFT LTISNVQSEDL AEYFC (SEQ ID NO: 1483) | QQYNS YPLT (SEQ ID NO: 42) | FGGGT KLEIK (SEQ ID NO: 959) |
| D34 | DIQMTQSPASLSA SVGETVTITCRAS (SEQ ID NO: 720) | ENSYSY (SEQ ID NO: 52) | LEWYQQK QGKSPQLL VY (SEQ ID NO: 1072) | NAK (SEQ ID NO: 28) | TLAEGVPSRFS GSGSGTQFSL KINSLQPEDFG TYYC (SEQ ID NO: 1399) | QHHYG TPYT (SEQ ID NO: 54) | FGGGT KLEIK (SEQ ID NO: 959) |
| D36 | DVVMTQSPASLSA SVGETVTITCRAS (SEQ ID NO: 890) | ENSYSY (SEQ ID NO: 52) | LEWYQQK QGKSPQLL VY (SEQ ID NO: 1072) | NAK (SEQ ID NO: 28) | TLAEGVPSRFS GSGSGTQFSL KINSLQPEDFG TYYC (SEQ ID NO: 1399) | QHHYG TPYT (SEQ ID NO: 54) | FGGGT KLEMK (SEQ ID NO: 961) |
| D5 | DIVMTQSQKFMST SVGDRVSVTCKAS (SEQ ID NO: 821) | QNVGTN (SEQ ID NO: 12) | VAWYQQK PGQSPKAL IY (SEQ ID NO: 1425) | SAS (SEQ ID NO: 13) | YRYSGVPDRF TGSGSGTDFT LTISNVQSEDL AEYFC (SEQ ID NO: 1483) | QQYNS YPYT (SEQ ID NO: 15) | FGGGT KLEMK (SEQ ID NO: 961) |
| BP003-T2P1C4 | DIQMTQSQKFMSA SVGDRVSVTCKAS (SEQ ID NO: 729) | QNVGTN (SEQ ID NO: 12) | VAWYQQK PGQSPKAL IY (SEQ ID NO: 1425) | SAS (SEQ ID NO: 13) | YRYSGVPDRF TGSGSGTDFT LTISNVQSEDL AEYFC (SEQ ID NO: 1483) | QQYNS YPYT (SEQ ID NO: 15) | FGGGT KLEMK (SEQ ID NO: 961) |
| BP003-T2P1D10 | DIVITQSQKFMSTS VGDRVSVTCKAS (SEQ ID NO: 766) | QNVGTN (SEQ ID NO: 12) | VAWYQQK PGQSPKAL IY (SEQ ID NO: 1425) | SAS (SEQ ID NO: 13) | YRYSGVPDRL TGSGSGTDFT LTISNVQSEDL AEYFC (SEQ ID NO: 1489) | QQYNR YPYT (SEQ ID NO: 1285) | FGGGT KLEIK (SEQ ID NO: 959) |
| BP003-T2P1D7 | DVVLTQTPLSLPV SLGDQASISCRSS (SEQ ID NO: 874) | QSIVHSN GNTY (SEQ ID NO: 1299) | LEWYLQK PGQSPKLL IY (SEQ ID NO: 1071) | KVS (SEQ ID NO: 1062) | NRFSGVPDRF SGSGSGTDFTL KISKVEAEDL GVYYC (SEQ ID NO: 1154) | FQGSH VPPT (SEQ ID NO: 966) | FGGGT KLEIK (SEQ ID NO: 959) |
| BP003-T2P1E3 | DIVLTQSQKFMST SVGDRVSVTCKAS (SEQ ID NO: 773) | QNVGTN (SEQ ID NO: 12) | VAWYQQK PGQSPKAL IY (SEQ ID NO: 1425) | SAS (SEQ ID NO: 13) | YRYSGVPDRF TGSGSGTDFT LTISNVQSEDL AEYFC (SEQ ID NO: 1483) | QQYNS YPYT (SEQ ID NO: 15) | FGGGT KLEIK (SEQ ID NO: 959) |
| BP003-T2P1D1 | DVVMTQSPASLSA SVGETVTITCRAS (SEQ ID NO: 890) | ENSYSY (SEQ ID NO: 52) | LEWYQQK QGKSPQLL VY (SEQ ID NO: 1072) | NAK (SEQ ID NO: 28) | TLAEGVPSRFS GSGSGTQFSL KINSLQPEDFG TYYC (SEQ ID NO: 1399) | QHHYG TPYT (SEQ ID NO: 54) | FGGGT KLEIK (SEQ ID NO: 959) |

TABLE 6

Heavy Chain CDRs

| Combination | CDRH1 | CDRH2 | CDRH3 |
|---|---|---|---|
| 1 | GDTFSSYV (SEQ ID NO: 167) | FNPYSDDI (SEQ ID NO: 242) | GSGYDGYYDWFAC (SEQ ID NO: 315) |
| 2 | GFAFSSYD (SEQ ID NO: 154) | ISSGGGST (SEQ ID NO: 227) | ARNYRSWFAY (SEQ ID NO: 300) |
| 3 | GFNIKDYY (SEQ ID NO: 977) | IDPDNGET (SEQ ID NO: 1003) | TVFWYGNNYAGFAY (SEQ ID NO: 1420) |
| 4 | GFNIKDYY (SEQ ID NO: 977) | IDPENGDT (SEQ ID NO: 1004) | NVITTATTWFAY (SEQ ID NO: 1165) |

TABLE 6-continued

Heavy Chain CDRs

| Combination | CDRH1 | CDRH2 | CDRH3 |
|---|---|---|---|
| 5 | GFSLSTSGMG (SEQ ID NO: 492) | IYWDDDK (SEQ ID NO: 515) | ARRAGDYGNPFPY (SEQ ID NO: 557) |
| 6 | GFSLSTSGMS (SEQ ID NO: 163) | IWWNDDK (SEQ ID NO: 238) | ARIGGNDGYYWYFDV (SEQ ID NO: 311) |
| 7 | GFSLTSYG (SEQ ID NO: 161) | IWAGGST (SEQ ID NO: 234) | ARGAYFDY (SEQ ID NO: 307) |
| 8 | GFSLTSYG (SEQ ID NO: 161) | IWAGGST (SEQ ID NO: 234) | AREGTGPWFAY (SEQ ID NO: 322) |
| 9 | GFTFNDAW (SEQ ID NO: 172) | IRSKANNHAT (SEQ ID NO: 239) | TNYGSNPLDY (SEQ ID NO: 321) |
| 10 | GFTFNTYA (SEQ ID NO: 182) | IRSKSNNYVT (SEQ ID NO: 257) | CERVRRCV (SEQ ID NO: 343) |
| 11 | GFTFSDAW (SEQ ID NO: 164) | IRSKANNHAT (SEQ ID NO: 239) | TPQFAY (SEQ ID NO: 312) |
| 12 | GFTFSDYY (SEQ ID NO: 160) | ISNGGGST (SEQ ID NO: 233) | ASPLGYDGFAY (SEQ ID NO: 306) |
| 13 | GFTFSGFW (SEQ ID NO: 176) | INSDGSAI (SEQ ID NO: 249) | MRYGSSYWYFD (SEQ ID NO: 328) |
| 14 | GFTFSNYR (SEQ ID NO: 183) | ITVKSDNYGA (SEQ ID NO: 258) | SRWFAY (SEQ ID NO: 344) |
| 15 | GFTFSNYR (SEQ ID NO: 183) | ITVKSDNYGA (SEQ ID NO: 258) | SRLFAY (SEQ ID NO: 534) |
| 16 | GFTFSNYW (SEQ ID NO: 166) | IRLKSNNYAT (SEQ ID NO: 241) | TGSDY (SEQ ID NO: 314) |
| 17 | GFTFSNYW (SEQ ID NO: 166) | IRLKSNNYAT (SEQ ID NO: 241) | TRIYDSGSSYTWYFDV (SEQ ID NO: 543) |
| 18 | GFTFSSFG (SEQ ID NO: 491) | ISGGGTI (SEQ ID NO: 514) | ARWRGGYFDY (SEQ ID NO: 555) |
| 19 | GFTFSSYA (SEQ ID NO: 151) | ISSGGST (SEQ ID NO: 224) | ARGEIWGKAWFAY (SEQ ID NO: 297) |
| 20 | GFTFSSYA (SEQ ID NO: 151) | ISSGGSYT (SEQ ID NO: 237) | ARGGMITPFAY (SEQ ID NO: 310) |
| 21 | GFTFSSYA (SEQ ID NO: 151) | ISSGGST (SEQ ID NO: 224) | ARGYGSSFAY (SEQ ID NO: 339) |
| 22 | GFTFSSYA (SEQ ID NO: 151) | ISSGGSYT (SEQ ID NO: 237) | ARRIGYDGGGSWFAY (SEQ ID NO: 342) |
| 23 | GFTFSSYG (SEQ ID NO: 165) | INSNGGST (SEQ ID NO: 240) | ASHYDEGY (SEQ ID NO: 313) |
| 24 | GFTFSSYG (SEQ ID NO: 165) | INSNGGST (SEQ ID NO: 240) | ARGGNPY (SEQ ID NO: 327) |
| 25 | GFTFSSYG (SEQ ID NO: 165) | ISSGGSYT (SEQ ID NO: 237) | ARHYYDYDYWYFDV (SEQ ID NO: 330) |
| 26 | GFTFSSYG (SEQ ID NO: 165) | INSNGGST (SEQ ID NO: 240) | ASLAY (SEQ ID NO: 548) |
| 27 | GFTFSSYT (SEQ ID NO: 485) | ISSGGGYT (SEQ ID NO: 508) | TRVSAKYFDV (SEQ ID NO: 539) |
| 28 | GFTFSSYW (SEQ ID NO: 177) | IRLKSDNYAT (SEQ ID NO: 250) | TRYYYGES (SEQ ID NO: 329) |
| 29 | GFTFSSYW (SEQ ID NO: 177) | IRLKSDNYAT (SEQ ID NO: 250) | TCDYDGGAWFAY (SEQ ID NO: 332) |
| 30 | GFTFTDYY (SEQ ID NO: 180) | IRNKANGYTT (SEQ ID NO: 255) | ARDKRITTVEAWFAY (SEQ ID NO: 338) |

TABLE 6-continued

Heavy Chain CDRs

| Combination | CDRH1 | CDRH2 | CDRH3 |
|---|---|---|---|
| 31 | GFTFTDYY (SEQ ID NO: 180) | IRNKANGYTT (SEQ ID NO: 255) | ARDGEVRRALAY (SEQ ID NO: 537) |
| 32 | GFTFTDYY (SEQ ID NO: 180) | IRNKANGYTT (SEQ ID NO: 255) | ARGWGNWFAY (SEQ ID NO: 554) |
| 33 | GLTFSSYG (SEQ ID NO: 171) | ISSGGSYI (SEQ ID NO: 244) | ARQDDGYYRIFDY (SEQ ID NO: 320) |
| 34 | GYAFSSYW (SEQ ID NO: 175) | IYPGDGDT (SEQ ID NO: 248) | ARSGYRYDAVFAY (SEQ ID NO: 326) |
| 35 | GYAFTNYL (SEQ ID NO: 155) | INPGSGGT (SEQ ID NO: 228) | ARKGSLTGVLAY (SEQ ID NO: 301) |
| 36 | GYAFTNYW (SEQ ID NO: 984) | IYPGGGYT (SEQ ID NO: 6) | ARVTPAS (SEQ ID NO: 8) |
| 37 | GYIFTNYW (SEQ ID NO: 156) | IDPSDSET (SEQ ID NO: 229) | ARRGLRAWFAY (SEQ ID NO: 302) |
| 38 | GYSFTKNG (SEQ ID NO: 168) | INTYTGEP (SEQ ID NO: 232) | AREPKTLDY (SEQ ID NO: 316) |
| 39 | GYSITSDYA (SEQ ID NO: 482) | ISYSGST (SEQ ID NO: 506) | ARSRGNYFDY (SEQ ID NO: 532) |
| 40 | GYSITSGYS (SEQ ID NO: 173) | IHYSGST (SEQ ID NO: 245) | ARDPPFAY (SEQ ID NO: 323) |
| 41 | GYTFNSHW (SEQ ID NO: 169) | IDPYDSET (SEQ ID NO: 235) | ARPYDYDGFAY (SEQ ID NO: 318) |
| 42 | GYTFSNY (SEQ ID NO: 985) | DIHPGGGYINYNEKFTG (SEQ ID NO: 695) | SRNFAN (SEQ ID NO: 1378) |
| 43 | GYTFSNYW (SEQ ID NO: 986) | IHPGGGYI (SEQ ID NO: 1014) | VSRNFAN (SEQ ID NO: 1445) |
| 44 | GYTFSNYW (SEQ ID NO: 986) | ILPGSGFT (SEQ ID NO: 1021) | ARGGTSVVHFDY (SEQ ID NO: 605) |
| 45 | GYTFSNYW (SEQ ID NO: 986) | ILPGSGFT (SEQ ID NO: 1021) | ARGGTSVVHFDS (SEQ ID NO: 604) |
| 46 | GYTFSNYW (SEQ ID NO: 986) | ILPGSGFT (SEQ ID NO: 1021) | ARGGTSVVHFDFDY (SEQ ID NO: 603) |
| 47 | GYTFSNYW (SEQ ID NO: 986) | ILPGSGFT (SEQ ID NO: 1021) | ARGGTSVVHFDS (SEQ ID NO: 604) |
| 48 | GYTFSNYW (SEQ ID NO: 986) | ILPGSGFT (SEQ ID NO: 1021) | ARGGTSVVHFDY (SEQ ID NO: 605) |
| 49 | GYTFSNYW (SEQ ID NO: 986) | ILPGSGYT (SEQ ID NO: 1022) | ARGGTSFVHFDY (SEQ ID NO: 602) |
| 50 | GYTFSSYW (SEQ ID NO: 179) | ILPGSGST (SEQ ID NO: 254) | ARRTYYGNAWFAY (SEQ ID NO: 337) |
| 51 | GYTFSSYW (SEQ ID NO: 179) | ILPGSGST (SEQ ID NO: 254) | ARSAHRYDAWFAY (SEQ ID NO: 551) |
| 52 | GYTFTDYA (SEQ ID NO: 19) | ISTYSGDV (SEQ ID NO: 46) | ARGVTFDS (SEQ ID NO: 48) |
| 53 | GYTFTDYA (SEQ ID NO: 19) | ISTYSGDA (SEQ ID NO: 21) | ARGVTFDY (SEQ ID NO: 23) |
| 54 | GYTFTDYA (SEQ ID NO: 19) | IITYSGDA (SEQ ID NO: 1020) | AXGVTFDY (SEQ ID NO: 619) |
| 55 | GYTFTDYA (SEQ ID NO: 19) | ISTYSGDV (SEQ ID NO: 46) | ARGVTFDS (SEQ ID NO: 48) |
| 56 | GYTFTDYA (SEQ ID NO: 19) | ISTYSGDA (SEQ ID NO: 21) | ARGVTFDY (SEQ ID NO: 23) |
| 57 | GYTFTDYA (SEQ ID NO: 19) | IXTYSGDV (SEQ ID NO: 1029) | ARGVTFDS (SEQ ID NO: 48) |

TABLE 6-continued

Heavy Chain CDRs

| Combination | CDRH1 | CDRH2 | CDRH3 |
|---|---|---|---|
| 58 | GYTFTDYA (SEQ ID NO: 19) | ISTYSGDA (SEQ ID NO: 21) | ARGVTFDY (SEQ ID NO: 23) |
| 59 | GYTFTDYA (SEQ ID NO: 19) | ISTYSGDA (SEQ ID NO: 21) | ARGVTFDY (SEQ ID NO: 23) |
| 60 | GYTFTDYA (SEQ ID NO: 19) | ISTYSGDV (SEQ ID NO: 46) | ARGVTFDS (SEQ ID NO: 48) |
| 61 | GYTFTDYA (SEQ ID NO: 19) | ISTYSGDA (SEQ ID NO: 21) | ARGVTFDY (SEQ ID NO: 23) |
| 62 | GYTFTDYE (SEQ ID NO: 174) | IHPGSGGT (SEQ ID NO: 247) | TRNGNGNWYFDV (SEQ ID NO: 325) |
| 63 | GYTFTDYE (SEQ ID NO: 174) | IHPGSGGT (SEQ ID NO: 247) | TRSDYGSSYEFAY (SEQ ID NO: 531) |
| 64 | GYTFTDYG (SEQ ID NO: 987) | ISTYSGDV (SEQ ID NO: 46) | ARGVTFDS (SEQ ID NO: 48) |
| 65 | GYTFTDYS (SEQ ID NO: 487) | INTETGEP (SEQ ID NO: 225) | ASFYYGNFAYYFDY (SEQ ID NO: 542) |
| 66 | GYTFTDYY (SEQ ID NO: 489) | IYPGSGNT (SEQ ID NO: 511) | ARVYSGFDV (SEQ ID NO: 549) |
| 67 | GYTFTKY (SEQ ID NO: 989) | DIHPGGGYINYNEKFTG (SEQ ID NO: 695) | SRNFAN (SEQ ID NO: 1378) |
| 68 | GYTFTNFY (SEQ ID NO: 486) | INPSNGGT (SEQ ID NO: 231) | TRSYYDYDWYFDV (SEQ ID NO: 540) |
| 69 | GYTFTNHH (SEQ ID NO: 170) | INPYNDYT (SEQ ID NO: 243) | ADGDYYFDY (SEQ ID NO: 319) |
| 70 | GYTFTNY (SEQ ID NO: 990) | DIHPGGDYSNYNEKFKG (SEQ ID NO: 692) | SRNFAY (SEQ ID NO: 1379) |
| 71 | GYTFTNY (SEQ ID NO: 990) | DIHPGGGYTNYNEKFKG (SEQ ID NO: 696) | SRNFAY (SEQ ID NO: 1379) |
| 72 | GYTFTNY (SEQ ID NO: 990) | DIHPGGSYTNYNENFKG (SEQ ID NO: 697) | SRNFAK (SEQ ID NO: 1377) |
| 73 | GYTFTNY (SEQ ID NO: 990) | DIHPGGGYIDYNEKFTG (SEQ ID NO: 694) | SRNFAK (SEQ ID NO: 1377) |
| 74 | GYTFTNY (SEQ ID NO: 990) | DIHPGGDYTNYNEKFKG (SEQ ID NO: 693) | GRNFAY (SEQ ID NO: 982) |
| 75 | GYTFTNY (SEQ ID NO: 990) | DFYPGGDYINYNEKFKG (SEQ ID NO: 691) | SRNFAY (SEQ ID NO: 1379) |
| 76 | GYTFTNYG (SEQ ID NO: 159) | INTYTGEP (SEQ ID NO: 232) | ASYYDSTYVGFAY (SEQ ID NO: 305) |
| 77 | GYTFTNYW (SEQ ID NO: 4) | IHPGGGYT (SEQ ID NO: 1015) | TSRNFAY (SEQ ID NO: 1419) |
| 78 | GYTFTNYW (SEQ ID NO: 4) | IYPGGGYT (SEQ ID NO: 6) | ARVSPAS (SEQ ID NO: 615) |
| 79 | GYTFTNYW (SEQ ID NO: 4) | IYPGGGYT (SEQ ID NO: 6) | ARVTPAS (SEQ ID NO: 8) |
| 80 | GYTFTNYW (SEQ ID NO: 4) | IHPGGDYT (SEQ ID NO: 1013) | TGRNFAY (SEQ ID NO: 1395) |
| 81 | GYTFTNYW (SEQ ID NO: 4) | IHPGGDYS (SEQ ID NO: 1012) | TSRNFAY (SEQ ID NO: 1419) |
| 82 | GYTFTNYW (SEQ ID NO: 4) | IHPGGGYI (SEQ ID NO: 1014) | VSRNFAN (SEQ ID NO: 1445) |
| 83 | GYTFTNYW (SEQ ID NO: 4) | INPGGGYT (SEQ ID NO: 1023) | TSRNFAY (SEQ ID NO: 1419) |
| 84 | GYTFTNYW (SEQ ID NO: 4) | IYPGGGYT (SEQ ID NO: 6) | VRVTPAS (SEQ ID NO: 1443) |

TABLE 6-continued

Heavy Chain CDRs

| Combination | CDRH1 | CDRH2 | CDRH3 |
|---|---|---|---|
| 85 | GYTFTNYW (SEQ ID NO: 4) | FYPGGDYI (SEQ ID NO: 973) | TSRNFAY (SEQ ID NO: 1419) |
| 86 | GYTFTNYW (SEQ ID NO: 4) | IYPGGGYT (SEQ ID NO: 6) | VRVTPAS (SEQ ID NO: 1443) |
| 87 | GYTFTNYW (SEQ ID NO: 4) | IHPGGGYT (SEQ ID NO: 1015) | TSRNFAY (SEQ ID NO: 1419) |
| 88 | GYTFTNYW (SEQ ID NO: 4) | INPGGGYT (SEQ ID NO: 1023) | TSRNFAY (SEQ ID NO: 1419) |
| 89 | GYTFTNYW (SEQ ID NO: 4) | IYPGGGYA (SEQ ID NO: 1035) | ARVTPAS (SEQ ID NO: 8) |
| 90 | GYTFTNYW (SEQ ID NO: 4) | IHPGGGYI (SEQ ID NO: 1014) | VSRNFAK (SEQ ID NO: 1444) |
| 91 | GYTFTNYW (SEQ ID NO: 4) | IHPGGGYT (SEQ ID NO: 1015) | TSRNFAY (SEQ ID NO: 1419) |
| 92 | GYTFTNYW (SEQ ID NO: 4) | IHPGGDYS (SEQ ID NO: 1012) | TSRNFAY (SEQ ID NO: 1419) |
| 93 | GYTFTNYW (SEQ ID NO: 4) | IYPGGGYT (SEQ ID NO: 6) | ARVTPAS (SEQ ID NO: 8) |
| 94 | GYTFTNYW (SEQ ID NO: 4) | IHPGGSYT (SEQ ID NO: 1016) | TSRNFAK (SEQ ID NO: 1418) |
| 95 | GYTFTNYW (SEQ ID NO: 4) | IYPGGGYT (SEQ ID NO: 6) | ARVTPAS (SEQ ID NO: 8) |
| 96 | GYTFTNYW (SEQ ID NO: 4) | IYPGGGYT (SEQ ID NO: 6) | ARVTPAS (SEQ ID NO: 8) |
| 97 | GYTFTNYY (SEQ ID NO: 490) | INPTNGGT (SEQ ID NO: 513) | TRGMAYRYDGAGWFAY (SEQ ID NO: 552) |
| 98 | GYTFTRFW (SEQ ID NO: 991) | INPSTDYT (SEQ ID NO: 1027) | ARGTVVDY (SEQ ID NO: 607) |
| 99 | GYTFTRYW (SEQ ID NO: 992) | INPSTGYT (SEQ ID NO: 230) | ARWGNFDY (SEQ ID NO: 617) |
| 100 | GYTFTRYW (SEQ ID NO: 992) | INPRTDYT (SEQ ID NO: 1025) | ARHGYFDY (SEQ ID NO: 611) |
| 101 | GYTFTRYW (SEQ ID NO: 992) | INPSSDYT (SEQ ID NO: 1026) | ARGTVVVDY (SEQ ID NO: 608) |
| 102 | GYTFTRYW (SEQ ID NO: 992) | INPSTDYT (SEQ ID NO: 1027) | VRSPILDY (SEQ ID NO: 1442) |
| 103 | GYTFTRYW (SEQ ID NO: 992) | INPRTDYT (SEQ ID NO: 1025) | ARHGYFDY (SEQ ID NO: 611) |
| 104 | GYTFTRYY (SEQ ID NO: 488) | INPSNGGT (SEQ ID NO: 231) | TKGGFYDFFAY (SEQ ID NO: 547) |
| 105 | GYTFTSST (SEQ ID NO: 484) | INPSSGYT (SEQ ID NO: 236) | VRHYYFDY (SEQ ID NO: 538) |
| 106 | GYTFTSYN (SEQ ID NO: 178) | IYPGNGDT (SEQ ID NO: 253) | TRSGGNLWFAY (SEQ ID NO: 336) |
| 107 | GYTFTSYT (SEQ ID NO: 162) | INPSSGYT (SEQ ID NO: 236) | ARWDGAY (SEQ ID NO: 309) |
| 108 | GYTFTSYT (SEQ ID NO: 162) | INPSSGYT (SEQ ID NO: 236) | AREGKNWYFDV (SEQ ID NO: 334) |
| 109 | GYTFTSYT (SEQ ID NO: 162) | INPSSGYT (SEQ ID NO: 236) | ARSGLRQAWFAY (SEQ ID NO: 533) |
| 110 | GYTFTSYV (SEQ ID NO: 153) | INPYNDGT (SEQ ID NO: 226) | ARDGYYVGPAY (SEQ ID NO: 299) |

TABLE 6-continued

Heavy Chain CDRs

| Combination | CDRH1 | CDRH2 | CDRH3 |
|---|---|---|---|
| 111 | GYTFTSYW (SEQ ID NO: 157) | IYPGSGST (SEQ ID NO: 251) | TRSGVEGLLHWYFD (SEQ ID NO: 1416) |
| 112 | GYTFTSYW (SEQ ID NO: 157) | IYPGSGST (SEQ ID NO: 251) | TRWITTDHYFDY (SEQ ID NO: 1417) |
| 113 | GYTFTSYW (SEQ ID NO: 157) | IYPGSGST (SEQ ID NO: 251) | TRSGVEGLLHWYFD (SEQ ID NO: 1416) |
| 114 | GYTFTSYW (SEQ ID NO: 157) | IDPYDSET (SEQ ID NO: 235) | AREASYYYGNAWFA (SEQ ID NO: 601) |
| 115 | GYTFTSYW (SEQ ID NO: 157) | INPSNGRT (SEQ ID NO: 510) | ARQLAAY (SEQ ID NO: 614) |
| 116 | GYTFTSYW (SEQ ID NO: 157) | INPSTGYT (SEQ ID NO: 230) | ARLDYYGSSRGFAY (SEQ ID NO: 303) |
| 117 | GYTFTSYW (SEQ ID NO: 157) | IDPYDSET (SEQ ID NO: 235) | ARSPAYYGNLWFAY (SEQ ID NO: 308) |
| 118 | GYTFTSYW (SEQ ID NO: 157) | IDPSDSET (SEQ ID NO: 229) | ANWAWFAY (SEQ ID NO: 317) |
| 119 | GYTFTSYW (SEQ ID NO: 157) | IDPSDSYT (SEQ ID NO: 246) | AREEITAWFAY (SEQ ID NO: 324) |
| 120 | GYTFTSYW (SEQ ID NO: 157) | IYPGSGST (SEQ ID NO: 251) | TRSGVEGLLHWYFDV (SEQ ID NO: 331) |
| 121 | GYTFTSYW (SEQ ID NO: 157) | IDPSNSET (SEQ ID NO: 252) | ARCDGYYDGLDY (SEQ ID NO: 333) |
| 122 | GYTFTSYW (SEQ ID NO: 157) | INPSNGGT (SEQ ID NO: 231) | ARRIYRTLDY (SEQ ID NO: 335) |
| 123 | GYTFTSYW (SEQ ID NO: 157) | INPSNGGT (SEQ ID NO: 231) | TITGFDV (SEQ ID NO: 535) |
| 124 | GYTFTSYW (SEQ ID NO: 157) | IYPSDSYT (SEQ ID NO: 509) | TRQNYYGSSHWYFDV (SEQ ID NO: 541) |
| 125 | GYTFTSYW (SEQ ID NO: 157) | IDPSDSET (SEQ ID NO: 229) | ANWAWFAY (SEQ ID NO: 317) |
| 126 | GYTFTSYW (SEQ ID NO: 157) | INPSNGRT (SEQ ID NO: 510) | ARDSSGYGAY (SEQ ID NO: 544) |
| 127 | GYTFTSYW (SEQ ID NO: 157) | INPSTGYT (SEQ ID NO: 230) | ARYDGYYYFDY (SEQ ID NO: 545) |
| 128 | GYTFTSYW (SEQ ID NO: 157) | IYPSDSYT (SEQ ID NO: 509) | TSHYYGRAWFAY (SEQ ID NO: 546) |
| 129 | GYTFTSYW (SEQ ID NO: 157) | IDPYDSET (SEQ ID NO: 235) | ARGGRGTWFAY (SEQ ID NO: 553) |
| 130 | GYTFTSYW (SEQ ID NO: 157) | IYPSDSYT (SEQ ID NO: 509) | TRTGGSTMTPWFAY (SEQ ID NO: 556) |
| 131 | GYTFTSYY (SEQ ID NO: 158) | INPSNGGT (SEQ ID NO: 231) | TNGGGWY (SEQ ID NO: 304) |
| 132 | GYTFTSYY (SEQ ID NO: 158) | INPSNSGT (SEQ ID NO: 256) | TRGGDYDASWFAY (SEQ ID NO: 340) |
| 133 | GYTFTSYY (SEQ ID NO: 158) | IYPGDGST (SEQ ID NO: 512) | ARGDGYFAWFAY (SEQ ID NO: 550) |
| 134 | GYTFTTST (SEQ ID NO: 993) | INPRSGYT (SEQ ID NO: 1024) | ARHYYFDY (SEQ ID NO: 612) |
| 135 | GYTFTTYW (SEQ ID NO: 483) | IFPGTGTT (SEQ ID NO: 507) | ARGGYYNSSPFAY (SEQ ID NO: 536) |

TABLE 6-continued

Heavy Chain CDRs

| Combination | CDRH1 | CDRH2 | CDRH3 |
|---|---|---|---|
| 136 | GYTLTDYS (SEQ ID NO: 152) | INTETGEP (SEQ ID NO: 225) | AWGNHY (SEQ ID NO: 298) |
| 137 | GYTLTDYV (SEQ ID NO: 181) | IYPGSGST (SEQ ID NO: 251) | ARRTARAFDY (SEQ ID NO: 341) |
| 138 | GYTSTAYW (SEQ ID NO: 994) | ITPSTGYT (SEQ ID NO: 1028) | ARGGYFDY (SEQ ID NO: 606) |
| 139 | GYTSTGYW (SEQ ID NO: 995) | INPSTGYT (SEQ ID NO: 230) | ARGGYFDY (SEQ ID NO: 606) |
| 140 | GYTSTNY (SEQ ID NO: 996) | DIHPGGDYSNYNEKFKG (SEQ ID NO: 692) | SRNFAY (SEQ ID NO: 1379) |
| 141 | GYTSTNYW (SEQ ID NO: 997) | IHPGGDYS (SEQ ID NO: 1012) | TSRNFAY (SEQ ID NO: 1419) |

TABLE 7

Light Chain CDRs

| Combination | CDRL1 | CDRL2 | CDRL3 |
|---|---|---|---|
| 1 | DNIYNY (SEQ ID NO: 833) | NAK (SEQ ID NO: 28) | QHHYGSPWT (SEQ ID NO: 1215) |
| 2 | EDIYNR (SEQ ID NO: 924) | GAT (SEQ ID NO: 976) | QQYWSTPPT (SEQ ID NO: 1292) |
| 3 | ENIYFS (SEQ ID NO: 927) | NAN (SEQ ID NO: 1142) | KQAYDVPWT (SEQ ID NO: 1058) |
| 4 | ENIYSY (SEQ ID NO: 930) | NAK (SEQ ID NO: 28) | QHHYDTPYT (SEQ ID NO: 30) |
| 5 | ENIYSY (SEQ ID NO: 930) | NAK (SEQ ID NO: 28) | QHHYGSPYT (SEQ ID NO: 1216) |
| 6 | ENIYSY (SEQ ID NO: 930) | NAK (SEQ ID NO: 28) | QHHYDTPYT (SEQ ID NO: 30) |
| 7 | ENIYSF (SEQ ID NO: 928) | NAK (SEQ ID NO: 28) | QHHYGTPYT (SEQ ID NO: 54) |
| 8 | ENIYSF (SEQ ID NO: 928) | NAK (SEQ ID NO: 28) | QHHYGIPYT (SEQ ID NO: 1214) |
| 9 | ENIYSN (SEQ ID NO: 929) | AAT (SEQ ID NO: 600) | QHFWGTPPT (SEQ ID NO: 1212) |
| 10 | ENIYSN (SEQ ID NO: 929) | AAT (SEQ ID NO: 600) | QHFWGTPWT (SEQ ID NO: 1213) |
| 11 | ENIYSN (SEQ ID NO: 929) | AAT (SEQ ID NO: 600) | QHFWGTPWT (SEQ ID NO: 1213) |
| 12 | ENIYSY (SEQ ID NO: 930) | NAK (SEQ ID NO: 28) | QHHYGSPYT (SEQ ID NO: 1216) |
| 13 | ENIYSY (SEQ ID NO: 930) | NAK (SEQ ID NO: 28) | QHHYGIPYT (SEQ ID NO: 1214) |
| 14 | ENIYSY (SEQ ID NO: 930) | NAK (SEQ ID NO: 28) | QHHYGTPYT (SEQ ID NO: 54) |
| 15 | ENIYSY (SEQ ID NO: 930) | NAK (SEQ ID NO: 28) | QHHYDTPYT (SEQ ID NO: 30) |
| 16 | ENIYSY (SEQ ID NO: 930) | NAK (SEQ ID NO: 28) | QHHYGTPWT (SEQ ID NO: 1217) |
| 17 | ENIYSY (SEQ ID NO: 930) | NAK (SEQ ID NO: 28) | QHHYGTPYT (SEQ ID NO: 54) |

TABLE 7-continued

| Light Chain CDRs | | | |
|---|---|---|---|
| Combination | CDRL1 | CDRL2 | CDRL3 |
| 18 | ENIYSY (SEQ ID NO: 930) | NAK (SEQ ID NO: 28) | QHHYDTPYT (SEQ ID NO: 30) |
| 19 | ENSYSY (SEQ ID NO: 52) | NAK (SEQ ID NO: 28) | QHHYGTPYT (SEQ ID NO: 54) |
| 20 | ENSYSY (SEQ ID NO: 52) | NAK (SEQ ID NO: 28) | QHHYGTPYT (SEQ ID NO: 54) |
| 21 | ENVATY (SEQ ID NO: 932) | GAS (SEQ ID NO: 975) | GQSYRYPYT (SEQ ID NO: 979) |
| 22 | ENVGTY (SEQ ID NO: 933) | GAS (SEQ ID NO: 975) | GQSYSYPYT (SEQ ID NO: 981) |
| 23 | ENVGTY (SEQ ID NO: 933) | GAS (SEQ ID NO: 975) | GQSYSYPYT (SEQ ID NO: 981) |
| 24 | ENVGTY (SEQ ID NO: 933) | GAS (SEQ ID NO: 975) | GQSYSYPWT (SEQ ID NO: 980) |
| 25 | ESVDNYGISF (SEQ ID NO: 934) | AAS (SEQ ID NO: 599) | QQSKEVPYT (SEQ ID NO: 1267) |
| 26 | ESVDSYGNSF (SEQ ID NO: 935) | LAS (SEQ ID NO: 1063) | QQNNEDPYT (SEQ ID NO: 1266) |
| 27 | ESVDSYGNSF (SEQ ID NO: 935) | RAS (SEQ ID NO: 1346) | QQSNEDPRT (SEQ ID NO: 1269) |
| 28 | KAGQNVGTNVA (SEQ ID NO: 1036) | SASYRYSG (SEQ ID NO: 1362) | QQYNSYPYT (SEQ ID NO: 15) |
| 29 | KASQNVGINVA (SEQ ID NO: 1037) | SASYRYSG (SEQ ID NO: 1362) | QQYNSYPYT (SEQ ID NO: 15) |
| 30 | KASQNVGTNVA (SEQ ID NO: 1038) | SASYRYSG (SEQ ID NO: 1362) | QQYNSYPYT (SEQ ID NO: 15) |
| 31 | KASQNVGTNVA (SEQ ID NO: 1038) | SASYRYSG (SEQ ID NO: 1362) | QQYNSYPWT (SEQ ID NO: 36) |
| 32 | KASQNVGTNVA (SEQ ID NO: 1038) | SASYRYSG (SEQ ID NO: 1362) | QQYNNSPLT (SEQ ID NO: 1282) |
| 33 | KASQSVGTNVA (SEQ ID NO: 1040) | SASYRYSG (SEQ ID NO: 1362) | QQYNNYPWT (SEQ ID NO: 1284) |
| 34 | KNSYSY (SEQ ID NO: 1057) | NAK (SEQ ID NO: 28) | QHHYGTPYT (SEQ ID NO: 54) |
| 35 | KSISKY (SEQ ID NO: 1059) | SGS (SEQ ID NO: 1365) | QQHNEYPWT (SEQ ID NO: 1257) |
| 36 | KSLLHSNGNTY (SEQ ID NO: 1060) | RMS (SEQ ID NO: 1360) | MQHLEYPYT (SEQ ID NO: 1136) |
| 37 | KSLLYKDGKTY (SEQ ID NO: 1061) | LMS (SEQ ID NO: 1081) | HQLVEYPYT (SEQ ID NO: 998) |
| 38 | QDIGLN (SEQ ID NO: 1198) | ATS (SEQ ID NO: 618) | LQYASSPFT (SEQ ID NO: 1097) |
| 39 | QDIGSS (SEQ ID NO: 1199) | ATS (SEQ ID NO: 618) | LQYASSPYT (SEQ ID NO: 1101) |
| 40 | QDIGSS (SEQ ID NO: 1199) | ATS (SEQ ID NO: 618) | LQYASSPWT (SEQ ID NO: 1100) |
| 41 | QDIGSS (SEQ ID NO: 1199) | ATS (SEQ ID NO: 618) | LQYASSPRT (SEQ ID NO: 1099) |
| 42 | QDIGSS (SEQ ID NO: 1199) | ATS (SEQ ID NO: 618) | LQYASSPHT (SEQ ID NO: 1098) |

TABLE 7-continued

| Light Chain CDRs | | | |
|---|---|---|---|
| Combination | CDRL1 | CDRL2 | CDRL3 |
| 43 | QDIGSS (SEQ ID NO: 1199) | ATS (SEQ ID NO: 618) | LQYATFPYT (SEQ ID NO: 1104) |
| 44 | QDINNF (SEQ ID NO: 1200) | RAN (SEQ ID NO: 1345) | LQYDEFPWT (SEQ ID NO: 1105) |
| 45 | QDINRY (SEQ ID NO: 1201) | RAN (SEQ ID NO: 1345) | LQYDEFPYT (SEQ ID NO: 1106) |
| 46 | QDINRY (SEQ ID NO: 1201) | RAN (SEQ ID NO: 1345) | LQYDEFPYT (SEQ ID NO: 1106) |
| 47 | QDIRNY (SEQ ID NO: 1202) | YTS (SEQ ID NO: 1495) | QQGNTLPPT (SEQ ID NO: 1253) |
| 48 | QDIRNY (SEQ ID NO: 1202) | YTS (SEQ ID NO: 1495) | QQGNTLPPT (SEQ ID NO: 1253) |
| 49 | QDISNY (SEQ ID NO: 27) | HTS (SEQ ID NO: 1002) | QQSNTLPPT (SEQ ID NO: 1272) |
| 50 | QDISNY (SEQ ID NO: 27) | HTS (SEQ ID NO: 1002) | QQSNSLPPT (SEQ ID NO: 1271) |
| 51 | QDISNY (SEQ ID NO: 27) | YTS (SEQ ID NO: 1495) | QQGNTLPPT (SEQ ID NO: 1253) |
| 52 | QDISNY (SEQ ID NO: 27) | YAS (SEQ ID NO: 1476) | QQGNTLPWT (SEQ ID NO: 1255) |
| 53 | QDISNY (SEQ ID NO: 27) | YTS (SEQ ID NO: 1495) | QQGNTLPPT (SEQ ID NO: 1253) |
| 54 | QDISNY (SEQ ID NO: 27) | HTS (SEQ ID NO: 1002) | QQSNSLPPT (SEQ ID NO: 1271) |
| 55 | QDISNY (SEQ ID NO: 27) | HTS (SEQ ID NO: 1002) | QQSNTLPPT (SEQ ID NO: 1272) |
| 56 | QDISNY (SEQ ID NO: 27) | HTS (SEQ ID NO: 1002) | QQGNTLPPT (SEQ ID NO: 1253) |
| 57 | QDISNY (SEQ ID NO: 27) | FTS (SEQ ID NO: 972) | QQGNTLPRT (SEQ ID NO: 1254) |
| 58 | QDISNY (SEQ ID NO: 27) | YTS (SEQ ID NO: 1495) | QQVYTLPWT (SEQ ID NO: 1273) |
| 59 | QDISNY (SEQ ID NO: 27) | YTS (SEQ ID NO: 1495) | QQGNTLPWT (SEQ ID NO: 1255) |
| 60 | QDISNY (SEQ ID NO: 27) | YTS (SEQ ID NO: 1495) | QQGNTLPPT (SEQ ID NO: 1253) |
| 61 | QDISNY (SEQ ID NO: 27) | HTS (SEQ ID NO: 1002) | QQSNSLPPT (SEQ ID NO: 1271) |
| 62 | QDISNY (SEQ ID NO: 27) | YTS (SEQ ID NO: 1495) | QQGHTLPPT (SEQ ID NO: 1252) |
| 63 | QDISNY (SEQ ID NO: 27) | NAK (SEQ ID NO: 28) | QHHYDTPYT (SEQ ID NO: 30) |
| 64 | QDVGTA (SEQ ID NO: 1204) | WAS (SEQ ID NO: 1450) | QQYSSYPLT (SEQ ID NO: 1291) |
| 65 | QDVITA (SEQ ID NO: 1205) | SAS (SEQ ID NO: 13) | QQHYSTPRT (SEQ ID NO: 1263) |
| 66 | QDVNTA (SEQ ID NO: 1206) | WAS (SEQ ID NO: 1450) | QQHYSSWT (SEQ ID NO: 1258) |
| 67 | QDVNTA (SEQ ID NO: 1206) | WAS (SEQ ID NO: 1450) | QQHYSSPWT (SEQ ID NO: 1258) |

TABLE 7-continued

Light Chain CDRs

| Combination | CDRL1 | CDRL2 | CDRL3 |
|---|---|---|---|
| 68 | QDVNTA (SEQ ID NO: 1206) | WAS (SEQ ID NO: 1450) | QQHYSSPWT (SEQ ID NO: 1258) |
| 69 | QDVNTA (SEQ ID NO: 1206) | SAS (SEQ ID NO: 13) | QQHFNSPYT (SEQ ID NO: 1256) |
| 70 | QDVNTA (SEQ ID NO: 1206) | WAS (SEQ ID NO: 1450) | QQHYSSPWT (SEQ ID NO: 1258) |
| 71 | QDVNTAVA (SEQ ID NO: 1207) | WAS (SEQ ID NO: 1450) | QQHYSSPWT (SEQ ID NO: 1258) |
| 72 | QDVRTA (SEQ ID NO: 1208) | STS (SEQ ID NO: 1386) | QQYSNYLTF (SEQ ID NO: 1290) |
| 73 | QDVSTA (SEQ ID NO: 1209) | SAS (SEQ ID NO: 13) | QQHYSTPYT (SEQ ID NO: 1265) |
| 74 | QDVSTA (SEQ ID NO: 1209) | SAS (SEQ ID NO: 13) | QQHYSTPWT (SEQ ID NO: 1264) |
| 75 | QDVSTA (SEQ ID NO: 1209) | SAS (SEQ ID NO: 13) | QQHYSTPPWT (SEQ ID NO: 1262) |
| 76 | QDVSTA (SEQ ID NO: 1209) | SAS (SEQ ID NO: 13) | QQHYSTPPT (SEQ ID NO: 1261) |
| 77 | QDVSTA (SEQ ID NO: 1209) | SAS (SEQ ID NO: 13) | QQHYSTPYT (SEQ ID NO: 1265) |
| 78 | QDVSTA (SEQ ID NO: 1209) | SAS (SEQ ID NO: 13) | QQHYSTHVH (SEQ ID NO: 1259) |
| 79 | QDVSTA (SEQ ID NO: 1209) | SAS (SEQ ID NO: 13) | QQHYSTPFT (SEQ ID NO: 1260) |
| 80 | QEISGY (SEQ ID NO: 1210) | AAS (SEQ ID NO: 599) | LQYASYPYT (SEQ ID NO: 1103) |
| 81 | QEISGY (SEQ ID NO: 1210) | AAS (SEQ ID NO: 599) | LQYISYPRT (SEQ ID NO: 1107) |
| 82 | QEISGY (SEQ ID NO: 1210) | AAS (SEQ ID NO: 599) | LQYASYPRT (SEQ ID NO: 1102) |
| 83 | QEISGY (SEQ ID NO: 1210) | AAS (SEQ ID NO: 599) | LQYASYPRT (SEQ ID NO: 1102) |
| 84 | QGISNY (SEQ ID NO: 1211) | YTS (SEQ ID NO: 1495) | QQYSKLPWT (SEQ ID NO: 1289) |
| 85 | QNVGIN (SEQ ID NO: 1243) | SAS (SEQ ID NO: 13) | QQYNSYPYT (SEQ ID NO: 15) |
| 86 | QNVGSN (SEQ ID NO: 1244) | SAS (SEQ ID NO: 13) | QQYDSYPYT (SEQ ID NO: 1280) |
| 87 | QNVGTN (SEQ ID NO: 12) | SAS (SEQ ID NO: 13) | QQYNSYPYT (SEQ ID NO: 15) |
| 88 | QNVGTN (SEQ ID NO: 12) | SAS (SEQ ID NO: 13) | QQYNTYPYT (SEQ ID NO: 1287) |
| 89 | QNVGTN (SEQ ID NO: 12) | SAS (SEQ ID NO: 13) | QQYNSYPYT (SEQ ID NO: 15) |
| 90 | QNVGTN (SEQ ID NO: 12) | SAS (SEQ ID NO: 13) | QQYNSYPWT (SEQ ID NO: 36) |
| 91 | QNVGTN (SEQ ID NO: 12) | SAS (SEQ ID NO: 13) | QQYNNYPWT (SEQ ID NO: 1284) |
| 92 | QNVGTN (SEQ ID NO: 12) | SAS (SEQ ID NO: 13) | QQYNTYPYT (SEQ ID NO: 1287) |

TABLE 7-continued

| | Light Chain CDRs | | |
|---|---|---|---|
| Combination | CDRL1 | CDRL2 | CDRL3 |
| 93 | QNVGTN (SEQ ID NO: 12) | SAS (SEQ ID NO: 13) | QQYNNHPYT (SEQ ID NO: 1281) |
| 94 | QNVGTN (SEQ ID NO: 12) | SAS (SEQ ID NO: 13) | QQYNNYPLT (SEQ ID NO: 1283) |
| 95 | QNVGTN (SEQ ID NO: 12) | SAS (SEQ ID NO: 13) | QQYNRYPYT (SEQ ID NO: 1285) |
| 96 | QNVGTN (SEQ ID NO: 12) | SAS (SEQ ID NO: 13) | XQYNSYPYT (SEQ ID NO: 1475) |
| 97 | QNVGTN (SEQ ID NO: 12) | SAS (SEQ ID NO: 13) | QQYNNSPLT (SEQ ID NO: 1282) |
| 98 | QNVGTN (SEQ ID NO: 12) | SAS (SEQ ID NO: 13) | QQYNSYPRT (SEQ ID NO: 1286) |
| 99 | QNVGTN (SEQ ID NO: 12) | SAS (SEQ ID NO: 13) | SQSTHVPYT (SEQ ID NO: 1375) |
| 100 | QNVGTN (SEQ ID NO: 12) | SAS (SEQ ID NO: 13) | QQYNSYPRT (SEQ ID NO: 1286) |
| 101 | QNVGTN (SEQ ID NO: 12) | SAS (SEQ ID NO: 13) | QQYNSYPYT (SEQ ID NO: 15) |
| 102 | QNVGTN (SEQ ID NO: 12) | SAS (SEQ ID NO: 13) | QQYNTYPYT (SEQ ID NO: 1287) |
| 103 | QNVGTN (SEQ ID NO: 12) | SAS (SEQ ID NO: 13) | QQYNSYPWT (SEQ ID NO: 36) |
| 104 | QNVGTN (SEQ ID NO: 12) | SAS (SEQ ID NO: 13) | QQYNSYPLT (SEQ ID NO: 42) |
| 105 | QNVGTN (SEQ ID NO: 12) | SAS (SEQ ID NO: 13) | QQYNSYPLT (SEQ ID NO: 42) |
| 106 | QNVGTN (SEQ ID NO: 12) | SAS (SEQ ID NO: 13) | QQYNRYPYT (SEQ ID NO: 1285) |
| 107 | QNVGTN (SEQ ID NO: 12) | SAS (SEQ ID NO: 13) | QQYNSYPYT (SEQ ID NO: 15) |
| 108 | QNVGTNVA (SEQ ID NO: 1246) | SAS (SEQ ID NO: 13) | QQYNSYPYT (SEQ ID NO: 15) |
| 109 | QNVRTA (SEQ ID NO: 1247) | MAS (SEQ ID NO: 1122) | LQHWNYPYT (SEQ ID NO: 1093) |
| 110 | QSISDY (SEQ ID NO: 1296) | YAS (SEQ ID NO: 1476) | QNGHSFPRT (SEQ ID NO: 1242) |
| 111 | QSIVHNNGNTY (SEQ ID NO: 1298) | KVS (SEQ ID NO: 1062) | FQGSYVPRT (SEQ ID NO: 971) |
| 112 | QSIVHSNGNTY (SEQ ID NO: 1299) | KVS (SEQ ID NO: 1062) | FQGSHVPPT (SEQ ID NO: 966) |
| 113 | QSIVHSNGNTY (SEQ ID NO: 1299) | KVS (SEQ ID NO: 1062) | FQGSHVPRT (SEQ ID NO: 967) |
| 114 | QSIVHSNGNTY (SEQ ID NO: 1299) | KVS (SEQ ID NO: 1062) | FQGSHVPTF (SEQ ID NO: 968) |
| 115 | QSIVHSNGNTY (SEQ ID NO: 1299) | KVS (SEQ ID NO: 1062) | FQGSHVPYT (SEQ ID NO: 970) |
| 116 | QSLENSNGNTY (SEQ ID NO: 1300) | RVS (SEQ ID NO: 1361) | LQVTHVPFA (SEQ ID NO: 1096) |
| 117 | QSLLDSDGKTY (SEQ ID NO: 1301) | LVS (SEQ ID NO: 1116) | WQGTHFPRT (SEQ ID NO: 1464) |

TABLE 7-continued

Light Chain CDRs

| Combination | CDRL1 | CDRL2 | CDRL3 |
|---|---|---|---|
| 118 | QSLLDSDGKTY (SEQ ID NO: 1301) | LVS (SEQ ID NO: 1116) | WQGTHFRT (SEQ ID NO: 1466) |
| 119 | QSLLDSDGKTY (SEQ ID NO: 1301) | LVS (SEQ ID NO: 1116) | WQGTHFPWT (SEQ ID NO: 1465) |
| 120 | QSLLDSDGKTY (SEQ ID NO: 1301) | LVS (SEQ ID NO: 1116) | WQGAHFPWT (SEQ ID NO: 1461) |
| 121 | QSLLDSDGKTY (SEQ ID NO: 1301) | LVS (SEQ ID NO: 1116) | WQGTHFPQT (SEQ ID NO: 1463) |
| 122 | QSLLDSDGKTY (SEQ ID NO: 1301) | LVS (SEQ ID NO: 1116) | WQGTFSSH (SEQ ID NO: 1462) |
| 123 | QSLLNSSNQKNY (SEQ ID NO: 1302) | FAS (SEQ ID NO: 957) | QQHYSTPYT (SEQ ID NO: 1265) |
| 124 | QSLLYSNGKTY (SEQ ID NO: 1303) | QVS (SEQ ID NO: 1344) | LQGTYYPTWT (SEQ ID NO: 1092) |
| 125 | QSLLYSSNQKNY (SEQ ID NO: 1304) | WAS (SEQ ID NO: 1450) | QQYYSYPWT (SEQ ID NO: 1294) |
| 126 | QSLLYSSNQKNY (SEQ ID NO: 1304) | WAS (SEQ ID NO: 1450) | QQYYSYRT (SEQ ID NO: 1295) |
| 127 | QSLLYSSNQKNY (SEQ ID NO: 1304) | WAS (SEQ ID NO: 1450) | QQYYSYP (SEQ ID NO: 1293) |
| 128 | QSLVHNNGNTY (SEQ ID NO: 1305) | KVS (SEQ ID NO: 1062) | SQSTHVPLT (SEQ ID NO: 1370) |
| 129 | QSLVHSNGNTY (SEQ ID NO: 1306) | EVS (SEQ ID NO: 944) | SQSTHVPYT (SEQ ID NO: 1375) |
| 130 | QSLVHSNGNTY (SEQ ID NO: 1306) | KVS (SEQ ID NO: 1062) | SQSTHVPPT (SEQ ID NO: 1371) |
| 131 | QSLVHSNGNTY (SEQ ID NO: 1306) | KVS (SEQ ID NO: 1062) | SQSTHVPWT (SEQ ID NO: 1374) |
| 132 | QSLVHSNGNTY (SEQ ID NO: 1306) | KVS (SEQ ID NO: 1062) | SQSTHVPT (SEQ ID NO: 1373) |
| 133 | QSLVHSNGNTY (SEQ ID NO: 1306) | KVS (SEQ ID NO: 1062) | SQSTHVPRT (SEQ ID NO: 1372) |
| 134 | QSLVHSNGNTY (SEQ ID NO: 1306) | KVS (SEQ ID NO: 1062) | SQSTHVYT (SEQ ID NO: 1376) |
| 135 | QSLVHSNGNTY (SEQ ID NO: 1306) | KVS (SEQ ID NO: 1062) | SQSTHVPLT (SEQ ID NO: 1370) |
| 136 | QSLVHSYGNTY (SEQ ID NO: 1307) | KVS (SEQ ID NO: 1062) | SQSTHVPHT (SEQ ID NO: 1369) |
| 137 | QSVDYDGDSY (SEQ ID NO: 1308) | AAS (SEQ ID NO: 599) | QQSNEDPYT (SEQ ID NO: 1270) |
| 138 | QSVDYDGDSY (SEQ ID NO: 1308) | ATS (SEQ ID NO: 618) | QQSNEDPLT (SEQ ID NO: 1268) |
| 139 | QSVNND (SEQ ID NO: 1309) | YAS (SEQ ID NO: 1476) | QQAYWSPYT (SEQ ID NO: 1248) |
| 140 | QSVNND (SEQ ID NO: 1309) | YAS (SEQ ID NO: 1476) | QQDYRSPYT (SEQ ID NO: 1249) |
| 141 | QSVNND (SEQ ID NO: 1309) | YAS (SEQ ID NO: 1476) | QQAYWSPYT (SEQ ID NO: 1248) |
| 142 | QSVSND (SEQ ID NO: 1310) | YAS (SEQ ID NO: 1476) | QQDYSSPWT (SEQ ID NO: 1251) |

TABLE 7-continued

Light Chain CDRs

| Combination | CDRL1 | CDRL2 | CDRL3 |
|---|---|---|---|
| 143 | QSVSND (SEQ ID NO: 1310) | YAS (SEQ ID NO: 1476) | QQDYSSPPT (SEQ ID NO: 1250) |
| 144 | QTLLHSDGNTY (SEQ ID NO: 1311) | QVS (SEQ ID NO: 1344) | FQGSHVPWT (SEQ ID NO: 969) |
| 145 | SRVTY (SEQ ID NO: 1380) | DTS (SEQ ID NO: 839) | HQRSGYSYT (SEQ ID NO: 1000) |
| 146 | SSIGY (SEQ ID NO: 1381) | DTS (SEQ ID NO: 839) | HQRGSYPWT (SEQ ID NO: 999) |
| 147 | SSISSSN (SEQ ID NO: 1382) | GTS (SEQ ID NO: 983) | QQWSSYPLT (SEQ ID NO: 1277) |
| 148 | SSVIY (SEQ ID NO: 1383) | DTS (SEQ ID NO: 839) | QQWTSNPPT (SEQ ID NO: 1279) |
| 149 | SSVSSSY (SEQ ID NO: 1384) | STS (SEQ ID NO: 1386) | HQYHRSPPT (SEQ ID NO: 1001) |
| 150 | SSVSY (SEQ ID NO: 1385) | DTS (SEQ ID NO: 839) | QQWSSNPPT (SEQ ID NO: 1274) |
| 151 | SSVSY (SEQ ID NO: 1385) | DTS (SEQ ID NO: 839) | QQWSSNPPYT (SEQ ID NO: 1275) |
| 152 | SSVSY (SEQ ID NO: 1385) | DTS (SEQ ID NO: 839) | QQWSSYPYT (SEQ ID NO: 1278) |
| 153 | SSVSY (SEQ ID NO: 1385) | LTP (SEQ ID NO: 1115) | QQWSSNPYT (SEQ ID NO: 1276) |
| 154 | TDIDDD (SEQ ID NO: 1391) | EGN (SEQ ID NO: 925) | LQSDNMPLT (SEQ ID NO: 1094) |
| 155 | TDIDDD (SEQ ID NO: 1391) | EGN (SEQ ID NO: 925) | LQSDNMPYT (SEQ ID NO: 1095) |

In some embodiments, the CD25 antibody comprises a "V-D-J-region" heavy chain sequence presented in any one of Table 2A, Table 2B, and Table 2C, and a "V-J-region" light chain sequence presented in any one of Table 3A, Table 3B, and Table 3C, humanized versions thereof, or an amino acid sequence comprising at least a 80%, at least a 85%, at least a 90%, or at least a 95% sequence identity thereto. In some embodiments, the antibody comprises the heavy chain variable region sequence from a particular antibody clone so named by its given "ID" (or a humanized version thereof) and the light chain variable region sequence from the same antibody clone (e.g. the light chain from clone identified by the same "ID") (or a humanized version thereof). Thus, the antibody clone of origin can be identified by the ID shown in Tables 2A-2C or 3A-3C. For example, in such embodiments, the CD25 antibody comprises the heavy chain variable region of antibody clone "AHH03760" as presented in row 1 of Table 2B (or a humanized version thereof) and the light chain variable region of antibody clone "AHH03760" as presented in row 3 of Table 3B (or a humanized version thereof). In other embodiments, the CD25 antibody comprises the heavy chain variable region sequence from a particular antibody clone so named by its given "ID" (or a humanized version thereof) and the light chain variable region sequence from a different antibody clone (e.g. the light chain from clone identified by the same "ID") (or a humanized version thereof).

In some embodiments, the CD25 antibody comprises a CDRH1, a CDRH2, and a CDRH3 presented in any one of Table 2A, Table 2B, and Table 2C, and a CDRL1, a CDRL2, and a CDRL3 presented in any one of Table 3A, Table 3B, and Table 3C. In such embodiments, the CD25 antibody comprises the CDRH1, CDRH2, and CDRH3 from a particular antibody clone and the CDRL1, CDRL2, and CDRL3 from the same antibody clone. As discussed above, the antibody clone of origin can be identified by the ID shown in Tables 2A-2C or 3A-3C.

In some embodiments, the CD25 antibody comprises a heavy chain variable region presented in Table 4A, humanized versions thereof, or an amino acid sequence comprising at least a 80%, at least a 85%, at least a 90%, or at least a 95% sequence identity thereto. The variable region may include the contiguous HFR1, CDRH1, HFR2, CDRH2, HFR3, CDRH3, HRF4 sequences to form a complete variable region, humanized versions thereof, or an amino acid sequence comprising at least a 80%, at least a 85%, at least a 90%, or at least a 95% sequence identity thereto. In some embodiments, the CD25 antibody comprises a light chain variable region presented in Table 4B, humanized versions thereof, or an amino acid sequence comprising at least a 80%, at least a 85%, at least a 90%, or at least a 95% sequence identity thereto. The variable region may include the contiguous LFR1, CDRL1, LFR2, CDRL2, LFR3, CDRL3, LRF4 sequences to form a complete variable region, humanized versions thereof, or an amino acid sequence comprising at least a 80%, at least a 85%, at least a 90%, or at least a 95% sequence identity thereto. In some embodiments, the CD25 antibody comprises a complete heavy chain variable region as presented in Table 4A and a complete light chain variable region as presented in Table 4B, including humanized versions thereof, and amino acid sequences comprising at least a 80%, at least a 85%, at least a 90%, or at least a 95% sequence identity thereto. In some embodiments, the CD25 antibody comprises the heavy chain variable region sequence from a particular antibody clone and the light chain variable region sequence from the same antibody clone, including humanized versions thereof and amino acid sequences comprising at least a 80%, at least a 85%, at least a 90%, or at least a 95% sequence identity thereto. In some embodiments, the CD25 antibody comprises the heavy chain variable region sequence from a particular antibody clone and the light chain variable region sequence from a different antibody clone, including humanized versions thereof and amino acid sequences comprising at least a 80%, at least a 85%, at least a 90%, or at least a 95% sequence identity thereto. The antibody clone of origin can be identified by the ID shown in Tables 4A and 4B.

In some embodiments, the CD25 antibody comprises a CDRH1, a CDRH2, and a CDRH3 presented in Table 4A, and a CDRL1, a CDRL2, and a CDRL3 presented in Table 4B. In some embodiments, the CD25 antibody comprises the CDRH1, CDRH2, and CDRH3 from a particular antibody clone and the CDRL1, CDRL2, and CDRL3 from the same antibody clone. In other embodiments, the CD25 antibody comprises the CDRH1, CDRH2, and CDRH3 from a particular antibody clone and the CDRL1, CDRL2, and CDRL3 from a different antibody clone. As discussed above, the antibody clone of origin can be identified by the ID shown in Tables 4A and 4B.

In some embodiments, the CD25 antibody comprises a heavy chain variable region presented in Table 5A, including humanized versions thereof and amino acid sequences comprising at least a 80%, at least a 85%, at least a 90%, or at least a 95% sequence identity thereto. The variable region may include the contiguous HFR1, CDRH1, HFR2, CDRH2, HFR3, CDRH3, HRF4 sequences to form a complete variable region, including humanized versions thereof and amino acid sequences comprising at least a 80%, at least a 85%, at least a 90%, or at least a 95% sequence identity thereto. In some embodiments, the CD25 antibody comprises a light chain variable region presented in Table 5B, including humanized versions thereof and amino acid sequences comprising at least a 80%, at least a 85%, at least a 90%, or at least a 95% sequence identity thereto. The variable region may include the contiguous LFR1, CDRL1, LFR2, CDRL2, LFR3, CDRL3, LRF4 sequences to form a complete variable region, including humanized versions thereof and amino acid sequences comprising at least a 80%, at least a 85%, at least a 90%, or at least a 95% sequence identity thereto. In some embodiments, the CD25 antibody comprises a complete heavy chain variable region as presented in Table 5A and a complete light chain variable region as presented in Table 5B, including humanized versions thereof and amino acid sequences comprising at least a 80%, at least a 85%, at least a 90%, or at least a 95% sequence identity thereto. In some embodiments, the CD25 antibody comprises the heavy chain variable region sequence from a particular antibody clone and the light chain variable region sequence from the same antibody clone, including humanized versions thereof and amino acid sequences comprising at least a 80%, at least a 85%, at least a 90%, or at least a 95% sequence identity thereto. In other embodiments, the CD25 antibody comprises the heavy chain variable region sequence from a particular antibody clone and the light chain variable region sequence from a different antibody clone, including humanized versions thereof and amino acid sequences comprising at least a 80%, at least a 85%, at least a 90%, or at least a 95% sequence identity thereto. The antibody clone of origin can be identified by the ID shown in Tables 5A and 5B.

In some embodiments, the CD25 antibody comprises a CDRH1, a CDRH2, and a CDRH3 presented in Table 5A, and a CDRL1, a CDRL2, and a CDRL3 presented in Table 5B. In some embodiments, the CD25 antibody comprises the CDRH1, CDRH2, and CDRH3 from a particular antibody clone and the CDRL1, CDRL2, and CDRL3 from the same antibody clone. In other embodiments, the CD25 antibody comprises the CDRH1, CDRH2, and CDRH3 from a particular antibody clone and the CDRL1, CDRL2, and CDRL3 from a different antibody clone. As discussed above, the antibody clone of origin can be identified by the ID shown in Tables 5A and 5B.

Figure 3A:
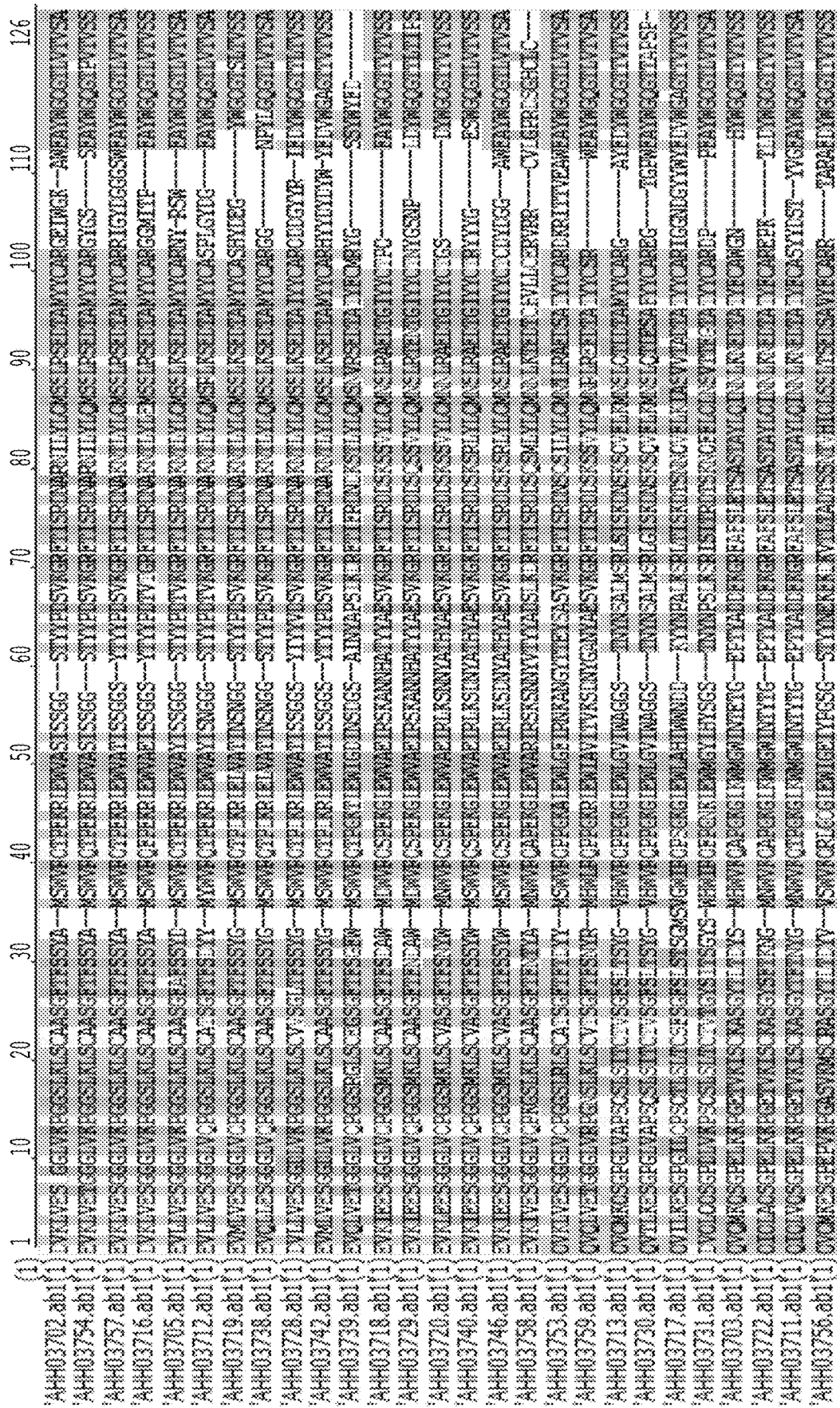
Figure 3B:
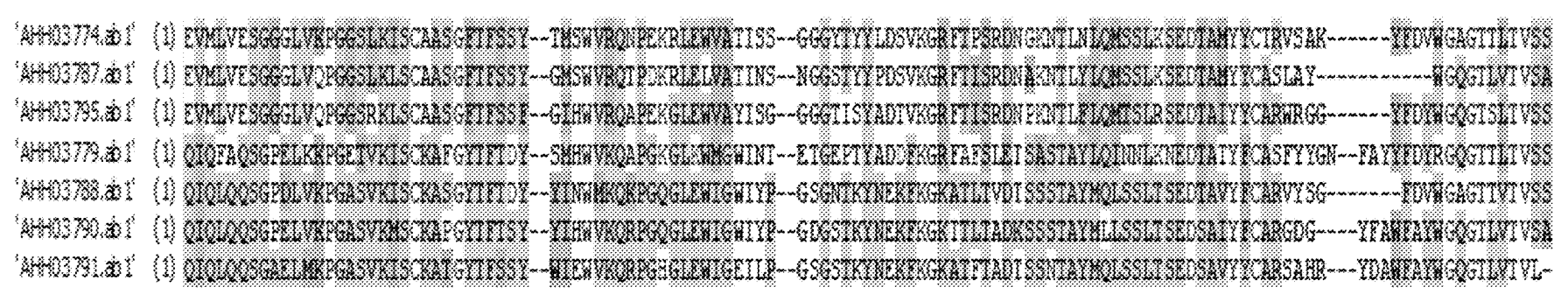
Figure 5:
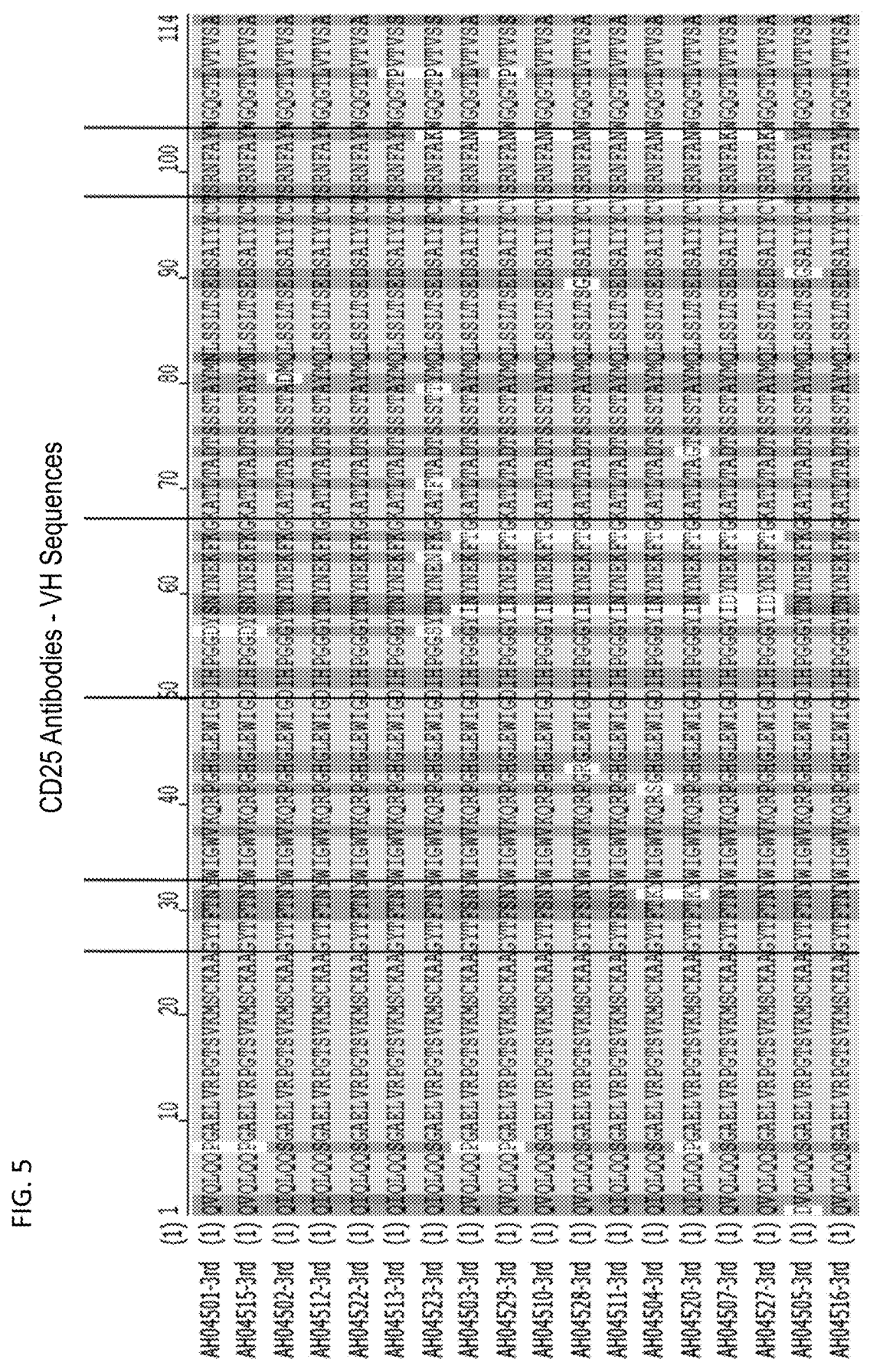

In some embodiments, the CD25 antibody comprises the amino acid sequence of any one of the variable heavy chains presented in Tables 1A, 1C, 1E, 1G, 1I, 1K, 2A, 2B, 2C, 4A, and 5A or FIGS. 3A, 3B and 5, or an amino acid sequence comprising at least a 80%, at least a 85%, at least a 90%, or at least a 95% sequence identity thereto. In some embodiments, the CD25 antibody comprises the amino acid sequence of any one of the variable heavy chains presented in Tables 1A, 1C, 1E, 1G, 1I, 1K, 2A, 2B, 2C, 4A, and 5A or FIGS. 3A, 3B and 5 that has been further humanized.

Figure 4A:
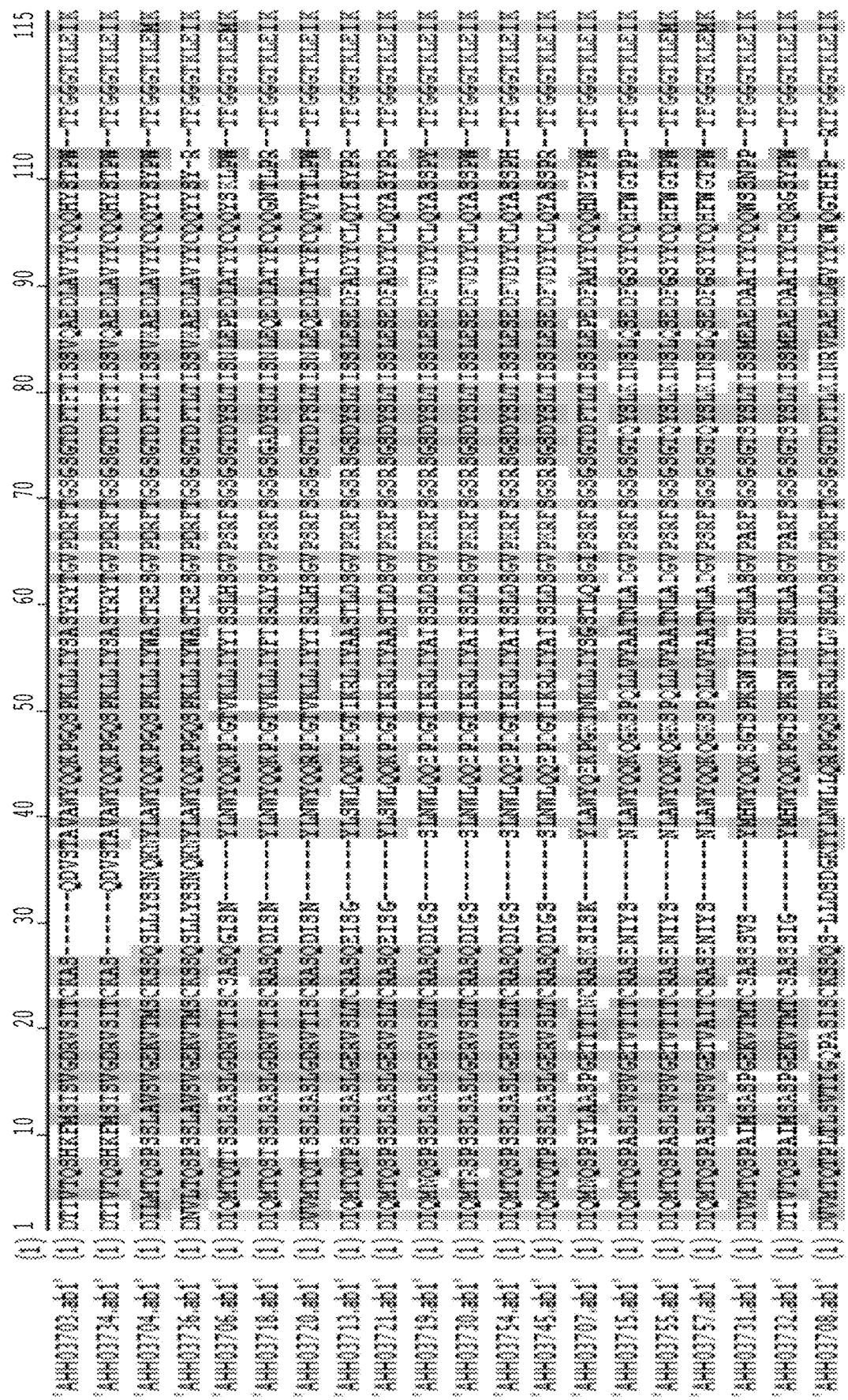
Figure 6:
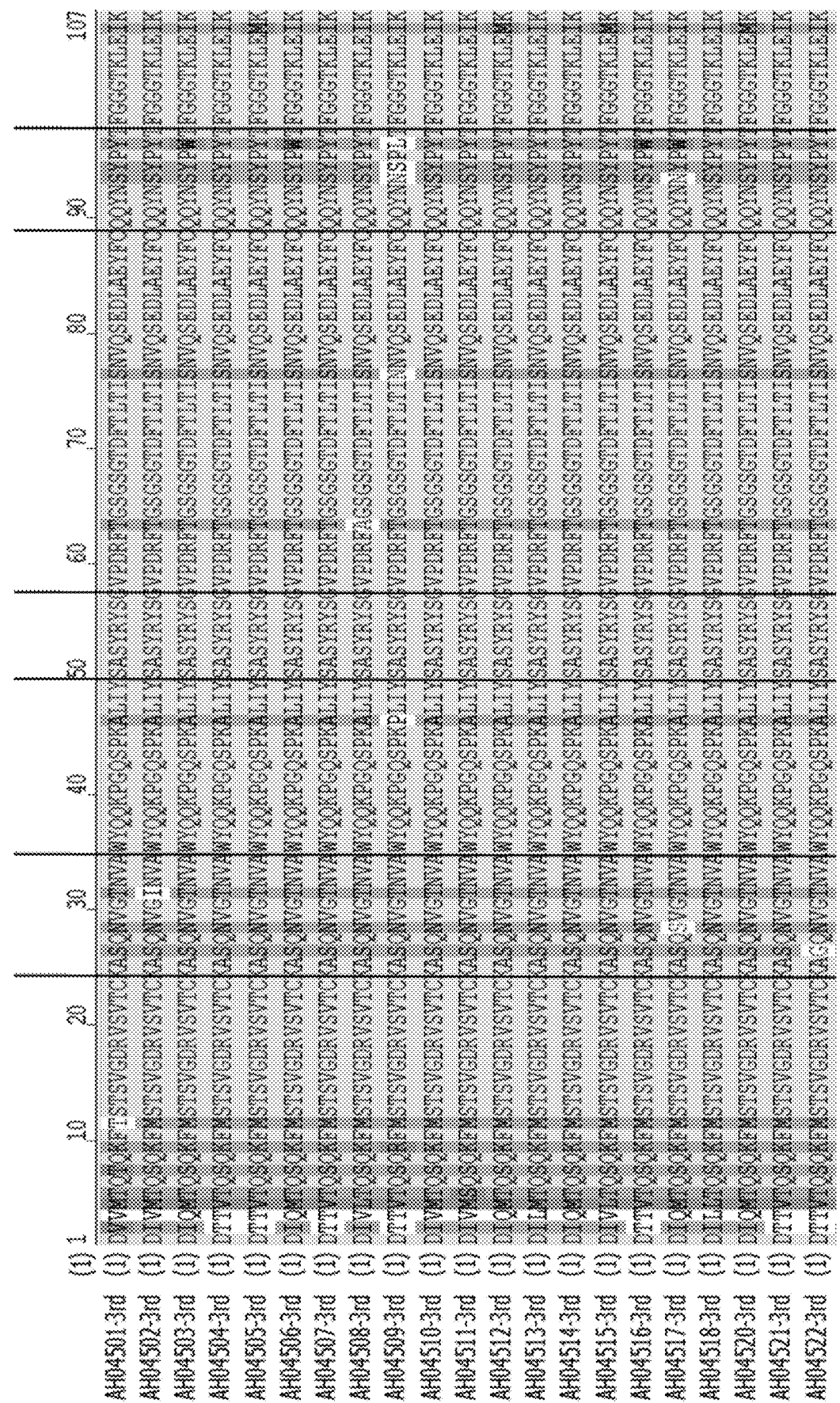
FIG. 6 depicts VL amino acid sequences of exemplary CD25 antibodies (SEQ ID NOs: 34, 701, 712, 735, 736, 737, 775, 777, 778, 795, 822, 823, 825, 838, 857, 859, 860, 861, 864, 895 and 912) of the disclosure.

In some embodiments, the CD25 antibody comprises the amino acid sequence of any one of the variable light chains presented in Tables 1B, 1D, 1F, 1H, 1J, 1L, 3A, 3B, 3C, 4B, and 5B or FIGS. 4A, 4B and 6, or an amino acid sequence comprising at least a 80%, at least a 85%, at least a 90%, or at least a 95% sequence identity thereto. In some embodiments, the CD25 antibody comprises the amino acid sequence of any one of the variable heavy chains presented in Tables 1B, 1D, 1F, 1H, 1J, 1L, 3A, 3B, 3C, 4B, and 5B or FIGS. 4A, 4B and 6 that has been further humanized, using conventional techniques In some embodiments, the CD25 antibody comprises the amino acid sequence of any one of the variable heavy chains presented in Tables 1A, 1C, 1E, 1G, 1I, 1K, 2A, 2B, 2C, 4A, and 5A or FIGS. 3A, 3B and 5, humanized versions thereof, or an amino acid sequence comprising at least a 80%, at least a 85%, at least a 90%, or at least a 95% sequence identity thereto; and the CD25 antibody comprises the amino acid sequence of any one of the variable light chains presented in Tables 1B, 1D, 1F, 1H, 1J, 1L, 3A, 3B, 3C, 4B, and 5B or FIGS. 4A, 4B and 6, humanized versions thereof, or an amino acid sequence comprising at least a 80%, at least a 85%, at least a 90%, or at least a 95% sequence identity thereto.

In some embodiments, VH of the CD25 antibody comprises the amino acid sequence of CDRH1, CDRH2, and CDRH3 as presented in Tables 1A, 1C, 1E, 1G, 1I, 1K, 2A, 2B, 2C, 4A, or 5A, or contained in the sequences presented in FIG. 3A, 3B or 5. In some embodiments, VH of the CD25 antibody comprises the amino acid sequence of CDRH1, CDRH2, and CDRH3 as presented in Table 6.

In some embodiments, VL of the CD25 antibody comprises the amino acid sequence of CDRL1, CDRL2, and CDRL3 as presented in Tables 1B, 1D, 1F, 1H, 1J, 1L, 3A, 3B, 3C, 4B, or 5B, or contained in the sequences presented in FIG. 4A, 4B or 6. In some embodiments, VL of the CD25 antibody comprises the amino acid sequence of CDRH1, CDRH2, and CDRH3 as presented in Table 7.

In some embodiments, VH of the CD25 antibody comprises the amino acid sequence of CDRH1, CDRH2, and CDRH3 as presented in Tables 1A, 1C, 1E, 1G, 1I, 1K, 2A, 2B, 2C, 4A, or 5A, or contained in the sequences presented in FIG. 3A, 3B or 5; and the VL of the CD25 antibody comprises the amino acid sequence of CDRL1, CDRL2, and CDRL3 as presented in Tables 1B, 1D, 1F, 1H, 1J, 1L, 3A, 3B, 3C, 4B, or 5B, or contained in the sequences presented in FIG. 4A, 4B or 6. In some embodiments, VH of the CD25 antibody comprises the amino acid sequence of CDRH1, CDRH2, and CDRH3 as presented in Table 6 and the VL of the CD25 antibody comprises the amino acid sequence of CDRH1, CDRH2, and CDRH3 as presented in Table 7.

In some embodiments, the VH of the antibody comprises the CDR1, CDR2, and CDR3 amino acid sequences presented in Table 5A. In some embodiments, the VL of the antibody comprises the CDR1, CDR2, and CDR3 amino acid sequences presented in Table 5B. In some embodiments, the antibody comprises a VH comprising the CDR1, CDR2, and CDR3 amino acid sequences presented in Table 5A, and a VL comprising the CDR1, CDR2, and CDR3 amino acid sequences presented in Table 5B.

In some embodiments, the antibody comprises the D5 CDR1, CDR2, and CDR3 amino acid sequences, the D5 VH and D5 VL amino acid sequences presented in Tables 1A and 1B, or humanized versions of the D5 VH and D5 VL amino acid sequences presented in Tables 1A and 1B.

In some embodiments, the antibody comprises the D11 CDR1, CDR2, and CDR3 amino acid sequences, the D11 VH and D11 VL amino acid sequences presented in Tables 1C and 1D, or humanized versions of the D11 VH and D11 VL amino acid sequences presented in Tables 1C and 1D.

In some embodiments, the antibody comprises the D16 CDR1, CDR2, and CDR3 amino acid sequences, the D16 VH and D16 VL amino acid sequences presented in Tables 1E and 1F, or humanized versions of the D16 VH and D16 VL amino acid sequences presented in Tables 1E and 1F.

In some embodiments, the antibody comprises the D17 CDR1, CDR2, and CDR3 amino acid sequences, the D17 VH and D17 VL amino acid sequences presented in Tables 1G and 1H, or humanized versions of the D17 VH and D17 VL amino acid sequences presented in Tables 1G and 1H.

In some embodiments, the antibody comprises the D34 CDR1, CDR2, and CDR3 amino acid sequences, the D34 VH and D34 VL amino acid sequences presented in Tables 1I and 1J, or humanized versions of the D34 VH and D34 VL amino acid sequences presented in Tables 1I and 1J.

In some embodiments, the antibody comprises the D36 CDR1, CDR2, and CDR3 amino acid sequences, the D36 VH and D36 VL amino acid sequences presented in Tables 1K and 1L, or the humanized versions of the D36 VH and D36 VL amino acid sequences presented in Tables 1K and 1L.

In some embodiments, the CD25 antibody comprises the CDRH1, CDRH2, and CDRH3 amino acid sequences of any one of the AH04507, AH04522, AH04526, AH04527, AH04734, AH04750, AH05214, AH05247, AH05249, AH05251, AH05256, AH05257, AH05258, AH05259, AH05268, AH05271, AH05274, AH05280, AH05285, AH05286, AH4501, AH4502, AH4503, AH4505, AH4509, AH4511, AH4518, AH4523, AH4524, AH4525, D11, D17, D34, D36, D5, BP003-T2P1C4, BP003-T2P1D10, BP003-T2P1D7, BP003-T2P1E3, or BP003-T2P1D1 clones presented in Table 5A.

In some embodiments, the CD25 antibody comprises the CDRL1, CDRL2, and CDRL3 amino acid sequences of any one of the AH04507, AH04522, AH04526, AH04527, AH04734, AH04750, AH05214, AH05247, AH05249, AH05251, AH05256, AH05257, AH05258, AH05259, AH05268, AH05271, AH05274, AH05280, AH05285, AH05286, AH4501, AH4502, AH4503, AH4505, AH4509, AH4511, AH4518, AH4523, AH4524, AH4525, D11, D17, D34, D36, D5, BP003-T2P1C4, BP003-T2P1D10, BP003-T2P1D7, BP003-T2P1E3, or BP003-T2P1D1 clones presented in Table 5B.

In some embodiments, the CD25 antibody comprises the CDRH1, CDRH2, and CDRH3 amino acid sequences of any one of the AH04507, AH04522, AH04526, AH04527, AH04734, AH04750, AH05214, AH05247, AH05249, AH05251, AH05256, AH05257, AH05258, AH05259, AH05268, AH05271, AH05274, AH05280, AH05285, AH05286, AH4501, AH4502, AH4503, AH4505, AH4509, AH4511, AH4518, AH4523, AH4524, AH4525, D11, D17, D34, D36, D5, BP003-T2P1C4, BP003-T2P1D10, BP003-T2P1D7, BP003-T2P1E3, or BP003-T2P1D1 clones presented in Table 5A; and the CD25 antibody comprises the CDRL1, CDRL2, and CDRL3 amino acid sequences of any one of the AH04507, AH04522, AH04526, AH04527, AH04734, AH04750, AH05214, AH05247, AH05249, AH05251, AH05256, AH05257, AH05258, AH05259, AH05268, AH05271, AH05274, AH05280, AH05285, AH05286, AH4501, AH4502, AH4503, AH4505, AH4509, AH4511, AH4518, AH4523, AH4524, AH4525, D11, D17, D34, D36, D5, BP003-T2P1C4, BP003-T2P1D10, BP003-T2P1D7, BP003-T2P1E3, or BP003-T2P1D1 clones presented in Table 5B.

In some embodiments, the CD25 antibody comprises the CDRH1, CDRH2, CDRH3, CDRL1, CDRL2, AND CDRL3 amino acid sequences of AH04507 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH04522 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH04526 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH04527 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH04734 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH04750 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH05214 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH05247 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH05249 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH05251 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH05256 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH05257 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH05258 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH05259 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH05268 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH05271 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH05274 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH05280 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH05285 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH05286 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH4501 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH4502 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH4503 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH4505 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH4509 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH4511 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH4518 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH4523 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH4524 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of AH4525 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of D11 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of D17 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of D34 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of D36 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of D5 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of BP003-T2P1C4 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of BP003-T2P1D10 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of BP003-T2P1D7 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of BP003-T2P1E3 (presented in Tables 5A and 5B respectively); in some embodiments, the CD25 antibody is a humanized antibody.

In some embodiments, the CD25 antibody comprises the CDRH1, CDRH2, CDRH3, CDRL1, CDRL2, AND CDRL3 amino acid sequences of BP003-T2P1D1 (presented in Tables 5A and 5B respectively); in some embodiments, the CD25 antibody is a humanized antibody.

In some embodiments, the CD25 antibody is conjugated for a variety of purposes including, but not limited to, for use in therapeutics and detection/diagnostics.

Also provided herein are nucleic acid sequences encoding any of the CD25 antibodies provided herein. Exemplary nucleic acid sequences encoding the D5, D11, D16, D17, D34, and D36 VH and VL regions are provided in Tables 1A-1L—one can use humanized versions thereof. Also provided herein are vectors comprising any of the nucleic acids encoding the antibodies, phage comprising such vectors, and host cells comprising such vectors.

Antibody Generation and Testing

Figure 2:
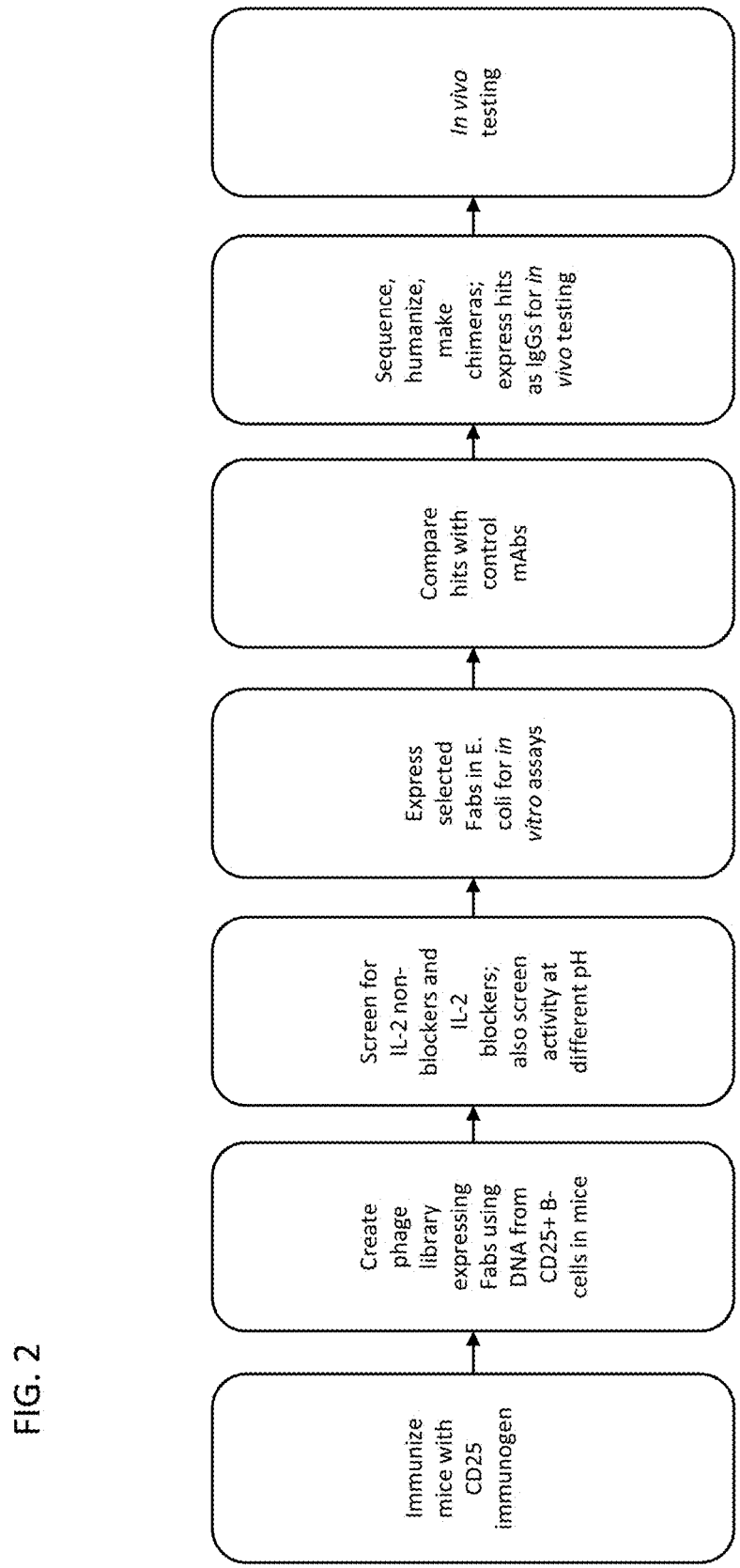
FIG. 2 is an exemplary workflow for CD25 antibody discovery, in vitro testing, and in vivo testing.

FIG. 2 is an exemplary non-limiting workflow for CD25 antibody discovery, in vitro testing, and in vivo testing, but one of skill in the art recognizes that there are alternative ways to approach antibody discovery and testing.

The CD25 antibodies described herein can be generated by injection of a CD25 complete or partial immunogen into an animal, e.g. a mouse or a rabbit. CD25 immunoge positive B-cells from the animal can be collected, and phage libraries generated therefrom. In some embodiments, the phage express Fab fragments of candidate CD25 antibodies. The phage can undergo multiple rounds of screening (referred to herein as phage panning), for example against successively lower concentrations of a CD25 antigen, to select for those Fab fragments capable of binding CD25 with high affinities. The phage can be screened against CD25 antigen coated beads, or some other substrate, for example. In some embodiments, the screening is carried out a physiological pH (e.g. about pH 7.4). In other embodiments, the screening is carried out at a lower pH, for example, at a pH of about 6.5 to screen for Fab fragments capable of binding the CD25 antigen at a lower pH, for example, for use in a therapeutic context, e.g. for use in a hypoxic, acidic tumor microenvironment.

The CD25 antibodies generated herein may be tested for efficacy using a number of in vitro, in vivo, ex vivo, and/or cell-based assays.

In some embodiments, the CD25 antibodies herein can be assayed for, and further selected based on their ability to deplete regulatory T cells. In particular embodiments, the CD25 antibodies herein can be assayed for, and further selected based on their ability to deplete regulatory T cells in an acidic environment, e.g at a pH lower than physiological pH, e.g. at pH 7.3, 7.2, 7.1, 7.0, 6.9, 6.8, 6.7, 6.6, 6.5, 6.4, 6.3, 6.2, 6.1, or lower.

In some embodiments, the CD25 antibodies herein can be assayed for, and further selected based on a pSTAT5 in vitro assay, to assay for the signaling through the IL-2/IL-2 receptor pathway, the maintenance of which indicates that the antibody is not an IL-2 blocking antibody.

In some embodiments, the CD25 antibodies herein can be assayed for using biosensor screening to characterize molecular interactions.

In some embodiments, the CD25 antibodies herein can be assayed for competition for binding against other known CD25 antibodies, with known mechanisms.

In some embodiments, the CD25 antibodies herein can be assayed for epitope specificity.

In some embodiments, the CD25 antibodies herein can be assayed for their capacity to be a non IL-2 blocker, an IL-2 blocker, or a partial IL-2 blocker.

Therapeutic Uses

Provided herein are CD25 antibodies for therapeutic use, e.g. for use in proliferative diseases or disorders such as cancer or for use in autoimmune diseases.

Accordingly provided herein are methods of treating a cancer comprising administering to a subject in need thereof a therapeutically effective amount of a therapeutic CD25 antibody. In some embodiments, the cancer is a primary cancer. In some embodiments, the cancer is a metastatic cancer. In some embodiments, the cancer involves a solid tumor; in other embodiments, the cancer involves a liquid tumor, e.g. a blood based cancer. In exemplary embodiments, the CD25 antibody is a non IL-2 blocking antibody.

Accordingly provided herein are methods of treating an autoimmune-related disease or disorder comprising administering to a subject in need thereof a therapeutically effective amount of a therapeutic CD25 antibody. In exemplary embodiments, the CD25 antibody is an IL-2 blocking antibody.

As used herein, a subject refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. Subjects may be male or female.

The administration of any of the therapeutic CD25 antibodies provided herein may be administered in combination with other known drugs/treatments (e.g. small molecule drugs, or biologics. The administration may be sequential or concurrent.

In vivo administration of the therapeutic CD25 antibodies described herein may be carried out intravenously, intratumorally, intracranially, intralesionally (e.g. intralesional injection, direct contact diffusion), intracavitary (intraperitoneal, intralpleural, intrauterine, intrarectal), intraperitoneally, intramuscularly, subcutaneously, topically, orally, transdermally, by implantation, by inhalation, intrathecally, intraventricularly, or intranasally. In an exemplary embodiment, the route of administration is by intravenous injection.

A therapeutically effective amount of the therapeutic antibody will be administered. The appropriate dosage of the therapeutic antibody may be determined based on the severity of the cancer, the clinical condition of the subject, the subject's clinical history and response to the treatment, and the discretion of the attending physician The dosage amounts of the CD25 antibodies provided herein may vary from about 1 ng/kg up to about 1000 mg/kg of a subject's body weight or more per day, depending upon the route of administration. For repeated administrations over several days or longer, depending on the severity of the cancer, the treatment may be sustained until a desired suppression of symptoms is achieved. Dosage regimens may be useful, depending on the pattern of pharmacokinetic decay that the physician wishes to achieve. For example, dosing an individual from one to twenty-one times a week is provided herein. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is may be monitored by conventional techniques and assays. The dosing regimen may vary over time independently of the dose used.

Diagnostic Uses

The CD25 antibodies provided herein may be used for diagnostic and detection purposes. Depending on the application, the CD25 antibody may be detected and quantified in vivo or in vitro.

The CD25 antibodies provided herein are amendable for use in a variety of immunoassays. These immunoassays include, but are not limited to enzyme-linked immunosorbent assay (ELISA), Western blot, radioimmunoassay (MA), flow cytometry, a radioimmunoassay, an immunofluorescence assay, spectrophotometry, radiography, electrophoresis, high performance liquid chromatography (HPLC), or thin layer chromatography (TLC).

The CD25 antibodies provided herein may be comprise a detectable label, for example detectable by spectroscopic, photochemical, biochemical, immunochemical, fluorescent, electrical, optical or chemical methods. Useful labels in the present disclosure include, but are not limited to fluorescent dyes, radiolabels, enzymes, colorimetric lables, avidin or biotin.

In some embodiments, the CD25 antibody is radiolabeled with an isotope, useful for imaging by nuclear medicine equipment (SPECT, PET, or scintigraphy).

Pharmaceutical Compositions

The disclosure provides compositions comprising therapeutic CD25 antibodies, In some embodiments the composition is sterile. The pharmaceutical compositions generally comprise an effective amount of the therapeutic antibody in a pharmaceutically acceptable excipient.

Kits and Articles of Manufacture

The disclosure also provides for kits comprising any of the CD25 antibodies described herein, e.g. for either therapeutic or diagnostic uses. In some embodiments, the kits further contain a component selected from any of secondary antibodies, reagents for immunohistochemistry analysis, pharmaceutically acceptable excipient and instruction manual and any combination thereof. In some embodiments, the kit comprises any one or more of the therapeutic compositions described herein, with one or more pharmaceutically acceptable excipients.

The present application also provides articles of manufacture comprising any one of the therapeutic or diagnostic compositions or kits described herein. Examples of an article of manufacture include vials (e.g. sealed vials).

The description provided herein sets forth numerous exemplary configurations, methods, parameters, and the like. It should be recognized, however, that such description is not intended as a limitation on the scope of the present disclosure, but is instead provided as a description of exemplary embodiments.

The following examples are included for illustrative purposes and are not intend to limit the scope of the invention.

ENUMERATED EMBODIMENTS

Embodiment 1. A monoclonal CD25 antibody which binds to human CD25, and possesses at least one of the following characteristics:

a. the antibody does not disrupt the binding of the IL-2 ligand to the alpha chain of the IL-2 receptor (CD25), and binds to a different epitope than to which 7G7B6 binds;

b. the antibody does not disrupt the binding of the IL-2 ligand to the alpha chain of the IL-2 receptor (CD25), but does disrupt the trimerization of the beta, gamma, and alpha (CD25) chains of the IL-2 receptor;

c. the antibody disrupts the binding of the IL-2 ligand to the alpha (CD25), beta, and/or gamma chains of the IL-2 receptor, and binds to a different epitope than to which daclizumab or baciliximab bind;

d. the antibody exhibits a higher affinity of binding to CD25 at pH lower than 7.4, when compared to the affinity of binding to CD25 at a pH of 7.4;

e. the antibody comprises the amino acid sequence of any one of the variable heavy chains presented in Tables 1A, 1C, 1E, 1G, 1I, 1K, 2A, 2B, 2C, 4A, and 5A or FIGS. 3A, 3B and 5, humanized versions thereof, or an amino acid sequence comprising at least a 80%, at least a 85%, at least a 90%, or at least a 95% sequence identity thereto;

f. the antibody comprises the amino acid sequence of any one of the variable light chains presented in Tables 1B, 1D, 1F, 1H, 1J, 1L, 3A, 3B, 3C, 4B, and 5B or FIGS. 4A, 4B and 6, humanized versions thereof, or an amino acid sequence comprising at least a 80%, at least a 85%, at least a 90%, or at least a 95% sequence identity thereto;

g. the VH of the antibody comprises any one of the amino acid sequence of CDRH1, CDRH2, and CDRH3 as presented in Tables 1A, 1C, 1E, 1G, 1I, 1K, 2A, 2B, 2C, 4A, 5A, and 6 or contained in the sequences presented in FIGS. 3A, 3B and 5;

h. the VL of the CD25 antibody comprises any one of the amino acid sequence of CDRL1, CDRL2, and CDRL3 as presented in Tables 1B, 1D, 1F, 1H, 1J, 1L, 3A, 3B, 3C, 4B, 5B and 7, or contained in the sequences presented in FIGS. 4A, 4B and 6; and i. the antibody comprises the amino acid sequence of CDRH1, CDRH2, and CDRH3 of any one of the combinations presented in Table 6 and the amino acid sequence of CDRL1, CDRL2, and CDRL3 of any one of the combinations presented in Table 7.

Embodiment 2. The antibody of embodiment 1, wherein the antibody possesses at least two, at least three, at least four, at least five, or at least six of the characteristics provided therein.

Embodiment 3. The antibody of embodiment 1, wherein the antibody does not disrupt the binding of the IL-2 ligand to the alpha chain of the IL-2 receptor (CD25), and binds to a different epitope than to which 7G7B6 binds.

Embodiment 4. The antibody of embodiment 1, wherein the antibody does not disrupt the binding of the IL-2 ligand to the alpha chain of the IL-2 receptor (CD25), but does disrupt the trimerization of the beta, gamma, and alpha (CD25) chains of the IL-2 receptor.

Embodiment 5. The antibody of embodiment 1, wherein the antibody disrupts the binding of the IL-2 ligand to the IL-2 receptor, and binds to a different epitope than to which Daclizumab or Baciliximab bind.

Embodiment 6. The antibody of embodiment 1, wherein the antibody exhibits a higher affinity of binding to CD25 at a pH lower than 7.4, when compared to the affinity of binding to CD25 at a pH of 7.4.

Embodiment 7. The antibody of embodiment 6, wherein the antibody exhibits a higher affinity of binding to CD25 at a pH of about 6.5.

Embodiment 8. The antibody of any one of embodiments 1 to 7, wherein the antibody comprises the amino acid sequence of any one of the variable heavy chains presented in Tables 1A, 1C, 1E, 1G, 1I, 1K, 2A, 2B, 2C, 4A, and 5A or FIGS. 3A, 3B and 5, humanized versions thereof, or an amino acid sequence comprising at least a 80%, at least a 85%, at least a 90%, or at least a 95% sequence identity thereto.

Embodiment 9. The antibody of any one of embodiments 1 to 8, wherein the antibody comprises the amino acid sequence of any one of the variable light chains presented in Tables 1B, 1D, 1F, 1H, 1J, 1L, 3A, 3B, 3C, 4B, and 5B or FIGS. 4A, 4B and 6, humanized versions thereof, or an amino acid sequence comprising at least a 80%, at least a 85%, at least a 90%, or at least a 95% sequence identity thereto.

Embodiment 10. The antibody of any one of embodiments 1 to 7, wherein the VH of the antibody comprises the amino acid sequence of CDRH1, CDRH2, and CDRH3 as presented in Tables 1A, 1C, 1E, 1G, 1I, 1K, 2A, 2B, 2C, 4A, or 5A, or contained in the sequences presented in FIG. 3A, 3B or 5.

Embodiment 11. The antibody of any one of embodiments 1 to 7 and embodiment 10, wherein the VL of the CD25 antibody comprises the amino acid sequence of CDRL1, CDRL2, and CDRL3 as presented in Tables 1B, 1D, 1F, 1H, 1J, 1L, 3A, 3B, 3C, 4B, or 5B, or contained in the sequences presented in FIG. 4A, 4B or 6.

Embodiment 12. The antibody of any one of embodiments 1 to 10, wherein the CD25 antibody comprises the amino acid sequence of CDRH1, CDRH2, and CDRH3 of any one of the combinations presented in Table 6.

Embodiment 13. The antibody of any one of embodiments 1 to 10, wherein the CD25 antibody comprises the amino acid sequence of CDRL1, CDRL2, and CDRL3 of any one of the combinations presented in Table 7.

Embodiment 14. The antibody of any one of embodiments 1 to 13, wherein the antibody is a human antibody.

Embodiment 15. The antibody of any one of embodiments 1 to 13, wherein the antibody is a humanized antibody.

Embodiment 16. The antibody of any one of embodiments 1 to 13, wherein the antibody is a chimeric antibody.

Embodiment 17. The antibody of embodiment 16, wherein the antibody comprises a mouse variable domain, and a human constant domain.

Embodiment 18. The antibody of any one of embodiments 1 to 15, wherein the antibody is an antibody fragment.

Embodiment 19. The antibody of any one of embodiments 1 to 18, wherein the antibody also binds cynomologous monkey CD25.

Embodiment 20. A pharmaceutical composition comprising any one of the antibodies of embodiments 1 to 19.

Embodiment 21. A nucleic acid sequence encoding any one of the antibodies of embodiments 1 to 19.

Embodiment 22. A vector comprising the nucleic acid sequence of embodiment 21.

Embodiment 23. A phage expressing any one of the antibodies of embodiments 1 to 19.

Embodiment 24. A method of treating a subject in need thereof comprising administering to the subject a therapeutically effective amount of any one of the antibodies of embodiments 1 to 19 or the pharmaceutical composition of embodiment 20.

Embodiment 25. A method of depleting the number of regulatory T cells in a subject comprising administering to the subject a therapeutically effective amount of any one of the antibodies of embodiments 1 to 19 or the pharmaceutical composition of embodiment 20.

Embodiment 26. The method of embodiment 24 or 25, wherein the subject suffers from cancer.

Embodiment 27. The method of embodiment 24 or 25, wherein the subject suffers from an autoimmune-related disease or disorder.

Embodiment 28. A method of depleting the number of regulatory T cells in a sample comprising peripheral blood mononuclear cells comprising contacting the sample with any one of the antibodies of embodiments 1 to 19.

Embodiment 29. A kit comprising any one of the antibodies of embodiments 1 to 19 or the pharmaceutical composition of embodiment 20.

EXAMPLES

Example 1: Immunization with CD25

Full length CD25 conjugated to KLH was injected into five difference BalbC mice. All injections were done via the tail vein. The immunization protocol was as follows:
Day 0: Immunization 1
Day 14: Immunization 2
Day 28: Immunization 3
Day 35: Bleed
Splenocytes and Leukocytes from four of the five mice were used to generate four phage libraries. The phage libraries contained phage, expressing antigen binding (Fab) fragments. More specifically, a M13 phagemid library using materials from the immunized animals was constructed as follows. (i) Total RNA from leukocytes and splenocytes was extracted; (ii) VH and VL genes were amplified with specific primers; and (iii) VH and VL fragments were inserted into GenScript's M13 phagemid vector by two-step cloning. The library size>$2\times10^8$; the insert rate was >90%, and the in-frame rate was >80%. The library was a high diversity library, with at >95% of unique sequences.

Example 2: Phage Panning for CD25 Binding 3 rounds of phage panning of the Fab-containing phage libraries were carried out, using an ELISA-based assay. The phage were screened against beads coated with CD25. Each round was carried out with a decreasing concentration of CD25. Individual phage clones were expressed in *E. coli* TG1 cells (plated on LB/carbenicillin). Single colonies were cultured in 0.4 ml 2YT broth for 30 min at 37° C., and then infected with M13 K07 helper phage for 3 hours at 37° C. Then 50 µg/ml carbenicillin and 10 µg/ml Kanamycin were added to the culture which was then grown overnight at 25° C. The next day, phage was harvested from the cultures.

Positive clones were sequenced as follows. Positive hit clones were cultured overnight and plasmid DNA was prepared with a Qiagen plasmid miniprep kit. Purified plasmids were submitted to Genewiz and ELIM Biopharmaceuticals for sanger sequencing. The VH sequence was obtained with the sequencing primers (ACGCCTGCGAAGTCACCCAT (SEQ ID NO: 1497)) or (AGAAACACAAAGTCTACGCCTGCGAAGTCAC (SEQ ID NO: 1498)). The VL sequence was obtained with the sequencing primer (AGCGGATAACAATTT-CACACAGGA (SEQ ID NO: 1499)), or CGGATAACAAT-TTCACACAG (SEQ ID NO: 1500).

FIGS. 3A, 3B, 4A, and 4B and Tables 2A, 2B, 3A, and 3B show VH and VL sequences of the Fabs selected after the second round of panning.

FIGS. 5 and 6, and Tables 2C and 3C show VH and VL sequences of the Fabs selected after the third round of panning.

Tables 4A, 4B, 5A, and 5B show additional clones after similar panning protocols.

Further pH-based phage panning was carried out.

Example 3: Phage Panning for CD25 Binding at pH 6.5

Further phage panning was carried out to select for Fab candidates that bind CD25 at lower pH ranges, to select for binders that could bind, for example, in a hypoxic, acidic tumor microenvironment.

The four mouse HuCD25 immunized phage libraries (7807, 7808, 7809, 7810) were transformed by electroporation in TG1 and phage propagated with the addition of CM13 using standard Phage Display protocols (Barbas et al., 2001). TG1 cultures secreting phage were PEG precipitated with PEG/NaCl after incubation on ice for one hour.

The phage libraries (7807, 7808, 7809, 7810) were used for specific pH selections using standard protocols. To deplete antibodies that bind with high affinity at physiological pH, subtractive panning was first carried out by counter-selection of 3×10^11 pfu phage (1000-fold representation of a 3×10^8) at pH 7.4 by absorption for 1 hour on ELISA plates coated with 10 ug/ml full-length CD25 (400 nM) in PBST pH 7.4. Resulting phage supernatant was collected and pH was adjusted to pH 6.5 with PB ST. Subsequent phage panning selections were carried out at pH 6.5

Panning selections were pre-cleared with 25 microliters streptavidin dynabeads with no CD25 antigen after 1 hour incubation. Phage were then added to new pre-blocked Eppendorf LoBind tube. Biotinylated full-length CD25 antigen was added at 100 nM concentration for one hour. Samples were then incubated with 25 microliters streptavidin beads RT for one hour. Samples were pelleted and washed using magnet/magnetic beads 7-9 times with PBST. Tubes were changed twice to remove residual phage.

To elute phage, 800 microliters Glycine pH 2.2 were added to beads and incubated for no more than ten minutes. They were then neutralized with high pH Tris 9.0. Eluted phage were added to 1 ml TG1 freshly grown (0D600-0.5), and incubated for 20-30 minutes. Fractional log dilution series were plated on plates, and the remainder was transferred to 25 ml 2×YT (2×Yeast Tryptone Broth). These steps were repeated two additional times for a total of three panning rounds, followed by Phage ELISA and Octet screening of periplasmic extracts.

Sequencing

Positive hit clones were cultured overnight and plasmid DNA was prepared with a Qiagen plasmid miniprep kit. Purified plasmids were submitted to Genewiz and ELIM Biopharmaceuticals for sanger sequencing. The VH sequence was obtained with the sequencing primer (ACGCCTGCGAAGTCACCCAT (SEQ ID NO: 1497)) or (AGAAACACAAAGTCTACGCCTGCGAAGTCAC (SEQ ID NO: 1498)). The VL sequence was obtained with the sequencing primer (AGCGGATAACAATTT-CACACAGGA (SEQ ID NO: 1499)) or (CGGATAACAAT-TTCACACAG (SEQ ID NO: 1500)). VH and VL V-D-J arrangements, nucleic acid alignments, and amino acid alignments were identified by IMGT High V-Quest.

Sequences for selected Fab clones D5, D11, D16, D17, D34, and D36 are presented in Tables 1A-1L.

Example 4: Phage ELISA Protocol and Biosensor/Octet Screening

ELISA/Extract Preparation

Phage ELISA, for assessing CD25 binding to Fab phage, and periplasmic extract preparation for Fab Octet screening were conducted essentially as described, with modifications noted (Schwimmer et al., 2013).

The CD25 antigen was diluted in PBS, pH 7.4. 50 microliters of antigen solution were made containing 1 ug of CD25 for each well of a 96-well plate to be coated. 50 microliters of antigen solution was added to the ELISA plate wells and incubate overnight at 4° C. Following the incubation, wells were washed twice with PBS, and wells were blocked by adding 200 microliters of 1×PBST 2.0% BSA and incubated for 2 hours at 25° C. Phage were diluted two-fold in 1×PBST 1.0% BSA, pH 6.5. 50 microliters were added per and incubated for 5 minutes at room temperature. The blocking solution was shaken out of the wells, and 50 ul of the dilute phage preparation was added to each well, and incubated for 1 hour at room temperature. The ELISA plate wells were washed 3-5 times with 200 microliters PBST pH 6.5. HRP-conjugated anti-M13 antibodies were diluted (Abcam, ab50370) 1:5000 with 1×PBST 1.0% BSA pH 6.5. 50 microliters of diluted secondary antibody conjugate was added to each well, and incubated for 1 hour at room temperature. ELISA plate wells were washed 3-5 times with 200 microliters PBST pH 6.5. The ECL Lumo substrate was prepared (e.g. Supersignal ELISA Pico Chemiluminescent Substrate) as described, into a 1:1 mixture. 50 microliters substrate solution was added to each well, incubated at room temperature for 5 to 60 minutes before reading.

Colonies were inoculated in 0.03-4 ml 2×YT 0.2% Glucose with 0.1 ml overnight culture (1 ml cultures in 96-well plate or 4 ml cultures in 14-ml falcon tubes). They were incubated at 250-700 rpm for 1.5-2 hours at 37° C. until the OD600~0.5-1.0. Cultures were induced with 50-400 ul IPTG 0.025-0.1M. In some cases, the temperature was reduced to 30° C. with shaking at 250 rpm. They were then incubated overnight. Next day cultures were harvested by pelleting 3400 rcf for 10-15 minutes. The supernatant was discarded.

Cultures were resuspended with 50-75 ul PPB buffer (30 mM Tris-HCl, pH 8.0, 1 mM EDTA, 20% Sucrose) with 1× Halt Protease Inhibitor and incubated on a rocking platform for 15 minutes at room temperature or 4° C. for 10 min. Cultures were resuspended with 150-225 ul of cold ddH20 with 1× Halt Protease Inhibitor and incubated on a rocking platform for one hour at room temperature or 4° C. for 1-2 hours. The lysate suspension was spun at 15000 rcf for 10-15 min at 4C. Supernatant was collected and diluted.

Fab Expression and Purification Protocol

Single E. coli colonies were inoculated and grown in 50 2×YT 0.2% Glucose with 0.03-0.5 ml overnight culture in plates or 50 mL cultures. Cultures were incubated at 250-700 rpm at 37° C. for 1.5-hours. Cultures were induced with 50 ul of 25 mM-1M IPTG. The temperature was reduced to 30° C. and rpm to 150. Incubation was done overnight. 50 ml cultures or plates were harvested by pelleting 3400 rcf for 15 minutes. The supernatant was discarded. Cell pellets from 50 mL cultures were placed in a −80° C. freezer for 1 hour, while cultures grown in plates had 75 uL of PPB added with 1× Halt protease inhibitor, EDTA-free (Thermo Fisher Scientific) and vortexed. Plates were shaken at 4° C. for 10 minutes at 1000 rpm. The volume of 225 uL of cold water with 1× Halt protease inhibitor, EDTA-free (Thermo Fisher Scientific) was added to each well. Samples were mixed and shaken at 4° C. for 1-2 hours at max speed i.e. 1000 rpm. Plates were spun at 3500 rpm for 10 mins at 4° C. The supernatant (PPE) was transferred to fresh plates and stored at −20° C. Cell pellets from the 50 mL cultures were removed from the freezer and 5 ml PBS, 10 mM Imidazole was added with 2.5 mg/ml lysozyme and 1× Halt protease inhibitor, EDTA-free (Thermo Fisher Scientific). These were incubated at room temperature for 30 minutes once pellet had fully thawed/mixed. The lysate was centrifuged for 15 minutes at 3400 rcf. The supernatant was removed and pellet discarded. 500 ul Ni-NTA resin was added (pre-washed and pelleted) or a Ni-NTA spin column was used for Fab purification. Incubate with cleared lysate for 30 min-1 hr. This was spun at 1500 rcf. These were washed 5 times with 1 ml PBS, 10 mM Imidazole. Buffer was discarded after each spin. 1 ml PBS, 200 mM Imidazole were added and mixed, incubated for 30 minutes and spun at 1500 rcf for 15 minutes. The eluted protein was stored at 4° C. or 20° C. after determining protein concentration. Zeba columns were used for desalting/buffer exchange.

Octet/Biosensor Screening of Fabs

For Octet Koff rate screening in raw supernatants, 50 ul of lysate was used in 384-well Pall ForteBio Octet plates. Data was collected on an Octet RED 384 (MD ForteBio). Briefly, Human CD25 was coupled to AR2G tips (1 ug/ml). For data collection, baseline was assessed in PBST 1% BSA buffer at pH 6.5 for 60 seconds. Tips were then moved to 50 ul lysate pH6.5 adjusted and association measured for 300 seconds. Finally, tips were moved to PBST 1% BSA buffer at pH 6.5. Tips were then regenerated with 200 mM Tris-Glycine, pH 2.5 and neutralization with PBST, 1% BSA, pH 6.5. For data analysis, Double referencing was performed on Octet HT 11.0 software (no CD25 on tip as well as blank reference well), for reference subtraction.

Biosensor assays were carried out to determine whether selected Fabs would block IL-2 binding to CD25.

Octet/Biosensor Screening of Human IgG1 Antibodies

A subset of selected 40 Fabs were reformatted to contain a human IgG1 (referred to herein as human IgG1 antibodies), and data were collected these. The Fabs selected for reformatting are show in Tables 5A (heavy chains) and Table 5B (light chains). The Koff rates and affinity of the different reformatted IgG1 antibodies were evaluated on a FortéBio® Octet RED384™ bio-layer interferometry instrument. Purified antibodies were covalently immobilized on amine reactive biosensors (Fortebio® AR2G), and excess reactive esters were blocked with ethanolamine. Sensors were then dipped into running buffer as a baseline, transferred to wells containing 300 nM full-length CD25, and then transferred back into running buffer. Association of CD25 and subsequent dissociation was recorded in duplicate. Association of running buffer only (to control for sensor drift), and additional sensors with immobilized IgG from human ND serum (to control for non-specific IgG binding), were run as controls. The observed on and off rates were fit using a 1:1 binding fit model, and the equilibrium binding constant (KD) was calculated.

Epitope binning of reformatted human IgG1 antibodies were done using cross-competition assays performed in the classical sandwich format, which involves collecting a baseline, immobilizing the sample antibody onto the biosensor, capturing the antigen, and then incubating with a competitive analyte. The competitive analyte can bind the captured CD25 only if its binding epitope does not overlap with that of the immobilized antibody. Purified antibodies were covalently immobilized on amine reactive biosensors (Fortebio® AR2G), and excess reactive esters were blocked with ethanolamine. Sensors were dipped into running buffer as a baseline, followed by full-length CD25. Then the sensors were transferred to wells containing a competitive analyte (IL-2, 7G7B6, Basiliximab, Dacluzumab) or running buffer as a reference. Sensors were regenerated when necessary by exposing them to 3 cycles of 0.1 M Glycine pH 2.0 for 10 seconds, followed by running buffer for 10 seconds.

Results

Figure 7:
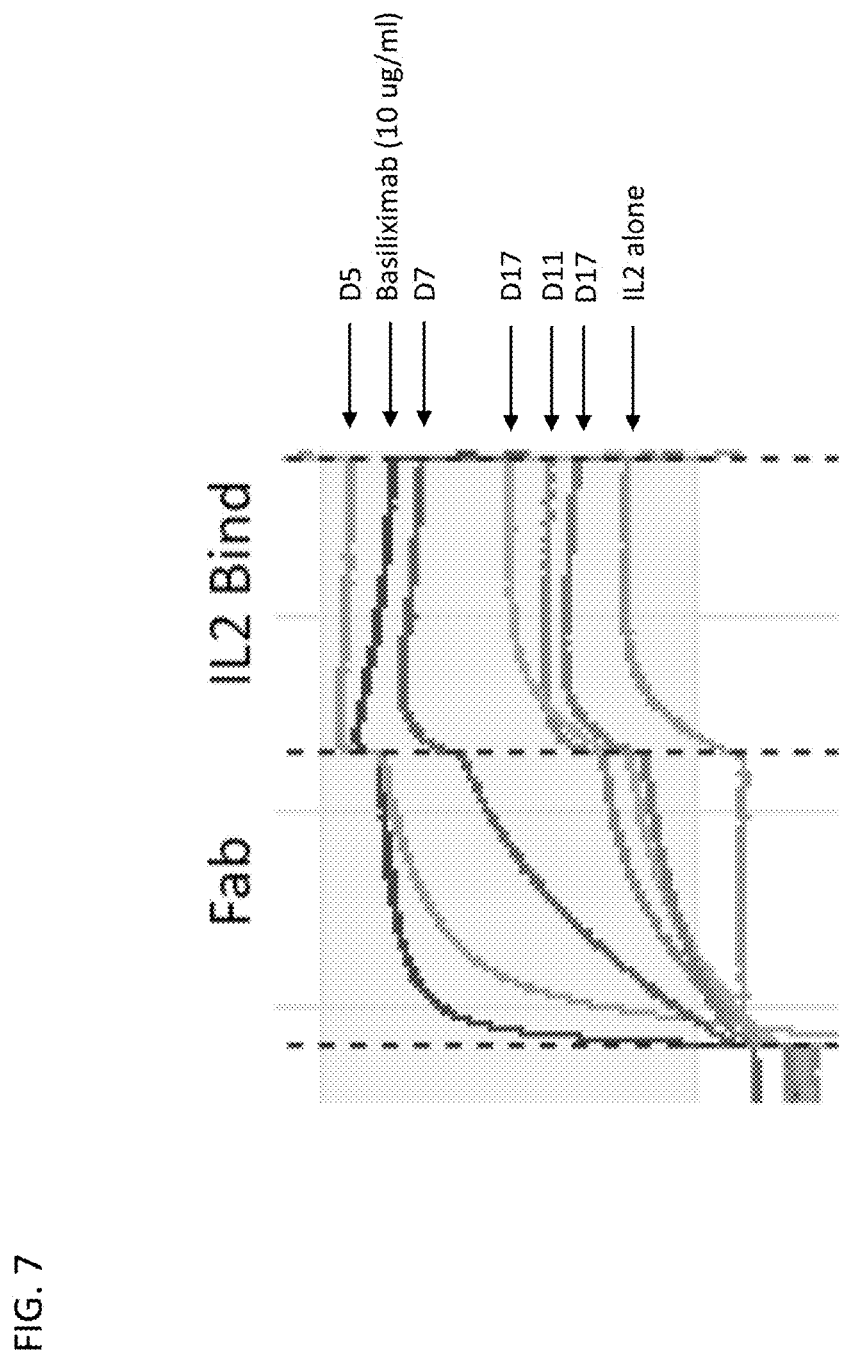
FIG. 7 depicts the identification of non IL-2 blockers, using a cross block assay, using a biosensor.

FIG. 7 depicts the identification of non IL-2 blockers and IL-2 blockers (Fabs), using a cross block assay at the molecular level. CD25 was coated on the biosensor tip, and brought into contact with the indicated Fab. IL2 was then added. An increase in signaling shows that the Fab and IL2 have different binding sites on CD25.

Table 8 shows that the Fab clones tested exhibited similar binding kinetics at physiological and acidic pH.

TABLE 8

| pH  | Sample ID | kdis (1/s) |
|-----|-----------|------------|
| 6.5 | D5        | 4.12E-03   |
| 7.4 | D5        | 3.45E-03   |
| 6.5 | D7        | 3.87E-03   |
| 7.4 | D7        | 2.80E-03   |
| 6.5 | D11       | 5.22E-03   |
| 7.4 | D11       | 4.52E-03   |
| 6.5 | D16       | 5.91E-03   |
| 7.4 | D16       | 4.00E-03   |
| 6.5 | D17       | 5.36E-03   |
| 7.4 | D17       | 3.37E-03   |
| 6.5 | D34       | 2.96E-03   |
| 7.4 | D34       | 2.85E-03   |
| 6.5 | D36       | 1.72E-03   |
| 7.4 | D36       | 8.98E-04   |

Figure 8:
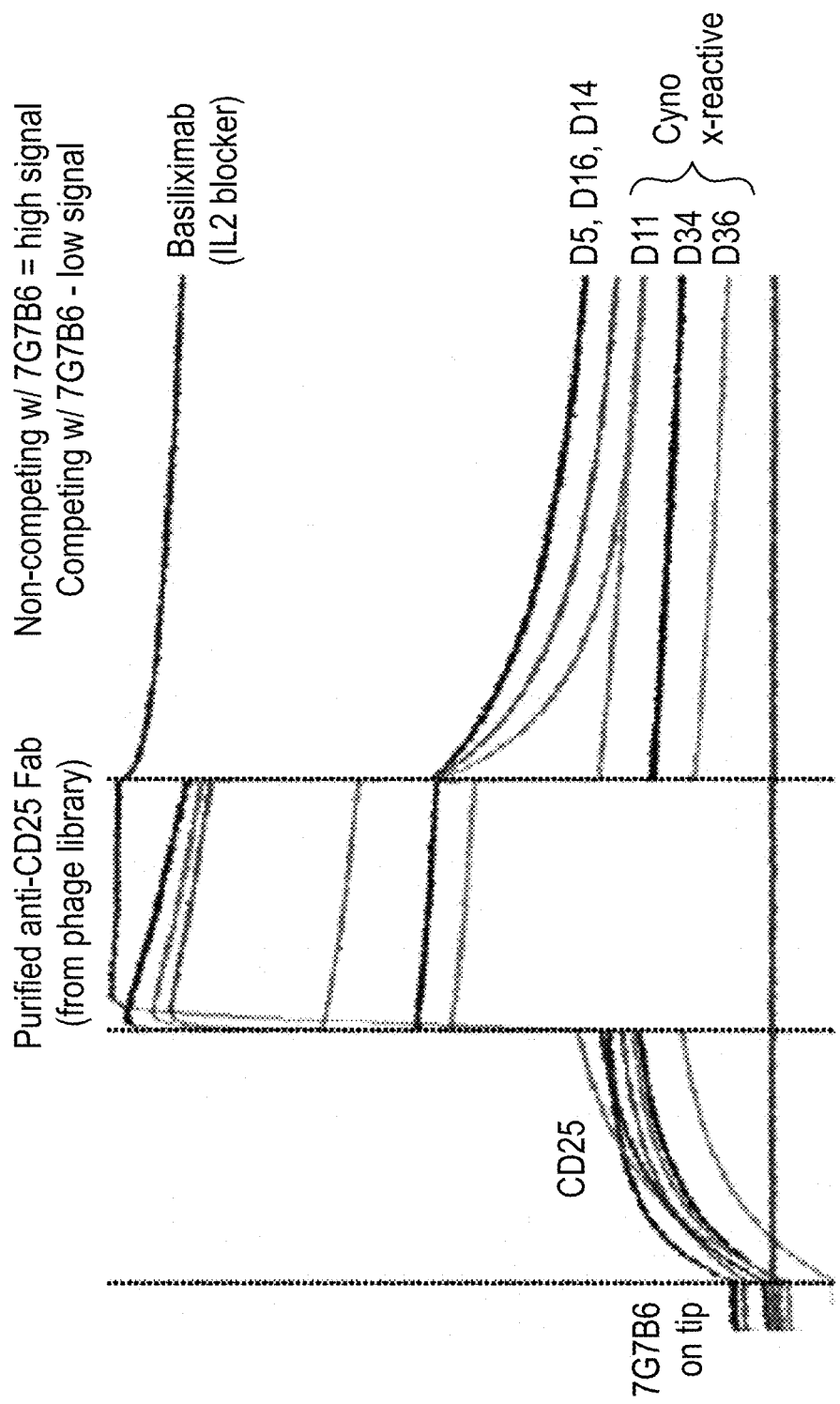
FIG. 8 depicts phage express Fabs of the disclosure that compete with IL-2 non-blocking antibody, 7G7B6, using a biosensor.

FIG. 8 depicts phage express Fabs of the disclosure that compete with IL-2 non-blocking antibody, 7G7B6. The biosensor tip was coated with the antibody 7G7B6, and brought into contact first with CD25, and then with the indicated Fab or Basiliximab, a known IL2 blocking antibody. Clones D11, D34, and D36 do not bind when 7G7B6 is bound to CD25. Clones D5, D16, and D17 bind, but rapidly come off, indicating a possible cross-blocking function.

Figure 13A:
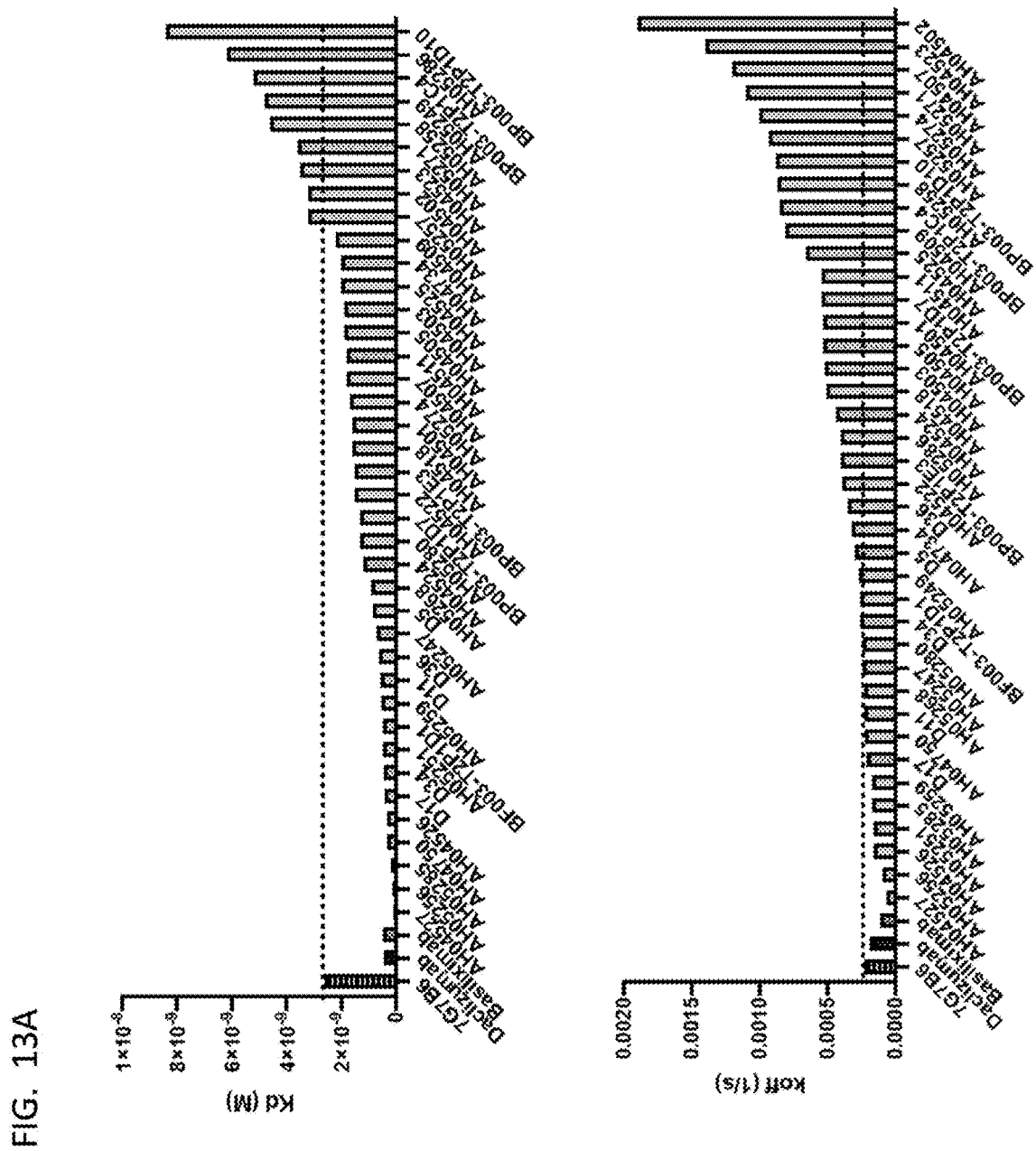
Figure 14C:
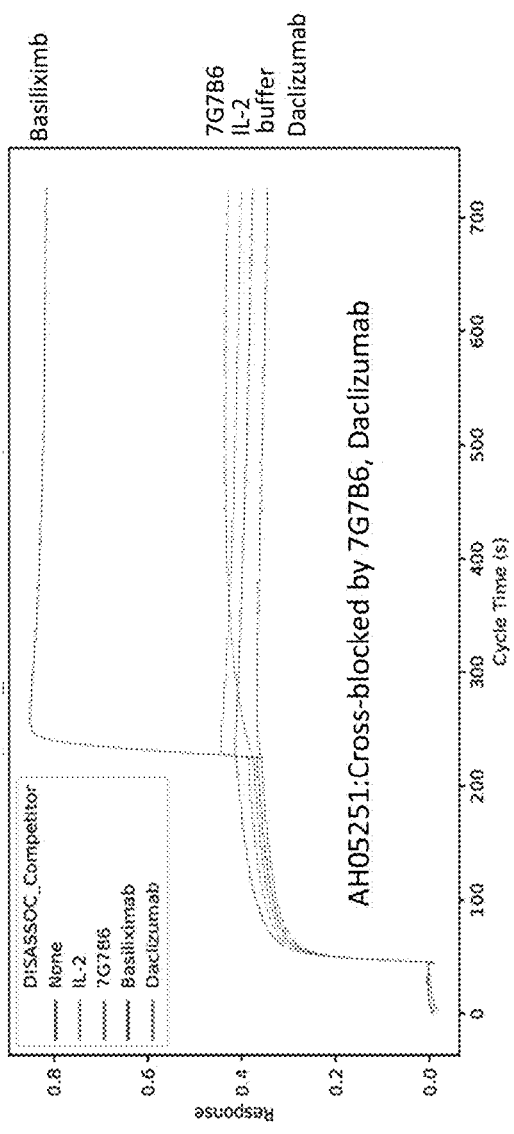
Figure 14D:
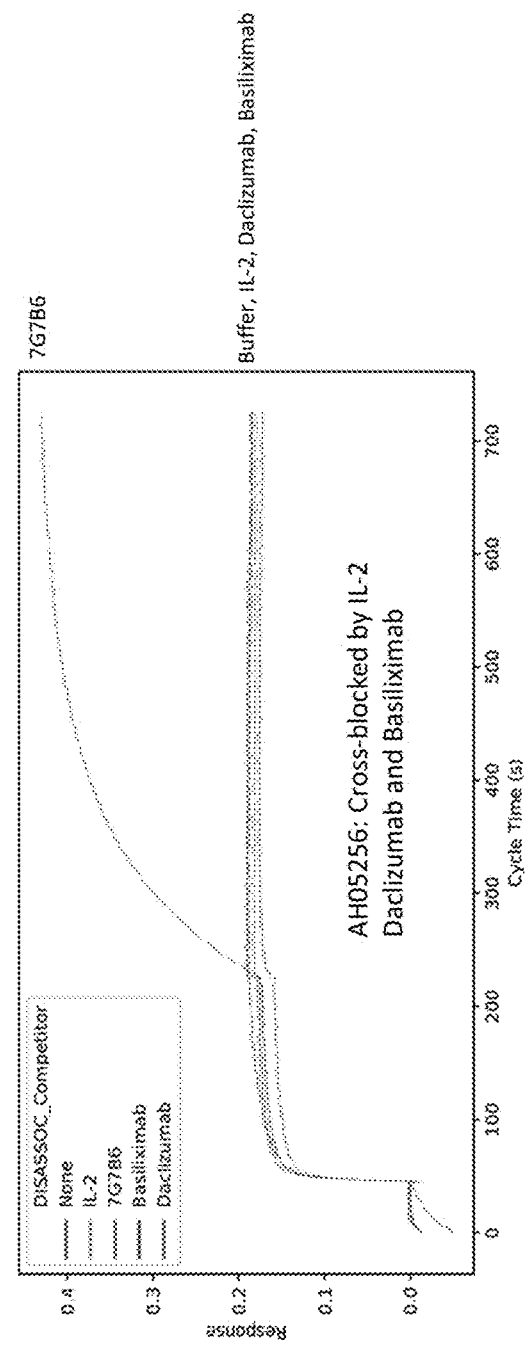

FIGS. 13A-13C shows kinetic analysis for Koff rates and affinity on the reformatted human IgG1 antibody clones (FIG. 13A). KD values of antibodies ranged from 4.4E-10 to 8.4 E-09 with Koff values from 6.4E-05 to 1.9E-03. Several antibodies had higher affinity (FIG. 13B) and Koff values (FIG. 13C) than commercially available antibodies 7G7B6, Daclizumab and Basiluxumab (Kd values 2.6E-09, 4.5E-10, 4.7E-10, respectively and Koff rates of 2.3E-04, 1.1E-04, 1.9E-04, respectively). The clones BP003-T2P1D7. AH0580, AH05268, D36, D11, AH05259, BF003-T2P1D1, and D34 have better Kd values than 7G7B6 in this analysis; the clones D17, AH04526, AH04750, AH05285, AH05256, and AH04527 have better Kd values than Daclizumab and Basiliximab in this analysis (FIG. 13B). The clones AH05256, AH04527, AH04526, AH05251, AH05285, AH05259, D17, AH04750 have better Koff rates than 7G7B6 in this analysis (FIG. 13C).

FIGS. 14A-14D Epitope binning was carried out to evaluate the binding of the reformatted human IgG1 Fabs to epitopes overlapping commercially available anti-human CD25 antibodies 7G7B6, Daclizumab and Basiliximab, as well as with IL-2. The blocking profiles of the clones are: (FIG. 14A) blocked by 7G7B6, but not by IL-2, Daclizumab or Basiliximab; (FIG. 14B) blocked by IL-2, Daclizumab, Basiliximab, but not by 7G7B6; (FIG. 14C) blocked by 7G7B6 and Daclizumab, but not by Basiliximab; (FIG. 14D) blocked by IL-2, Daclizumab and Basiliximab. These blocking profiles indicate binding of the antibodies to different epitopes from different approach angles.

Additional epitope mapping of functional epitopes will be performed by Alanine Mutagensis. This method is used as an orthogonal method for binning antibodies as it operates on the functional epitope, rather than the structural epitope defined by competition assays. Various pairs of surface-accessible residues are selected for mutagenesis. Computational modeling is used to confirm that the alanine mutations selected for use in these assays do not impact global or local stability.

Example 5: Binding Assays

Cell Binding Assays for CD25 Specific Binding of Human IgG Antibodies

To validate antibody binding to CD25 on cells and for specificity, three cell lines SUDHL-1 and SUDHL-2 (human large diffuse histiocytic lymphoma cell lines, ATCC) and HEK IL-2 reporter cells (Invivogen) were used to test for CD25 binding. SUDHL-1 and HEK IL-2 reporter cell lines are CD25+, while SUDHL-2 are CD25− cells. For each cell line, 100,000 cells were plated in a 96 well round bottom plate in cell buffer (PBS+2% HI FBS) and centrifuged. Antibody concentrations from 1-10 ug/mL were used to test the binding of each antibody. Cell were resuspended in 100 uL of antibodies/well and incubated for 20 minutes on ice. After incubation, cells were centrifuged at 300×g for 5 minutes at room temperature, and resuspended and washed with ice cold cell buffer. Cells were then stained with an anti-human Fc secondary antibody conjugated to AF647 (Biolegend) and incubated on ice for 20 min in the dark. Cells were centrifuged, washed and resuspended in cold cell buffer with DAPI and analyzed using flow cytometry (Cytoflex, Becton Dickinson). DAPI+ cell were excluded from analysis. The mean fluorescence intensity was calculated using the median (FlowJo, TreeStar).

Recombinant CD25 Cynomolgus Monkey Binding of Human IgG1 Clones

To test for binding to recombinant cynomolgus monkey (cyno) CD25, microtiter plates were coated with 80 ul of 1 ug/ml Cyno CD25 in 50 mM sodium carbonate pH 9.6) at 4° C. overnight. The next day, remove the protein from the wells and block with 200 ul PBS/0.1% BSA/0.05% tween20. The plate was incubated for 1 hour at room temperature. Human IgG1 reformatted Fab clones (human IgG1 antibodies) starting 25 nM and 3 fold serially were diluted in PBT buffer and added to the plate for incubation at RT for 1 hour. The plate was then washed and then 1:2500 dilution of HRP conjugate anti-Fab antibody was added. The plate was washed 5-10 times with PBS/tween20 to remove non-specific binders. TMB perxidase substrate and peroxidase solution were added and incubated for the time needed to develop with 80 uL of ELISA stop solution added at the end. OD measurements were then taken at 450 nM using a plate reader (SpectraMax iD3 Plate Reader, Molecular Devices).

Figure 15A:
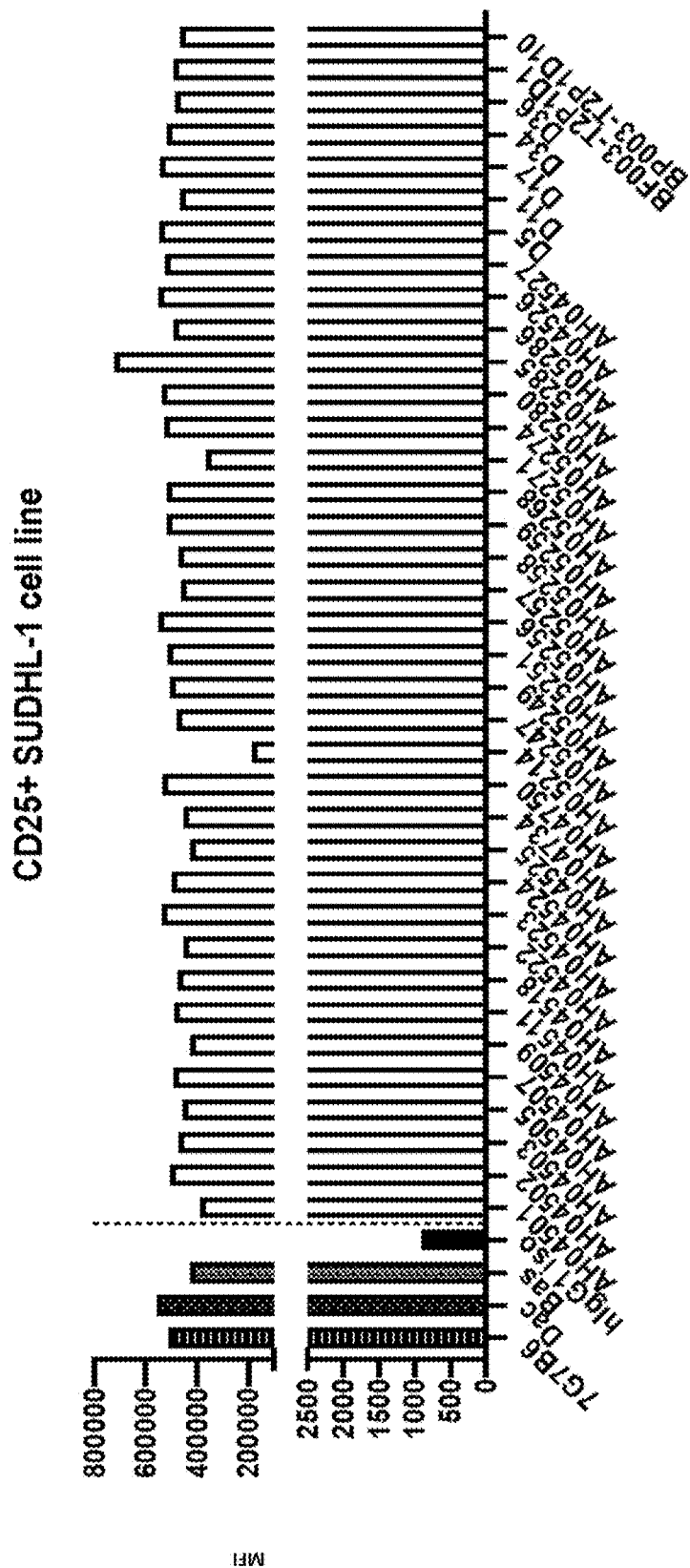
Figure 15A:
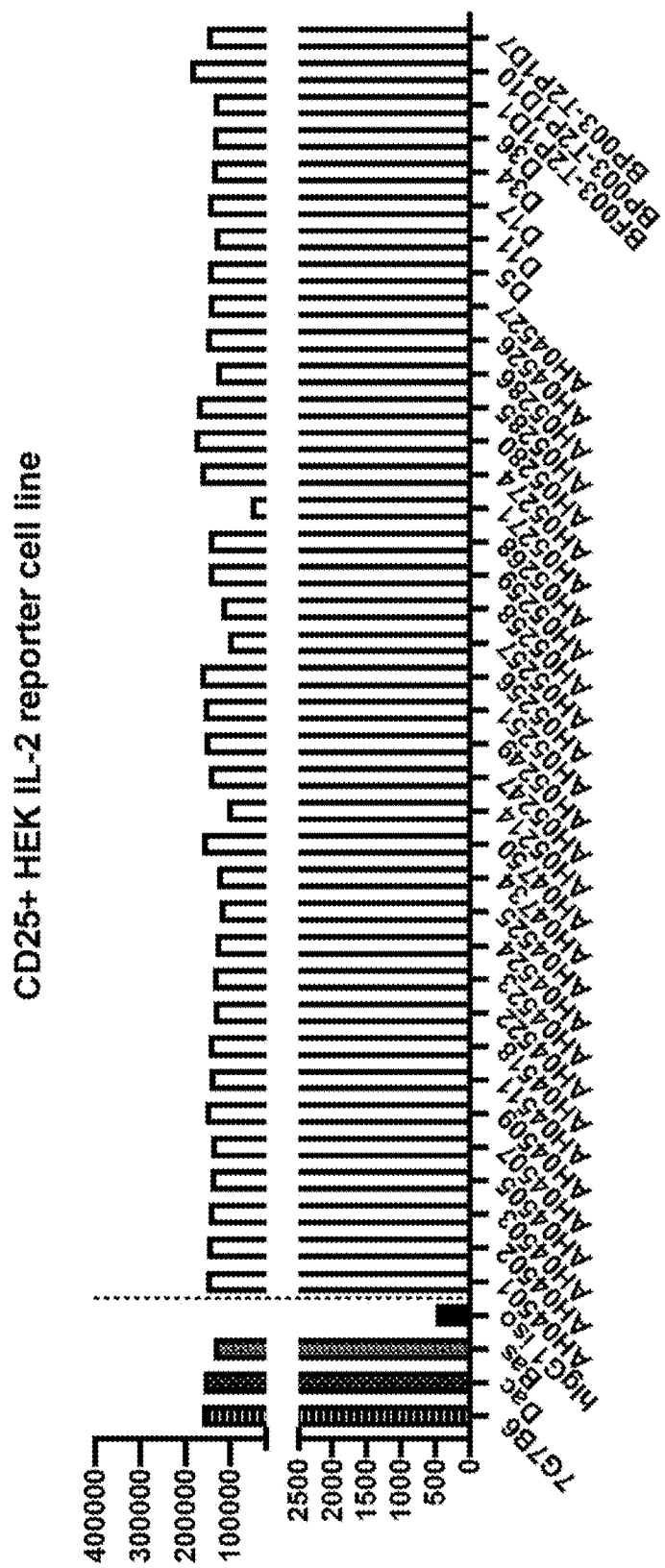

FIGS. 15A-15B shows validation and specific binding of all antibody clones (10 ug/mL) to both CD25+ cells lines, SUDHL-1 and HEK cells, and no binding on CD25−SUDHL-2 cell line. Additionally, the majority of antibodies bound similarly to controls, 7G7B6, Daclizumab, Basiliximab.

Figure 16A:
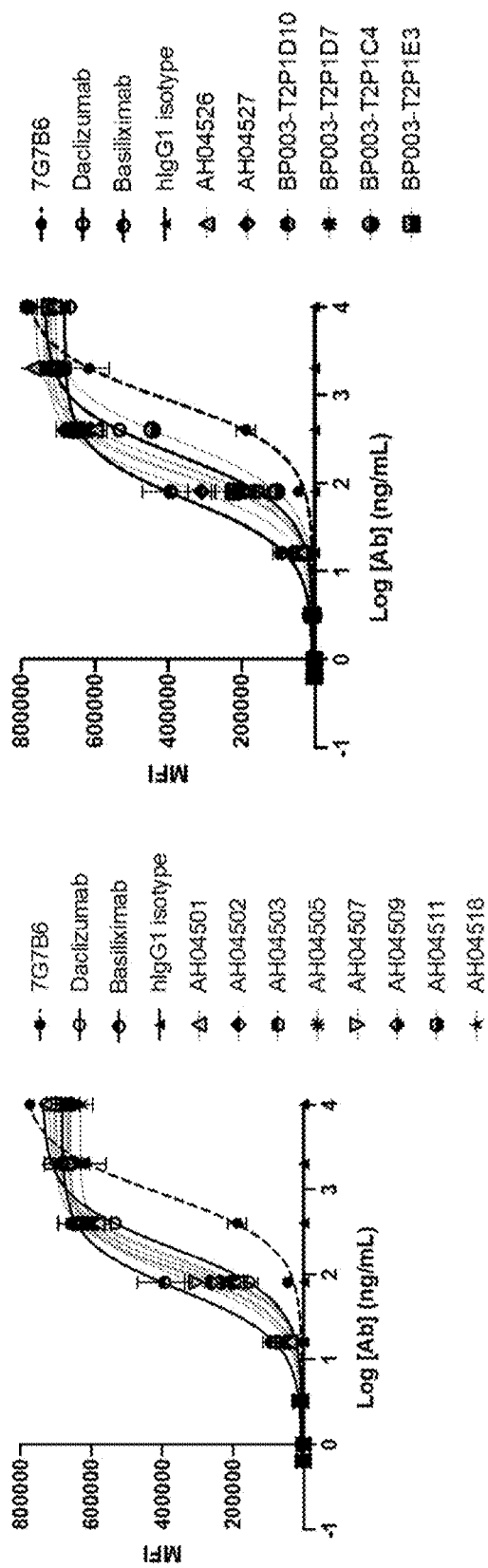
FIGS. 16A-16B show representative dose response curves of human IgG1 reformatted Fab clones on CD25+ cell line SUDHL-1 compared to commercially available antibodies 7G7B6, Daclizumab and Basiliximab (FIG. 16A). Several clones show better EC50 values than IL-2 non-blocker 7G7B6 (FIG. 16B).
Figure 16B:
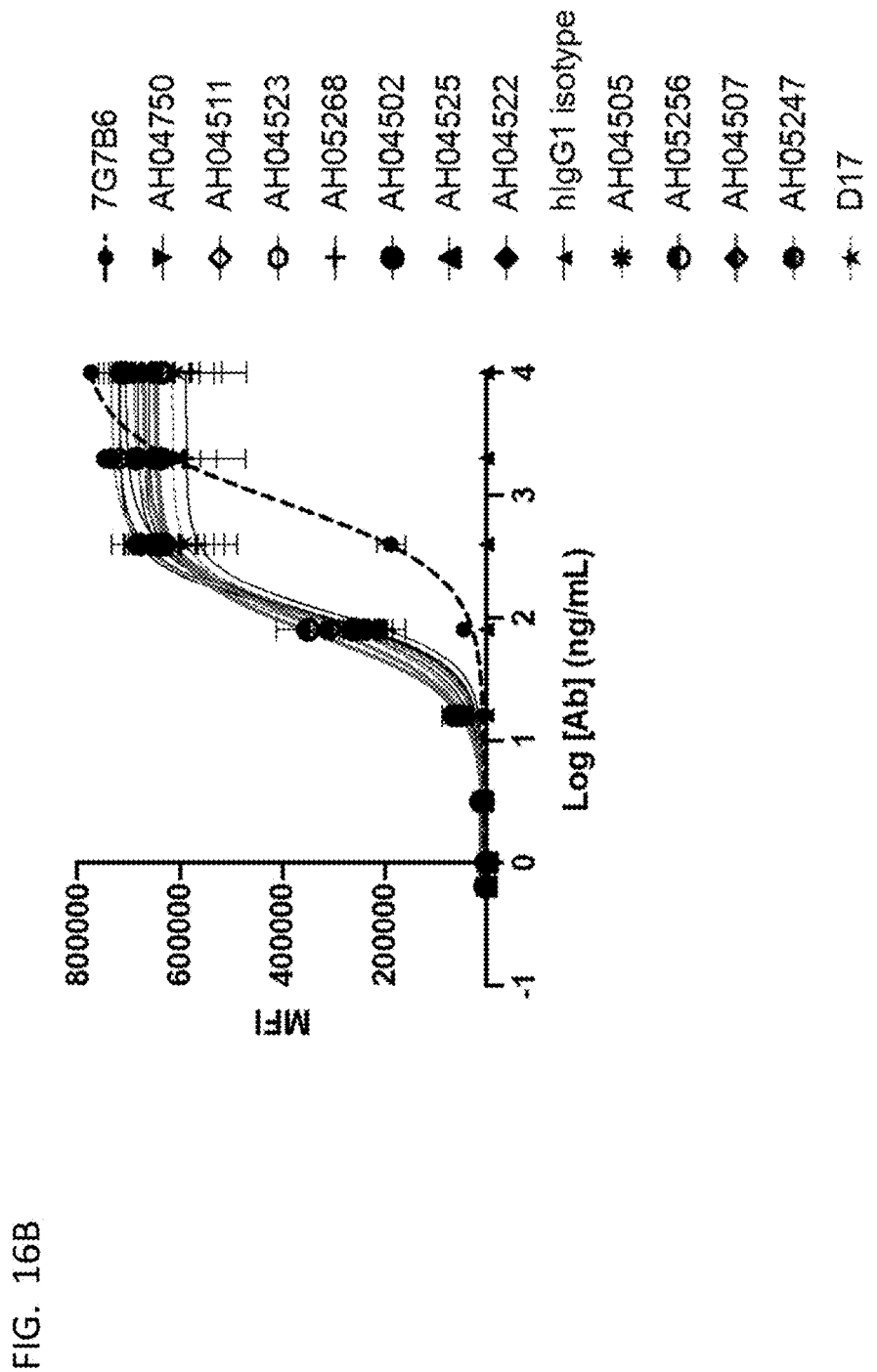

FIGS. 16A-16B show dose response curves of clones starting at 10 ug/mL with 5 fold serial dilutions binding on SUDHL-1 CD25+ cell line (FIG. 16A). A majority of clones bound in a dose dependent manner and had better EC50 values than commercially available 7G7B6 (FIG. 16B, Table 9), clone names referring to those presented in the above tables of the disclosure. Several Clones in Table 9 have better EC50 values than 7G7B6.

TABLE 9

| Clone | EC50 (ng/mL) |
|---|---|
| 7G7B6 | 902.8 |
| Daclizumab | 190.7 |
| Basilixumab | 57.285 |
| AH05256 | 71.48 |
| AH04507 | 88.95 |
| D17 | 95.7 |
| AH04527 | 95.91 |
| AH05247 | 97.73 |
| AH04505 | 105.7 |
| AH04750 | 107.2 |
| AH04511 | 107.6 |
| AH04523 | 108.2 |
| AH05268 | 108.2 |
| AH04502 | 108.9 |
| AH04525 | 109.1 |
| AH04522 | 109.6 |
| AH05257 | 113.3 |
| AH04518 | 114.4 |
| AH04524 | 115.8 |
| AH05259 | 120.7 |
| AH04509 | 121.3 |
| BP003-T2P1D7 | 124.8 |
| BP003-T2P1E3 | 124.9 |
| AH05251 | 132.2 |
| AH04503 | 144.6 |
| AH04501 | 158.9 |
| AH04526 | 164.3 |
| BP003-T2P1D10 | 165.4 |
| AH05258 | 183.9 |
| AH05274 | 227.9 |
| AH05271 | 249.6 |
| BP003-T2P1C4 | 294 |
| AH05280 | 387 |
| D5 | 602.9 |
| AH05286 | 777.5 |
| AH05249 | 896.9 |
| D34 | 1098 |
| D36 | 1491 |
| AH04734 | 1906 |
| D11 | 2120 |
| AH05214 | ~51090 |

Figure 17:
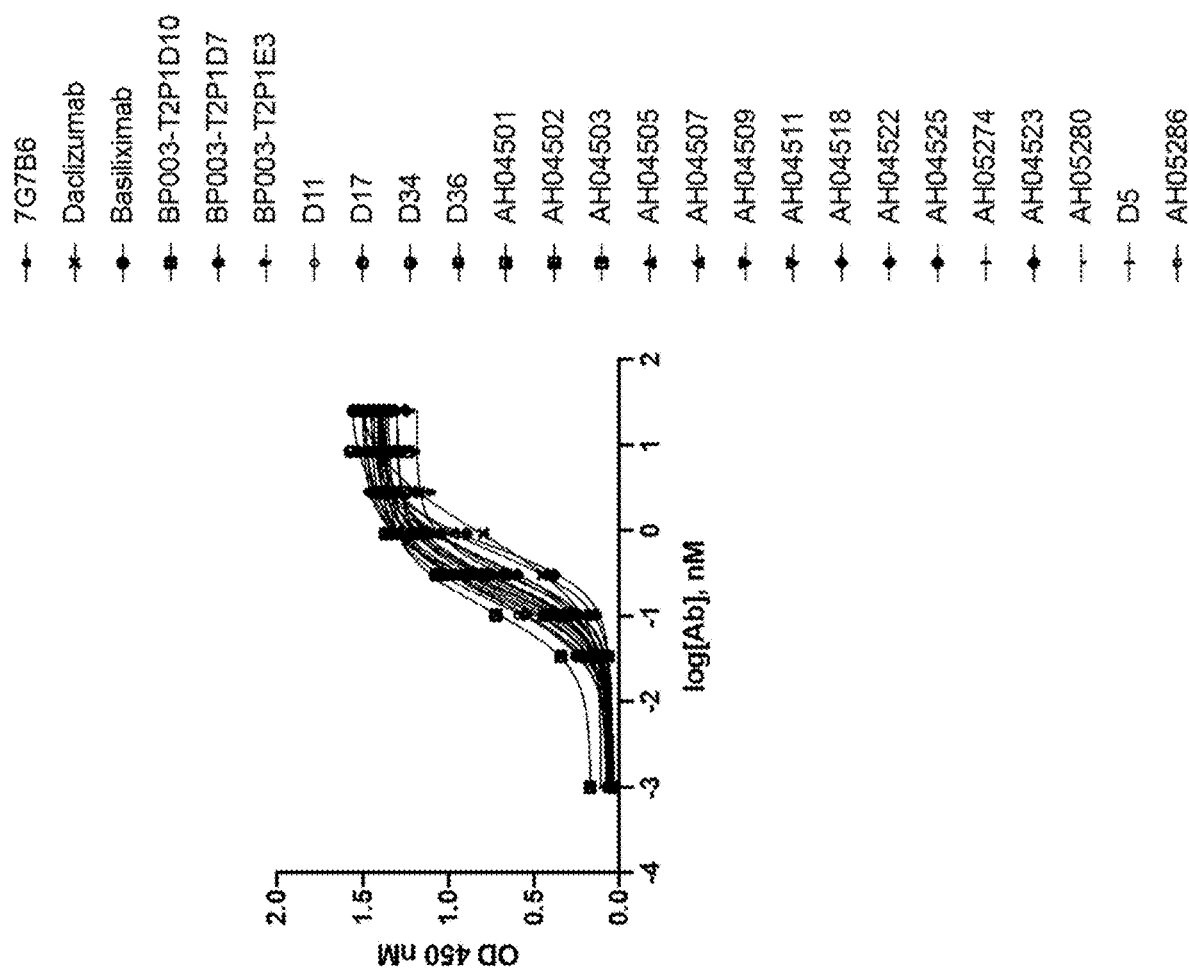
FIG. 17. show representative data of human IgG1 reformatted Fab clones that bind to recombinant cynomolgus monkey CD25 protein (25 nM). Majority of clones bind in a dose dependent manner (starting at 25 nM with 3 fold dilutions).

FIG. 17 show dose response curves of several clones that bound to recombinant cyno CD25. Daclizumab and Basiliximab were used as positive controls.

Example 6: pSTAT5 Assay Using Primary Cells pSTAT5 Assay for Screening Biological Activity of Fab Clones on Highly Purified Human Regulatory T Cells The IL-2/JAK3/STAT-5 signaling pathway is involved in the survival and expansion of Tregs. This pathway initiates and maintains the expression of the transcription factor Foxp3, a factor that is essential for the suppressive activity of Tregs. When IL-2 binds to IL-2R, JAK proteins get activated; they are tyrosine kinases that are bound to the cytoplasmic regions of IL-2 receptors. This initiates trans-phosphorylation on specific tyrosine residues generating docking sites for STAT proteins to be recruited and phosphorylated. Dimerized and phosphorylated STATs are then translocated to the nucleus to bind specific DNA sequences, regulating the transcription of several target genes, such as Foxp3 and CD25 in Tregs.

In this example, the functionality of selected Fabs when bound to CD25 on primary human regulatory T cells was assessed. This assay allowed for determination which are IL-2 blockers, non-blockers and partial blockers, as well as potency, based on pSTAT5 levels. Controls used in the assay include a known IL-2 blocker (Daclizumab) and IL-2 non-blocker (7G7B6). First, fresh PBMC cells were isolated from leukocyte reduction system chambers (Stanford Blood Center). Equal volume of cell buffer (PBS+2% HI FBS) was added to each blood sample and added to a Ficoll Paque filled inside a 50 mL SepMate conical tube (Stem Cell Technologies) and followed standard protocol for PBMC isolation using SepMate tubes. To isolate human T regulatory cells from PBMCs, the EasySep Human CD4+ CD127low CD25+ Regulatory T cell isolation kit (Stem Cell Technologies) and Regulatory Human CD4+CD25+ T cell kit (Dynabeads) were used. Respective isolation kit protocols were used for magnetic based isolation of cells. Treg isolation was confirmed by staining cells with anti-human CD4, CD25, CD127 antibodies and intracellular Foxp3 staining (BD Biosciences). For the pSTAT5 assay, 100,000 Tregs were plated in a 96 well round bottom plate and centrifuged. Antibody concentrations from 1-5 ug/mL were used. Tregs were resuspended in 50 uL of antibodies/well and incubated for 15 minutes in 37° C. incubator. Next, dilutions for IL-2 were prepared starting at 100 ng/mL concentration with 10 fold dilutions in cell media. IL-2 dilutions were added to the wells at 50 uL/well for 10 minutes in 37° C. incubator. After incubation, the plate was centrifuged at 300×g for 5 minutes at room temperature, and resuspended in 100 uL/well of room temperature fixation buffer (BD Biosciences), for 15 min at room temperature. Cells were spun down and resuspended in cold cell buffer (PBS+2% HI FBS). Cells were then resuspended in 100 uL/well of ice cold permeabilization buffer (BD Biosciences) and incubated on ice for 15 minutes. Cells were washed with cell buffer and resuspended in 50 uL of prepared pSTAT5 antibody for analysis using flow cytometry (Cytoflex, Becton Dickinson).

pSTAT5 Assay for Screening Biological Activity of Antibody Clones Using HEK IL-2 Reporter Cells In this example, clones were tested using the HEK IL-2 reporter cell line (Invivogen). This cell line was generated by Invivogen to monitor the activation of the JAK-STAT pathway with the binding of IL-2. To obtain a fully active human IL-2 signaling pathway, the reporter cell line was created by stably transfecting HEK293 cells with human IL-2Rα, IL-2Rβ and IL-2Rγ genes, and JAK3 and STAT5 genes. This assay presents a high throughput method for evaluating IL-2 physiology and characterization of IL-2 blockers, non-blockers, partial blockers, with the addition of antibodies and competitors in the presence of IL-2, based on pSTAT5 levels. Controls used in the assay include a known IL-2 blocker (Daclizumab and Basiliximab) and IL-2 non-blocker (7G7B6). For a pSTAT5 assay, 100,000 cells were plated in a 96 well round bottom plate and centrifuged. Antibody concentrations from 1-5 ug/mL) were used. HEK cells were resuspended in 50 uL of antibodies/well and incubated for 15 minutes in 37° C. incubator. Next, dilutions for IL-2 were prepared starting at 10 ng/mL concentration with 10 fold dilutions in cell media. IL-2 dilutions were added to the wells at 50 uL/well for 10 minutes in 37° C. incubator. After incubation, the plate was centrifuged at 300×g for 5 minutes at room temperature, and resuspended in 100 uL/well of room temperature fixation buffer (BD Biosciences), for 15 min at room temperature. Cells were spun down and resuspended in cold cell buffer (PBS+2% HI FBS). Cells were then resuspended in 100 uL/well of ice cold permeabilization buffer (BD Biosciences) and incubated on ice for 15 minutes. Cells were washed with cell buffer and resuspended in 50 uL of prepared pSTAT5 antibody for analysis using flow cytometry (Cytoflex, Becton Dickinson). Percent pSTAT5+ cells were quantified based on the parental population and values were normalized to IL-2 at 10 ng/mL concentration.

Results

Figure 9:
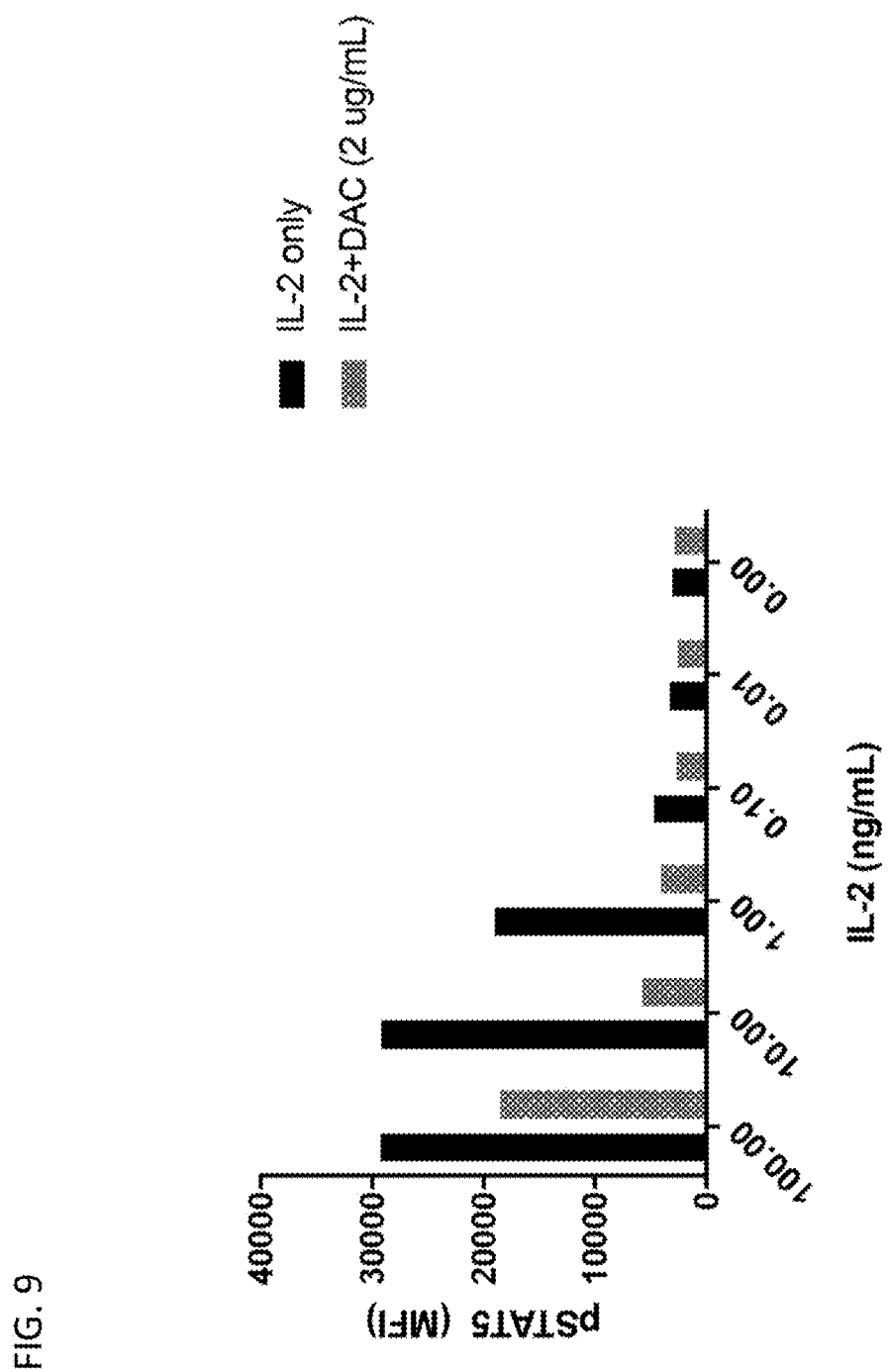
FIG. 9 shows that pSTAT5 levels are IL-2 dose dependent and inhibited with an IL-2 blocking antibody, Daclizumab.

FIG. 9 shows that pSTAT5 signal is IL-2 dose dependent and is inhibited with Daclizumab (IL-2 blocker). pSTAT5 levels were correlated with doses of IL-2, with high IL-2 doses increasing pSTAT5 levels, while lower levels of IL-2 yielded lower levels of pSTAT5. In addition, when Daclizumab, an anti-human IL-2 antibody IL-2 blocker was added at fixed concentration of 2 ug/mL, it inhibited JAK/STAT5 signaling pathway, yielding less pSTAT5 levels.

Figure 10:
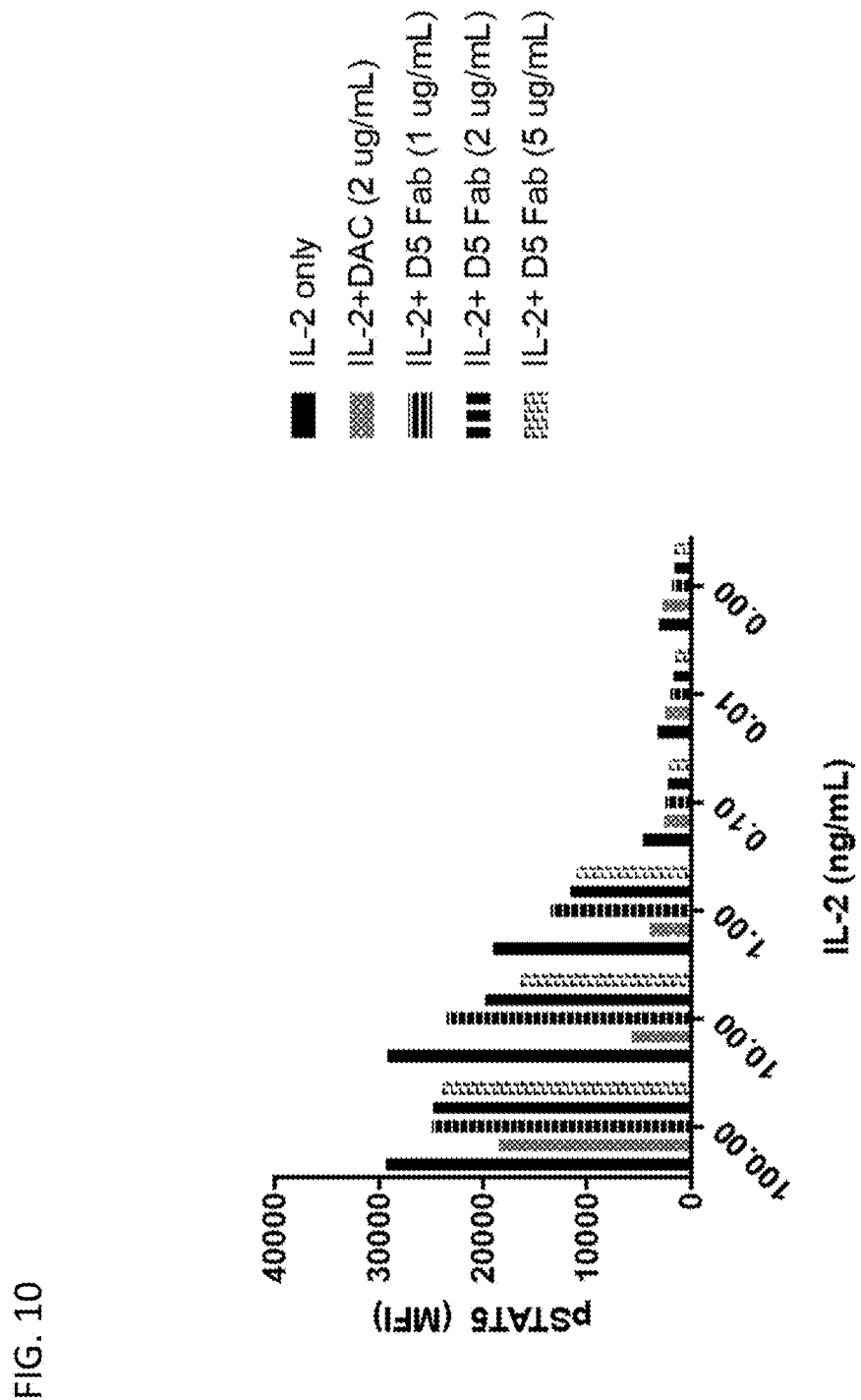
FIG. 10 depicts the effect of the D5 Fab of the disclosure on pSTAT5 levels. The data indicate that the D5 Fab is a partial IL-2 blocker.
Figure 11:
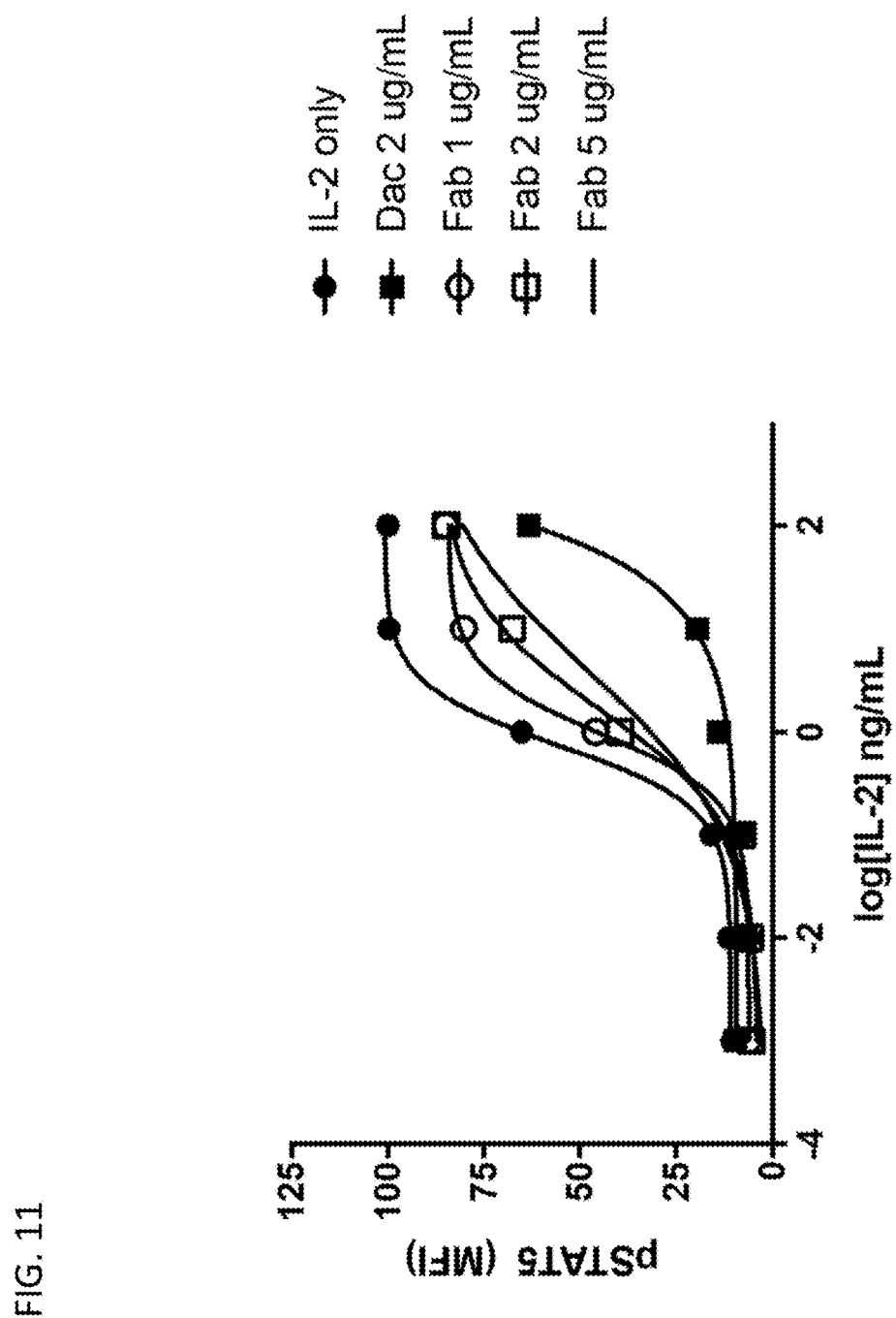
FIG. 11 depicts the effect of the D5 Fab at different concentrations on pSTAT5 levels, relative to maximum IL-2 pSTAT5 levels.

FIG. 10 and FIG. 11 show testing of the D5 Fab in the pSTAT5 assay. The data in FIG. 10 show that the pSTAT5 assay was able to distinguish differences in D5 Fab activity at 1, 2 and 5 ug/mL compared to Daclizumab and IL-2 only. At the different concentrations of D5 there was a dose-dependent decrease in levels of pSTAT5, suggesting that D5 is partially blocking IL-2 binding to IL-2R, even at the lowest concentration of 1 ug/mL. The data is represented by raw MFI levels (mean fluorescence intensity) and by comparing pSTAT5 levels relative to maximum pSTAT5 level generated by the highest dose of IL-2 (100 ng/mL) (FIG. 11).

Figure 12:
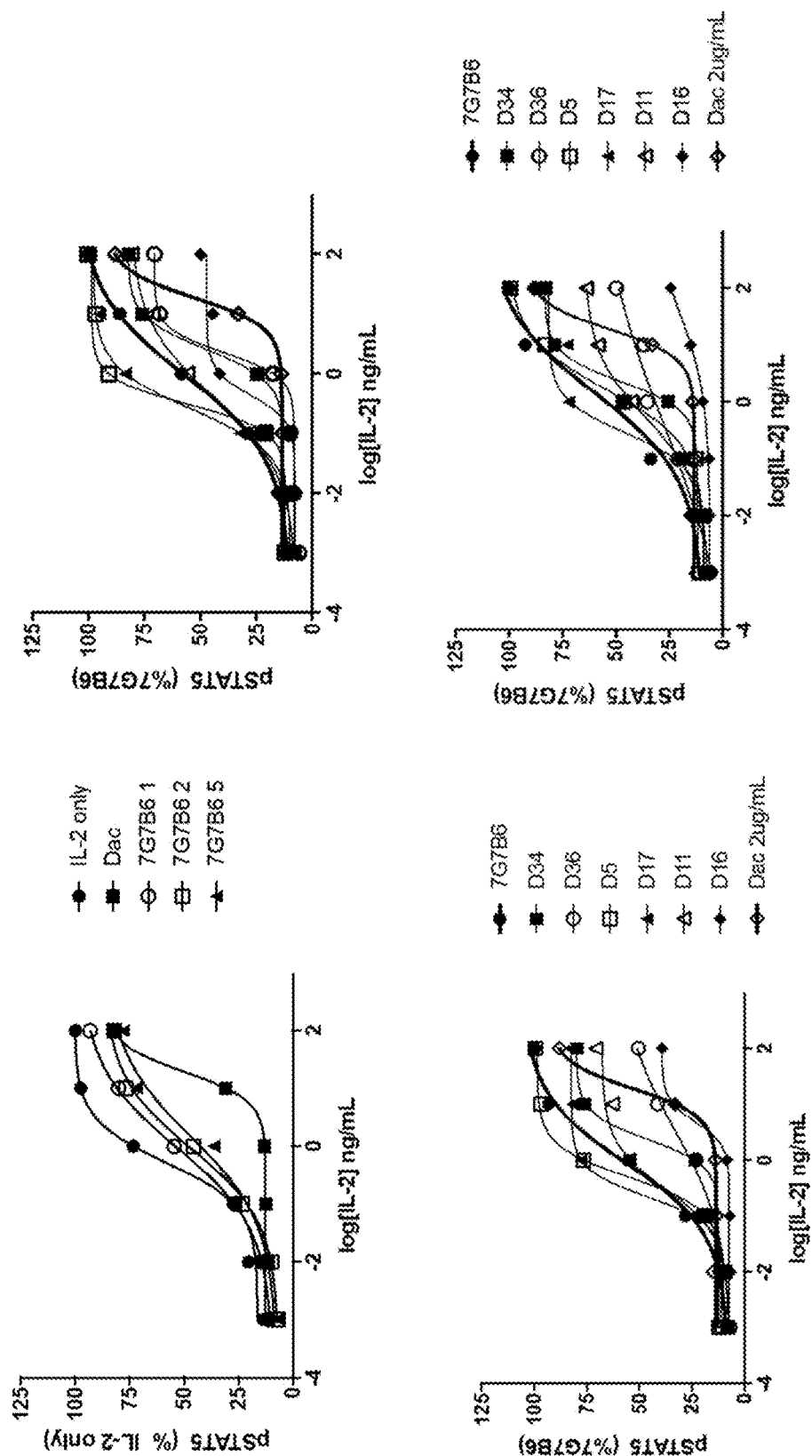
FIG. 12 depicts differences in pSTAT5 levels between several Fab clones at 1, 2 and 5 ug/mL compared to the controls (IL-2 only, Daclizumab (Dac) and 7G7B6.

FIG. 12 shows preliminary Fab screen data from one donor. This assay from one donor shows differences in pSTAT5 levels between several Fab clones at 1, 2 and 5 ug/mL compared to the controls (IL-2 only, Daclizumab (Dac, an IL-2 blocker) and 7G7B6 (non IL-2 blocker). Some clones seem to be better IL-2 non-blockers than 7G7B6 while others are better IL-2 blockers than Daclizumab. Complete IL-2 non-blockers would be expected to have similar pSTAT5 levels as IL-2 and would not be expected to be concentration dependent. The data are represented by raw MFI levels (mean fluorescence intensity) and by comparing pSTAT5 levels relative to maximum pSTAT5 level generated by 7G7B6. In addition, the data can be used to observe differences in IC50 potency values of the Fab clones. (Table 10).

TABLE 10

| Ab | IC50 (1 ug/mL) [ng/ml] | IC50 (2 ug/mL) [ng/ml] | IC50 (5 ug/mL) [ng/ml] |
|---|---|---|---|
| 7G7B6 | 0.9629 | 0.9058 | 1.47 |
| Dac |  | 18.69 |  |
| D34 | 2.558 | 2.355 | 2.275 |
| D36 | 2.233 | 3.446 | 0.3782 |
| D5 | 0.3032 | 0.4881 | 1.653 |
| D17 | 0.2511 | 0.2173 | 0.2826 |

TABLE 10-continued

| Ab | IC50 (1 ug/mL) [ng/ml] | IC50 (2 ug/mL) [ng/ml] | IC50 (5 ug/mL) [ng/ml] |
|---|---|---|---|
| D11 | 0.4137 | 0.3032 | 0.5087 |
| D16 | 0.43 | 4.77 | 40.33 |

Subsequent assays will include the Fab form of Daclizumab and 7G7B6 as well as testing the same Fab clones on multiple donors. In addition, the pSTAT5 assay will be performed at lower pH levels (pH 6.4-6.7) to recapitulate pH of the tumor microenvironment against clone activity at physiological pH.

Figure 18A:
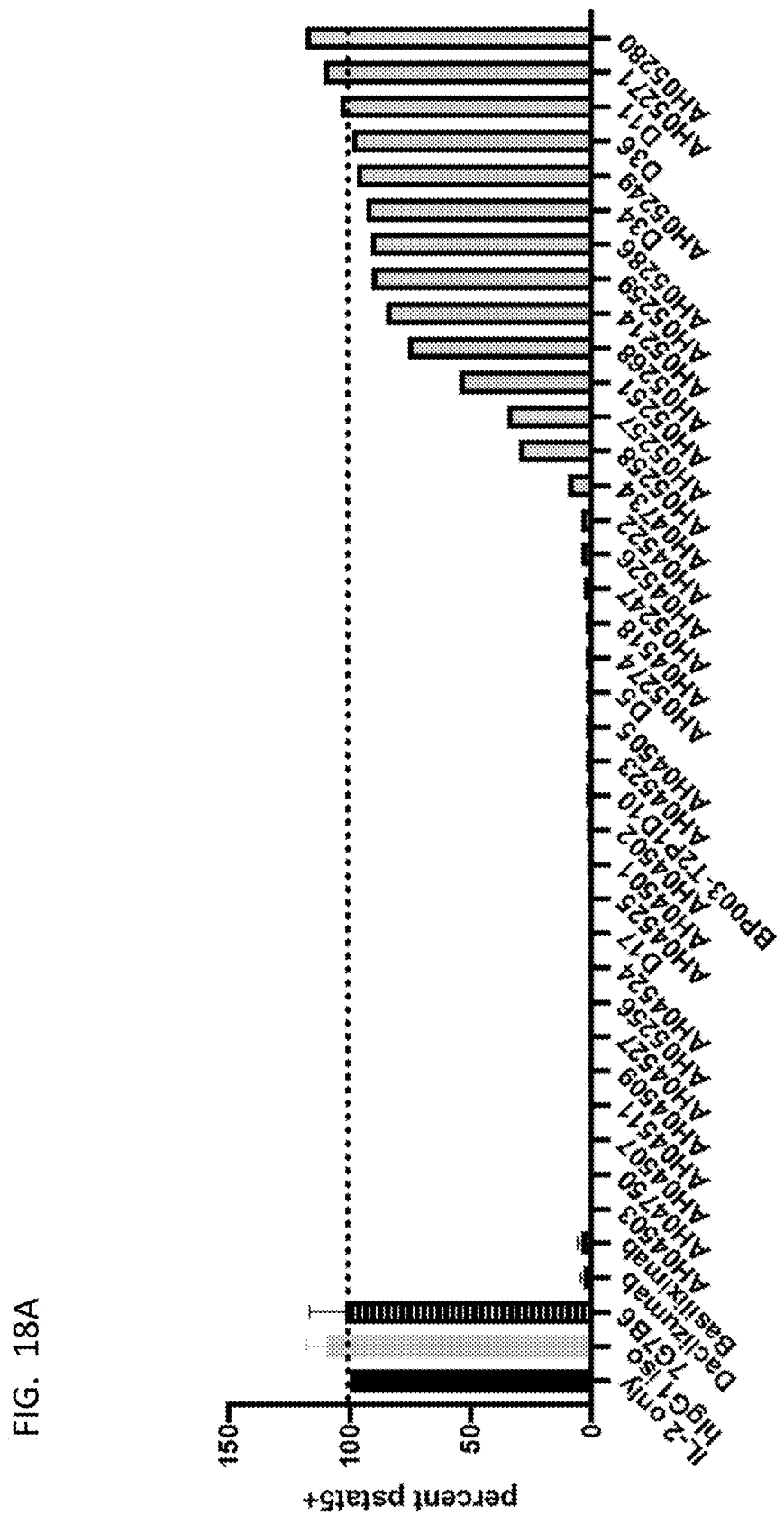

FIGS. 18A-18B show functional characterization of reformatted human IgG1clones (at 5 ug/mL) as IL-2 blockers, non-blockers and partial blockers by measuring pSTAT5 in HEK IL-2 reporter cell lines starting at IL-2 concentration of 10 ng/ml with 10 fold serial dilutions. At IL-2 concentration of 0.1 ng/mL (closer to physiological levels), clones such as AH04503, AH04750 are better IL-2 blockers than either Daclizumab or Basiliximab, while clones AH05280 and AH02571 may be better IL-2 non-blockers than 7G7B6 at 5 ug/mL (A). Clones AH05251, AH05257 are examples of IL-2 partial blockers (FIG. 18A). IL-2 dose response curves clearly depict clones that are IL-2 non-blockers from those that are IL-2 blockers, with curves shifting to the left with 7G7B6 and curves shifting to the right with Daclizumab and Basiliximab, respectively (FIG. 18B).

Continued pSTAT5 studies may be done to test these antibody clones using primary Tregs and multiple donors.

Example 7: Antibody-Dependent Cell Cytotoxicity (ADCC)

Functional Cell Killing Assay ADCC and ADCP

One of the mechanisms for Treg depletion is through antibody-dependent cell cytotoxicity (ADCC). This is a cell-mediated immune defense mechanism that usually causes cell death, triggered by the recognition of immune/effector cells to antibodies bound to a specific antigen on a target cell. To elicit ADCC, antibodies with the human Fc subclass, IgG1, is commonly chosen for its effector functions with the ability to bind to the three Fc receptors: FcγRI (CD64), FCγRII (CD32), and FcγRIIIA (CD16), that are expressed on immune cells such as NK cells, monocytes and granulocytes. NK cells predominantly express FcγRIIIA and considered to be the main effector cell in ADCC In this example, ADCC was quantified using a Lactate dehydrogenase (LDH) Cytotoxicity plate-based colorimetric assay (Thermo Fisher). In this assay, the release of LDH is proportional to the amount of cell killing. Lactate dehydrogenase (LDH) is a cytosolic enzyme, present in all cells, that is released when the plasma membrane is damaged. Extracellular LDH in the media is quantified by a coupled enzymatic reaction in which LDH catalyzes the conversion of lactate to pyruvate via NAD+ reduction to NADH. By addition of diaphorase, NADH is reduced to a tetrazolium salt (INT) to form a formazan product that can be measured at 490 nm. Controls for the assay include the use of Rituximab (anti-CD20 antibody) on human Raji lymphoma cell line and Daclizumab on SUDHL-1 cells (both antibodies are known to induce ADCC). Additional controls include: non-glycosylated human IgG1, as a negative control and non-fucosylated human IgG1, as a positive control. As a first initial screen, reformatted clones were tested in the ADCC assay at one concentration (10 ug/mL) using PBMCs from a single donor. Human PBMCs (ASTARTE Biologics) were thawed the day before and cultured overnight with X-VIVO 15 or 20 media (Lonza) at 37C in 5% CO2 incubator. On the day of experiment, PBMCs and SUDHL-1 target cells were counted and resuspended in X-VIVO 15 (Lonza, phenol red) serum free medium. Antibody dilutions were prepared starting with 10 ug/ml with 5 fold serial dilutions. Target cells were then plated in a 96 well 50 µL/well in a 96-well white flat bottom opaque plate (CORNING Ref #3917) and 10 µL/well antibody dilution was added to the target cells and incubated at 37° C. and 5% CO2 incubator for 30 min. After the incubation, PBMCs were added to the target cells (50 µL/well). For control target cells for spontaneous and max LDH release calculation, 50 µL/well of assay medium (X-VIVO15, phenol red free) was added. The co-incubation (ADCC induction) was done by incubating the plate for 4 h at 37° C. and 5% CO2 incubator 45 min before the co-incubation completed, 10% Triton X100 solution (in PBS) was added to the wells to calculate Max LDH release (10 µL/well, 11× dilution factor). After the incubation, 50 µL/well of the reaction substrate was plated in a 96-well plate (clear flat bottom) and then 50 µL/well of the supernatant of the assay plate was transferred to the reaction substrate. The plate was developed in the dark at RT for 30 min. After the incubation, 50 µL/well of stop solution was added and absorbance 490 nm and 680 nm was measured by using a plate reader (SpectraMax iD3 Plate Reader, Molecular Devices).

Additionally, function antibody-dependent cell phagocytosis (ADCP) assays will also be performed to test activity of macrophages to phagocytose Treg cells upon antibody binding. This may be an additional mechanism of action for Treg depletion. Fc receptor FcγRIIa (CD32b) on macrophages is thought to be the dominant inducer for ADCP. In this assay, primary Tregs will be used as target cells with human monocyte-derived macrophages as effector cells. PBMCs will be isolated from leukocyte reduction system chambers (Stanford Blood Center) for monocyte isolation using CD14 microbeads (Miltenyi Biotec) and for Tregs using Regulatory Human CD4+CD25+ T cell kit (Dynabeads) and Human Treg Cell Differentiation kit (R&D Systems). Monocytes will be cultured for 5-7 days with human serum or M-CSF in media. At days 5-7, macrophages will be cocultured with pre-labeled Tregs (labeled with a fixable viability dye (Invitrogen)) for 2-4 hours at 10 to 1 effector to target ratio with addition of anti-CD25 antibodies and controls, and fixed with fixation buffer (BD Biosciences). Macrophages will be stained with CD14 to identify macrophages from labeled Tregs, and analyzed for the phagocytic population defined as CD14+ and Treg labeled+ population using flow cytometry. Anti-CD25 antibodies are expected to also induce ADCP.

Results

Figure 19A:
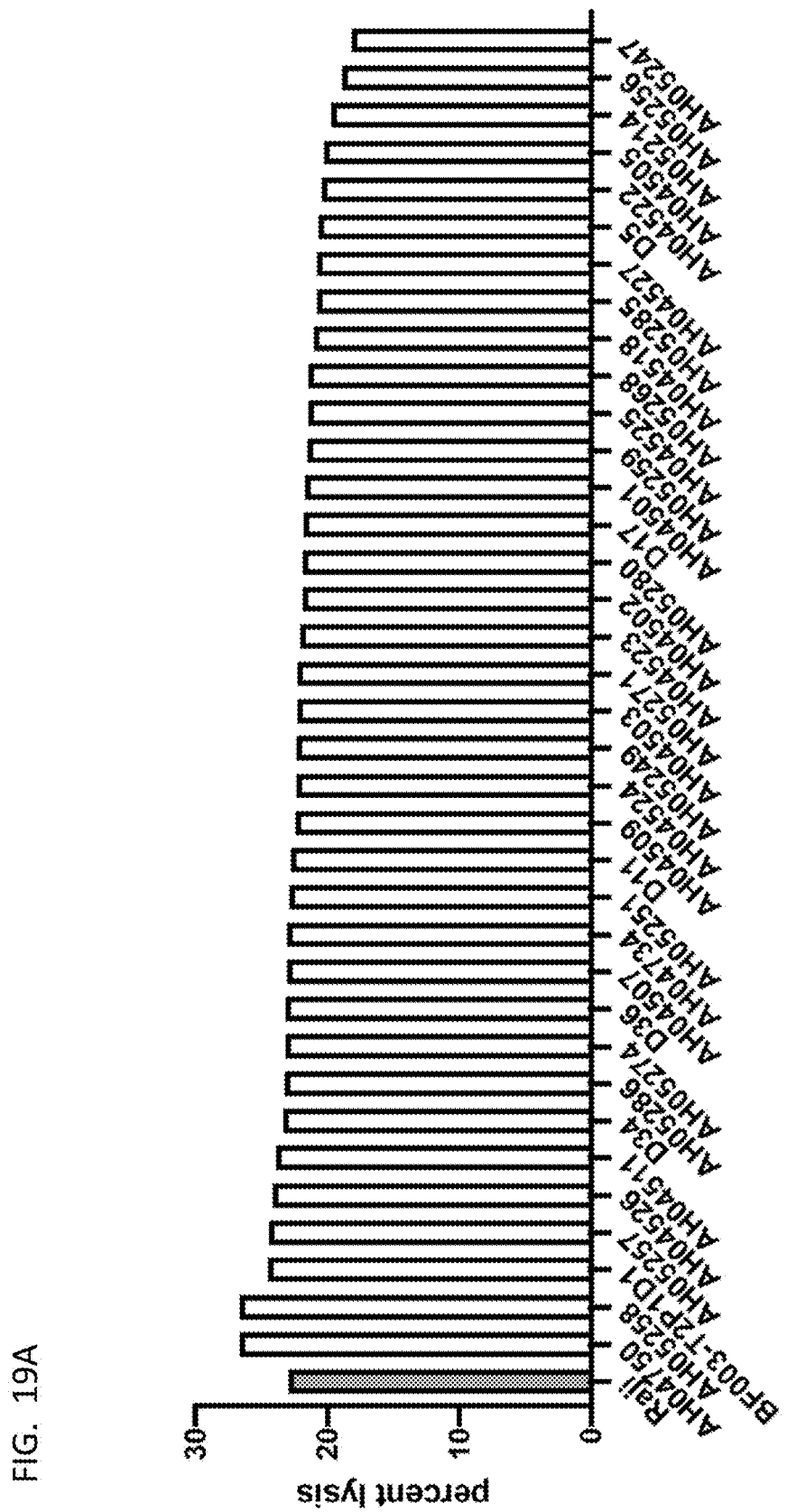
FIGS. 19A-19B. show representative data of human IgG1 reformatted Fab clones at 20 ug/mL, that elicited cell killing in an ADCC assay using PBMCs as effector cells and SUHL-1 cells as targets (FIG. 19A). Several clones showed higher ADCC than 7G7B6 starting at 10 ug/mL with 5 fold dilutions of antibody (FIG. 19B).
Figure 19B:
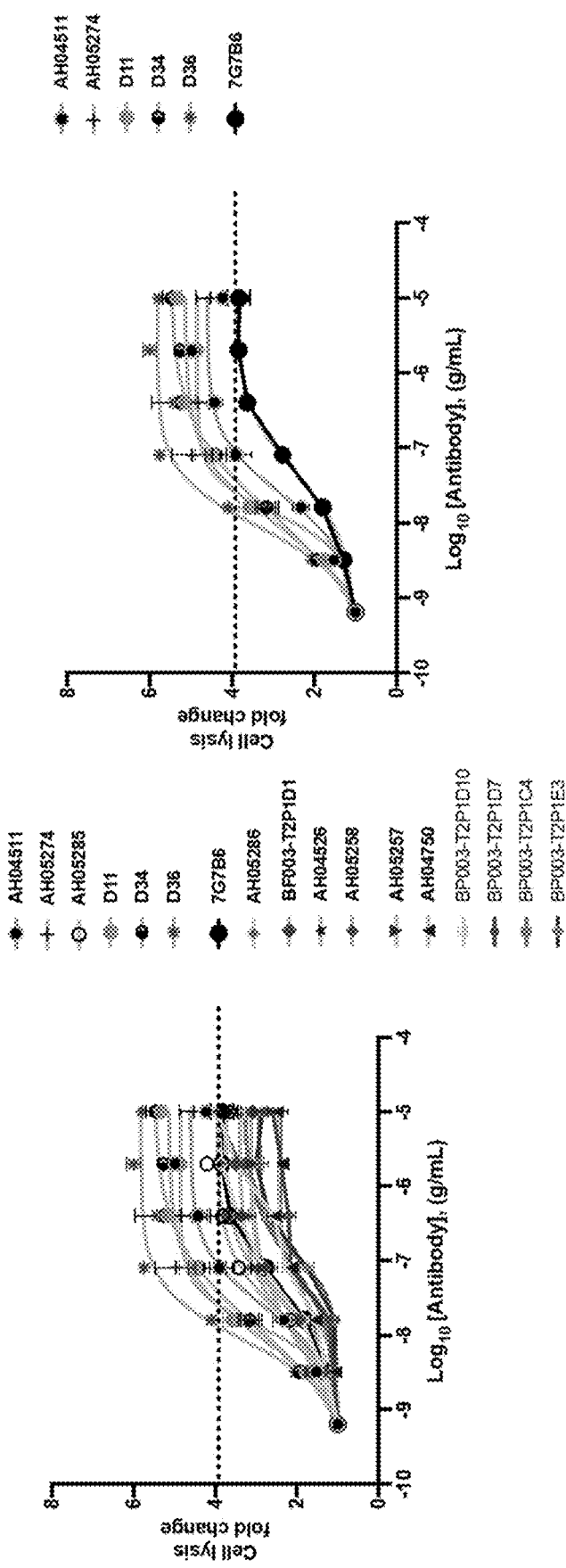

FIGS. 19A-19B show functional ADCC activity of all reformatted clones. In the first screen, clones bound to CD25+ cells, and ADCC was induced with cell killing ranging from 18.2% to 26.7% lysis (Raji cell killing is used as a reference; (FIG. 19A) To verify these findings, the assay was repeated with a dose response curve for select clones. The results show a range of ADCC activity from 2 to 6-fold over baseline lysis, with clones AH04511, AH05274, D11, D34, D36 eliciting the most potent ADCC and with greater potency than the 7G7B6 antibody, as measured by fold change over % background lysis.

Subsequent studies will include additional donors of PBMCs and NK cells as effectors for functional ADCC killing assays.

Example 8: Functional Characterization of CD25 Antibodies

Characterization, In Vitro

Subsequent in vitro characterizations will include T-cell activation and Treg suppression studies to evaluate the impact of CD25 antibodies on T-effector cell responses in the absence and presence of Treg cells. Readouts for activation will include intracellular granzyme B, proliferation and cytokine release (e.g. IL-2, IFNγ, TNF-α). Specifically, human primary conventional T cells (T cony cells) from healthy donors and donors with specific antigen responses (e.g. human cytomegalovirus or influenza flu antigens) will be labeled with a cell proliferation dye (e.g. ThermoFisher) and treated with varying concentrations of CD25 and control antibodies (1-10 ug/mL), followed by activation using CD3/CD28 beads and incubated with and without Tregs for incubation at 37° C., 5% CO2 for 48-72 hours. To evaluate T cell activation, supernatants will be collected for cytokine analysis and cells will be stained with fixable viability dye (e.g. Thermofisher) and with surface anti human T cell markers: CD3, CD4, CD8, CD45RA, CD25, followed by fixation and permeabilization for staining of intracellular Granzyme B and Foxp3. Cells will be analyzed using flow cytometry for Granzyme B positive and proliferating cells.

Characterization, In Vivo

In vivo activity of CD25 antibodies using a mouse xenograft tumor model. These experiments will help to distinguish differences in CD25 antibodies based on CD25+ tumor depletion via ADCC and/or ADCP. Candidate antibodies will be produced as mouse IgG2a isotype antibodies and used in immunodeficient RAG−/− knockout mice (with functional NK and APC cells, but no mature B or T lymphocytes). Animals will be subcutaneously engrafted with CD25+ human cell lines (e.g SUDHL-1, a CD25+ anaplastic large cell lymphoma). Various size tumors (palpable, 100-500 mm3) may be used to discern the differences between antibodies. Animals will be treated with different doses of CD25 antibodies (e.g. 1-10 mg/kg, 3× weekly or once daily) and monitored for changes in body weight and TGI.

Drug Efficacy and MOA Studies in Mouse Xenograft Tumor Models in Humanized Mice.

The more effective antibodies for tumor growth inhibition via Treg depletion and increased intratumoral Teff/Treg ratio with increased T effector cell activity will be tested in various human tumor models (e.g. liver, breast, melanoma, gastric, NSCLC and colon cancer) to establish efficacy and mechanism of action. Some studies may include using the triple negative breast cancer cell line MDA-MB-231, a gastric cell line, melanoma cell line A375 and liver cancer cell line Huh-7 as well as human PDX models that have been well characterized and have either shown correlations between infiltrated Tregs and tumor growth and/or have been treated with PD-1 antibody combinations in humanized mice engrafted with human PBMCs and/or CD34+ cells. In these models, tumors will be subcutaneously engrafted until tumors reach a range of sizes from palpable to 100-500 mm3, and treated with various doses of CD25 antibodies and dosing schedules (e.g. 1-10 mg/kg, 3× weekly or once daily). Animal health scoring, bodyweight, tumor growth as well as immunophenotyping of blood and tumors will be performed to characterize tumor and immune cell composition and tumor infiltrating cells, and cytokine secretion using flow cytometry, Meso Scale Discovery multiplex plates and histology.

Combination studies in mouse xenograft tumor models in humanized mice. Once the lead candidate and indication is established based on efficacy and MOA studies, we will perform combination studies using a wide range of agents to increase immunogenicity and activation of other pathways for immune activation (e.g. chemotherapy, checkpoint inhibitors, TLR agonists, vaccines). Combination experiments will be conducted in similar tumor models used in efficacy and MOA studies.

All patents, patent applications, publications, documents, web links, and articles cited herein are incorporated herein by reference in their entireties.

The invention claimed is:

1. A monoclonal CD25 antibody which binds to human CD25 comprising:
an amino acid sequence of complementarity determining regions of the heavy chain variable regions (CDRH1, CDRH2, and CDRH3) and amino acid sequences of light chain variable regions (CDRL1, CDRL2, and CDRL3) for each antibody as set forth in the table below:

| ID | CDRH1 | CDRH2 | CDRH3 |
|---|---|---|---|
| D11 | GYTFTDYA (SEQ ID NO: 19) | ISTYSGDA (SEQ ID NO: 21) | ARGVTFDY (SEQ ID NO: 23) |
| D17 | GYTFTNYW (SEQ ID NO: 4) | IYPGGGYT (SEQ ID NO: 6) | ARVTPAS (SEQ ID NO: 8) |
| D34 | GYTFTDYA (SEQ ID NO: 19) | ISTYSGDV (SEQ ID NO: 46) | ARGVTFDS (SEQ ID NO: 48) |
| D36 | GYTFTDYA (SEQ ID NO: 19) | ISTYSGDA (SEQ ID NO: 21) | ARGVTFDY (SEQ ID NO: 23) |
| D5 | GYTFTNYW (SEQ ID NO: 4) | IYPGGGYT (SEQ ID NO: 6) | ARVTPAS (SEQ ID NO: 8) |
| AHH03702 | GFTFSSYA (SEQ ID NO: 151) | ISSGGST (SEQ ID NO: 224) | ARGEIWGKAWFAY (SEQ ID NO: 297) |
| AHH03703 | GYTLTDYS (SEQ ID NO: 152) | INTETGEP (SEQ ID NO: 225) | AWGNHY (SEQ ID NO: 298) |
| AHH03704 | GYTFTSYV (SEQ ID NO: 153) | INPYNDGT (SEQ ID NO: 226) | ARDGYYVGPAY (SEQ ID NO: 299) |
| AHH03705 | GFAFSSYD (SEQ ID NO: 154) | ISSGGGST (SEQ ID NO: 227) | ARNYRSWFAY (SEQ ID NO: 300) |
| AHH03706 | GYAFTNYL (SEQ ID NO: 155) | INPGSGGT (SEQ ID NO: 228) | ARKGSLTGVLAY (SEQ ID NO: 301) |
| AHH03707 | GYIFTNYW (SEQ ID NO: 156) | IDPSDSET (SEQ ID NO: 229) | ARRGLRAWFAY (SEQ ID NO: 302) |
| AHH03708 | GYTFTSYW (SEQ ID NO: 157) | INPSTGYT (SEQ ID NO: 230) | ARLDYYGSSRGFAY (SEQ ID NO: 303) |
| AHH03709 | GYTFTSYY (SEQ ID NO: 158) | INPSNGGT (SEQ ID NO: 231) | TNGGGWY (SEQ ID NO: 304) |
| AHH03711 | GYTFTNYG (SEQ ID NO: 159) | INTYTGEP (SEQ ID NO: 232) | ASYYDSTYVGFAY (SEQ ID NO: 305) |
| AHH03712 | GFTFSDYY (SEQ ID NO: 160) | ISNGGGST (SEQ ID NO: 233) | ASPLGYDGFAY (SEQ ID NO: 306) |
| AHH03713 | GFSLTSYG (SEQ ID NO: 161) | IWAGGST (SEQ ID NO: 234) | ARGAYFDY (SEQ ID NO: 307) |
| AHH03714 | GYTFTSYW (SEQ ID NO: 157) | IDPYDSET (SEQ ID NO: 235) | ARSPAYYGNLWFAY (SEQ ID NO: 308) |
| AHH03715 | GYTFTSYT (SEQ ID NO: 162) | INPSSGYT (SEQ ID NO: 236) | ARWDGAY (SEQ ID NO: 309) |
| AHH03716 | GFTFSSYA (SEQ ID NO: 151) | ISSGGSYT (SEQ ID NO: 237) | ARGGMITPFAY (SEQ ID NO: 310) |
| AHH03717 | GFSLSTSGMS (SEQ ID NO: 163) | IWWNDDK (SEQ ID NO: 238) | ARIGGNDGYYWYFDV (SEQ ID NO: 311) |
| AHH03718 | GFTFSDAW (SEQ ID NO: 164) | IRSKANNHAT (SEQ ID NO: 239) | TPQFAY (SEQ ID NO: 312) |
| AHH03719 | GFTFSSYG (SEQ ID NO: 165) | INSNGGST (SEQ ID NO: 240) | ASHYDEGY (SEQ ID NO: 313) |
| AHH03720 | GFTFSNYW (SEQ ID NO: 166) | IRLKSNNYAT (SEQ ID NO: 241) | TGSDY (SEQ ID NO: 314) |
| AHH03721 | GDTFSSYV (SEQ ID NO: 167) | FNPYSDDI (SEQ ID NO: 242) | GSGYDGYYDWFAC (SEQ ID NO: 315) |
| AHH03722 | GYSFTKNG (SEQ ID NO: 168) | INTYTGEP (SEQ ID NO: 232) | AREPKTLDY (SEQ ID NO: 316) |
| AHH03724 | GYTFTSYW (SEQ ID NO: 157) | IDPSDSET (SEQ ID NO: 229) | ANWAWFAY (SEQ ID NO: 317) |
| AHH03726 | GYTFNSHW (SEQ ID NO: 169) | IDPYDSET (SEQ ID NO: 235) | ARPYDGFAY (SEQ ID NO: 318) |
| AHH03727 | GYTFTNHH (SEQ ID NO: 170) | INPYNDYT (SEQ ID NO: 243) | ADGDYYFDY (SEQ ID NO: 319) |
| AHH03728 | GLTFSSYG (SEQ ID NO: 171) | ISSGGSYI (SEQ ID NO: 244) | ARQDDGYYRIFDY (SEQ ID NO: 320) |
| AHH03729 | GFTFNDAW (SEQ ID NO: 172) | IRSKANNHAT (SEQ ID NO: 239) | TNYGSNPLDY (SEQ ID NO: 321) |

| | | | |
|---|---|---|---|
| AHH03730 | GFSLTSYG (SEQ ID NO: 161) | IWAGGST (SEQ ID NO: 234) | AREGTGPWF AY (SEQ ID NO: 322) |
| AHH03731 | GYSITSGYS (SEQ ID NO: 173) | IHYSGST (SEQ ID NO: 245) | ARDPPFAY (SEQ ID NO: 323) |
| AHH03733 | GYTFTSYW (SEQ ID NO: 157) | IDPSDSYT (SEQ ID NO: 246) | AREEITAWF AY (SEQ ID NO: 324) |
| AHH03734 | GYTFTDYE (SEQ ID NO: 174) | IHPGSGGT (SEQ ID NO: 247) | TRNGNGNW YFDV (SEQ ID NO: 325) |
| AHH03737 | GYAFSSYW (SEQ ID NO: 175) | IYPGDGDT (SEQ ID NO: 248) | ARSGYRYDA VFAY (SEQ ID NO: 326) |
| AHH03738 | GFTFSSYG (SEQ ID NO: 165) | INSNGGST (SEQ ID NO: 240) | ARGGNPY (SEQ ID NO: 327) |
| AHH03739 | GFTFSGFW (SEQ ID NO: 176) | INSDGSAI (SEQ ID NO: 249) | MRYGSSYW YFD (SEQ ID NO: 328) |
| AHH03740 | GFTFSSYW (SEQ ID NO: 177) | IRLKSDNYA T (SEQ ID NO: 250) | TRYYYGES (SEQ ID NO: 329) |
| AHH03742 | GFTFSSYG (SEQ ID NO: 165) | ISSGGSYT (SEQ ID NO: 237) | ARHYYDYD YWFDV (SEQ ID NO: 330) |
| AHH03743 | GYTFTSYW (SEQ ID NO: 157) | IYPGSGST (SEQ ID NO: 251) | TRSGVEGLL HWYFDV (SEQ ID NO: 331) |
| AHH03746 | GFTFSSYW (SEQ ID NO: 177) | IRLKSDNYA T (SEQ ID NO: 250) | TCDYDGGA WFAY (SEQ ID NO: 332) |
| AHH03748 | GYTFTSYW (SEQ ID NO: 157) | IDPSNSET (SEQ ID NO: 252) | ARCDGYYD GLDY (SEQ ID NO: 333) |
| AHH03749 | GYTFTSYT (SEQ ID NO: 162) | INPSSGYT (SEQ ID NO: 236) | AREGKNWY FDV (SEQ ID NO: 334) |
| AHH03750 | GYTFTSYW (SEQ ID NO: 157) | INPSNGGT (SEQ ID NO: 231) | ARRIYRTLD Y (SEQ ID NO: 335) |
| AHH03751 | GYTFTSYN (SEQ ID NO: 178) | IYPGNGDT (SEQ ID NO: 253) | TRSGGNLWF AY (SEQ ID NO: 336) |
| AHH03752 | GYTFSSYW (SEQ ID NO: 179) | ILPGSGST (SEQ ID NO: 254) | ARRTYYGN AWFAY (SEQ ID NO: 337) |
| AHH03753 | GFTFTDYY (SEQ ID NO: 180) | IRNKANGY TT (SEQ ID NO: 255) | ARDKRITTV EAWFAY (SEQ ID NO: 338) |
| AHH03754 | GFTFSSYA (SEQ ID NO: 151) | ISSGGST (SEQ ID NO: 224) | ARGYGSSFA Y (SEQ ID NO: 339) |
| AHH03755 | GYTFTSYY (SEQ ID NO: 158) | INPSNSGT (SEQ ID NO: 256) | TRGGDYDAS WFAY (SEQ ID NO: 340) |
| AHH03756 | GYTLTDYV (SEQ ID NO: 181) | IYPGSGST (SEQ ID NO: 251) | ARRTARAFD Y (SEQ ID NO: 341) |
| AHH03757 | GFTFSSYA (SEQ ID NO: 151) | ISSGGSYT (SEQ ID NO: 237) | ARRIGYDGG GSWFAY (SEQ ID NO: 342) |
| H03758 | ITYA (SEQ ID NO: 182) | NNYVT (SEQ ID NO: 257) | RRCV (SEQ ID NO: 343) |
| H03759 | SNYR (SEQ ID NO: 183) | DNYGA (SEQ ID NO: 258) | FAY (SEQ ID NO: 344) |
| AHH03760 | GYTFTDYE (SEQ ID NO: 174) | IHPGSGGT (SEQ ID NO: 247) | TRSDYGSSY EFAY (SEQ ID NO: 531) |
| AHH03765 | GYSITSDYA (SEQ ID NO: 482) | ISYSGST (SEQ ID NO: 506) | ARSRGNYFD Y (SEQ ID NO: 532) |
| AHH03767 | GYTFTSYT (SEQ ID NO: 162) | INPSSGYT (SEQ ID NO: 236) | ARSGLRQA WFAY (SEQ ID NO: 533) |
| AHH03768 | GFTFSNYR (SEQ ID NO: 183) | ITVKSDNY GA (SEQ ID NO: 258) | SRLFAY (SEQ ID NO: 534) |
| AHH03770 | GYTFTSYW (SEQ ID NO: 157) | INPSNGGT (SEQ ID NO: 231) | TITGFDV (SEQ ID NO: 535) |
| AHH03771 | GYTFTTYW (SEQ ID NO: 483) | IFPGTGTT (SEQ ID NO: 507) | ARGGYYNSS PFAY (SEQ ID NO: 536) |
| AHH03772 | GFTFTDYY (SEQ ID NO: 180) | IRNKANGY TT (SEQ ID NO: 255) | ARDGEVRRA LAY (SEQ ID NO: 537) |
| AHH03773 | GYTFTSST (SEQ ID NO: 484) | INPSSGYT (SEQ ID NO: 236) | VRHYYFDY (SEQ ID NO: 538) |
| AHH03774 | GFTFSSYT (SEQ ID NO: 485) | ISSGGGYT (SEQ ID NO: 508) | TRVSAKYFD V (SEQ ID NO: 539) |
| AHH03776 | GYTFTNFY (SEQ ID NO: 486) | INPSNGGT (SEQ ID NO: 231) | TRSYYDYD WYFDV (SEQ ID NO: 540) |
| AHH03777 | GYTFTSYW (SEQ ID NO: 157) | IYPSDSYT (SEQ ID NO: 509) | TRQNYYGSS HWYFDV (SEQ ID NO: 541) |
| AHH03778 | GYTFTSYW (SEQ ID NO: 157) | IDPSDSET (SEQ ID NO: 229) | ANWAWFAY (SEQ ID NO: 317) |
| AHH03779 | GYTFTDYS (SEQ ID NO: 487) | INTETGEP (SEQ ID NO: 225) | ASFYYGNFA YYFDY (SEQ ID NO: 542) |
| AHH03780 | GFTFSNYW (SEQ ID NO: 166) | IRLKSNNYA T (SEQ ID NO: 241) | TRIYDSGSSY TWYFDV (SEQ ID NO: 543) |
| AHH03782 | GFSLSTSGM S (SEQ ID NO: 163) | IWWNDDK (SEQ ID NO: 238) | ARIGGNDGY YWYFDV (SEQ ID NO: 311) |

| | | | |
|---|---|---|---|
| AHH03783 | GYTFTSYW (SEQ ID NO: 157) | INPSNGRT (SEQ ID NO: 510) | ARDSSGYGAY (SEQ ID NO: 544) |
| AHH03784 | GYTFTSYW (SEQ ID NO: 157) | INPSTGYT (SEQ ID NO: 230) | ARYDGYYYFDY (SEQ ID NO: 545) |
| AHH03785 | GYTFTSYW (SEQ ID NO: 157) | IYPSDSYT (SEQ ID NO: 509) | TSHYYGRAWFAY (SEQ ID NO: 546) |
| AHH03786 | GYTFTRYY (SEQ ID NO: 488) | INPSNGGT (SEQ ID NO: 231) | TKGGFYDFFAY (SEQ ID NO: 547) |
| AHH03787 | GFTFSSYG (SEQ ID NO: 165) | INSNGGST (SEQ ID NO: 240) | ASLAY (SEQ ID NO: 548) |
| AHH03788 | GYTFTDYY (SEQ ID NO: 489) | IYPGSGNT (SEQ ID NO: 511) | ARVYSGFDV (SEQ ID NO: 549) |
| AHH03790 | GYTFTSYY (SEQ ID NO: 158) | IYPGDGST (SEQ ID NO: 512) | ARGDGYFAWFAY (SEQ ID NO: 550) |
| AHH03791 | GYTFSSYW (SEQ ID NO: 179) | ILPGSGST (SEQ ID NO: 254) | ARSAHRYDAWFAY (SEQ ID NO: 551) |
| AHH03792 | GYTFTNYY (SEQ ID NO: 490) | INPTNGGT (SEQ ID NO: 513) | TRGMAYRYDGAGWFAY (SEQ ID NO: 552) |
| AHH03793 | GYTFTSYW (SEQ ID NO: 157) | IDPYDSET (SEQ ID NO: 235) | ARGGRGTWFAY (SEQ ID NO: 553) |
| AHH03794 | GFTFTDYY (SEQ ID NO: 180) | IRNKANGYTT (SEQ ID NO: 255) | ARGWGNWFAY (SEQ ID NO: 554) |
| AHH03795 | GFTFSSFG (SEQ ID NO: 491) | ISGGGGTI (SEQ ID NO: 514) | ARWRGGYFDY (SEQ ID NO: 555) |
| AHH03797 | GYTFTSYW (SEQ ID NO: 157) | IYPSDSYT (SEQ ID NO: 509) | TRTGGSTMTPWFAY (SEQ ID NO: 556) |
| AHH03799 | GFSLSTSGMG (SEQ ID NO: 492) | IYWDDDK (SEQ ID NO: 515) | ARRAGDYGNPPPY (SEQ ID NO: 557) |
| >AH04501-VH | GYTFTNY (SEQ ID NO: 990) | DIHPGGDYSNYNEKFKG (SEQ ID NO: 692) | SRNFAY (SEQ ID NO: 1379) |
| >AH04515-VH | GYTFTNY (SEQ ID NO: 990) | DIHPGGDYSNYNEKFKG (SEQ ID NO: 692) | SRNFAY (SEQ ID NO: 1379) |
| >AH04502-VH | GYTFTNY (SEQ ID NO: 990) | DIHPGGGYTNYNEKFKG (SEQ ID NO: 696) | SRNFAY (SEQ ID NO: 1379) |
| >AH04512-VH | GYTFTNY (SEQ ID NO: 990) | DIHPGGGYTNYNEKFKG (SEQ ID NO: 696) | SRNFAY (SEQ ID NO: 1379) |
| >AH04522-VH | GYTFTNY (SEQ ID NO: 990) | DIHPGGGYTNYNEKFKG (SEQ ID NO: 696) | SRNFAY (SEQ ID NO: 1379) |
| >AH04513-VH | GYTFTNY (SEQ ID NO: 990) | DIHPGGGYTNYNEKFKG (SEQ ID NO: 696) | SRNFAY (SEQ ID NO: 1379) |
| >AH04523-VH | GYTFTNY (SEQ ID NO: 990) | DIHPGGSYTNYNENFKG (SEQ ID NO: 697) | SRNFAK (SEQ ID NO: 1377) |
| >AH04503-VH | GYTFSNY (SEQ ID NO: 985) | DIHPGGGYINYNEKFTG (SEQ ID NO: 695) | SRNFAN (SEQ ID NO: 1378) |
| >AH04529-VH | GYTFSNY (SEQ ID NO: 985) | DIHPGGGYINYNEKFTG (SEQ ID NO: 695) | SRNFAN (SEQ ID NO: 1378) |
| >AH04510-VH | GYTFSNY (SEQ ID NO: 985) | DIHPGGGYINYNEKFTG (SEQ ID NO: 695) | SRNFAN (SEQ ID NO: 1378) |
| >AH04528-VH | GYTFSNY (SEQ ID NO: 985) | DIHPGGGYINYNEKFTG (SEQ ID NO: 695) | SRNFAN (SEQ ID NO: 1378) |
| >AH04511-VH | GYTFSNY (SEQ ID NO: 985) | DIHPGGGYINYNEKFTG (SEQ ID NO: 695) | SRNFAN (SEQ ID NO: 1378) |
| >AH04504-VH | GYTFTKY (SEQ ID NO: 989) | DIHPGGGYINYNEKFTG (SEQ ID NO: 695) | SRNFAN (SEQ ID NO: 1378) |
| >AH04520-VH | GYTFTKY (SEQ ID NO: 989) | DIHPGGGYINYNEKFTG (SEQ ID NO: 695) | SRNFAN (SEQ ID NO: 1378) |
| >AH04507-VH | GYTFTNY (SEQ ID NO: 990) | DIHPGGGYIDYNEKFTG (SEQ ID NO: 694) | SRNFAK (SEQ ID NO: 1377) |
| >AH04527-VH | GYTFTNY (SEQ ID NO: 990) | DIHPGGGYIDYNEKFTG (SEQ ID NO: 694) | SRNFAK (SEQ ID NO: 1377) |
| >AH04505-VH | GYTFTNY (SEQ ID NO: 990) | DIHPGGGYTNYNEKFKG (SEQ ID NO: 696) | SRNFAY (SEQ ID NO: 1379) |
| >AH04516-VH | GYTFTNY (SEQ ID NO: 990) | DIHPGGGYTNYNEKFKG (SEQ ID NO: 696) | SRNFAY (SEQ ID NO: 1379) |
| >AH04525-VH | GYTFTNY (SEQ ID NO: 990) | DIHPGGDYTNYNEKFKG (SEQ ID NO: 693) | GRNFAY (SEQ ID NO: 982) |
| >AH04509-VH | GYTFTNY (SEQ ID NO: 990) | DFYPGGDYINYNEKFKG (SEQ ID NO: 691) | SRNFAY (SEQ ID NO: 1379) |

| | | | |
|---|---|---|---|
| >AH04521-VH | GYTFTNY (SEQ ID NO: 990) | DFYPGGDYINYNEKFKG (SEQ ID NO: 691) | SRNFAY (SEQ ID NO: 1379) |
| >AH04526-VH | GYTFTNY (SEQ ID NO: 990) | DIHPGGDYSNYNEKFKG (SEQ ID NO: 692) | SRNFAY (SEQ ID NO: 1379) |
| >AH04514-VH | GYTFTNY (SEQ ID NO: 990) | DIHPGGDYSNYNEKFKG (SEQ ID NO: 692) | SRNFAY (SEQ ID NO: 1379) |
| >AH04524-VH | GYTFTNY (SEQ ID NO: 990) | DIHPGGDYSNYNEKFKG (SEQ ID NO: 692) | SRNFAY (SEQ ID NO: 1379) |
| >AH04530-VH | GYTSTNY (SEQ ID NO: 996) | DIHPGGDYSNYNEKFKG (SEQ ID NO: 692) | SRNFAY (SEQ ID NO: 1379) |
| >AH04517-VH | GYTFTNY (SEQ ID NO: 990) | DIHPGGDYSNYNEKFKG (SEQ ID NO: 692) | SRNFAY (SEQ ID NO: 1379) |
| >AH04506-VH | GYTFTNY (SEQ ID NO: 990) | DIHPGGDYSNYNEKFKG (SEQ ID NO: 692) | SRNFAY (SEQ ID NO: 1379) |
| >AH04508-VH | GYTFTNY (SEQ ID NO: 990) | DIHPGGDYSNYNEKFKG (SEQ ID NO: 692) | SRNFAY (SEQ ID NO: 1379) |
| >AH04518-VH | GYTFTNY (SEQ ID NO: 990) | DIHPGGDYSNYNEKFKG (SEQ ID NO: 692) | SRNFAY (SEQ ID NO: 1379) |
| AH04734 | GYTFTTST (SEQ ID NO: 993) | INPRSGYT (SEQ ID NO: 1024) | ARHYYFDY (SEQ ID NO: 612) |
| AH04750 | GYTSTAYW (SEQ ID NO: 994) | ITPSTGYT (SEQ ID NO: 1028) | ARGGYFDY (SEQ ID NO: 606) |
| AH05214 | GYTFTSYW (SEQ ID NO: 157) | INPSNGRT (SEQ ID NO: 510) | ARQLAAY (SEQ ID NO: 614) |
| AH05247 | GYTFSNYW (SEQ ID NO: 986) | ILPGSGFT (SEQ ID NO: 1021) | ARGGTSVVHFDS (SEQ ID NO: 604) |
| AH05249 | GYTFSNYW (SEQ ID NO: 986) | ILPGSGFT (SEQ ID NO: 1021) | ARGGTSVVHFDS (SEQ ID NO: 604) |
| AH05251 | GFNIKDYY (SEQ ID NO: 977) | IDPDNGET (SEQ ID NO: 1003) | TVFWYGNNYAGFAY (SEQ ID NO: 1420) |
| AH05256 | GYTFTRYW (SEQ ID NO: 992) | INPRTDYT (SEQ ID NO: 1025) | ARHGYFDY (SEQ ID NO: 611) |
| AH05257 | GYTFTDYA (SEQ ID NO: 19) | ISTYSGDA (SEQ ID NO: 21) | ARGVTFDY (SEQ ID NO: 23) |
| AH05258 | GYTFTDYA (SEQ ID NO: 19) | ISTYSGDV (SEQ ID NO: 46) | ARGVTFDS (SEQ ID NO: 48) |
| AH05259 | GYTFTDYA (SEQ ID NO: 19) | ISTYSGDV (SEQ ID NO: 46) | ARGVTFDS (SEQ ID NO: 48) |
| AH05268 | GYTFTDYA (SEQ ID NO: 19) | ISTYSGDA (SEQ ID NO: 21) | ARGVTEDY (SEQ ID NO: 23) |
| AH05271 | GYTFTDYA (SEQ ID NO: 19) | ISTYSGDV (SEQ ID NO: 46) | ARGVTFDS (SEQ ID NO: 48) |
| AH05274 | GYTFTNYW (SEQ ID NO: 4) | IYPGGGYT (SEQ ID NO: 6) | ARVTPAS (SEQ ID NO: 8) |
| AH05280 | GYTFSNYW (SEQ ID NO: 986) | ILPGSGFT (SEQ ID NO: 1021) | ARGGTSVVHFDY (SEQ ID NO: 605) |
| AH05285 | GYTFTRFW (SEQ ID NO: 991) | INPSTDYT (SEQ ID NO: 1027) | ARGTVVDY (SEQ ID NO: 607) |
| AH05286 | GYTFSNYW (SEQ ID NO: 986) | ILPGSGYT (SEQ ID NO: 1022) | ARGGTSFVHFDY (SEQ ID NO: 602) |
| AH4501 | GYTFTNYW (SEQ ID NO: 4) | IHPGGDYS (SEQ ID NO: 1012) | TSRNFAY (SEQ ID NO: 1419) |
| AH4502 | GYTFTNYW (SEQ ID NO: 4) | IHPGGGYT (SEQ ID NO: 1015) | TSRNFAY (SEQ ID NO: 1419) |
| AH4503 | GYTFSNYW (SEQ ID NO: 986) | IHPGGGYI (SEQ ID NO: 1014) | VSRNFAN (SEQ ID NO: 1445) |
| AH4505 | GYTFTNYW (SEQ ID NO: 4) | IHPGGGYT (SEQ ID NO: 1015) | TSRNFAY (SEQ ID NO: 1419) |
| AH4509 | GYTFTNYW (SEQ ID NO: 4) | FYPGGDYI (SEQ ID NO: 973) | TSRNFAY (SEQ ID NO: 1419) |
| AH4511 | GYTFSNYW (SEQ ID NO: 986) | IHPGGGYI (SEQ ID NO: 1014) | VSRNFAN (SEQ ID NO: 1445) |
| AH4518 | GYTFTNYW (SEQ ID NO: 4) | IHPGGDYS (SEQ ID NO: 1012) | TSRNFAY (SEQ ID NO: 1419) |
| AH4523 | GYTFTNYW (SEQ ID NO: 4) | IHPGGSYT (SEQ ID NO: 1016) | TSRNFAK (SEQ ID NO: 1418) |
| AH4524 | GYTFTNYW (SEQ ID NO: 4) | IHPGGDYS (SEQ ID NO: 1012) | TSRNFAY (SEQ ID NO: 1419) |
| AH4525 | GYTFTNYW (SEQ ID NO: 4) | IHPGGDYT (SEQ ID NO: 1013) | TGRNFAY (SEQ ID NO: 1395) |
| BP003-T2P1C4 | GYTFTNYW (SEQ ID NO: 4) | IYPGGGYT (SEQ ID NO: 6) | ARVTPAS (SEQ ID NO: 8) |
| BP003-T2P1D10 | GYTFTNYW (SEQ ID NO: 4) | IYPGGGYT (SEQ ID NO: 6) | ARVTPAS (SEQ ID NO: 8) |

| | | | |
|---|---|---|---|
| BP003-T2P1D7 | GFNIKDYY (SEQ ID NO: 977) | IDPDNGET (SEQ ID NO: 1003) | TVFWYGNNYAGFAY (SEQ ID NO: 1420) |
| BP003-T2P1E3 | GYTFTNYW (SEQ ID NO: 4) | IHPGGGYT (SEQ ID NO: 1015) | TSRNFAY (SEQ ID NO: 1419) |
| BP003-T2P1D1 | GYTFTDYA (SEQ ID NO: 19) | ISTYSGDA (SEQ ID NO: 21) | ARGVTFDY (SEQ ID NO: 23) |
| BL_592989-2015_G2_P8_G02 | GYTFTNYW (SEQ ID NO: 4) | IHPGGGYT (SEQ ID NO: 1015) | TSRNFAY (SEQ ID NO: 1419) |
| BL_592989-2016_H2_P8_H02 | GYTFTSYW (SEQ ID NO: 157) | IYPGSGST (SEQ ID NO: 251) | TRSGVEGLLHWYFD (SEQ ID NO: 1416) |
| BL_592989-2017_A3_P8_A03 | GYTFTSYW (SEQ ID NO: 157) | IYPGSGST (SEQ ID NO: 251) | TRWITTDHYPDY (SEQ ID NO: 1417) |
| BL_592989-2018_B3_P8_B03 | GYTFTNYW (SEQ ID NO: 4) | IYPGGGYT (SEQ ID NO: 6) | ARVSPAS (SEQ ID NO: 615) |
| BL_592989-2019_C3_P8_C03 | GYTFTNYW (SEQ ID NO: 4) | IYPGGGYT (SEQ ID NO: 6) | ARVTPAS (SEQ ID NO: 8) |
| BL_592989-2021_E3_P8_E03 | GYTFTNYW (SEQ ID NO: 4) | IHPGGGYT (SEQ ID NO: 1015) | TSRNFAY (SEQ ID NO: 1419) |
| BL_592989-2022_F3_P8_F03 | GYTFTNYW (SEQ ID NO: 4) | IHPGGGYT (SEQ ID NO: 1015) | TSRNFAY (SEQ ID NO: 1419) |
| BL_592989-2023_G3_P8_G03 | GYTFTSYW (SEQ ID NO: 157) | IYPGSGST (SEQ ID NO: 251) | TRSGVEGLLHWYFD (SEQ ID NO: 1416) |
| BL_592989-2024_H3_P8_H03 | GYTSTGYW (SEQ ID NO: 995) | INPSTGYT (SEQ ID NO: 230) | ARGGYFDY (SEQ ID NO: 606) |
| BL_592989-2025_A4_P8_A04 | GYTFTNYW (SEQ ID NO: 4) | IYPGGGYT (SEQ ID NO: 6) | ARVTPAS (SEQ ID NO: 8) |
| BL_592989-2026_B4_P8_B04 | GYTFTDYA (SEQ ID NO: 19) | ISTYSGDV (SEQ ID NO: 46) | ARGVTFDS (SEQ ID NO: 48) |
| BL_592989-2027_C4_P8_C04 | GYTFTNYW (SEQ ID NO: 4) | IYPGGGYT (SEQ ID NO: 6) | ARVTPAS (SEQ ID NO: 8) |
| BL_592989-2029_E4_P8_E04 | GYTFTNYW (SEQ ID NO: 4) | IHPGGDYT (SEQ ID NO: 1013) | TGRNFAY (SEQ ID NO: 1395) |
| BL_592989-2030_F4_P8_F04 | GYTFTNYW (SEQ ID NO: 4) | IHPGGGYT (SEQ ID NO: 1015) | TSRNFAY (SEQ ID NO: 1419) |
| BL_592989-2031_G4_P8_G04 | GYTFTNYW (SEQ ID NO: 4) | IHPGGGYT (SEQ ID NO: 1015) | TSRNFAY (SEQ ID NO: 1419) |
| BL_592989-2032_H4_P8_H04 | GYTFSNYW (SEQ ID NO: 986) | IHPGGGYI (SEQ ID NO: 1014) | VSRNFAN (SEQ ID NO: 1445) |
| BL_592989-2033_A5_P8_A05 | GYTFTDYA (SEQ ID NO: 19) | ISTYSGDV (SEQ ID NO: 46) | ARGVTFDS (SEQ ID NO: 48) |
| BL_592989-2034_B5_P8_B05 | GYTFTNYW (SEQ ID NO: 4) | IYPGGGYT (SEQ ID NO: 6) | ARVTPAS (SEQ ID NO: 8) |
| BL_592989-2035_C5_P8_C05 | GYTFTNYW (SEQ ID NO: 4) | IYPGGGYT (SEQ ID NO: 6) | ARVTPAS (SEQ ID NO: 8) |
| BL_592989-2037_E5_P8_E05 | GYTFTNYW (SEQ ID NO: 4) | IHPGGDYS (SEQ ID NO: 1012) | TSRNFAY (SEQ ID NO: 1419) |
| BL_592989-2038_F5_P8_F05 | GYTFTNYW (SEQ ID NO: 4) | IHPGGGYI (SEQ ID NO: 1014) | VSRNFAN (SEQ ID NO: 1445) |
| BL_592989-2039_G5_P8_G05 | GYTFTNYW (SEQ ID NO: 4) | IHPGGGYT (SEQ ID NO: 1015) | TSRNFAY (SEQ ID NO: 1419) |
| BL_592989-2040_H5_P8_H05 | GYTFTNYW (SEQ ID NO: 4) | IHPGGGYT (SEQ ID NO: 1015) | TSRNFAY (SEQ ID NO: 1419) |
| BL_592989-2041_A6_P8_A06 | GYTFTDYA (SEQ ID NO: 19) | ISTYSGDA (SEQ ID NO: 21) | ARGVTFDY (SEQ ID NO: 23) |
| BL_592989-2042_B6_P8_B06 | GYTFTDYA (SEQ ID NO: 19) | ISTYSGDV (SEQ ID NO: 46) | ARGVTFDS (SEQ ID NO: 48) |
| BL_592989-2043_C6_P8_C06 | GYTFTDYA (SEQ ID NO: 19) | ISTYSGDV (SEQ ID NO: 46) | ARGVTFDS (SEQ ID NO: 48) |
| BL_592989-2044_D6_P8_D06 | GYTFTNYW (SEQ ID NO: 4) | IYPGGGYT (SEQ ID NO: 6) | ARVTPAS (SEQ ID NO: 8) |
| BL_592989-2045_E6_P8_E06 | GYTFTNYW (SEQ ID NO: 4) | IHPGGDYS (SEQ ID NO: 1012) | TSRNFAY (SEQ ID NO: 1419) |
| BL_592989-2046_F6_P8_F06 | GYTFTNYW (SEQ ID NO: 4) | IHPGGDYS (SEQ ID NO: 1012) | TSRNFAY (SEQ ID NO: 1419) |

| | | | |
|---|---|---|---|
| BL_592989-2047_G6_P8_G06 | GYTFTNYW (SEQ ID NO: 4) | IHPGGGYT (SEQ ID NO: 1015) | TSRNFAY (SEQ ID NO: 1419) |
| BL_592989-2048_H6_P8_H06 | GYTFTNYW (SEQ ID NO: 4) | IHPGGDYS (SEQ ID NO: 1012) | TSRNFAY (SEQ ID NO: 1419) |
| BL_592989-2049_A7_P8_A07 | GYTFTDYA (SEQ ID NO: 19) | ISTYSGDV (SEQ ID NO: 46) | ARGVTFDS (SEQ ID NO: 48) |
| BL_592989-2051_C7_P8_C07 | GYTFTNYW (SEQ ID NO: 4) | IYPGGGYT (SEQ ID NO: 6) | ARVTPAS (SEQ ID NO: 8) |
| BL_592989-2052_D7_P8_D07 | GFNIKDYY (SEQ ID NO: 977) | IDPDNGET (SEQ ID NO: 1003) | TVFWYGNNYAGFAY (SEQ ID NO: 1420) |
| BL_592989-2054_F7_P8_F07 | GYTFTNYW (SEQ ID NO: 4) | IHPGGDYS (SEQ ID NO: 1012) | TSRNFAY (SEQ ID NO: 1419) |
| BL_592989-2055_G7_P8_G07 | GYTFTNYW (SEQ ID NO: 4) | INPGGGYT (SEQ ID NO: 1023) | TSRNFAY (SEQ ID NO: 1419) |
| BL_592989-2059_C8_P8_C08 | GYTFTNYW (SEQ ID NO: 4) | IYPGGGYT (SEQ ID NO: 6) | VRVTPAS (SEQ ID NO: 1443) |
| BL_592989-2060_D8_P8_D08 | GYTFTDYA (SEQ ID NO: 19) | ISTYSGDA (SEQ ID NO: 21) | ARGVTFDY (SEQ ID NO: 23) |
| BL_592989-2061_E8_P8_E08 | GYTFTNYW (SEQ ID NO: 4) | IHPGGGYI (SEQ ID NO: 1014) | VSRNFAN (SEQ ID NO: 1445) |
| BL_592989-2062_F8_P8_F08 | GYTFTDYA (SEQ ID NO: 19) | IITYSGDA (SEQ ID NO: 1020) | AXGVTFDY (SEQ ID NO: 619) |
| BL_592989-2063_G8_P8_G08 | GYTFTSYW (SEQ ID NO: 157) | IDPYDSET (SEQ ID NO: 235) | AREASYYYGNAWFA (SEQ ID NO: 601) |
| BL_592989-2064_H8_P8_H08 | GYTSTNYW (SEQ ID NO: 997) | IHPGGDYS (SEQ ID NO: 1012) | TSRNFAY (SEQ ID NO: 1419) |
| BL_592989-2065_A9_P8_A09 | GYTFTDYA (SEQ ID NO: 19) | ISTYSGDA (SEQ ID NO: 21) | ARGVTFDY (SEQ ID NO: 23) |
| BL_592989-2067_C9_P8_C09 | GYAFTNYW (SEQ ID NO: 984) | IYPGGGYT (SEQ ID NO: 6) | ARVTPAS (SEQ ID NO: 8) |
| BL_592989-2068_D9_P8_D09 | GYTFTDYA (SEQ ID NO: 19) | ISTYSGDA (SEQ ID NO: 21) | ARGVTFDY (SEQ ID NO: 23) |
| BL_592989-2069_E9_P8_E09 | GYTFTNYW (SEQ ID NO: 4) | IHPGGDYS (SEQ ID NO: 1012) | TSRNFAY (SEQ ID NO: 1419) |
| BL_592989-2070_F9_P8_F09 | GYTFTDYA (SEQ ID NO: 19) | ISTYSGDV (SEQ ID NO: 46) | ARGVTFDS (SEQ ID NO: 48) |
| BL_592989-2071_G9_P8_G09 | GYTFTNYW (SEQ ID NO: 4) | IHPGGGYT (SEQ ID NO: 1015) | TSRNFAY (SEQ ID NO: 1419) |
| BL_592989-2074_B10_P8_B10 | GYTFTNYW (SEQ ID NO: 4) | IYPGGGYT (SEQ ID NO: 6) | ARVTPAS (SEQ ID NO: 8) |
| BL_592989-2076_D10_P8_D10 | GYTFTNYW (SEQ ID NO: 4) | IYPGGGYT (SEQ ID NO: 6) | ARVTPAS (SEQ ID NO: 8) |
| BL_592989-2077_E10_P8_E10 | GYTFTNYW (SEQ ID NO: 4) | IHPGGGYT (SEQ ID NO: 1015) | TSRNFAY (SEQ ID NO: 1419) |
| BL_592989-2078_F10_P8_F10 | GYTFTNYW (SEQ ID NO: 4) | IHPGGDYS (SEQ ID NO: 1012) | TSRNFAY (SEQ ID NO: 1419) |
| BL_592989-2079_G10_P8_G10 | GYTFTNYW (SEQ ID NO: 4) | FYPGGDYI (SEQ ID NO: 973) | TSRNFAY (SEQ ID NO: 1419) |
| BL_592989-2080_H10_P8_H10 | GYTFTRYW (SEQ ID NO: 992) | INPSTGYT (SEQ ID NO: 230) | ARWGNFDY (SEQ ID NO: 617) |
| BP003-T2P1A7 | GYTFTDYA (SEQ ID NO: 19) | ISTYSGDV (SEQ ID NO: 46) | ARGVTFDS (SEQ ID NO: 48) |
| BP003-T2P1C8 | GYTFTNYW (SEQ ID NO: 4) | IYPGGGYT (SEQ ID NO: 6) | VRVTPAS (SEQ ID NO: 1443) |
| BP003-T2P1F4 | GYTFTNYW (SEQ ID NO: 4) | IHPGGGYT (SEQ ID NO: 1015) | TSRNFAY (SEQ ID NO: 1419) |
| BP003-T2P1G2 | GYTFTNYW (SEQ ID NO: 4) | IHPGGGYT (SEQ ID NO: 1015) | TSRNFAY (SEQ ID NO: 1419) |
| BP003-T2P1G4 | GYTFTNYW (SEQ ID NO: 4) | IHPGGGYT (SEQ ID NO: 1015) | TSRNFAY (SEQ ID NO: 1419) |

| Name | CDR1 | CDR2 | CDR3 |
|---|---|---|---|
| BP003-T2P1G7 | GYTFTNYW (SEQ ID NO: 4) | INPGGGYT (SEQ ID NO: 1023) | TSRNFAY (SEQ ID NO: 1419) |
| BP003-T2P1H5 | GYTFTNYW (SEQ ID NO: 4) | IHPGGGYT (SEQ ID NO: 1015) | TSRNFAY (SEQ ID NO: 1419) |
| BP003T3P2-1 | GYTFTDYA (SEQ ID NO: 19) | ISTYSGDA (SEQ ID NO: 21) | ARGVTFDY (SEQ ID NO: 23) |
| BP003T3P2-10 | GYTFTDYA (SEQ ID NO: 19) | ISTYSGDA (SEQ ID NO: 21) | ARGVTFDY (SEQ ID NO: 23) |
| BP003T3P2-11 | GYTFTDYA (SEQ ID NO: 19) | ISTYSGDA (SEQ ID NO: 21) | ARGVTFDY (SEQ ID NO: 23) |
| BP003T3P2-12 | GYTFTDYA (SEQ ID NO: 19) | ISTYSGDA (SEQ ID NO: 21) | ARGVTFDY (SEQ ID NO: 23) |
| BP003T3P2-13 | GYTFTDYA (SEQ ID NO: 19) | ISTYSGDA (SEQ ID NO: 21) | ARGVTFDY (SEQ ID NO: 23) |
| BP003T3P2-14 | GYTFTDYA (SEQ ID NO: 19) | ISTYSGDA (SEQ ID NO: 21) | ARGVTFDY (SEQ ID NO: 23) |
| BP003T3P2-15 | GYTFTDYA (SEQ ID NO: 19) | ISTYSGDA (SEQ ID NO: 21) | ARGVTFDY (SEQ ID NO: 23) |
| BP003T3P2-16 | GYTFTDYA (SEQ ID NO: 19) | ISTYSGDA (SEQ ID NO: 21) | ARGVTFDY (SEQ ID NO: 23) |
| BP003T3P2-17 | GYTFTDYA (SEQ ID NO: 19) | ISTYSGDA (SEQ ID NO: 21) | ARGVTFDY (SEQ ID NO: 23) |
| BP003T3P2-18 | GYTFTDYA (SEQ ID NO: 19) | ISTYSGDA (SEQ ID NO: 21) | ARGVTFDY (SEQ ID NO: 23) |
| BP003T3P2-19 | GYTFTDYA (SEQ ID NO: 19) | ISTYSGDA (SEQ ID NO: 21) | ARGVTFDY (SEQ ID NO: 23) |
| BP003T3P2-2 | GYTFTDYA (SEQ ID NO: 19) | ISTYSGDA (SEQ ID NO: 21) | ARGVTEDY (SEQ ID NO: 23) |
| BP003T3P2-20 | GYTFTDYA (SEQ ID NO: 19) | ISTYSGDA (SEQ ID NO: 21) | ARGVTFDY (SEQ ID NO: 23) |
| BP003T3P2-21 | GYTFTDYA (SEQ ID NO: 19) | ISTYSGDA (SEQ ID NO: 21) | ARGVTFDY (SEQ ID NO: 23) |
| BP003T3P2-22 | GYTFTDYA (SEQ ID NO: 19) | ISTYSGDA (SEQ ID NO: 21) | ARGVTFDY (SEQ ID NO: 23) |
| BP003T3P2-23 | GYTFTDYA (SEQ ID NO: 19) | ISTYSGDV (SEQ ID NO: 46) | ARGVTFDS (SEQ ID NO: 48) |
| BP003T3P2-24 | GYTFTDYA (SEQ ID NO: 19) | ISTYSGDV (SEQ ID NO: 46) | ARGVTFDS (SEQ ID NO: 48) |
| BP003T3P2-25 | GYTFTDYA (SEQ ID NO: 19) | ISTYSGDV (SEQ ID NO: 46) | ARGVTFDS (SEQ ID NO: 48) |
| BP003T3P2-26 | GYTFTDYA (SEQ ID NO: 19) | IXTYSGDV (SEQ ID NO: 1029) | ARGVTFDS (SEQ ID NO: 48) |
| BP003T3P2-27 | GYTFTDYG (SEQ ID NO: 987) | ISTYSGDV (SEQ ID NO: 46) | ARGVTFDS (SEQ ID NO: 48) |
| BP003T3P2-28 | GYTFTRYW (SEQ ID NO: 992) | INPRTDYT (SEQ ID NO: 1025) | ARHGYFDY (SEQ ID NO: 611) |
| BP003T3P2-29 | GYTFTRYW (SEQ ID NO: 992) | INPRTDYT (SEQ ID NO: 1025) | ARHGYFDY (SEQ ID NO: 611) |
| BP003T3P2-3 | GYTFTDYA (SEQ ID NO: 19) | ISTYSGDA (SEQ ID NO: 21) | ARGVTFDY (SEQ ID NO: 23) |
| BP003T3P2-30 | GYTFTRYW (SEQ ID NO: 992) | INPRTDYT (SEQ ID NO: 1025) | ARHGYFDY (SEQ ID NO: 611) |
| BP003T3P2-31 | GYTFTRYW (SEQ ID NO: 992) | INPRTDYT (SEQ ID NO: 1025) | ARHGYFDY (SEQ ID NO: 611) |
| BP003T3P2-32 | GYTFTRYW (SEQ ID NO: 992) | INPRTDYT (SEQ ID NO: 1025) | ARHGYFDY (SEQ ID NO: 611) |
| BP003T3P2-33 | GYTFTRYW (SEQ ID NO: 992) | INPRTDYT (SEQ ID NO: 1025) | ARHGYFDY (SEQ ID NO: 611) |
| BP003T3P2-34 | GYTFTRYW (SEQ ID NO: 992) | INPRTDYT (SEQ ID NO: 1025) | ARHGYFDY (SEQ ID NO: 611) |
| BP003T3P2-35 | GYTFTRYW (SEQ ID NO: 992) | INPRTDYT (SEQ ID NO: 1025) | ARHGYFDY (SEQ ID NO: 611) |
| BP003T3P2-36 | GYTFTRYW (SEQ ID NO: 992) | INPRTDYT (SEQ ID NO: 1025) | ARHGYFDY (SEQ ID NO: 611) |
| BP003T3P2-37 | GYTFTRYW (SEQ ID NO: 992) | INPRTDYT (SEQ ID NO: 1025) | ARHGYFDY (SEQ ID NO: 611) |
| BP003T3P2-38 | GYTFTRYW (SEQ ID NO: 992) | INPSSDYT (SEQ ID NO: 1026) | ARGTVVVDY (SEQ ID NO: 608) |
| BP003T3P2-39 | GYTFTRYW (SEQ ID NO: 992) | INPSTDYT (SEQ ID NO: 1027) | VRSPILDY (SEQ ID NO: 1442) |
| BP003T3P2-4 | GYTFTDYA (SEQ ID NO: 19) | ISTYSGDA (SEQ ID NO: 21) | ARGVTFDY (SEQ ID NO: 23) |
| BP003T3P2-40 | GYTFTNYW (SEQ ID NO: 4) | IYPGGGYT (SEQ ID NO: 6) | ARVTPAS (SEQ ID NO: 8) |
| BP003T3P2-41 | GYTFTNYW (SEQ ID NO: 4) | IYPGGGYT (SEQ ID NO: 6) | ARVTPAS (SEQ ID NO: 8) |

| | | | |
|---|---|---|---|
| BP003T 3P2-42 | GYTFTNYW (SEQ ID NO: 4) | IYPGGGYT (SEQ ID NO: 6) | ARVTPAS (SEQ ID NO: 8) |
| BP003T 3P2-43 | GYTFTNYW (SEQ ID NO: 4) | IYPGGGYT (SEQ ID NO: 6) | ARVTPAS (SEQ ID NO: 8) |
| BP003T 3P2-44 | GYTFTNYW (SEQ ID NO: 4) | IYPGGGYT (SEQ ID NO: 6) | ARVTPAS (SEQ ID NO: 8) |
| BP003T 3P2-45 | GYTFTNYW (SEQ ID NO: 4) | IYPGGGYT (SEQ ID NO: 6) | ARVTPAS (SEQ ID NO: 8) |
| BP003T 3P2-46 | GYTFTNYW (SEQ ID NO: 4) | IYPGGGYT (SEQ ID NO: 6) | ARVTPAS (SEQ ID NO: 8) |
| BP003T 3P2-47 | GYTFTNYW (SEQ ID NO: 4) | IYPGGGYT (SEQ ID NO: 6) | ARVTPAS (SEQ ID NO: 8) |
| BP003T 3P2-48 | GYTFTNYW (SEQ ID NO: 4) | IYPGGGYT (SEQ ID NO: 6) | ARVTPAS (SEQ ID NO: 8) |
| BP003T 3P2-49 | GYTFTNYW (SEQ ID NO: 4) | IYPGGGYT (SEQ ID NO: 6) | ARVTPAS (SEQ ID NO: 8) |
| BP003T 3P2-5 | GYTFTDYA (SEQ ID NO: 19) | ISTYSGDA (SEQ ID NO: 21) | ARGVTFDY (SEQ ID NO: 23) |
| BP003T 3P2-50 | GYTFTNYW (SEQ ID NO: 4) | IYPGGGYT (SEQ ID NO: 6) | ARVTPAS (SEQ ID NO: 8) |
| BP003T 3P2-51 | GYTFTNYW (SEQ ID NO: 4) | IYPGGGYT (SEQ ID NO: 6) | ARVTPAS (SEQ ID NO: 8) |
| BP003T 3P2-52 | GYTFTNYW (SEQ ID NO: 4) | IYPGGGYT (SEQ ID NO: 6) | ARVTPAS (SEQ ID NO: 8) |
| BP003T 3P2-53 | GYTFTNYW (SEQ ID NO: 4) | IYPGGGYT (SEQ ID NO: 6) | ARVTPAS (SEQ ID NO: 8) |
| BP003T 3P2-54 | GYTFTNYW (SEQ ID NO: 4) | IYPGGGYA (SEQ ID NO: 1035) | ARVTPAS (SEQ ID NO: 8) |
| BP003T 3P2-55 | GYTFTNYW (SEQ ID NO: 4) | IYPGGGYT (SEQ ID NO: 6) | ARVTPAS (SEQ ID NO: 8) |
| BP003T 3P2-56 | GYTFTNYW (SEQ ID NO: 4) | IYPGGGYT (SEQ ID NO: 6) | ARVTPAS (SEQ ID NO: 8) |
| BP003T 3P2-57 | GYTFTNYW (SEQ ID NO: 4) | IYPGGGYT (SEQ ID NO: 6) | ARVTPAS (SEQ ID NO: 8) |
| BP003T 3P2-58 | GYTFTNYW (SEQ ID NO: 4) | IYPGGGYT (SEQ ID NO: 6) | ARVTPAS (SEQ ID NO: 8) |
| BP003T 3P2-59 | GYTFTNYW (SEQ ID NO: 4) | IYPGGGYT (SEQ ID NO: 6) | ARVTPAS (SEQ ID NO: 8) |
| BP003T 3P2-6 | GYTFTDYA (SEQ ID NO: 19) | ISTYSGDA (SEQ ID NO: 21) | ARGVTFDY (SEQ ID NO: 23) |
| BP003T 3P2-60 | GYTFTNYW (SEQ ID NO: 4) | IYPGGGYT (SEQ ID NO: 6) | ARVTPAS (SEQ ID NO: 8) |
| BP003T 3P2-61 | GYTFTNYW (SEQ ID NO: 4) | IYPGGGYT (SEQ ID NO: 6) | ARVTPAS (SEQ ID NO: 8) |
| BP003T 3P2-62 | GYTFSNYW (SEQ ID NO: 986) | ILPGSGFT (SEQ ID NO: 1021) | ARGGTSVV HFDY (SEQ ID NO: 605) |
| BP003T 3P2-63 | GYTFSNYW (SEQ ID NO: 986) | ILPGSGFT (SEQ ID NO: 1021) | ARGGTSVV HFDS (SEQ ID NO: 604) |
| BP003T 3P2-64 | GYTFSNYW (SEQ ID NO: 986) | ILPGSGFT (SEQ ID NO: 1021) | ARGGTSVV HFDY (SEQ ID NO: 605) |
| BP003T 3P2-65 | GYTFSNYW (SEQ ID NO: 986) | ILPGSGFT (SEQ ID NO: 1021) | ARGGTSVV HFDFDY (SEQ ID NO: 603) |
| BP003T 3P2-66 | GFNIKDYY (SEQ ID NO: 977) | IDPENGDT (SEQ ID NO: 1004) | NVITTATTW FAY (SEQ ID NO: 1165) |
| BP003T 3P2-67 | GFNIKDYY (SEQ ID NO: 977) | IDPDNGET (SEQ ID NO: 1003) | TVFWYGNN YAGFAY (SEQ ID NO: 1420) |
| BP003T 3P2-68 | GFNIKDYY (SEQ ID NO: 977) | IDPDNGET (SEQ ID NO: 1003) | TVFWYGNN YAGFAY (SEQ ID NO: 1420) |
| BP003T 3P2-69 | GFNIKDYY (SEQ ID NO: 977) | IDPDNGET (SEQ ID NO: 1003) | TVFWYGNN YAGFAY (SEQ ID NO: 1420) |
| BP003T 3P2-7 | GYTFTDYA (SEQ ID NO: 19) | ISTYSGDA (SEQ ID NO: 21) | ARGVTFDY (SEQ ID NO: 23) |
| BP003T 3P2-70 | GFNIKDYY (SEQ ID NO: 977) | IDPDNGET (SEQ ID NO: 1003) | TVFWYGNN YAGFAY (SEQ ID NO: 1420) |
| BP003T 3P2-71 | GFNIKDYY (SEQ ID NO: 977) | IDPDNGET (SEQ ID NO: 1003) | TVFWYGNN YAGFAY (SEQ ID NO: 1420) |
| BP003T 3P2-72 | GFNIKDYY (SEQ ID NO: 977) | IDPDNGET (SEQ ID NO: 1003) | TVFWYGNN YAGFAY (SEQ ID NO: 1420) |
| BP003T 3P2-73 | GFNIKDYY (SEQ ID NO: 977) | IDPDNGET (SEQ ID NO: 1003) | TVFWYGNN YAGFAY (SEQ ID NO: 1420) |
| BP003T 3P2-74 | GFNIKDYY (SEQ ID NO: 977) | IDPDNGET (SEQ ID NO: 1003) | TVFWYGNN YAGFAY (SEQ ID NO: 1420) |

| ID | CDRL1 | CDRL2 | CDRL3 |
|---|---|---|---|
| BP003T3P2-75 | GYTFTDYA (SEQ ID NO: 19) | ISTYSGDV (SEQ ID NO: 46) | ARGVTFDS (SEQ ID NO: 48) |
| BP003T3P2-8 | GYTFTDYA (SEQ ID NO: 19) | ISTYSGDA (SEQ ID NO: 21) | ARGVTFDY (SEQ ID NO: 23) |
| BP003T3P2-9 | GYTFTDYA (SEQ ID NO: 19) | ISTYSGDA (SEQ ID NO: 21) | ARGVTFDY (SEQ ID NO: 23) |

| ID | CDRL1 | CDRL2 | CDRL3 |
|---|---|---|---|
| D11 | QDISNY (SEQ ID NO: 27) | NAK (SEQ ID NO: 28) | QHHYDTPYT (SEQ ID NO: 30) |
| D17 | QNVGTN (SEQ ID NO: 12) | SAS (SEQ ID NO: 13) | QQYNSYPLT (SEQ ID NO: 42) |
| D34 | ENSYSY (SEQ ID NO: 52) | NAK (SEQ ID NO: 28) | QHHYGTPYT (SEQ ID NO: 54) |
| D36 | ENSYSY (SEQ ID NO: 52) | NAK (SEQ ID NO: 28) | QHHYGTPYT (SEQ ID NO: 54) |
| D5 | QNVGTN (SEQ ID NO: 12) | SAS (SEQ ID NO: 13) | QQYNSYPYT (SEQ ID NO: 15) |
| AHH03702 | QDVSTA (SEQ ID NO: 1209) | SAS (SEQ ID NO: 13) | QQHYSTPWT (SEQ ID NO: 1264) |
| AHH03703 | QDVSTA (SEQ ID NO: 1209) | SAS (SEQ ID NO: 13) | QQHYSTPWT (SEQ ID NO: 1264) |
| AHH03704 | QSLLYSSNQKNY (SEQ ID NO: 1304) | WAS (SEQ ID NO: 1450) | QQYYSYPWT (SEQ ID NO: 1294) |
| AHH03705 | QSLLYSSNQKNY (SEQ ID NO: 1304) | WAS (SEQ ID NO: 1450) | QQYYSYPWT (SEQ ID NO: 1294) |
| AHH03706 | QGISNY (SEQ ID NO: 1211) | YTS (SEQ ID NO: 1495) | QQYSKLPWT (SEQ ID NO: 1289) |
| AHH03707 | KSISKY (SEQ ID NO: 1059) | SGS (SEQ ID NO: 1365) | QQHNEYPWT (SEQ ID NO: 1257) |
| AHH03708 | QSLLDSDGKTY (SEQ ID NO: 1301) | LVS (SEQ ID NO: 1116) | WQGTHFPRT (SEQ ID NO: 1464) |
| AHH03709 | ENVGTY (SEQ ID NO: 933) | GAS (SEQ ID NO: 975) | GQSYSYPYT (SEQ ID NO: 981) |
| AHH03711 | QNVRTA (SEQ ID NO: 1247) | MAS (SEQ ID NO: 1122) | LQHWNYPYT (SEQ ID NO: 1093) |
| AHH03712 | QSVSND (SEQ ID NO: 1310) | YAS (SEQ ID NO: 1476) | QQDYSSPWT (SEQ ID NO: 1251) |
| AHH03713 | QEISGY (SEQ ID NO: 1210) | AAS (SEQ ID NO: 599) | LQYISYPRT (SEQ ID NO: 1107) |
| AHH03714 | QNVGTN (SEQ ID NO: 12) | SAS (SEQ ID NO: 13) | QQYNSYPRT (SEQ ID NO: 1286) |
| AHH03715 | ENIYSN (SEQ ID NO: 929) | AAT (SEQ ID NO: 600) | QHFWGTPPT (SEQ ID NO: 1212) |
| AHH03716 | QSLLDSDGKTY (SEQ ID NO: 1301) | LVS (SEQ ID NO: 1116) | WQGTHFRT (SEQ ID NO: 1466) |
| AHH03717 | QSLVHNNGNTY (SEQ ID NO: 1305) | KVS (SEQ ID NO: 1062) | SQSTHVPLT (SEQ ID NO: 1370) |
| AHH03718 | QDISNY (SEQ ID NO: 27) | FTS (SEQ ID NO: 972) | QQGNTLPRT (SEQ ID NO: 1254) |
| AHH03719 | QDIGSS (SEQ ID NO: 1199) | ATS (SEQ ID NO: 618) | LQYASSPYT (SEQ ID NO: 1101) |
| AHH03720 | QDISNY (SEQ ID NO: 27) | YTS (SEQ ID NO: 1495) | QQVYTLPWT (SEQ ID NO: 1273) |
| AHH03721 | QEISGY (SEQ ID NO: 1210) | AAS (SEQ ID NO: 599) | LQYASYPRT (SEQ ID NO: 1102) |
| AHH03722 | QEISGY (SEQ ID NO: 1210) | AAS (SEQ ID NO: 599) | LQYASYPRT (SEQ ID NO: 1102) |
| AHH03724 | QSVDYDGDSY (SEQ ID NO: 1308) | AAS (SEQ ID NO: 599) | QQSNEDPYT (SEQ ID NO: 1270) |
| AHH03726 | QSVDYDGDSY (SEQ ID NO: 1308) | AAS (SEQ ID NO: 599) | QQSNEDPYT (SEQ ID NO: 1270) |
| AHH03727 | QSLVHSNGNTY (SEQ ID NO: 1306) | KVS (SEQ ID NO: 1062) | SQSTHVPWT (SEQ ID NO: 1374) |
| AHH03728 | QDVNTA (SEQ ID NO: 1206) | SAS (SEQ ID NO: 13) | QQHFNSPYT (SEQ ID NO: 1256) |
| AHH03729 | QSVDYDGDSY (SEQ ID NO: 1308) | ATS (SEQ ID NO: 618) | QQSNEDPLT (SEQ ID NO: 1268) |
| AHH03730 | QDIGSS (SEQ ID NO: 1199) | ATS (SEQ ID NO: 618) | LQYASSPWT (SEQ ID NO: 1100) |
| AHH03731 | SSVSY (SEQ ID NO: 1385) | DTS (SEQ ID NO: 839) | QQWSSNPPT (SEQ ID NO: 1274) |
| AHH03733 | SSIGY (SEQ ID NO: 1381) | DTS (SEQ ID NO: 839) | HQRGSYPWT (SEQ ID NO: 999) |

| | | | |
|---|---|---|---|
| AHH03734 | QDVSTA (SEQ ID NO: 1209) | SAS (SEQ ID NO: 13) | QQHYSTPWT (SEQ ID NO: 1264) |
| AHH03737 | ENVATY (SEQ ID NO: 932) | GAS (SEQ ID NO: 975) | GQSYRYPYT (SEQ ID NO: 979) |
| AHH03738 | QSLVHSNGNTY (SEQ ID NO: 1306) | KVS (SEQ ID NO: 1062) | SQSTHVPT (SEQ ID NO: 1373) |
| AHH03739 | ESVDSYGNSF (SEQ ID NO: 935) | LAS (SEQ ID NO: 1063) | QQNNEDPYT (SEQ ID NO: 1266) |
| AHH03740 | QNVGTN (SEQ ID NO: 12) | SAS (SEQ ID NO: 13) | QQYNSYPYT (SEQ ID NO: 15) |
| AHH03742 | ENVGTY (SEQ ID NO: 933) | GAS (SEQ ID NO: 975) | GQSYSYPYT (SEQ ID NO: 981) |
| AHH03743 | QDVSTA (SEQ ID NO: 1209) | SAS (SEQ ID NO: 13) | QQHYSTPPWT (SEQ ID NO: 1262) |
| AHH03746 | QSLLYSNGKTY (SEQ ID NO: 1303) | QVS (SEQ ID NO: 1344) | LQGTYYPTWT (SEQ ID NO: 1092) |
| AHH03748 | QSLVHSNGNTY (SEQ ID NO: 1306) | KVS (SEQ ID NO: 1062) | SQSTHVPWT (SEQ ID NO: 1374) |
| AHH03749 | QDVSTA (SEQ ID NO: 1209) | SAS (SEQ ID NO: 13) | QQHYSTPPT (SEQ ID NO: 1261) |
| AHH03750 | QSLLDSDGKTY (SEQ ID NO: 1301) | LVS (SEQ ID NO: 1116) | WQGTHFPWT (SEQ ID NO: 1465) |
| AHH03751 | QSLLDSDGKTY (SEQ ID NO: 1301) | LVS (SEQ ID NO: 1116) | WQGAHFPWT (SEQ ID NO: 1461) |
| AHH03752 | QSLLDSDGKTY (SEQ ID NO: 1301) | LVS (SEQ ID NO: 1116) | WQGTHFPQT (SEQ ID NO: 1463) |
| AHH03753 | QNVGSN (SEQ ID NO: 1244) | SAS (SEQ ID NO: 13) | QQYDSYPYT (SEQ ID NO: 1280) |
| AHH03754 | QDIGSS (SEQ ID NO: 1199) | ATS (SEQ ID NO: 618) | LQYASSPHT (SEQ ID NO: 1098) |
| AHH03755 | ENIYSN (SEQ ID NO: 929) | AAT (SEQ ID NO: 600) | QHFWGTPWT (SEQ ID NO: 1213) |
| AHH03756 | QDVSTA (SEQ ID NO: 1209) | SAS (SEQ ID NO: 13) | QQHYSTPYT (SEQ ID NO: 1265) |
| AHH03757 | ENIYSN (SEQ ID NO: 929) | AAT (SEQ ID NO: 600) | QHFWGTPWT (SEQ ID NO: 1213) |
| H03758 | DDD (SEQ ID NO: 1391) | (SEQ ID NO: 925) | DNMPLT (SEQ ID NO: 1094) |
| H03759 | VDYDGDSY (SEQ ID NO: 1308) | (SEQ ID NO: 599) | NEDPYT (SEQ ID NO: 1270) |
| AHH03760 | QSVSND (SEQ ID NO: 1310) | YAS (SEQ ID NO: 1476) | QQDYSSPPT (SEQ ID NO: 1250) |
| AHH03765 | SSVSY (SEQ ID NO: 1385) | DTS (SEQ ID NO: 839) | QQWSSNPPYT (SEQ ID NO: 1275) |
| AHH03767 | QSLLDSDGKTY (SEQ ID NO: 1301) | LVS (SEQ ID NO: 1116) | WQGTHFPRT (SEQ ID NO: 1464) |
| AHH03768 | EDIYNR (SEQ ID NO: 924) | GAT (SEQ ID NO: 976) | QQYWSTPPT (SEQ ID NO: 1292) |
| AHH03770 | QSLLYSSNQKNY (SEQ ID NO: 1304) | WAS (SEQ ID NO: 1450) | QQYYSYP (SEQ ID NO: 1293) |
| AHH03771 | QSLVHSNGNTY (SEQ ID NO: 1306) | KVS (SEQ ID NO: 1062) | SQSTHVYT (SEQ ID NO: 1376) |
| AHH03772 | ENIYSY (SEQ ID NO: 930) | NAK (SEQ ID NO: 28) | QHHYGTPWT (SEQ ID NO: 1217) |
| AHH03773 | QSLVHSNGNTY (SEQ ID NO: 1306) | KVS (SEQ ID NO: 1062) | SQSTHVPT (SEQ ID NO: 1373) |
| AHH03774 | SSVSY (SEQ ID NO: 1385) | DTS (SEQ ID NO: 839) | QQWSSYPYT (SEQ ID NO: 1278) |
| AHH03776 | TDIDDD (SEQ ID NO: 1391) | EGN (SEQ ID NO: 925) | LQSDNMPYT (SEQ ID NO: 1095) |
| AHH03777 | QSLLDSDGKTY (SEQ ID NO: 1301) | LVS (SEQ ID NO: 1116) | WQGTFSSH (SEQ ID NO: 1462) |
| AHH03778 | QDVITA (SEQ ID NO: 1205) | SAS (SEQ ID NO: 13) | QQHYSTPRT (SEQ ID NO: 1263) |
| AHH03779 | QEISGY (SEQ ID NO: 1210) | AAS (SEQ ID NO: 599) | LQYASYPRT (SEQ ID NO: 1102) |
| AHH03780 | ESVDSYGNSF (SEQ ID NO: 935) | RAS (SEQ ID NO: 1346) | QQSNEDPRT (SEQ ID NO: 1269) |
| AHH03782 | QSLVHSNGNTY (SEQ ID NO: 1306) | KVS (SEQ ID NO: 1062) | SQSTHVPWT (SEQ ID NO: 1374) |
| AHH03783 | QSVDYDGDSY (SEQ ID NO: 1308) | AAS (SEQ ID NO: 599) | QQSNEDPYT (SEQ ID NO: 1270) |

| | | | | | | |
|---|---|---|---|---|---|---|
| AHH03784 | QSLLNSSN QKNY (SEQ ID NO: 1302) | FAS (SEQ ID NO: 957) | QQHYSTPYT (SEQ ID NO: 1265) | | | |
| AHH03785 | QDVSTA (SEQ ID NO: 1209) | SAS (SEQ ID NO: 13) | QQHYSTHV H (SEQ ID NO: 1259) | | | |
| AHH03786 | QSLVHSNG NTY (SEQ ID NO: 1306) | KVS (SEQ ID NO: 1062) | SQSTHVPWT (SEQ ID NO: 1374) | | | |
| AHH03787 | SSVIY (SEQ ID NO: 1383) | DTS (SEQ ID NO: 839) | QQWTSNPPT (SEQ ID NO: 1279) | | | |
| AHH03788 | QNVGTN (SEQ ID NO: 12) | SAS (SEQ ID NO: 13) | SQSTHVPYT (SEQ ID NO: 1375) | | | |
| AHH03790 | SRVTY (SEQ ID NO: 1380) | DTS (SEQ ID NO: 839) | HQRSGYSYT (SEQ ID NO: 1000) | | | |
| AHH03791 | SRVTY (SEQ ID NO: 1380) | DTS (SEQ ID NO: 839) | HQRSGYSYT (SEQ ID NO: 1000) | | | |
| AHH03792 | QNVGTN (SEQ ID NO: 12) | SAS (SEQ ID NO: 13) | QQYNSYPRT (SEQ ID NO: 1286) | | | |
| AHH03793 | KSLLHSNG NTY (SEQ ID NO: 1060) | RMS (SEQ ID NO: 1360) | MQHLEYPY T (SEQ ID NO: 1136) | | | |
| AHH03794 | QDISNY (SEQ ID NO: 27) | YTS (SEQ ID NO: 1495) | QQGNTLPW T (SEQ ID NO: 1255) | | | |
| AHH03795 | QDISNY (SEQ ID NO: 27) | YTS (SEQ ID NO: 1495) | QQGNTLPW T (SEQ ID NO: 1255) | | | |
| AHH03797 | QSLENSNG NTY (SEQ ID NO: 1300) | RVS (SEQ ID NO: 1361) | LQVTHVPFA (SEQ ID NO: 1096) | | | |
| AHH03799 | QSLVHSYG NTY (SEQ ID NO: 1307) | KVS (SEQ ID NO: 1062) | SQSTHVPHT (SEQ ID NO: 1369) | | | |
| >AH04501-VH | KASQNVGT NVA (SEQ ID NO: 1038) | SASYRYS G (SEQ ID NO: 1362) | QQYNSYPY T (SEQ ID NO: 15) | | | |
| >AH04515-VH | KASQNVGT NVA (SEQ ID NO: 1038) | SASYRYS G (SEQ ID NO: 1362) | QQYNSYPY T (SEQ ID NO: 15) | | | |
| >AH04502-VH | KASQNVGI NVA (SEQ ID NO: 1037) | SASYRYS G (SEQ ID NO: 1362) | QQYNSYPY T (SEQ ID NO: 15) | | | |
| >AH04512-VH | KASQNVGT NVA (SEQ ID NO: 1038) | SASYRYS G (SEQ ID NO: 1362) | QQYNSYPY T (SEQ ID NO: 15) | | | |
| >AH04522-VH | KAGQNVG TNVA (SEQ ID NO: 1036) | SASYRYS G (SEQ ID NO: 1362) | QQYNSYPY T (SEQ ID NO: 15) | | | |
| >AH04513-VH | KASQNVGT NVA (SEQ ID NO: 1038) | SASYRYS G (SEQ ID NO: 1362) | QQYNSYPY T (SEQ ID NO: 15) | | | |
| >AH04523-VH | KASQNVGT NVA (SEQ ID NO: 1038) | SASYRYS G (SEQ ID NO: 1362) | QQYNSYPY T (SEQ ID NO: 15) | | | |
| >AH04503-VH | KASQNVGT NVA (SEQ ID NO: 1038) | SASYRYS G (SEQ ID NO: 1362) | QQYNSYPW T (SEQ ID NO: 36) | | | |
| >AH04529-VH | KASQNVGT NVA (SEQ ID NO: 1038) | SASYRYS G (SEQ ID NO: 1362) | QQYNSYPY T (SEQ ID NO: 15) | | | |
| >AH04510-VH | KASQNVGT NVA (SEQ ID NO: 1038) | SASYRYS G (SEQ ID NO: 1362) | QQYNSYPY T (SEQ ID NO: 15) | | | |
| >AH04528-VH | KASQNVGT NVA (SEQ ID NO: 1038) | SASYRYS G (SEQ ID NO: 1362) | QQYNSYPY T (SEQ ID NO: 15) | | | |
| >AH04511-VH | KASQNVGT NVA (SEQ ID NO: 1038) | SASYRYS G (SEQ ID NO: 1362) | QQYNSYPY T (SEQ ID NO: 15) | | | |
| >AH04504-VH | KASQNVGT NVA (SEQ ID NO: 1038) | SASYRYS G (SEQ ID NO: 1362) | QQYNSYPY T (SEQ ID NO: 15) | | | |
| >AH04520-VH | KASQNVGT NVA (SEQ ID NO: 1038) | SASYRYS G (SEQ ID NO: 1362) | QQYNSYPY T (SEQ ID NO: 15) | | | |
| >AH04507-VH | KASQNVGT NVA (SEQ ID NO: 1038) | SASYRYS G (SEQ ID NO: 1362) | QQYNSYPY T (SEQ ID NO: 15) | | | |
| >AH04527-VH | KASQNVGT NVA (SEQ ID NO: 1038) | SASYRYS G (SEQ ID NO: 1362) | QQYNSYPY T (SEQ ID NO: 15) | | | |
| >AH04505-VH | KASQNVGT NVA (SEQ ID NO: 1038) | SASYRYS G (SEQ ID NO: 1362) | QQYNSYPY T (SEQ ID NO: 15) | | | |
| >AH04516-VH | KASQNVGT NVA (SEQ ID NO: 1038) | SASYRYS G (SEQ ID NO: 1362) | QQYNSYPW T (SEQ ID NO: 36) | | | |
| >AH04525-VH | KASQNVGT NVA (SEQ ID NO: 1038) | SASYRYS G (SEQ ID NO: 1362) | QQYNSYPY T (SEQ ID NO: 15) | | | |
| >AH04509-VH | KASQNVGT NVA (SEQ ID NO: 1038) | SASYRYS G (SEQ ID NO: 1362) | QQYNNSPLT (SEQ ID NO: 1282) | | | |

| | | | |
|---|---|---|---|
| >AH04521-VH | KASQNVGTNVA (SEQ ID NO: 1038) | SASYRYSG (SEQ ID NO: 1362) | QQYNSYPYT (SEQ ID NO: 15) |
| >AH04526-VH | KASQNVGTNVA (SEQ ID NO: 1038) | SASYRYSG (SEQ ID NO: 1362) | QQYNSYPYT (SEQ ID NO: 15) |
| >AH04514-VH | KASQNVGTNVA (SEQ ID NO: 1038) | SASYRYSG (SEQ ID NO: 1362) | QQYNSYPYT (SEQ ID NO: 15) |
| >AH04524-VH | KASQNVGTNVA (SEQ ID NO: 1038) | SASYRYSG (SEQ ID NO: 1362) | QQYNSYPYT (SEQ ID NO: 15) |
| >AH04530-VH | KASQNVGTNVA (SEQ ID NO: 1038) | SASYRYSG (SEQ ID NO: 1362) | QQYNSYPWT (SEQ ID NO: 36) |
| >AH04517-VH | KASQSVGTNVA (SEQ ID NO: 1040) | SASYRYSG (SEQ ID NO: 1362) | QQYNNYPWT (SEQ ID NO: 1284) |
| >AH04506-VH | KASQNVGTNVA (SEQ ID NO: 1038) | SASYRYSG (SEQ ID NO: 1362) | QQYNSYPWT (SEQ ID NO: 36) |
| >AH04508-VH | KASQNVGTNVA (SEQ ID NO: 1038) | SASYRYSG (SEQ ID NO: 1362) | QQYNSYPYT (SEQ ID NO: 15) |
| >AH04518-VH | KASQNVGTNVA (SEQ ID NO: 1038) | SASYRYSG (SEQ ID NO: 1362) | QQYNSYPYT (SEQ ID NO: 15) |
| AH04734 | QDIRNY (SEQ ID NO: 1202) | YTS (SEQ ID NO: 1495) | QQGNTLPPT (SEQ ID NO: 1253) |
| AH04750 | QDISNY (SEQ ID NO: 27) | YTS (SEQ ID NO: 1495) | QQGNTLPPT (SEQ ID NO: 1253) |
| AH05214 | SSISSSN (SEQ ID NO: 1382) | GTS (SEQ ID NO: 983) | QQWSSYPLT (SEQ ID NO: 1277) |
| AH05247 | QNVGTN (SEQ ID NO: 12) | SAS (SEQ ID NO: 13) | QQYNSYPLT (SEQ ID NO: 42) |
| AH05249 | QSVNND (SEQ ID NO: 1309) | YAS (SEQ ID NO: 1476) | QQDYRSPYT (SEQ ID NO: 1249) |
| AH05251 | QSIVHSNGNTY (SEQ ID NO: 1299) | KVS (SEQ ID NO: 1062) | FQGSHVPPT (SEQ ID NO: 966) |
| AH05256 | QDISNY (SEQ ID NO: 27) | HTS (SEQ ID NO: 1002) | QQSNSLPPT (SEQ ID NO: 1271) |
| AH05257 | QDISNY (SEQ ID NO: 27) | YTS (SEQ ID NO: 1495) | QQGHTLPPT (SEQ ID NO: 1252) |
| AH05258 | QDVSTA (SEQ ID NO: 1209) | SAS (SEQ ID NO: 13) | QQHYSTPFT (SEQ ID NO: 1260) |
| AH05259 | ENIYSF (SEQ ID NO: 928) | NAK (SEQ ID NO: 28) | QHHYGIPYT (SEQ ID NO: 1214) |
| AH05268 | QDINRY (SEQ ID NO: 1201) | RAN (SEQ ID NO: 1345) | LQYDEFPYT (SEQ ID NO: 1106) |
| AH05271 | ENIYFS (SEQ ID NO: 927) | NAN (SEQ ID NO: 1142) | KQAYDVPWT (SEQ ID NO: 1058) |
| AH05274 | QNVGTN (SEQ ID NO: 12) | SAS (SEQ ID NO: 13) | QQYNSYPYT (SEQ ID NO: 15) |
| AH05280 | QSVNND (SEQ ID NO: 1309) | YAS (SEQ ID NO: 1476) | QQAYWSPYT (SEQ ID NO: 1248) |
| AH05285 | QDISNY (SEQ ID NO: 27) | YTS (SEQ ID NO: 1495) | QQGNTLPPT (SEQ ID NO: 1253) |
| AH05286 | QDVNTA (SEQ ID NO: 1206) | WAS (SEQ ID NO: 1450) | QQHYSSPWT (SEQ ID NO: 1258) |
| AH4501 | QNVGTN (SEQ ID NO: 12) | SAS (SEQ ID NO: 13) | QQYNSYPYT (SEQ ID NO: 15) |
| AH4502 | QNVGIN (SEQ ID NO: 1243) | SAS (SEQ ID NO: 13) | QQYNSYPYT (SEQ ID NO: 15) |
| AH4503 | QNVGTN (SEQ ID NO: 12) | SAS (SEQ ID NO: 13) | QQYNSYPWT (SEQ ID NO: 36) |
| AH4505 | QNVGTN (SEQ ID NO: 12) | SAS (SEQ ID NO: 13) | QQYNSYPYT (SEQ ID NO: 15) |
| AH4509 | QNVGTN (SEQ ID NO: 12) | SAS (SEQ ID NO: 13) | QQYNNSPLT (SEQ ID NO: 1282) |
| AH4511 | QNVGTN (SEQ ID NO: 12) | SAS (SEQ ID NO: 13) | QQYNSYPYT (SEQ ID NO: 15) |
| AH4518 | QNVGTN (SEQ ID NO: 12) | SAS (SEQ ID NO: 13) | QQYNSYPYT (SEQ ID NO: 15) |
| AH4523 | QNVGTN (SEQ ID NO: 12) | SAS (SEQ ID NO: 13) | QQYNSYPYT (SEQ ID NO: 15) |
| AH4524 | QNVGTN (SEQ ID NO: 12) | SAS (SEQ ID NO: 13) | QQYNSYPYT (SEQ ID NO: 15) |
| AH4525 | QNVGTN (SEQ ID NO: 12) | SAS (SEQ ID NO: 13) | QQYNSYPYT (SEQ ID NO: 15) |
| BP003-T2P1C4 | QNVGTN (SEQ ID NO: 12) | SAS (SEQ ID NO: 13) | QQYNSYPYT (SEQ ID NO: 15) |
| BP003-T2P1D10 | QNVGTN (SEQ ID NO: 12) | SAS (SEQ ID NO: 13) | QQYNRYPYT (SEQ ID NO: 1285) |

| | | | |
|---|---|---|---|
| BP003-T2P1D7 | QSIVHSNGNTY (SEQ ID NO: 1299) | KVS (SEQ ID NO: 1062) | FQGSHVPPT (SEQ ID NO: 966) |
| BP003-T2P1E3 | QNVGTN (SEQ ID NO: 12) | SAS (SEQ ID NO: 13) | QQYNSYPYT (SEQ ID NO: 15) |
| BP003-T2P1D1 | ENSYSY (SEQ ID NO: 52) | NAK (SEQ ID NO: 28) | QHHYGTPYT (SEQ ID NO: 54) |
| BL_592989-2015_G2_P8_G02 | QNVGTN (SEQ ID NO: 12) | SAS (SEQ ID NO: 13) | QQYNSYPYT (SEQ ID NO: 15) |
| BL_592989-2016_H2_P8_H02 | QSLVHSNGNTY (SEQ ID NO: 1306) | EVS (SEQ ID NO: 944) | SQSTHVPYT (SEQ ID NO: 1375) |
| BL_592989-2017_A3_P8_A03 | QDVNTAVA (SEQ ID NO: 1207) | WAS (SEQ ID NO: 1450) | QQHYSSPWT (SEQ ID NO: 1258) |
| BL_592989-2018_B3_P8_B03 | QNVGTN (SEQ ID NO: 12) | SAS (SEQ ID NO: 13) | QQYNSYPYT (SEQ ID NO: 15) |
| BL_592989-2019_C3_P8_C03 | QNVGTN (SEQ ID NO: 12) | SAS (SEQ ID NO: 13) | QQYNSYPYT (SEQ ID NO: 15) |
| BL_592989-2021_E3_P8_E03 | QNVGTN (SEQ ID NO: 12) | SAS (SEQ ID NO: 13) | QQYNSYPYT (SEQ ID NO: 15) |
| BL_592989-2022_F3_P8_F03 | QNVGTN (SEQ ID NO: 12) | SAS (SEQ ID NO: 13) | QQYNSYPYT (SEQ ID NO: 15) |
| BL_592989-2023_G3_P8_G03 | QSLVHSNGNTY (SEQ ID NO: 1306) | EVS (SEQ ID NO: 944) | SQSTHVPYT (SEQ ID NO: 1375) |
| BL_592989-2024_H3_P8_H03 | QDIRNY (SEQ ID NO: 1202) | YTS (SEQ ID NO: 1495) | QQGNTLPPT (SEQ ID NO: 1253) |
| BL_592989-2025_A4_P8_A04 | QNVGTN (SEQ ID NO: 12) | SAS (SEQ ID NO: 13) | QQYNSYPYT (SEQ ID NO: 15) |
| BL_592989-2026_B4_P8_B04 | ENIYSY (SEQ ID NO: 930) | NAK (SEQ ID NO: 28) | QHHYGSPYT (SEQ ID NO: 1216) |
| BL_592989-2027_C4_P8_C04 | QNVGTN (SEQ ID NO: 12) | SAS (SEQ ID NO: 13) | QQYNSYPYT (SEQ ID NO: 15) |
| BL_592989-2029_E4_P8_E04 | QNVGTN (SEQ ID NO: 12) | SAS (SEQ ID NO: 13) | QQYNSYPYT (SEQ ID NO: 15) |
| BL_592989-2030_F4_P8_F04 | QNVGTN (SEQ ID NO: 12) | SAS (SEQ ID NO: 13) | QQYNSYPWT (SEQ ID NO: 36) |
| BL_592989-2031_G4_P8_G04 | QNVGTN (SEQ ID NO: 12) | SAS (SEQ ID NO: 13) | QQYNSYPYT (SEQ ID NO: 15) |
| BL_592989-2032_H4_P8_H04 | QNVGTN (SEQ ID NO: 12) | SAS (SEQ ID NO: 13) | QQYNSYPYT (SEQ ID NO: 15) |
| BL_592989-2033_A5_P8_A05 | ENIYSY (SEQ ID NO: 930) | NAK (SEQ ID NO: 28) | QHHYGIPYT (SEQ ID NO: 1214) |
| BL_592989-2034_B5_P8_B05 | QNVGTN (SEQ ID NO: 12) | SAS (SEQ ID NO: 13) | QQYNSYPYT (SEQ ID NO: 15) |
| BL_592989-2035_C5_P8_C05 | QNVGTN (SEQ ID NO: 12) | SAS (SEQ ID NO: 13) | QQYNSYPYT (SEQ ID NO: 15) |
| BL_592989-2037_E5_P8_E05 | QNVGTN (SEQ ID NO: 12) | SAS (SEQ ID NO: 13) | QQYNSYPYT (SEQ ID NO: 15) |
| BL_592989-2038_F5_P8_F05 | QNVGTN (SEQ ID NO: 12) | SAS (SEQ ID NO: 13) | QQYNSYPYT (SEQ ID NO: 15) |
| BL_592989-2039_G5_P8_G05 | QNVGTN (SEQ ID NO: 12) | SAS (SEQ ID NO: 13) | QQYNNYPWT (SEQ ID NO: 1284) |
| BL_592989-2040_H5_P8_H05 | QNVGTN (SEQ ID NO: 12) | SAS (SEQ ID NO: 13) | QQYNSYPYT (SEQ ID NO: 15) |
| BL_592989-2041_A6_P8_A06 | ENSYSY (SEQ ID NO: 52) | NAK (SEQ ID NO: 28) | QHHYGTPYT (SEQ ID NO: 54) |
| BL_592989-2042_B6_P8_B06 | ENSYSY (SEQ ID NO: 52) | NAK (SEQ ID NO: 28) | QHHYGTPYT (SEQ ID NO: 54) |
| BL_592989-2043_C6_P8_C06 | ENIYSY (SEQ ID NO: 930) | NAK (SEQ ID NO: 28) | QHHYGTPYT (SEQ ID NO: 54) |
| BL_592989-2044_D6_P8_D06 | QNVGTN (SEQ ID NO: 12) | SAS (SEQ ID NO: 13) | QQYNTYPYT (SEQ ID NO: 1287) |
| BL_592989-2045_E6_P8_E06 | QNVGTN (SEQ ID NO: 12) | SAS (SEQ ID NO: 13) | QQYNSYPYT (SEQ ID NO: 15) |
| BL_592989-2046_F6_P8_F06 | QNVGTN (SEQ ID NO: 12) | SAS (SEQ ID NO: 13) | QQYNSYPYT (SEQ ID NO: 15) |

| | | | |
|---|---|---|---|
| BL_592 989-2047_G6_P8_G06 | QNVGTN (SEQ ID NO: 12) | SAS (SEQ ID NO: 13) | QQYNNYPWT (SEQ ID NO: 1284) |
| BL_592 989-2048_H6_P8_H06 | QNVGTN (SEQ ID NO: 12) | SAS (SEQ ID NO: 13) | QQYNSYPYT (SEQ ID NO: 15) |
| BL_592 989-2049_A7_P8_A07 | ENIYSY (SEQ ID NO: 930) | NAK (SEQ ID NO: 28) | QHHYGTPYT (SEQ ID NO: 54) |
| BL_592 989-2051_C7_P8_C07 | QNVGTN (SEQ ID NO: 12) | SAS (SEQ ID NO: 13) | QQYNSYPYT (SEQ ID NO: 15) |
| BL_592 989-2052_D7_P8_D07 | QSIVHSNGNTY (SEQ ID NO: 1299) | KVS (SEQ ID NO: 1062) | FQGSHVPPT (SEQ ID NO: 966) |
| BL_592 989-2054_F7_P8_F07 | QNVGTN (SEQ ID NO: 12) | SAS (SEQ ID NO: 13) | QQYNNHPYT (SEQ ID NO: 1281) |
| BL_592 989-2055_G7_P8_G07 | QNVGTN (SEQ ID NO: 12) | SAS (SEQ ID NO: 13) | QQYNSYPWT (SEQ ID NO: 36) |
| BL_592 989-2059_C8_P8_C08 | QNVGTN (SEQ ID NO: 12) | SAS (SEQ ID NO: 13) | QQYNTYPYT (SEQ ID NO: 1287) |
| BL_592 989-2060_D8_P8_D08 | ENIYSY (SEQ ID NO: 930) | NAK (SEQ ID NO: 28) | QHHYGSPYT (SEQ ID NO: 1216) |
| BL_592 989-2061_E8_P8_E08 | QNVGTN (SEQ ID NO: 12) | SAS (SEQ ID NO: 13) | QQYNSYPYT (SEQ ID NO: 15) |
| BL_592 989-2062_F8_P8_F08 | ENIYSF (SEQ ID NO: 928) | NAK (SEQ ID NO: 28) | QHHYGTPYT (SEQ ID NO: 54) |
| BL_592 989-2063_G8_P8_G08 | QNVGTNVA (SEQ ID NO: 1246) | SAS (SEQ ID NO: 13) | QQYNSYPYT (SEQ ID NO: 15) |
| BL_592 989-2064_H8_P8_H08 | QNVGTN (SEQ ID NO: 12) | SAS (SEQ ID NO: 13) | QQYNSYPWT (SEQ ID NO: 36) |
| BL_592 989-2065_A9_P8_A09 | ENIYSF (SEQ ID NO: 928) | NAK (SEQ ID NO: 28) | QHHYGTPYT (SEQ ID NO: 54) |
| BL_592 989-2067_C9_P8_C09 | QNVGTN (SEQ ID NO: 12) | SAS (SEQ ID NO: 13) | QQYNNYPLT (SEQ ID NO: 1283) |
| BL_592 989-2068_D9_P8_D09 | ENIYSY (SEQ ID NO: 930) | NAK (SEQ ID NO: 28) | QHHYDTPYT (SEQ ID NO: 30) |
| BL_592 989-2069_E9_P8_E09 | QNVGTN (SEQ ID NO: 12) | SAS (SEQ ID NO: 13) | QQYNSYPYT (SEQ ID NO: 15) |
| BL_592 989-2070_F9_P8_F09 | ENIYSY (SEQ ID NO: 930) | NAK (SEQ ID NO: 28) | QHHYGSPYT (SEQ ID NO: 1216) |
| BL_592 989-2071_G9_P8_G09 | QNVGTN (SEQ ID NO: 12) | SAS (SEQ ID NO: 13) | QQYNSYPYT (SEQ ID NO: 15) |
| BL_592 989-2074_B10_P8_B10 | QNVGTN (SEQ ID NO: 12) | SAS (SEQ ID NO: 13) | QQYNSYPYT (SEQ ID NO: 15) |
| BL_592 989-2076_D10_P8_D10 | QNVGTN (SEQ ID NO: 12) | SAS (SEQ ID NO: 13) | QQYNRYPYT (SEQ ID NO: 1285) |
| BL_592 989-2077_E10_P8_E10 | QNVGTN (SEQ ID NO: 12) | SAS (SEQ ID NO: 13) | QQYNSYPWT (SEQ ID NO: 36) |
| BL_592 989-2078_F10_P8_F10 | QNVGTN (SEQ ID NO: 12) | SAS (SEQ ID NO: 13) | QQYNSYPYT (SEQ ID NO: 15) |
| BL_592 989-2079_G10_P8_G10 | QNVGTN (SEQ ID NO: 12) | SAS (SEQ ID NO: 13) | QQYNSYPWT (SEQ ID NO: 36) |
| BL_592 989-2080_H10_P8_H10 | QDIRNY (SEQ ID NO: 1202) | YTS (SEQ ID NO: 1495) | QQGNTLPPT (SEQ ID NO: 1253) |
| BP003-T2P1A7 | ENIYSY (SEQ ID NO: 930) | NAK (SEQ ID NO: 28) | QHHYGTPYT (SEQ ID NO: 54) |
| BP003-T2P1C8 | QNVGTN SEQ ID NO: 12 | SAS (SEQ ID NO: 13) | QQYNTYPYT (SEQ ID NO: 1287) |
| BP003-T2P1F4 | QNVGTN (SEQ ID NO: 12) | SAS (SEQ ID NO: 13) | QQYNSYPWT (SEQ ID NO: 36) |
| BP003-T2P1G2 | QNVGTN (SEQ ID NO: 12) | SAS (SEQ ID NO: 13) | QQYNSYPYT (SEQ ID NO: 15) |
| BP003-T2P1G4 | QNVGTN SEQ ID NO: 12 | SAS (SEQ ID NO: 13) | QQYNSYPYT (SEQ ID NO: 15) |
| BP003-T2P1G7 | QNVGTN (SEQ ID NO: 12) | SAS (SEQ ID NO: 13) | QQYNSYPWT (SEQ ID NO: 36) |

| | | | |
|---|---|---|---|
| BP003-T2P1H5 | QNVGTN (SEQ ID NO: 12) | SAS (SEQ ID NO: 13) | QQYNSYPYT (SEQ ID NO: 15) |
| BP003T3P2-1 | ENIYSY (SEQ ID NO: 930) | NAK (SEQ ID NO: 28) | QHHYDTPYT (SEQ ID NO: 30) |
| BP003T3P2-10 | QDINRY (SEQ ID NO: 1201) | RAN (SEQ ID NO: 1345) | LQYDEFPYT (SEQ ID NO: 1106) |
| BP003T3P2-11 | QDINRY (SEQ ID NO: 1201) | RAN (SEQ ID NO: 1345) | LQYDEFPYT (SEQ ID NO: 1106) |
| BP003T3P2-12 | QDINNF (SEQ ID NO: 1200) | RAN (SEQ ID NO: 1345) | LQYDEFPWT (SEQ ID NO: 1105) |
| BP003T3P2-13 | ENIYSY (SEQ ID NO: 930) | NAK (SEQ ID NO: 28) | QHHYGSPYT (SEQ ID NO: 1216) |
| BP003T3P2-14 | ENIYSY (SEQ ID NO: 930) | NAK (SEQ ID NO: 28) | QHHYDTPYT (SEQ ID NO: 30) |
| BP003T3P2-15 | ENSYSY (SEQ ID NO: 52) | NAK (SEQ ID NO: 28) | QHHYGTPYT (SEQ ID NO: 54) |
| BP003T3P2-16 | ENIYSY (SEQ ID NO: 930) | NAK (SEQ ID NO: 28) | QHHYDTPYT (SEQ ID NO: 30) |
| BP003T3P2-17 | ENIYSY (SEQ ID NO: 930) | NAK (SEQ ID NO: 28) | QHHYDTPYT (SEQ ID NO: 30) |
| BP003T3P2-18 | ENIYSY (SEQ ID NO: 930) | NAK (SEQ ID NO: 28) | QHHYGSPYT (SEQ ID NO: 1216) |
| BP003T3P2-19 | ENIYSY (SEQ ID NO: 930) | NAK (SEQ ID NO: 28) | QHHYDTPYT (SEQ ID NO: 30) |
| BP003T3P2-2 | ENIYSY (SEQ ID NO: 930) | NAK (SEQ ID NO: 28) | QHHYDTPYT (SEQ ID NO: 30) |
| BP003T3P2-20 | KNSYSY (SEQ ID NO: 1057) | NAK (SEQ ID NO: 28) | QHHYGTPYT (SEQ ID NO: 54) |
| BP003T3P2-21 | ENIYSY (SEQ ID NO: 930) | NAK (SEQ ID NO: 28) | QHHYGTPYT (SEQ ID NO: 54) |
| BP003T3P2-22 | ENSYSY (SEQ ID NO: 52) | NAK (SEQ ID NO: 28) | QHHYGTPYT (SEQ ID NO: 54) |
| BP003T3P2-23 | ENSYSY (SEQ ID NO: 52) | NAK (SEQ ID NO: 28) | QHHYGSPYT (SEQ ID NO: 1216) |
| BP003T3P2-24 | ENSYSY (SEQ ID NO: 52) | NAK (SEQ ID NO: 28) | QHHYGSPYT (SEQ ID NO: 1216) |
| BP003T3P2-25 | ENSYSY (SEQ ID NO: 52) | NAK (SEQ ID NO: 28) | QHHYGSPYT (SEQ ID NO: 1216) |
| BP003T3P2-26 | ENIYSY (SEQ ID NO: 930) | NAK (SEQ ID NO: 28) | QHHYGSPYT (SEQ ID NO: 1216) |
| BP003T3P2-27 | QDISNY (SEQ ID NO: 27) | YAS (SEQ ID NO: 1476) | QQGNTLPWT (SEQ ID NO: 1255) |
| BP003T3P2-28 | QDISNY (SEQ ID NO: 27) | HTS (SEQ ID NO: 1002) | QQSNTLPPT (SEQ ID NO: 1272) |
| BP003T3P2-29 | QDISNY (SEQ ID NO: 27) | HTS (SEQ ID NO: 1002) | QQSNSLPPT (SEQ ID NO: 1271) |
| BP003T3P2-3 | ENIYSY (SEQ ID NO: 930) | NAK (SEQ ID NO: 28) | QHHYDTPYT (SEQ ID NO: 30) |
| BP003T3P2-30 | QDISNY (SEQ ID NO: 27) | HTS (SEQ ID NO: 1002) | QQSNSLPPT (SEQ ID NO: 1271) |
| BP003T3P2-31 | QDISNY (SEQ ID NO: 27) | HTS (SEQ ID NO: 1002) | QQSNSLPPT (SEQ ID NO: 1271) |
| BP003T3P2-32 | QDISNY (SEQ ID NO: 27) | YTS (SEQ ID NO: 1495) | QQGNTLPPT (SEQ ID NO: 1253) |
| BP003T3P2-33 | QDISNY (SEQ ID NO: 27) | HTS (SEQ ID NO: 1002) | QQSNSLPPT (SEQ ID NO: 1271) |
| BP003T3P2-34 | QDISNY (SEQ ID NO: 27) | HTS (SEQ ID NO: 1002) | QQSNSLPPT (SEQ ID NO: 1271) |
| BP003T3P2-35 | QDISNY (SEQ ID NO: 27) | HTS (SEQ ID NO: 1002) | QQSNTLPPT SEQ ID NO: 1272) |
| BP003T3P2-36 | QDISNY (SEQ ID NO: 27) | HTS (SEQ ID NO: 1002) | QQSNTLPPT (SEQ ID NO: 1272) |
| BP003T3P2-37 | QDISNY (SEQ ID NO: 27) | HTS (SEQ ID NO: 1002) | QQGNTLPPT (SEQ ID NO: 1253) |
| BP003T3P2-38 | QDISNY (SEQ ID NO: 27) | YTS (SEQ ID NO: 1495) | QQGNTLPPT (SEQ ID NO: 1253) |
| BP003T3P2-39 | QDISNY (SEQ ID NO: 27) | HTS (SEQ ID NO: 1002) | QQGNTLPPT (SEQ ID NO: 1253) |
| BP003T3P2-4 | ENIYSY (SEQ ID NO: 930) | NAK (SEQ ID NO: 28) | QHHYDTPYT (SEQ ID NO: 30) |
| BP003T3P2-40 | QNVGTN (SEQ ID NO: 12) | SAS (SEQ ID NO: 13) | QQYNSYPYT (SEQ ID NO: 15) |
| BP003T3P2-41 | QNVGTN (SEQ ID NO: 12) | SAS (SEQ ID NO: 13) | QQYNSYPYT (SEQ ID NO: 15) |
| BP003T3P2-42 | QNVGTN (SEQ ID NO: 12) | SAS (SEQ ID NO: 13) | QQYNSYPYT (SEQ ID NO: 15) |
| BP003T3P2-43 | QNVGTN (SEQ ID NO: 12) | SAS (SEQ ID NO: 13) | QQYNTYPYT (SEQ ID NO: 1287) |

| | | | |
|---|---|---|---|
| BP003T 3P2-44 | QNVGTN (SEQ ID NO: 12) | SAS (SEQ ID NO: 13) | QQYNSYPYT (SEQ ID NO: 15) |
| BP003T 3P2-45 | QNVGTN (SEQ ID NO: 12) | SAS (SEQ ID NO: 13) | QQYNTYPYT (SEQ ID NO: 1287) |
| BP003T 3P2-46 | QDIGLN (SEQ ID NO: 1198) | ATS (SEQ ID NO: 618) | LQYASSPFT (SEQ ID NO: 1097) |
| BP003T 3P2-47 | QNVGTN (SEQ ID NO: 12) | SAS (SEQ ID NO: 13) | QQYNTYPYT (SEQ ID NO: 1287) |
| BP003T 3P2-48 | QNVGTN (SEQ ID NO: 12) | SAS (SEQ ID NO: 13) | QQYNSYPYT (SEQ ID NO: 15) |
| BP003T 3P2-49 | QNVGTN (SEQ ID NO: 12) | SAS (SEQ ID NO: 13) | QQYNSYPYT (SEQ ID NO: 15) |
| BP003T 3P2-5 | ENIYSY (SEQ ID NO: 930) | NAK (SEQ ID NO: 28) | QHHYDTPYT (SEQ ID NO: 30) |
| BP003T 3P2-50 | QNVGTN (SEQ ID NO: 12) | SAS (SEQ ID NO: 13) | QQYNSYPYT (SEQ ID NO: 15) |
| BP003T 3P2-51 | QSLVHSNGNTY (SEQ ID NO: 1306) | KVS (SEQ ID NO: 1062) | SQSTHVPPT (SEQ ID NO: 1371) |
| BP003T 3P2-52 | QNVGTN (SEQ ID NO: 12) | SAS (SEQ ID NO: 13) | QQYNSYPYT (SEQ ID NO: 15) |
| BP003T 3P2-53 | QNVGTN (SEQ ID NO: 12) | SAS (SEQ ID NO: 13) | QQYNSYPYT (SEQ ID NO: 15) |
| BP003T 3P2-54 | QNVGTN (SEQ ID NO: 12) | SAS (SEQ ID NO: 13) | QQYNSYPYT (SEQ ID NO: 15) |
| BP003T 3P2-55 | QNVGTN (SEQ ID NO: 12) | SAS (SEQ ID NO: 13) | QQYNSYPYT (SEQ ID NO: 15) |
| BP003T 3P2-56 | QNVGTN (SEQ ID NO: 12) | SAS (SEQ ID NO: 13) | QQYNSYPYT (SEQ ID NO: 15) |
| BP003T 3P2-57 | QNVGTN (SEQ ID NO: 12) | SAS (SEQ ID NO: 13) | QQYNSYPYT (SEQ ID NO: 15) |
| BP003T 3P2-58 | QNVGTN (SEQ ID NO: 12) | SAS (SEQ ID NO: 13) | QQYNSYPYT (SEQ ID NO: 15) |
| BP003T 3P2-59 | QDVRTA (SEQ ID NO: 1208) | STS (SEQ ID NO: 1386) | QQYSNYLTF (SEQ ID NO: 1290) |
| BP003T 3P2-6 | ENIYSY (SEQ ID NO: 930) | NAK (SEQ ID NO: 28) | QHHYDTPYT (SEQ ID NO: 30) |
| BP003T 3P2-60 | QNVGTN (SEQ ID NO: 12) | SAS (SEQ ID NO: 13) | QQYNTYPYT (SEQ ID NO: 1287) |
| BP003T 3P2-61 | QNVGTN (SEQ ID NO: 12) | SAS (SEQ ID NO: 13) | XQYNSYPYT (SEQ ID NO: 1475) |
| BP003T 3P2-62 | QSVNND (SEQ ID NO: 1309) | YAS (SEQ ID NO: 1476) | QQAYWSPYT (SEQ ID NO: 1248) |
| BP003T 3P2-63 | QDVNTA (SEQ ID NO: 1206) | WAS (SEQ ID NO: 1450) | QQHYSSPWT (SEQ ID NO: 1258) |
| BP003T 3P2-64 | QDVNTA (SEQ ID NO: 1206) | WAS (SEQ ID NO: 1450) | QQHYSSPWT (SEQ ID NO: 1258) |
| BP003T 3P2-65 | QDVNTA (SEQ ID NO: 1206) | WAS (SEQ ID NO: 1450) | QQHYSSPWT (SEQ ID NO: 1258) |
| BP003T 3P2-66 | QEISGY (SEQ ID NO: 1210) | AAS (SEQ ID NO: 599) | LQYASYPYT (SEQ ID NO: 1103) |
| BP003T 3P2-67 | QSIVHSNGNTY (SEQ ID NO: 1299) | KVS (SEQ ID NO: 1062) | FQGSHVPPT (SEQ ID NO: 966) |
| BP003T 3P2-68 | QSIVHSNGNTY (SEQ ID NO: 1299) | KVS (SEQ ID NO: 1062) | FQGSHVPRT (SEQ ID NO: 967) |
| BP003T 3P2-69 | QSIVHNNGNTY (SEQ ID NO: 1298) | KVS (SEQ ID NO: 1062) | FQGSYVPRT (SEQ ID NO: 971) |
| BP003T 3P2-7 | ENIYSY (SEQ ID NO: 930) | NAK (SEQ ID NO: 28) | QHHYDTPYT (SEQ ID NO: 30) |
| BP003T 3P2-70 | QSIVHSNGNTY (SEQ ID NO: 1299) | KVS (SEQ ID NO: 1062) | FQGSHVPPT (SEQ ID NO: 966) |
| BP003T 3P2-71 | QSIVHSNGNTY (SEQ ID NO: 1299) | KVS (SEQ ID NO: 1062) | FQGSHVPPT (SEQ ID NO: 966) |
| BP003T 3P2-72 | QSIVHSNGNTY (SEQ ID NO: 1299) | KVS (SEQ ID NO: 1062) | FQGSHVPTF (SEQ ID NO: 968) |
| BP003T 3P2-73 | QSIVHSNGNTY (SEQ ID NO: 1299) | KVS (SEQ ID NO: 1062) | FQGSHVPPT (SEQ ID NO: 966) |
| BP003T 3P2-74 | QSIVHSNGNTY (SEQ ID NO: 1299) | KVS (SEQ ID NO: 1062) | FQGSHVPPT (SEQ ID NO: 966) |
| BP003T 3P2-75 | QDVSTA (SEQ ID NO: 1209) | SAS (SEQ ID NO: 13) | QQHYSTPYT (SEQ ID NO: 1265) |
| BP003T 3P2-8 | ENIYSY (SEQ ID NO: 930) | NAK (SEQ ID NO: 28) | QHHYDTPYT (SEQ ID NO: 30) |

| | | | |
|---|---|---|---|
| BP003T 3P2-9 | DNIYNY (SEQ ID NO: 833) | NAK (SEQ ID NO: 28) | QHHYGSPW T (SEQ ID NO: 1215). |

2. The antibody of claim 1, wherein the antibody does not disrupt the binding of the IL-2 ligand to the alpha chain of the IL-2 receptor (CD25), and binds to a different epitope than to which 7G7B6 binds selected from D5, D16, D17, D11, D34, D36, AH05259, AH05268, AH05271, AH05280, and AH05286.

3. The antibody of claim 1, wherein the antibody does not disrupt the binding of the IL-2 ligand to the alpha chain of the IL-2 receptor (CD25), but does disrupt the trimerization of the beta, gamma, and alpha (CD25) chains of the IL-2 receptor selected from D5, D7, D11, D17, D34, D36, AH04501, AH04502, AH04503, AH04505, AH04507, AH04509, AH04511, AH04518, AH04522, AH04523, AH04525, AH04526, AH04527, AH04547, AH04750, AH05256, AH05247, AH05268, BP003-T2P1D10, BP003-T2P1D7, BP003-T2P1C4, and BP003-T2P1E3.

4. The antibody of claim 1, wherein the antibody disrupts the binding of the IL-2 ligand to the IL-2 receptor, and binds to a different epitope than to which Daclizumab or Bacilix-imab bind, wherein the antibody is D34, AH04511, AH05274, and AH04503.

5. The antibody of claim 1, wherein the antibody exhibits a higher affinity of binding to CD25 at a pH lower than 7.4, when compared to the affinity of binding to CD25 at a pH of 7.4.

6. The antibody of claim 5, wherein the antibody exhibits a higher affinity of binding to CD25 at a pH of about 6.5.

7. The antibody of claim 1, wherein the antibody comprises the amino acid sequence of any one of the variable heavy chain sequences presented in SEQ ID NOS: 2, 4, 6, 8, 17, 19, 21, 23, 32, 38, 44, 46, 48, 56, 60-107, 114, 157, 190, 195, 230, 235, 251, 265, 269, 398, 413, 421, 422, 424, 425, 431-460, 473, 601, 603-606, 608, 611, 615, 617, 619, 868, 869, 936-940, 942, 943, 945-952, 954, 955, 973, 977, 984, 986, 987, 992, 995, 997, 1003-1008, 1010-1015, 1017, 1018, 1020, 1021, 1023, 1025-1027, 1029-1035, 1074, 1075, 1118, 1119, 1123-1128, 1137-1139, 1165-1172, 1174-1179, 1181-1185, 1187, 1188, 1190-1197, 1218, 1220, 1222, 1223-1241, 1313-1318, 1321-1343, 1387-1389, 1395, 1416, 1417, 1419, 1420, 1442-1445, 1453-1455, 1448, 1474, 1496, humanized versions thereof, or an amino acid sequence comprising at least a 80%, at least a 85%, at least a 90%, or at least a 95% sequence identity thereto.

8. The antibody of claim 1, wherein the antibody comprises the amino acid sequence of any one of the variable light chain sequences presented in SEQ ID NOS: 10, 12, 13, 15, 25, 27, 28, 30, 34, 36, 40, 42, 50, 52, 54, 59, 599, 618, 700, 701, 703, 705, 707, 709, 711, 712, 713, 715, 717-720, 722, 724, 725, 727-732, 734-740, 742, 744, 745, 747, 749-752, 754-757, 759, 760, 762, 765-767, 769, 770, 773, 775-778, 780, 781, 783, 785, 787, 789, 791, 793, 794, 795, 797, 799, 801, 803, 804, 806, 807, 809-811, 813, 815, 816, 818, 821-825, 827-833, 835, 837, 838, 841, 842, 844, 846, 848, 849, 851, 853, 854, 857, 858-861, 864, 865, 870-880, 882, 884, 886, 888, 889, 890, 892, 894, 895, 897, 899, 900-903, 905-909, 912, 914, 915, 917-922, 926-928, 930, 944, 958, 959, 961, 963, 966-968, 971, 974, 978, 983, 1002, 1057, 1058, 1062, 1070-1072, 1076, 1085, 1088, 1091, 1097, 1103, 1105, 1106, 1109, 1110, 1112, 1117, 1132, 1142, 1151, 1154, 1157-1159, 1164, 1198, 1200-1202, 1206-1210, 1214-1216, 1243, 1246, 1248, 1249, 1252, 1253, 1255, 1258, 1260, 1265, 1271, 1272, 1277, 1281-1285, 1287, 1290, 1298, 1299, 1306, 1309, 1345, 1347-1350, 1352, 1353, 1355-1357, 1359, 1366, 1371, 1375, 1382, 1386, 1396-1402, 1404, 1408, 1413, 1414, 1423-1425, 1427, 1429, 1430, 1432, 1433, 1436, 1447, 1449, 1450, 1470, 1471, 1475-1478, 1481-1483, 1486-1491, 1495, humanized versions thereof, or an amino acid sequence comprising at least a 80%, at least a 85%, at least a 90%, or at least a 95% sequence identity thereto.

9. The antibody of claim 1, wherein the antibody is a human antibody.

10. The antibody of claim 1, wherein the antibody is a humanized antibody.

11. The antibody of claim 1, wherein the antibody is a chimeric antibody.

12. The antibody of claim 11, wherein the antibody comprises a mouse variable domain, and a human constant domain.

13. The antibody of claim 1, wherein the antibody is an antibody fragment.

14. The antibody of claim 1, wherein the antibody also binds cynomologous monkey CD25.

15. A pharmaceutical composition comprising the antibody of claim 1.

16. A composition comprising a nucleic acid sequence encoding the antibody of claim 1.

17. A vector comprising the nucleic acid sequence of claim 16.

18. A phage expressing any the-antibody of claim 1.

19. A method of treating a subject in need thereof comprising administering to the subject a therapeutically effective amount of the antibody of claim 1.

20. A method of depleting the number of regulatory T cells in a subject comprising administering to the subject a therapeutically effective amount of the antibody of claim 1.

21. The method of claim 19, wherein the subject suffers from cancer or an autoimmune-related disease or disorder.

22. The method of claim 19, wherein the subject suffers from an autoimmune-related disease or disorder.

23. A method of depleting the number of regulatory T cells in a sample comprising peripheral blood mononuclear cells comprising contacting the sample the antibody of claim 1.

24. A kit comprising the antibody of claim 1.

\* \* \* \* \*

SEQUENCE LISTING

```
<160> NUMBER OF SEQ ID NOS: 1501

<210> SEQ ID NO 1
<211> LENGTH: 343
<212> TYPE: DNA
<213> ORGANISM: Mus musculus

<400> SEQUENCE: 1
catgtgcaac tgcagcagtc tggagctgag ctggtaaggc ctgggacttc agtgaagata     60
tcctgcaagg cttctggcta caccttcact aactactggc taggttgggt aaagcagagg    120
cctggacatg gacttgagtg gattggagat atttaccctg gaggtggtta tactaactac    180
aatgagaagt tcaagggcaa ggccacactg actgcagaca catcctccag cactgcctac    240
atgcagctca gtagcctgac atctgaggac tctgctgtct atttctgtgc aagagttact    300
ccggcttcct ggggccaagg caccagtctc acagtctcct cgg                      343

<210> SEQ ID NO 2
<211> LENGTH: 114
<212> TYPE: PRT
<213> ORGANISM: Mus musculus

<400> SEQUENCE: 2
```

-continued

```
His Val Gln Leu Gln Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
                35                  40                  45

Gly Asp Ile Tyr Pro Gly Gly Gly Tyr Thr Asn Tyr Asn Glu Lys Phe
50                  55                  60

Lys Gly Lys Ala Thr Leu Thr Ala Asp Thr Ser Ser Thr Ala Tyr
65                  70                  75                  80

Met Gln Leu Ser Ser Leu Thr Ser Glu Asp Ser Ala Val Tyr Phe Cys
            85                  90                  95

Ala Arg Val Thr Pro Ala Ser Trp Gly Gln Gly Thr Ser Leu Thr Val
                100                 105                 110

Ser Ser
```

<210> SEQ ID NO 3
<211> LENGTH: 24
<212> TYPE: DNA
<213> ORGANISM: Mus musculus

<400> SEQUENCE: 3
ggctacacct tcactaacta ctgg                                    24

<210> SEQ ID NO 4
<211> LENGTH: 8
<212> TYPE: PRT
<213> ORGANISM: Mus musculus

<400> SEQUENCE: 4

Gly Tyr Thr Phe Thr Asn Tyr Trp
1               5

<210> SEQ ID NO 5
<211> LENGTH: 24
<212> TYPE: DNA
<213> ORGANISM: Mus musculus

<400> SEQUENCE: 5
atttaccctg gaggtggtta tact                                    24

<210> SEQ ID NO 6
<211> LENGTH: 8
<212> TYPE: PRT
<213> ORGANISM: Mus musculus

<400> SEQUENCE: 6

Ile Tyr Pro Gly Gly Gly Tyr Thr
1               5

<210> SEQ ID NO 7
<211> LENGTH: 21
<212> TYPE: DNA
<213> ORGANISM: Mus musculus

<400> SEQUENCE: 7
gcaagagtta ctccggcttc c                                       21

<210> SEQ ID NO 8
<211> LENGTH: 7

```
<212> TYPE: PRT
<213> ORGANISM: Mus musculus

<400> SEQUENCE: 8

Ala Arg Val Thr Pro Ala Ser
1               5

<210> SEQ ID NO 9
<211> LENGTH: 322
<212> TYPE: DNA
<213> ORGANISM: Mus musculus

<400> SEQUENCE: 9
gatattgtga tgacccagtc tcaaaaattc atgtccacat cagtaggaga cagggtcagc      60
gtcacctgca aggccagtca gaatgtgggt actaatgtag cctggtatca acagaaacca     120
gggcaatctc ctaaagcact gatttactcg gcatcctacc ggtacagtgg agtccctgat     180
cgcttcacag gcagtggatc tgggacagat ttcactctca ccatcagcaa tgtgcagtct     240
gaagacttgg cagagtattt ctgtcagcaa tataacagct atccgtacac gttcggaggg     300
gggaccaagc tggaaatgaa ac                                              322

<210> SEQ ID NO 10
<211> LENGTH: 107
<212> TYPE: PRT
<213> ORGANISM: Mus musculus

<400> SEQUENCE: 10

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Met Lys
            100                 105

<210> SEQ ID NO 11
<211> LENGTH: 18
<212> TYPE: DNA
<213> ORGANISM: Mus musculus

<400> SEQUENCE: 11
cagaatgtgg gtactaat                                                    18

<210> SEQ ID NO 12
<211> LENGTH: 6
<212> TYPE: PRT
<213> ORGANISM: Mus musculus

<400> SEQUENCE: 12

Gln Asn Val Gly Thr Asn
1               5
```

<210> SEQ ID NO 13
<211> LENGTH: 3
<212> TYPE: PRT
<213> ORGANISM: Mus musculus

<400> SEQUENCE: 13

Ser Ala Ser
1

<210> SEQ ID NO 14
<211> LENGTH: 27
<212> TYPE: DNA
<213> ORGANISM: Mus musculus

<400> SEQUENCE: 14
cagcaatata acagctatcc gtacacg                                        27

<210> SEQ ID NO 15
<211> LENGTH: 9
<212> TYPE: PRT
<213> ORGANISM: Mus musculus

<400> SEQUENCE: 15

Gln Gln Tyr Asn Ser Tyr Pro Tyr Thr
1               5

<210> SEQ ID NO 16
<211> LENGTH: 346
<212> TYPE: DNA
<213> ORGANISM: Mus musculus

<400> SEQUENCE: 16
cagatccaac tgcagcagcc tggggctgag ctggtgaggc ctggggtttc actgaaaatt     60
tcctgcaagg gttctggcta cacattcact gattatgcta tgcactgggt gaggcagagt    120
catgcaaaga gtctagagtg gattggagtt attagtactt actctggtga tgctatctac    180
aaccagaagt tcaagggcaa ggccacaatg actgtcgaca atcctccag cacagcctat     240 ctggaacttg ccagactgac atctgacgat tctgccatct attactgtgc aagaggggta    300
acttttgact actggggcca aggcaccact gtcacagtct cctcgg                   346

<210> SEQ ID NO 17
<211> LENGTH: 115
<212> TYPE: PRT
<213> ORGANISM: Mus musculus

<400> SEQUENCE: 17

Gln Ile Gln Leu Gln Gln Pro Gly Ala Glu Leu Val Arg Pro Gly Val
1               5                   10                  15

Ser Leu Lys Ile Ser Cys Lys Gly Ser Gly Tyr Thr Phe Thr Asp Tyr
            20                  25                  30

Ala Met His Trp Val Arg Gln Ser His Ala Lys Ser Leu Glu Trp Ile
        35                  40                  45

Gly Val Ile Ser Thr Tyr Ser Gly Asp Ala Ile Tyr Asn Gln Lys Phe
    50                  55                  60

Lys Gly Lys Ala Thr Met Thr Val Asp Lys Ser Ser Thr Ala Tyr
65                  70                  75                  80

Leu Glu Leu Ala Arg Leu Thr Ser Asp Asp Ser Ala Ile Tyr Tyr Cys
                85                  90                  95

Ala Arg Gly Val Thr Phe Asp Tyr Trp Gly Gln Gly Thr Thr Val Thr
            100                 105                 110

Val Ser Ser
        115

<210> SEQ ID NO 18
<211> LENGTH: 24
<212> TYPE: DNA
<213> ORGANISM: Mus musculus

<400> SEQUENCE: 18
ggctacacat tcactgatta tgct                                          24

<210> SEQ ID NO 19
<211> LENGTH: 8
<212> TYPE: PRT
<213> ORGANISM: Mus musculus

<400> SEQUENCE: 19

Gly Tyr Thr Phe Thr Asp Tyr Ala
1               5

<210> SEQ ID NO 20
<211> LENGTH: 24
<212> TYPE: DNA
<213> ORGANISM: Mus musculus

<400> SEQUENCE: 20
attagtactt actctggtga tgct                                          24

<210> SEQ ID NO 21
<211> LENGTH: 8
<212> TYPE: PRT
<213> ORGANISM: Mus musculus

<400> SEQUENCE: 21

Ile Ser Thr Tyr Ser Gly Asp Ala
1               5

<210> SEQ ID NO 22
<211> LENGTH: 24
<212> TYPE: DNA
<213> ORGANISM: Mus musculus

<400> SEQUENCE: 22
gcaagagggg taacttttga ctac                                          24

<210> SEQ ID NO 23
<211> LENGTH: 8
<212> TYPE: PRT
<213> ORGANISM: Mus musculus

<400> SEQUENCE: 23

Ala Arg Gly Val Thr Phe Asp Tyr
1               5

<210> SEQ ID NO 24
<211> LENGTH: 322
<212> TYPE: DNA
<213> ORGANISM: Mus musculus

<400> SEQUENCE: 24
gacatccaga tgacacagac tacatcctcc ctgtctgcct ctctgggaga cagagtcacc    60
atcacttgca gggcaagtca ggacattagc aattatttag aatggtatca gcagaaacag   120

```
ggaaaatctc ctcagctcct ggtctataat gcaaaaacct tagcagaagg tgtgccatca    180
aggttcagtg gcagtggatc aggcacacag ttttctctga agatcaacag cctgcagcct    240
gaagattttg gagttatta ctgtcaacat cattatgata ctccgtacac gttcggaggg     300
gggaccaagc tggaaataaa ac                                              322
```

<210> SEQ ID NO 25
<211> LENGTH: 107
<212> TYPE: PRT
<213> ORGANISM: Mus musculus

<400> SEQUENCE: 25

```
Asp Ile Gln Met Thr Gln Thr Thr Ser Ser Leu Ser Ala Ser Leu Gly
1               5                   10                  15

Asp Arg Val Thr Ile Thr Cys Arg Ala Ser Gln Asp Ile Ser Asn Tyr
            20                  25                  30

Leu Glu Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Asp Thr Pro Tyr
                85                  90                  95

Thr Phe Gly Gly Gly Thr Lys Leu Glu Ile Lys
            100                 105
```

<210> SEQ ID NO 26
<211> LENGTH: 18
<212> TYPE: DNA
<213> ORGANISM: Mus musculus

<400> SEQUENCE: 26

```
caggacatta gcaattat                                                    18
```

<210> SEQ ID NO 27
<211> LENGTH: 6
<212> TYPE: PRT
<213> ORGANISM: Mus musculus

<400> SEQUENCE: 27

```
Gln Asp Ile Ser Asn Tyr
1               5
```

<210> SEQ ID NO 28
<211> LENGTH: 3
<212> TYPE: PRT
<213> ORGANISM: Mus musculus

<400> SEQUENCE: 28

```
Asn Ala Lys
1
```

<210> SEQ ID NO 29
<211> LENGTH: 27
<212> TYPE: PRT
<213> ORGANISM: Mus musculus

<400> SEQUENCE: 29

```
Cys Ala Ala Cys Ala Thr Cys Ala Thr Thr Ala Thr Gly Ala Thr Ala
1               5                   10                  15
```

Cys Thr Cys Cys Gly Thr Ala Cys Ala Cys Gly
                20                  25

<210> SEQ ID NO 30
<211> LENGTH: 9
<212> TYPE: PRT
<213> ORGANISM: Mus musculus

<400> SEQUENCE: 30

Gln His His Tyr Asp Thr Pro Tyr Thr
1               5

<210> SEQ ID NO 31
<211> LENGTH: 343
<212> TYPE: DNA
<213> ORGANISM: Mus musculus

<400> SEQUENCE: 31
caggtgcaaa tgcagcagtc tggagctgag ctggtaaggc ctgggacttc agtgaagata      60
tcctgcaagg cttctggcta caccttcact aactactggc taggttgggt aaagcagagg     120
cctggacatg gacttgagtg gattggagat atttaccctg aggtggtta tactaactac      180 aatgagaagt tcaagggcaa ggccacactg actgcagaca catcctccag cactgcctac     240
atgcagctca gtagcctgac atctgaggac tctgctgtct atttctgtgc aagagttact     300
ccggcttcct ggggccaagg caccactctc acagtctcct cgg                       343

<210> SEQ ID NO 32
<211> LENGTH: 114
<212> TYPE: PRT
<213> ORGANISM: Mus musculus

<400> SEQUENCE: 32

Gln Val Gln Met Gln Gln Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
                20                  25                  30

Trp Leu Gly Trp Val Lys Gln Arg Pro Gly His Gly Leu Glu Trp Ile
            35                  40                  45

Gly Asp Ile Tyr Pro Gly Gly Gly Tyr Thr Asn Tyr Asn Glu Lys Phe
        50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val Thr Pro Ala Ser Trp Gly Gln Gly Thr Thr Leu Thr Val
            100                 105                 110

Ser Ser

<210> SEQ ID NO 33
<211> LENGTH: 322
<212> TYPE: DNA
<213> ORGANISM: Mus musculus

<400> SEQUENCE: 33
gatatccaga tgacccagtc tcaaaaattc atgtccacat cagtaggaga cagggtcagc      60
gtcacctgca aggccagtca gaatgtgggt actaatgtag cctggtatca acagaaacca     120
gggcaatctc ctaaagcact gatttactcg gcatcctacc ggtacagtgg agtccctgat     180
cgcttcacag gcagtggatc tgggacagat ttcactctca ccatcagcaa tgtgcagtct    240
gaagacttgg cagagtattt ctgtcagcaa tataacagct atccgtggac gttcggtgga    300
ggcaccaagc tggaaatcaa ac    322

<210> SEQ ID NO 34
<211> LENGTH: 107
<212> TYPE: PRT
<213> ORGANISM: Mus musculus

<400> SEQUENCE: 34

Asp Ile Gln Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Trp
                85                  90                  95

Thr Phe Gly Gly Gly Thr Lys Leu Glu Ile Lys
            100                 105

<210> SEQ ID NO 35
<211> LENGTH: 27
<212> TYPE: DNA
<213> ORGANISM: Mus musculus

<400> SEQUENCE: 35
cagcaatata acagctatcc gtggacg    27

<210> SEQ ID NO 36
<211> LENGTH: 9
<212> TYPE: PRT
<213> ORGANISM: Mus musculus

<400> SEQUENCE: 36

Gln Gln Tyr Asn Ser Tyr Pro Trp Thr
1               5

<210> SEQ ID NO 37
<211> LENGTH: 343
<212> TYPE: DNA
<213> ORGANISM: Mus musculus

<400> SEQUENCE: 37
cagatccaac tgcagcagtc tggagctgag ctggtaaggc ctgggacttc agtgaagata     60
tcctgcaagg cttctggcta caccttcact aactactggc taggttgggt aaagcagagg    120
cctggacatg gacttgagtg gattggagat atttaccctg gaggtggtta tactaactac    180
aatgagaagt tcaagggcaa ggccacactg actgcagaca catcctccag cactgcctac    240
atgcagctca gtagcctgac atctgaggac tctgctgtct atttctgtgc aagagttact    300
ccggcttcct ggggccaagg caccactctc acagtctctg cgg    343

<210> SEQ ID NO 38

<211> LENGTH: 114
<212> TYPE: PRT
<213> ORGANISM: Mus musculus

<400> SEQUENCE: 38

Gln Ile Gln Leu Gln Gln Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
                20                  25                  30

Trp Leu Gly Trp Val Lys Gln Arg Pro Gly His Gly Leu Glu Trp Ile
            35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Thr Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val Thr Pro Ala Ser Trp Gly Gln Gly Thr Thr Leu Thr Val
            100                 105                 110

Ser Ala

<210> SEQ ID NO 39
<211> LENGTH: 322
<212> TYPE: DNA
<213> ORGANISM: Mus musculus

<400> SEQUENCE: 39
gacattctgc tgacccagtc tcaaaaattc atgtccacat cagtaggaga cagggtcagc      60
gtcacctgca aggccagtca gaatgtgggt actaatgtag cctggtatca acagaaacca     120
gggcaatctc ctaaagcact gatttactcg gcatcctacc ggtacagtgg agtccctgat     180
cgcttcacag gcagtggatc tgggacagat ttcactctca ccatcagcaa tgtgcagtct     240
gaagacttgg cagagtattt ctgtcagcaa tataacagct atcctctcac gttcggaggg     300
gggaccaagc tggaaataaa ac                                              322

<210> SEQ ID NO 40
<211> LENGTH: 107
<212> TYPE: PRT
<213> ORGANISM: Mus musculus

<400> SEQUENCE: 40

Asp Ile Leu Leu Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
                20                  25                  30

Val Ala Trp Tyr Gln Gln Lys Pro Gly Gln Ser Pro Lys Ala Leu Ile
            35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Gly Gly Thr Lys Leu Glu Ile Lys
            100                 105

<210> SEQ ID NO 41
<211> LENGTH: 27
<212> TYPE: DNA
<213> ORGANISM: Mus musculus

<400> SEQUENCE: 41
cagcaatata acagctatcc tctcacg    27

<210> SEQ ID NO 42
<211> LENGTH: 9
<212> TYPE: PRT
<213> ORGANISM: Mus musculus

<400> SEQUENCE: 42

Gln Gln Tyr Asn Ser Tyr Pro Leu Thr
1               5

<210> SEQ ID NO 43
<211> LENGTH: 345
<212> TYPE: DNA
<213> ORGANISM: Mus musculus

<400> SEQUENCE: 43
caggtccaac tgcagcagtc tggggctgag ctggtgaggc ctggggtctc agtgaagatt    60
tcctgcaagg gttctggcta cacattcact gattatgcta tgcactgggt gaagcagagt   120
catgcaaaga gtctagagtg gattggagtt attagtactt actctggtga tgttagttac   180
aaccagaagt tcaagggcaa ggccacaatg actgtcgaca atcctccag cacagcctat    240 atggaacttg ccagactgac atctgaggat tctgccatct attactgtgc aagaggggta   300
acttttgact cctggggcca aggcaccacg gtcaccgtct cctcg                   345

<210> SEQ ID NO 44
<211> LENGTH: 115
<212> TYPE: PRT
<213> ORGANISM: Mus musculus

<400> SEQUENCE: 44

Gln Val Gln Leu Gln Gln Ser Gly Ala Glu Leu Val Arg Pro Gly Val
1               5                   10                  15

Ser Val Lys Ile Ser Cys Lys Gly Ser Gly Tyr Thr Phe Thr Asp Tyr
                20                  25                  30

Ala Met His Trp Val Lys Gln Ser His Ala Lys Ser Leu Glu Trp Ile
            35                  40                  45

Gly Val Ile Ser Thr Tyr Ser Gly Asp Val Ser Tyr Asn Gln Lys Phe
        50                  55                  60

Lys Gly Lys Ala Thr Met Thr Val Asp Lys Ser Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Gly Val Thr Phe Asp Ser Trp Gly Gln Gly Thr Thr Val Thr
            100                 105                 110

Val Ser Ser
        115

<210> SEQ ID NO 45
<211> LENGTH: 24
<212> TYPE: DNA
<213> ORGANISM: Mus musculus

<400> SEQUENCE: 45

```
attagtactt actctggtga tgtt                                          24
```

<210> SEQ ID NO 46
<211> LENGTH: 8
<212> TYPE: PRT
<213> ORGANISM: Mus musculus

<400> SEQUENCE: 46

Ile Ser Thr Tyr Ser Gly Asp Val
1               5

<210> SEQ ID NO 47
<211> LENGTH: 24
<212> TYPE: DNA
<213> ORGANISM: Mus musculus

<400> SEQUENCE: 47

```
gcaagagggg taactttga ctcc                                           24
```

<210> SEQ ID NO 48
<211> LENGTH: 8
<212> TYPE: PRT
<213> ORGANISM: Mus musculus

<400> SEQUENCE: 48

Ala Arg Gly Val Thr Phe Asp Ser
1               5

<210> SEQ ID NO 49
<211> LENGTH: 322
<212> TYPE: DNA
<213> ORGANISM: Mus musculus

<400> SEQUENCE: 49

```
gacatccaga tgacacagtc tccagcctcc ctatctgcat ctgtgggaga aactgtcacc    60
atcacatgtc gagcaagtga aatagttac agttatttag aatggtatca gcagaaacag   120
ggaaaatctc ctcagctcct ggtctataat gcaaaaactt tagcagaagg tgtgccatca   180
aggttcagtg gcagtggatc aggcacacag ttttctctga agatcaacag cctgcagcct   240
gaagattttg ggacttatta ctgtcaacat cattatggta ctccgtacac gttcggaggg   300
gggaccaagc tggaaataaa ac                                           322
```

<210> SEQ ID NO 50
<211> LENGTH: 107
<212> TYPE: PRT
<213> ORGANISM: Mus musculus

<400> SEQUENCE: 50

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ser Tyr Ser Tyr
            20                  25                  30

Leu Glu Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Thr Tyr Tyr Cys Gln His His Tyr Gly Thr Pro Tyr

```
                    85                  90                  95
Thr Phe Gly Gly Gly Thr Lys Leu Glu Ile Lys
            100                 105

<210> SEQ ID NO 51
<211> LENGTH: 18
<212> TYPE: DNA
<213> ORGANISM: Mus musculus

<400> SEQUENCE: 51
gagaatagtt acagttat                                               18

<210> SEQ ID NO 52
<211> LENGTH: 6
<212> TYPE: PRT
<213> ORGANISM: Mus musculus

<400> SEQUENCE: 52

Glu Asn Ser Tyr Ser Tyr
1               5

<210> SEQ ID NO 53
<211> LENGTH: 27
<212> TYPE: DNA
<213> ORGANISM: Mus musculus

<400> SEQUENCE: 53
caacatcatt atggtactcc gtacacg                                     27

<210> SEQ ID NO 54
<211> LENGTH: 9
<212> TYPE: PRT
<213> ORGANISM: Mus musculus

<400> SEQUENCE: 54

Gln His His Tyr Gly Thr Pro Tyr Thr
1               5

<210> SEQ ID NO 55
<211> LENGTH: 346
<212> TYPE: DNA
<213> ORGANISM: Mus musculus

<400> SEQUENCE: 55
caggtccaac tgcagcagcc tggggctgag ctggtgaggc ctggggtttc actgaagatt    60
tcctgcaagg gttctggcta cacattcact gattatgcta tgcactgggt gaggcagagt   120
catgcaaaga gtctagagtg gattggagtt attagtactt actctggtga tgctctctac   180
aaccagaagt tcaagggcaa ggccacaatg actgtcgaca atcctccag cacagcctat    240 ctggaacttg ccagactgac atctgaggat tctgccatct attactgtgc gcgaggggta   300
acttttgact actggggcca aggcaccact ctcacagtct cctcgg                 346

<210> SEQ ID NO 56
<211> LENGTH: 115
<212> TYPE: PRT
<213> ORGANISM: Mus musculus

<400> SEQUENCE: 56

Gln Val Gln Leu Gln Gln Pro Gly Ala Glu Leu Val Arg Pro Gly Val
1               5                   10                  15

Ser Leu Lys Ile Ser Cys Lys Gly Ser Gly Tyr Thr Phe Thr Asp Tyr
```

```
                20                  25                  30
Ala Met His Trp Val Arg Gln Ser His Ala Lys Ser Leu Glu Trp Ile
            35                  40                  45

Gly Val Ile Ser Thr Tyr Ser Gly Asp Ala Leu Tyr Asn Gln Lys Phe
        50                  55                  60

Lys Gly Lys Ala Thr Met Thr Val Asp Lys Ser Ser Thr Ala Tyr
65                  70                  75                  80

Leu Glu Leu Ala Arg Leu Thr Ser Glu Asp Ser Ala Ile Tyr Tyr Cys
                85                  90                  95

Ala Arg Gly Val Thr Phe Asp Tyr Trp Gly Gln Gly Thr Thr Leu Thr
                100                 105                 110

Val Ser Ser
        115

<210> SEQ ID NO 57
<211> LENGTH: 24
<212> TYPE: DNA
<213> ORGANISM: Mus musculus

<400> SEQUENCE: 57
gcgcgagggg taacttttga ctac                                              24

<210> SEQ ID NO 58
<211> LENGTH: 322
<212> TYPE: DNA
<213> ORGANISM: Mus musculus

<400> SEQUENCE: 58
gatgttgtga tgacccagtc tccagcctcc ctatctgcat ctgtgggaga aactgtcacc       60
atcacatgtc gagcaagtga aatagttac agttatttag aatggtatca gcagaaacag      120
ggaaaatctc ctcagctcct ggtctataat gcaaaaactt tagcagaagg tgtgccatca      180
aggttcagtg cagtggatc aggcacacag ttttctctga agatcaacag cctgcagcct      240
gaagattttg ggacttatta ctgtcaacat cattatggta ctccgtacac gttcggaggg      300
gggaccaagc tggaaatgaa ac                                              322

<210> SEQ ID NO 59
<211> LENGTH: 107
<212> TYPE: PRT
<213> ORGANISM: Mus musculus

<400> SEQUENCE: 59

Asp Val Val Met Thr Gln Ser Pro Ala Ser Leu Ser Ala Ser Val Gly
1               5                   10                  15

Glu Thr Val Thr Ile Thr Cys Arg Ala Ser Glu Asn Ser Tyr Ser Tyr
            20                  25                  30

Leu Glu Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Thr Tyr Tyr Cys Gln His His Tyr Gly Thr Pro Tyr
                85                  90                  95

Thr Phe Gly Gly Gly Thr Lys Leu Glu Met Lys
            100                 105
```

```
<210> SEQ ID NO 60
<211> LENGTH: 119
<212> TYPE: PRT
<213> ORGANISM: Mus musculus

<400> SEQUENCE: 60

Asp Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Ser Ile Ser Ser Gly Gly Ser Thr Tyr Tyr Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
                85                  90                  95

Arg Gly Glu Ile Trp Gly Lys Ala Trp Phe Ala Tyr Trp Gly Gln Gly
            100                 105                 110

Thr Leu Val Thr Val Ser Ala
        115

<210> SEQ ID NO 61
<211> LENGTH: 113
<212> TYPE: PRT
<213> ORGANISM: Mus musculus

<400> SEQUENCE: 61

Gln Val Gln Met Lys Gln Ser Gly Pro Glu Leu Lys Lys Pro Gly Glu
1               5                   10                  15

Thr Val Lys Ile Ser Cys Lys Ala Ser Gly Tyr Thr Leu Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Trp Gly Asn His Tyr Trp Gly Gln Gly Thr Thr Val Thr Val Ser
            100                 105                 110

Ser

<210> SEQ ID NO 62
<211> LENGTH: 118
<212> TYPE: PRT
<213> ORGANISM: Mus musculus

<400> SEQUENCE: 62

Gln Ile Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45
```

Gly Tyr Ile Asn Pro Tyr Asn Asp Gly Thr Lys Tyr Asn Glu Lys Phe
            50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Asp Gly Tyr Tyr Val Gly Pro Ala Tyr Trp Gly Gln Gly Thr
                100                 105                 110

Leu Val Thr Val Ser Ala
            115

<210> SEQ ID NO 63
<211> LENGTH: 117
<212> TYPE: PRT
<213> ORGANISM: Mus musculus

<400> SEQUENCE: 63

Glu Val Leu Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ser Tyr
            20                  25                  30

Asp Met Ser Trp Val Arg Gln Thr Pro Glu Lys Arg Leu Glu Trp Val
        35                  40                  45

Ala Tyr Ile Ser Ser Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Asn Tyr Arg Ser Trp Phe Ala Tyr Trp Gly Gln Gly Thr Leu
                100                 105                 110

Val Thr Val Ser Ala
            115

<210> SEQ ID NO 64
<211> LENGTH: 119
<212> TYPE: PRT
<213> ORGANISM: Mus musculus

<400> SEQUENCE: 64

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Lys Gly Ser Leu Thr Gly Val Leu Ala Tyr Trp Gly Gln Gly
                100                 105                 110

Thr Leu Val Thr Val Ser Ala
            115

<210> SEQ ID NO 65
<211> LENGTH: 118
<212> TYPE: PRT
<213> ORGANISM: Mus musculus

<400> SEQUENCE: 65

Gln Val Gln Leu Gln Gln Ser Gly Ala Glu Leu Val Arg Pro Gly Ala
1               5                   10                  15
Ser Val Lys Leu Ser Cys Lys Ala Ser Gly Tyr Ile Phe Thr Asn Tyr
            20                  25                  30
Trp Met Asn Trp Val Lys Gln Arg Pro Gly Gln Gly Leu Glu Trp Ile
        35                  40                  45
Gly Met Ile Asp Pro Ser Asp Ser Glu Thr His Tyr Asn Gln Met Ser
    50                  55                  60
Lys Asp Lys Ala Thr Leu Thr Val Asp Lys Ser Ser Thr Ala Tyr
65                  70                  75                  80
Met Gln Leu Ser Ser Leu Thr Ser Glu Asp Ser Ala Val Tyr Tyr Cys
                85                  90                  95
Ala Arg Arg Gly Leu Arg Ala Trp Phe Ala Tyr Trp Gly Gln Gly Thr
            100                 105                 110
Leu Val Thr Val Ser Ala
        115

<210> SEQ ID NO 66
<211> LENGTH: 121
<212> TYPE: PRT
<213> ORGANISM: Mus musculus

<400> SEQUENCE: 66

Gln Val Gln Leu Gln Pro Gly Ala Glu Leu Ala Lys Pro Gly Ala
1               5                   10                  15
Ser Val Lys Met Ser Cys Lys Ala Ser Gly Tyr Thr Phe Thr Ser Tyr
            20                  25                  30
Trp Met His Trp Val Lys Gln Arg Pro Gly Gln Gly Leu Glu Trp Ile
        35                  40                  45
Gly Tyr Ile Asn Pro Ser Thr Gly Tyr Thr Glu Tyr Asn Gln Lys Phe
    50                  55                  60
Lys Asp Lys Ala Thr Leu Thr Ala Asp Lys Ser Ser Ser Thr Ala Tyr
65                  70                  75                  80
Met Gln Leu Ser Ser Leu Thr Ser Glu Asp Ser Ala Val Tyr Tyr Cys
                85                  90                  95
Ala Arg Leu Asp Tyr Tyr Gly Ser Ser Arg Gly Phe Ala Tyr Trp Gly
            100                 105                 110
Gln Gly Thr Leu Val Thr Val Ser Ala
        115                 120

<210> SEQ ID NO 67
<211> LENGTH: 114
<212> TYPE: PRT
<213> ORGANISM: Mus musculus

<400> SEQUENCE: 67

Gln Val Gln Leu Gln Gln Ser Gly Ala Glu Leu Val Lys Pro Gly Ala
1               5                   10                  15
Ser Val Lys Leu Ser Cys Lys Ala Ser Gly Tyr Thr Phe Thr Ser Tyr
            20                  25                  30

```
Tyr Met Tyr Trp Val Lys Gln Arg Pro Gly Gln Gly Leu Glu Trp Ile
            35                  40                  45

Gly Glu Ile Asn Pro Ser Asn Gly Gly Thr Asn Phe Asn Glu Lys Phe
 50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Asn Gly Gly Gly Trp Tyr Trp Gly Gln Gly Thr Thr Val Thr Val
            100                 105                 110

Ser Ser

<210> SEQ ID NO 68
<211> LENGTH: 120
<212> TYPE: PRT
<213> ORGANISM: Mus musculus

<400> SEQUENCE: 68

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asn Tyr
            20                  25                  30

Gly Met Asn Trp Val Lys Gln Thr Pro Gly Lys Gly Leu Lys Trp Met
            35                  40                  45

Gly Trp Ile Asn Thr Tyr Thr Gly Glu Pro Thr Tyr Ala Asp Asp Phe
 50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Ser Tyr Tyr Asp Ser Thr Tyr Val Gly Phe Ala Tyr Trp Gly Gln
            100                 105                 110

Gly Thr Leu Val Thr Val Ser Ala
            115                 120

<210> SEQ ID NO 69
<211> LENGTH: 118
<212> TYPE: PRT
<213> ORGANISM: Mus musculus

<400> SEQUENCE: 69

Glu Val Leu Leu Val Glu Ser Gly Gly Gly Leu Val Gln Pro Gly Gly
 1               5                  10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
            35                  40                  45

Ala Tyr Ile Ser Asn Gly Gly Gly Ser Thr Tyr Tyr Pro Asp Thr Val
 50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Ser Pro Leu Gly Tyr Asp Gly Phe Ala Tyr Trp Gly Gln Gly Thr
            100                 105                 110

Leu Val Thr Val Ser Ala
```

-continued

115

<210> SEQ ID NO 70
<211> LENGTH: 114
<212> TYPE: PRT
<213> ORGANISM: Mus musculus

<400> SEQUENCE: 70

Gln Val Gln Met Lys Gln Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Gly Ala Tyr Phe Asp Tyr Trp Gly Gln Gly Thr Thr Val Thr Val
            100                 105                 110

Ser Ser

<210> SEQ ID NO 71
<211> LENGTH: 121
<212> TYPE: PRT
<213> ORGANISM: Mus musculus

<400> SEQUENCE: 71

Gln Val Gln Leu Gln Gln Ser Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Glu Gln Gly Leu Glu Trp Ile
        35                  40                  45

Gly Arg Ile Asp Pro Tyr Asp Ser Glu Thr His Tyr Asn Gln Lys Phe
    50                  55                  60

Lys Asp Lys Ala Ile Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Pro Ala Tyr Tyr Gly Asn Leu Trp Phe Ala Tyr Trp Gly
            100                 105                 110

Gln Gly Thr Leu Val Thr Val Ser Ala
        115                 120

<210> SEQ ID NO 72
<211> LENGTH: 114
<212> TYPE: PRT
<213> ORGANISM: Mus musculus

<400> SEQUENCE: 72

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

```
Thr Ile His Trp Val Lys Gln Arg Pro Gly Gln Gly Leu Glu Trp Ile
         35                  40                  45

Gly Tyr Ile Asn Pro Ser Ser Gly Tyr Thr Asn Tyr Asn Gln Lys Phe
 50                      55                  60

Lys Asp Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Trp Asp Gly Ala Tyr Trp Gly Gln Gly Thr Pro Val Thr Val
             100                 105                 110

Ser Ser
```

<210> SEQ ID NO 73
<211> LENGTH: 118
<212> TYPE: PRT
<213> ORGANISM: Mus musculus

<400> SEQUENCE: 73

```
Asp Val Lys Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Ser Tyr
             20                  25                  30

Ala Met Ser Trp Val Arg Gln Phe Pro Glu Lys Arg Leu Glu Trp Val
         35                  40                  45

Ala Glu Ile Ser Ser Gly Gly Ser Tyr Thr Tyr Tyr Pro Asp Thr Val
 50                      55                  60

Thr Gly Arg Phe Thr Ile Ser Arg Asp Asn Ala Lys Asn Thr Leu Tyr
 65                  70                  75                  80

Leu Glu Met Ser Ser Leu Arg Ser Glu Asp Thr Ala Met Tyr Tyr Cys
                 85                  90                  95

Ala Arg Gly Gly Met Ile Thr Pro Phe Ala Tyr Trp Gly Gln Gly Thr
             100                 105                 110

Leu Val Thr Val Ser Ser
        115
```

<210> SEQ ID NO 74
<211> LENGTH: 123
<212> TYPE: PRT
<213> ORGANISM: Mus musculus

<400> SEQUENCE: 74

```
Gln Val Ile Leu Lys Glu Ser Gly Pro Gly Ile Leu Gln Pro Ser Gln
 1               5                  10                  15

Thr Leu Ser Leu Thr Cys Ser Phe Ser Gly Phe Ser Leu Ser Thr Ser
             20                  25                  30

Gly Met Ser Val Gly Trp Ile Arg Gln Pro Ser Gly Lys Gly Leu Glu
         35                  40                  45

Trp Leu Ala His Ile Trp Trp Asn Asp Asp Lys Tyr Tyr Asn Pro Ala
 50                      55                  60

Leu Lys Ser Arg Leu Thr Ile Ser Lys Asp Thr Ser Asn Asn Gln Val
 65                  70                  75                  80

Phe Leu Lys Ile Ala Ser Val Val Thr Ala Asp Thr Ala Thr Tyr Tyr
                 85                  90                  95

Cys Ala Arg Ile Gly Gly Asn Asp Gly Tyr Tyr Trp Tyr Phe Asp Val
             100                 105                 110

Trp Gly Ala Gly Thr Thr Val Thr Val Ser Ser
```

-continued

```
            115                 120
```

<210> SEQ ID NO 75
<211> LENGTH: 115
<212> TYPE: PRT
<213> ORGANISM: Mus musculus

<400> SEQUENCE: 75

```
Glu Val Lys Ile Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Ser Lys Ala Asn Asn His Ala Thr Tyr Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Ala Glu Asp Thr Gly Ile Tyr
                85                  90                  95

Tyr Cys Thr Pro Gln Phe Ala Tyr Trp Gly Gln Gly Thr Thr Val Thr
            100                 105                 110

Val Ser Ser
        115
```

<210> SEQ ID NO 76
<211> LENGTH: 115
<212> TYPE: PRT
<213> ORGANISM: Mus musculus

<400> SEQUENCE: 76

```
Glu Val Met Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Leu Val
        35                  40                  45

Ala Thr Ile Asn Ser Asn Gly Gly Ser Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Ser His Tyr Asp Glu Gly Tyr Trp Gly Gln Gly Thr Ser Leu Thr
            100                 105                 110

Val Ser Ser
        115
```

<210> SEQ ID NO 77
<211> LENGTH: 114
<212> TYPE: PRT
<213> ORGANISM: Mus musculus

<400> SEQUENCE: 77

```
Glu Val Lys Leu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
    50                  55                  60
```

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Gly Ser Asp Tyr Trp Gly Gln Gly Thr Thr Val Thr Val
            100                 105                 110

Ser Ser

<210> SEQ ID NO 78
<211> LENGTH: 120
<212> TYPE: PRT
<213> ORGANISM: Mus musculus

<400> SEQUENCE: 78

Gln Val Gln Leu Gln Gln Ser Gly Pro Glu Leu Val Lys Pro Gly Ala
1               5                   10                  15

Ser Val Lys Met Ser Cys Lys Ala Ser Gly Asp Thr Phe Ser Ser Tyr
            20                  25                  30

Val Ile His Trp Val Lys Gln Lys Pro Gly Gln Gly Leu Glu Trp Ile
        35                  40                  45

Gly Tyr Phe Asn Pro Tyr Ser Asp Asp Ile Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Gly Ser Gly Tyr Asp Gly Tyr Tyr Asp Trp Phe Ala Cys Trp Gly Gln
            100                 105                 110

Gly Thr Leu Val Thr Val Ser Ala
        115                 120

<210> SEQ ID NO 79
<211> LENGTH: 116
<212> TYPE: PRT
<213> ORGANISM: Mus musculus

<400> SEQUENCE: 79

Gln Ile Gln Leu Ala Gln Ser Gly Pro Glu Leu Lys Lys Pro Gly Glu
1               5                   10                  15

Thr Val Lys Ile Ser Cys Lys Ala Ser Gly Tyr Ser Phe Thr Lys Asn
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Glu Pro Lys Thr Leu Asp Tyr Trp Gly Gln Gly Thr Thr Val
            100                 105                 110

Thr Val Ser Ser
        115

<210> SEQ ID NO 80
<211> LENGTH: 115
<212> TYPE: PRT

<213> ORGANISM: Mus musculus

<400> SEQUENCE: 80

Gln Val Gln Leu Gln Gln Ser Gly Ala Glu Leu Val Lys Pro Gly Ala
1               5                   10                  15

Pro Val Lys Leu Ser Cys Lys Ala Ser Gly Tyr Thr Phe Thr Ser Tyr
                20                  25                  30

Trp Met Asn Trp Val Lys Gln Arg Pro Gly Arg Gly Leu Glu Trp Ile
            35                  40                  45

Gly Arg Ile Asp Pro Ser Asp Ser Glu Thr His Tyr Asn Gln Lys Phe
        50                  55                  60

Lys Asp Lys Ala Thr Leu Thr Val Asp Lys Ser Ser Thr Ala Tyr
65                  70                  75                  80

Ile Gln Leu Ser Ser Leu Thr Ser Glu Asp Ser Ala Val Tyr Tyr Cys
                85                  90                  95

Ala Asn Trp Ala Trp Phe Ala Tyr Trp Gly Gln Gly Thr Leu Val Thr
            100                 105                 110

Val Ser Ala
        115

<210> SEQ ID NO 81
<211> LENGTH: 118
<212> TYPE: PRT
<213> ORGANISM: Mus musculus

<400> SEQUENCE: 81

Gln Met Gln Leu Lys Glu Ser Gly Thr Glu Leu Val Arg Pro Gly Ala
1               5                   10                  15

Ser Val Lys Leu Ser Cys Lys Ala Ser Gly Tyr Thr Phe Asn Ser His
                20                  25                  30

Trp Met Asn Trp Val Lys Gln Arg Pro Glu Gln Gly Leu Glu Trp Ile
            35                  40                  45

Gly Lys Ile Asp Pro Tyr Asp Ser Glu Thr His Tyr Asn Gln Lys Phe
        50                  55                  60

Lys Asp Lys Ala Ile Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Pro Tyr Asp Tyr Asp Gly Phe Ala Tyr Trp Gly Gln Gly Thr
            100                 105                 110

Leu Val Thr Val Ser Ala
        115

<210> SEQ ID NO 82
<211> LENGTH: 116
<212> TYPE: PRT
<213> ORGANISM: Mus musculus

<400> SEQUENCE: 82

Gln Ile Gln Leu Gln Gln Ser Gly Ala Glu Leu Val Arg Pro Gly Ala
1               5                   10                  15

Ser Val Lys Ile Ser Cys Lys Ala Phe Gly Tyr Thr Phe Thr Asn His
                20                  25                  30

His Ile Asn Trp Val Lys Gln Arg Pro Gly Gln Gly Leu Asp Trp Ile
            35                  40                  45

Gly Tyr Ile Asn Pro Tyr Asn Asp Tyr Thr Ser Tyr Asn Gln Lys Phe
        50                  55                  60

```
Lys Gly Lys Ala Thr Leu Thr Val Asp Lys Ser Ser Thr Ala Tyr
 65                  70                  75                  80

Met Glu Leu Ser Ser Leu Thr Ser Glu Asp Ser Ala Val Tyr Tyr Cys
                 85                  90                  95

Ala Asp Gly Asp Tyr Tyr Phe Asp Tyr Trp Gly Gln Gly Thr Ser Leu
            100                 105                 110

Thr Val Ser Ser
        115

<210> SEQ ID NO 83
<211> LENGTH: 120
<212> TYPE: PRT
<213> ORGANISM: Mus musculus

<400> SEQUENCE: 83

Asp Val Leu Val Glu Ser Gly Gly Asp Leu Val Lys Pro Gly Gly
  1               5                  10                  15

Ser Leu Lys Leu Ser Cys Val Val Ser Gly Leu Thr Phe Ser Ser Tyr
                 20                  25                  30

Gly Met Ser Trp Val Arg Gln Thr Pro Asp Lys Arg Leu Glu Trp Val
             35                  40                  45

Ala Thr Ile Ser Ser Gly Gly Ser Tyr Ile Tyr Tyr Val Asp Ser Val
 50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Ile Tyr Tyr Cys
                 85                  90                  95

Ala Arg Gln Asp Asp Gly Tyr Tyr Arg Ile Phe Asp Tyr Trp Gly Gln
            100                 105                 110

Gly Thr Thr Leu Thr Val Ser Ser
            115                 120

<210> SEQ ID NO 84
<211> LENGTH: 119
<212> TYPE: PRT
<213> ORGANISM: Mus musculus

<400> SEQUENCE: 84

Glu Val Lys Ile Glu Glu Ser Gly Gly Gly Leu Val Gln Pro Gly Gly
  1               5                  10                  15

Ser Met Lys Leu Ser Cys Ala Ala Ser Gly Phe Thr Phe Asn Asp Ala
                 20                  25                  30

Trp Met Asp Trp Val Arg Gln Ser Pro Glu Lys Gly Leu Glu Trp Val
             35                  40                  45

Ala Glu Ile Arg Ser Lys Ala Asn Asn His Ala Thr Tyr Tyr Ala Glu
 50                  55                  60

Ser Val Lys Gly Arg Phe Thr Ile Ser Arg Asp Asp Ser Gln Ser Ser
 65                  70                  75                  80

Val Tyr Leu Gln Met Asn Ser Leu Arg Thr Glu Asn Thr Gly Ile Tyr
                 85                  90                  95

Tyr Cys Thr Asn Tyr Gly Ser Asn Pro Leu Asp Tyr Trp Gly Gln Gly
            100                 105                 110

Thr Thr Leu Thr Ile Pro Ser
        115

<210> SEQ ID NO 85
```

```
<211> LENGTH: 116
<212> TYPE: PRT
<213> ORGANISM: Mus musculus

<400> SEQUENCE: 85

Gln Val Thr Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Gly Ile Ser Lys Asp Asn Ser Lys Ser Gln Val Phe Leu
65                  70                  75                  80

Lys Met Asn Ser Leu Gln Thr Asp Glu Ser Ala Phe Tyr Tyr Cys Ala
                85                  90                  95

Arg Glu Gly Thr Gly Pro Trp Phe Ala Tyr Trp Gly Gln Gly Thr Thr
            100                 105                 110

Ala Pro Ser Pro
        115

<210> SEQ ID NO 86
<211> LENGTH: 115
<212> TYPE: PRT
<213> ORGANISM: Mus musculus

<400> SEQUENCE: 86

Asp Val Gln Leu Gln Gln Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Gly Tyr Ile His Tyr Ser Gly Ser Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Gly Thr Ala Thr Tyr Tyr Cys
                85                  90                  95

Ala Arg Asp Pro Pro Phe Ala Tyr Trp Gly Gln Gly Thr Leu Val Thr
            100                 105                 110

Val Ser Ala
        115

<210> SEQ ID NO 87
<211> LENGTH: 118
<212> TYPE: PRT
<213> ORGANISM: Mus musculus

<400> SEQUENCE: 87

Gln Val Gln Leu Gln Gln Ser Gly Ala Glu Leu Val Lys Pro Gly Ala
1               5                   10                  15

Ser Val Arg Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45
```

Gly Glu Ile Asp Pro Ser Asp Ser Tyr Thr Asn Tyr Asn Gln Lys Phe
    50                  55                  60

Lys Gly Lys Ala Thr Leu Ala Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Glu Ile Thr Ala Trp Phe Ala Tyr Trp Gly Gln Gly Thr
                100                 105                 110

Leu Val Thr Val Ser Ala
        115

<210> SEQ ID NO 88
<211> LENGTH: 119
<212> TYPE: PRT
<213> ORGANISM: Mus musculus

<400> SEQUENCE: 88

Gln Val Gln Leu Gln Gln Pro Gly Ala Glu Leu Val Arg Pro Gly Ala
1               5                   10                  15

Ser Val Lys Leu Ser Cys Lys Ala Leu Gly Tyr Thr Phe Thr Asp Tyr
                20                  25                  30

Glu Met His Trp Val Lys Gln Thr Pro Val His Gly Leu Glu Trp Ile
            35                  40                  45

Gly Ala Ile His Pro Gly Ser Gly Gly Thr Ala Tyr Asn Gln Lys Phe
    50                  55                  60

Lys Gly Lys Ala Thr Leu Thr Ala Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Thr Arg Asn Gly Asn Gly Asn Trp Tyr Phe Asp Val Trp Gly Ala Gly
                100                 105                 110

Thr Thr Leu Thr Val Ser Ser
        115

<210> SEQ ID NO 89
<211> LENGTH: 120
<212> TYPE: PRT
<213> ORGANISM: Mus musculus

<400> SEQUENCE: 89

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Tyr Pro Gly Asp Gly Asp Thr Tyr Tyr Asn Gly Lys Phe
    50                  55                  60

Lys Asp Lys Ala Thr Leu Thr Ala Asp Lys Ser Ser Ser Thr Ala Tyr
65                  70                  75                  80

Met His Leu Ser Ser Leu Thr Ser Glu Asp Ser Ala Val Tyr Phe Cys
                85                  90                  95

Ala Arg Ser Gly Tyr Arg Tyr Asp Ala Val Phe Ala Tyr Trp Gly Pro
                100                 105                 110

Gly Thr Leu Val Thr Val Ser Ala
        115                 120

<210> SEQ ID NO 90
<211> LENGTH: 114
<212> TYPE: PRT
<213> ORGANISM: Mus musculus

<400> SEQUENCE: 90

Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Leu Val
        35                  40                  45

Ala Thr Ile Asn Ser Asn Gly Gly Ser Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Gly Gly Asn Pro Tyr Leu Gly Gln Gly Thr Leu Val Thr Val
            100                 105                 110

Ser Ala

<210> SEQ ID NO 91
<211> LENGTH: 107
<212> TYPE: PRT
<213> ORGANISM: Mus musculus

<400> SEQUENCE: 91

Glu Val Gln Leu Val Glu Thr Gly Gly Gly Leu Val Gln Pro Gly Gly
1               5                   10                  15

Ser Arg Gly Leu Ser Cys Glu Gly Ser Gly Phe Thr Phe Ser Gly Phe
            20                  25                  30

Trp Met Ser Trp Val Arg Gln Thr Pro Gly Lys Thr Leu Glu Trp Ile
        35                  40                  45

Gly Asp Ile Asn Ser Asp Gly Ser Ala Ile Asn Tyr Ala Pro Ser Ile
    50                  55                  60

Lys Asp Arg Phe Thr Ile Phe Arg Asp Asn Asp Lys Ser Thr Leu Tyr
65                  70                  75                  80

Leu Gln Met Ser Asn Val Arg Ser Glu Asp Thr Ala Thr Tyr Phe Cys
                85                  90                  95

Met Arg Tyr Gly Ser Ser Tyr Trp Tyr Phe Asp
            100                 105

<210> SEQ ID NO 92
<211> LENGTH: 117
<212> TYPE: PRT
<213> ORGANISM: Mus musculus

<400> SEQUENCE: 92

Glu Val Lys Ile Glu Glu Ser Gly Gly Gly Leu Val Gln Pro Gly Gly
1               5                   10                  15

Ser Met Lys Leu Ser Cys Val Ala Ser Gly Phe Thr Phe Ser Ser Tyr
            20                  25                  30

Trp Met Ser Trp Val Arg Gln Ser Pro Glu Lys Gly Leu Glu Trp Val
        35                  40                  45

Ala Glu Ile Arg Leu Lys Ser Asp Asn Tyr Ala Thr His Tyr Ala Glu
    50                  55                  60

```
Ser Val Lys Gly Lys Phe Thr Ile Ser Arg Asp Asp Ser Lys Ser Arg
 65                  70                  75                  80

Leu Tyr Leu Gln Met Asn Ser Leu Arg Ala Glu Asp Thr Gly Ile Tyr
                 85                  90                  95

Tyr Cys Thr Arg Tyr Tyr Tyr Gly Glu Ser Trp Gly Gln Gly Thr Leu
            100                 105                 110

Val Thr Val Ser Ser
            115

<210> SEQ ID NO 93
<211> LENGTH: 121
<212> TYPE: PRT
<213> ORGANISM: Mus musculus

<400> SEQUENCE: 93

Glu Val Met Leu Val Glu Ser Gly Gly Asp Leu Val Lys Pro Gly Gly
  1               5                  10                  15

Ser Leu Lys Leu Ser Cys Ala Ala Ser Gly Phe Thr Phe Ser Ser Tyr
                 20                  25                  30

Gly Met Ser Trp Val Arg Gln Thr Pro Asp Lys Arg Leu Glu Trp Val
             35                  40                  45

Ala Thr Ile Ser Ser Gly Gly Ser Tyr Thr Tyr Tyr Pro Asp Ser Val
     50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Arg His Tyr Tyr Asp Tyr Asp Tyr Trp Tyr Phe Asp Val Trp Gly
            100                 105                 110

Ala Gly Thr Thr Val Thr Val Ser Ser
            115                 120

<210> SEQ ID NO 94
<211> LENGTH: 122
<212> TYPE: PRT
<213> ORGANISM: Mus musculus

<400> SEQUENCE: 94

Gln Val Gln Leu Gln Gln Pro Gly Ser Glu Leu Val Arg Pro Gly Ala
  1               5                  10                  15

Ser Val Lys Leu Ser Cys Lys Ala Ser Gly Tyr Thr Phe Thr Ser Tyr
                 20                  25                  30

Trp Met His Trp Val Lys Gln Arg Tyr Gly Gln Gly Leu Glu Trp Ile
             35                  40                  45

Gly Asn Ile Tyr Pro Gly Ser Gly Ser Thr Asn Tyr Asp Glu Lys Phe
     50                  55                  60

Lys Ser Lys Gly Thr Leu Thr Val Asp Thr Ser Ser Ser Thr Ala Tyr
 65                  70                  75                  80

Met His Leu Ser Ser Leu Thr Ser Glu Asp Ser Ala Val Tyr Tyr Cys
                 85                  90                  95

Thr Arg Ser Gly Val Glu Gly Leu Leu His Trp Tyr Phe Asp Val Trp
            100                 105                 110

Gly Ala Gly Thr Ser Leu Thr Val Ser Ser
            115                 120

<210> SEQ ID NO 95
```

```
<211> LENGTH: 121
<212> TYPE: PRT
<213> ORGANISM: Mus musculus

<400> SEQUENCE: 95

Glu Val Lys Ile Glu Glu Ser Gly Gly Gly Leu Val Gln Pro Gly Gly
1               5                   10                  15

Ser Met Lys Leu Ser Cys Val Ala Ser Gly Phe Thr Phe Ser Ser Tyr
            20                  25                  30

Trp Met Ser Trp Val Arg Gln Ser Pro Glu Lys Gly Leu Glu Trp Val
        35                  40                  45

Ala Glu Ile Arg Leu Lys Ser Asp Asn Tyr Ala Thr His Tyr Ala Glu
    50                  55                  60

Ser Val Lys Gly Lys Phe Thr Ile Ser Arg Asp Asp Ser Lys Ser Arg
65                  70                  75                  80

Leu Tyr Leu Gln Met Asn Ser Leu Arg Ala Glu Asp Thr Gly Ile Tyr
                85                  90                  95

Tyr Cys Thr Cys Asp Tyr Asp Gly Gly Ala Trp Phe Ala Tyr Trp Gly
            100                 105                 110

Gln Gly Thr Leu Val Thr Val Ser Ala
        115                 120

<210> SEQ ID NO 96
<211> LENGTH: 119
<212> TYPE: PRT
<213> ORGANISM: Mus musculus

<400> SEQUENCE: 96

Gln Ile Gln Leu Gln Gln Pro Gly Pro Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Met Ile Asp Pro Ser Asn Ser Glu Thr Arg Leu Asn Gln Lys Phe
    50                  55                  60

Lys Asp Lys Ala Thr Leu Asn Val Asp Lys Ser Ser Asn Thr Ala Cys
65                  70                  75                  80

Met Gln Leu Ser Ser Leu Thr Ser Glu Asp Ser Ala Val Tyr Tyr Cys
                85                  90                  95

Ala Arg Cys Asp Gly Tyr Tyr Asp Gly Leu Asp Tyr Trp Gly Gln Gly
            100                 105                 110

Thr Thr Leu Thr Val Ser Ser
        115

<210> SEQ ID NO 97
<211> LENGTH: 118
<212> TYPE: PRT
<213> ORGANISM: Mus musculus

<400> SEQUENCE: 97

Gln Val Gln Leu Gln Gln Pro Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Ile His Trp Val Lys Gln Arg Pro Gly Gln Gly Leu Glu Trp Ile
        35                  40                  45
```

-continued

Gly Tyr Ile Asn Pro Ser Ser Gly Tyr Thr Asn Tyr Asn Gln Lys Phe
            50                  55                  60

Lys Asp Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Glu Gly Lys Asn Trp Tyr Phe Asp Val Trp Gly Ala Gly Thr
                100                 105                 110

Thr Val Thr Val Ser Ser
            115

<210> SEQ ID NO 98
<211> LENGTH: 117
<212> TYPE: PRT
<213> ORGANISM: Mus musculus

<400> SEQUENCE: 98

Gln Ile Gln Leu Gln Gln Ser Gly Ala Glu Leu Val Arg Pro Gly Val
 1               5                  10                  15

Ser Val Lys Leu Ser Cys Lys Ala Ser Gly Tyr Thr Phe Thr Ser Tyr
            20                  25                  30

Trp Met His Trp Ile Lys Gln Arg Pro Glu Gln Gly Leu Glu Arg Ile
            35                  40                  45

Gly Glu Ile Asn Pro Ser Asn Gly Gly Thr Asn Tyr Asn Glu Lys Phe
            50                  55                  60

Lys Ser Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Arg Ile Tyr Arg Thr Leu Asp Tyr Trp Gly Gln Gly Thr Thr
                100                 105                 110

Val Thr Val Ser Ser
            115

<210> SEQ ID NO 99
<211> LENGTH: 118
<212> TYPE: PRT
<213> ORGANISM: Mus musculus

<400> SEQUENCE: 99

Glu Val Gln Leu Gln Gln Ser Gly Ala Glu Leu Val Lys Pro Gly Ala
 1               5                  10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
            35                  40                  45

Gly Val Ile Tyr Pro Gly Asn Gly Asp Thr Ala Tyr Asn Gln Lys Phe
            50                  55                  60

Lys Gly Lys Ala Thr Val Thr Ala Asp Arg Ser Ser Thr Ala Tyr
 65                  70                  75                  80

Met Gln Leu Ser Ser Leu Thr Ser Glu Asp Ser Ala Val Tyr Tyr Cys
                 85                  90                  95

Thr Arg Ser Gly Gly Asn Leu Trp Phe Ala Tyr Trp Gly Gln Gly Thr
                100                 105                 110

Leu Val Thr Val Ser Ala
            115

<210> SEQ ID NO 100
<211> LENGTH: 120
<212> TYPE: PRT
<213> ORGANISM: Mus musculus

<400> SEQUENCE: 100

```
Gln Ile Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Asn Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Arg Thr Tyr Tyr Gly Asn Ala Trp Phe Ala Tyr Trp Gly Gln
            100                 105                 110

Gly Thr Leu Val Thr Val Ser Ala
        115                 120
```

<210> SEQ ID NO 101
<211> LENGTH: 124
<212> TYPE: PRT
<213> ORGANISM: Mus musculus

<400> SEQUENCE: 101

```
Gln Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Ala Arg Asp Lys Arg Ile Thr Thr Val Glu Ala Trp Phe Ala
            100                 105                 110

Tyr Trp Gly Gln Gly Thr Leu Val Thr Val Ser Ala
        115                 120
```

<210> SEQ ID NO 102
<211> LENGTH: 116
<212> TYPE: PRT
<213> ORGANISM: Mus musculus

<400> SEQUENCE: 102

```
Glu Val Lys Leu Val Glu Thr Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
```

```
                35                  40                  45
Ala Ser Ile Ser Ser Gly Gly Ser Thr Tyr Tyr Pro Asp Ser Val Lys
        50                  55                  60
Gly Arg Phe Thr Ile Ser Arg Asp Asn Ala Arg Asn Ile Leu Tyr Leu
65                  70                  75                  80
Gln Met Ser Ser Leu Arg Ser Glu Asp Thr Ala Met Tyr Tyr Cys Ala
                85                  90                  95
Arg Gly Tyr Gly Ser Ser Phe Ala Tyr Trp Gly Gln Gly Thr Pro Val
                100                 105                 110
Thr Val Ser Ser
        115

<210> SEQ ID NO 103
<211> LENGTH: 120
<212> TYPE: PRT
<213> ORGANISM: Mus musculus

<400> SEQUENCE: 103

Gln Val Gln Leu Gln Gln Ser Gly Ala Glu Leu Val Lys Pro Gly Ala
1               5                   10                  15
Ser Val Lys Leu Ser Cys Lys Ala Ser Gly Tyr Thr Phe Thr Ser Tyr
                20                  25                  30
Tyr Met Tyr Trp Val Lys Gln Arg Pro Gly Gln Gly Leu Glu Trp Ile
                35                  40                  45
Gly Glu Ile Asn Pro Ser Asn Ser Gly Thr Asn Phe Asn Glu Lys Phe
        50                  55                  60
Lys Ser Lys Ala Thr Leu Thr Val Asp Lys Ser Ser Thr Ala Tyr
65                  70                  75                  80
Met Gln Leu Ser Ser Leu Thr Ser Glu Asp Ser Ala Val Tyr Tyr Cys
                85                  90                  95
Thr Arg Gly Gly Asp Tyr Asp Ala Ser Trp Phe Ala Tyr Trp Gly Gln
                100                 105                 110
Gly Thr Leu Val Thr Val Ser Ala
        115                 120

<210> SEQ ID NO 104
<211> LENGTH: 117
<212> TYPE: PRT
<213> ORGANISM: Mus musculus

<400> SEQUENCE: 104

Gln Val Gln Met Lys Glu Ser Gly Pro Glu Pro Val Lys Pro Gly Ala
1               5                   10                  15
Ser Val Lys Met Ser Cys Arg Ala Ser Gly Tyr Thr Leu Thr Asp Tyr
                20                  25                  30
Val Val Ser Trp Val Lys Gln Arg Leu Gly Gln Gly Leu Glu Trp Ile
                35                  40                  45
Gly Glu Ile Tyr Pro Gly Ser Gly Ser Thr Tyr Tyr Asn Glu Lys Phe
        50                  55                  60
Lys Asp Lys Val Thr Leu Thr Ala Asp Thr Ser Ser Asn Thr Val His
65                  70                  75                  80
Ile Gln Leu Ser Ser Leu Thr Ser Glu Asp Ser Ala Val Tyr Phe Cys
                85                  90                  95
Ala Arg Arg Thr Ala Arg Ala Phe Asp Tyr Trp Gly Gln Gly Thr Thr
                100                 105                 110
Val Thr Val Ser Ser
```

-continued

```
            115

<210> SEQ ID NO 105
<211> LENGTH: 122
<212> TYPE: PRT
<213> ORGANISM: Mus musculus

<400> SEQUENCE: 105

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Arg Ile Gly Tyr Asp Gly Gly Gly Ser Trp Phe Ala Tyr Trp
            100                 105                 110

Gly Gln Gly Thr Leu Val Thr Val Ser Ala
        115                 120

<210> SEQ ID NO 106
<211> LENGTH: 117
<212> TYPE: PRT
<213> ORGANISM: Mus musculus

<400> SEQUENCE: 106

Glu Val Lys Ile Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Glu Lys Gly Leu Glu Trp Val
        35                  40                  45

Ala Arg Ile Arg Ser Lys Ser Asn Asn Tyr Val Thr Tyr Tyr Ala Asp
    50                  55                  60

Ser Leu Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Cys His Val
                85                  90                  95

Leu Leu Cys Glu Arg Val Arg Arg Cys Val Leu Gly Pro Arg Asp Ser
            100                 105                 110

Gly His Cys Leu Cys
        115

<210> SEQ ID NO 107
<211> LENGTH: 115
<212> TYPE: PRT
<213> ORGANISM: Mus musculus

<400> SEQUENCE: 107

Gln Val Gln Leu Val Glu Thr Gly Gly Gly Leu Val Arg Pro Gly Asn
1               5                   10                  15

Ser Leu Lys Leu Ser Cys Val Thr Ser Gly Phe Thr Phe Ser Asn Tyr
            20                  25                  30
```

-continued

```
Arg Met His Trp Leu Arg Gln Pro Gly Lys Arg Leu Glu Trp Ile
         35                  40                  45

Ala Val Ile Thr Val Lys Ser Asp Asn Tyr Gly Ala Asn Tyr Ala Glu
 50                  55                  60

Ser Val Lys Gly Arg Phe Thr Ile Ser Arg Asp Asp Ser Lys Ser Ser
 65                  70                  75                  80

Val Tyr Leu Gln Met Asn Arg Leu Arg Glu Glu Asp Thr Ala Thr Tyr
                 85                  90                  95

Tyr Cys Ser Arg Trp Phe Ala Tyr Trp Gly Gln Gly Thr Leu Val Thr
            100                 105                 110

Val Ser Ala
        115

<210> SEQ ID NO 108
<211> LENGTH: 25
<212> TYPE: PRT
<213> ORGANISM: Mus musculus

<400> SEQUENCE: 108

Asp Val Lys Leu Val Glu Ser Gly Gly Gly Leu Val Lys Pro Gly Gly
1               5                   10                  15

Ser Leu Lys Leu Ser Cys Ala Ala Ser
            20                  25

<210> SEQ ID NO 109
<211> LENGTH: 25
<212> TYPE: PRT
<213> ORGANISM: Mus musculus

<400> SEQUENCE: 109

Gln Val Gln Met Lys Gln Ser Gly Pro Glu Leu Lys Lys Pro Gly Glu
1               5                   10                  15

Thr Val Lys Ile Ser Cys Lys Ala Ser
            20                  25

<210> SEQ ID NO 110
<211> LENGTH: 25
<212> TYPE: PRT
<213> ORGANISM: Mus musculus

<400> SEQUENCE: 110

Gln Ile Gln Leu Gln Gln Ser Gly Pro Glu Leu Val Lys Pro Gly Ala
1               5                   10                  15

Ser Val Lys Met Ser Cys Lys Ala Ser
            20                  25

<210> SEQ ID NO 111
<211> LENGTH: 25
<212> TYPE: PRT
<213> ORGANISM: Mus musculus

<400> SEQUENCE: 111

Glu Val Leu Leu Val Glu Ser Gly Gly Gly Leu Val Lys Pro Gly Gly
1               5                   10                  15

Ser Leu Lys Leu Ser Cys Ala Ala Ser
            20                  25

<210> SEQ ID NO 112
<211> LENGTH: 25
<212> TYPE: PRT
```

<213> ORGANISM: Mus musculus

<400> SEQUENCE: 112

Gln Val Gln Leu Gln Gln Ser Gly Ala Glu Leu Val Arg Pro Gly Thr
1               5                   10                  15

Ser Val Lys Val Ser Cys Lys Ala Ser
            20                  25

<210> SEQ ID NO 113
<211> LENGTH: 25
<212> TYPE: PRT
<213> ORGANISM: Mus musculus

<400> SEQUENCE: 113

Gln Val Gln Leu Gln Gln Ser Gly Ala Glu Leu Val Arg Pro Gly Ala
1               5                   10                  15

Ser Val Lys Leu Ser Cys Lys Ala Ser
            20                  25

<210> SEQ ID NO 114
<211> LENGTH: 25
<212> TYPE: PRT
<213> ORGANISM: Mus musculus

<400> SEQUENCE: 114

Gln Val Gln Leu Gln Gln Pro Gly Ala Glu Leu Ala Lys Pro Gly Ala
1               5                   10                  15

Ser Val Lys Met Ser Cys Lys Ala Ser
            20                  25

<210> SEQ ID NO 115
<211> LENGTH: 25
<212> TYPE: PRT
<213> ORGANISM: Mus musculus

<400> SEQUENCE: 115

Gln Val Gln Leu Gln Gln Ser Gly Ala Glu Leu Val Lys Pro Gly Ala
1               5                   10                  15

Ser Val Lys Leu Ser Cys Lys Ala Ser
            20                  25

<210> SEQ ID NO 116
<211> LENGTH: 25
<212> TYPE: PRT
<213> ORGANISM: Mus musculus

<400> SEQUENCE: 116

Gln Ile Gln Leu Val Gln Ser Gly Pro Glu Leu Lys Lys Pro Gly Glu
1               5                   10                  15

Thr Val Lys Ile Ser Cys Lys Ala Ser
            20                  25

<210> SEQ ID NO 117
<211> LENGTH: 25
<212> TYPE: PRT
<213> ORGANISM: Mus musculus

<400> SEQUENCE: 117

Glu Val Leu Leu Val Glu Ser Gly Gly Gly Leu Val Gln Pro Gly Gly
1               5                   10                  15

Ser Leu Lys Leu Ser Cys Ala Thr Ser
            20                  25

```
<210> SEQ ID NO 118
<211> LENGTH: 25
<212> TYPE: PRT
<213> ORGANISM: Mus musculus

<400> SEQUENCE: 118

Gln Val Gln Met Lys Gln Ser Gly Pro Gly Leu Val Ala Pro Ser Gln
1               5                   10                  15

Ser Leu Ser Ile Thr Cys Thr Val Ser
            20                  25

<210> SEQ ID NO 119
<211> LENGTH: 25
<212> TYPE: PRT
<213> ORGANISM: Mus musculus

<400> SEQUENCE: 119

Gln Val Gln Leu Gln Gln Ser Gly Ala Glu Leu Ala Arg Pro Gly Ala
1               5                   10                  15

Ser Val Lys Met Ser Cys Lys Ala Ser
            20                  25

<210> SEQ ID NO 120
<211> LENGTH: 25
<212> TYPE: PRT
<213> ORGANISM: Mus musculus

<400> SEQUENCE: 120

Gln Val Ile Leu Lys Glu Ser Gly Pro Gly Ile Leu Gln Pro Ser Gln
1               5                   10                  15

Thr Leu Ser Leu Thr Cys Ser Phe Ser
            20                  25

<210> SEQ ID NO 121
<211> LENGTH: 25
<212> TYPE: PRT
<213> ORGANISM: Mus musculus

<400> SEQUENCE: 121

Glu Val Lys Ile Glu Glu Ser Gly Gly Gly Leu Val Gln Pro Gly Gly
1               5                   10                  15

Ser Met Lys Leu Ser Cys Ala Ala Ser
            20                  25

<210> SEQ ID NO 122
<211> LENGTH: 25
<212> TYPE: PRT
<213> ORGANISM: Mus musculus

<400> SEQUENCE: 122

Glu Val Met Leu Val Glu Ser Gly Gly Gly Leu Val Gln Pro Gly Gly
1               5                   10                  15

Ser Leu Lys Leu Ser Cys Ala Ala Ser
            20                  25

<210> SEQ ID NO 123
<211> LENGTH: 25
<212> TYPE: PRT
<213> ORGANISM: Mus musculus

<400> SEQUENCE: 123
```

```
Glu Val Lys Leu Glu Glu Ser Gly Gly Gly Leu Val Gln Pro Gly Gly
1               5                   10                  15

Ser Met Lys Leu Ser Cys Val Ala Ser
                20                  25
```

<210> SEQ ID NO 124
<211> LENGTH: 25
<212> TYPE: PRT
<213> ORGANISM: Mus musculus

<400> SEQUENCE: 124

```
Gln Val Gln Leu Gln Gln Ser Gly Pro Glu Leu Val Lys Pro Gly Ala
1               5                   10                  15

Ser Val Lys Met Ser Cys Lys Ala Ser
                20                  25
```

<210> SEQ ID NO 125
<211> LENGTH: 25
<212> TYPE: PRT
<213> ORGANISM: Mus musculus

<400> SEQUENCE: 125

```
Gln Ile Gln Leu Ala Gln Ser Gly Pro Glu Leu Lys Lys Pro Gly Glu
1               5                   10                  15

Thr Val Lys Ile Ser Cys Lys Ala Ser
                20                  25
```

<210> SEQ ID NO 126
<211> LENGTH: 25
<212> TYPE: PRT
<213> ORGANISM: Mus musculus

<400> SEQUENCE: 126

```
Gln Val Gln Leu Gln Gln Ser Gly Ala Glu Leu Val Lys Pro Gly Ala
1               5                   10                  15

Pro Val Lys Leu Ser Cys Lys Ala Ser
                20                  25
```

<210> SEQ ID NO 127
<211> LENGTH: 25
<212> TYPE: PRT
<213> ORGANISM: Mus musculus

<400> SEQUENCE: 127

```
Gln Met Gln Leu Lys Glu Ser Gly Thr Glu Leu Val Arg Pro Gly Ala
1               5                   10                  15

Ser Val Lys Leu Ser Cys Lys Ala Ser
                20                  25
```

<210> SEQ ID NO 128
<211> LENGTH: 25
<212> TYPE: PRT
<213> ORGANISM: Mus musculus

<400> SEQUENCE: 128

```
Gln Ile Gln Leu Gln Gln Ser Gly Ala Glu Leu Val Arg Pro Gly Ala
1               5                   10                  15

Ser Val Lys Ile Ser Cys Lys Ala Phe
                20                  25
```

<210> SEQ ID NO 129
<211> LENGTH: 25

```
<212> TYPE: PRT
<213> ORGANISM: Mus musculus

<400> SEQUENCE: 129

Asp Val Leu Val Glu Ser Gly Gly Asp Leu Val Lys Pro Gly Gly
1               5                   10                  15

Ser Leu Lys Leu Ser Cys Val Val Ser
            20                  25

<210> SEQ ID NO 130
<211> LENGTH: 25
<212> TYPE: PRT
<213> ORGANISM: Mus musculus

<400> SEQUENCE: 130

Gln Val Thr Leu Lys Glu Ser Gly Pro Gly Leu Val Ala Pro Ser Gln
1               5                   10                  15

Ser Leu Ser Ile Thr Cys Thr Val Ser
            20                  25

<210> SEQ ID NO 131
<211> LENGTH: 25
<212> TYPE: PRT
<213> ORGANISM: Mus musculus

<400> SEQUENCE: 131

Asp Val Gln Leu Gln Gln Ser Gly Pro Asp Leu Val Lys Pro Ser Gln
1               5                   10                  15

Ser Leu Ser Leu Thr Cys Thr Val Thr
            20                  25

<210> SEQ ID NO 132
<211> LENGTH: 25
<212> TYPE: PRT
<213> ORGANISM: Mus musculus

<400> SEQUENCE: 132

Gln Val Gln Leu Gln Gln Ser Gly Ala Glu Leu Val Lys Pro Gly Ala
1               5                   10                  15

Ser Val Arg Leu Ser Cys Lys Ala Ser
            20                  25

<210> SEQ ID NO 133
<211> LENGTH: 25
<212> TYPE: PRT
<213> ORGANISM: Mus musculus

<400> SEQUENCE: 133

Gln Val Gln Leu Gln Gln Pro Gly Ala Glu Leu Val Arg Pro Gly Ala
1               5                   10                  15

Ser Val Lys Leu Ser Cys Lys Ala Leu
            20                  25

<210> SEQ ID NO 134
<211> LENGTH: 25
<212> TYPE: PRT
<213> ORGANISM: Mus musculus

<400> SEQUENCE: 134

Gln Val Gln Leu Gln Gln Ser Gly Ala Glu Leu Val Arg Pro Gly Ser
1               5                   10                  15

Ser Val Lys Ile Ser Cys Lys Ala Ser
```

20                  25

<210> SEQ ID NO 135
<211> LENGTH: 25
<212> TYPE: PRT
<213> ORGANISM: Mus musculus

<400> SEQUENCE: 135

Glu Val Gln Leu Leu Glu Ser Gly Gly Gly Leu Val Gln Pro Gly Gly
1               5                   10                  15

Ser Leu Lys Leu Ser Cys Ala Ala Ser
            20                  25

<210> SEQ ID NO 136
<211> LENGTH: 25
<212> TYPE: PRT
<213> ORGANISM: Mus musculus

<400> SEQUENCE: 136

Glu Val Gln Leu Val Glu Thr Gly Gly Gly Leu Val Gln Pro Gly Gly
1               5                   10                  15

Ser Arg Gly Leu Ser Cys Glu Gly Ser
            20                  25

<210> SEQ ID NO 137
<211> LENGTH: 25
<212> TYPE: PRT
<213> ORGANISM: Mus musculus

<400> SEQUENCE: 137

Glu Val Lys Ile Glu Glu Ser Gly Gly Gly Leu Val Gln Pro Gly Gly
1               5                   10                  15

Ser Met Lys Leu Ser Cys Val Ala Ser
            20                  25

<210> SEQ ID NO 138
<211> LENGTH: 25
<212> TYPE: PRT
<213> ORGANISM: Mus musculus

<400> SEQUENCE: 138

Glu Val Met Leu Val Glu Ser Gly Gly Asp Leu Val Lys Pro Gly Gly
1               5                   10                  15

Ser Leu Lys Leu Ser Cys Ala Ala Ser
            20                  25

<210> SEQ ID NO 139
<211> LENGTH: 25
<212> TYPE: PRT
<213> ORGANISM: Mus musculus

<400> SEQUENCE: 139

Gln Val Gln Leu Gln Gln Pro Gly Ser Glu Leu Val Arg Pro Gly Ala
1               5                   10                  15

Ser Val Lys Leu Ser Cys Lys Ala Ser
            20                  25

<210> SEQ ID NO 140
<211> LENGTH: 25
<212> TYPE: PRT
<213> ORGANISM: Mus musculus

<400> SEQUENCE: 140

Gln Ile Gln Leu Gln Gln Pro Gly Pro Glu Leu Val Arg Pro Gly Ala
1               5                   10                  15

Ser Val Lys Met Ser Cys Lys Ala Ser
            20                  25

<210> SEQ ID NO 141
<211> LENGTH: 25
<212> TYPE: PRT
<213> ORGANISM: Mus musculus

<400> SEQUENCE: 141

Gln Val Gln Leu Gln Gln Pro Gly Ala Glu Leu Ala Arg Pro Gly Ala
1               5                   10                  15

Ser Val Lys Met Ser Cys Lys Ala Ser
            20                  25

<210> SEQ ID NO 142
<211> LENGTH: 25
<212> TYPE: PRT
<213> ORGANISM: Mus musculus

<400> SEQUENCE: 142

Gln Ile Gln Leu Gln Gln Ser Gly Ala Glu Leu Val Arg Pro Gly Val
1               5                   10                  15

Ser Val Lys Leu Ser Cys Lys Ala Ser
            20                  25

<210> SEQ ID NO 143
<211> LENGTH: 25
<212> TYPE: PRT
<213> ORGANISM: Mus musculus

<400> SEQUENCE: 143

Glu Val Gln Leu Gln Gln Ser Gly Ala Glu Leu Val Lys Pro Gly Ala
1               5                   10                  15

Ser Val Lys Met Ser Cys Lys Ala Ser
            20                  25

<210> SEQ ID NO 144
<211> LENGTH: 25
<212> TYPE: PRT
<213> ORGANISM: Mus musculus

<400> SEQUENCE: 144

Gln Ile Gln Leu Gln Gln Ser Gly Ala Glu Leu Met Lys Pro Gly Ala
1               5                   10                  15

Ser Val Lys Ile Ser Cys Lys Ala Thr
            20                  25

<210> SEQ ID NO 145
<211> LENGTH: 25
<212> TYPE: PRT
<213> ORGANISM: Mus musculus

<400> SEQUENCE: 145

Gln Val Lys Leu Val Glu Ser Gly Gly Gly Leu Val Gln Pro Gly Gly
1               5                   10                  15

Ser Leu Arg Leu Ser Cys Ala Thr Ser
            20                  25

<210> SEQ ID NO 146

```
<211> LENGTH: 25
<212> TYPE: PRT
<213> ORGANISM: Mus musculus

<400> SEQUENCE: 146

Glu Val Lys Leu Val Glu Thr Gly Gly Gly Leu Val Lys Pro Gly Gly
1               5                   10                  15

Ser Leu Lys Leu Ser Cys Ala Ala Ser
            20                  25

<210> SEQ ID NO 147
<211> LENGTH: 25
<212> TYPE: PRT
<213> ORGANISM: Mus musculus

<400> SEQUENCE: 147

Gln Val Gln Met Lys Glu Ser Gly Pro Glu Pro Val Lys Pro Gly Ala
1               5                   10                  15

Ser Val Lys Met Ser Cys Arg Ala Ser
            20                  25

<210> SEQ ID NO 148
<211> LENGTH: 25
<212> TYPE: PRT
<213> ORGANISM: Mus musculus

<400> SEQUENCE: 148

Glu Val Lys Leu Val Glu Ser Gly Gly Gly Leu Val Lys Pro Gly Gly
1               5                   10                  15

Ser Leu Lys Leu Ser Cys Ala Ala Ser
            20                  25

<210> SEQ ID NO 149
<211> LENGTH: 25
<212> TYPE: PRT
<213> ORGANISM: Mus musculus

<400> SEQUENCE: 149

Glu Val Lys Ile Val Glu Ser Gly Gly Gly Leu Val Gln Pro Lys Gly
1               5                   10                  15

Ser Leu Lys Leu Ser Cys Ala Ala Ser
            20                  25

<210> SEQ ID NO 150
<211> LENGTH: 25
<212> TYPE: PRT
<213> ORGANISM: Mus musculus

<400> SEQUENCE: 150

Gln Val Gln Leu Val Glu Thr Gly Gly Gly Leu Val Arg Pro Gly Asn
1               5                   10                  15

Ser Leu Lys Leu Ser Cys Val Thr Ser
            20                  25

<210> SEQ ID NO 151
<211> LENGTH: 8
<212> TYPE: PRT
<213> ORGANISM: Mus musculus

<400> SEQUENCE: 151

Gly Phe Thr Phe Ser Ser Tyr Ala
1               5
```

<210> SEQ ID NO 152
<211> LENGTH: 8
<212> TYPE: PRT
<213> ORGANISM: Mus musculus

<400> SEQUENCE: 152

Gly Tyr Thr Leu Thr Asp Tyr Ser
1               5

<210> SEQ ID NO 153
<211> LENGTH: 8
<212> TYPE: PRT
<213> ORGANISM: Mus musculus

<400> SEQUENCE: 153

Gly Tyr Thr Phe Thr Ser Tyr Val
1               5

<210> SEQ ID NO 154
<211> LENGTH: 8
<212> TYPE: PRT
<213> ORGANISM: Mus musculus

<400> SEQUENCE: 154

Gly Phe Ala Phe Ser Ser Tyr Asp
1               5

<210> SEQ ID NO 155
<211> LENGTH: 8
<212> TYPE: PRT
<213> ORGANISM: Mus musculus

<400> SEQUENCE: 155

Gly Tyr Ala Phe Thr Asn Tyr Leu
1               5

<210> SEQ ID NO 156
<211> LENGTH: 8
<212> TYPE: PRT
<213> ORGANISM: Mus musculus

<400> SEQUENCE: 156

Gly Tyr Ile Phe Thr Asn Tyr Trp
1               5

<210> SEQ ID NO 157
<211> LENGTH: 8
<212> TYPE: PRT
<213> ORGANISM: Mus musculus

<400> SEQUENCE: 157

Gly Tyr Thr Phe Thr Ser Tyr Trp
1               5

<210> SEQ ID NO 158
<211> LENGTH: 8
<212> TYPE: PRT
<213> ORGANISM: Mus musculus

<400> SEQUENCE: 158

Gly Tyr Thr Phe Thr Ser Tyr Tyr
1               5

<210> SEQ ID NO 159

```
<211> LENGTH: 8
<212> TYPE: PRT
<213> ORGANISM: Mus musculus

<400> SEQUENCE: 159

Gly Tyr Thr Phe Thr Asn Tyr Gly
1               5

<210> SEQ ID NO 160
<211> LENGTH: 8
<212> TYPE: PRT
<213> ORGANISM: Mus musculus

<400> SEQUENCE: 160

Gly Phe Thr Phe Ser Asp Tyr Tyr
1               5

<210> SEQ ID NO 161
<211> LENGTH: 8
<212> TYPE: PRT
<213> ORGANISM: Mus musculus

<400> SEQUENCE: 161

Gly Phe Ser Leu Thr Ser Tyr Gly
1               5

<210> SEQ ID NO 162
<211> LENGTH: 8
<212> TYPE: PRT
<213> ORGANISM: Mus musculus

<400> SEQUENCE: 162

Gly Tyr Thr Phe Thr Ser Tyr Thr
1               5

<210> SEQ ID NO 163
<211> LENGTH: 10
<212> TYPE: PRT
<213> ORGANISM: Mus musculus

<400> SEQUENCE: 163

Gly Phe Ser Leu Ser Thr Ser Gly Met Ser
1               5                   10

<210> SEQ ID NO 164
<211> LENGTH: 8
<212> TYPE: PRT
<213> ORGANISM: Mus musculus

<400> SEQUENCE: 164

Gly Phe Thr Phe Ser Asp Ala Trp
1               5

<210> SEQ ID NO 165
<211> LENGTH: 8
<212> TYPE: PRT
<213> ORGANISM: Mus musculus

<400> SEQUENCE: 165

Gly Phe Thr Phe Ser Ser Tyr Gly
1               5

<210> SEQ ID NO 166
<211> LENGTH: 8
<212> TYPE: PRT
```

<213> ORGANISM: Mus musculus

<400> SEQUENCE: 166

Gly Phe Thr Phe Ser Asn Tyr Trp
1               5

<210> SEQ ID NO 167
<211> LENGTH: 8
<212> TYPE: PRT
<213> ORGANISM: Mus musculus

<400> SEQUENCE: 167

Gly Asp Thr Phe Ser Ser Tyr Val
1               5

<210> SEQ ID NO 168
<211> LENGTH: 8
<212> TYPE: PRT
<213> ORGANISM: Mus musculus

<400> SEQUENCE: 168

Gly Tyr Ser Phe Thr Lys Asn Gly
1               5

<210> SEQ ID NO 169
<211> LENGTH: 8
<212> TYPE: PRT
<213> ORGANISM: Mus musculus

<400> SEQUENCE: 169

Gly Tyr Thr Phe Asn Ser His Trp
1               5

<210> SEQ ID NO 170
<211> LENGTH: 8
<212> TYPE: PRT
<213> ORGANISM: Mus musculus

<400> SEQUENCE: 170

Gly Tyr Thr Phe Thr Asn His His
1               5

<210> SEQ ID NO 171
<211> LENGTH: 8
<212> TYPE: PRT
<213> ORGANISM: Mus musculus

<400> SEQUENCE: 171

Gly Leu Thr Phe Ser Ser Tyr Gly
1               5

<210> SEQ ID NO 172
<211> LENGTH: 8
<212> TYPE: PRT
<213> ORGANISM: Mus musculus

<400> SEQUENCE: 172

Gly Phe Thr Phe Asn Asp Ala Trp
1               5

<210> SEQ ID NO 173
<211> LENGTH: 9
<212> TYPE: PRT
<213> ORGANISM: Mus musculus

```
<400> SEQUENCE: 173

Gly Tyr Ser Ile Thr Ser Gly Tyr Ser
1               5

<210> SEQ ID NO 174
<211> LENGTH: 8
<212> TYPE: PRT
<213> ORGANISM: Mus musculus

<400> SEQUENCE: 174

Gly Tyr Thr Phe Thr Asp Tyr Glu
1               5

<210> SEQ ID NO 175
<211> LENGTH: 8
<212> TYPE: PRT
<213> ORGANISM: Mus musculus

<400> SEQUENCE: 175

Gly Tyr Ala Phe Ser Ser Tyr Trp
1               5

<210> SEQ ID NO 176
<211> LENGTH: 8
<212> TYPE: PRT
<213> ORGANISM: Mus musculus

<400> SEQUENCE: 176

Gly Phe Thr Phe Ser Gly Phe Trp
1               5

<210> SEQ ID NO 177
<211> LENGTH: 8
<212> TYPE: PRT
<213> ORGANISM: Mus musculus

<400> SEQUENCE: 177

Gly Phe Thr Phe Ser Ser Tyr Trp
1               5

<210> SEQ ID NO 178
<211> LENGTH: 8
<212> TYPE: PRT
<213> ORGANISM: Mus musculus

<400> SEQUENCE: 178

Gly Tyr Thr Phe Thr Ser Tyr Asn
1               5

<210> SEQ ID NO 179
<211> LENGTH: 8
<212> TYPE: PRT
<213> ORGANISM: Mus musculus

<400> SEQUENCE: 179

Gly Tyr Thr Phe Ser Ser Tyr Trp
1               5

<210> SEQ ID NO 180
<211> LENGTH: 8
<212> TYPE: PRT
<213> ORGANISM: Mus musculus

<400> SEQUENCE: 180
```

```
Gly Phe Thr Phe Thr Asp Tyr Tyr
1               5

<210> SEQ ID NO 181
<211> LENGTH: 8
<212> TYPE: PRT
<213> ORGANISM: Mus musculus

<400> SEQUENCE: 181

Gly Tyr Thr Leu Thr Asp Tyr Val
1               5

<210> SEQ ID NO 182
<211> LENGTH: 8
<212> TYPE: PRT
<213> ORGANISM: Mus musculus

<400> SEQUENCE: 182

Gly Phe Thr Phe Asn Thr Tyr Ala
1               5

<210> SEQ ID NO 183
<211> LENGTH: 8
<212> TYPE: PRT
<213> ORGANISM: Mus musculus

<400> SEQUENCE: 183

Gly Phe Thr Phe Ser Asn Tyr Arg
1               5

<210> SEQ ID NO 184
<211> LENGTH: 17
<212> TYPE: PRT
<213> ORGANISM: Mus musculus

<400> SEQUENCE: 184

Met Ser Trp Val Arg Gln Thr Pro Glu Lys Arg Leu Glu Trp Val Ala
1               5                   10                  15

Ser

<210> SEQ ID NO 185
<211> LENGTH: 17
<212> TYPE: PRT
<213> ORGANISM: Mus musculus

<400> SEQUENCE: 185

Met His Trp Val Lys Gln Ala Pro Gly Lys Gly Leu Lys Trp Met Gly
1               5                   10                  15

Trp

<210> SEQ ID NO 186
<211> LENGTH: 17
<212> TYPE: PRT
<213> ORGANISM: Mus musculus

<400> SEQUENCE: 186

Met His Trp Val Lys Gln Lys Pro Gly Gln Gly Leu Glu Trp Ile Gly
1               5                   10                  15

Tyr

<210> SEQ ID NO 187
<211> LENGTH: 17
<212> TYPE: PRT
```

```
<213> ORGANISM: Mus musculus

<400> SEQUENCE: 187

Met Ser Trp Val Arg Gln Thr Pro Glu Lys Arg Leu Glu Trp Val Ala
1               5                   10                  15
Tyr

<210> SEQ ID NO 188
<211> LENGTH: 17
<212> TYPE: PRT
<213> ORGANISM: Mus musculus

<400> SEQUENCE: 188

Ile Glu Trp Val Lys Gln Arg Pro Gly Gln Gly Leu Glu Trp Ile Gly
1               5                   10                  15
Val

<210> SEQ ID NO 189
<211> LENGTH: 17
<212> TYPE: PRT
<213> ORGANISM: Mus musculus

<400> SEQUENCE: 189

Met Asn Trp Val Lys Gln Arg Pro Gly Gln Gly Leu Glu Trp Ile Gly
1               5                   10                  15
Met

<210> SEQ ID NO 190
<211> LENGTH: 17
<212> TYPE: PRT
<213> ORGANISM: Mus musculus

<400> SEQUENCE: 190

Met His Trp Val Lys Gln Arg Pro Gly Gln Gly Leu Glu Trp Ile Gly
1               5                   10                  15
Tyr

<210> SEQ ID NO 191
<211> LENGTH: 17
<212> TYPE: PRT
<213> ORGANISM: Mus musculus

<400> SEQUENCE: 191

Met Tyr Trp Val Lys Gln Arg Pro Gly Gln Gly Leu Glu Trp Ile Gly
1               5                   10                  15
Glu

<210> SEQ ID NO 192
<211> LENGTH: 17
<212> TYPE: PRT
<213> ORGANISM: Mus musculus

<400> SEQUENCE: 192

Met Asn Trp Val Lys Gln Thr Pro Gly Lys Gly Leu Lys Trp Met Gly
1               5                   10                  15
Trp

<210> SEQ ID NO 193
<211> LENGTH: 17
<212> TYPE: PRT
<213> ORGANISM: Mus musculus
```

<400> SEQUENCE: 193

Met Tyr Trp Val Arg Gln Thr Pro Glu Lys Arg Leu Glu Trp Val Ala
1               5                   10                  15

Tyr

<210> SEQ ID NO 194
<211> LENGTH: 17
<212> TYPE: PRT
<213> ORGANISM: Mus musculus

<400> SEQUENCE: 194

Val His Trp Val Arg Gln Pro Pro Gly Lys Gly Leu Glu Trp Leu Gly
1               5                   10                  15

Val

<210> SEQ ID NO 195
<211> LENGTH: 17
<212> TYPE: PRT
<213> ORGANISM: Mus musculus

<400> SEQUENCE: 195

Met Asn Trp Val Lys Gln Arg Pro Glu Gln Gly Leu Glu Trp Ile Gly
1               5                   10                  15

Arg

<210> SEQ ID NO 196
<211> LENGTH: 17
<212> TYPE: PRT
<213> ORGANISM: Mus musculus

<400> SEQUENCE: 196

Ile His Trp Val Lys Gln Arg Pro Gly Gln Gly Leu Glu Trp Ile Gly
1               5                   10                  15

Tyr

<210> SEQ ID NO 197
<211> LENGTH: 17
<212> TYPE: PRT
<213> ORGANISM: Mus musculus

<400> SEQUENCE: 197

Met Ser Trp Val Arg Gln Phe Pro Glu Lys Arg Leu Glu Trp Val Ala
1               5                   10                  15

Glu

<210> SEQ ID NO 198
<211> LENGTH: 17
<212> TYPE: PRT
<213> ORGANISM: Mus musculus

<400> SEQUENCE: 198

Val Gly Trp Ile Arg Gln Pro Ser Gly Lys Gly Leu Glu Trp Leu Ala
1               5                   10                  15

His

<210> SEQ ID NO 199
<211> LENGTH: 17
<212> TYPE: PRT
<213> ORGANISM: Mus musculus

```
<400> SEQUENCE: 199

Met Asp Trp Val Arg Gln Ser Pro Glu Lys Gly Leu Glu Trp Val Ala
1               5                   10                  15
Glu

<210> SEQ ID NO 200
<211> LENGTH: 17
<212> TYPE: PRT
<213> ORGANISM: Mus musculus

<400> SEQUENCE: 200

Met Ser Trp Val Arg Gln Thr Pro Asp Lys Arg Leu Glu Leu Val Ala
1               5                   10                  15
Thr

<210> SEQ ID NO 201
<211> LENGTH: 17
<212> TYPE: PRT
<213> ORGANISM: Mus musculus

<400> SEQUENCE: 201

Met Asn Trp Val Arg Gln Ser Pro Glu Lys Gly Leu Glu Trp Val Ala
1               5                   10                  15
Glu

<210> SEQ ID NO 202
<211> LENGTH: 17
<212> TYPE: PRT
<213> ORGANISM: Mus musculus

<400> SEQUENCE: 202

Ile His Trp Val Lys Gln Lys Pro Gly Gln Gly Leu Glu Trp Ile Gly
1               5                   10                  15
Tyr

<210> SEQ ID NO 203
<211> LENGTH: 17
<212> TYPE: PRT
<213> ORGANISM: Mus musculus

<400> SEQUENCE: 203

Met Asn Trp Val Lys Gln Ala Pro Gly Lys Gly Leu Lys Trp Met Gly
1               5                   10                  15
Trp

<210> SEQ ID NO 204
<211> LENGTH: 17
<212> TYPE: PRT
<213> ORGANISM: Mus musculus

<400> SEQUENCE: 204

Met Asn Trp Val Lys Gln Arg Pro Gly Arg Gly Leu Glu Trp Ile Gly
1               5                   10                  15
Arg

<210> SEQ ID NO 205
<211> LENGTH: 17
<212> TYPE: PRT
<213> ORGANISM: Mus musculus

<400> SEQUENCE: 205
```

```
Met Asn Trp Val Lys Gln Arg Pro Glu Gln Gly Leu Glu Trp Ile Gly
1               5                   10                  15

Lys

<210> SEQ ID NO 206
<211> LENGTH: 17
<212> TYPE: PRT
<213> ORGANISM: Mus musculus

<400> SEQUENCE: 206

Ile Asn Trp Val Lys Gln Arg Pro Gly Gln Gly Leu Asp Trp Ile Gly
1               5                   10                  15

Tyr

<210> SEQ ID NO 207
<211> LENGTH: 17
<212> TYPE: PRT
<213> ORGANISM: Mus musculus

<400> SEQUENCE: 207

Met Ser Trp Val Arg Gln Thr Pro Asp Lys Arg Leu Glu Trp Val Ala
1               5                   10                  15

Thr

<210> SEQ ID NO 208
<211> LENGTH: 17
<212> TYPE: PRT
<213> ORGANISM: Mus musculus

<400> SEQUENCE: 208

Trp His Trp Ile Arg Gln Phe Pro Gly Asn Lys Leu Glu Trp Met Gly
1               5                   10                  15

Tyr

<210> SEQ ID NO 209
<211> LENGTH: 17
<212> TYPE: PRT
<213> ORGANISM: Mus musculus

<400> SEQUENCE: 209

Met His Trp Val Lys Gln Arg Pro Gly Gln Gly Leu Glu Trp Ile Gly
1               5                   10                  15

Glu

<210> SEQ ID NO 210
<211> LENGTH: 17
<212> TYPE: PRT
<213> ORGANISM: Mus musculus

<400> SEQUENCE: 210

Met His Trp Val Lys Gln Thr Pro Val His Gly Leu Glu Trp Ile Gly
1               5                   10                  15

Ala

<210> SEQ ID NO 211
<211> LENGTH: 17
<212> TYPE: PRT
<213> ORGANISM: Mus musculus

<400> SEQUENCE: 211
```

Met Asn Trp Val Lys Gln Arg Pro Gly Gln Gly Leu Glu Trp Ile Gly
1               5                   10                  15

Gln

<210> SEQ ID NO 212
<211> LENGTH: 17
<212> TYPE: PRT
<213> ORGANISM: Mus musculus

<400> SEQUENCE: 212

Met Ser Trp Val Arg Gln Thr Pro Gly Lys Thr Leu Glu Trp Ile Gly
1               5                   10                  15

Asp

<210> SEQ ID NO 213
<211> LENGTH: 17
<212> TYPE: PRT
<213> ORGANISM: Mus musculus

<400> SEQUENCE: 213

Met Ser Trp Val Arg Gln Ser Pro Glu Lys Gly Leu Glu Trp Val Ala
1               5                   10                  15

Glu

<210> SEQ ID NO 214
<211> LENGTH: 17
<212> TYPE: PRT
<213> ORGANISM: Mus musculus

<400> SEQUENCE: 214

Met His Trp Val Lys Gln Arg Tyr Gly Gln Gly Leu Glu Trp Ile Gly
1               5                   10                  15

Asn

<210> SEQ ID NO 215
<211> LENGTH: 17
<212> TYPE: PRT
<213> ORGANISM: Mus musculus

<400> SEQUENCE: 215

Met His Trp Val Lys Gln Arg Pro Gly Gln Gly Leu Glu Trp Ile Gly
1               5                   10                  15

Met

<210> SEQ ID NO 216
<211> LENGTH: 17
<212> TYPE: PRT
<213> ORGANISM: Mus musculus

<400> SEQUENCE: 216

Met His Trp Ile Lys Gln Arg Pro Glu Gln Gly Leu Glu Arg Ile Gly
1               5                   10                  15

Glu

<210> SEQ ID NO 217
<211> LENGTH: 17
<212> TYPE: PRT
<213> ORGANISM: Mus musculus

<400> SEQUENCE: 217

Met His Trp Val Lys Gln Thr Pro Gly Gln Gly Leu Glu Trp Ile Gly

<210> SEQ ID NO 218
<211> LENGTH: 17
<212> TYPE: PRT
<213> ORGANISM: Mus musculus

<400> SEQUENCE: 218

Ile Glu Trp Val Lys Gln Arg Pro Gly His Gly Leu Glu Trp Ile Gly
1               5                   10                  15
Glu

<210> SEQ ID NO 219
<211> LENGTH: 17
<212> TYPE: PRT
<213> ORGANISM: Mus musculus

<400> SEQUENCE: 219

Met Ser Trp Val Arg Gln Pro Pro Gly Lys Ala Leu Glu Trp Leu Gly
1               5                   10                  15
Phe

<210> SEQ ID NO 220
<211> LENGTH: 17
<212> TYPE: PRT
<213> ORGANISM: Mus musculus

<400> SEQUENCE: 220

Val Ser Trp Val Lys Gln Arg Leu Gly Gln Gly Leu Glu Trp Ile Gly
1               5                   10                  15
Glu

<210> SEQ ID NO 221
<211> LENGTH: 17
<212> TYPE: PRT
<213> ORGANISM: Mus musculus

<400> SEQUENCE: 221

Met Ser Trp Val Arg Gln Thr Pro Glu Lys Arg Leu Glu Trp Val Ala
1               5                   10                  15
Thr

<210> SEQ ID NO 222
<211> LENGTH: 17
<212> TYPE: PRT
<213> ORGANISM: Mus musculus

<400> SEQUENCE: 222

Met Asn Trp Val Arg Gln Ala Pro Glu Lys Gly Leu Glu Trp Val Ala
1               5                   10                  15
Arg

<210> SEQ ID NO 223
<211> LENGTH: 17
<212> TYPE: PRT
<213> ORGANISM: Mus musculus

<400> SEQUENCE: 223

Met His Trp Leu Arg Gln Pro Pro Gly Lys Arg Leu Glu Trp Ile Ala
1               5                   10                  15

Val

<210> SEQ ID NO 224
<211> LENGTH: 7
<212> TYPE: PRT
<213> ORGANISM: Mus musculus

<400> SEQUENCE: 224

Ile Ser Ser Gly Gly Ser Thr
1               5

<210> SEQ ID NO 225
<211> LENGTH: 8
<212> TYPE: PRT
<213> ORGANISM: Mus musculus

<400> SEQUENCE: 225

Ile Asn Thr Glu Thr Gly Glu Pro
1               5

<210> SEQ ID NO 226
<211> LENGTH: 8
<212> TYPE: PRT
<213> ORGANISM: Mus musculus

<400> SEQUENCE: 226

Ile Asn Pro Tyr Asn Asp Gly Thr
1               5

<210> SEQ ID NO 227
<211> LENGTH: 8
<212> TYPE: PRT
<213> ORGANISM: Mus musculus

<400> SEQUENCE: 227

Ile Ser Ser Gly Gly Ser Thr
1               5

<210> SEQ ID NO 228
<211> LENGTH: 8
<212> TYPE: PRT
<213> ORGANISM: Mus musculus

<400> SEQUENCE: 228

Ile Asn Pro Gly Ser Gly Gly Thr
1               5

<210> SEQ ID NO 229
<211> LENGTH: 8
<212> TYPE: PRT
<213> ORGANISM: Mus musculus

<400> SEQUENCE: 229

Ile Asp Pro Ser Asp Ser Glu Thr
1               5

<210> SEQ ID NO 230
<211> LENGTH: 8
<212> TYPE: PRT
<213> ORGANISM: Mus musculus

<400> SEQUENCE: 230

Ile Asn Pro Ser Thr Gly Tyr Thr
1               5

```
<210> SEQ ID NO 231
<211> LENGTH: 8
<212> TYPE: PRT
<213> ORGANISM: Mus musculus

<400> SEQUENCE: 231

Ile Asn Pro Ser Asn Gly Gly Thr
1               5

<210> SEQ ID NO 232
<211> LENGTH: 8
<212> TYPE: PRT
<213> ORGANISM: Mus musculus

<400> SEQUENCE: 232

Ile Asn Thr Tyr Thr Gly Glu Pro
1               5

<210> SEQ ID NO 233
<211> LENGTH: 8
<212> TYPE: PRT
<213> ORGANISM: Mus musculus

<400> SEQUENCE: 233

Ile Ser Asn Gly Gly Gly Ser Thr
1               5

<210> SEQ ID NO 234
<211> LENGTH: 7
<212> TYPE: PRT
<213> ORGANISM: Mus musculus

<400> SEQUENCE: 234

Ile Trp Ala Gly Gly Ser Thr
1               5

<210> SEQ ID NO 235
<211> LENGTH: 8
<212> TYPE: PRT
<213> ORGANISM: Mus musculus

<400> SEQUENCE: 235

Ile Asp Pro Tyr Asp Ser Glu Thr
1               5

<210> SEQ ID NO 236
<211> LENGTH: 8
<212> TYPE: PRT
<213> ORGANISM: Mus musculus

<400> SEQUENCE: 236

Ile Asn Pro Ser Ser Gly Tyr Thr
1               5

<210> SEQ ID NO 237
<211> LENGTH: 8
<212> TYPE: PRT
<213> ORGANISM: Mus musculus

<400> SEQUENCE: 237

Ile Ser Ser Gly Gly Ser Tyr Thr
1               5
```

```
<210> SEQ ID NO 238
<211> LENGTH: 7
<212> TYPE: PRT
<213> ORGANISM: Mus musculus

<400> SEQUENCE: 238

Ile Trp Trp Asn Asp Asp Lys
1               5

<210> SEQ ID NO 239
<211> LENGTH: 10
<212> TYPE: PRT
<213> ORGANISM: Mus musculus

<400> SEQUENCE: 239

Ile Arg Ser Lys Ala Asn Asn His Ala Thr
1               5                   10

<210> SEQ ID NO 240
<211> LENGTH: 8
<212> TYPE: PRT
<213> ORGANISM: Mus musculus

<400> SEQUENCE: 240

Ile Asn Ser Asn Gly Gly Ser Thr
1               5

<210> SEQ ID NO 241
<211> LENGTH: 10
<212> TYPE: PRT
<213> ORGANISM: Mus musculus

<400> SEQUENCE: 241

Ile Arg Leu Lys Ser Asn Asn Tyr Ala Thr
1               5                   10

<210> SEQ ID NO 242
<211> LENGTH: 8
<212> TYPE: PRT
<213> ORGANISM: Mus musculus

<400> SEQUENCE: 242

Phe Asn Pro Tyr Ser Asp Asp Ile
1               5

<210> SEQ ID NO 243
<211> LENGTH: 8
<212> TYPE: PRT
<213> ORGANISM: Mus musculus

<400> SEQUENCE: 243

Ile Asn Pro Tyr Asn Asp Tyr Thr
1               5

<210> SEQ ID NO 244
<211> LENGTH: 8
<212> TYPE: PRT
<213> ORGANISM: Mus musculus

<400> SEQUENCE: 244

Ile Ser Ser Gly Gly Ser Tyr Ile
1               5

<210> SEQ ID NO 245
<211> LENGTH: 7
```

```
<212> TYPE: PRT
<213> ORGANISM: Mus musculus

<400> SEQUENCE: 245

Ile His Tyr Ser Gly Ser Thr
1               5

<210> SEQ ID NO 246
<211> LENGTH: 8
<212> TYPE: PRT
<213> ORGANISM: Mus musculus

<400> SEQUENCE: 246

Ile Asp Pro Ser Asp Ser Tyr Thr
1               5

<210> SEQ ID NO 247
<211> LENGTH: 8
<212> TYPE: PRT
<213> ORGANISM: Mus musculus

<400> SEQUENCE: 247

Ile His Pro Gly Ser Gly Gly Thr
1               5

<210> SEQ ID NO 248
<211> LENGTH: 8
<212> TYPE: PRT
<213> ORGANISM: Mus musculus

<400> SEQUENCE: 248

Ile Tyr Pro Gly Asp Gly Asp Thr
1               5

<210> SEQ ID NO 249
<211> LENGTH: 8
<212> TYPE: PRT
<213> ORGANISM: Mus musculus

<400> SEQUENCE: 249

Ile Asn Ser Asp Gly Ser Ala Ile
1               5

<210> SEQ ID NO 250
<211> LENGTH: 10
<212> TYPE: PRT
<213> ORGANISM: Mus musculus

<400> SEQUENCE: 250

Ile Arg Leu Lys Ser Asp Asn Tyr Ala Thr
1               5                   10

<210> SEQ ID NO 251
<211> LENGTH: 8
<212> TYPE: PRT
<213> ORGANISM: Mus musculus

<400> SEQUENCE: 251

Ile Tyr Pro Gly Ser Gly Ser Thr
1               5

<210> SEQ ID NO 252
<211> LENGTH: 8
<212> TYPE: PRT
<213> ORGANISM: Mus musculus
```

<400> SEQUENCE: 252

Ile Asp Pro Ser Asn Ser Glu Thr
1               5

<210> SEQ ID NO 253
<211> LENGTH: 8
<212> TYPE: PRT
<213> ORGANISM: Mus musculus

<400> SEQUENCE: 253

Ile Tyr Pro Gly Asn Gly Asp Thr
1               5

<210> SEQ ID NO 254
<211> LENGTH: 8
<212> TYPE: PRT
<213> ORGANISM: Mus musculus

<400> SEQUENCE: 254

Ile Leu Pro Gly Ser Gly Ser Thr
1               5

<210> SEQ ID NO 255
<211> LENGTH: 10
<212> TYPE: PRT
<213> ORGANISM: Mus musculus

<400> SEQUENCE: 255

Ile Arg Asn Lys Ala Asn Gly Tyr Thr Thr
1               5                   10

<210> SEQ ID NO 256
<211> LENGTH: 8
<212> TYPE: PRT
<213> ORGANISM: Mus musculus

<400> SEQUENCE: 256

Ile Asn Pro Ser Asn Ser Gly Thr
1               5

<210> SEQ ID NO 257
<211> LENGTH: 10
<212> TYPE: PRT
<213> ORGANISM: Mus musculus

<400> SEQUENCE: 257

Ile Arg Ser Lys Ser Asn Asn Tyr Val Thr
1               5                   10

<210> SEQ ID NO 258
<211> LENGTH: 10
<212> TYPE: PRT
<213> ORGANISM: Mus musculus

<400> SEQUENCE: 258

Ile Thr Val Lys Ser Asp Asn Tyr Gly Ala
1               5                   10

<210> SEQ ID NO 259
<211> LENGTH: 38
<212> TYPE: PRT
<213> ORGANISM: Mus musculus

<400> SEQUENCE: 259

```
Tyr Tyr Pro Asp Ser Val Lys Gly Arg Phe Thr Ile Ser Arg Asp Asn
1               5                   10                  15

Ala Arg Asn Ile Leu Tyr Leu Gln Met Ser Ser Leu Arg Ser Glu Asp
            20                  25                  30

Thr Ala Met Tyr Tyr Cys
        35

<210> SEQ ID NO 260
<211> LENGTH: 38
<212> TYPE: PRT
<213> ORGANISM: Mus musculus

<400> SEQUENCE: 260

Thr Tyr Ala Asp Asp Phe Lys Gly Arg Phe Ala Phe Ser Leu Glu Thr
1               5                   10                  15

Ser Ala Ser Thr Ala Tyr Leu Gln Ile Asn Asn Leu Lys Asn Glu Asp
            20                  25                  30

Thr Ala Thr Tyr Phe Cys
        35

<210> SEQ ID NO 261
<211> LENGTH: 38
<212> TYPE: PRT
<213> ORGANISM: Mus musculus

<400> SEQUENCE: 261

Lys Tyr Asn Glu Lys Phe Lys Gly Lys Ala Thr Leu Thr Ser Asp Lys
1               5                   10                  15

Ser Ser Ser Thr Ala Tyr Met Glu Leu Ser Ser Leu Thr Ser Glu Asp
            20                  25                  30

Ser Ala Val Tyr Tyr Cys
        35

<210> SEQ ID NO 262
<211> LENGTH: 38
<212> TYPE: PRT
<213> ORGANISM: Mus musculus

<400> SEQUENCE: 262

Tyr Tyr Pro Asp Thr Val Lys Gly Arg Phe Thr Ile Ser Arg Asp Asn
1               5                   10                  15

Ala Lys Asn Thr Leu Tyr Leu Gln Met Ser Ser Leu Lys Ser Glu Asp
            20                  25                  30

Thr Ala Met Tyr Tyr Cys
        35

<210> SEQ ID NO 263
<211> LENGTH: 38
<212> TYPE: PRT
<213> ORGANISM: Mus musculus

<400> SEQUENCE: 263

Asn Tyr Asn Glu Lys Phe Lys Gly Lys Ala Thr Leu Thr Ala Asp Lys
1               5                   10                  15

Ser Ser Ser Thr Ala Tyr Met Gln Leu Ser Ser Leu Thr Ser Asp Asp
            20                  25                  30

Ser Ala Val Tyr Phe Cys
        35
```

```
<210> SEQ ID NO 264
<211> LENGTH: 38
<212> TYPE: PRT
<213> ORGANISM: Mus musculus

<400> SEQUENCE: 264

His Tyr Asn Gln Met Ser Lys Asp Lys Ala Thr Leu Thr Val Asp Lys
1               5                   10                  15

Ser Ser Ser Thr Ala Tyr Met Gln Leu Ser Ser Leu Thr Ser Glu Asp
            20                  25                  30

Ser Ala Val Tyr Tyr Cys
        35

<210> SEQ ID NO 265
<211> LENGTH: 38
<212> TYPE: PRT
<213> ORGANISM: Mus musculus

<400> SEQUENCE: 265

Glu Tyr Asn Gln Lys Phe Lys Asp Lys Ala Thr Leu Thr Ala Asp Lys
1               5                   10                  15

Ser Ser Ser Thr Ala Tyr Met Gln Leu Ser Ser Leu Thr Ser Glu Asp
            20                  25                  30

Ser Ala Val Tyr Tyr Cys
        35

<210> SEQ ID NO 266
<211> LENGTH: 38
<212> TYPE: PRT
<213> ORGANISM: Mus musculus

<400> SEQUENCE: 266

Asn Phe Asn Glu Lys Phe Lys Ser Lys Ala Thr Leu Thr Val Asp Lys
1               5                   10                  15

Ser Ser Ser Thr Ala Tyr Met Gln Leu Ser Ser Leu Thr Ser Glu Asp
            20                  25                  30

Ser Ala Val Tyr Tyr Cys
        35

<210> SEQ ID NO 267
<211> LENGTH: 38
<212> TYPE: PRT
<213> ORGANISM: Mus musculus

<400> SEQUENCE: 267

Tyr Tyr Pro Asp Thr Val Lys Gly Arg Phe Thr Ile Ser Arg Asp Asn
1               5                   10                  15

Ala Lys Asn Thr Leu Tyr Leu Gln Met Ser Arg Leu Lys Ser Glu Asp
            20                  25                  30

Thr Ala Met Tyr Tyr Cys
        35

<210> SEQ ID NO 268
<211> LENGTH: 38
<212> TYPE: PRT
<213> ORGANISM: Mus musculus

<400> SEQUENCE: 268

Asn Tyr Asn Ser Ala Leu Met Ser Arg Leu Ser Ile Ser Lys Asp Asn
1               5                   10                  15

Ser Lys Ser Gln Val Phe Leu Lys Met Asn Ser Leu Gln Thr Asp Asp
```

```
                  20                  25                  30

Thr Ala Met Tyr Tyr Cys
            35

<210> SEQ ID NO 269
<211> LENGTH: 38
<212> TYPE: PRT
<213> ORGANISM: Mus musculus

<400> SEQUENCE: 269

His Tyr Asn Gln Lys Phe Lys Asp Lys Ala Ile Leu Thr Val Asp Lys
1               5                   10                  15

Ser Ser Ser Thr Ala Tyr Met Gln Leu Ser Ser Leu Thr Ser Glu Asp
            20                  25                  30

Ser Ala Val Tyr Tyr Cys
            35

<210> SEQ ID NO 270
<211> LENGTH: 38
<212> TYPE: PRT
<213> ORGANISM: Mus musculus

<400> SEQUENCE: 270

Asn Tyr Asn Gln Lys Phe Lys Asp Lys Ala Thr Leu Thr Ala Asp Lys
1               5                   10                  15

Ser Ser Ser Thr Ala Tyr Met Gln Leu Ser Ser Leu Thr Ser Glu Asp
            20                  25                  30

Ser Ala Val Tyr Tyr Cys
            35

<210> SEQ ID NO 271
<211> LENGTH: 38
<212> TYPE: PRT
<213> ORGANISM: Mus musculus

<400> SEQUENCE: 271

Tyr Tyr Pro Asp Thr Val Thr Gly Arg Phe Thr Ile Ser Arg Asp Asn
1               5                   10                  15

Ala Lys Asn Thr Leu Tyr Leu Glu Met Ser Ser Leu Arg Ser Glu Asp
            20                  25                  30

Thr Ala Met Tyr Tyr Cys
            35

<210> SEQ ID NO 272
<211> LENGTH: 38
<212> TYPE: PRT
<213> ORGANISM: Mus musculus

<400> SEQUENCE: 272

Tyr Tyr Asn Pro Ala Leu Lys Ser Arg Leu Thr Ile Ser Lys Asp Thr
1               5                   10                  15

Ser Asn Asn Gln Val Phe Leu Lys Ile Ala Ser Val Val Thr Ala Asp
            20                  25                  30

Thr Ala Thr Tyr Tyr Cys
            35

<210> SEQ ID NO 273
<211> LENGTH: 38
<212> TYPE: PRT
<213> ORGANISM: Mus musculus
```

```
<400> SEQUENCE: 273

Tyr Tyr Ala Glu Ser Val Lys Gly Arg Phe Thr Ile Ser Arg Asp Asp
1               5                   10                  15

Ser Lys Ser Ser Val Tyr Leu Gln Met Asn Ser Leu Arg Ala Glu Asp
            20                  25                  30

Thr Gly Ile Tyr Tyr Cys
            35

<210> SEQ ID NO 274
<211> LENGTH: 38
<212> TYPE: PRT
<213> ORGANISM: Mus musculus

<400> SEQUENCE: 274

Tyr Tyr Pro Asp Ser Val Lys Gly Arg Phe Thr Ile Ser Arg Asp Asn
1               5                   10                  15

Ala Lys Asn Thr Leu Tyr Leu Gln Met Ser Ser Leu Lys Ser Glu Asp
            20                  25                  30

Thr Ala Met Tyr Tyr Cys
            35

<210> SEQ ID NO 275
<211> LENGTH: 38
<212> TYPE: PRT
<213> ORGANISM: Mus musculus

<400> SEQUENCE: 275

His Tyr Ala Glu Ser Val Lys Gly Arg Phe Thr Ile Ser Arg Asp Asp
1               5                   10                  15

Ser Lys Ser Ser Val Tyr Leu Gln Met Asn Asn Leu Arg Ala Glu Asp
            20                  25                  30

Thr Gly Ile Tyr Tyr Cys
            35

<210> SEQ ID NO 276
<211> LENGTH: 38
<212> TYPE: PRT
<213> ORGANISM: Mus musculus

<400> SEQUENCE: 276

His Tyr Asn Gln Lys Phe Lys Asp Lys Ala Thr Leu Thr Val Asp Lys
1               5                   10                  15

Ser Ser Ser Thr Ala Tyr Ile Gln Leu Ser Ser Leu Thr Ser Glu Asp
            20                  25                  30

Ser Ala Val Tyr Tyr Cys
            35

<210> SEQ ID NO 277
<211> LENGTH: 38
<212> TYPE: PRT
<213> ORGANISM: Mus musculus

<400> SEQUENCE: 277

Ser Tyr Asn Gln Lys Phe Lys Gly Lys Ala Thr Leu Thr Val Asp Lys
1               5                   10                  15

Ser Ser Ser Thr Ala Tyr Met Glu Leu Ser Ser Leu Thr Ser Glu Asp
            20                  25                  30

Ser Ala Val Tyr Tyr Cys
            35
```

```
<210> SEQ ID NO 278
<211> LENGTH: 38
<212> TYPE: PRT
<213> ORGANISM: Mus musculus

<400> SEQUENCE: 278

Tyr Tyr Val Asp Ser Val Lys Gly Arg Phe Thr Ile Ser Arg Asp Asn
1               5                   10                  15

Ala Lys Asn Thr Leu Tyr Leu Gln Met Ser Ser Leu Lys Ser Glu Asp
            20                  25                  30

Thr Ala Ile Tyr Tyr Cys
        35

<210> SEQ ID NO 279
<211> LENGTH: 38
<212> TYPE: PRT
<213> ORGANISM: Mus musculus

<400> SEQUENCE: 279

Tyr Tyr Ala Glu Ser Val Lys Gly Arg Phe Thr Ile Ser Arg Asp Asp
1               5                   10                  15

Ser Gln Ser Ser Val Tyr Leu Gln Met Asn Ser Leu Arg Thr Glu Asn
            20                  25                  30

Thr Gly Ile Tyr Tyr Cys
        35

<210> SEQ ID NO 280
<211> LENGTH: 38
<212> TYPE: PRT
<213> ORGANISM: Mus musculus

<400> SEQUENCE: 280

Asn Tyr Asn Ser Ala Leu Met Ser Arg Leu Gly Ile Ser Lys Asp Asn
1               5                   10                  15

Ser Lys Ser Gln Val Phe Leu Lys Met Asn Ser Leu Gln Thr Asp Glu
            20                  25                  30

Ser Ala Phe Tyr Tyr Cys
        35

<210> SEQ ID NO 281
<211> LENGTH: 38
<212> TYPE: PRT
<213> ORGANISM: Mus musculus

<400> SEQUENCE: 281

Asn Tyr Asn Pro Ser Leu Lys Ser Arg Ile Ser Ile Thr Arg Asp Thr
1               5                   10                  15

Ser Lys Asn Gln Phe Phe Leu Gln Leu Asn Ser Val Thr Thr Glu Gly
            20                  25                  30

Thr Ala Thr Tyr Tyr Cys
        35

<210> SEQ ID NO 282
<211> LENGTH: 38
<212> TYPE: PRT
<213> ORGANISM: Mus musculus

<400> SEQUENCE: 282

Asn Tyr Asn Gln Lys Phe Lys Gly Lys Ala Thr Leu Ala Val Asp Lys
1               5                   10                  15
```

Ser Ser Ser Thr Ala Tyr Met Gln Leu Ser Ser Leu Thr Ser Glu Asp
            20                  25                  30

Ser Ala Val Tyr Tyr Cys
        35

<210> SEQ ID NO 283
<211> LENGTH: 38
<212> TYPE: PRT
<213> ORGANISM: Mus musculus

<400> SEQUENCE: 283

Ala Tyr Asn Gln Lys Phe Lys Gly Lys Ala Thr Leu Thr Ala Asp Lys
1               5                   10                  15

Ser Ser Ser Thr Ala Tyr Met Glu Leu Ser Ser Leu Thr Ser Glu Asp
            20                  25                  30

Ser Ala Val Tyr Tyr Cys
        35

<210> SEQ ID NO 284
<211> LENGTH: 38
<212> TYPE: PRT
<213> ORGANISM: Mus musculus

<400> SEQUENCE: 284

Tyr Tyr Asn Gly Lys Phe Lys Asp Lys Ala Thr Leu Thr Ala Asp Lys
1               5                   10                  15

Ser Ser Ser Thr Ala Tyr Met His Leu Ser Ser Leu Thr Ser Glu Asp
            20                  25                  30

Ser Ala Val Tyr Phe Cys
        35

<210> SEQ ID NO 285
<211> LENGTH: 38
<212> TYPE: PRT
<213> ORGANISM: Mus musculus

<400> SEQUENCE: 285

Asn Tyr Ala Pro Ser Ile Lys Asp Arg Phe Thr Ile Phe Arg Asp Asn
1               5                   10                  15

Asp Lys Ser Thr Leu Tyr Leu Gln Met Ser Asn Val Arg Ser Glu Asp
            20                  25                  30

Thr Ala Thr Tyr Phe Cys
        35

<210> SEQ ID NO 286
<211> LENGTH: 38
<212> TYPE: PRT
<213> ORGANISM: Mus musculus

<400> SEQUENCE: 286

His Tyr Ala Glu Ser Val Lys Gly Lys Phe Thr Ile Ser Arg Asp Asp
1               5                   10                  15

Ser Lys Ser Arg Leu Tyr Leu Gln Met Asn Ser Leu Arg Ala Glu Asp
            20                  25                  30

Thr Gly Ile Tyr Tyr Cys
        35

<210> SEQ ID NO 287
<211> LENGTH: 38
<212> TYPE: PRT
<213> ORGANISM: Mus musculus

<400> SEQUENCE: 287

Asn Tyr Asp Glu Lys Phe Lys Ser Lys Gly Thr Leu Thr Val Asp Thr
1               5                   10                  15

Ser Ser Ser Thr Ala Tyr Met His Leu Ser Ser Leu Thr Ser Glu Asp
            20                  25                  30

Ser Ala Val Tyr Tyr Cys
            35

<210> SEQ ID NO 288
<211> LENGTH: 38
<212> TYPE: PRT
<213> ORGANISM: Mus musculus

<400> SEQUENCE: 288

Arg Leu Asn Gln Lys Phe Lys Asp Lys Ala Thr Leu Asn Val Asp Lys
1               5                   10                  15

Ser Ser Asn Thr Ala Cys Met Gln Leu Ser Ser Leu Thr Ser Glu Asp
            20                  25                  30

Ser Ala Val Tyr Tyr Cys
            35

<210> SEQ ID NO 289
<211> LENGTH: 38
<212> TYPE: PRT
<213> ORGANISM: Mus musculus

<400> SEQUENCE: 289

Asn Tyr Asn Glu Lys Phe Lys Ser Lys Ala Thr Leu Thr Val Asp Lys
1               5                   10                  15

Ser Ser Ser Thr Ala Tyr Met Gln Leu Ser Ser Leu Thr Ser Glu Asp
            20                  25                  30

Ser Ala Val Tyr Tyr Cys
            35

<210> SEQ ID NO 290
<211> LENGTH: 38
<212> TYPE: PRT
<213> ORGANISM: Mus musculus

<400> SEQUENCE: 290

Ala Tyr Asn Gln Lys Phe Lys Gly Lys Ala Thr Val Thr Ala Asp Arg
1               5                   10                  15

Ser Ser Ser Thr Ala Tyr Met Gln Leu Ser Ser Leu Ser Glu Asp
            20                  25                  30

Ser Ala Val Tyr Tyr Cys
            35

<210> SEQ ID NO 291
<211> LENGTH: 38
<212> TYPE: PRT
<213> ORGANISM: Mus musculus

<400> SEQUENCE: 291

Asn Tyr Asn Glu Lys Phe Lys Gly Lys Ala Thr Phe Thr Ala Asp Thr
1               5                   10                  15

Ser Ser Asn Thr Ala Tyr Met Gln Leu Ser Ser Leu Thr Ser Glu Asp
            20                  25                  30

Ser Ala Val Tyr Tyr Cys
            35

<210> SEQ ID NO 292
<211> LENGTH: 38
<212> TYPE: PRT
<213> ORGANISM: Mus musculus

<400> SEQUENCE: 292

Glu Tyr Ser Ala Ser Val Lys Gly Arg Phe Thr Ile Ser Arg Asp Asn
1               5                   10                  15

Ser Gln Ser Ile Leu Tyr Leu Gln Met Asn Thr Leu Arg Ala Glu Asp
            20                  25                  30

Ser Ala Thr Tyr Tyr Cys
        35

<210> SEQ ID NO 293
<211> LENGTH: 38
<212> TYPE: PRT
<213> ORGANISM: Mus musculus

<400> SEQUENCE: 293

Tyr Tyr Asn Glu Lys Phe Lys Asp Lys Val Thr Leu Thr Ala Asp Thr
1               5                   10                  15

Ser Ser Asn Thr Val His Ile Gln Leu Ser Ser Leu Thr Ser Glu Asp
            20                  25                  30

Ser Ala Val Tyr Phe Cys
        35

<210> SEQ ID NO 294
<211> LENGTH: 38
<212> TYPE: PRT
<213> ORGANISM: Mus musculus

<400> SEQUENCE: 294

Tyr Tyr Pro Asp Ser Val Lys Gly Arg Phe Thr Ile Ser Arg Asp Asn
1               5                   10                  15

Ala Lys Asn Thr Leu Tyr Leu Gln Met Ser Ser Leu Arg Ser Glu Asp
            20                  25                  30

Thr Ala Met Tyr Tyr Cys
        35

<210> SEQ ID NO 295
<211> LENGTH: 38
<212> TYPE: PRT
<213> ORGANISM: Mus musculus

<400> SEQUENCE: 295

Tyr Tyr Ala Asp Ser Leu Lys Asp Arg Phe Thr Ile Ser Arg Asp Asp
1               5                   10                  15

Ser Gln Ser Met Leu Tyr Leu Gln Met Asn Asn Leu Lys Thr Glu Asp
            20                  25                  30

Thr Cys His Val Leu Leu
        35

<210> SEQ ID NO 296
<211> LENGTH: 38
<212> TYPE: PRT
<213> ORGANISM: Mus musculus

<400> SEQUENCE: 296

Asn Tyr Ala Glu Ser Val Lys Gly Arg Phe Thr Ile Ser Arg Asp Asp
1               5                   10                  15

```
Ser Lys Ser Ser Val Tyr Leu Gln Met Asn Arg Leu Arg Glu Glu Asp
            20                  25                  30

Thr Ala Thr Tyr Tyr Cys
        35

<210> SEQ ID NO 297
<211> LENGTH: 13
<212> TYPE: PRT
<213> ORGANISM: Mus musculus

<400> SEQUENCE: 297

Ala Arg Gly Glu Ile Trp Gly Lys Ala Trp Phe Ala Tyr
1               5                   10

<210> SEQ ID NO 298
<211> LENGTH: 6
<212> TYPE: PRT
<213> ORGANISM: Mus musculus

<400> SEQUENCE: 298

Ala Trp Gly Asn His Tyr
1               5

<210> SEQ ID NO 299
<211> LENGTH: 11
<212> TYPE: PRT
<213> ORGANISM: Mus musculus

<400> SEQUENCE: 299

Ala Arg Asp Gly Tyr Tyr Val Gly Pro Ala Tyr
1               5                   10

<210> SEQ ID NO 300
<211> LENGTH: 10
<212> TYPE: PRT
<213> ORGANISM: Mus musculus

<400> SEQUENCE: 300

Ala Arg Asn Tyr Arg Ser Trp Phe Ala Tyr
1               5                   10

<210> SEQ ID NO 301
<211> LENGTH: 12
<212> TYPE: PRT
<213> ORGANISM: Mus musculus

<400> SEQUENCE: 301

Ala Arg Lys Gly Ser Leu Thr Gly Val Leu Ala Tyr
1               5                   10

<210> SEQ ID NO 302
<211> LENGTH: 11
<212> TYPE: PRT
<213> ORGANISM: Mus musculus

<400> SEQUENCE: 302

Ala Arg Arg Gly Leu Arg Ala Trp Phe Ala Tyr
1               5                   10

<210> SEQ ID NO 303
<211> LENGTH: 14
<212> TYPE: PRT
<213> ORGANISM: Mus musculus
```

<400> SEQUENCE: 303

Ala Arg Leu Asp Tyr Tyr Gly Ser Ser Arg Gly Phe Ala Tyr
1               5                   10

<210> SEQ ID NO 304
<211> LENGTH: 7
<212> TYPE: PRT
<213> ORGANISM: Mus musculus

<400> SEQUENCE: 304

Thr Asn Gly Gly Gly Trp Tyr
1               5

<210> SEQ ID NO 305
<211> LENGTH: 13
<212> TYPE: PRT
<213> ORGANISM: Mus musculus

<400> SEQUENCE: 305

Ala Ser Tyr Tyr Asp Ser Thr Tyr Val Gly Phe Ala Tyr
1               5                   10

<210> SEQ ID NO 306
<211> LENGTH: 11
<212> TYPE: PRT
<213> ORGANISM: Mus musculus

<400> SEQUENCE: 306

Ala Ser Pro Leu Gly Tyr Asp Gly Phe Ala Tyr
1               5                   10

<210> SEQ ID NO 307
<211> LENGTH: 8
<212> TYPE: PRT
<213> ORGANISM: Mus musculus

<400> SEQUENCE: 307

Ala Arg Gly Ala Tyr Phe Asp Tyr
1               5

<210> SEQ ID NO 308
<211> LENGTH: 14
<212> TYPE: PRT
<213> ORGANISM: Mus musculus

<400> SEQUENCE: 308

Ala Arg Ser Pro Ala Tyr Tyr Gly Asn Leu Trp Phe Ala Tyr
1               5                   10

<210> SEQ ID NO 309
<211> LENGTH: 7
<212> TYPE: PRT
<213> ORGANISM: Mus musculus

<400> SEQUENCE: 309

Ala Arg Trp Asp Gly Ala Tyr
1               5

<210> SEQ ID NO 310
<211> LENGTH: 11
<212> TYPE: PRT
<213> ORGANISM: Mus musculus

<400> SEQUENCE: 310

Ala Arg Gly Gly Met Ile Thr Pro Phe Ala Tyr
1               5                   10

<210> SEQ ID NO 311
<211> LENGTH: 15
<212> TYPE: PRT
<213> ORGANISM: Mus musculus

<400> SEQUENCE: 311

Ala Arg Ile Gly Gly Asn Asp Gly Tyr Tyr Trp Tyr Phe Asp Val
1               5                   10                  15

<210> SEQ ID NO 312
<211> LENGTH: 6
<212> TYPE: PRT
<213> ORGANISM: Mus musculus

<400> SEQUENCE: 312

Thr Pro Gln Phe Ala Tyr
1               5

<210> SEQ ID NO 313
<211> LENGTH: 8
<212> TYPE: PRT
<213> ORGANISM: Mus musculus

<400> SEQUENCE: 313

Ala Ser His Tyr Asp Glu Gly Tyr
1               5

<210> SEQ ID NO 314
<211> LENGTH: 5
<212> TYPE: PRT
<213> ORGANISM: Mus musculus

<400> SEQUENCE: 314

Thr Gly Ser Asp Tyr
1               5

<210> SEQ ID NO 315
<211> LENGTH: 13
<212> TYPE: PRT
<213> ORGANISM: Mus musculus

<400> SEQUENCE: 315

Gly Ser Gly Tyr Asp Gly Tyr Tyr Asp Trp Phe Ala Cys
1               5                   10

<210> SEQ ID NO 316
<211> LENGTH: 9
<212> TYPE: PRT
<213> ORGANISM: Mus musculus

<400> SEQUENCE: 316

Ala Arg Glu Pro Lys Thr Leu Asp Tyr
1               5

<210> SEQ ID NO 317
<211> LENGTH: 8
<212> TYPE: PRT
<213> ORGANISM: Mus musculus

<400> SEQUENCE: 317

Ala Asn Trp Ala Trp Phe Ala Tyr
1               5

<210> SEQ ID NO 318
<211> LENGTH: 11
<212> TYPE: PRT
<213> ORGANISM: Mus musculus

<400> SEQUENCE: 318

Ala Arg Pro Tyr Asp Tyr Asp Gly Phe Ala Tyr
1               5                   10

<210> SEQ ID NO 319
<211> LENGTH: 9
<212> TYPE: PRT
<213> ORGANISM: Mus musculus

<400> SEQUENCE: 319

Ala Asp Gly Asp Tyr Tyr Phe Asp Tyr
1               5

<210> SEQ ID NO 320
<211> LENGTH: 13
<212> TYPE: PRT
<213> ORGANISM: Mus musculus

<400> SEQUENCE: 320

Ala Arg Gln Asp Asp Gly Tyr Tyr Arg Ile Phe Asp Tyr
1               5                   10

<210> SEQ ID NO 321
<211> LENGTH: 10
<212> TYPE: PRT
<213> ORGANISM: Mus musculus

<400> SEQUENCE: 321

Thr Asn Tyr Gly Ser Asn Pro Leu Asp Tyr
1               5                   10

<210> SEQ ID NO 322
<211> LENGTH: 11
<212> TYPE: PRT
<213> ORGANISM: Mus musculus

<400> SEQUENCE: 322

Ala Arg Glu Gly Thr Gly Pro Trp Phe Ala Tyr
1               5                   10

<210> SEQ ID NO 323
<211> LENGTH: 8
<212> TYPE: PRT
<213> ORGANISM: Mus musculus

<400> SEQUENCE: 323

Ala Arg Asp Pro Pro Phe Ala Tyr
1               5

<210> SEQ ID NO 324
<211> LENGTH: 11
<212> TYPE: PRT
<213> ORGANISM: Mus musculus

<400> SEQUENCE: 324

Ala Arg Glu Glu Ile Thr Ala Trp Phe Ala Tyr
1               5                   10

```
<210> SEQ ID NO 325
<211> LENGTH: 12
<212> TYPE: PRT
<213> ORGANISM: Mus musculus

<400> SEQUENCE: 325

Thr Arg Asn Gly Asn Gly Asn Trp Tyr Phe Asp Val
1               5                   10

<210> SEQ ID NO 326
<211> LENGTH: 13
<212> TYPE: PRT
<213> ORGANISM: Mus musculus

<400> SEQUENCE: 326

Ala Arg Ser Gly Tyr Arg Tyr Asp Ala Val Phe Ala Tyr
1               5                   10

<210> SEQ ID NO 327
<211> LENGTH: 7
<212> TYPE: PRT
<213> ORGANISM: Mus musculus

<400> SEQUENCE: 327

Ala Arg Gly Gly Asn Pro Tyr
1               5

<210> SEQ ID NO 328
<211> LENGTH: 11
<212> TYPE: PRT
<213> ORGANISM: Mus musculus

<400> SEQUENCE: 328

Met Arg Tyr Gly Ser Ser Tyr Trp Tyr Phe Asp
1               5                   10

<210> SEQ ID NO 329
<211> LENGTH: 8
<212> TYPE: PRT
<213> ORGANISM: Mus musculus

<400> SEQUENCE: 329

Thr Arg Tyr Tyr Tyr Gly Glu Ser
1               5

<210> SEQ ID NO 330
<211> LENGTH: 14
<212> TYPE: PRT
<213> ORGANISM: Mus musculus

<400> SEQUENCE: 330

Ala Arg His Tyr Tyr Asp Tyr Asp Tyr Trp Tyr Phe Asp Val
1               5                   10

<210> SEQ ID NO 331
<211> LENGTH: 15
<212> TYPE: PRT
<213> ORGANISM: Mus musculus

<400> SEQUENCE: 331

Thr Arg Ser Gly Val Glu Gly Leu Leu His Trp Tyr Phe Asp Val
1               5                   10                  15

<210> SEQ ID NO 332
<211> LENGTH: 12
```

```
<212> TYPE: PRT
<213> ORGANISM: Mus musculus

<400> SEQUENCE: 332

Thr Cys Asp Tyr Asp Gly Gly Ala Trp Phe Ala Tyr
1               5                   10

<210> SEQ ID NO 333
<211> LENGTH: 12
<212> TYPE: PRT
<213> ORGANISM: Mus musculus

<400> SEQUENCE: 333

Ala Arg Cys Asp Gly Tyr Tyr Asp Gly Leu Asp Tyr
1               5                   10

<210> SEQ ID NO 334
<211> LENGTH: 11
<212> TYPE: PRT
<213> ORGANISM: Mus musculus

<400> SEQUENCE: 334

Ala Arg Glu Gly Lys Asn Trp Tyr Phe Asp Val
1               5                   10

<210> SEQ ID NO 335
<211> LENGTH: 10
<212> TYPE: PRT
<213> ORGANISM: Mus musculus

<400> SEQUENCE: 335

Ala Arg Arg Ile Tyr Arg Thr Leu Asp Tyr
1               5                   10

<210> SEQ ID NO 336
<211> LENGTH: 11
<212> TYPE: PRT
<213> ORGANISM: Mus musculus

<400> SEQUENCE: 336

Thr Arg Ser Gly Gly Asn Leu Trp Phe Ala Tyr
1               5                   10

<210> SEQ ID NO 337
<211> LENGTH: 13
<212> TYPE: PRT
<213> ORGANISM: Mus musculus

<400> SEQUENCE: 337

Ala Arg Arg Thr Tyr Tyr Gly Asn Ala Trp Phe Ala Tyr
1               5                   10

<210> SEQ ID NO 338
<211> LENGTH: 15
<212> TYPE: PRT
<213> ORGANISM: Mus musculus

<400> SEQUENCE: 338

Ala Arg Asp Lys Arg Ile Thr Thr Val Glu Ala Trp Phe Ala Tyr
1               5                   10                  15

<210> SEQ ID NO 339
<211> LENGTH: 10
<212> TYPE: PRT
<213> ORGANISM: Mus musculus
```

<400> SEQUENCE: 339

Ala Arg Gly Tyr Gly Ser Ser Phe Ala Tyr
1               5                   10

<210> SEQ ID NO 340
<211> LENGTH: 13
<212> TYPE: PRT
<213> ORGANISM: Mus musculus

<400> SEQUENCE: 340

Thr Arg Gly Gly Asp Tyr Asp Ala Ser Trp Phe Ala Tyr
1               5                   10

<210> SEQ ID NO 341
<211> LENGTH: 10
<212> TYPE: PRT
<213> ORGANISM: Mus musculus

<400> SEQUENCE: 341

Ala Arg Arg Thr Ala Arg Ala Phe Asp Tyr
1               5                   10

<210> SEQ ID NO 342
<211> LENGTH: 15
<212> TYPE: PRT
<213> ORGANISM: Mus musculus

<400> SEQUENCE: 342

Ala Arg Arg Ile Gly Tyr Asp Gly Gly Gly Ser Trp Phe Ala Tyr
1               5                   10                  15

<210> SEQ ID NO 343
<211> LENGTH: 8
<212> TYPE: PRT
<213> ORGANISM: Mus musculus

<400> SEQUENCE: 343

Cys Glu Arg Val Arg Arg Cys Val
1               5

<210> SEQ ID NO 344
<211> LENGTH: 6
<212> TYPE: PRT
<213> ORGANISM: Mus musculus

<400> SEQUENCE: 344

Ser Arg Trp Phe Ala Tyr
1               5

<210> SEQ ID NO 345
<211> LENGTH: 15
<212> TYPE: PRT
<213> ORGANISM: Mus musculus

<400> SEQUENCE: 345

Cys Ala Arg Gly Glu Ile Trp Gly Lys Ala Trp Phe Ala Tyr Trp
1               5                   10                  15

<210> SEQ ID NO 346
<211> LENGTH: 8
<212> TYPE: PRT
<213> ORGANISM: Mus musculus

<400> SEQUENCE: 346

```
Cys Ala Trp Gly Asn His Tyr Trp
1               5

<210> SEQ ID NO 347
<211> LENGTH: 13
<212> TYPE: PRT
<213> ORGANISM: Mus musculus

<400> SEQUENCE: 347

Cys Ala Arg Asp Gly Tyr Tyr Val Gly Pro Ala Tyr Trp
1               5                   10

<210> SEQ ID NO 348
<211> LENGTH: 12
<212> TYPE: PRT
<213> ORGANISM: Mus musculus

<400> SEQUENCE: 348

Cys Ala Arg Asn Tyr Arg Ser Trp Phe Ala Tyr Trp
1               5                   10

<210> SEQ ID NO 349
<211> LENGTH: 14
<212> TYPE: PRT
<213> ORGANISM: Mus musculus

<400> SEQUENCE: 349

Cys Ala Arg Lys Gly Ser Leu Thr Gly Val Leu Ala Tyr Trp
1               5                   10

<210> SEQ ID NO 350
<211> LENGTH: 13
<212> TYPE: PRT
<213> ORGANISM: Mus musculus

<400> SEQUENCE: 350

Cys Ala Arg Arg Gly Leu Arg Ala Trp Phe Ala Tyr Trp
1               5                   10

<210> SEQ ID NO 351
<211> LENGTH: 16
<212> TYPE: PRT
<213> ORGANISM: Mus musculus

<400> SEQUENCE: 351

Cys Ala Arg Leu Asp Tyr Tyr Gly Ser Ser Arg Gly Phe Ala Tyr Trp
1               5                   10                  15

<210> SEQ ID NO 352
<211> LENGTH: 9
<212> TYPE: PRT
<213> ORGANISM: Mus musculus

<400> SEQUENCE: 352

Cys Thr Asn Gly Gly Gly Trp Tyr Trp
1               5

<210> SEQ ID NO 353
<211> LENGTH: 15
<212> TYPE: PRT
<213> ORGANISM: Mus musculus

<400> SEQUENCE: 353

Cys Ala Ser Tyr Tyr Asp Ser Thr Tyr Val Gly Phe Ala Tyr Trp
```

```
1               5                   10                  15
```

<210> SEQ ID NO 354
<211> LENGTH: 13
<212> TYPE: PRT
<213> ORGANISM: Mus musculus

<400> SEQUENCE: 354

```
Cys Ala Ser Pro Leu Gly Tyr Asp Gly Phe Ala Tyr Trp
1               5                   10
```

<210> SEQ ID NO 355
<211> LENGTH: 10
<212> TYPE: PRT
<213> ORGANISM: Mus musculus

<400> SEQUENCE: 355

```
Cys Ala Arg Gly Ala Tyr Phe Asp Tyr Trp
1               5                   10
```

<210> SEQ ID NO 356
<211> LENGTH: 16
<212> TYPE: PRT
<213> ORGANISM: Mus musculus

<400> SEQUENCE: 356

```
Cys Ala Arg Ser Pro Ala Tyr Tyr Gly Asn Leu Trp Phe Ala Tyr Trp
1               5                   10                  15
```

<210> SEQ ID NO 357
<211> LENGTH: 9
<212> TYPE: PRT
<213> ORGANISM: Mus musculus

<400> SEQUENCE: 357

```
Cys Ala Arg Trp Asp Gly Ala Tyr Trp
1               5
```

<210> SEQ ID NO 358
<211> LENGTH: 13
<212> TYPE: PRT
<213> ORGANISM: Mus musculus

<400> SEQUENCE: 358

```
Cys Ala Arg Gly Gly Met Ile Thr Pro Phe Ala Tyr Trp
1               5                   10
```

<210> SEQ ID NO 359
<211> LENGTH: 17
<212> TYPE: PRT
<213> ORGANISM: Mus musculus

<400> SEQUENCE: 359

```
Cys Ala Arg Ile Gly Gly Asn Asp Gly Tyr Tyr Trp Tyr Phe Asp Val
1               5                   10                  15

Trp
```

<210> SEQ ID NO 360
<211> LENGTH: 8
<212> TYPE: PRT
<213> ORGANISM: Mus musculus

<400> SEQUENCE: 360

```
Cys Thr Pro Gln Phe Ala Tyr Trp
```

```
<210> SEQ ID NO 361
<211> LENGTH: 10
<212> TYPE: PRT
<213> ORGANISM: Mus musculus

<400> SEQUENCE: 361

Cys Ala Ser His Tyr Asp Glu Gly Tyr Trp
1               5                   10

<210> SEQ ID NO 362
<211> LENGTH: 7
<212> TYPE: PRT
<213> ORGANISM: Mus musculus

<400> SEQUENCE: 362

Cys Thr Gly Ser Asp Tyr Trp
1               5

<210> SEQ ID NO 363
<211> LENGTH: 15
<212> TYPE: PRT
<213> ORGANISM: Mus musculus

<400> SEQUENCE: 363

Cys Gly Ser Gly Tyr Asp Gly Tyr Tyr Asp Trp Phe Ala Cys Trp
1               5                   10                  15

<210> SEQ ID NO 364
<211> LENGTH: 11
<212> TYPE: PRT
<213> ORGANISM: Mus musculus

<400> SEQUENCE: 364

Cys Ala Arg Glu Pro Lys Thr Leu Asp Tyr Trp
1               5                   10

<210> SEQ ID NO 365
<211> LENGTH: 10
<212> TYPE: PRT
<213> ORGANISM: Mus musculus

<400> SEQUENCE: 365

Cys Ala Asn Trp Ala Trp Phe Ala Tyr Trp
1               5                   10

<210> SEQ ID NO 366
<211> LENGTH: 13
<212> TYPE: PRT
<213> ORGANISM: Mus musculus

<400> SEQUENCE: 366

Cys Ala Arg Pro Tyr Asp Tyr Asp Gly Phe Ala Tyr Trp
1               5                   10

<210> SEQ ID NO 367
<211> LENGTH: 11
<212> TYPE: PRT
<213> ORGANISM: Mus musculus

<400> SEQUENCE: 367

Cys Ala Asp Gly Asp Tyr Tyr Phe Asp Tyr Trp
1               5                   10
```

<210> SEQ ID NO 368
<211> LENGTH: 15
<212> TYPE: PRT
<213> ORGANISM: Mus musculus

<400> SEQUENCE: 368

Cys Ala Arg Gln Asp Asp Gly Tyr Tyr Arg Ile Phe Asp Tyr Trp
1               5                   10                  15

<210> SEQ ID NO 369
<211> LENGTH: 12
<212> TYPE: PRT
<213> ORGANISM: Mus musculus

<400> SEQUENCE: 369

Cys Thr Asn Tyr Gly Ser Asn Pro Leu Asp Tyr Trp
1               5                   10

<210> SEQ ID NO 370
<211> LENGTH: 13
<212> TYPE: PRT
<213> ORGANISM: Mus musculus

<400> SEQUENCE: 370

Cys Ala Arg Glu Gly Thr Gly Pro Trp Phe Ala Tyr Trp
1               5                   10

<210> SEQ ID NO 371
<211> LENGTH: 10
<212> TYPE: PRT
<213> ORGANISM: Mus musculus

<400> SEQUENCE: 371

Cys Ala Arg Asp Pro Pro Phe Ala Tyr Trp
1               5                   10

<210> SEQ ID NO 372
<211> LENGTH: 13
<212> TYPE: PRT
<213> ORGANISM: Mus musculus

<400> SEQUENCE: 372

Cys Ala Arg Glu Glu Ile Thr Ala Trp Phe Ala Tyr Trp
1               5                   10

<210> SEQ ID NO 373
<211> LENGTH: 14
<212> TYPE: PRT
<213> ORGANISM: Mus musculus

<400> SEQUENCE: 373

Cys Thr Arg Asn Gly Asn Gly Asn Trp Tyr Phe Asp Val Trp
1               5                   10

<210> SEQ ID NO 374
<211> LENGTH: 15
<212> TYPE: PRT
<213> ORGANISM: Mus musculus

<400> SEQUENCE: 374

Cys Ala Arg Ser Gly Tyr Arg Tyr Asp Ala Val Phe Ala Tyr Trp
1               5                   10                  15

<210> SEQ ID NO 375

```
<211> LENGTH: 9
<212> TYPE: PRT
<213> ORGANISM: Mus musculus

<400> SEQUENCE: 375

Cys Ala Arg Gly Gly Asn Pro Tyr Leu
1               5

<210> SEQ ID NO 376
<211> LENGTH: 10
<212> TYPE: PRT
<213> ORGANISM: Mus musculus

<400> SEQUENCE: 376

Cys Thr Arg Tyr Tyr Tyr Gly Glu Ser Trp
1               5                   10

<210> SEQ ID NO 377
<211> LENGTH: 16
<212> TYPE: PRT
<213> ORGANISM: Mus musculus

<400> SEQUENCE: 377

Cys Ala Arg His Tyr Tyr Asp Tyr Asp Tyr Trp Tyr Phe Asp Val Trp
1               5                   10                  15

<210> SEQ ID NO 378
<211> LENGTH: 17
<212> TYPE: PRT
<213> ORGANISM: Mus musculus

<400> SEQUENCE: 378

Cys Thr Arg Ser Gly Val Glu Gly Leu Leu His Trp Tyr Phe Asp Val
1               5                   10                  15

Trp

<210> SEQ ID NO 379
<211> LENGTH: 14
<212> TYPE: PRT
<213> ORGANISM: Mus musculus

<400> SEQUENCE: 379

Cys Thr Cys Asp Tyr Asp Gly Gly Ala Trp Phe Ala Tyr Trp
1               5                   10

<210> SEQ ID NO 380
<211> LENGTH: 14
<212> TYPE: PRT
<213> ORGANISM: Mus musculus

<400> SEQUENCE: 380

Cys Ala Arg Cys Asp Gly Tyr Tyr Asp Gly Leu Asp Tyr Trp
1               5                   10

<210> SEQ ID NO 381
<211> LENGTH: 13
<212> TYPE: PRT
<213> ORGANISM: Mus musculus

<400> SEQUENCE: 381

Cys Ala Arg Glu Gly Lys Asn Trp Tyr Phe Asp Val Trp
1               5                   10

<210> SEQ ID NO 382
```

```
<211> LENGTH: 12
<212> TYPE: PRT
<213> ORGANISM: Mus musculus

<400> SEQUENCE: 382

Cys Ala Arg Arg Ile Tyr Arg Thr Leu Asp Tyr Trp
1               5                   10

<210> SEQ ID NO 383
<211> LENGTH: 13
<212> TYPE: PRT
<213> ORGANISM: Mus musculus

<400> SEQUENCE: 383

Cys Thr Arg Ser Gly Gly Asn Leu Trp Phe Ala Tyr Trp
1               5                   10

<210> SEQ ID NO 384
<211> LENGTH: 15
<212> TYPE: PRT
<213> ORGANISM: Mus musculus

<400> SEQUENCE: 384

Cys Ala Arg Arg Thr Tyr Tyr Gly Asn Ala Trp Phe Ala Tyr Trp
1               5                   10                  15

<210> SEQ ID NO 385
<211> LENGTH: 17
<212> TYPE: PRT
<213> ORGANISM: Mus musculus

<400> SEQUENCE: 385

Cys Ala Arg Asp Lys Arg Ile Thr Thr Val Glu Ala Trp Phe Ala Tyr
1               5                   10                  15

Trp

<210> SEQ ID NO 386
<211> LENGTH: 12
<212> TYPE: PRT
<213> ORGANISM: Mus musculus

<400> SEQUENCE: 386

Cys Ala Arg Gly Tyr Gly Ser Ser Phe Ala Tyr Trp
1               5                   10

<210> SEQ ID NO 387
<211> LENGTH: 15
<212> TYPE: PRT
<213> ORGANISM: Mus musculus

<400> SEQUENCE: 387

Cys Thr Arg Gly Gly Asp Tyr Asp Ala Ser Trp Phe Ala Tyr Trp
1               5                   10                  15

<210> SEQ ID NO 388
<211> LENGTH: 12
<212> TYPE: PRT
<213> ORGANISM: Mus musculus

<400> SEQUENCE: 388

Cys Ala Arg Arg Thr Ala Arg Ala Phe Asp Tyr Trp
1               5                   10

<210> SEQ ID NO 389
```

```
<211> LENGTH: 17
<212> TYPE: PRT
<213> ORGANISM: Mus musculus

<400> SEQUENCE: 389

Cys Ala Arg Arg Ile Gly Tyr Asp Gly Gly Gly Ser Trp Phe Ala Tyr
1               5                   10                  15

Trp

<210> SEQ ID NO 390
<211> LENGTH: 10
<212> TYPE: PRT
<213> ORGANISM: Mus musculus

<400> SEQUENCE: 390

Leu Cys Glu Arg Val Arg Arg Cys Val Leu
1               5                   10

<210> SEQ ID NO 391
<211> LENGTH: 8
<212> TYPE: PRT
<213> ORGANISM: Mus musculus

<400> SEQUENCE: 391

Cys Ser Arg Trp Phe Ala Tyr Trp
1               5

<210> SEQ ID NO 392
<211> LENGTH: 15
<212> TYPE: PRT
<213> ORGANISM: Mus musculus

<400> SEQUENCE: 392

Trp Phe Ala Tyr Trp Gly Gln Gly Thr Leu Val Thr Val Ser Ala
1               5                   10                  15

<210> SEQ ID NO 393
<211> LENGTH: 12
<212> TYPE: PRT
<213> ORGANISM: Mus musculus

<400> SEQUENCE: 393

Tyr Trp Gly Gln Gly Thr Thr Val Thr Val Ser Ser
1               5                   10

<210> SEQ ID NO 394
<211> LENGTH: 13
<212> TYPE: PRT
<213> ORGANISM: Mus musculus

<400> SEQUENCE: 394

Ala Tyr Trp Gly Gln Gly Thr Leu Val Thr Val Ser Ala
1               5                   10

<210> SEQ ID NO 395
<211> LENGTH: 14
<212> TYPE: PRT
<213> ORGANISM: Mus musculus

<400> SEQUENCE: 395

Phe Ala Tyr Trp Gly Gln Gly Thr Leu Val Thr Val Ser Ala
1               5                   10

<210> SEQ ID NO 396
```

```
<210> SEQ ID NO 396
<211> LENGTH: 15
<212> TYPE: PRT
<213> ORGANISM: Mus musculus

<400> SEQUENCE: 396

Gly Gly Trp Tyr Trp Gly Gln Gly Thr Thr Val Thr Val Ser Ser
1               5                   10                  15

<210> SEQ ID NO 397
<211> LENGTH: 15
<212> TYPE: PRT
<213> ORGANISM: Mus musculus

<400> SEQUENCE: 397

Tyr Phe Asp Tyr Trp Gly Gln Gly Thr Thr Val Thr Val Ser Ser
1               5                   10                  15

<210> SEQ ID NO 398
<211> LENGTH: 11
<212> TYPE: PRT
<213> ORGANISM: Mus musculus

<400> SEQUENCE: 398

Trp Gly Gln Gly Thr Pro Val Thr Val Ser Ser
1               5                   10

<210> SEQ ID NO 399
<211> LENGTH: 14
<212> TYPE: PRT
<213> ORGANISM: Mus musculus

<400> SEQUENCE: 399

Phe Ala Tyr Trp Gly Gln Gly Thr Leu Val Thr Val Ser Ser
1               5                   10

<210> SEQ ID NO 400
<211> LENGTH: 17
<212> TYPE: PRT
<213> ORGANISM: Mus musculus

<400> SEQUENCE: 400

Tyr Trp Tyr Phe Asp Val Trp Gly Ala Gly Thr Thr Val Thr Val Ser
1               5                   10                  15

Ser

<210> SEQ ID NO 401
<211> LENGTH: 14
<212> TYPE: PRT
<213> ORGANISM: Mus musculus

<400> SEQUENCE: 401

Phe Ala Tyr Trp Gly Gln Gly Thr Thr Val Thr Val Ser Ser
1               5                   10

<210> SEQ ID NO 402
<211> LENGTH: 12
<212> TYPE: PRT
<213> ORGANISM: Mus musculus

<400> SEQUENCE: 402

Tyr Trp Gly Gln Gly Thr Ser Leu Thr Val Ser Ser
1               5                   10

<210> SEQ ID NO 403
```

-continued

<211> LENGTH: 13
<212> TYPE: PRT
<213> ORGANISM: Mus musculus

<400> SEQUENCE: 403

Asp Tyr Trp Gly Gln Gly Thr Thr Val Thr Val Ser Ser
1               5                   10

<210> SEQ ID NO 404
<211> LENGTH: 15
<212> TYPE: PRT
<213> ORGANISM: Mus musculus

<400> SEQUENCE: 404

Trp Phe Ala Cys Trp Gly Gln Gly Thr Leu Val Thr Val Ser Ala
1               5                   10                  15

<210> SEQ ID NO 405
<211> LENGTH: 15
<212> TYPE: PRT
<213> ORGANISM: Mus musculus

<400> SEQUENCE: 405

Tyr Phe Asp Tyr Trp Gly Gln Gly Thr Ser Leu Thr Val Ser Ser
1               5                   10                  15

<210> SEQ ID NO 406
<211> LENGTH: 14
<212> TYPE: PRT
<213> ORGANISM: Mus musculus

<400> SEQUENCE: 406

Phe Asp Tyr Trp Gly Gln Gly Thr Thr Leu Thr Val Ser Ser
1               5                   10

<210> SEQ ID NO 407
<211> LENGTH: 13
<212> TYPE: PRT
<213> ORGANISM: Mus musculus

<400> SEQUENCE: 407

Asp Tyr Trp Gly Gln Gly Thr Thr Leu Thr Ile Pro Ser
1               5                   10

<210> SEQ ID NO 408
<211> LENGTH: 14
<212> TYPE: PRT
<213> ORGANISM: Mus musculus

<400> SEQUENCE: 408

Trp Phe Ala Tyr Trp Gly Gln Gly Thr Thr Ala Pro Ser Pro
1               5                   10

<210> SEQ ID NO 409
<211> LENGTH: 16
<212> TYPE: PRT
<213> ORGANISM: Mus musculus

<400> SEQUENCE: 409

Trp Tyr Phe Asp Val Trp Gly Ala Gly Thr Thr Leu Thr Val Ser Ser
1               5                   10                  15

<210> SEQ ID NO 410
<211> LENGTH: 14
<212> TYPE: PRT

```
<213> ORGANISM: Mus musculus

<400> SEQUENCE: 410

Phe Ala Tyr Trp Gly Pro Gly Thr Leu Val Thr Val Ser Ala
1               5                   10

<210> SEQ ID NO 411
<211> LENGTH: 12
<212> TYPE: PRT
<213> ORGANISM: Mus musculus

<400> SEQUENCE: 411

Tyr Leu Gly Gln Gly Thr Leu Val Thr Val Ser Ala
1               5                   10

<210> SEQ ID NO 412
<211> LENGTH: 6
<212> TYPE: PRT
<213> ORGANISM: Mus musculus

<400> SEQUENCE: 412

Leu Leu Val Leu Arg Cys
1               5

<210> SEQ ID NO 413
<211> LENGTH: 11
<212> TYPE: PRT
<213> ORGANISM: Mus musculus

<400> SEQUENCE: 413

Trp Gly Gln Gly Thr Leu Val Thr Val Ser Ser
1               5                   10

<210> SEQ ID NO 414
<211> LENGTH: 16
<212> TYPE: PRT
<213> ORGANISM: Mus musculus

<400> SEQUENCE: 414

Trp Tyr Phe Asp Val Trp Gly Ala Gly Thr Ser Leu Thr Val Ser Ser
1               5                   10                  15

<210> SEQ ID NO 415
<211> LENGTH: 15
<212> TYPE: PRT
<213> ORGANISM: Mus musculus

<400> SEQUENCE: 415

Gly Leu Asp Tyr Trp Gly Gln Gly Thr Thr Leu Thr Val Ser Ser
1               5                   10                  15

<210> SEQ ID NO 416
<211> LENGTH: 16
<212> TYPE: PRT
<213> ORGANISM: Mus musculus

<400> SEQUENCE: 416

Trp Tyr Phe Asp Val Trp Gly Ala Gly Thr Thr Val Thr Val Ser Ser
1               5                   10                  15

<210> SEQ ID NO 417
<211> LENGTH: 15
<212> TYPE: PRT
<213> ORGANISM: Mus musculus
```

```
<400> SEQUENCE: 417

Thr Leu Asp Tyr Trp Gly Gln Gly Thr Thr Val Thr Val Ser Ser
1               5                   10                  15

<210> SEQ ID NO 418
<211> LENGTH: 15
<212> TYPE: PRT
<213> ORGANISM: Mus musculus

<400> SEQUENCE: 418

Ser Phe Ala Tyr Trp Gly Gln Gly Thr Pro Val Thr Val Ser Ser
1               5                   10                  15

<210> SEQ ID NO 419
<211> LENGTH: 14
<212> TYPE: PRT
<213> ORGANISM: Mus musculus

<400> SEQUENCE: 419

Phe Asp Tyr Trp Gly Gln Gly Thr Thr Val Thr Val Ser Ser
1               5                   10

<210> SEQ ID NO 420
<211> LENGTH: 13
<212> TYPE: PRT
<213> ORGANISM: Mus musculus

<400> SEQUENCE: 420

Cys Val Leu Gly Pro Arg Asp Ser Gly His Cys Leu Cys
1               5                   10

<210> SEQ ID NO 421
<211> LENGTH: 11
<212> TYPE: PRT
<213> ORGANISM: Mus musculus

<400> SEQUENCE: 421

Trp Gly Gln Gly Thr Leu Val Thr Val Ser Ala
1               5                   10

<210> SEQ ID NO 422
<211> LENGTH: 11
<212> TYPE: PRT
<213> ORGANISM: Mus musculus

<400> SEQUENCE: 422

Trp Gly Gln Gly Thr Thr Val Thr Val Ser Ser
1               5                   10

<210> SEQ ID NO 423
<211> LENGTH: 11
<212> TYPE: PRT
<213> ORGANISM: Mus musculus

<400> SEQUENCE: 423

Trp Gly Ala Gly Thr Thr Val Thr Val Ser Ser
1               5                   10

<210> SEQ ID NO 424
<211> LENGTH: 11
<212> TYPE: PRT
<213> ORGANISM: Mus musculus

<400> SEQUENCE: 424
```

Trp Gly Gln Gly Thr Ser Leu Thr Val Ser Ser
1               5                   10

<210> SEQ ID NO 425
<211> LENGTH: 11
<212> TYPE: PRT
<213> ORGANISM: Mus musculus

<400> SEQUENCE: 425

Trp Gly Gln Gly Thr Thr Leu Thr Val Ser Ser
1               5                   10

<210> SEQ ID NO 426
<211> LENGTH: 11
<212> TYPE: PRT
<213> ORGANISM: Mus musculus

<400> SEQUENCE: 426

Trp Gly Gln Gly Thr Thr Leu Thr Ile Pro Ser
1               5                   10

<210> SEQ ID NO 427
<211> LENGTH: 10
<212> TYPE: PRT
<213> ORGANISM: Mus musculus

<400> SEQUENCE: 427

Trp Gly Gln Gly Thr Thr Ala Pro Ser Pro
1               5                   10

<210> SEQ ID NO 428
<211> LENGTH: 11
<212> TYPE: PRT
<213> ORGANISM: Mus musculus

<400> SEQUENCE: 428

Trp Gly Ala Gly Thr Thr Leu Thr Val Ser Ser
1               5                   10

<210> SEQ ID NO 429
<211> LENGTH: 11
<212> TYPE: PRT
<213> ORGANISM: Mus musculus

<400> SEQUENCE: 429

Trp Gly Pro Gly Thr Leu Val Thr Val Ser Ala
1               5                   10

<210> SEQ ID NO 430
<211> LENGTH: 11
<212> TYPE: PRT
<213> ORGANISM: Mus musculus

<400> SEQUENCE: 430

Leu Gly Gln Gly Thr Leu Val Thr Val Ser Ala
1               5                   10

<210> SEQ ID NO 431
<211> LENGTH: 11
<212> TYPE: PRT
<213> ORGANISM: Mus musculus

<400> SEQUENCE: 431

Trp Gly Ala Gly Thr Ser Leu Thr Val Ser Ser
1               5                   10

<210> SEQ ID NO 432
<211> LENGTH: 120
<212> TYPE: PRT
<213> ORGANISM: Mus musculus

<400> SEQUENCE: 432

Gln Val Gln Leu Gln Gln Ser Gly Ala Glu Leu Val Arg Pro Gly Ala
1               5                   10                  15

Ser Val Lys Leu Ser Cys Lys Ala Leu Gly Tyr Thr Phe Thr Asp Tyr
                20                  25                  30

Glu Met His Trp Val Lys Gln Thr Pro Val His Gly Leu Gly Trp Ile
            35                  40                  45

Gly Ala Ile His Pro Gly Ser Gly Gly Thr Ala Tyr Asn Gln Lys Phe
        50                  55                  60

Lys Gly Lys Ala Thr Leu Thr Ala Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Thr Arg Ser Asp Tyr Gly Ser Ser Tyr Glu Phe Ala Tyr Trp Gly Gln
                100                 105                 110

Gly Thr Leu Val Thr Val Ser Ser
        115                 120

<210> SEQ ID NO 433
<211> LENGTH: 117
<212> TYPE: PRT
<213> ORGANISM: Mus musculus

<400> SEQUENCE: 433

Gln Ile Gln Leu Lys Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
                20                  25                  30

Tyr Ala Trp Asn Trp Ile Arg Gln Phe Pro Gly Asn Lys Leu Glu Trp
            35                  40                  45

Met Gly Tyr Ile Ser Tyr Ser Gly Ser Thr Ser Tyr Asn Pro Ser Leu
        50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Ser Arg Gly Asn Tyr Phe Asp Tyr Trp Gly Gln Gly Thr Thr
                100                 105                 110

Val Thr Val Ser Ser
        115

<210> SEQ ID NO 434
<211> LENGTH: 119
<212> TYPE: PRT
<213> ORGANISM: Mus musculus

<400> SEQUENCE: 434

Gln Ile Gln Leu Gln Gln Ser Gly Ala Glu Leu Ala Arg Pro Gly Ala
1               5                   10                  15

Ser Val Arg Met Ser Cys Lys Ala Ser Gly Tyr Thr Phe Thr Ser Tyr
                20                  25                  30

```
Thr Ile His Trp Val Lys Gln Arg Pro Gly Gln Gly Leu Glu Trp Ile
         35                  40                  45

Gly Tyr Ile Asn Pro Ser Ser Gly Tyr Thr Asn Tyr Asn Gln Lys Phe
 50                  55                  60

Lys Asp Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Ser Gly Leu Arg Gln Ala Trp Phe Ala Tyr Trp Gly Gln Gly
                100                 105                 110

Thr Leu Val Thr Val Ser Ala
        115
```

<210> SEQ ID NO 435
<211> LENGTH: 115
<212> TYPE: PRT
<213> ORGANISM: Mus musculus

<400> SEQUENCE: 435

```
Gln Val Gln Leu Val Glu Thr Gly Gly Gly Leu Val Arg Pro Gly Asn
 1               5                  10                  15

Ser Leu Lys Leu Ser Cys Val Thr Ser Gly Phe Thr Phe Ser Asn Tyr
                 20                  25                  30

Arg Met His Trp Leu Arg Gln Pro Leu Gly Lys Arg Leu Glu Trp Ile
         35                  40                  45

Ala Val Ile Thr Val Lys Ser Asp Asn Tyr Gly Ala Asn Tyr Ala Glu
 50                  55                  60

Ser Val Lys Gly Arg Phe Thr Ile Ser Arg Asp Asp Ser Lys Ser Ser
 65                  70                  75                  80

Val Tyr Leu Gln Met Asn Arg Leu Arg Glu Glu Asp Thr Ala Thr Tyr
                 85                  90                  95

Tyr Cys Ser Arg Leu Phe Ala Tyr Trp Gly Gln Gly Thr Leu Val Thr
                100                 105                 110

Val Ser Ala
        115
```

<210> SEQ ID NO 436
<211> LENGTH: 114
<212> TYPE: PRT
<213> ORGANISM: Mus musculus

<400> SEQUENCE: 436

```
Gln Val Gln Leu Gln Gln Pro Gly Ala Glu Leu Val Lys Pro Gly Ala
 1               5                  10                  15

Ser Val Lys Leu Ser Cys Lys Ala Ser Gly Tyr Thr Phe Thr Ser Tyr
                 20                  25                  30

Trp Met His Trp Val Lys Leu Arg Pro Gly Gln Gly Phe Glu Trp Ile
         35                  40                  45

Gly Glu Ile Asn Pro Ser Asn Gly Gly Thr Asn Tyr Asn Glu Lys Phe
 50                  55                  60

Lys Arg Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Thr Ile Thr Gly Phe Asp Val Trp Gly Ala Gly Thr Thr Val Thr Val
                100                 105                 110
```

Ser Ser

<210> SEQ ID NO 437
<211> LENGTH: 120
<212> TYPE: PRT
<213> ORGANISM: Mus musculus

<400> SEQUENCE: 437

Gln Ile Gln Leu Gln Gln Ser Gly Ala Glu Leu Val Lys Pro Gly Ala
1               5                   10                  15

Ser Val Lys Leu Ser Cys Lys Thr Ser Gly Tyr Thr Phe Thr Thr Tyr
                20                  25                  30

Trp Ile Gln Trp Val Lys Gln Arg Pro Gly Gln Gly Leu Gly Trp Ile
            35                  40                  45

Gly Glu Ile Phe Pro Gly Thr Gly Thr Thr Tyr Tyr Asn Glu Lys Phe
    50                  55                  60

Lys Gly Lys Ala Thr Leu Thr Ile Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Gly Tyr Tyr Asn Ser Ser Pro Phe Ala Tyr Trp Gly Gln
                100                 105                 110

Gly Thr Leu Val Thr Val Ser Ala
            115                 120

<210> SEQ ID NO 438
<211> LENGTH: 121
<212> TYPE: PRT
<213> ORGANISM: Mus musculus

<400> SEQUENCE: 438

Asp Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
                20                  25                  30

Tyr Met Ser Trp Val Arg Gln Pro Pro Gly Lys Ala Leu Glu Trp Leu
            35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Ala Arg Asp Gly Glu Val Arg Arg Ala Leu Ala Tyr Trp Gly
                100                 105                 110

Gln Gly Thr Leu Val Thr Val Ser Ala
            115                 120

<210> SEQ ID NO 439
<211> LENGTH: 115
<212> TYPE: PRT
<213> ORGANISM: Mus musculus

<400> SEQUENCE: 439

Gln Val Gln Leu Gln Gln Pro Ala Ala Glu Leu Ala Arg Pro Gly Ala
1               5                   10                  15

Ser Val Lys Met Ser Cys Lys Ala Ser Gly Tyr Thr Phe Thr Ser Ser
                20                  25                  30

Thr Met His Trp Val Lys Gln Arg Pro Gly Gln Gly Leu Glu Trp Ile
                35                  40                  45

Gly Tyr Ile Asn Pro Ser Ser Gly Tyr Thr Glu Tyr Asn Gln Lys Phe
        50                  55                  60

Lys Asp Lys Thr Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Val Arg His Tyr Tyr Phe Asp Tyr Trp Gly Gln Gly Thr Thr Val Thr
                100                 105                 110

Val Ser Ser
        115

<210> SEQ ID NO 440
<211> LENGTH: 117
<212> TYPE: PRT
<213> ORGANISM: Mus musculus

<400> SEQUENCE: 440

Glu Val Met Leu Val Glu Ser Gly Gly Gly Leu Val Lys Pro Gly Gly
1               5                   10                  15

Ser Leu Lys Ile Ser Cys Ala Ala Ser Gly Phe Thr Phe Ser Ser Tyr
                20                  25                  30

Thr Met Ser Trp Val Arg Gln Asn Pro Glu Lys Arg Leu Glu Trp Val
                35                  40                  45

Ala Thr Ile Ser Ser Gly Gly Tyr Thr Tyr Tyr Leu Asp Ser Val
        50                  55                  60

Lys Gly Arg Phe Thr Pro Ser Arg Asp Asn Gly Lys Asn Thr Leu Asn
65                  70                  75                  80

Leu Gln Met Ser Ser Leu Lys Ser Glu Asp Thr Ala Met Tyr Tyr Cys
                85                  90                  95

Thr Arg Val Ser Ala Lys Tyr Phe Asp Val Trp Gly Ala Gly Thr Thr
                100                 105                 110

Leu Thr Val Ser Ser
        115

<210> SEQ ID NO 441
<211> LENGTH: 120
<212> TYPE: PRT
<213> ORGANISM: Mus musculus

<400> SEQUENCE: 441

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Asn Phe
                20                  25                  30

Tyr Leu Tyr Trp Val Lys Gln Arg Pro Gly Gln Gly Leu Glu Trp Ile
                35                  40                  45

Gly Gly Ile Asn Pro Ser Asn Gly Gly Thr Asn Phe Asn Glu Lys Phe
        50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Ser Tyr Tyr Asp Tyr Asp Trp Tyr Phe Asp Val Trp Gly Ala
                100                 105                 110

```
Gly Thr Thr Val Thr Val Ser Ser
        115                 120
```

<210> SEQ ID NO 442
<211> LENGTH: 122
<212> TYPE: PRT
<213> ORGANISM: Mus musculus

<400> SEQUENCE: 442

```
Gln Val Gln Leu Gln Gln Ser Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Gln Asn Tyr Tyr Gly Ser Ser His Trp Tyr Phe Asp Val Trp
            100                 105                 110

Gly Ala Gly Thr Thr Leu Thr Val Ser Ser
        115                 120
```

<210> SEQ ID NO 443
<211> LENGTH: 115
<212> TYPE: PRT
<213> ORGANISM: Mus musculus

<400> SEQUENCE: 443

```
Gln Val Gln Leu Gln Gln Pro Gly Ala Glu Leu Val Lys Pro Gly Ala
1               5                   10                  15

Pro Val Lys Leu Ser Cys Lys Ala Ser Gly Tyr Thr Phe Thr Ser Tyr
            20                  25                  30

Trp Met Asn Trp Val Lys Gln Arg Pro Gly Arg Gly Leu Glu Trp Ile
        35                  40                  45

Gly Arg Ile Asp Pro Ser Asp Ser Glu Thr His Tyr Asn Gln Lys Phe
    50                  55                  60

Lys Asp Lys Ala Thr Leu Thr Val Asp Lys Ser Ser Ser Thr Ala Tyr
65                  70                  75                  80

Ile Gln Leu Ser Ser Leu Thr Ser Glu Asp Ser Ala Val Tyr Tyr Cys
                85                  90                  95

Ala Asn Trp Ala Trp Phe Ala Tyr Trp Gly Gln Gly Thr Leu Val Thr
            100                 105                 110

Val Ser Ser
        115
```

<210> SEQ ID NO 444
<211> LENGTH: 121
<212> TYPE: PRT
<213> ORGANISM: Mus musculus

<400> SEQUENCE: 444

```
Gln Ile Gln Phe Ala Gln Ser Gly Pro Glu Leu Lys Lys Pro Gly Glu
1               5                   10                  15
```

Thr Val Lys Ile Ser Cys Lys Ala Phe Gly Tyr Thr Phe Thr Asp Tyr
        20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Ser Phe Tyr Tyr Gly Asn Phe Ala Tyr Tyr Phe Asp Tyr Arg Gly
                100                 105                 110

Gln Gly Thr Thr Leu Thr Val Ser Ser
        115                 120

<210> SEQ ID NO 445
<211> LENGTH: 125
<212> TYPE: PRT
<213> ORGANISM: Mus musculus

<400> SEQUENCE: 445

Glu Val Lys Ile Glu Glu Ser Gly Gly Gly Leu Val Gln Pro Gly Gly
1               5                   10                  15

Ala Met Lys Leu Ser Cys Val Ala Ser Gly Phe Thr Phe Ser Asn Tyr
        20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr Tyr Tyr Ala Glu
50                  55                  60

Ser Val Lys Gly Arg Phe Thr Ile Ser Arg Asp Asp Ser Gln Ser Ser
65                  70                  75                  80

Val Tyr Leu Gln Met Asn Asp Leu Arg Thr Glu Asp Thr Gly Ile Tyr
                85                  90                  95

Tyr Cys Thr Arg Ile Tyr Asp Ser Gly Ser Ser Tyr Thr Trp Tyr Phe
                100                 105                 110

Asp Val Trp Gly Ala Gly Thr Thr Val Thr Val Ser Ser
        115                 120                 125

<210> SEQ ID NO 446
<211> LENGTH: 123
<212> TYPE: PRT
<213> ORGANISM: Mus musculus

<400> SEQUENCE: 446

Gln Val Ile Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
        20                  25                  30

Gly Met Ser Val Gly Trp Ile Arg Gln Pro Ser Gly Lys Gly Leu Glu
        35                  40                  45

Trp Leu Ala His Ile Trp Trp Asn Asp Asp Lys Tyr Tyr Asn Pro Ala
50                  55                  60

Leu Lys Ser Arg Leu Thr Ile Ser Lys Asp Thr Pro Asn Asn Gln Val
65                  70                  75                  80

Phe Leu Lys Ile Ala Ser Val Val Thr Ala Asp Thr Ala Thr Tyr Tyr
                85                  90                  95

Cys Ala Arg Ile Gly Gly Asn Asp Gly Tyr Tyr Trp Tyr Phe Asp Val
            100                 105                 110
Trp Gly Ala Gly Thr Ser Leu Thr Val Ser Ser
        115                 120

<210> SEQ ID NO 447
<211> LENGTH: 117
<212> TYPE: PRT
<213> ORGANISM: Mus musculus

<400> SEQUENCE: 447

Gln Ile Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Ser Ser Gly Tyr Gly Ala Tyr Trp Gly Gln Gly Thr Leu
            100                 105                 110

Val Thr Val Ser Ser
        115

<210> SEQ ID NO 448
<211> LENGTH: 118
<212> TYPE: PRT
<213> ORGANISM: Mus musculus

<400> SEQUENCE: 448

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Asp Gly Tyr Tyr Tyr Phe Asp Tyr Trp Gly Gln Gly Thr
            100                 105                 110

Thr Leu Thr Val Ser Ser
        115

<210> SEQ ID NO 449
<211> LENGTH: 118
<212> TYPE: PRT
<213> ORGANISM: Mus musculus

<400> SEQUENCE: 449

Gln Val Gln Leu Gln Gln Ser Gly Ala Glu Leu Val Arg Pro Gly Ala

```
              1               5                  10                 15
Ser Val Lys Leu Ser Cys Lys Ala Ser Gly Tyr Thr Phe Thr Ser Tyr
            20                  25                 30

Trp Ile Asn Trp Val Lys Gln Arg Pro Gly Gln Gly Leu Glu Trp Ile
            35                  40                 45

Gly Asn Ile Tyr Pro Ser Ser Tyr Thr Asn Tyr Asn Gln Lys Phe
            50                  55                 60

Lys Asp Lys Ala Thr Leu Thr Val Asp Lys Ser Ser Ser Thr Ala Tyr
 65                 70                  75                     80

Met Gln Leu Ser Ser Pro Thr Ser Glu Asp Ser Ala Val Tyr Tyr Cys
                85                  90                 95

Thr Ser His Tyr Tyr Gly Arg Ala Trp Phe Ala Tyr Trp Gly Gln Gly
               100                 105                110

Thr Leu Val Thr Val Leu
           115
```

<210> SEQ ID NO 450
<211> LENGTH: 118
<212> TYPE: PRT
<213> ORGANISM: Mus musculus

<400> SEQUENCE: 450

```
Gln Ile Gln Leu Gln Gln Pro Gly Ala Glu Leu Val Lys Pro Gly Ala
 1               5                  10                 15

Ser Val Lys Leu Ser Cys Lys Ala Ser Gly Tyr Thr Phe Thr Arg Tyr
            20                  25                 30

Tyr Met Tyr Trp Val Lys Gln Arg Pro Gly Gln Gly Leu Glu Trp Ile
            35                  40                 45

Gly Glu Ile Asn Pro Ser Asn Gly Gly Thr Asn Phe Asn Glu Lys Phe
            50                  55                 60

Lys Ser Lys Ala Thr Leu Thr Val Asp Lys Ser Ser Ser Thr Ala Tyr
 65                 70                  75                     80

Met Gln Leu Asn Ser Leu Thr Ser Asp Asp Ser Ala Val Tyr Tyr Cys
                85                  90                 95

Thr Lys Gly Gly Phe Tyr Asp Phe Phe Ala Tyr Trp Gly Gln Gly Thr
               100                 105                110

Leu Val Thr Val Ser Ala
           115
```

<210> SEQ ID NO 451
<211> LENGTH: 112
<212> TYPE: PRT
<213> ORGANISM: Mus musculus

<400> SEQUENCE: 451

```
Glu Val Met Leu Val Glu Ser Gly Gly Leu Val Gln Pro Gly Gly
 1               5                  10                 15

Ser Leu Lys Leu Ser Cys Ala Ala Ser Gly Phe Thr Phe Ser Ser Tyr
            20                  25                 30

Gly Met Ser Trp Val Arg Gln Thr Pro Asp Lys Arg Leu Glu Leu Val
            35                  40                 45

Ala Thr Ile Asn Ser Asn Gly Gly Ser Thr Tyr Tyr Pro Asp Ser Val
            50                  55                 60

Lys Gly Arg Phe Thr Ile Ser Arg Asp Asn Ala Lys Asn Thr Leu Tyr
 65                 70                  75                     80

Leu Gln Met Ser Ser Leu Lys Ser Glu Asp Thr Ala Met Tyr Tyr Cys
```

```
                    85                  90                  95

Ala Ser Leu Ala Tyr Trp Gly Gln Gly Thr Leu Val Thr Val Ser Ala
                100                 105                 110

<210> SEQ ID NO 452
<211> LENGTH: 116
<212> TYPE: PRT
<213> ORGANISM: Mus musculus

<400> SEQUENCE: 452

Gln Ile Gln Leu Gln Gln Ser Gly Pro Asp Leu Val Lys Pro Gly Ala
1               5                   10                  15

Ser Val Lys Ile Ser Cys Lys Ala Ser Gly Tyr Thr Phe Thr Asp Tyr
                20                  25                  30

Tyr Ile Asn Trp Met Lys Gln Lys Pro Gly Gln Gly Leu Glu Trp Ile
            35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ser Thr Ala Tyr
65                  70                  75                  80

Met Gln Leu Ser Ser Leu Thr Ser Glu Asp Thr Ala Val Tyr Phe Cys
                85                  90                  95

Ala Arg Val Tyr Ser Gly Phe Asp Val Trp Gly Ala Gly Thr Thr Val
                100                 105                 110

Thr Val Ser Ser
        115

<210> SEQ ID NO 453
<211> LENGTH: 119
<212> TYPE: PRT
<213> ORGANISM: Mus musculus

<400> SEQUENCE: 453

Gln Ile Gln Leu Gln Gln Ser Gly Pro Glu Leu Val Lys Pro Gly Ala
1               5                   10                  15

Ser Val Lys Met Ser Cys Lys Ala Pro Gly Tyr Thr Phe Thr Ser Tyr
                20                  25                  30

Tyr Ile His Trp Val Lys Gln Arg Pro Gly Gln Gly Leu Glu Trp Ile
            35                  40                  45

Gly Trp Ile Tyr Pro Gly Asp Gly Ser Thr Lys Tyr Asn Glu Lys Phe
    50                  55                  60

Lys Gly Lys Thr Thr Leu Thr Ala Asp Lys Ser Ser Ser Thr Ala Tyr
65                  70                  75                  80

Met Leu Leu Ser Ser Leu Thr Ser Glu Asp Ser Ala Ile Tyr Phe Cys
                85                  90                  95

Ala Arg Gly Asp Gly Tyr Phe Ala Trp Phe Ala Tyr Trp Gly Gln Gly
                100                 105                 110

Thr Leu Val Thr Val Ser Ala
        115

<210> SEQ ID NO 454
<211> LENGTH: 119
<212> TYPE: PRT
<213> ORGANISM: Mus musculus

<400> SEQUENCE: 454

Gln Ile Gln Leu Gln Gln Ser Gly Ala Glu Leu Met Lys Pro Gly Ala
1               5                   10                  15
```

Ser Val Lys Ile Ser Cys Lys Ala Thr Gly Tyr Thr Phe Ser Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Lys Tyr Asn Glu Lys Phe
50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Ala His Arg Tyr Asp Ala Trp Phe Ala Tyr Trp Gly Gln
            100                 105                 110

Gly Thr Leu Val Thr Val Leu
            115

<210> SEQ ID NO 455
<211> LENGTH: 123
<212> TYPE: PRT
<213> ORGANISM: Mus musculus

<400> SEQUENCE: 455

Gln Ile Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Tyr Met Tyr Trp Val Asn Gln Arg Pro Gly Gln Gly Leu Glu Trp Ile
        35                  40                  45

Gly Gly Ile Asn Pro Thr Asn Gly Gly Thr Asn Phe Asn Ala Lys Phe
50                  55                  60

Lys Asn Lys Ala Thr Leu Thr Val Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Thr Arg Gly Met Ala Tyr Arg Tyr Asp Gly Ala Gly Trp Phe Ala Tyr
            100                 105                 110

Trp Gly Gln Gly Thr Pro Val Thr Val Ser Ser
            115                 120

<210> SEQ ID NO 456
<211> LENGTH: 118
<212> TYPE: PRT
<213> ORGANISM: Mus musculus

<400> SEQUENCE: 456

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Glu Gln Gly Leu Glu Trp Ile
        35                  40                  45

Gly Arg Ile Asp Pro Tyr Asp Ser Glu Thr His Tyr Asn Gln Lys Phe
50                  55                  60

Lys Asp Lys Ala Ile Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

```
Ala Arg Gly Gly Arg Gly Thr Trp Phe Ala Tyr Trp Gly Gln Gly Thr
            100                 105                 110

Leu Val Thr Val Ser Ala
        115

<210> SEQ ID NO 457
<211> LENGTH: 119
<212> TYPE: PRT
<213> ORGANISM: Mus musculus

<400> SEQUENCE: 457

Asp Val Met Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Ala Arg Gly Trp Gly Asn Trp Phe Ala Tyr Trp Gly Gln Gly
            100                 105                 110

Thr Leu Val Thr Val Ser Ala
        115

<210> SEQ ID NO 458
<211> LENGTH: 117
<212> TYPE: PRT
<213> ORGANISM: Mus musculus

<400> SEQUENCE: 458

Glu Val Met Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Ile His Trp Val Arg Gln Ala Pro Glu Lys Gly Leu Glu Trp Val
        35                  40                  45

Ala Tyr Ile Ser Gly Gly Gly Thr Ile Ser Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Ile Tyr Tyr Cys
                85                  90                  95

Ala Arg Trp Arg Gly Gly Tyr Phe Asp Tyr Trp Gly Gln Gly Thr Ser
            100                 105                 110

Leu Thr Val Ser Ser
        115

<210> SEQ ID NO 459
<211> LENGTH: 121
<212> TYPE: PRT
<213> ORGANISM: Mus musculus

<400> SEQUENCE: 459
```

Gln Ile Gln Leu Gln Gln Ser Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
            35                  40                  45

Gly Asn Ile Tyr Pro Ser Asp Ser Tyr Thr Asn Tyr Asn Gln Lys Phe
        50                  55                  60

Lys Asp Lys Ala Thr Leu Thr Val Asp Lys Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Thr Gly Gly Ser Thr Met Thr Pro Trp Phe Ala Tyr Trp Gly
            100                 105                 110

Gln Gly Thr Leu Val Thr Val Ser Ser
            115                 120

```
<210> SEQ ID NO 460
<211> LENGTH: 121
<212> TYPE: PRT
<213> ORGANISM: Mus musculus

<400> SEQUENCE: 460
```

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
            35                  40                  45

Trp Leu Ala His Ile Tyr Trp Asp Asp Lys Arg Tyr Asn Pro Ser
        50                  55                  60

Leu Lys Ser Arg Leu Thr Ile Ser Lys Asp Thr Ser Arg Asn Gln Val
65                  70                  75                  80

Phe Leu Lys Ile Thr Ser Val Asp Thr Thr Asp Thr Ala Thr Tyr Tyr
                85                  90                  95

Cys Ala Arg Arg Ala Gly Asp Tyr Gly Asn Pro Phe Pro Tyr Trp Gly
            100                 105                 110

Gln Gly Thr Leu Val Thr Val Ser Ala
            115                 120

```
<210> SEQ ID NO 461
<211> LENGTH: 25
<212> TYPE: PRT
<213> ORGANISM: Mus musculus

<400> SEQUENCE: 461
```

Gln Val Gln Leu Gln Gln Ser Gly Ala Glu Leu Val Arg Pro Gly Ala
1               5                   10                  15

Ser Val Lys Leu Ser Cys Lys Ala Leu
            20                  25

```
<210> SEQ ID NO 462
<211> LENGTH: 25
<212> TYPE: PRT
<213> ORGANISM: Mus musculus

<400> SEQUENCE: 462
```

Gln Ile Gln Leu Lys Glu Ser Gly Pro Gly Leu Val Lys Pro Ser Gln
1               5                   10                  15

```
                1               5                   10                  15
Ser Leu Ser Leu Thr Cys Thr Val Thr
            20                  25

<210> SEQ ID NO 463
<211> LENGTH: 25
<212> TYPE: PRT
<213> ORGANISM: Mus musculus

<400> SEQUENCE: 463

Gln Ile Gln Leu Gln Gln Ser Gly Ala Glu Leu Ala Arg Pro Gly Ala
1               5                   10                  15

Ser Val Arg Met Ser Cys Lys Ala Ser
            20                  25

<210> SEQ ID NO 464
<211> LENGTH: 25
<212> TYPE: PRT
<213> ORGANISM: Mus musculus

<400> SEQUENCE: 464

Gln Val Gln Leu Gln Gln Pro Gly Ala Glu Leu Val Lys Pro Gly Ala
1               5                   10                  15

Ser Val Lys Leu Ser Cys Lys Ala Ser
            20                  25

<210> SEQ ID NO 465
<211> LENGTH: 25
<212> TYPE: PRT
<213> ORGANISM: Mus musculus

<400> SEQUENCE: 465

Gln Ile Gln Leu Gln Gln Ser Gly Ala Glu Leu Val Lys Pro Gly Ala
1               5                   10                  15

Ser Val Lys Leu Ser Cys Lys Thr Ser
            20                  25

<210> SEQ ID NO 466
<211> LENGTH: 25
<212> TYPE: PRT
<213> ORGANISM: Mus musculus

<400> SEQUENCE: 466

Asp Val Gln Leu Val Glu Ser Gly Gly Gly Leu Val Gln Pro Gly Gly
1               5                   10                  15

Ser Leu Arg Leu Ser Cys Ala Thr Ser
            20                  25

<210> SEQ ID NO 467
<211> LENGTH: 25
<212> TYPE: PRT
<213> ORGANISM: Mus musculus

<400> SEQUENCE: 467

Gln Val Gln Leu Gln Gln Pro Ala Ala Glu Leu Ala Arg Pro Gly Ala
1               5                   10                  15

Ser Val Lys Met Ser Cys Lys Ala Ser
            20                  25

<210> SEQ ID NO 468
<211> LENGTH: 25
<212> TYPE: PRT
```

```
<213> ORGANISM: Mus musculus

<400> SEQUENCE: 468

Glu Val Met Leu Val Glu Ser Gly Gly Gly Leu Val Lys Pro Gly Gly
1               5                   10                  15

Ser Leu Lys Ile Ser Cys Ala Ala Ser
            20                  25

<210> SEQ ID NO 469
<211> LENGTH: 25
<212> TYPE: PRT
<213> ORGANISM: Mus musculus

<400> SEQUENCE: 469

Gln Val Gln Leu Gln Gln Pro Gly Ala Glu Leu Val Lys Pro Gly Ala
1               5                   10                  15

Pro Val Lys Leu Ser Cys Lys Ala Ser
            20                  25

<210> SEQ ID NO 470
<211> LENGTH: 25
<212> TYPE: PRT
<213> ORGANISM: Mus musculus

<400> SEQUENCE: 470

Gln Ile Gln Phe Ala Gln Ser Gly Pro Glu Leu Lys Lys Pro Gly Glu
1               5                   10                  15

Thr Val Lys Ile Ser Cys Lys Ala Phe
            20                  25

<210> SEQ ID NO 471
<211> LENGTH: 25
<212> TYPE: PRT
<213> ORGANISM: Mus musculus

<400> SEQUENCE: 471

Glu Val Lys Ile Glu Glu Ser Gly Gly Gly Leu Val Gln Pro Gly Gly
1               5                   10                  15

Ala Met Lys Leu Ser Cys Val Ala Ser
            20                  25

<210> SEQ ID NO 472
<211> LENGTH: 25
<212> TYPE: PRT
<213> ORGANISM: Mus musculus

<400> SEQUENCE: 472

Gln Ile Gln Leu Gln Gln Ser Gly Ala Glu Leu Val Lys Pro Gly Ala
1               5                   10                  15

Ser Val Lys Leu Ser Cys Lys Ala Ser
            20                  25

<210> SEQ ID NO 473
<211> LENGTH: 25
<212> TYPE: PRT
<213> ORGANISM: Mus musculus

<400> SEQUENCE: 473

Gln Val Gln Leu Gln Gln Ser Gly Ala Glu Leu Ala Lys Pro Gly Ala
1               5                   10                  15

Ser Val Lys Met Ser Cys Lys Ala Ser
            20                  25
```

<210> SEQ ID NO 474
<211> LENGTH: 25
<212> TYPE: PRT
<213> ORGANISM: Mus musculus

<400> SEQUENCE: 474

Gln Ile Gln Leu Gln Gln Pro Gly Ala Glu Leu Val Lys Pro Gly Ala
1               5                   10                  15

Ser Val Lys Leu Ser Cys Lys Ala Ser
            20                  25

<210> SEQ ID NO 475
<211> LENGTH: 25
<212> TYPE: PRT
<213> ORGANISM: Mus musculus

<400> SEQUENCE: 475

Gln Ile Gln Leu Gln Gln Ser Gly Pro Asp Leu Val Lys Pro Gly Ala
1               5                   10                  15

Ser Val Lys Ile Ser Cys Lys Ala Ser
            20                  25

<210> SEQ ID NO 476
<211> LENGTH: 25
<212> TYPE: PRT
<213> ORGANISM: Mus musculus

<400> SEQUENCE: 476

Gln Ile Gln Leu Gln Ser Gly Pro Glu Leu Val Lys Pro Gly Ala
1               5                   10                  15

Ser Val Lys Met Ser Cys Lys Ala Pro
            20                  25

<210> SEQ ID NO 477
<211> LENGTH: 25
<212> TYPE: PRT
<213> ORGANISM: Mus musculus

<400> SEQUENCE: 477

Gln Val Gln Leu Gln Gln Pro Gly Ala Glu Leu Val Arg Pro Gly Ala
1               5                   10                  15

Ser Val Lys Leu Ser Cys Lys Ala Ser
            20                  25

<210> SEQ ID NO 478
<211> LENGTH: 25
<212> TYPE: PRT
<213> ORGANISM: Mus musculus

<400> SEQUENCE: 478

Asp Val Met Leu Val Glu Ser Gly Gly Gly Leu Val Gln Pro Gly Gly
1               5                   10                  15

Ser Leu Arg Leu Ser Cys Ala Thr Ser
            20                  25

<210> SEQ ID NO 479
<211> LENGTH: 25
<212> TYPE: PRT
<213> ORGANISM: Mus musculus

<400> SEQUENCE: 479

Glu Val Met Leu Val Glu Ser Gly Gly Gly Leu Val Gln Pro Gly Gly
1               5                   10                  15

Ser Arg Lys Leu Ser Cys Ala Ala Ser
            20                  25

<210> SEQ ID NO 480
<211> LENGTH: 25
<212> TYPE: PRT
<213> ORGANISM: Mus musculus

<400> SEQUENCE: 480

Gln Ile Gln Leu Gln Gln Ser Gly Ala Glu Leu Val Arg Pro Gly Ala
1               5                   10                  15

Ser Val Lys Leu Ser Cys Lys Ala Ser
            20                  25

<210> SEQ ID NO 481
<211> LENGTH: 25
<212> TYPE: PRT
<213> ORGANISM: Mus musculus

<400> SEQUENCE: 481

Gln Val Thr Leu Lys Glu Ser Gly Pro Gly Ile Leu Gln Pro Ser Gln
1               5                   10                  15

Thr Leu Ser Leu Thr Cys Ser Phe Ser
            20                  25

<210> SEQ ID NO 482
<211> LENGTH: 9
<212> TYPE: PRT
<213> ORGANISM: Mus musculus

<400> SEQUENCE: 482

Gly Tyr Ser Ile Thr Ser Asp Tyr Ala
1               5

<210> SEQ ID NO 483
<211> LENGTH: 8
<212> TYPE: PRT
<213> ORGANISM: Mus musculus

<400> SEQUENCE: 483

Gly Tyr Thr Phe Thr Thr Tyr Trp
1               5

<210> SEQ ID NO 484
<211> LENGTH: 8
<212> TYPE: PRT
<213> ORGANISM: Mus musculus

<400> SEQUENCE: 484

Gly Tyr Thr Phe Thr Ser Ser Thr
1               5

<210> SEQ ID NO 485
<211> LENGTH: 8
<212> TYPE: PRT
<213> ORGANISM: Mus musculus

<400> SEQUENCE: 485

Gly Phe Thr Phe Ser Ser Tyr Thr
1               5

```
<210> SEQ ID NO 486
<211> LENGTH: 8
<212> TYPE: PRT
<213> ORGANISM: Mus musculus

<400> SEQUENCE: 486

Gly Tyr Thr Phe Thr Asn Phe Tyr
1               5

<210> SEQ ID NO 487
<211> LENGTH: 8
<212> TYPE: PRT
<213> ORGANISM: Mus musculus

<400> SEQUENCE: 487

Gly Tyr Thr Phe Thr Asp Tyr Ser
1               5

<210> SEQ ID NO 488
<211> LENGTH: 8
<212> TYPE: PRT
<213> ORGANISM: Mus musculus

<400> SEQUENCE: 488

Gly Tyr Thr Phe Thr Arg Tyr Tyr
1               5

<210> SEQ ID NO 489
<211> LENGTH: 8
<212> TYPE: PRT
<213> ORGANISM: Mus musculus

<400> SEQUENCE: 489

Gly Tyr Thr Phe Thr Asp Tyr Tyr
1               5

<210> SEQ ID NO 490
<211> LENGTH: 8
<212> TYPE: PRT
<213> ORGANISM: Mus musculus

<400> SEQUENCE: 490

Gly Tyr Thr Phe Thr Asn Tyr Tyr
1               5

<210> SEQ ID NO 491
<211> LENGTH: 8
<212> TYPE: PRT
<213> ORGANISM: Mus musculus

<400> SEQUENCE: 491

Gly Phe Thr Phe Ser Ser Phe Gly
1               5

<210> SEQ ID NO 492
<211> LENGTH: 10
<212> TYPE: PRT
<213> ORGANISM: Mus musculus

<400> SEQUENCE: 492

Gly Phe Ser Leu Ser Thr Ser Gly Met Gly
1               5                   10

<210> SEQ ID NO 493
<211> LENGTH: 17
```

```
<212> TYPE: PRT
<213> ORGANISM: Mus musculus

<400> SEQUENCE: 493

Met His Trp Val Lys Gln Thr Pro Val His Gly Leu Gly Trp Ile Gly
1               5                   10                  15

Ala

<210> SEQ ID NO 494
<211> LENGTH: 17
<212> TYPE: PRT
<213> ORGANISM: Mus musculus

<400> SEQUENCE: 494

Trp Asn Trp Ile Arg Gln Phe Pro Gly Asn Lys Leu Glu Trp Met Gly
1               5                   10                  15

Tyr

<210> SEQ ID NO 495
<211> LENGTH: 17
<212> TYPE: PRT
<213> ORGANISM: Mus musculus

<400> SEQUENCE: 495

Met His Trp Leu Arg Gln Pro Leu Gly Lys Arg Leu Glu Trp Ile Ala
1               5                   10                  15

Val

<210> SEQ ID NO 496
<211> LENGTH: 17
<212> TYPE: PRT
<213> ORGANISM: Mus musculus

<400> SEQUENCE: 496

Met His Trp Val Lys Leu Arg Pro Gly Gln Gly Phe Glu Trp Ile Gly
1               5                   10                  15

Glu

<210> SEQ ID NO 497
<211> LENGTH: 17
<212> TYPE: PRT
<213> ORGANISM: Mus musculus

<400> SEQUENCE: 497

Ile Gln Trp Val Lys Gln Arg Pro Gly Gln Gly Leu Gly Trp Ile Gly
1               5                   10                  15

Glu

<210> SEQ ID NO 498
<211> LENGTH: 17
<212> TYPE: PRT
<213> ORGANISM: Mus musculus

<400> SEQUENCE: 498

Met Ser Trp Val Arg Gln Asn Pro Glu Lys Arg Leu Glu Trp Val Ala
1               5                   10                  15

Thr

<210> SEQ ID NO 499
<211> LENGTH: 17
<212> TYPE: PRT
```

-continued

<213> ORGANISM: Mus musculus

<400> SEQUENCE: 499

Leu Tyr Trp Val Lys Gln Arg Pro Gly Gln Gly Leu Glu Trp Ile Gly
1               5                   10                  15

Gly

<210> SEQ ID NO 500
<211> LENGTH: 17
<212> TYPE: PRT
<213> ORGANISM: Mus musculus

<400> SEQUENCE: 500

Ile Asn Trp Val Lys Gln Arg Pro Gly Gln Gly Leu Glu Trp Ile Gly
1               5                   10                  15

Asn

<210> SEQ ID NO 501
<211> LENGTH: 17
<212> TYPE: PRT
<213> ORGANISM: Mus musculus

<400> SEQUENCE: 501

Ile Asn Trp Met Lys Gln Lys Pro Gly Gln Gly Leu Glu Trp Ile Gly
1               5                   10                  15

Trp

<210> SEQ ID NO 502
<211> LENGTH: 17
<212> TYPE: PRT
<213> ORGANISM: Mus musculus

<400> SEQUENCE: 502

Ile His Trp Val Lys Gln Arg Pro Gly Gln Gly Leu Glu Trp Ile Gly
1               5                   10                  15

Trp

<210> SEQ ID NO 503
<211> LENGTH: 17
<212> TYPE: PRT
<213> ORGANISM: Mus musculus

<400> SEQUENCE: 503

Met Tyr Trp Val Asn Gln Arg Pro Gly Gln Gly Leu Glu Trp Ile Gly
1               5                   10                  15

Gly

<210> SEQ ID NO 504
<211> LENGTH: 17
<212> TYPE: PRT
<213> ORGANISM: Mus musculus

<400> SEQUENCE: 504

Ile His Trp Val Arg Gln Ala Pro Glu Lys Gly Leu Glu Trp Val Ala
1               5                   10                  15

Tyr

<210> SEQ ID NO 505
<211> LENGTH: 17
<212> TYPE: PRT
<213> ORGANISM: Mus musculus

```
<400> SEQUENCE: 505

Val Ser Trp Ile Arg Gln Pro Ser Gly Lys Gly Leu Glu Trp Leu Ala
1               5                   10                  15

His

<210> SEQ ID NO 506
<211> LENGTH: 7
<212> TYPE: PRT
<213> ORGANISM: Mus musculus

<400> SEQUENCE: 506

Ile Ser Tyr Ser Gly Ser Thr
1               5

<210> SEQ ID NO 507
<211> LENGTH: 8
<212> TYPE: PRT
<213> ORGANISM: Mus musculus

<400> SEQUENCE: 507

Ile Phe Pro Gly Thr Gly Thr Thr
1               5

<210> SEQ ID NO 508
<211> LENGTH: 8
<212> TYPE: PRT
<213> ORGANISM: Mus musculus

<400> SEQUENCE: 508

Ile Ser Ser Gly Gly Gly Tyr Thr
1               5

<210> SEQ ID NO 509
<211> LENGTH: 8
<212> TYPE: PRT
<213> ORGANISM: Mus musculus

<400> SEQUENCE: 509

Ile Tyr Pro Ser Asp Ser Tyr Thr
1               5

<210> SEQ ID NO 510
<211> LENGTH: 8
<212> TYPE: PRT
<213> ORGANISM: Mus musculus

<400> SEQUENCE: 510

Ile Asn Pro Ser Asn Gly Arg Thr
1               5

<210> SEQ ID NO 511
<211> LENGTH: 8
<212> TYPE: PRT
<213> ORGANISM: Mus musculus

<400> SEQUENCE: 511

Ile Tyr Pro Gly Ser Gly Asn Thr
1               5

<210> SEQ ID NO 512
<211> LENGTH: 8
<212> TYPE: PRT
<213> ORGANISM: Mus musculus
```

<400> SEQUENCE: 512

Ile Tyr Pro Gly Asp Gly Ser Thr
1               5

<210> SEQ ID NO 513
<211> LENGTH: 8
<212> TYPE: PRT
<213> ORGANISM: Mus musculus

<400> SEQUENCE: 513

Ile Asn Pro Thr Asn Gly Gly Thr
1               5

<210> SEQ ID NO 514
<211> LENGTH: 8
<212> TYPE: PRT
<213> ORGANISM: Mus musculus

<400> SEQUENCE: 514

Ile Ser Gly Gly Gly Gly Thr Ile
1               5

<210> SEQ ID NO 515
<211> LENGTH: 7
<212> TYPE: PRT
<213> ORGANISM: Mus musculus

<400> SEQUENCE: 515

Ile Tyr Trp Asp Asp Asp Lys
1               5

<210> SEQ ID NO 516
<211> LENGTH: 38
<212> TYPE: PRT
<213> ORGANISM: Mus musculus

<400> SEQUENCE: 516

Ser Tyr Asn Pro Ser Leu Lys Ser Arg Ile Ser Ile Thr Arg Asp Thr
1               5                   10                  15

Ser Lys Asn Gln Phe Phe Leu Gln Leu Asn Ser Val Thr Thr Glu Asp
                20                  25                  30

Thr Ala Thr Tyr Tyr Cys
            35

<210> SEQ ID NO 517
<211> LENGTH: 38
<212> TYPE: PRT
<213> ORGANISM: Mus musculus

<400> SEQUENCE: 517

Asn Tyr Asn Glu Lys Phe Lys Arg Lys Ala Thr Leu Thr Val Asp Lys
1               5                   10                  15

Ser Ser Ser Thr Ala Tyr Met Gln Leu Ser Ser Leu Thr Ser Glu Asp
                20                  25                  30

Ser Ala Val Tyr Tyr Cys
            35

<210> SEQ ID NO 518
<211> LENGTH: 38
<212> TYPE: PRT
<213> ORGANISM: Mus musculus

```
<400> SEQUENCE: 518

Tyr Tyr Asn Glu Lys Phe Lys Gly Lys Ala Thr Leu Thr Ile Asp Thr
1               5                   10                  15

Ser Ser Ser Thr Ala Tyr Met Gln Leu Ser Ser Leu Thr Ser Glu Asp
                20                  25                  30

Ser Ala Val Tyr Phe Cys
            35

<210> SEQ ID NO 519
<211> LENGTH: 38
<212> TYPE: PRT
<213> ORGANISM: Mus musculus

<400> SEQUENCE: 519

Glu Tyr Asn Gln Lys Phe Lys Asp Lys Thr Thr Leu Thr Ala Asp Lys
1               5                   10                  15

Ser Ser Ser Thr Ala Tyr Met Gln Leu Ser Ser Leu Thr Ser Glu Asp
                20                  25                  30

Ser Ala Val Tyr Tyr Cys
            35

<210> SEQ ID NO 520
<211> LENGTH: 38
<212> TYPE: PRT
<213> ORGANISM: Mus musculus

<400> SEQUENCE: 520

Tyr Tyr Leu Asp Ser Val Lys Gly Arg Phe Thr Pro Ser Arg Asp Asn
1               5                   10                  15

Gly Lys Asn Thr Leu Asn Leu Gln Met Ser Ser Leu Lys Ser Glu Asp
                20                  25                  30

Thr Ala Met Tyr Tyr Cys
            35

<210> SEQ ID NO 521
<211> LENGTH: 38
<212> TYPE: PRT
<213> ORGANISM: Mus musculus

<400> SEQUENCE: 521

Asn Tyr Asn Gln Lys Phe Lys Asp Lys Ala Thr Leu Thr Val Asp Lys
1               5                   10                  15

Ser Ser Ser Thr Ala Tyr Met Gln Leu Ser Ser Pro Thr Ser Glu Asp
                20                  25                  30

Ser Ala Val Tyr Tyr Cys
            35

<210> SEQ ID NO 522
<211> LENGTH: 38
<212> TYPE: PRT
<213> ORGANISM: Mus musculus

<400> SEQUENCE: 522

Tyr Tyr Ala Glu Ser Val Lys Gly Arg Phe Thr Ile Ser Arg Asp Asp
1               5                   10                  15

Ser Gln Ser Ser Val Tyr Leu Gln Met Asn Asp Leu Arg Thr Glu Asp
                20                  25                  30

Thr Gly Ile Tyr Tyr Cys
            35
```

<210> SEQ ID NO 523
<211> LENGTH: 38
<212> TYPE: PRT
<213> ORGANISM: Mus musculus

<400> SEQUENCE: 523

Tyr Tyr Asn Pro Ala Leu Lys Ser Arg Leu Thr Ile Ser Lys Asp Thr
1               5                   10                  15

Pro Asn Asn Gln Val Phe Leu Lys Ile Ala Ser Val Val Thr Ala Asp
            20                  25                  30

Thr Ala Thr Tyr Tyr Cys
        35

<210> SEQ ID NO 524
<211> LENGTH: 38
<212> TYPE: PRT
<213> ORGANISM: Mus musculus

<400> SEQUENCE: 524

Asn Phe Asn Glu Lys Phe Lys Ser Lys Ala Thr Leu Thr Val Asp Lys
1               5                   10                  15

Ser Ser Ser Thr Ala Tyr Met Gln Leu Asn Ser Leu Thr Ser Asp Asp
            20                  25                  30

Ser Ala Val Tyr Tyr Cys
        35

<210> SEQ ID NO 525
<211> LENGTH: 38
<212> TYPE: PRT
<213> ORGANISM: Mus musculus

<400> SEQUENCE: 525

Lys Tyr Asn Glu Lys Phe Lys Gly Lys Ala Thr Leu Thr Val Asp Thr
1               5                   10                  15

Ser Ser Ser Thr Ala Tyr Met Gln Leu Ser Ser Leu Thr Ser Glu Asp
            20                  25                  30

Thr Ala Val Tyr Phe Cys
        35

<210> SEQ ID NO 526
<211> LENGTH: 38
<212> TYPE: PRT
<213> ORGANISM: Mus musculus

<400> SEQUENCE: 526

Lys Tyr Asn Glu Lys Phe Lys Gly Lys Thr Thr Leu Thr Ala Asp Lys
1               5                   10                  15

Ser Ser Ser Thr Ala Tyr Met Leu Leu Ser Ser Leu Thr Ser Glu Asp
            20                  25                  30

Ser Ala Ile Tyr Phe Cys
        35

<210> SEQ ID NO 527
<211> LENGTH: 38
<212> TYPE: PRT
<213> ORGANISM: Mus musculus

<400> SEQUENCE: 527

Lys Tyr Asn Glu Lys Phe Lys Gly Lys Ala Thr Phe Thr Ala Asp Thr
1               5                   10                  15

-continued

```
Ser Ser Asn Thr Ala Tyr Met Gln Leu Ser Ser Leu Thr Ser Glu Asp
            20                  25                  30

Ser Ala Val Tyr Tyr Cys
            35

<210> SEQ ID NO 528
<211> LENGTH: 38
<212> TYPE: PRT
<213> ORGANISM: Mus musculus

<400> SEQUENCE: 528

Asn Phe Asn Ala Lys Phe Lys Asn Lys Ala Thr Leu Thr Val Asp Lys
1               5                   10                  15

Ser Ser Asn Thr Ala Tyr Met Gln Leu Ser Ser Leu Thr Ser Glu Asp
            20                  25                  30

Ser Ala Val Tyr Tyr Cys
            35

<210> SEQ ID NO 529
<211> LENGTH: 38
<212> TYPE: PRT
<213> ORGANISM: Mus musculus

<400> SEQUENCE: 529

Ser Tyr Ala Asp Thr Val Lys Gly Arg Phe Thr Ile Ser Arg Asp Asn
1               5                   10                  15

Pro Lys Asn Thr Leu Phe Leu Gln Met Thr Ser Leu Arg Ser Glu Asp
            20                  25                  30

Thr Ala Ile Tyr Tyr Cys
            35

<210> SEQ ID NO 530
<211> LENGTH: 38
<212> TYPE: PRT
<213> ORGANISM: Mus musculus

<400> SEQUENCE: 530

Arg Tyr Asn Pro Ser Leu Lys Ser Arg Leu Thr Ile Ser Lys Asp Thr
1               5                   10                  15

Ser Arg Asn Gln Val Phe Leu Lys Ile Thr Ser Val Asp Thr Thr Asp
            20                  25                  30

Thr Ala Thr Tyr Tyr Cys
            35

<210> SEQ ID NO 531
<211> LENGTH: 13
<212> TYPE: PRT
<213> ORGANISM: Mus musculus

<400> SEQUENCE: 531

Thr Arg Ser Asp Tyr Gly Ser Ser Tyr Glu Phe Ala Tyr
1               5                   10

<210> SEQ ID NO 532
<211> LENGTH: 10
<212> TYPE: PRT
<213> ORGANISM: Mus musculus

<400> SEQUENCE: 532

Ala Arg Ser Arg Gly Asn Tyr Phe Asp Tyr
1               5                   10
```

<210> SEQ ID NO 533
<211> LENGTH: 12
<212> TYPE: PRT
<213> ORGANISM: Mus musculus

<400> SEQUENCE: 533

Ala Arg Ser Gly Leu Arg Gln Ala Trp Phe Ala Tyr
1               5                   10

<210> SEQ ID NO 534
<211> LENGTH: 6
<212> TYPE: PRT
<213> ORGANISM: Mus musculus

<400> SEQUENCE: 534

Ser Arg Leu Phe Ala Tyr
1               5

<210> SEQ ID NO 535
<211> LENGTH: 7
<212> TYPE: PRT
<213> ORGANISM: Mus musculus

<400> SEQUENCE: 535

Thr Ile Thr Gly Phe Asp Val
1               5

<210> SEQ ID NO 536
<211> LENGTH: 13
<212> TYPE: PRT
<213> ORGANISM: Mus musculus

<400> SEQUENCE: 536

Ala Arg Gly Gly Tyr Tyr Asn Ser Ser Pro Phe Ala Tyr
1               5                   10

<210> SEQ ID NO 537
<211> LENGTH: 12
<212> TYPE: PRT
<213> ORGANISM: Mus musculus

<400> SEQUENCE: 537

Ala Arg Asp Gly Glu Val Arg Arg Ala Leu Ala Tyr
1               5                   10

<210> SEQ ID NO 538
<211> LENGTH: 8
<212> TYPE: PRT
<213> ORGANISM: Mus musculus

<400> SEQUENCE: 538

Val Arg His Tyr Tyr Phe Asp Tyr
1               5

<210> SEQ ID NO 539
<211> LENGTH: 10
<212> TYPE: PRT
<213> ORGANISM: Mus musculus

<400> SEQUENCE: 539

Thr Arg Val Ser Ala Lys Tyr Phe Asp Val
1               5                   10

<210> SEQ ID NO 540

```
<211> LENGTH: 13
<212> TYPE: PRT
<213> ORGANISM: Mus musculus

<400> SEQUENCE: 540

Thr Arg Ser Tyr Tyr Asp Tyr Asp Trp Tyr Phe Asp Val
1               5                   10

<210> SEQ ID NO 541
<211> LENGTH: 15
<212> TYPE: PRT
<213> ORGANISM: Mus musculus

<400> SEQUENCE: 541

Thr Arg Gln Asn Tyr Tyr Gly Ser Ser His Trp Tyr Phe Asp Val
1               5                   10                  15

<210> SEQ ID NO 542
<211> LENGTH: 14
<212> TYPE: PRT
<213> ORGANISM: Mus musculus

<400> SEQUENCE: 542

Ala Ser Phe Tyr Tyr Gly Asn Phe Ala Tyr Tyr Phe Asp Tyr
1               5                   10

<210> SEQ ID NO 543
<211> LENGTH: 16
<212> TYPE: PRT
<213> ORGANISM: Mus musculus

<400> SEQUENCE: 543

Thr Arg Ile Tyr Asp Ser Gly Ser Ser Tyr Thr Trp Tyr Phe Asp Val
1               5                   10                  15

<210> SEQ ID NO 544
<211> LENGTH: 10
<212> TYPE: PRT
<213> ORGANISM: Mus musculus

<400> SEQUENCE: 544

Ala Arg Asp Ser Ser Gly Tyr Gly Ala Tyr
1               5                   10

<210> SEQ ID NO 545
<211> LENGTH: 11
<212> TYPE: PRT
<213> ORGANISM: Mus musculus

<400> SEQUENCE: 545

Ala Arg Tyr Asp Gly Tyr Tyr Tyr Phe Asp Tyr
1               5                   10

<210> SEQ ID NO 546
<211> LENGTH: 12
<212> TYPE: PRT
<213> ORGANISM: Mus musculus

<400> SEQUENCE: 546

Thr Ser His Tyr Tyr Gly Arg Ala Trp Phe Ala Tyr
1               5                   10

<210> SEQ ID NO 547
<211> LENGTH: 11
<212> TYPE: PRT
```

<213> ORGANISM: Mus musculus

<400> SEQUENCE: 547

Thr Lys Gly Gly Phe Tyr Asp Phe Phe Ala Tyr
1               5                   10

<210> SEQ ID NO 548
<211> LENGTH: 5
<212> TYPE: PRT
<213> ORGANISM: Mus musculus

<400> SEQUENCE: 548

Ala Ser Leu Ala Tyr
1               5

<210> SEQ ID NO 549
<211> LENGTH: 9
<212> TYPE: PRT
<213> ORGANISM: Mus musculus

<400> SEQUENCE: 549

Ala Arg Val Tyr Ser Gly Phe Asp Val
1               5

<210> SEQ ID NO 550
<211> LENGTH: 12
<212> TYPE: PRT
<213> ORGANISM: Mus musculus

<400> SEQUENCE: 550

Ala Arg Gly Asp Gly Tyr Phe Ala Trp Phe Ala Tyr
1               5                   10

<210> SEQ ID NO 551
<211> LENGTH: 13
<212> TYPE: PRT
<213> ORGANISM: Mus musculus

<400> SEQUENCE: 551

Ala Arg Ser Ala His Arg Tyr Asp Ala Trp Phe Ala Tyr
1               5                   10

<210> SEQ ID NO 552
<211> LENGTH: 16
<212> TYPE: PRT
<213> ORGANISM: Mus musculus

<400> SEQUENCE: 552

Thr Arg Gly Met Ala Tyr Arg Tyr Asp Gly Ala Gly Trp Phe Ala Tyr
1               5                   10                  15

<210> SEQ ID NO 553
<211> LENGTH: 11
<212> TYPE: PRT
<213> ORGANISM: Mus musculus

<400> SEQUENCE: 553

Ala Arg Gly Gly Arg Gly Thr Trp Phe Ala Tyr
1               5                   10

<210> SEQ ID NO 554
<211> LENGTH: 10
<212> TYPE: PRT
<213> ORGANISM: Mus musculus

<400> SEQUENCE: 554

Ala Arg Gly Trp Gly Asn Trp Phe Ala Tyr
1               5                   10

<210> SEQ ID NO 555
<211> LENGTH: 10
<212> TYPE: PRT
<213> ORGANISM: Mus musculus

<400> SEQUENCE: 555

Ala Arg Trp Arg Gly Gly Tyr Phe Asp Tyr
1               5                   10

<210> SEQ ID NO 556
<211> LENGTH: 14
<212> TYPE: PRT
<213> ORGANISM: Mus musculus

<400> SEQUENCE: 556

Thr Arg Thr Gly Gly Ser Thr Met Thr Pro Trp Phe Ala Tyr
1               5                   10

<210> SEQ ID NO 557
<211> LENGTH: 13
<212> TYPE: PRT
<213> ORGANISM: Mus musculus

<400> SEQUENCE: 557

Ala Arg Arg Ala Gly Asp Tyr Gly Asn Pro Phe Pro Tyr
1               5                   10

<210> SEQ ID NO 558
<211> LENGTH: 15
<212> TYPE: PRT
<213> ORGANISM: Mus musculus

<400> SEQUENCE: 558

Cys Thr Arg Ser Asp Tyr Gly Ser Ser Tyr Glu Phe Ala Tyr Trp
1               5                   10                  15

<210> SEQ ID NO 559
<211> LENGTH: 12
<212> TYPE: PRT
<213> ORGANISM: Mus musculus

<400> SEQUENCE: 559

Cys Ala Arg Ser Arg Gly Asn Tyr Phe Asp Tyr Trp
1               5                   10

<210> SEQ ID NO 560
<211> LENGTH: 14
<212> TYPE: PRT
<213> ORGANISM: Mus musculus

<400> SEQUENCE: 560

Cys Ala Arg Ser Gly Leu Arg Gln Ala Trp Phe Ala Tyr Trp
1               5                   10

<210> SEQ ID NO 561
<211> LENGTH: 8
<212> TYPE: PRT
<213> ORGANISM: Mus musculus

<400> SEQUENCE: 561

```
Cys Ser Arg Leu Phe Ala Tyr Trp
1               5
```

<210> SEQ ID NO 562
<211> LENGTH: 9
<212> TYPE: PRT
<213> ORGANISM: Mus musculus

<400> SEQUENCE: 562

```
Cys Thr Ile Thr Gly Phe Asp Val Trp
1               5
```

<210> SEQ ID NO 563
<211> LENGTH: 15
<212> TYPE: PRT
<213> ORGANISM: Mus musculus

<400> SEQUENCE: 563

```
Cys Ala Arg Gly Gly Tyr Tyr Asn Ser Ser Pro Phe Ala Tyr Trp
1               5                   10                  15
```

<210> SEQ ID NO 564
<211> LENGTH: 14
<212> TYPE: PRT
<213> ORGANISM: Mus musculus

<400> SEQUENCE: 564

```
Cys Ala Arg Asp Gly Glu Val Arg Arg Ala Leu Ala Tyr Trp
1               5                   10
```

<210> SEQ ID NO 565
<211> LENGTH: 10
<212> TYPE: PRT
<213> ORGANISM: Mus musculus

<400> SEQUENCE: 565

```
Cys Val Arg His Tyr Tyr Phe Asp Tyr Trp
1               5                   10
```

<210> SEQ ID NO 566
<211> LENGTH: 12
<212> TYPE: PRT
<213> ORGANISM: Mus musculus

<400> SEQUENCE: 566

```
Cys Thr Arg Val Ser Ala Lys Tyr Phe Asp Val Trp
1               5                   10
```

<210> SEQ ID NO 567
<211> LENGTH: 15
<212> TYPE: PRT
<213> ORGANISM: Mus musculus

<400> SEQUENCE: 567

```
Cys Thr Arg Ser Tyr Tyr Asp Tyr Asp Trp Tyr Phe Asp Val Trp
1               5                   10                  15
```

<210> SEQ ID NO 568
<211> LENGTH: 17
<212> TYPE: PRT
<213> ORGANISM: Mus musculus

<400> SEQUENCE: 568

```
Cys Thr Arg Gln Asn Tyr Tyr Gly Ser Ser His Trp Tyr Phe Asp Val
1               5                   10                  15
```

Trp

<210> SEQ ID NO 569
<211> LENGTH: 16
<212> TYPE: PRT
<213> ORGANISM: Mus musculus

<400> SEQUENCE: 569

Cys Ala Ser Phe Tyr Tyr Gly Asn Phe Ala Tyr Tyr Phe Asp Tyr Arg
1               5                   10                  15

<210> SEQ ID NO 570
<211> LENGTH: 18
<212> TYPE: PRT
<213> ORGANISM: Mus musculus

<400> SEQUENCE: 570

Cys Thr Arg Ile Tyr Asp Ser Gly Ser Ser Tyr Thr Trp Tyr Phe Asp
1               5                   10                  15

Val Trp

<210> SEQ ID NO 571
<211> LENGTH: 12
<212> TYPE: PRT
<213> ORGANISM: Mus musculus

<400> SEQUENCE: 571

Cys Ala Arg Asp Ser Ser Gly Tyr Gly Ala Tyr Trp
1               5                   10

<210> SEQ ID NO 572
<211> LENGTH: 13
<212> TYPE: PRT
<213> ORGANISM: Mus musculus

<400> SEQUENCE: 572

Cys Ala Arg Tyr Asp Gly Tyr Tyr Tyr Phe Asp Tyr Trp
1               5                   10

<210> SEQ ID NO 573
<211> LENGTH: 14
<212> TYPE: PRT
<213> ORGANISM: Mus musculus

<400> SEQUENCE: 573

Cys Thr Ser His Tyr Tyr Gly Arg Ala Trp Phe Ala Tyr Trp
1               5                   10

<210> SEQ ID NO 574
<211> LENGTH: 13
<212> TYPE: PRT
<213> ORGANISM: Mus musculus

<400> SEQUENCE: 574

Cys Thr Lys Gly Gly Phe Tyr Asp Phe Phe Ala Tyr Trp
1               5                   10

<210> SEQ ID NO 575
<211> LENGTH: 7
<212> TYPE: PRT
<213> ORGANISM: Mus musculus

<400> SEQUENCE: 575

```
Cys Ala Ser Leu Ala Tyr Trp
1               5

<210> SEQ ID NO 576
<211> LENGTH: 11
<212> TYPE: PRT
<213> ORGANISM: Mus musculus

<400> SEQUENCE: 576

Cys Ala Arg Val Tyr Ser Gly Phe Asp Val Trp
1               5                   10

<210> SEQ ID NO 577
<211> LENGTH: 14
<212> TYPE: PRT
<213> ORGANISM: Mus musculus

<400> SEQUENCE: 577

Cys Ala Arg Gly Asp Gly Tyr Phe Ala Trp Phe Ala Tyr Trp
1               5                   10

<210> SEQ ID NO 578
<211> LENGTH: 15
<212> TYPE: PRT
<213> ORGANISM: Mus musculus

<400> SEQUENCE: 578

Cys Ala Arg Ser Ala His Arg Tyr Asp Ala Trp Phe Ala Tyr Trp
1               5                   10                  15

<210> SEQ ID NO 579
<211> LENGTH: 18
<212> TYPE: PRT
<213> ORGANISM: Mus musculus

<400> SEQUENCE: 579

Cys Thr Arg Gly Met Ala Tyr Arg Tyr Asp Gly Ala Gly Trp Phe Ala
1               5                   10                  15

Tyr Trp

<210> SEQ ID NO 580
<211> LENGTH: 13
<212> TYPE: PRT
<213> ORGANISM: Mus musculus

<400> SEQUENCE: 580

Cys Ala Arg Gly Gly Arg Gly Thr Trp Phe Ala Tyr Trp
1               5                   10

<210> SEQ ID NO 581
<211> LENGTH: 12
<212> TYPE: PRT
<213> ORGANISM: Mus musculus

<400> SEQUENCE: 581

Cys Ala Arg Gly Trp Gly Asn Trp Phe Ala Tyr Trp
1               5                   10

<210> SEQ ID NO 582
<211> LENGTH: 12
<212> TYPE: PRT
<213> ORGANISM: Mus musculus

<400> SEQUENCE: 582
```

```
Cys Ala Arg Trp Arg Gly Gly Tyr Phe Asp Tyr Trp
1               5                   10
```

<210> SEQ ID NO 583
<211> LENGTH: 16
<212> TYPE: PRT
<213> ORGANISM: Mus musculus

<400> SEQUENCE: 583

```
Cys Thr Arg Thr Gly Gly Ser Thr Met Thr Pro Trp Phe Ala Tyr Trp
1               5                   10                  15
```

<210> SEQ ID NO 584
<211> LENGTH: 15
<212> TYPE: PRT
<213> ORGANISM: Mus musculus

<400> SEQUENCE: 584

```
Cys Ala Arg Arg Ala Gly Asp Tyr Gly Asn Pro Phe Pro Tyr Trp
1               5                   10                  15
```

<210> SEQ ID NO 585
<211> LENGTH: 14
<212> TYPE: PRT
<213> ORGANISM: Mus musculus

<400> SEQUENCE: 585

```
Phe Asp Val Trp Gly Ala Gly Thr Thr Val Thr Val Ser Ser
1               5                   10
```

<210> SEQ ID NO 586
<211> LENGTH: 15
<212> TYPE: PRT
<213> ORGANISM: Mus musculus

<400> SEQUENCE: 586

```
Tyr Phe Asp Val Trp Gly Ala Gly Thr Thr Leu Thr Val Ser Ser
1               5                   10                  15
```

<210> SEQ ID NO 587
<211> LENGTH: 17
<212> TYPE: PRT
<213> ORGANISM: Mus musculus

<400> SEQUENCE: 587

```
Asp Trp Tyr Phe Asp Val Trp Gly Ala Gly Thr Thr Val Thr Val Ser
1               5                   10                  15
Ser
```

<210> SEQ ID NO 588
<211> LENGTH: 15
<212> TYPE: PRT
<213> ORGANISM: Mus musculus

<400> SEQUENCE: 588

```
Trp Phe Ala Tyr Trp Gly Gln Gly Thr Leu Val Thr Val Ser Ser
1               5                   10                  15
```

<210> SEQ ID NO 589
<211> LENGTH: 15
<212> TYPE: PRT
<213> ORGANISM: Mus musculus

<400> SEQUENCE: 589

Tyr Phe Asp Tyr Arg Gly Gln Gly Thr Thr Leu Thr Val Ser Ser
1               5                   10                  15

<210> SEQ ID NO 590
<211> LENGTH: 17
<212> TYPE: PRT
<213> ORGANISM: Mus musculus

<400> SEQUENCE: 590

Tyr Trp Tyr Phe Asp Val Trp Gly Ala Gly Thr Ser Leu Thr Val Ser
1               5                   10                  15

Ser

<210> SEQ ID NO 591
<211> LENGTH: 15
<212> TYPE: PRT
<213> ORGANISM: Mus musculus

<400> SEQUENCE: 591

Tyr Gly Ala Tyr Trp Gly Gln Gly Thr Leu Val Thr Val Ser Ser
1               5                   10                  15

<210> SEQ ID NO 592
<211> LENGTH: 15
<212> TYPE: PRT
<213> ORGANISM: Mus musculus

<400> SEQUENCE: 592

Tyr Phe Asp Tyr Trp Gly Gln Gly Thr Thr Leu Thr Val Ser Ser
1               5                   10                  15

<210> SEQ ID NO 593
<211> LENGTH: 14
<212> TYPE: PRT
<213> ORGANISM: Mus musculus

<400> SEQUENCE: 593

Trp Phe Ala Tyr Trp Gly Gln Gly Thr Leu Val Thr Val Leu
1               5                   10

<210> SEQ ID NO 594
<211> LENGTH: 15
<212> TYPE: PRT
<213> ORGANISM: Mus musculus

<400> SEQUENCE: 594

Phe Phe Ala Tyr Trp Gly Gln Gly Thr Leu Val Thr Val Ser Ala
1               5                   10                  15

<210> SEQ ID NO 595
<211> LENGTH: 15
<212> TYPE: PRT
<213> ORGANISM: Mus musculus

<400> SEQUENCE: 595

Trp Phe Ala Tyr Trp Gly Gln Gly Thr Pro Val Thr Val Ser Ser
1               5                   10                  15

<210> SEQ ID NO 596
<211> LENGTH: 14
<212> TYPE: PRT
<213> ORGANISM: Mus musculus

<400> SEQUENCE: 596

```
Phe Pro Tyr Trp Gly Gln Gly Thr Leu Val Thr Val Ser Ala
1               5                   10
```

<210> SEQ ID NO 597
<211> LENGTH: 11
<212> TYPE: PRT
<213> ORGANISM: Mus musculus

<400> SEQUENCE: 597

```
Arg Gly Gln Gly Thr Thr Leu Thr Val Ser Ser
1               5                   10
```

<210> SEQ ID NO 598
<211> LENGTH: 10
<212> TYPE: PRT
<213> ORGANISM: Mus musculus

<400> SEQUENCE: 598

```
Trp Gly Gln Gly Thr Leu Val Thr Val Leu
1               5                   10
```

<210> SEQ ID NO 599
<211> LENGTH: 3
<212> TYPE: PRT
<213> ORGANISM: Mus musculus

<400> SEQUENCE: 599

```
Ala Ala Ser
1
```

<210> SEQ ID NO 600
<211> LENGTH: 3
<212> TYPE: PRT
<213> ORGANISM: Mus musculus

<400> SEQUENCE: 600

```
Ala Ala Thr
1
```

<210> SEQ ID NO 601
<211> LENGTH: 14
<212> TYPE: PRT
<213> ORGANISM: Mus musculus

<400> SEQUENCE: 601

```
Ala Arg Glu Ala Ser Tyr Tyr Tyr Gly Asn Ala Trp Phe Ala
1               5                   10
```

<210> SEQ ID NO 602
<211> LENGTH: 12
<212> TYPE: PRT
<213> ORGANISM: Mus musculus

<400> SEQUENCE: 602

```
Ala Arg Gly Gly Thr Ser Phe Val His Phe Asp Tyr
1               5                   10
```

<210> SEQ ID NO 603
<211> LENGTH: 14
<212> TYPE: PRT
<213> ORGANISM: Mus musculus

<400> SEQUENCE: 603

```
Ala Arg Gly Gly Thr Ser Val Val His Phe Asp Phe Asp Tyr
1               5                   10
```

<210> SEQ ID NO 604
<211> LENGTH: 12
<212> TYPE: PRT
<213> ORGANISM: Mus musculus

<400> SEQUENCE: 604

Ala Arg Gly Gly Thr Ser Val Val His Phe Asp Ser
1               5                   10

<210> SEQ ID NO 605
<211> LENGTH: 12
<212> TYPE: PRT
<213> ORGANISM: Mus musculus

<400> SEQUENCE: 605

Ala Arg Gly Gly Thr Ser Val Val His Phe Asp Tyr
1               5                   10

<210> SEQ ID NO 606
<211> LENGTH: 8
<212> TYPE: PRT
<213> ORGANISM: Mus musculus

<400> SEQUENCE: 606

Ala Arg Gly Gly Tyr Phe Asp Tyr
1               5

<210> SEQ ID NO 607
<211> LENGTH: 8
<212> TYPE: PRT
<213> ORGANISM: Mus musculus

<400> SEQUENCE: 607

Ala Arg Gly Thr Val Val Asp Tyr
1               5

<210> SEQ ID NO 608
<211> LENGTH: 9
<212> TYPE: PRT
<213> ORGANISM: Mus musculus

<400> SEQUENCE: 608

Ala Arg Gly Thr Val Val Val Asp Tyr
1               5

<210> SEQ ID NO 609
<211> LENGTH: 8
<212> TYPE: PRT
<213> ORGANISM: Mus musculus

<400> SEQUENCE: 609

Ala Arg Gly Val Thr Phe Asp Ser
1               5

<210> SEQ ID NO 610
<211> LENGTH: 8
<212> TYPE: PRT
<213> ORGANISM: Mus musculus

<400> SEQUENCE: 610

Ala Arg Gly Val Thr Phe Asp Tyr
1               5

```
<210> SEQ ID NO 611
<211> LENGTH: 8
<212> TYPE: PRT
<213> ORGANISM: Mus musculus

<400> SEQUENCE: 611

Ala Arg His Gly Tyr Phe Asp Tyr
1               5

<210> SEQ ID NO 612
<211> LENGTH: 8
<212> TYPE: PRT
<213> ORGANISM: Mus musculus

<400> SEQUENCE: 612

Ala Arg His Tyr Tyr Phe Asp Tyr
1               5

<210> SEQ ID NO 613
<211> LENGTH: 8
<212> TYPE: PRT
<213> ORGANISM: Mus musculus

<400> SEQUENCE: 613

Ala Arg His Tyr Tyr Phe Asp Tyr
1               5

<210> SEQ ID NO 614
<211> LENGTH: 7
<212> TYPE: PRT
<213> ORGANISM: Mus musculus

<400> SEQUENCE: 614

Ala Arg Gln Leu Ala Ala Tyr
1               5

<210> SEQ ID NO 615
<211> LENGTH: 7
<212> TYPE: PRT
<213> ORGANISM: Mus musculus

<400> SEQUENCE: 615

Ala Arg Val Ser Pro Ala Ser
1               5

<210> SEQ ID NO 616
<211> LENGTH: 7
<212> TYPE: PRT
<213> ORGANISM: Mus musculus

<400> SEQUENCE: 616

Ala Arg Val Thr Pro Ala Ser
1               5

<210> SEQ ID NO 617
<211> LENGTH: 8
<212> TYPE: PRT
<213> ORGANISM: Mus musculus

<400> SEQUENCE: 617

Ala Arg Trp Gly Asn Phe Asp Tyr
1               5

<210> SEQ ID NO 618
<211> LENGTH: 3
```

```
<212> TYPE: PRT
<213> ORGANISM: Mus musculus

<400> SEQUENCE: 618

Ala Thr Ser
1

<210> SEQ ID NO 619
<211> LENGTH: 8
<212> TYPE: PRT
<213> ORGANISM: Mus musculus
<220> FEATURE:
<221> NAME/KEY: misc_feature
<222> LOCATION: (2)..(2)
<223> OTHER INFORMATION: Xaa can be any naturally occurring amino acid

<400> SEQUENCE: 619

Ala Xaa Gly Val Thr Phe Asp Tyr
1               5

<210> SEQ ID NO 620
<211> LENGTH: 11
<212> TYPE: PRT
<213> ORGANISM: Mus musculus

<400> SEQUENCE: 620

Cys Phe Gln Gly Ser His Val Pro Trp Thr Phe
1               5                   10

<210> SEQ ID NO 621
<211> LENGTH: 11
<212> TYPE: PRT
<213> ORGANISM: Mus musculus

<400> SEQUENCE: 621

Cys Phe Gln Gly Ser His Val Pro Tyr Thr Phe
1               5                   10

<210> SEQ ID NO 622
<211> LENGTH: 11
<212> TYPE: PRT
<213> ORGANISM: Mus musculus

<400> SEQUENCE: 622

Cys Gly Gln Ser Tyr Arg Tyr Pro Tyr Thr Phe
1               5                   10

<210> SEQ ID NO 623
<211> LENGTH: 11
<212> TYPE: PRT
<213> ORGANISM: Mus musculus

<400> SEQUENCE: 623

Cys Gly Gln Ser Tyr Ser Tyr Pro Trp Thr Phe
1               5                   10

<210> SEQ ID NO 624
<211> LENGTH: 11
<212> TYPE: PRT
<213> ORGANISM: Mus musculus

<400> SEQUENCE: 624

Cys Gly Gln Ser Tyr Ser Tyr Pro Tyr Thr Phe
1               5                   10
```

```
<210> SEQ ID NO 625
<211> LENGTH: 11
<212> TYPE: PRT
<213> ORGANISM: Mus musculus

<400> SEQUENCE: 625

Cys His Gln Leu Val Glu Tyr Pro Tyr Thr Phe
1               5                   10

<210> SEQ ID NO 626
<211> LENGTH: 11
<212> TYPE: PRT
<213> ORGANISM: Mus musculus

<400> SEQUENCE: 626

Cys His Gln Arg Gly Ser Tyr Pro Trp Thr Phe
1               5                   10

<210> SEQ ID NO 627
<211> LENGTH: 11
<212> TYPE: PRT
<213> ORGANISM: Mus musculus

<400> SEQUENCE: 627

Cys His Gln Arg Ser Gly Tyr Ser Tyr Thr Phe
1               5                   10

<210> SEQ ID NO 628
<211> LENGTH: 11
<212> TYPE: PRT
<213> ORGANISM: Mus musculus

<400> SEQUENCE: 628

Cys His Gln Tyr His Arg Ser Pro Pro Thr Phe
1               5                   10

<210> SEQ ID NO 629
<211> LENGTH: 12
<212> TYPE: PRT
<213> ORGANISM: Mus musculus

<400> SEQUENCE: 629

Cys Leu Gln Gly Thr Tyr Tyr Pro Thr Trp Thr Phe
1               5                   10

<210> SEQ ID NO 630
<211> LENGTH: 11
<212> TYPE: PRT
<213> ORGANISM: Mus musculus

<400> SEQUENCE: 630

Cys Leu Gln His Trp Asn Tyr Pro Tyr Thr Phe
1               5                   10

<210> SEQ ID NO 631
<211> LENGTH: 11
<212> TYPE: PRT
<213> ORGANISM: Mus musculus

<400> SEQUENCE: 631

Cys Leu Gln Ser Asp Asn Met Pro Leu Thr Phe
1               5                   10

<210> SEQ ID NO 632
<211> LENGTH: 11
```

```
<212> TYPE: PRT
<213> ORGANISM: Mus musculus

<400> SEQUENCE: 632

Cys Leu Gln Ser Asp Asn Met Pro Tyr Thr Phe
1               5                   10

<210> SEQ ID NO 633
<211> LENGTH: 11
<212> TYPE: PRT
<213> ORGANISM: Mus musculus

<400> SEQUENCE: 633

Cys Leu Gln Val Thr His Val Pro Phe Ala Phe
1               5                   10

<210> SEQ ID NO 634
<211> LENGTH: 11
<212> TYPE: PRT
<213> ORGANISM: Mus musculus

<400> SEQUENCE: 634

Cys Leu Gln Tyr Ala Ser Ser Pro His Thr Phe
1               5                   10

<210> SEQ ID NO 635
<211> LENGTH: 11
<212> TYPE: PRT
<213> ORGANISM: Mus musculus

<400> SEQUENCE: 635

Cys Leu Gln Tyr Ala Ser Ser Pro Arg Thr Phe
1               5                   10

<210> SEQ ID NO 636
<211> LENGTH: 11
<212> TYPE: PRT
<213> ORGANISM: Mus musculus

<400> SEQUENCE: 636

Cys Leu Gln Tyr Ala Ser Ser Pro Trp Thr Phe
1               5                   10

<210> SEQ ID NO 637
<211> LENGTH: 11
<212> TYPE: PRT
<213> ORGANISM: Mus musculus

<400> SEQUENCE: 637

Cys Leu Gln Tyr Ala Ser Ser Pro Tyr Thr Phe
1               5                   10

<210> SEQ ID NO 638
<211> LENGTH: 11
<212> TYPE: PRT
<213> ORGANISM: Mus musculus

<400> SEQUENCE: 638

Cys Leu Gln Tyr Ala Ser Tyr Pro Arg Thr Phe
1               5                   10

<210> SEQ ID NO 639
<211> LENGTH: 11
<212> TYPE: PRT
<213> ORGANISM: Mus musculus
```

<400> SEQUENCE: 639

Cys Leu Gln Tyr Ala Thr Phe Pro Tyr Thr Phe
1               5                   10

<210> SEQ ID NO 640
<211> LENGTH: 11
<212> TYPE: PRT
<213> ORGANISM: Mus musculus

<400> SEQUENCE: 640

Cys Leu Gln Tyr Ile Ser Tyr Pro Arg Thr Phe
1               5                   10

<210> SEQ ID NO 641
<211> LENGTH: 11
<212> TYPE: PRT
<213> ORGANISM: Mus musculus

<400> SEQUENCE: 641

Cys Met Gln His Leu Glu Tyr Pro Tyr Thr Phe
1               5                   10

<210> SEQ ID NO 642
<211> LENGTH: 11
<212> TYPE: PRT
<213> ORGANISM: Mus musculus

<400> SEQUENCE: 642

Cys Gln His Phe Trp Gly Thr Pro Pro Thr Phe
1               5                   10

<210> SEQ ID NO 643
<211> LENGTH: 11
<212> TYPE: PRT
<213> ORGANISM: Mus musculus

<400> SEQUENCE: 643

Cys Gln His Phe Trp Gly Thr Pro Trp Thr Phe
1               5                   10

<210> SEQ ID NO 644
<211> LENGTH: 11
<212> TYPE: PRT
<213> ORGANISM: Mus musculus

<400> SEQUENCE: 644

Cys Gln His His Tyr Gly Thr Pro Trp Thr Phe
1               5                   10

<210> SEQ ID NO 645
<211> LENGTH: 11
<212> TYPE: PRT
<213> ORGANISM: Mus musculus

<400> SEQUENCE: 645

Cys Gln Asn Gly His Ser Phe Pro Arg Thr Phe
1               5                   10

<210> SEQ ID NO 646
<211> LENGTH: 11
<212> TYPE: PRT
<213> ORGANISM: Mus musculus

<400> SEQUENCE: 646

```
Cys Gln Gln Asp Tyr Ser Ser Pro Pro Thr Phe
1               5                   10
```

<210> SEQ ID NO 647
<211> LENGTH: 11
<212> TYPE: PRT
<213> ORGANISM: Mus musculus

<400> SEQUENCE: 647

```
Cys Gln Gln Asp Tyr Ser Ser Pro Trp Thr Phe
1               5                   10
```

<210> SEQ ID NO 648
<211> LENGTH: 11
<212> TYPE: PRT
<213> ORGANISM: Mus musculus

<400> SEQUENCE: 648

```
Cys Gln Gln Gly Asn Thr Leu Pro Arg Thr Phe
1               5                   10
```

<210> SEQ ID NO 649
<211> LENGTH: 11
<212> TYPE: PRT
<213> ORGANISM: Mus musculus

<400> SEQUENCE: 649

```
Cys Gln Gln Gly Asn Thr Leu Pro Trp Thr Phe
1               5                   10
```

<210> SEQ ID NO 650
<211> LENGTH: 11
<212> TYPE: PRT
<213> ORGANISM: Mus musculus

<400> SEQUENCE: 650

```
Cys Gln Gln His Phe Asn Ser Pro Tyr Thr Phe
1               5                   10
```

<210> SEQ ID NO 651
<211> LENGTH: 11
<212> TYPE: PRT
<213> ORGANISM: Mus musculus

<400> SEQUENCE: 651

```
Cys Gln Gln His Asn Glu Tyr Pro Trp Thr Phe
1               5                   10
```

<210> SEQ ID NO 652
<211> LENGTH: 11
<212> TYPE: PRT
<213> ORGANISM: Mus musculus

<400> SEQUENCE: 652

```
Cys Gln Gln His Tyr Ser Thr His Val His Val
1               5                   10
```

<210> SEQ ID NO 653
<211> LENGTH: 11
<212> TYPE: PRT
<213> ORGANISM: Mus musculus

<400> SEQUENCE: 653

```
Cys Gln Gln His Tyr Ser Thr Pro Pro Thr Phe
```

```
1               5                   10
```

<210> SEQ ID NO 654
<211> LENGTH: 12
<212> TYPE: PRT
<213> ORGANISM: Mus musculus

<400> SEQUENCE: 654

```
Cys Gln Gln His Tyr Ser Thr Pro Pro Trp Thr Phe
1               5                   10
```

<210> SEQ ID NO 655
<211> LENGTH: 11
<212> TYPE: PRT
<213> ORGANISM: Mus musculus

<400> SEQUENCE: 655

```
Cys Gln Gln His Tyr Ser Thr Pro Arg Thr Phe
1               5                   10
```

<210> SEQ ID NO 656
<211> LENGTH: 11
<212> TYPE: PRT
<213> ORGANISM: Mus musculus

<400> SEQUENCE: 656

```
Cys Gln Gln His Tyr Ser Thr Pro Trp Thr Phe
1               5                   10
```

<210> SEQ ID NO 657
<211> LENGTH: 11
<212> TYPE: PRT
<213> ORGANISM: Mus musculus

<400> SEQUENCE: 657

```
Cys Gln Gln His Tyr Ser Thr Pro Tyr Thr Phe
1               5                   10
```

<210> SEQ ID NO 658
<211> LENGTH: 11
<212> TYPE: PRT
<213> ORGANISM: Mus musculus

<400> SEQUENCE: 658

```
Cys Gln Gln Asn Asn Glu Asp Pro Tyr Thr Phe
1               5                   10
```

<210> SEQ ID NO 659
<211> LENGTH: 11
<212> TYPE: PRT
<213> ORGANISM: Mus musculus

<400> SEQUENCE: 659

```
Cys Gln Gln Ser Lys Glu Val Pro Tyr Thr Phe
1               5                   10
```

<210> SEQ ID NO 660
<211> LENGTH: 11
<212> TYPE: PRT
<213> ORGANISM: Mus musculus

<400> SEQUENCE: 660

```
Cys Gln Gln Ser Asn Glu Asp Pro Leu Thr Phe
1               5                   10
```

<210> SEQ ID NO 661
<211> LENGTH: 11
<212> TYPE: PRT
<213> ORGANISM: Mus musculus

<400> SEQUENCE: 661

Cys Gln Gln Ser Asn Glu Asp Pro Arg Thr Phe
1               5                   10

<210> SEQ ID NO 662
<211> LENGTH: 11
<212> TYPE: PRT
<213> ORGANISM: Mus musculus

<400> SEQUENCE: 662

Cys Gln Gln Ser Asn Glu Asp Pro Tyr Thr Phe
1               5                   10

<210> SEQ ID NO 663
<211> LENGTH: 11
<212> TYPE: PRT
<213> ORGANISM: Mus musculus

<400> SEQUENCE: 663

Cys Gln Gln Val Tyr Thr Leu Pro Trp Thr Phe
1               5                   10

<210> SEQ ID NO 664
<211> LENGTH: 11
<212> TYPE: PRT
<213> ORGANISM: Mus musculus

<400> SEQUENCE: 664

Cys Gln Gln Trp Ser Ser Asn Pro Pro Thr Phe
1               5                   10

<210> SEQ ID NO 665
<211> LENGTH: 12
<212> TYPE: PRT
<213> ORGANISM: Mus musculus

<400> SEQUENCE: 665

Cys Gln Gln Trp Ser Ser Asn Pro Pro Tyr Thr Phe
1               5                   10

<210> SEQ ID NO 666
<211> LENGTH: 11
<212> TYPE: PRT
<213> ORGANISM: Mus musculus

<400> SEQUENCE: 666

Cys Gln Gln Trp Ser Ser Asn Pro Tyr Thr Phe
1               5                   10

<210> SEQ ID NO 667
<211> LENGTH: 11
<212> TYPE: PRT
<213> ORGANISM: Mus musculus

<400> SEQUENCE: 667

Cys Gln Gln Trp Ser Ser Tyr Pro Tyr Thr Ser
1               5                   10

<210> SEQ ID NO 668

```
<211> LENGTH: 11
<212> TYPE: PRT
<213> ORGANISM: Mus musculus

<400> SEQUENCE: 668

Cys Gln Gln Trp Thr Ser Asn Pro Pro Thr Phe
1               5                   10

<210> SEQ ID NO 669
<211> LENGTH: 11
<212> TYPE: PRT
<213> ORGANISM: Mus musculus

<400> SEQUENCE: 669

Cys Gln Gln Tyr Asp Ser Tyr Pro Tyr Thr Phe
1               5                   10

<210> SEQ ID NO 670
<211> LENGTH: 11
<212> TYPE: PRT
<213> ORGANISM: Mus musculus

<400> SEQUENCE: 670

Cys Gln Gln Tyr Asn Ser Tyr Pro Arg Thr Phe
1               5                   10

<210> SEQ ID NO 671
<211> LENGTH: 11
<212> TYPE: PRT
<213> ORGANISM: Mus musculus

<400> SEQUENCE: 671

Cys Gln Gln Tyr Asn Ser Tyr Pro Tyr Thr Phe
1               5                   10

<210> SEQ ID NO 672
<211> LENGTH: 11
<212> TYPE: PRT
<213> ORGANISM: Mus musculus

<400> SEQUENCE: 672

Cys Gln Gln Tyr Ser Lys Leu Pro Trp Thr Phe
1               5                   10

<210> SEQ ID NO 673
<211> LENGTH: 11
<212> TYPE: PRT
<213> ORGANISM: Mus musculus

<400> SEQUENCE: 673

Cys Gln Gln Tyr Ser Ser Tyr Pro Leu Thr Phe
1               5                   10

<210> SEQ ID NO 674
<211> LENGTH: 11
<212> TYPE: PRT
<213> ORGANISM: Mus musculus

<400> SEQUENCE: 674

Cys Gln Gln Tyr Trp Ser Thr Pro Pro Thr Phe
1               5                   10

<210> SEQ ID NO 675
<211> LENGTH: 9
<212> TYPE: PRT
```

<213> ORGANISM: Mus musculus

<400> SEQUENCE: 675

Cys Gln Gln Tyr Tyr Ser Tyr Pro Phe
1               5

<210> SEQ ID NO 676
<211> LENGTH: 11
<212> TYPE: PRT
<213> ORGANISM: Mus musculus

<400> SEQUENCE: 676

Cys Gln Gln Tyr Tyr Ser Tyr Pro Trp Thr Phe
1               5                   10

<210> SEQ ID NO 677
<211> LENGTH: 10
<212> TYPE: PRT
<213> ORGANISM: Mus musculus

<400> SEQUENCE: 677

Cys Gln Gln Tyr Tyr Ser Tyr Arg Thr Phe
1               5                   10

<210> SEQ ID NO 678
<211> LENGTH: 11
<212> TYPE: PRT
<213> ORGANISM: Mus musculus

<400> SEQUENCE: 678

Cys Ser Gln Ser Thr His Val Pro His Thr Phe
1               5                   10

<210> SEQ ID NO 679
<211> LENGTH: 11
<212> TYPE: PRT
<213> ORGANISM: Mus musculus

<400> SEQUENCE: 679

Cys Ser Gln Ser Thr His Val Pro Leu Thr Phe
1               5                   10

<210> SEQ ID NO 680
<211> LENGTH: 11
<212> TYPE: PRT
<213> ORGANISM: Mus musculus

<400> SEQUENCE: 680

Cys Ser Gln Ser Thr His Val Pro Arg Thr Phe
1               5                   10

<210> SEQ ID NO 681
<211> LENGTH: 10
<212> TYPE: PRT
<213> ORGANISM: Mus musculus

<400> SEQUENCE: 681

Cys Ser Gln Ser Thr His Val Pro Thr Phe
1               5                   10

<210> SEQ ID NO 682
<211> LENGTH: 11
<212> TYPE: PRT
<213> ORGANISM: Mus musculus

```
<400> SEQUENCE: 682

Cys Ser Gln Ser Thr His Val Pro Trp Thr Phe
1               5                   10

<210> SEQ ID NO 683
<211> LENGTH: 11
<212> TYPE: PRT
<213> ORGANISM: Mus musculus

<400> SEQUENCE: 683

Cys Ser Gln Ser Thr His Val Pro Tyr Thr Phe
1               5                   10

<210> SEQ ID NO 684
<211> LENGTH: 10
<212> TYPE: PRT
<213> ORGANISM: Mus musculus

<400> SEQUENCE: 684

Cys Ser Gln Ser Thr His Val Tyr Thr Phe
1               5                   10

<210> SEQ ID NO 685
<211> LENGTH: 11
<212> TYPE: PRT
<213> ORGANISM: Mus musculus

<400> SEQUENCE: 685

Cys Trp Gln Gly Ala His Phe Pro Trp Thr Phe
1               5                   10

<210> SEQ ID NO 686
<211> LENGTH: 10
<212> TYPE: PRT
<213> ORGANISM: Mus musculus

<400> SEQUENCE: 686

Cys Trp Gln Gly Thr Phe Ser Ser His Val
1               5                   10

<210> SEQ ID NO 687
<211> LENGTH: 11
<212> TYPE: PRT
<213> ORGANISM: Mus musculus

<400> SEQUENCE: 687

Cys Trp Gln Gly Thr His Phe Pro Gln Thr Phe
1               5                   10

<210> SEQ ID NO 688
<211> LENGTH: 11
<212> TYPE: PRT
<213> ORGANISM: Mus musculus

<400> SEQUENCE: 688

Cys Trp Gln Gly Thr His Phe Pro Arg Thr Phe
1               5                   10

<210> SEQ ID NO 689
<211> LENGTH: 11
<212> TYPE: PRT
<213> ORGANISM: Mus musculus

<400> SEQUENCE: 689
```

```
Cys Trp Gln Gly Thr His Phe Pro Trp Thr Phe
1               5                   10
```

<210> SEQ ID NO 690
<211> LENGTH: 10
<212> TYPE: PRT
<213> ORGANISM: Mus musculus

<400> SEQUENCE: 690

```
Cys Trp Gln Gly Thr His Phe Arg Thr Phe
1               5                   10
```

<210> SEQ ID NO 691
<211> LENGTH: 17
<212> TYPE: PRT
<213> ORGANISM: Mus musculus

<400> SEQUENCE: 691

```
Asp Phe Tyr Pro Gly Gly Asp Tyr Ile Asn Tyr Asn Glu Lys Phe Lys
1               5                   10                  15

Gly
```

<210> SEQ ID NO 692
<211> LENGTH: 17
<212> TYPE: PRT
<213> ORGANISM: Mus musculus

<400> SEQUENCE: 692

```
Asp Ile His Pro Gly Gly Asp Tyr Ser Asn Tyr Asn Glu Lys Phe Lys
1               5                   10                  15

Gly
```

<210> SEQ ID NO 693
<211> LENGTH: 17
<212> TYPE: PRT
<213> ORGANISM: Mus musculus

<400> SEQUENCE: 693

```
Asp Ile His Pro Gly Gly Asp Tyr Thr Asn Tyr Asn Glu Lys Phe Lys
1               5                   10                  15

Gly
```

<210> SEQ ID NO 694
<211> LENGTH: 17
<212> TYPE: PRT
<213> ORGANISM: Mus musculus

<400> SEQUENCE: 694

```
Asp Ile His Pro Gly Gly Gly Tyr Ile Asp Tyr Asn Glu Lys Phe Thr
1               5                   10                  15

Gly
```

<210> SEQ ID NO 695
<211> LENGTH: 17
<212> TYPE: PRT
<213> ORGANISM: Mus musculus

<400> SEQUENCE: 695

```
Asp Ile His Pro Gly Gly Gly Tyr Ile Asn Tyr Asn Glu Lys Phe Thr
1               5                   10                  15

Gly
```

<210> SEQ ID NO 696
<211> LENGTH: 17
<212> TYPE: PRT
<213> ORGANISM: Mus musculus

<400> SEQUENCE: 696

Asp Ile His Pro Gly Gly Tyr Thr Asn Tyr Asn Glu Lys Phe Lys
1               5                   10                  15

Gly

<210> SEQ ID NO 697
<211> LENGTH: 17
<212> TYPE: PRT
<213> ORGANISM: Mus musculus

<400> SEQUENCE: 697

Asp Ile His Pro Gly Gly Ser Tyr Thr Asn Tyr Asn Glu Asn Phe Lys
1               5                   10                  15

Gly

<210> SEQ ID NO 698
<211> LENGTH: 26
<212> TYPE: PRT
<213> ORGANISM: Mus musculus

<400> SEQUENCE: 698

Asp Ile Leu Leu Thr Gln Ser Pro Ala Leu Met Ala Ala Ser Pro Gly
1               5                   10                  15

Glu Lys Val Thr Ile Thr Cys Ser Val Ser
            20                  25

<210> SEQ ID NO 699
<211> LENGTH: 23
<212> TYPE: PRT
<213> ORGANISM: Mus musculus

<400> SEQUENCE: 699

Asp Ile Leu Leu Thr Gln Ser Gln Lys Phe Met Ser Thr Ser Val Gly
1               5                   10                  15

Asp Arg Val Ser Val Thr Cys
            20

<210> SEQ ID NO 700
<211> LENGTH: 26
<212> TYPE: PRT
<213> ORGANISM: Mus musculus

<400> SEQUENCE: 700

Asp Ile Leu Leu Thr Gln Ser Gln Lys Phe Met Ser Thr Ser Val Gly
1               5                   10                  15

Asp Arg Val Ser Val Thr Cys Lys Ala Ser
            20                  25

<210> SEQ ID NO 701
<211> LENGTH: 107
<212> TYPE: PRT
<213> ORGANISM: Mus musculus

<400> SEQUENCE: 701

Asp Ile Leu Leu Thr Gln Ser Gln Lys Phe Met Ser Thr Ser Val Gly
1               5                   10                  15

-continued

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys
            100                 105

<210> SEQ ID NO 702
<211> LENGTH: 26
<212> TYPE: PRT
<213> ORGANISM: Mus musculus

<400> SEQUENCE: 702

Asp Ile Leu Met Thr Gln Ser Pro Ala Ile Met Ser Ala Ser Pro Gly
1               5                   10                  15

Glu Lys Val Thr Met Thr Cys Ser Ala Ser
            20                  25

<210> SEQ ID NO 703
<211> LENGTH: 106
<212> TYPE: PRT
<213> ORGANISM: Mus musculus

<400> SEQUENCE: 703

Asp Ile Leu Met Thr Gln Ser Pro Ala Ile Met Ser Ala Ser Pro Gly
1               5                   10                  15

Glu Lys Val Thr Met Thr Cys Ser Ala Ser Ser Ser Val Ile Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Ser Ile Ser Ser Met Glu Thr Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105

<210> SEQ ID NO 704
<211> LENGTH: 26
<212> TYPE: PRT
<213> ORGANISM: Mus musculus

<400> SEQUENCE: 704

Asp Ile Leu Met Thr Gln Ser Pro Ala Ser Leu Ser Val Ala Thr Gly
1               5                   10                  15

Glu Lys Val Thr Ile Arg Cys Ile Thr Ser
            20                  25

<210> SEQ ID NO 705
<211> LENGTH: 107
<212> TYPE: PRT

<213> ORGANISM: Mus musculus

<400> SEQUENCE: 705

Asp Ile Leu Met Thr Gln Ser Pro Ala Ser Leu Ser Val Ala Thr Gly
1               5                   10                  15

Glu Lys Val Thr Ile Arg Cys Ile Thr Ser Thr Asp Ile Asp Asp Asp
            20                  25                  30

Met Asn Trp Tyr Gln Gln Lys Pro Gly Glu Pro Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Thr Leu Ser
65                  70                  75                  80

Glu Asp Val Ala Asp Tyr Tyr Cys Leu Gln Ser Asp Asn Met Pro Leu
                85                  90                  95

Thr Phe Gly Gly Gly Thr Lys Leu Glu Ile Lys
            100                 105

<210> SEQ ID NO 706
<211> LENGTH: 26
<212> TYPE: PRT
<213> ORGANISM: Mus musculus

<400> SEQUENCE: 706

Asp Ile Leu Met Thr Gln Ser Pro Ala Thr Leu Ser Val Thr Pro Gly
1               5                   10                  15

Asp Arg Val Ser Leu Ser Cys Arg Ala Ser
            20                  25

<210> SEQ ID NO 707
<211> LENGTH: 107
<212> TYPE: PRT
<213> ORGANISM: Mus musculus

<400> SEQUENCE: 707

Asp Ile Leu Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Arg
                85                  90                  95

Thr Phe Gly Gly Gly Thr Lys Leu Glu Ile Lys
            100                 105

<210> SEQ ID NO 708
<211> LENGTH: 26
<212> TYPE: PRT
<213> ORGANISM: Mus musculus

<400> SEQUENCE: 708

Asp Ile Leu Met Thr Gln Ser Pro Ser Ser Leu Ala Val Ser Val Gly
1               5                   10                  15

```
Glu Lys Val Thr Met Ser Cys Lys Ser Ser
            20                  25
```

```
<210> SEQ ID NO 709
<211> LENGTH: 113
<212> TYPE: PRT
<213> ORGANISM: Mus musculus

<400> SEQUENCE: 709
```

```
Asp Ile Leu Met Thr Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Trp Thr Phe Gly Gly Gly Thr Lys Leu Glu Met
            100                 105                 110

Lys
```

```
<210> SEQ ID NO 710
<211> LENGTH: 23
<212> TYPE: PRT
<213> ORGANISM: Mus musculus

<400> SEQUENCE: 710
```

```
Asp Ile Leu Met Thr Gln Ser Gln Lys Phe Met Ser Thr Ser Val Gly
1               5                   10                  15

Asp Arg Val Ser Val Thr Cys
            20
```

```
<210> SEQ ID NO 711
<211> LENGTH: 26
<212> TYPE: PRT
<213> ORGANISM: Mus musculus

<400> SEQUENCE: 711
```

```
Asp Ile Leu Met Thr Gln Ser Gln Lys Phe Met Ser Thr Ser Val Gly
1               5                   10                  15

Asp Arg Val Ser Val Thr Cys Lys Ala Ser
            20                  25
```

```
<210> SEQ ID NO 712
<211> LENGTH: 107
<212> TYPE: PRT
<213> ORGANISM: Mus musculus

<400> SEQUENCE: 712
```

```
Asp Ile Leu Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45
```

```
Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys
            100                 105

<210> SEQ ID NO 713
<211> LENGTH: 26
<212> TYPE: PRT
<213> ORGANISM: Mus musculus

<400> SEQUENCE: 713

Asp Ile Gln Met Asn Gln Ser His Lys Phe Met Ser Thr Ser Val Gly
1               5                   10                  15

Asp Arg Val Ser Ile Thr Cys Lys Ala Ser
            20                  25

<210> SEQ ID NO 714
<211> LENGTH: 26
<212> TYPE: PRT
<213> ORGANISM: Mus musculus

<400> SEQUENCE: 714

Asp Ile Gln Met Asn Gln Ser Pro Ser Ser Leu Ser Ala Ser Leu Gly
1               5                   10                  15

Glu Arg Val Ser Leu Thr Cys Arg Ala Ser
            20                  25

<210> SEQ ID NO 715
<211> LENGTH: 107
<212> TYPE: PRT
<213> ORGANISM: Mus musculus

<400> SEQUENCE: 715

Asp Ile Gln Met Asn Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Asn Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Ser Ser Pro Tyr
                85                  90                  95

Thr Phe Gly Gly Gly Thr Lys Leu Glu Ile Lys
            100                 105

<210> SEQ ID NO 716
<211> LENGTH: 26
<212> TYPE: PRT
<213> ORGANISM: Mus musculus

<400> SEQUENCE: 716

Asp Ile Gln Met Asn Gln Ser Pro Ser Tyr Leu Ala Ala Ser Pro Gly
1               5                   10                  15
```

```
Glu Thr Ile Thr Ile Asn Cys Arg Ala Ser
            20                  25

<210> SEQ ID NO 717
<211> LENGTH: 107
<212> TYPE: PRT
<213> ORGANISM: Mus musculus

<400> SEQUENCE: 717

Asp Ile Gln Met Asn Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Trp
                85                  90                  95

Thr Phe Gly Gly Gly Thr Lys Leu Glu Ile Lys
            100                 105

<210> SEQ ID NO 718
<211> LENGTH: 26
<212> TYPE: PRT
<213> ORGANISM: Mus musculus

<400> SEQUENCE: 718

Asp Ile Gln Met Thr Gln Ser Pro Ala Ser Leu Ser Ala Ser Val Gly
1               5                   10                  15

Glu Ser Val Thr Ile Thr Cys Arg Ala Ser
            20                  25

<210> SEQ ID NO 719
<211> LENGTH: 26
<212> TYPE: PRT
<213> ORGANISM: Mus musculus

<400> SEQUENCE: 719

Asp Ile Gln Met Thr Gln Ser Pro Ala Ser Leu Ser Ala Ser Val Gly
1               5                   10                  15

Glu Ser Val Thr Ile Thr Cys Arg Thr Ser
            20                  25

<210> SEQ ID NO 720
<211> LENGTH: 26
<212> TYPE: PRT
<213> ORGANISM: Mus musculus

<400> SEQUENCE: 720

Asp Ile Gln Met Thr Gln Ser Pro Ala Ser Leu Ser Ala Ser Val Gly
1               5                   10                  15

Glu Thr Val Thr Ile Thr Cys Arg Ala Ser
            20                  25

<210> SEQ ID NO 721
<211> LENGTH: 26
<212> TYPE: PRT
```

```
<213> ORGANISM: Mus musculus

<400> SEQUENCE: 721

Asp Ile Gln Met Thr Gln Ser Pro Ala Ser Leu Ser Val Ser Val Gly
1               5                   10                  15

Glu Thr Val Ala Ile Thr Cys Arg Ala Ser
            20                  25

<210> SEQ ID NO 722
<211> LENGTH: 107
<212> TYPE: PRT
<213> ORGANISM: Mus musculus

<400> SEQUENCE: 722

Asp Ile Gln Met Thr Gln Ser Pro Ala Ser Leu Ser Val Ser Val Gly
1               5                   10                  15

Glu Thr Val Ala Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Trp
                85                  90                  95

Thr Phe Gly Gly Gly Thr Lys Leu Glu Met Lys
            100                 105

<210> SEQ ID NO 723
<211> LENGTH: 26
<212> TYPE: PRT
<213> ORGANISM: Mus musculus

<400> SEQUENCE: 723

Asp Ile Gln Met Thr Gln Ser Pro Ala Ser Leu Ser Val Ser Val Gly
1               5                   10                  15

Glu Thr Val Thr Ile Thr Cys Arg Ala Ser
            20                  25

<210> SEQ ID NO 724
<211> LENGTH: 107
<212> TYPE: PRT
<213> ORGANISM: Mus musculus

<400> SEQUENCE: 724

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Pro
                85                  90                  95
```

```
Thr Phe Gly Gly Gly Thr Lys Leu Glu Ile Lys
            100                 105

<210> SEQ ID NO 725
<211> LENGTH: 107
<212> TYPE: PRT
<213> ORGANISM: Mus musculus

<400> SEQUENCE: 725

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Trp
                85                  90                  95

Thr Phe Gly Gly Gly Thr Lys Leu Glu Met Lys
            100                 105

<210> SEQ ID NO 726
<211> LENGTH: 26
<212> TYPE: PRT
<213> ORGANISM: Mus musculus

<400> SEQUENCE: 726

Asp Ile Gln Met Thr Gln Ser Pro Ser Ser Leu Ser Ala Ser Leu Gly
1               5                   10                  15

Glu Arg Val Ser Leu Thr Cys Arg Ala Ser
            20                  25

<210> SEQ ID NO 727
<211> LENGTH: 107
<212> TYPE: PRT
<213> ORGANISM: Mus musculus

<400> SEQUENCE: 727

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Asn Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Ser Ser Pro His
                85                  90                  95

Thr Phe Gly Gly Gly Thr Lys Leu Glu Ile Lys
            100                 105

<210> SEQ ID NO 728
<211> LENGTH: 107
<212> TYPE: PRT
```

<213> ORGANISM: Mus musculus

<400> SEQUENCE: 728

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Arg
                85                  90                  95

Thr Phe Gly Gly Gly Thr Lys Leu Glu Ile Lys
            100                 105

<210> SEQ ID NO 729
<211> LENGTH: 26
<212> TYPE: PRT
<213> ORGANISM: Mus musculus

<400> SEQUENCE: 729

Asp Ile Gln Met Thr Gln Ser Gln Lys Phe Met Ser Ala Ser Val Gly
1               5                   10                  15

Asp Arg Val Ser Val Thr Cys Lys Ala Ser
            20                  25

<210> SEQ ID NO 730
<211> LENGTH: 26
<212> TYPE: PRT
<213> ORGANISM: Mus musculus

<400> SEQUENCE: 730

Asp Ile Gln Met Thr Gln Ser Gln Lys Phe Met Ser Thr Ser Ala Gly
1               5                   10                  15

Asp Arg Val Ser Val Thr Cys Lys Ala Ser
            20                  25

<210> SEQ ID NO 731
<211> LENGTH: 26
<212> TYPE: PRT
<213> ORGANISM: Mus musculus

<400> SEQUENCE: 731

Asp Ile Gln Met Thr Gln Ser Gln Lys Phe Met Ser Thr Ser Val Gly
1               5                   10                  15

Asp Arg Ala Ser Val Thr Cys Lys Ala Ser
            20                  25

<210> SEQ ID NO 732
<211> LENGTH: 26
<212> TYPE: PRT
<213> ORGANISM: Mus musculus

<400> SEQUENCE: 732

Asp Ile Gln Met Thr Gln Ser Gln Lys Phe Met Ser Thr Ser Val Gly
1               5                   10                  15

Asp Arg Val Gly Val Thr Cys Lys Ala Ser

```
                        20                  25

<210> SEQ ID NO 733
<211> LENGTH: 23
<212> TYPE: PRT
<213> ORGANISM: Mus musculus

<400> SEQUENCE: 733

Asp Ile Gln Met Thr Gln Ser Gln Lys Phe Met Ser Thr Ser Val Gly
1               5                   10                  15

Asp Arg Val Ser Val Thr Cys
            20

<210> SEQ ID NO 734
<211> LENGTH: 26
<212> TYPE: PRT
<213> ORGANISM: Mus musculus

<400> SEQUENCE: 734

Asp Ile Gln Met Thr Gln Ser Gln Lys Phe Met Ser Thr Ser Val Gly
1               5                   10                  15

Asp Arg Val Ser Val Thr Cys Lys Ala Ser
            20                  25

<210> SEQ ID NO 735
<211> LENGTH: 107
<212> TYPE: PRT
<213> ORGANISM: Mus musculus

<400> SEQUENCE: 735

Asp Ile Gln Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Met Lys
            100                 105

<210> SEQ ID NO 736
<211> LENGTH: 107
<212> TYPE: PRT
<213> ORGANISM: Mus musculus

<400> SEQUENCE: 736

Asp Ile Gln Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60
```

```
Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln Tyr Asn Ser Tyr Pro Tyr
                 85                  90                  95

Thr Phe Gly Gly Gly Thr Lys Leu Glu Ile Lys
            100                 105

<210> SEQ ID NO 737
<211> LENGTH: 107
<212> TYPE: PRT
<213> ORGANISM: Mus musculus

<400> SEQUENCE: 737

Asp Ile Gln Met Thr Gln Ser Gln Lys Phe Met Ser Thr Ser Val Gly
 1               5                  10                  15

Asp Arg Val Ser Val Thr Cys Lys Ala Ser Gln Ser Val Gly Thr Asn
                20                  25                  30

Val Ala Trp Tyr Gln Gln Lys Pro Gly Gln Ser Pro Lys Ala Leu Ile
             35                  40                  45

Tyr Ser Ala Ser Tyr Arg Tyr Ser Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln Tyr Asn Asn Tyr Pro Trp
                 85                  90                  95

Thr Phe Gly Gly Gly Thr Lys Leu Glu Ile Lys
            100                 105

<210> SEQ ID NO 738
<211> LENGTH: 26
<212> TYPE: PRT
<213> ORGANISM: Mus musculus

<400> SEQUENCE: 738

Asp Ile Gln Met Thr Gln Ser Thr Ser Ser Leu Ser Ala Ser Leu Gly
 1               5                  10                  15

Asp Arg Val Thr Ile Ser Cys Arg Ala Ser
                20                  25

<210> SEQ ID NO 739
<211> LENGTH: 107
<212> TYPE: PRT
<213> ORGANISM: Mus musculus

<400> SEQUENCE: 739

Asp Ile Gln Met Thr Gln Ser Thr Ser Ser Leu Ser Ala Ser Leu Gly
 1               5                  10                  15

Asp Arg Val Thr Ile Ser Cys Arg Ala Ser Gln Asp Ile Ser Asn Tyr
                20                  25                  30

Leu Asn Trp Tyr Gln Gln Lys Pro Asp Gly Thr Val Lys Leu Leu Ile
             35                  40                  45

Tyr Phe Thr Ser Arg Leu Tyr Ser Gly Val Pro Ser Arg Phe Ser Gly
 50                  55                  60

Ser Gly Ser Gly Ala Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Arg
                 85                  90                  95

Thr Phe Gly Gly Gly Thr Lys Leu Glu Ile Lys
```

<210> SEQ ID NO 740
<211> LENGTH: 26
<212> TYPE: PRT
<213> ORGANISM: Mus musculus

<400> SEQUENCE: 740

Asp Ile Gln Met Thr Gln Ser Thr Ser Ser Leu Ser Ala Ser Leu Gly
1               5                   10                  15

Asp Arg Val Thr Ile Thr Cys Arg Ala Ser
            20                  25

<210> SEQ ID NO 741
<211> LENGTH: 26
<212> TYPE: PRT
<213> ORGANISM: Mus musculus

<400> SEQUENCE: 741

Asp Ile Gln Met Thr Gln Thr His Lys Phe Met Ser Thr Ser Val Gly
1               5                   10                  15

Asp Arg Val Ser Ile Thr Cys Lys Ala Ser
            20                  25

<210> SEQ ID NO 742
<211> LENGTH: 107
<212> TYPE: PRT
<213> ORGANISM: Mus musculus

<400> SEQUENCE: 742

Asp Ile Gln Met Thr Gln Thr His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr His Val
                85                  90                  95

His Val Arg Arg Gly Asp Gln Ala Gly Asn Gln
            100                 105

<210> SEQ ID NO 743
<211> LENGTH: 26
<212> TYPE: PRT
<213> ORGANISM: Mus musculus

<400> SEQUENCE: 743

Asp Ile Gln Met Thr Gln Thr Pro Ala Ser Leu Ala Ala Ser Val Gly
1               5                   10                  15

Glu Thr Val Thr Ile Thr Cys Arg Ala Ser
            20                  25

<210> SEQ ID NO 744
<211> LENGTH: 26
<212> TYPE: PRT
<213> ORGANISM: Mus musculus

```
<400> SEQUENCE: 744

Asp Ile Gln Met Thr Gln Thr Pro Ala Ser Leu Ser Ala Ser Val Gly
1               5                   10                  15

Glu Thr Val Thr Ile Thr Cys Arg Ala Ser
            20                  25

<210> SEQ ID NO 745
<211> LENGTH: 107
<212> TYPE: PRT
<213> ORGANISM: Mus musculus

<400> SEQUENCE: 745

Asp Ile Gln Met Thr Gln Thr Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Trp
                85                  90                  95

Thr Phe Gly Gly Gly Thr Lys Leu Glu Ile Lys
            100                 105

<210> SEQ ID NO 746
<211> LENGTH: 26
<212> TYPE: PRT
<213> ORGANISM: Mus musculus

<400> SEQUENCE: 746

Asp Ile Gln Met Thr Gln Thr Pro Lys Phe Leu Leu Val Ser Ala Gly
1               5                   10                  15

Asp Arg Val Thr Ile Thr Cys Lys Ala Ser
            20                  25

<210> SEQ ID NO 747
<211> LENGTH: 107
<212> TYPE: PRT
<213> ORGANISM: Mus musculus

<400> SEQUENCE: 747

Asp Ile Gln Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Trp
                85                  90                  95

Thr Phe Gly Gly Gly Thr Lys Leu Glu Ile Lys
            100                 105
```

```
<210> SEQ ID NO 748
<211> LENGTH: 26
<212> TYPE: PRT
<213> ORGANISM: Mus musculus

<400> SEQUENCE: 748

Asp Ile Gln Met Thr Gln Thr Pro Leu Thr Leu Ser Val Thr Ile Gly
1               5                   10                  15

Gln Pro Ala Ser Ile Ser Cys Lys Ser Ser
            20                  25

<210> SEQ ID NO 749
<211> LENGTH: 112
<212> TYPE: PRT
<213> ORGANISM: Mus musculus

<400> SEQUENCE: 749

Asp Ile Gln Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Ala His Phe Pro Trp Thr Phe Gly Gly Gly Thr Lys Leu Glu Ile Lys
            100                 105                 110

<210> SEQ ID NO 750
<211> LENGTH: 112
<212> TYPE: PRT
<213> ORGANISM: Mus musculus

<400> SEQUENCE: 750

Asp Ile Gln Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Met Lys
            100                 105                 110

<210> SEQ ID NO 751
<211> LENGTH: 112
<212> TYPE: PRT
<213> ORGANISM: Mus musculus
```

-continued

<400> SEQUENCE: 751

Asp Ile Gln Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Arg Thr Phe Gly Gly Gly Thr Lys Leu Glu Ile Lys
            100                 105                 110

<210> SEQ ID NO 752
<211> LENGTH: 111
<212> TYPE: PRT
<213> ORGANISM: Mus musculus

<400> SEQUENCE: 752

Asp Ile Gln Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr Phe Ser Ser His Val Arg Arg Gly Asp Gln Ala Gly Asn Glu
            100                 105                 110

<210> SEQ ID NO 753
<211> LENGTH: 26
<212> TYPE: PRT
<213> ORGANISM: Mus musculus

<400> SEQUENCE: 753

Asp Ile Gln Met Thr Gln Thr Pro Ser Ser Leu Ser Ala Ser Leu Gly
1               5                   10                  15

Glu Arg Val Ser Leu Thr Cys Arg Ala Ser
            20                  25

<210> SEQ ID NO 754
<211> LENGTH: 107
<212> TYPE: PRT
<213> ORGANISM: Mus musculus

<400> SEQUENCE: 754

Asp Ile Gln Met Thr Gln Thr Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Asn Trp Leu Gln Gln Glu Pro Asp Gly Thr Ile Lys Arg Leu Ile
        35                  40                  45

Ser Ala Thr Ser Ser Leu Asp Ser Gly Val Pro Lys Arg Phe Ser Gly
 50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Thr Phe Pro Tyr
                 85                  90                  95

Thr Phe Gly Gly Gly Thr Lys Leu Glu Ile Lys
            100                 105

<210> SEQ ID NO 755
<211> LENGTH: 107
<212> TYPE: PRT
<213> ORGANISM: Mus musculus

<400> SEQUENCE: 755

Asp Ile Gln Met Thr Gln Thr Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Asn Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
 50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Ser Ser Pro Arg
                 85                  90                  95

Thr Phe Gly Gly Gly Thr Lys Leu Glu Ile Lys
            100                 105

<210> SEQ ID NO 756
<211> LENGTH: 107
<212> TYPE: PRT
<213> ORGANISM: Mus musculus

<400> SEQUENCE: 756

Asp Ile Gln Met Thr Gln Thr Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
 50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ile Ser Tyr Pro Arg
                 85                  90                  95

Thr Phe Gly Gly Gly Thr Lys Leu Glu Ile Lys
            100                 105

<210> SEQ ID NO 757
<211> LENGTH: 26
<212> TYPE: PRT
<213> ORGANISM: Mus musculus

<400> SEQUENCE: 757

Asp Ile Gln Met Thr Gln Thr Gln Lys Phe Met Ser Thr Ser Val Gly
1               5                   10                  15

Asp Arg Val Ser Val Thr Cys Lys Ala Ser
            20                  25

<210> SEQ ID NO 758
<211> LENGTH: 26
<212> TYPE: PRT
<213> ORGANISM: Mus musculus

<400> SEQUENCE: 758

Asp Ile Gln Met Thr Gln Thr Ser Ser Phe Ser Val Ser Leu Gly
1               5                   10                  15

Asp Arg Val Thr Ile Thr Cys Lys Ala Ser
            20                  25

<210> SEQ ID NO 759
<211> LENGTH: 107
<212> TYPE: PRT
<213> ORGANISM: Mus musculus

<400> SEQUENCE: 759

Asp Ile Gln Met Thr Gln Thr Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Pro
                85                  90                  95

Thr Phe Gly Gly Gly Thr Lys Leu Glu Ile Lys
            100                 105

<210> SEQ ID NO 760
<211> LENGTH: 26
<212> TYPE: PRT
<213> ORGANISM: Mus musculus

<400> SEQUENCE: 760

Asp Ile Gln Met Thr Gln Thr Thr Ser Ser Leu Ser Ala Ser Leu Gly
1               5                   10                  15

Asp Arg Val Thr Ile Ser Cys Arg Ala Ser
            20                  25

<210> SEQ ID NO 761
<211> LENGTH: 26
<212> TYPE: PRT
<213> ORGANISM: Mus musculus

<400> SEQUENCE: 761

Asp Ile Gln Met Thr Gln Thr Thr Ser Ser Leu Ser Ala Ser Leu Gly
1               5                   10                  15

Asp Arg Val Thr Ile Ser Cys Ser Ala Ser
            20                  25

<210> SEQ ID NO 762
<211> LENGTH: 107
<212> TYPE: PRT
<213> ORGANISM: Mus musculus

<400> SEQUENCE: 762

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Trp
                85                  90                  95

Thr Phe Gly Gly Gly Thr Lys Leu Glu Met Lys
            100                 105

<210> SEQ ID NO 763
<211> LENGTH: 26
<212> TYPE: PRT
<213> ORGANISM: Mus musculus

<400> SEQUENCE: 763

Asp Ile Gln Met Thr Gln Thr Thr Ser Ser Leu Ser Ala Ser Leu Gly
1               5                   10                  15

Asp Arg Val Thr Ile Thr Cys Arg Ala Ser
            20                  25

<210> SEQ ID NO 764
<211> LENGTH: 26
<212> TYPE: PRT
<213> ORGANISM: Mus musculus

<400> SEQUENCE: 764

Asp Ile Gln Met Thr Arg Ser Pro Ser Ser Leu Ser Ala Ser Leu Gly
1               5                   10                  15

Glu Arg Val Ser Leu Thr Cys Arg Ala Ser
            20                  25

<210> SEQ ID NO 765
<211> LENGTH: 107
<212> TYPE: PRT
<213> ORGANISM: Mus musculus

<400> SEQUENCE: 765

Asp Ile Gln Met Thr Arg Ser Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Asn Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser

```
                65                  70                  75                  80
Glu Asp Phe Val Asp Tyr Tyr Cys Leu Gln Tyr Ala Ser Ser Pro Trp
                    85                  90                  95

Thr Phe Gly Gly Gly Thr Lys Leu Glu Ile Lys
            100                 105

<210> SEQ ID NO 766
<211> LENGTH: 26
<212> TYPE: PRT
<213> ORGANISM: Mus musculus

<400> SEQUENCE: 766

Asp Ile Val Ile Thr Gln Ser Gln Lys Phe Met Ser Thr Ser Val Gly
1               5                   10                  15

Asp Arg Val Ser Val Thr Cys Lys Ala Ser
            20                  25

<210> SEQ ID NO 767
<211> LENGTH: 107
<212> TYPE: PRT
<213> ORGANISM: Mus musculus

<400> SEQUENCE: 767

Asp Ile Val Ile Thr Gln Ser Gln Lys Phe Met Ser Thr Ser Val Gly
1               5                   10                  15

Asp Arg Val Ser Val Thr Cys Lys Ala Ser Gln Asn Val Gly Ser Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asp Ser Tyr Pro Tyr
                85                  90                  95

Thr Phe Gly Gly Gly Thr Lys Leu Glu Ile Lys
            100                 105

<210> SEQ ID NO 768
<211> LENGTH: 26
<212> TYPE: PRT
<213> ORGANISM: Mus musculus

<400> SEQUENCE: 768

Asp Ile Val Leu Thr Gln Ser Pro Ala Ser Leu Ala Val Ser Leu Gly
1               5                   10                  15

Gln Arg Ala Thr Ile Ser Cys Arg Ala Ser
            20                  25

<210> SEQ ID NO 769
<211> LENGTH: 111
<212> TYPE: PRT
<213> ORGANISM: Mus musculus

<400> SEQUENCE: 769

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30
```

```
Gly Ile Ser Phe Met Asn Trp Phe Gln Lys Lys Pro Gly Gln Pro Pro
            35                  40                  45

Lys Leu Leu Ile Tyr Ala Ala Ser Asn Gln Gly Ser Gly Val Pro Ala
 50                      55                  60

Arg Phe Ser Gly Ser Gly Ser Gly Thr Asp Phe Ser Leu Asn Ile His
 65                  70                  75                  80

Pro Met Glu Glu Asp Asp Thr Ala Met Tyr Phe Cys Gln Gln Ser Lys
                 85                  90                  95

Glu Val Pro Tyr Thr Phe Gly Gly Gly Thr Lys Leu Glu Ile Lys
            100                 105                 110
```

<210> SEQ ID NO 770
<211> LENGTH: 26
<212> TYPE: PRT
<213> ORGANISM: Mus musculus

<400> SEQUENCE: 770

```
Asp Ile Val Leu Thr Gln Ser Pro Ala Ser Leu Ser Ala Ser Val Gly
 1               5                  10                  15

Glu Ser Val Thr Ile Thr Cys Arg Ala Ser
            20                  25
```

<210> SEQ ID NO 771
<211> LENGTH: 26
<212> TYPE: PRT
<213> ORGANISM: Mus musculus

<400> SEQUENCE: 771

```
Asp Ile Val Leu Thr Gln Ser Pro Pro Thr Leu Ser Leu Ser Pro Gly
 1               5                  10                  15

Glu Arg Val Thr Leu Ser Cys Lys Ala Ser
            20                  25
```

<210> SEQ ID NO 772
<211> LENGTH: 23
<212> TYPE: PRT
<213> ORGANISM: Mus musculus

<400> SEQUENCE: 772

```
Asp Ile Val Leu Thr Gln Ser Gln Lys Phe Met Ser Thr Ser Val Gly
 1               5                  10                  15

Asp Arg Val Ser Val Thr Cys
            20
```

<210> SEQ ID NO 773
<211> LENGTH: 26
<212> TYPE: PRT
<213> ORGANISM: Mus musculus

<400> SEQUENCE: 773

```
Asp Ile Val Leu Thr Gln Ser Gln Lys Phe Met Ser Thr Ser Val Gly
 1               5                  10                  15

Asp Arg Val Ser Val Thr Cys Lys Ala Ser
            20                  25
```

<210> SEQ ID NO 774
<211> LENGTH: 26
<212> TYPE: PRT
<213> ORGANISM: Mus musculus

<400> SEQUENCE: 774

-continued

Asp Ile Val Leu Thr Gln Ser Gln Lys Phe Met Ser Thr Ser Val Gly
1               5                   10                  15

Asp Arg Val Ser Val Thr Cys Lys Ala Ser
            20                  25

<210> SEQ ID NO 775
<211> LENGTH: 107
<212> TYPE: PRT
<213> ORGANISM: Mus musculus

<400> SEQUENCE: 775

Asp Ile Val Leu Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Ala Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys
            100                 105

<210> SEQ ID NO 776
<211> LENGTH: 107
<212> TYPE: PRT
<213> ORGANISM: Mus musculus

<400> SEQUENCE: 776

Asp Ile Val Leu Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Lys Ile Ser Arg Val Glu Ala
65                  70                  75                  80

Glu Asp Leu Gly Val Tyr Phe Cys Ser Gln Ser Thr His Val Pro Tyr
                85                  90                  95

Thr Phe Gly Gly Gly Thr Lys Leu Glu Ile Lys
            100                 105

<210> SEQ ID NO 777
<211> LENGTH: 107
<212> TYPE: PRT
<213> ORGANISM: Mus musculus

<400> SEQUENCE: 777

Asp Ile Val Leu Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile

```
              35                  40                  45
Tyr Ser Ala Ser Tyr Arg Tyr Ser Gly Val Pro Asp Arg Phe Thr Gly
         50                  55                  60
Ser Gly Ser Gly Thr Asp Phe Thr Leu Thr Ile Ser Asn Val Gln Ser
 65                  70                  75                  80
Glu Asp Leu Ala Glu Tyr Phe Cys Gln Gln Tyr Asn Ser Tyr Pro Tyr
                 85                  90                  95
Thr Phe Gly Gly Gly Thr Lys Leu Glu Met Lys
            100                 105
```

<210> SEQ ID NO 778
<211> LENGTH: 107
<212> TYPE: PRT
<213> ORGANISM: Mus musculus

<400> SEQUENCE: 778

```
Asp Ile Val Leu Thr Gln Ser Gln Lys Phe Met Ser Thr Ser Val Gly
  1               5                  10                  15
Asp Arg Val Ser Val Thr Cys Lys Ala Ser Gln Asn Val Gly Thr Asn
                 20                  25                  30
Val Ala Trp Tyr Gln Gln Lys Pro Gly Gln Ser Pro Lys Ala Leu Ile
              35                  40                  45
Tyr Ser Ala Ser Tyr Arg Tyr Ser Gly Val Pro Asp Arg Phe Thr Gly
         50                  55                  60
Ser Gly Ser Gly Thr Asp Phe Thr Leu Thr Ile Ser Asn Val Gln Ser
 65                  70                  75                  80
Glu Asp Leu Ala Glu Tyr Phe Cys Gln Gln Tyr Asn Ser Tyr Pro Tyr
                 85                  90                  95
Thr Phe Gly Gly Gly Thr Lys Leu Glu Ile Lys
            100                 105
```

<210> SEQ ID NO 779
<211> LENGTH: 26
<212> TYPE: PRT
<213> ORGANISM: Mus musculus

<400> SEQUENCE: 779

```
Asp Ile Val Met Ser Gln Ser His Lys Phe Met Ser Thr Ser Val Gly
  1               5                  10                  15
Asp Arg Val Ser Ile Thr Cys Lys Ala Ser
                 20                  25
```

<210> SEQ ID NO 780
<211> LENGTH: 107
<212> TYPE: PRT
<213> ORGANISM: Mus musculus

<400> SEQUENCE: 780

```
Asp Ile Val Met Ser Gln Ser His Lys Phe Met Ser Thr Ser Val Gly
  1               5                  10                  15
Asp Arg Val Ser Ile Thr Cys Lys Ala Ser Gln Asp Val Gly Thr Ala
                 20                  25                  30
Val Ala Trp Tyr Gln Gln Lys Pro Gly Gln Ser Pro Lys Leu Leu Ile
              35                  40                  45
Tyr Trp Ala Ser Thr Arg His Thr Gly Val Pro Asp Arg Phe Thr Gly
         50                  55                  60
Ser Gly Ser Gly Thr Asp Phe Thr Leu Thr Ile Ser Ile Val Gln Ser
 65                  70                  75                  80
```

-continued

Glu Asp Leu Ala Asp Tyr Phe Cys Gln Gln Tyr Ser Ser Tyr Pro Leu
                85                  90                  95

Thr Phe Gly Gly Gly Thr Lys Leu Glu Ile Lys
            100                 105

<210> SEQ ID NO 781
<211> LENGTH: 107
<212> TYPE: PRT
<213> ORGANISM: Mus musculus

<400> SEQUENCE: 781

Asp Ile Val Met Ser Gln Ser His Lys Phe Met Ser Thr Ser Val Gly
1               5                   10                  15

Asp Arg Val Ser Ile Thr Cys Lys Ala Ser Gln Asp Val Ile Thr Ala
            20                  25                  30

Val Ala Trp Tyr Gln Gln Lys Pro Gly Gln Ser Pro Lys Leu Pro Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Arg
                85                  90                  95

Thr Phe Gly Gly Gly Thr Lys Leu Glu Ile Lys
            100                 105

<210> SEQ ID NO 782
<211> LENGTH: 26
<212> TYPE: PRT
<213> ORGANISM: Mus musculus

<400> SEQUENCE: 782

Asp Ile Val Met Ser Gln Ser Pro Ala Ile Leu Ser Ala Ser Pro Gly
1               5                   10                  15

Glu Lys Val Thr Met Thr Cys Ser Ala Ser
            20                  25

<210> SEQ ID NO 783
<211> LENGTH: 106
<212> TYPE: PRT
<213> ORGANISM: Mus musculus

<400> SEQUENCE: 783

Asp Ile Val Met Ser Gln Ser Pro Ala Ile Leu Ser Ala Ser Pro Gly
1               5                   10                  15

Glu Lys Val Thr Met Thr Cys Ser Ala Ser Ser Arg Val Thr Tyr Met
            20                  25                  30

His Trp Tyr Gln Gln Lys Pro Gly Thr Ser Pro Lys Arg Trp Ile Tyr
        35                  40                  45

Asp Thr Ser Thr Leu Thr Ser Gly Val Pro Ala Arg Phe Ser Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys His Gln Arg Ser Gly Tyr Ser Tyr Thr
                85                  90                  95

Phe Gly Gly Gly Thr Lys Leu Glu Met Lys
            100                 105

<210> SEQ ID NO 784
<211> LENGTH: 26
<212> TYPE: PRT
<213> ORGANISM: Mus musculus

<400> SEQUENCE: 784

Asp Ile Val Met Ser Gln Ser Pro Ala Ile Met Ser Ala Ser Pro Gly
1               5                   10                  15

Glu Lys Val Thr Met Thr Arg Ser Ala Ser
            20                  25

<210> SEQ ID NO 785
<211> LENGTH: 106
<212> TYPE: PRT
<213> ORGANISM: Mus musculus

<400> SEQUENCE: 785

Asp Ile Val Met Ser Gln Ser Pro Ala Ile Met Ser Ala Ser Pro Gly
1               5                   10                  15

Glu Lys Val Thr Met Thr Arg Ser Ala Ser Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Tyr Thr
                85                  90                  95

Ser Gly Gly Gly Thr Lys Leu Glu Ile Lys
            100                 105

<210> SEQ ID NO 786
<211> LENGTH: 26
<212> TYPE: PRT
<213> ORGANISM: Mus musculus

<400> SEQUENCE: 786

Asp Ile Val Met Ser Gln Ser Pro Ala Ser Leu Ala Val Ser Leu Gly
1               5                   10                  15

Gln Arg Ala Thr Ile Ser Cys Lys Ala Ser
            20                  25

<210> SEQ ID NO 787
<211> LENGTH: 111
<212> TYPE: PRT
<213> ORGANISM: Mus musculus

<400> SEQUENCE: 787

Asp Ile Val Met Ser Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Thr Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

```
Pro Val Glu Glu Glu Asp Ala Ala Thr Tyr Tyr Cys Gln Gln Ser Asn
                85                  90                  95

Glu Asp Pro Leu Thr Phe Gly Ala Gly Thr Lys Leu Glu Ile Lys
            100                 105                 110
```

<210> SEQ ID NO 788
<211> LENGTH: 26
<212> TYPE: PRT
<213> ORGANISM: Mus musculus

<400> SEQUENCE: 788

```
Asp Ile Val Met Ser Gln Ser Pro Ala Ser Leu Ser Val Ala Thr Gly
1               5                   10                  15

Glu Lys Val Thr Ile Arg Cys Ile Thr Ser
            20                  25
```

<210> SEQ ID NO 789
<211> LENGTH: 107
<212> TYPE: PRT
<213> ORGANISM: Mus musculus

<400> SEQUENCE: 789

```
Asp Ile Val Met Ser Gln Ser Pro Ala Ser Leu Ser Val Ala Thr Gly
1               5                   10                  15

Glu Lys Val Thr Ile Arg Cys Ile Thr Ser Thr Asp Ile Asp Asp Asp
            20                  25                  30

Met Asn Trp Tyr Gln Gln Lys Pro Gly Glu Pro Pro Lys Leu Leu Ile
        35                  40                  45

Ser Glu Gly Asn Thr Leu Arg Pro Gly Val Pro Ser Arg Phe Ser Ser
50                  55                  60

Ser Gly Tyr Gly Thr Asp Phe Val Phe Thr Ile Glu Asn Thr Leu Ser
65                  70                  75                  80

Glu Asp Val Ala Asp Tyr Tyr Cys Leu Gln Ser Asp Asn Met Pro Tyr
                85                  90                  95

Thr Phe Gly Gly Gly Thr Lys Leu Glu Ile Lys
            100                 105
```

<210> SEQ ID NO 790
<211> LENGTH: 26
<212> TYPE: PRT
<213> ORGANISM: Mus musculus

<400> SEQUENCE: 790

```
Asp Ile Val Met Ser Gln Ser Pro Ser Ser Leu Ala Val Ser Val Gly
1               5                   10                  15

Glu Lys Val Thr Met Ser Cys Lys Ser Ser
            20                  25
```

<210> SEQ ID NO 791
<211> LENGTH: 111
<212> TYPE: PRT
<213> ORGANISM: Mus musculus

<400> SEQUENCE: 791

```
Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
```

```
                35                  40                  45
Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                 85                  90                  95

Tyr Tyr Ser Tyr Pro Phe Gly Gly Gly Thr Lys Leu Glu Ile Lys
            100                 105                 110

<210> SEQ ID NO 792
<211> LENGTH: 23
<212> TYPE: PRT
<213> ORGANISM: Mus musculus

<400> SEQUENCE: 792

Asp Ile Val Met Ser Gln Ser Gln Lys Phe Met Ser Thr Ser Val Gly
 1               5                  10                  15

Asp Arg Val Ser Val Thr Cys
             20

<210> SEQ ID NO 793
<211> LENGTH: 26
<212> TYPE: PRT
<213> ORGANISM: Mus musculus

<400> SEQUENCE: 793

Asp Ile Val Met Ser Gln Ser Gln Lys Phe Met Ser Thr Ser Val Gly
 1               5                  10                  15

Asp Arg Val Ser Val Thr Cys Lys Ala Ser
             20                  25

<210> SEQ ID NO 794
<211> LENGTH: 107
<212> TYPE: PRT
<213> ORGANISM: Mus musculus

<400> SEQUENCE: 794

Asp Ile Val Met Ser Gln Ser Gln Lys Phe Met Ser Thr Ser Val Gly
 1               5                  10                  15

Asp Arg Val Ser Val Thr Cys Lys Ala Ser Gln Asn Val Gly Thr Asn
             20                  25                  30

Val Ala Trp Tyr Gln Gln Lys Pro Gly Gln Ser Pro Lys Ala Leu Ile
         35                  40                  45

Tyr Ser Ala Ser Tyr Arg Tyr Ser Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln Tyr Asn Ser Tyr Pro Arg
                 85                  90                  95

Thr Phe Gly Gly Gly Thr Lys Leu Glu Ile Lys
            100                 105

<210> SEQ ID NO 795
<211> LENGTH: 107
<212> TYPE: PRT
<213> ORGANISM: Mus musculus

<400> SEQUENCE: 795
```

```
Asp Ile Val Met Ser Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys
                100                 105
```

<210> SEQ ID NO 796
<211> LENGTH: 26
<212> TYPE: PRT
<213> ORGANISM: Mus musculus

<400> SEQUENCE: 796

```
Asp Ile Val Met Thr Gln Ala Ala Pro Ser Val Pro Val Thr Pro Gly
1               5                   10                  15

Glu Ser Val Ser Ile Ser Cys Arg Ser Ser
            20                  25
```

<210> SEQ ID NO 797
<211> LENGTH: 112
<212> TYPE: PRT
<213> ORGANISM: Mus musculus

<400> SEQUENCE: 797

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
                100                 105                 110
```

<210> SEQ ID NO 798
<211> LENGTH: 26
<212> TYPE: PRT
<213> ORGANISM: Mus musculus

<400> SEQUENCE: 798

```
Asp Ile Val Met Thr Gln Asp Glu Leu Ser Asn Pro Val Thr Ser Gly
1               5                   10                  15

Glu Ser Val Ser Ile Ser Cys Arg Ser Ser
            20                  25
```

-continued

<210> SEQ ID NO 799
<211> LENGTH: 112
<212> TYPE: PRT
<213> ORGANISM: Mus musculus

<400> SEQUENCE: 799

Asp Ile Val Met Thr Gln Asp Glu Leu Ser Asn Pro Val Thr Ser Gly
1               5                   10                  15

Glu Ser Val Ser Ile Ser Cys Arg Ser Ser Lys Ser Leu Leu Tyr Lys
            20                  25                  30

Asp Gly Lys Thr Tyr Leu Asn Cys Phe Leu Gln Arg Pro Gly Gln Ser
        35                  40                  45

Pro Gln Leu Leu Ile Tyr Leu Met Ser Thr Arg Ala Ser Gly Val Ser
    50                  55                  60

Asn Arg Phe Ser Gly Ser Gly Ser Gly Thr Asp Phe Thr Leu Glu Ile
65                  70                  75                  80

Ser Arg Val Lys Ala Glu Asp Val Gly Val Tyr Tyr Cys His Gln Leu
                85                  90                  95

Val Glu Tyr Pro Tyr Thr Phe Gly Gly Gly Thr Lys Leu Glu Met Lys
            100                 105                 110

<210> SEQ ID NO 800
<211> LENGTH: 26
<212> TYPE: PRT
<213> ORGANISM: Mus musculus

<400> SEQUENCE: 800

Asp Ile Val Met Thr Gln Ser His Lys Phe Met Ser Thr Ser Val Gly
1               5                   10                  15

Asp Arg Val Ser Ile Thr Cys Lys Ala Ser
            20                  25

<210> SEQ ID NO 801
<211> LENGTH: 107
<212> TYPE: PRT
<213> ORGANISM: Mus musculus

<400> SEQUENCE: 801

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

His Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Pro
                85                  90                  95

Thr Phe Gly Gly Gly Thr Lys Leu Glu Ile Lys
            100                 105

<210> SEQ ID NO 802
<211> LENGTH: 26
<212> TYPE: PRT
<213> ORGANISM: Mus musculus

<400> SEQUENCE: 802

-continued

Asp Ile Val Met Thr Gln Ser Pro Ala Ile Met Ser Ala Ser Pro Gly
1               5                   10                  15

Glu Lys Val Thr Met Thr Cys Ser Ala Ser
            20                  25

<210> SEQ ID NO 803
<211> LENGTH: 106
<212> TYPE: PRT
<213> ORGANISM: Mus musculus

<400> SEQUENCE: 803

Asp Ile Val Met Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Leu Glu Ile Lys
            100                 105

<210> SEQ ID NO 804
<211> LENGTH: 107
<212> TYPE: PRT
<213> ORGANISM: Mus musculus

<400> SEQUENCE: 804

Asp Ile Val Met Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Tyr
                85                  90                  95

Thr Phe Gly Gly Gly Thr Lys Leu Glu Met Lys
            100                 105

<210> SEQ ID NO 805
<211> LENGTH: 26
<212> TYPE: PRT
<213> ORGANISM: Mus musculus

<400> SEQUENCE: 805

Asp Ile Val Met Thr Gln Ser Pro Ala Leu Met Ser Ala Ser Pro Gly
1               5                   10                  15

Glu Lys Val Thr Met Thr Cys Ser Ala Ser
            20                  25

```
<210> SEQ ID NO 806
<211> LENGTH: 106
<212> TYPE: PRT
<213> ORGANISM: Mus musculus

<400> SEQUENCE: 806

Asp Ile Val Met Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Pro Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Tyr Thr
                85                  90                  95

Phe Gly Gly Gly Thr Lys Leu Glu Ile Lys
            100                 105

<210> SEQ ID NO 807
<211> LENGTH: 26
<212> TYPE: PRT
<213> ORGANISM: Mus musculus

<400> SEQUENCE: 807

Asp Ile Val Met Thr Gln Ser Pro Ala Ser Leu Ser Ala Ser Val Gly
1               5                   10                  15

Glu Thr Val Thr Ile Thr Cys Arg Ala Ser
            20                  25

<210> SEQ ID NO 808
<211> LENGTH: 26
<212> TYPE: PRT
<213> ORGANISM: Mus musculus

<400> SEQUENCE: 808

Asp Ile Val Met Thr Gln Ser Pro Lys Ser Met Ser Met Ser Val Gly
1               5                   10                  15

Glu Arg Val Thr Leu Ser Cys Lys Ala Ser
            20                  25

<210> SEQ ID NO 809
<211> LENGTH: 107
<212> TYPE: PRT
<213> ORGANISM: Mus musculus

<400> SEQUENCE: 809

Asp Ile Val Met Thr Gln Ser Pro Lys Ser Met Ser Met Ser Val Gly
1               5                   10                  15

Glu Arg Val Thr Leu Ser Cys Lys Ala Ser Glu Asn Val Ala Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80
```

-continued

```
Glu Asp Leu Ala Asp Tyr Arg Cys Gly Gln Ser Tyr Arg Tyr Pro Tyr
                85                  90                  95

Thr Phe Gly Gly Gly Thr Lys Leu Glu Met Lys
            100                 105

<210> SEQ ID NO 810
<211> LENGTH: 107
<212> TYPE: PRT
<213> ORGANISM: Mus musculus

<400> SEQUENCE: 810

Asp Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Ser Tyr Pro Tyr
                85                  90                  95

Thr Phe Gly Gly Gly Thr Lys Leu Glu Ile Lys
            100                 105

<210> SEQ ID NO 811
<211> LENGTH: 107
<212> TYPE: PRT
<213> ORGANISM: Mus musculus

<400> SEQUENCE: 811

Asp Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Ser Tyr Pro Trp
                85                  90                  95

Thr Phe Gly Gly Gly Thr Lys Leu Glu Ile Lys
            100                 105

<210> SEQ ID NO 812
<211> LENGTH: 26
<212> TYPE: PRT
<213> ORGANISM: Mus musculus

<400> SEQUENCE: 812

Asp Ile Val Met Thr Gln Ser Pro Leu Ser Leu Ser Val Thr Ile Gly
1               5                   10                  15

Gln Pro Ala Ser Ile Ser Cys Lys Ser Ser
            20                  25
```

```
<210> SEQ ID NO 813
<211> LENGTH: 113
<212> TYPE: PRT
<213> ORGANISM: Mus musculus

<400> SEQUENCE: 813
```

Asp Ile Val Met Thr Gln Ser Pro Leu Ser Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Gln Gln Arg Pro Gly Gln Ala
        35                  40                  45

Pro Lys His Leu Met Tyr Gln Val Ser Lys Leu Asp Pro Gly Ile Pro
    50                  55                  60

Asp Arg Phe Ser Gly Ser Gly Ser Glu Thr Asp Phe Thr Leu Lys Ile
65                  70                  75                  80

Ser Arg Val Glu Ala Glu Asp Leu Gly Val Tyr Tyr Cys Leu Gln Gly
                85                  90                  95

Thr Tyr Tyr Pro Thr Trp Thr Phe Gly Gly Gly Thr Lys Leu Glu Ile
            100                 105                 110

Lys

```
<210> SEQ ID NO 814
<211> LENGTH: 26
<212> TYPE: PRT
<213> ORGANISM: Mus musculus

<400> SEQUENCE: 814
```

Asp Ile Val Met Thr Gln Ser Pro Leu Thr Leu Ser Val Thr Ile Gly
1               5                   10                  15

Gln Pro Ala Ser Ile Ser Cys Lys Ser Ser
            20                  25

```
<210> SEQ ID NO 815
<211> LENGTH: 112
<212> TYPE: PRT
<213> ORGANISM: Mus musculus

<400> SEQUENCE: 815
```

Asp Ile Val Met Thr Gln Ser Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Trp Thr Phe Gly Gly Gly Thr Lys Leu Glu Ile Lys
            100                 105                 110

```
<210> SEQ ID NO 816
<211> LENGTH: 26
<212> TYPE: PRT
<213> ORGANISM: Mus musculus
```

<400> SEQUENCE: 816

Asp Ile Val Met Thr Gln Ser Pro Pro Thr Leu Ser Leu Ser Pro Gly
1               5                   10                  15

Glu Arg Val Thr Leu Ser Cys Lys Ala Ser
            20                  25

<210> SEQ ID NO 817
<211> LENGTH: 26
<212> TYPE: PRT
<213> ORGANISM: Mus musculus

<400> SEQUENCE: 817

Asp Ile Val Met Thr Gln Ser Pro Ser Pro Leu Ser Ala Ser Leu Gly
1               5                   10                  15

Glu Arg Val Ser Leu Thr Cys Arg Ala Ser
            20                  25

<210> SEQ ID NO 818
<211> LENGTH: 107
<212> TYPE: PRT
<213> ORGANISM: Mus musculus

<400> SEQUENCE: 818

Asp Ile Val Met Thr Gln Ser Pro Ser Pro Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Arg
                85                  90                  95

Thr Phe Gly Gly Gly Thr Lys Leu Glu Ile Lys
            100                 105

<210> SEQ ID NO 819
<211> LENGTH: 23
<212> TYPE: PRT
<213> ORGANISM: Mus musculus

<400> SEQUENCE: 819

Asp Ile Val Met Thr Gln Ser Gln Lys Phe Met Ser Thr Ser Val Gly
1               5                   10                  15

Asp Arg Val Ser Val Thr Cys
            20

<210> SEQ ID NO 820
<211> LENGTH: 23
<212> TYPE: PRT
<213> ORGANISM: Mus musculus

<400> SEQUENCE: 820

Asp Ile Val Met Thr Gln Ser Gln Lys Phe Met Ser Thr Ser Val Gly
1               5                   10                  15

Asp Arg Val Ser Val Thr Cys
            20

<210> SEQ ID NO 821
<211> LENGTH: 26
<212> TYPE: PRT
<213> ORGANISM: Mus musculus

<400> SEQUENCE: 821

Asp Ile Val Met Thr Gln Ser Gln Lys Phe Met Ser Thr Ser Val Gly
1               5                   10                  15

Asp Arg Val Ser Val Thr Cys Lys Ala Ser
            20                  25

<210> SEQ ID NO 822
<211> LENGTH: 107
<212> TYPE: PRT
<213> ORGANISM: Mus musculus

<400> SEQUENCE: 822

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Ile Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys
            100                 105

<210> SEQ ID NO 823
<211> LENGTH: 107
<212> TYPE: PRT
<213> ORGANISM: Mus musculus

<400> SEQUENCE: 823

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys
            100                 105

<210> SEQ ID NO 824
<211> LENGTH: 107
<212> TYPE: PRT
<213> ORGANISM: Mus musculus

<400> SEQUENCE: 824

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Leu Cys Gln Gln Tyr Asn Ser Tyr Pro Arg
                85                  90                  95

Thr Phe Gly Gly Gly Thr Lys Leu Glu Ile Lys
            100                 105

<210> SEQ ID NO 825
<211> LENGTH: 107
<212> TYPE: PRT
<213> ORGANISM: Mus musculus

<400> SEQUENCE: 825

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys
            100                 105

<210> SEQ ID NO 826
<211> LENGTH: 26
<212> TYPE: PRT
<213> ORGANISM: Mus musculus

<400> SEQUENCE: 826

Asp Ile Val Met Thr Gln Ser Gln Lys Phe Met Ser Thr Ser Val Gly
1               5                   10                  15

Asp Arg Val Thr Ile Thr Cys Lys Ala Ser
            20                  25

<210> SEQ ID NO 827
<211> LENGTH: 107
<212> TYPE: PRT
<213> ORGANISM: Mus musculus

<400> SEQUENCE: 827

Asp Ile Val Met Thr Gln Ser Gln Lys Phe Met Ser Thr Ser Val Gly
1               5                   10                  15

Asp Arg Val Thr Ile Thr Cys Lys Ala Ser Gln Asn Val Arg Thr Ala
            20                  25                  30

-continued

```
Val Ala Trp Tyr His Gln Lys Pro Gly Gln Ser Pro Lys Ala Leu Ile
            35                  40                  45

Tyr Met Ala Ser Asn Arg His Thr Gly Val Pro Asp Arg Phe Thr Gly
 50                  55                  60

Ser Gly Ser Gly Ala Asp Phe Thr Leu Thr Ile Thr Asn Val Gln Ser
65                  70                  75                  80

Glu Asp Leu Ala Asp Tyr Phe Cys Leu Gln His Trp Asn Tyr Pro Tyr
                85                  90                  95

Thr Phe Gly Gly Gly Thr Lys Leu Glu Ile Lys
            100                 105

<210> SEQ ID NO 828
<211> LENGTH: 26
<212> TYPE: PRT
<213> ORGANISM: Mus musculus

<400> SEQUENCE: 828

Asp Ile Val Met Thr Gln Ser Thr Ser Ser Leu Ser Ala Ser Leu Gly
1               5                  10                  15

Asp Arg Val Thr Ile Ser Cys Arg Ala Ser
            20                  25

<210> SEQ ID NO 829
<211> LENGTH: 107
<212> TYPE: PRT
<213> ORGANISM: Mus musculus

<400> SEQUENCE: 829

Asp Ile Val Met Thr Gln Ser Thr Ser Ser Leu Ser Ala Ser Leu Gly
1               5                  10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 830
<211> LENGTH: 26
<212> TYPE: PRT
<213> ORGANISM: Mus musculus

<400> SEQUENCE: 830

Asp Ile Val Met Thr Gln Thr Pro Lys Phe Leu Leu Val Ser Ala Gly
1               5                  10                  15

Asp Arg Val Thr Ile Thr Cys Lys Ala Ser
            20                  25

<210> SEQ ID NO 831
<211> LENGTH: 26
<212> TYPE: PRT
<213> ORGANISM: Mus musculus

<400> SEQUENCE: 831
```

```
Asp Ile Val Met Thr Gln Thr Thr Ser Ser Leu Ser Ala Ser Leu Gly
1               5                   10                  15

Asp Arg Val Thr Ile Ser Cys Arg Ala Ser
            20                  25

<210> SEQ ID NO 832
<211> LENGTH: 26
<212> TYPE: PRT
<213> ORGANISM: Mus musculus
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 832

Asp Ile Xaa Met Thr Gln Ser Thr Ser Ser Leu Ser Ala Ser Leu Gly
1               5                   10                  15

Asp Arg Xaa Thr Ile Thr Cys Arg Ala Ser
            20                  25

<210> SEQ ID NO 833
<211> LENGTH: 6
<212> TYPE: PRT
<213> ORGANISM: Mus musculus

<400> SEQUENCE: 833

Asp Asn Ile Tyr Asn Tyr
1               5

<210> SEQ ID NO 834
<211> LENGTH: 26
<212> TYPE: PRT
<213> ORGANISM: Mus musculus

<400> SEQUENCE: 834

Asp Asn Val Leu Thr Gln Ser Pro Ser Ser Leu Ala Val Ser Val Gly
1               5                   10                  15

Glu Lys Val Thr Met Ser Cys Lys Ser Ser
            20                  25

<210> SEQ ID NO 835
<211> LENGTH: 112
<212> TYPE: PRT
<213> ORGANISM: Mus musculus

<400> SEQUENCE: 835

Asp Asn Val Leu Thr Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95
```

```
Tyr Tyr Ser Tyr Arg Thr Phe Gly Gly Gly Thr Lys Leu Glu Ile Lys
            100                 105                 110
```

<210> SEQ ID NO 836
<211> LENGTH: 23
<212> TYPE: PRT
<213> ORGANISM: Mus musculus

<400> SEQUENCE: 836

```
Asp Asn Val Leu Thr Gln Ser Gln Lys Phe Met Ser Thr Ser Val Gly
1               5                   10                  15

Asp Arg Val Ser Val Thr Cys
            20
```

<210> SEQ ID NO 837
<211> LENGTH: 26
<212> TYPE: PRT
<213> ORGANISM: Mus musculus

<400> SEQUENCE: 837

```
Asp Asn Val Leu Thr Gln Ser Gln Lys Phe Met Ser Thr Ser Val Gly
1               5                   10                  15

Asp Arg Val Ser Val Thr Cys Lys Ala Ser
            20                  25
```

<210> SEQ ID NO 838
<211> LENGTH: 107
<212> TYPE: PRT
<213> ORGANISM: Mus musculus

<400> SEQUENCE: 838

```
Asp Asn Val Leu Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Met Lys
            100                 105
```

<210> SEQ ID NO 839
<211> LENGTH: 3
<212> TYPE: PRT
<213> ORGANISM: Mus musculus

<400> SEQUENCE: 839

```
Asp Thr Ser
1
```

<210> SEQ ID NO 840
<211> LENGTH: 26
<212> TYPE: PRT
<213> ORGANISM: Mus musculus

<400> SEQUENCE: 840

-continued

Asp Thr Thr Val Thr Gln Ser His Lys Phe Met Ser Thr Ser Val Gly
1               5                   10                  15

Asp Arg Val Ser Ile Thr Cys Lys Ala Ser
            20                  25

<210> SEQ ID NO 841
<211> LENGTH: 107
<212> TYPE: PRT
<213> ORGANISM: Mus musculus

<400> SEQUENCE: 841

Asp Thr Thr Val Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys
            100                 105

<210> SEQ ID NO 842
<211> LENGTH: 107
<212> TYPE: PRT
<213> ORGANISM: Mus musculus

<400> SEQUENCE: 842

Asp Thr Thr Val Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Tyr
                85                  90                  95

Thr Phe Gly Gly Gly Thr Lys Leu Glu Ile Lys
            100                 105

<210> SEQ ID NO 843
<211> LENGTH: 26
<212> TYPE: PRT
<213> ORGANISM: Mus musculus

<400> SEQUENCE: 843

Asp Thr Thr Val Thr Gln Ser His Arg Phe Met Ser Thr Ser Val Glu
1               5                   10                  15

Asp Arg Val Thr Ile Ala Cys Lys Ala Ser
            20                  25

<210> SEQ ID NO 844
<211> LENGTH: 107
<212> TYPE: PRT
<213> ORGANISM: Mus musculus

<400> SEQUENCE: 844

Asp Thr Thr Val Thr Gln Ser His Arg Phe Met Ser Thr Ser Val Glu
1               5                   10                  15

Asp Arg Val Thr Ile Ala Cys Lys Ala Ser Gln Asp Val Asn Thr Ala
            20                  25                  30

Val Ala Trp Tyr Gln His Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Arg Thr Asp Phe Thr Phe Thr Ile Ser Ser Val Gln Ala
65                  70                  75                  80

Glu Asp Leu Ala Val Tyr Tyr Cys Gln Gln His Phe Asn Ser Pro Tyr
                85                  90                  95

Thr Phe Gly Gly Gly Thr Lys Leu Glu Ile Lys
            100                 105

<210> SEQ ID NO 845
<211> LENGTH: 26
<212> TYPE: PRT
<213> ORGANISM: Mus musculus

<400> SEQUENCE: 845

Asp Thr Thr Val Thr Gln Ser Pro Ala Ile Met Ser Ala Ser Pro Gly
1               5                   10                  15

Glu Lys Val Thr Met Thr Cys Ser Ala Ser
            20                  25

<210> SEQ ID NO 846
<211> LENGTH: 106
<212> TYPE: PRT
<213> ORGANISM: Mus musculus

<400> SEQUENCE: 846

Asp Thr Thr Val Thr Gln Ser Pro Ala Ile Met Ser Ala Ser Pro Gly
1               5                   10                  15

Glu Lys Val Thr Met Thr Cys Ser Ala Ser Ser Ser Ile Gly Tyr Met
            20                  25                  30

His Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Gly Ser Tyr Pro Trp Thr
                85                  90                  95

Phe Gly Gly Gly Thr Lys Leu Glu Ile Lys
            100                 105

<210> SEQ ID NO 847
<211> LENGTH: 26
<212> TYPE: PRT
<213> ORGANISM: Mus musculus

<400> SEQUENCE: 847

-continued

Asp Thr Thr Val Thr Gln Ser Pro Ala Ser Leu Ala Val Ser Leu Gly
1               5                   10                  15

Gln Arg Ala Thr Ile Ser Cys Lys Ala Ser
            20                  25

<210> SEQ ID NO 848
<211> LENGTH: 111
<212> TYPE: PRT
<213> ORGANISM: Mus musculus

<400> SEQUENCE: 848

Asp Thr Thr Val Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Tyr Thr Phe Gly Gly Gly Thr Lys Leu Glu Met Lys
            100                 105                 110

<210> SEQ ID NO 849
<211> LENGTH: 111
<212> TYPE: PRT
<213> ORGANISM: Mus musculus

<400> SEQUENCE: 849

Asp Thr Thr Val Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110

<210> SEQ ID NO 850
<211> LENGTH: 26
<212> TYPE: PRT
<213> ORGANISM: Mus musculus

<400> SEQUENCE: 850

Asp Thr Thr Val Thr Gln Ser Pro Ala Ser Leu Ala Val Ser Leu Gly
1               5                   10                  15

Gln Arg Ala Thr Ile Ser Cys Arg Ala Ser
            20                  25

<210> SEQ ID NO 851
<211> LENGTH: 111
<212> TYPE: PRT
<213> ORGANISM: Mus musculus

<400> SEQUENCE: 851

Asp Thr Thr Val Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Gly Phe Thr Leu Thr Ile Asn
65                  70                  75                  80

Pro Val Glu Ala Asp Val Ala Thr Tyr Tyr Cys Gln Gln Ser Asn
                85                  90                  95

Glu Asp Pro Arg Thr Phe Gly Gly Gly Thr Lys Leu Glu Met Lys
            100                 105                 110

<210> SEQ ID NO 852
<211> LENGTH: 26
<212> TYPE: PRT
<213> ORGANISM: Mus musculus

<400> SEQUENCE: 852

Asp Thr Thr Val Thr Gln Ser Pro Ser Ser Leu Ala Met Ser Val Gly
1               5                   10                  15

Gln Lys Val Thr Met Ser Cys Lys Ser Ser
            20                  25

<210> SEQ ID NO 853
<211> LENGTH: 113
<212> TYPE: PRT
<213> ORGANISM: Mus musculus

<400> SEQUENCE: 853

Asp Thr Thr Val Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Tyr Thr Phe Gly Gly Gly Thr Lys Leu Glu Ile
            100                 105                 110

Lys

<210> SEQ ID NO 854
<211> LENGTH: 26
<212> TYPE: PRT
<213> ORGANISM: Mus musculus -continued

<400> SEQUENCE: 854

Asp Thr Thr Val Thr Gln Ser Gln Lys Phe Met Ser Thr Ser Val Gly
1               5                   10                  15

Asp Arg Val Ser Val Ala Cys Lys Ala Ser
            20                  25

<210> SEQ ID NO 855
<211> LENGTH: 23
<212> TYPE: PRT
<213> ORGANISM: Mus musculus

<400> SEQUENCE: 855

Asp Thr Thr Val Thr Gln Ser Gln Lys Phe Met Ser Thr Ser Val Gly
1               5                   10                  15

Asp Arg Val Ser Val Thr Cys
            20

<210> SEQ ID NO 856
<211> LENGTH: 26
<212> TYPE: PRT
<213> ORGANISM: Mus musculus

<400> SEQUENCE: 856

Asp Thr Thr Val Thr Gln Ser Gln Lys Phe Met Ser Thr Ser Val Gly
1               5                   10                  15

Asp Arg Val Ser Val Thr Cys Lys Ala Gly
            20                  25

<210> SEQ ID NO 857
<211> LENGTH: 107
<212> TYPE: PRT
<213> ORGANISM: Mus musculus

<400> SEQUENCE: 857

Asp Thr Thr Val Thr Gln Ser Gln Lys Phe Met Ser Thr Ser Val Gly
1               5                   10                  15

Asp Arg Val Ser Val Thr Cys Lys Ala Gly Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys
            100                 105

<210> SEQ ID NO 858
<211> LENGTH: 26
<212> TYPE: PRT
<213> ORGANISM: Mus musculus

<400> SEQUENCE: 858

Asp Thr Thr Val Thr Gln Ser Gln Lys Phe Met Ser Thr Ser Val Gly
1               5                   10                  15

Asp Arg Val Ser Val Thr Cys Lys Ala Ser
            20                  25

<210> SEQ ID NO 859
<211> LENGTH: 107
<212> TYPE: PRT
<213> ORGANISM: Mus musculus

<400> SEQUENCE: 859

Asp Thr Thr Val Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys
            100                 105

<210> SEQ ID NO 860
<211> LENGTH: 107
<212> TYPE: PRT
<213> ORGANISM: Mus musculus

<400> SEQUENCE: 860

Asp Thr Thr Val Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Met Lys
            100                 105

<210> SEQ ID NO 861
<211> LENGTH: 107
<212> TYPE: PRT
<213> ORGANISM: Mus musculus

<400> SEQUENCE: 861

Asp Thr Thr Val Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

```
Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln Tyr Asn Ser Tyr Pro Trp
                 85                  90                  95

Thr Phe Gly Gly Gly Thr Lys Leu Glu Ile Lys
                100                 105

<210> SEQ ID NO 862
<211> LENGTH: 23
<212> TYPE: PRT
<213> ORGANISM: Mus musculus

<400> SEQUENCE: 862

Asp Thr Thr Val Thr Gln Ser Gln Arg Phe Met Ser Thr Ser Val Gly
  1               5                  10                  15

Asp Arg Val Ser Val Thr Cys
             20

<210> SEQ ID NO 863
<211> LENGTH: 26
<212> TYPE: PRT
<213> ORGANISM: Mus musculus

<400> SEQUENCE: 863

Asp Thr Thr Val Thr Gln Ser Gln Arg Phe Met Ser Thr Ser Val Gly
  1               5                  10                  15

Asp Arg Val Ser Val Thr Cys Lys Ala Ser
             20                  25

<210> SEQ ID NO 864
<211> LENGTH: 107
<212> TYPE: PRT
<213> ORGANISM: Mus musculus

<400> SEQUENCE: 864

Asp Thr Thr Val Thr Gln Ser Gln Arg Phe Met Ser Thr Ser Val Gly
  1               5                  10                  15

Asp Arg Val Ser Val Thr Cys Lys Ala Ser Gln Asn Val Gly Thr Asn
             20                  25                  30

Val Ala Trp Tyr Gln Gln Lys Pro Gly Gln Ser Pro Lys Pro Leu Ile
         35                  40                  45

Tyr Ser Ala Ser Tyr Arg Tyr Ser Gly Val Pro Asp Arg Phe Thr Gly
 50                  55                  60

Ser Gly Ser Gly Thr Asp Phe Thr Leu Thr Ile Asn Asn Val Gln Ser
 65                  70                  75                  80

Glu Asp Leu Ala Glu Tyr Phe Cys Gln Gln Tyr Asn Asn Ser Pro Leu
                 85                  90                  95

Thr Phe Gly Gly Gly Thr Lys Leu Glu Ile Lys
                100                 105

<210> SEQ ID NO 865
<211> LENGTH: 26
<212> TYPE: PRT
<213> ORGANISM: Mus musculus

<400> SEQUENCE: 865

Asp Val His Met Asn Gln Ser Gln Lys Phe Met Ser Thr Ser Val Gly
  1               5                  10                  15

Asn Arg Val Ser Val Thr Cys Lys Gly Ser
             20                  25
```

<210> SEQ ID NO 866
<211> LENGTH: 25
<212> TYPE: PRT
<213> ORGANISM: Mus musculus

<400> SEQUENCE: 866

Asp Val Gln Leu Gln Glu Ser Gly Ala Glu Leu Ala Lys Pro Gly Ala
1               5                   10                  15

Ser Val Lys Met Ser Cys Lys Ala Ser
            20                  25

<210> SEQ ID NO 867
<211> LENGTH: 25
<212> TYPE: PRT
<213> ORGANISM: Mus musculus

<400> SEQUENCE: 867

Asp Val Gln Leu Gln Gln Ser Gly Ala Glu Leu Val Arg Pro Gly Thr
1               5                   10                  15

Ser Val Lys Met Ser Cys Lys Ala Ala
            20                  25

<210> SEQ ID NO 868
<211> LENGTH: 114
<212> TYPE: PRT
<213> ORGANISM: Mus musculus

<400> SEQUENCE: 868

Asp Val Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn Tyr
            20                  25                  30

Trp Ile Gly Trp Val Lys Gln Arg Pro Gly His Gly Leu Glu Trp Ile
        35                  40                  45

Gly Asp Ile His Pro Gly Gly Asp Tyr Ser Asn Tyr Asn Glu Lys Phe
    50                  55                  60

Lys Gly Lys Ala Thr Leu Thr Ala Asp Thr Ser Ser Thr Ala Tyr
65                  70                  75                  80

Met Asn Leu Ser Ser Leu Thr Ser Glu Asp Ser Ala Ile Tyr Tyr Cys
                85                  90                  95

Thr Ser Arg Asn Phe Ala Tyr Trp Gly Gln Gly Thr Leu Val Thr Val
            100                 105                 110

Ser Ala

<210> SEQ ID NO 869
<211> LENGTH: 114
<212> TYPE: PRT
<213> ORGANISM: Mus musculus

<400> SEQUENCE: 869

Asp Val Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn Tyr
            20                  25                  30

Trp Ile Gly Trp Val Lys Gln Arg Pro Gly His Gly Leu Glu Trp Ile
        35                  40                  45

Gly Asp Ile His Pro Gly Gly Gly Tyr Thr Asn Tyr Asn Glu Lys Phe
    50                  55                  60

```
Lys Gly Lys Ala Thr Leu Thr Ala Asp Thr Ser Ser Thr Ala Tyr
65                  70                  75                  80

Met Gln Leu Ser Ser Leu Thr Ser Glu Gly Ser Ala Ile Tyr Tyr Cys
            85                  90                  95

Thr Ser Arg Asn Phe Ala Tyr Trp Gly Gln Gly Thr Leu Val Thr Val
            100                 105                 110

Ser Ala

<210> SEQ ID NO 870
<211> LENGTH: 26
<212> TYPE: PRT
<213> ORGANISM: Mus musculus

<400> SEQUENCE: 870

Asp Val Gln Met Asn Gln Ser Pro Ser Ser Met Tyr Ala Ser Leu Gly
1               5                   10                  15

Glu Arg Val Thr Ile Thr Cys Lys Ala Ser
            20                  25

<210> SEQ ID NO 871
<211> LENGTH: 26
<212> TYPE: PRT
<213> ORGANISM: Mus musculus

<400> SEQUENCE: 871

Asp Val Gln Met Thr Gln Ser Pro Ala Ser Leu Ser Ala Ser Val Gly
1               5                   10                  15

Glu Thr Val Thr Ile Thr Cys Arg Ala Ser
            20                  25

<210> SEQ ID NO 872
<211> LENGTH: 26
<212> TYPE: PRT
<213> ORGANISM: Mus musculus

<400> SEQUENCE: 872

Asp Val Gln Met Thr Gln Ser Pro Ser Ser Met Tyr Ala Ser Leu Gly
1               5                   10                  15

Glu Arg Val Thr Phe Thr Cys Lys Ala Ser
            20                  25

<210> SEQ ID NO 873
<211> LENGTH: 26
<212> TYPE: PRT
<213> ORGANISM: Mus musculus

<400> SEQUENCE: 873

Asp Val Gln Met Thr Gln Ser Gln Lys Phe Met Ser Thr Ser Val Gly
1               5                   10                  15

Asp Arg Val Ser Val Thr Cys Lys Ala Ser
            20                  25

<210> SEQ ID NO 874
<211> LENGTH: 26
<212> TYPE: PRT
<213> ORGANISM: Mus musculus

<400> SEQUENCE: 874

Asp Val Val Leu Thr Gln Thr Pro Leu Ser Leu Pro Val Ser Leu Gly
1               5                   10                  15
```

Asp Gln Ala Ser Ile Ser Cys Arg Ser Ser
            20                  25

<210> SEQ ID NO 875
<211> LENGTH: 112
<212> TYPE: PRT
<213> ORGANISM: Mus musculus

<400> SEQUENCE: 875

Asp Val Val Leu Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 876
<211> LENGTH: 112
<212> TYPE: PRT
<213> ORGANISM: Mus musculus

<400> SEQUENCE: 876

Asp Val Val Leu Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 877
<211> LENGTH: 112
<212> TYPE: PRT
<213> ORGANISM: Mus musculus

<400> SEQUENCE: 877

Asp Val Val Leu Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro

```
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Trp Thr Phe Gly Gly Gly Thr Lys Leu Glu Met Lys
                100                 105                 110
```

<210> SEQ ID NO 878
<211> LENGTH: 112
<212> TYPE: PRT
<213> ORGANISM: Mus musculus

<400> SEQUENCE: 878

```
Asp Val Val Leu Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Arg Thr Phe Gly Gly Gly Thr Lys Leu Glu Ile Lys
                100                 105                 110
```

<210> SEQ ID NO 879
<211> LENGTH: 111
<212> TYPE: PRT
<213> ORGANISM: Mus musculus

<400> SEQUENCE: 879

```
Asp Val Val Leu Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Thr Phe Gly Gly Gly Thr Lys Leu Glu Ile Lys
                100                 105                 110
```

<210> SEQ ID NO 880
<211> LENGTH: 112
<212> TYPE: PRT
<213> ORGANISM: Mus musculus

<400> SEQUENCE: 880

```
Asp Val Val Leu Thr Gln Thr Pro Leu Ser Leu Pro Val Ser Leu Gly
 1               5                  10                  15
```

```
Asp Gln Ala Ser Ile Ser Cys Arg Ser Ser Gln Ser Leu Val His Ser
            20                  25                  30

Tyr Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro His Thr Phe Gly Gly Gly Thr Lys Leu Glu Met Lys
            100                 105                 110
```

<210> SEQ ID NO 881
<211> LENGTH: 26
<212> TYPE: PRT
<213> ORGANISM: Mus musculus

<400> SEQUENCE: 881

```
Asp Val Val Leu Thr Gln Thr Pro Leu Ser Leu Pro Val Ser Leu Gly
1               5                   10                  15

Asp Gln Val Ser Ile Ser Cys Arg Ser Gly
            20                  25
```

<210> SEQ ID NO 882
<211> LENGTH: 112
<212> TYPE: PRT
<213> ORGANISM: Mus musculus

<400> SEQUENCE: 882

```
Asp Val Val Leu Thr Gln Thr Pro Leu Ser Leu Pro Val Ser Leu Gly
1               5                   10                  15

Asp Gln Val Ser Ile Ser Cys Arg Ser Gly Gln Ser Leu Val His Asn
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Ile Lys
            100                 105                 110
```

<210> SEQ ID NO 883
<211> LENGTH: 26
<212> TYPE: PRT
<213> ORGANISM: Mus musculus

<400> SEQUENCE: 883

```
Asp Val Val Leu Thr Gln Thr Pro Leu Ser Leu Pro Val Thr Leu Gly
1               5                   10                  15

Asp Pro Ala Ser Ile Ser Cys Arg Ser Ser
            20                  25
```

<210> SEQ ID NO 884
<211> LENGTH: 112

```
<212> TYPE: PRT
<213> ORGANISM: Mus musculus

<400> SEQUENCE: 884

Asp Val Val Leu Thr Gln Thr Pro Leu Ser Leu Pro Val Thr Leu Gly
1               5                   10                  15

Asp Pro Ala Ser Ile Ser Cys Arg Ser Ser Gln Thr Leu Leu His Ser
            20                  25                  30

Asp Gly Asn Thr Tyr Leu Lys Trp Tyr Leu Gln Lys Pro Gly Gln Ser
        35                  40                  45

Pro Lys Leu Leu Ile Tyr Gln Val Ser Asn Arg Phe Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr His Cys Phe Gln Gly
                85                  90                  95

Ser His Val Pro Trp Thr Phe Gly Gly Gly Thr Lys Leu Glu Ile Lys
            100                 105                 110

<210> SEQ ID NO 885
<211> LENGTH: 26
<212> TYPE: PRT
<213> ORGANISM: Mus musculus

<400> SEQUENCE: 885

Asp Val Val Met Thr Gln Ser His Lys Phe Met Ser Thr Ser Val Gly
1               5                   10                  15

Asp Arg Val Ser Ile Thr Cys Lys Ala Ser
            20                  25

<210> SEQ ID NO 886
<211> LENGTH: 108
<212> TYPE: PRT
<213> ORGANISM: Mus musculus

<400> SEQUENCE: 886

Asp Val Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Pro
                85                  90                  95

Trp Thr Phe Gly Arg Gly Thr Lys Leu Glu Ile Lys
            100                 105

<210> SEQ ID NO 887
<211> LENGTH: 26
<212> TYPE: PRT
<213> ORGANISM: Mus musculus

<400> SEQUENCE: 887

Asp Val Val Met Thr Gln Ser Pro Ala Ile Met Ser Ala Ser Leu Gly
1               5                   10                  15
```

```
Glu Arg Val Thr Met Thr Cys Thr Ala Ser
            20                  25

<210> SEQ ID NO 888
<211> LENGTH: 108
<212> TYPE: PRT
<213> ORGANISM: Mus musculus

<400> SEQUENCE: 888

Asp Val Val Met Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Pro Thr Phe Gly Gly Gly Thr Lys Leu Glu Ile Lys
            100                 105

<210> SEQ ID NO 889
<211> LENGTH: 26
<212> TYPE: PRT
<213> ORGANISM: Mus musculus

<400> SEQUENCE: 889

Asp Val Val Met Thr Gln Ser Pro Ala Ser Leu Ser Ala Ser Val Gly
1               5                   10                  15

Glu Ser Val Thr Ile Thr Cys Arg Ala Ser
            20                  25

<210> SEQ ID NO 890
<211> LENGTH: 26
<212> TYPE: PRT
<213> ORGANISM: Mus musculus

<400> SEQUENCE: 890

Asp Val Val Met Thr Gln Ser Pro Ala Ser Leu Ser Ala Ser Val Gly
1               5                   10                  15

Glu Thr Val Thr Ile Thr Cys Arg Ala Ser
            20                  25

<210> SEQ ID NO 891
<211> LENGTH: 26
<212> TYPE: PRT
<213> ORGANISM: Mus musculus

<400> SEQUENCE: 891

Asp Val Val Met Thr Gln Ser Gln Lys Phe Met Ser Thr Ser Val Gly
1               5                   10                  15

Asp Arg Val Asn Val Thr Cys Lys Ala Ser
            20                  25

<210> SEQ ID NO 892
<211> LENGTH: 107
<212> TYPE: PRT
```

<213> ORGANISM: Mus musculus

<400> SEQUENCE: 892

Asp Val Val Met Thr Gln Ser Gln Lys Phe Met Ser Thr Ser Val Gly
1               5                   10                  15

Asp Arg Val Asn Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys
            100                 105

<210> SEQ ID NO 893
<211> LENGTH: 23
<212> TYPE: PRT
<213> ORGANISM: Mus musculus

<400> SEQUENCE: 893

Asp Val Val Met Thr Gln Ser Gln Lys Phe Met Ser Thr Ser Val Gly
1               5                   10                  15

Asp Arg Val Ser Val Thr Cys
            20

<210> SEQ ID NO 894
<211> LENGTH: 26
<212> TYPE: PRT
<213> ORGANISM: Mus musculus

<400> SEQUENCE: 894

Asp Val Val Met Thr Gln Ser Gln Lys Phe Met Ser Thr Ser Val Gly
1               5                   10                  15

Asp Arg Val Ser Val Thr Cys Lys Ala Ser
            20                  25

<210> SEQ ID NO 895
<211> LENGTH: 107
<212> TYPE: PRT
<213> ORGANISM: Mus musculus

<400> SEQUENCE: 895

Asp Val Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

-continued

Thr Phe Gly Gly Gly Thr Lys Leu Glu Ile Lys
            100                 105

<210> SEQ ID NO 896
<211> LENGTH: 26
<212> TYPE: PRT
<213> ORGANISM: Mus musculus

<400> SEQUENCE: 896

Asp Val Val Met Thr Gln Thr Pro Lys Phe Leu Leu Val Ser Ala Gly
1               5                   10                  15

Asp Arg Val Thr Ile Thr Cys Lys Ala Ser
            20                  25

<210> SEQ ID NO 897
<211> LENGTH: 107
<212> TYPE: PRT
<213> ORGANISM: Mus musculus

<400> SEQUENCE: 897

Asp Val Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Pro
                85                  90                  95

Thr Phe Gly Gly Gly Thr Lys Leu Glu Ile Lys
            100                 105

<210> SEQ ID NO 898
<211> LENGTH: 26
<212> TYPE: PRT
<213> ORGANISM: Mus musculus

<400> SEQUENCE: 898

Asp Val Val Met Thr Gln Thr Pro Leu Ser Leu Pro Val Asn Leu Gly
1               5                   10                  15

Asp Gln Ala Ser Ile Ser Cys Arg Ser Ser
            20                  25

<210> SEQ ID NO 899
<211> LENGTH: 26
<212> TYPE: PRT
<213> ORGANISM: Mus musculus

<400> SEQUENCE: 899

Asp Val Val Met Thr Gln Thr Pro Leu Ser Leu Pro Val Ser Leu Gly
1               5                   10                  15

Asp Gln Ala Ser Ile Ser Cys Arg Ser Asn
            20                  25

<210> SEQ ID NO 900
<211> LENGTH: 26
<212> TYPE: PRT
<213> ORGANISM: Mus musculus -continued

<400> SEQUENCE: 900

Asp Val Val Met Thr Gln Thr Pro Leu Ser Leu Pro Val Ser Leu Gly
1               5                   10                  15

Asp Gln Ala Ser Ile Ser Cys Arg Ser Ser
            20                  25

<210> SEQ ID NO 901
<211> LENGTH: 112
<212> TYPE: PRT
<213> ORGANISM: Mus musculus

<400> SEQUENCE: 901

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 902
<211> LENGTH: 112
<212> TYPE: PRT
<213> ORGANISM: Mus musculus

<400> SEQUENCE: 902

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Ile Lys
            100                 105                 110

<210> SEQ ID NO 903
<211> LENGTH: 112
<212> TYPE: PRT
<213> ORGANISM: Mus musculus

<400> SEQUENCE: 903

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser 20                  25                  30

Asn Gly Asn Thr Tyr Leu Arg Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 904
<211> LENGTH: 26
<212> TYPE: PRT
<213> ORGANISM: Mus musculus

<400> SEQUENCE: 904

Asp Val Val Met Thr Gln Thr Pro Leu Thr Leu Ser Val Thr Ile Gly
1               5                   10                  15

Gln Pro Ala Ser Ile Ser Cys Lys Ser Ser
            20                  25

<210> SEQ ID NO 905
<211> LENGTH: 112
<212> TYPE: PRT
<213> ORGANISM: Mus musculus

<400> SEQUENCE: 905

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Asn Arg Val Glu Ala Glu Asp Leu Gly Val Tyr Tyr Cys Trp Gln Gly
                85                  90                  95

Thr His Phe Pro Arg Thr Phe Gly Gly Gly Thr Lys Leu Glu Ile Lys
            100                 105                 110

<210> SEQ ID NO 906
<211> LENGTH: 111
<212> TYPE: PRT
<213> ORGANISM: Mus musculus

<400> SEQUENCE: 906

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

```
Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Arg Thr Phe Gly Gly Gly Thr Lys Leu Glu Met Lys
            100                 105                 110

<210> SEQ ID NO 907
<211> LENGTH: 112
<212> TYPE: PRT
<213> ORGANISM: Mus musculus

<400> SEQUENCE: 907

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Trp Thr Phe Gly Gly Gly Thr Lys Leu Glu Ile Lys
            100                 105                 110

<210> SEQ ID NO 908
<211> LENGTH: 112
<212> TYPE: PRT
<213> ORGANISM: Mus musculus

<400> SEQUENCE: 908

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Gly Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Arg Thr Phe Gly Gly Gly Thr Lys Leu Glu Ile Lys
            100                 105                 110

<210> SEQ ID NO 909
<211> LENGTH: 26
<212> TYPE: PRT
<213> ORGANISM: Mus musculus

<400> SEQUENCE: 909

Asp Val Val Met Thr Gln Thr Gln Lys Phe Met Ser Thr Ser Val Gly
1               5                   10                  15
```

```
Asp Arg Val Ser Val Thr Cys Lys Ala Ser
            20                  25

<210> SEQ ID NO 910
<211> LENGTH: 23
<212> TYPE: PRT
<213> ORGANISM: Mus musculus

<400> SEQUENCE: 910

Asp Val Val Met Thr Gln Thr Gln Lys Phe Thr Ser Thr Ser Val Gly
1               5                   10                  15

Asp Arg Val Ser Val Thr Cys
            20

<210> SEQ ID NO 911
<211> LENGTH: 26
<212> TYPE: PRT
<213> ORGANISM: Mus musculus

<400> SEQUENCE: 911

Asp Val Val Met Thr Gln Thr Gln Lys Phe Thr Ser Thr Ser Val Gly
1               5                   10                  15

Asp Arg Val Ser Val Thr Cys Lys Ala Ser
            20                  25

<210> SEQ ID NO 912
<211> LENGTH: 107
<212> TYPE: PRT
<213> ORGANISM: Mus musculus

<400> SEQUENCE: 912

Asp Val Val Met Thr Gln Thr Gln Lys Phe Thr Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys
            100                 105

<210> SEQ ID NO 913
<211> LENGTH: 26
<212> TYPE: PRT
<213> ORGANISM: Mus musculus

<400> SEQUENCE: 913

Asp Val Val Met Thr Gln Thr Thr Ser Ser Leu Ser Ala Ser Leu Gly
1               5                   10                  15

Asp Arg Val Thr Ile Ser Cys Arg Ala Ser
            20                  25

<210> SEQ ID NO 914
<211> LENGTH: 107
<212> TYPE: PRT
```

<400> SEQUENCE: 914

Asp Val Val Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Arg Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Ser Leu Thr Ile Ser Asn Leu Glu Gln
65                  70                  75                  80

Glu Asp Ile Ala Thr Tyr Phe Cys Gln Gln Val Tyr Thr Leu Pro Trp
                85                  90                  95

Thr Phe Gly Gly Gly Thr Lys Leu Glu Ile Lys
            100                 105

<210> SEQ ID NO 915
<211> LENGTH: 26
<212> TYPE: PRT
<213> ORGANISM: Mus musculus

<400> SEQUENCE: 915

Asp Val Val Met Thr Gln Thr Thr Ser Ser Leu Ser Ala Ser Leu Gly
1               5                   10                  15

Asp Arg Val Thr Ile Thr Cys Arg Ala Ser
            20                  25

<210> SEQ ID NO 916
<211> LENGTH: 26
<212> TYPE: PRT
<213> ORGANISM: Mus musculus

<400> SEQUENCE: 916

Asp Val Val Val Thr Gln Ser Pro Ala Ser Leu Ala Val Ser Leu Gly
1               5                   10                  15

Gln Arg Ala Thr Ile Ser Cys Arg Ala Ser
            20                  25

<210> SEQ ID NO 917
<211> LENGTH: 111
<212> TYPE: PRT
<213> ORGANISM: Mus musculus

<400> SEQUENCE: 917

Asp Val Val Val Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Ala Ala Thr Tyr Tyr Cys Gln Gln Asn Asn
                85                  90                  95

Glu Asp Pro Tyr Thr Phe Gly Gly Gly Thr Lys Leu Glu Ile Lys

<210> SEQ ID NO 918
<211> LENGTH: 26
<212> TYPE: PRT
<213> ORGANISM: Mus musculus

<400> SEQUENCE: 918

Asp Val Val Val Thr Gln Thr Pro Leu Ser Leu Pro Val Ser Leu Gly
1               5                   10                  15

Asp Gln Ala Ser Ile Ser Cys Arg Ser Ser
            20                  25

<210> SEQ ID NO 919
<211> LENGTH: 112
<212> TYPE: PRT
<213> ORGANISM: Mus musculus

<400> SEQUENCE: 919

Asp Val Val Val Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Ser
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Asn Arg Phe Ser Gly Val Leu
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
                85                  90                  95

Thr His Val Pro Phe Ala Phe Gly Ser Gly Thr Lys Leu Glu Ile Lys
                100                 105                 110

<210> SEQ ID NO 920
<211> LENGTH: 111
<212> TYPE: PRT
<213> ORGANISM: Mus musculus

<400> SEQUENCE: 920

Asp Val Val Val Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Thr Phe Gly Gly Gly Thr Lys Leu Glu Ile Lys
                100                 105                 110

<210> SEQ ID NO 921
<211> LENGTH: 111
<212> TYPE: PRT
<213> ORGANISM: Mus musculus

<400> SEQUENCE: 921

Asp Val Val Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Asp Ala Glu Asp Leu Gly Val Tyr Phe Cys Ser Gln Ser
                85                  90                  95

Thr His Val Tyr Thr Phe Gly Gly Gly Thr Lys Leu Glu Met Lys
            100                 105                 110

<210> SEQ ID NO 922
<211> LENGTH: 112
<212> TYPE: PRT
<213> ORGANISM: Mus musculus

<400> SEQUENCE: 922

Asp Val Val Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 923
<211> LENGTH: 38
<212> TYPE: PRT
<213> ORGANISM: Mus musculus

<400> SEQUENCE: 923

Asp Tyr Asn Glu Lys Phe Thr Gly Lys Ala Thr Leu Thr Ala Asp Thr
1               5                   10                  15

Ser Ser Ser Thr Ala Tyr Met Gln Leu Ser Ser Leu Thr Ser Glu Asp
            20                  25                  30

Ser Ala Ile Tyr Tyr Cys
            35

<210> SEQ ID NO 924
<211> LENGTH: 6
<212> TYPE: PRT
<213> ORGANISM: Mus musculus

<400> SEQUENCE: 924

Glu Asp Ile Tyr Asn Arg

```
<210> SEQ ID NO 925
<211> LENGTH: 3
<212> TYPE: PRT
<213> ORGANISM: Mus musculus

<400> SEQUENCE: 925

Glu Gly Asn
1

<210> SEQ ID NO 926
<211> LENGTH: 26
<212> TYPE: PRT
<213> ORGANISM: Mus musculus

<400> SEQUENCE: 926

Glu Ile Val Met Thr Gln Ser Pro Pro Thr Leu Ser Leu Ser Pro Gly
1               5                   10                  15

Glu Arg Val Thr Leu Ser Cys Lys Ala Ser
            20                  25

<210> SEQ ID NO 927
<211> LENGTH: 6
<212> TYPE: PRT
<213> ORGANISM: Mus musculus

<400> SEQUENCE: 927

Glu Asn Ile Tyr Phe Ser
1               5

<210> SEQ ID NO 928
<211> LENGTH: 6
<212> TYPE: PRT
<213> ORGANISM: Mus musculus

<400> SEQUENCE: 928

Glu Asn Ile Tyr Ser Phe
1               5

<210> SEQ ID NO 929
<211> LENGTH: 6
<212> TYPE: PRT
<213> ORGANISM: Mus musculus

<400> SEQUENCE: 929

Glu Asn Ile Tyr Ser Asn
1               5

<210> SEQ ID NO 930
<211> LENGTH: 6
<212> TYPE: PRT
<213> ORGANISM: Mus musculus

<400> SEQUENCE: 930

Glu Asn Ile Tyr Ser Tyr
1               5

<210> SEQ ID NO 931
<211> LENGTH: 6
<212> TYPE: PRT
<213> ORGANISM: Mus musculus

<400> SEQUENCE: 931
```

Glu Asn Ser Tyr Ser Tyr
1               5

<210> SEQ ID NO 932
<211> LENGTH: 6
<212> TYPE: PRT
<213> ORGANISM: Mus musculus

<400> SEQUENCE: 932

Glu Asn Val Ala Thr Tyr
1               5

<210> SEQ ID NO 933
<211> LENGTH: 6
<212> TYPE: PRT
<213> ORGANISM: Mus musculus

<400> SEQUENCE: 933

Glu Asn Val Gly Thr Tyr
1               5

<210> SEQ ID NO 934
<211> LENGTH: 10
<212> TYPE: PRT
<213> ORGANISM: Mus musculus

<400> SEQUENCE: 934

Glu Ser Val Asp Asn Tyr Gly Ile Ser Phe
1               5                   10

<210> SEQ ID NO 935
<211> LENGTH: 10
<212> TYPE: PRT
<213> ORGANISM: Mus musculus

<400> SEQUENCE: 935

Glu Ser Val Asp Ser Tyr Gly Asn Ser Phe
1               5                   10

<210> SEQ ID NO 936
<211> LENGTH: 25
<212> TYPE: PRT
<213> ORGANISM: Mus musculus

<400> SEQUENCE: 936

Glu Val His Leu Gln Gln Ser Gly Ala Glu Leu Val Arg Ser Gly Ala
1               5                   10                  15

Ser Val Lys Leu Ser Cys Thr Ala Ser
            20                  25

<210> SEQ ID NO 937
<211> LENGTH: 25
<212> TYPE: PRT
<213> ORGANISM: Mus musculus

<400> SEQUENCE: 937

Glu Val Leu Leu Gln Gln Phe Gly Ala Glu Leu Val Arg Ser Gly Ala
1               5                   10                  15

Ser Val Lys Leu Ser Cys Thr Ala Ser
            20                  25

<210> SEQ ID NO 938
<211> LENGTH: 25
<212> TYPE: PRT

```
<213> ORGANISM: Mus musculus

<400> SEQUENCE: 938

Glu Val Leu Leu Gln Gln Ser Gly Ala Asp Leu Met Lys Pro Gly Ala
1               5                   10                  15

Ser Val Lys Ile Ser Cys Lys Ala Ser
            20                  25

<210> SEQ ID NO 939
<211> LENGTH: 25
<212> TYPE: PRT
<213> ORGANISM: Mus musculus

<400> SEQUENCE: 939

Glu Val Gln Leu Gln Glu Ser Gly Ala Asp Leu Met Lys Pro Gly Ala
1               5                   10                  15

Ser Val Lys Ile Ser Cys Lys Ala Ser
            20                  25

<210> SEQ ID NO 940
<211> LENGTH: 25
<212> TYPE: PRT
<213> ORGANISM: Mus musculus

<400> SEQUENCE: 940

Glu Val Gln Leu Gln Gln Ser Gly Ala Glu Leu Val Arg Pro Gly Val
1               5                   10                  15

Ser Leu Lys Ile Ser Cys Lys Gly Ser
            20                  25

<210> SEQ ID NO 941
<211> LENGTH: 25
<212> TYPE: PRT
<213> ORGANISM: Mus musculus

<400> SEQUENCE: 941

Glu Val Arg Leu Gln Gln Ser Gly Ala Asp Leu Met Lys Pro Gly Ala
1               5                   10                  15

Ser Val Lys Ile Ser Cys Lys Thr Ser
            20                  25

<210> SEQ ID NO 942
<211> LENGTH: 25
<212> TYPE: PRT
<213> ORGANISM: Mus musculus

<400> SEQUENCE: 942

Glu Val Arg Leu Gln Gln Ser Gly Ala Glu Leu Val Arg Ser Gly Ala
1               5                   10                  15

Ser Val Lys Leu Pro Cys Thr Ala Ser
            20                  25

<210> SEQ ID NO 943
<211> LENGTH: 25
<212> TYPE: PRT
<213> ORGANISM: Mus musculus

<400> SEQUENCE: 943

Glu Val Arg Leu Gln Gln Ser Gly Ala Glu Leu Val Arg Ser Gly Ala
1               5                   10                  15

Ser Val Lys Leu Ser Cys Thr Ala Ser
            20                  25
```

<210> SEQ ID NO 944
<211> LENGTH: 3
<212> TYPE: PRT
<213> ORGANISM: Mus musculus

<400> SEQUENCE: 944

Glu Val Ser
1

<210> SEQ ID NO 945
<211> LENGTH: 37
<212> TYPE: PRT
<213> ORGANISM: Mus musculus

<400> SEQUENCE: 945

Glu Tyr Ala Pro Lys Phe Gly Lys Ala Thr Met Thr Ala Asp Thr
1               5                   10                  15

Ser Asn Thr Ala His Leu Gln Leu Ser Ser Leu Thr Ser Glu Asp Thr
            20                  25                  30

Ala Val Tyr Tyr Cys
        35

<210> SEQ ID NO 946
<211> LENGTH: 38
<212> TYPE: PRT
<213> ORGANISM: Mus musculus

<400> SEQUENCE: 946

Glu Tyr Ala Pro Lys Phe Gln Gly Lys Ala Thr Met Thr Ala Asp Thr
1               5                   10                  15

Ser Ser Asn Thr Ala His Leu Gln Leu Ser Ser Leu Thr Ser Glu Asp
            20                  25                  30

Thr Ala Val Tyr Tyr Cys
        35

<210> SEQ ID NO 947
<211> LENGTH: 38
<212> TYPE: PRT
<213> ORGANISM: Mus musculus

<400> SEQUENCE: 947

Glu Tyr Ala Pro Lys Phe Gln Gly Lys Ala Thr Met Thr Ala Asp Thr
1               5                   10                  15

Ser Ser Asn Thr Ala Tyr Leu Gln Leu Ser Ser Leu Thr Ser Glu Asp
            20                  25                  30

Thr Ala Val Tyr Tyr Cys
        35

<210> SEQ ID NO 948
<211> LENGTH: 38
<212> TYPE: PRT
<213> ORGANISM: Mus musculus

<400> SEQUENCE: 948

Glu Tyr Ala Pro Lys Phe Gln Gly Lys Ala Thr Met Thr Thr Asp Thr
1               5                   10                  15

Ser Ser Asn Thr Ala His Leu Gln Leu Ser Ser Leu Thr Ser Glu Asp
            20                  25                  30

Thr Ala Val Tyr Tyr Cys
        35

<210> SEQ ID NO 949
<211> LENGTH: 37
<212> TYPE: PRT
<213> ORGANISM: Mus musculus

<400> SEQUENCE: 949

Glu Tyr Asn Glu Lys Phe Asp Lys Ala Thr Leu Thr Ala Asp Lys Ser
1               5                   10                  15

Ser Ser Thr Ala Tyr Met Gln Leu Ser Ser Leu Thr Ser Glu Asp Ser
            20                  25                  30

Ala Val Tyr Phe Cys
        35

<210> SEQ ID NO 950
<211> LENGTH: 38
<212> TYPE: PRT
<213> ORGANISM: Mus musculus

<400> SEQUENCE: 950

Glu Tyr Asn Glu Lys Phe Glu Asp Lys Ala Thr Leu Thr Ala Asp Lys
1               5                   10                  15

Ser Ser Ser Thr Ala Tyr Met Gln Leu Ser Ser Leu Thr Ser Glu Asp
            20                  25                  30

Ser Ala Val Tyr Tyr Cys
        35

<210> SEQ ID NO 951
<211> LENGTH: 37
<212> TYPE: PRT
<213> ORGANISM: Mus musculus

<400> SEQUENCE: 951

Glu Tyr Asn Gln Lys Phe Asp Lys Ala Thr Leu Thr Ala Asp Lys Ser
1               5                   10                  15

Ser Ser Thr Ala Tyr Met Gln Leu Ser Ser Leu Thr Ser Asp Asp Ser
            20                  25                  30

Ala Val Tyr Tyr Cys
        35

<210> SEQ ID NO 952
<211> LENGTH: 37
<212> TYPE: PRT
<213> ORGANISM: Mus musculus
<220> FEATURE:
<221> NAME/KEY: misc_feature
<222> LOCATION: (25)..(25)
<223> OTHER INFORMATION: Xaa can be any naturally occurring amino acid

<400> SEQUENCE: 952

Glu Tyr Asn Gln Lys Phe Asp Lys Ala Thr Leu Thr Ala Asp Lys Ser
1               5                   10                  15

Ser Ser Thr Ala Tyr Met Gln Leu Xaa Ser Leu Thr Ser Asp Asp Ser
            20                  25                  30

Ala Val Tyr Tyr Cys
        35

<210> SEQ ID NO 953
<211> LENGTH: 38
<212> TYPE: PRT
<213> ORGANISM: Mus musculus

<400> SEQUENCE: 953

Glu Tyr Asn Gln Lys Phe Glu Asp Lys Ala Thr Leu Thr Ala Asp Lys
1               5                   10                  15

Ser Ser Asn Thr Ala Tyr Met Gln Leu Asn Ser Leu Thr Ser Glu Asp
            20                  25                  30

Ser Ala Val Tyr Tyr Cys
        35

<210> SEQ ID NO 954
<211> LENGTH: 38
<212> TYPE: PRT
<213> ORGANISM: Mus musculus

<400> SEQUENCE: 954

Glu Tyr Asn Gln Lys Phe Glu Asp Lys Ala Thr Leu Thr Ala Asp Lys
1               5                   10                  15

Ser Ser Asn Thr Ala Tyr Met Gln Leu Ser Ser Leu Thr Ser Glu Asp
            20                  25                  30

Ser Ala Val Tyr Tyr Cys
        35

<210> SEQ ID NO 955
<211> LENGTH: 38
<212> TYPE: PRT
<213> ORGANISM: Mus musculus

<400> SEQUENCE: 955

Glu Tyr Asn Gln Lys Phe Lys Asp Lys Ala Thr Leu Thr Ala Asp Lys
1               5                   10                  15

Ser Ser Ser Thr Ala Tyr Met Gln Leu Ser Ser Leu Thr Ser Asp Asp
            20                  25                  30

Ser Ala Val Tyr Tyr Cys
        35

<210> SEQ ID NO 956
<211> LENGTH: 12
<212> TYPE: PRT
<213> ORGANISM: Mus musculus

<400> SEQUENCE: 956

Phe Ala Phe Gly Ser Gly Thr Lys Leu Glu Ile Lys
1               5                   10

<210> SEQ ID NO 957
<211> LENGTH: 3
<212> TYPE: PRT
<213> ORGANISM: Mus musculus

<400> SEQUENCE: 957

Phe Ala Ser
1

<210> SEQ ID NO 958
<211> LENGTH: 10
<212> TYPE: PRT
<213> ORGANISM: Mus musculus

<400> SEQUENCE: 958

Phe Gly Ala Gly Thr Lys Leu Glu Ile Lys
1               5                   10

```
<210> SEQ ID NO 959
<211> LENGTH: 10
<212> TYPE: PRT
<213> ORGANISM: Mus musculus

<400> SEQUENCE: 959

Phe Gly Gly Gly Thr Lys Leu Glu Ile Lys
1               5                   10

<210> SEQ ID NO 960
<211> LENGTH: 10
<212> TYPE: PRT
<213> ORGANISM: Mus musculus

<400> SEQUENCE: 960

Phe Gly Gly Gly Thr Lys Leu Glu Ile Lys
1               5                   10

<210> SEQ ID NO 961
<211> LENGTH: 10
<212> TYPE: PRT
<213> ORGANISM: Mus musculus

<400> SEQUENCE: 961

Phe Gly Gly Gly Thr Lys Leu Glu Met Lys
1               5                   10

<210> SEQ ID NO 962
<211> LENGTH: 10
<212> TYPE: PRT
<213> ORGANISM: Mus musculus

<400> SEQUENCE: 962

Phe Gly Gly Gly Thr Lys Leu Glu Met Lys
1               5                   10

<210> SEQ ID NO 963
<211> LENGTH: 10
<212> TYPE: PRT
<213> ORGANISM: Mus musculus
<220> FEATURE:
<221> NAME/KEY: misc_feature
<222> LOCATION: (6)..(6)
<223> OTHER INFORMATION: Xaa can be any naturally occurring amino acid

<400> SEQUENCE: 963

Phe Gly Gly Gly Thr Xaa Leu Glu Ile Lys
1               5                   10

<210> SEQ ID NO 964
<211> LENGTH: 10
<212> TYPE: PRT
<213> ORGANISM: Mus musculus

<400> SEQUENCE: 964

Phe Gly Arg Gly Thr Lys Leu Glu Ile Lys
1               5                   10

<210> SEQ ID NO 965
<211> LENGTH: 10
<212> TYPE: PRT
<213> ORGANISM: Mus musculus

<400> SEQUENCE: 965

Phe Gly Ser Gly Thr Lys Leu Glu Ile Lys
1               5                   10
```

<210> SEQ ID NO 966
<211> LENGTH: 9
<212> TYPE: PRT
<213> ORGANISM: Mus musculus

<400> SEQUENCE: 966

Phe Gln Gly Ser His Val Pro Pro Thr
1               5

<210> SEQ ID NO 967
<211> LENGTH: 9
<212> TYPE: PRT
<213> ORGANISM: Mus musculus

<400> SEQUENCE: 967

Phe Gln Gly Ser His Val Pro Arg Thr
1               5

<210> SEQ ID NO 968
<211> LENGTH: 9
<212> TYPE: PRT
<213> ORGANISM: Mus musculus

<400> SEQUENCE: 968

Phe Gln Gly Ser His Val Pro Thr Phe
1               5

<210> SEQ ID NO 969
<211> LENGTH: 9
<212> TYPE: PRT
<213> ORGANISM: Mus musculus

<400> SEQUENCE: 969

Phe Gln Gly Ser His Val Pro Trp Thr
1               5

<210> SEQ ID NO 970
<211> LENGTH: 9
<212> TYPE: PRT
<213> ORGANISM: Mus musculus

<400> SEQUENCE: 970

Phe Gln Gly Ser His Val Pro Tyr Thr
1               5

<210> SEQ ID NO 971
<211> LENGTH: 9
<212> TYPE: PRT
<213> ORGANISM: Mus musculus

<400> SEQUENCE: 971

Phe Gln Gly Ser Tyr Val Pro Arg Thr
1               5

<210> SEQ ID NO 972
<211> LENGTH: 3
<212> TYPE: PRT
<213> ORGANISM: Mus musculus

<400> SEQUENCE: 972

Phe Thr Ser
1

<210> SEQ ID NO 973
<211> LENGTH: 8
<212> TYPE: PRT
<213> ORGANISM: Mus musculus

<400> SEQUENCE: 973

Phe Tyr Pro Gly Gly Asp Tyr Ile
1               5

<210> SEQ ID NO 974
<211> LENGTH: 9
<212> TYPE: PRT
<213> ORGANISM: Mus musculus

<400> SEQUENCE: 974

Gly Ala Gly Thr Lys Leu Glu Ile Lys
1               5

<210> SEQ ID NO 975
<211> LENGTH: 3
<212> TYPE: PRT
<213> ORGANISM: Mus musculus

<400> SEQUENCE: 975

Gly Ala Ser
1

<210> SEQ ID NO 976
<211> LENGTH: 3
<212> TYPE: PRT
<213> ORGANISM: Mus musculus

<400> SEQUENCE: 976

Gly Ala Thr
1

<210> SEQ ID NO 977
<211> LENGTH: 8
<212> TYPE: PRT
<213> ORGANISM: Mus musculus

<400> SEQUENCE: 977

Gly Phe Asn Ile Lys Asp Tyr Tyr
1               5

<210> SEQ ID NO 978
<211> LENGTH: 10
<212> TYPE: PRT
<213> ORGANISM: Mus musculus

<400> SEQUENCE: 978

Gly Gly Gly Thr Lys Lys Leu Glu Ile Lys
1               5                   10

<210> SEQ ID NO 979
<211> LENGTH: 9
<212> TYPE: PRT
<213> ORGANISM: Mus musculus

<400> SEQUENCE: 979

Gly Gln Ser Tyr Arg Tyr Pro Tyr Thr
1               5

<210> SEQ ID NO 980
<211> LENGTH: 9

```
<212> TYPE: PRT
<213> ORGANISM: Mus musculus

<400> SEQUENCE: 980

Gly Gln Ser Tyr Ser Tyr Pro Trp Thr
1               5

<210> SEQ ID NO 981
<211> LENGTH: 9
<212> TYPE: PRT
<213> ORGANISM: Mus musculus

<400> SEQUENCE: 981

Gly Gln Ser Tyr Ser Tyr Pro Tyr Thr
1               5

<210> SEQ ID NO 982
<211> LENGTH: 6
<212> TYPE: PRT
<213> ORGANISM: Mus musculus

<400> SEQUENCE: 982

Gly Arg Asn Phe Ala Tyr
1               5

<210> SEQ ID NO 983
<211> LENGTH: 3
<212> TYPE: PRT
<213> ORGANISM: Mus musculus

<400> SEQUENCE: 983

Gly Thr Ser
1

<210> SEQ ID NO 984
<211> LENGTH: 8
<212> TYPE: PRT
<213> ORGANISM: Mus musculus

<400> SEQUENCE: 984

Gly Tyr Ala Phe Thr Asn Tyr Trp
1               5

<210> SEQ ID NO 985
<211> LENGTH: 7
<212> TYPE: PRT
<213> ORGANISM: Mus musculus

<400> SEQUENCE: 985

Gly Tyr Thr Phe Ser Asn Tyr
1               5

<210> SEQ ID NO 986
<211> LENGTH: 8
<212> TYPE: PRT
<213> ORGANISM: Mus musculus

<400> SEQUENCE: 986

Gly Tyr Thr Phe Ser Asn Tyr Trp
1               5

<210> SEQ ID NO 987
<211> LENGTH: 8
<212> TYPE: PRT
<213> ORGANISM: Mus musculus
```

<400> SEQUENCE: 987

Gly Tyr Thr Phe Thr Asp Tyr Gly
1               5

<210> SEQ ID NO 988
<211> LENGTH: 8
<212> TYPE: PRT
<213> ORGANISM: Mus musculus

<400> SEQUENCE: 988

Gly Tyr Thr Phe Thr Asp Tyr Ser
1               5

<210> SEQ ID NO 989
<211> LENGTH: 7
<212> TYPE: PRT
<213> ORGANISM: Mus musculus

<400> SEQUENCE: 989

Gly Tyr Thr Phe Thr Lys Tyr
1               5

<210> SEQ ID NO 990
<211> LENGTH: 7
<212> TYPE: PRT
<213> ORGANISM: Mus musculus

<400> SEQUENCE: 990

Gly Tyr Thr Phe Thr Asn Tyr
1               5

<210> SEQ ID NO 991
<211> LENGTH: 8
<212> TYPE: PRT
<213> ORGANISM: Mus musculus

<400> SEQUENCE: 991

Gly Tyr Thr Phe Thr Arg Phe Trp
1               5

<210> SEQ ID NO 992
<211> LENGTH: 8
<212> TYPE: PRT
<213> ORGANISM: Mus musculus

<400> SEQUENCE: 992

Gly Tyr Thr Phe Thr Arg Tyr Trp
1               5

<210> SEQ ID NO 993
<211> LENGTH: 8
<212> TYPE: PRT
<213> ORGANISM: Mus musculus

<400> SEQUENCE: 993

Gly Tyr Thr Phe Thr Thr Ser Thr
1               5

<210> SEQ ID NO 994
<211> LENGTH: 8
<212> TYPE: PRT
<213> ORGANISM: Mus musculus

<400> SEQUENCE: 994

Gly Tyr Thr Ser Thr Ala Tyr Trp
1               5

<210> SEQ ID NO 995
<211> LENGTH: 8
<212> TYPE: PRT
<213> ORGANISM: Mus musculus

<400> SEQUENCE: 995

Gly Tyr Thr Ser Thr Gly Tyr Trp
1               5

<210> SEQ ID NO 996
<211> LENGTH: 7
<212> TYPE: PRT
<213> ORGANISM: Mus musculus

<400> SEQUENCE: 996

Gly Tyr Thr Ser Thr Asn Tyr
1               5

<210> SEQ ID NO 997
<211> LENGTH: 8
<212> TYPE: PRT
<213> ORGANISM: Mus musculus

<400> SEQUENCE: 997

Gly Tyr Thr Ser Thr Asn Tyr Trp
1               5

<210> SEQ ID NO 998
<211> LENGTH: 9
<212> TYPE: PRT
<213> ORGANISM: Mus musculus

<400> SEQUENCE: 998

His Gln Leu Val Glu Tyr Pro Tyr Thr
1               5

<210> SEQ ID NO 999
<211> LENGTH: 9
<212> TYPE: PRT
<213> ORGANISM: Mus musculus

<400> SEQUENCE: 999

His Gln Arg Gly Ser Tyr Pro Trp Thr
1               5

<210> SEQ ID NO 1000
<211> LENGTH: 9
<212> TYPE: PRT
<213> ORGANISM: Mus musculus

<400> SEQUENCE: 1000

His Gln Arg Ser Gly Tyr Ser Tyr Thr
1               5

<210> SEQ ID NO 1001
<211> LENGTH: 9
<212> TYPE: PRT
<213> ORGANISM: Mus musculus

<400> SEQUENCE: 1001

His Gln Tyr His Arg Ser Pro Pro Thr

```
1               5

<210> SEQ ID NO 1002
<211> LENGTH: 3
<212> TYPE: PRT
<213> ORGANISM: Mus musculus

<400> SEQUENCE: 1002

His Thr Ser
1

<210> SEQ ID NO 1003
<211> LENGTH: 8
<212> TYPE: PRT
<213> ORGANISM: Mus musculus

<400> SEQUENCE: 1003

Ile Asp Pro Asp Asn Gly Glu Thr
1               5

<210> SEQ ID NO 1004
<211> LENGTH: 8
<212> TYPE: PRT
<213> ORGANISM: Mus musculus

<400> SEQUENCE: 1004

Ile Asp Pro Glu Asn Gly Asp Thr
1               5

<210> SEQ ID NO 1005
<211> LENGTH: 17
<212> TYPE: PRT
<213> ORGANISM: Mus musculus

<400> SEQUENCE: 1005

Ile Glu Trp Ile Lys Gln Arg Pro Gly His Gly Leu Glu Trp Ile Gly
1               5                   10                  15

Glu

<210> SEQ ID NO 1006
<211> LENGTH: 17
<212> TYPE: PRT
<213> ORGANISM: Mus musculus

<400> SEQUENCE: 1006

Ile Glu Trp Ile Lys Gln Arg Pro Gly His Gly Leu Glu Trp Val Gly
1               5                   10                  15

Glu

<210> SEQ ID NO 1007
<211> LENGTH: 17
<212> TYPE: PRT
<213> ORGANISM: Mus musculus

<400> SEQUENCE: 1007

Ile Gly Trp Ile Lys Gln Arg Pro Gly His Gly Leu Glu Trp Ile Gly
1               5                   10                  15

Asp

<210> SEQ ID NO 1008
<211> LENGTH: 17
<212> TYPE: PRT
<213> ORGANISM: Mus musculus
```

```
<400> SEQUENCE: 1008

Ile Gly Trp Val Lys Leu Arg Pro Gly His Gly Leu Glu Trp Ile Gly
1               5                   10                  15

Asp

<210> SEQ ID NO 1009
<211> LENGTH: 17
<212> TYPE: PRT
<213> ORGANISM: Mus musculus

<400> SEQUENCE: 1009

Ile Gly Trp Val Lys Gln Arg Pro Gly His Asp Leu Glu Trp Ile Gly
1               5                   10                  15

Asp

<210> SEQ ID NO 1010
<211> LENGTH: 17
<212> TYPE: PRT
<213> ORGANISM: Mus musculus

<400> SEQUENCE: 1010

Ile Gly Trp Val Lys Gln Arg Pro Gly His Gly Leu Glu Trp Ile Gly
1               5                   10                  15

Asp

<210> SEQ ID NO 1011
<211> LENGTH: 17
<212> TYPE: PRT
<213> ORGANISM: Mus musculus

<400> SEQUENCE: 1011

Ile Gly Trp Val Lys Gln Arg Pro Gly His Gly Leu Glu Trp Val Gly
1               5                   10                  15

Asp

<210> SEQ ID NO 1012
<211> LENGTH: 8
<212> TYPE: PRT
<213> ORGANISM: Mus musculus

<400> SEQUENCE: 1012

Ile His Pro Gly Gly Asp Tyr Ser
1               5

<210> SEQ ID NO 1013
<211> LENGTH: 8
<212> TYPE: PRT
<213> ORGANISM: Mus musculus

<400> SEQUENCE: 1013

Ile His Pro Gly Gly Asp Tyr Thr
1               5

<210> SEQ ID NO 1014
<211> LENGTH: 8
<212> TYPE: PRT
<213> ORGANISM: Mus musculus

<400> SEQUENCE: 1014

Ile His Pro Gly Gly Gly Tyr Ile
1               5
```

```
<210> SEQ ID NO 1015
<211> LENGTH: 8
<212> TYPE: PRT
<213> ORGANISM: Mus musculus

<400> SEQUENCE: 1015

Ile His Pro Gly Gly Gly Tyr Thr
1               5

<210> SEQ ID NO 1016
<211> LENGTH: 8
<212> TYPE: PRT
<213> ORGANISM: Mus musculus

<400> SEQUENCE: 1016

Ile His Pro Gly Gly Ser Tyr Thr
1               5

<210> SEQ ID NO 1017
<211> LENGTH: 17
<212> TYPE: PRT
<213> ORGANISM: Mus musculus

<400> SEQUENCE: 1017

Ile His Trp Val Lys Gln Arg Pro Glu Gln Gly Leu Glu Trp Ile Gly
1               5                   10                  15

Trp

<210> SEQ ID NO 1018
<211> LENGTH: 17
<212> TYPE: PRT
<213> ORGANISM: Mus musculus

<400> SEQUENCE: 1018

Ile His Trp Val Lys Gln Arg Pro Gly Gln Asp Leu Glu Trp Ile Gly
1               5                   10                  15

Tyr

<210> SEQ ID NO 1019
<211> LENGTH: 17
<212> TYPE: PRT
<213> ORGANISM: Mus musculus

<400> SEQUENCE: 1019

Ile His Trp Val Lys Gln Arg Pro Gly Gln Asp Leu Glu Trp Ile Gly
1               5                   10                  15

Tyr

<210> SEQ ID NO 1020
<211> LENGTH: 8
<212> TYPE: PRT
<213> ORGANISM: Mus musculus

<400> SEQUENCE: 1020

Ile Ile Thr Tyr Ser Gly Asp Ala
1               5

<210> SEQ ID NO 1021
<211> LENGTH: 8
<212> TYPE: PRT
<213> ORGANISM: Mus musculus
```

```
<400> SEQUENCE: 1021

Ile Leu Pro Gly Ser Gly Phe Thr
1               5

<210> SEQ ID NO 1022
<211> LENGTH: 8
<212> TYPE: PRT
<213> ORGANISM: Mus musculus

<400> SEQUENCE: 1022

Ile Leu Pro Gly Ser Gly Tyr Thr
1               5

<210> SEQ ID NO 1023
<211> LENGTH: 8
<212> TYPE: PRT
<213> ORGANISM: Mus musculus

<400> SEQUENCE: 1023

Ile Asn Pro Gly Gly Gly Tyr Thr
1               5

<210> SEQ ID NO 1024
<211> LENGTH: 8
<212> TYPE: PRT
<213> ORGANISM: Mus musculus

<400> SEQUENCE: 1024

Ile Asn Pro Arg Ser Gly Tyr Thr
1               5

<210> SEQ ID NO 1025
<211> LENGTH: 8
<212> TYPE: PRT
<213> ORGANISM: Mus musculus

<400> SEQUENCE: 1025

Ile Asn Pro Arg Thr Asp Tyr Thr
1               5

<210> SEQ ID NO 1026
<211> LENGTH: 8
<212> TYPE: PRT
<213> ORGANISM: Mus musculus

<400> SEQUENCE: 1026

Ile Asn Pro Ser Ser Asp Tyr Thr
1               5

<210> SEQ ID NO 1027
<211> LENGTH: 8
<212> TYPE: PRT
<213> ORGANISM: Mus musculus

<400> SEQUENCE: 1027

Ile Asn Pro Ser Thr Asp Tyr Thr
1               5

<210> SEQ ID NO 1028
<211> LENGTH: 8
<212> TYPE: PRT
<213> ORGANISM: Mus musculus

<400> SEQUENCE: 1028
```

```
Ile Thr Pro Ser Thr Gly Tyr Thr
1               5

<210> SEQ ID NO 1029
<211> LENGTH: 8
<212> TYPE: PRT
<213> ORGANISM: Mus musculus
<220> FEATURE:
<221> NAME/KEY: misc_feature
<222> LOCATION: (2)..(2)
<223> OTHER INFORMATION: Xaa can be any naturally occurring amino acid

<400> SEQUENCE: 1029

Ile Xaa Thr Tyr Ser Gly Asp Val
1               5

<210> SEQ ID NO 1030
<211> LENGTH: 37
<212> TYPE: PRT
<213> ORGANISM: Mus musculus

<400> SEQUENCE: 1030

Ile Tyr Asn Gln Lys Phe Asp Lys Ala Thr Met Thr Val Asp Lys Ser
1               5                   10                  15

Ser Ser Thr Ala Tyr Leu Glu Leu Ala Arg Leu Thr Ser Glu Asp Ser
            20                  25                  30

Ala Ile Tyr Tyr Cys
            35

<210> SEQ ID NO 1031
<211> LENGTH: 37
<212> TYPE: PRT
<213> ORGANISM: Mus musculus

<400> SEQUENCE: 1031

Ile Tyr Asn Gln Lys Phe Gly Lys Ala Thr Met Thr Val Asp Lys Ser
1               5                   10                  15

Ser Ser Thr Ala Tyr Leu Glu Leu Ala Arg Leu Thr Ser Asp Asp Ser
            20                  25                  30

Ala Ile Tyr Tyr Cys
            35

<210> SEQ ID NO 1032
<211> LENGTH: 37
<212> TYPE: PRT
<213> ORGANISM: Mus musculus

<400> SEQUENCE: 1032

Ile Tyr Asn Gln Lys Phe Gly Lys Ala Thr Met Thr Val Asp Lys Ser
1               5                   10                  15

Ser Ser Thr Ala Tyr Leu Glu Leu Ala Arg Leu Thr Ser Glu Asp Ser
            20                  25                  30

Ala Ile Tyr Tyr Cys
            35

<210> SEQ ID NO 1033
<211> LENGTH: 38
<212> TYPE: PRT
<213> ORGANISM: Mus musculus

<400> SEQUENCE: 1033

Ile Tyr Asn Gln Lys Phe Lys Gly Lys Ala Thr Met Thr Val Asp Lys
1               5                   10                  15
```

```
Ser Ser Ser Thr Ala Tyr Leu Glu Leu Ala Arg Leu Thr Ser Asp Asp
            20                  25                  30

Ser Ala Ile Tyr Tyr Cys
            35

<210> SEQ ID NO 1034
<211> LENGTH: 38
<212> TYPE: PRT
<213> ORGANISM: Mus musculus

<400> SEQUENCE: 1034

Ile Tyr Asn Gln Lys Phe Lys Gly Lys Ala Thr Met Thr Val Asp Lys
1               5                   10                  15

Ser Ser Ser Thr Ala Tyr Leu Glu Leu Ala Arg Leu Thr Ser Glu Asp
            20                  25                  30

Ser Ala Ile Tyr Tyr Cys
            35

<210> SEQ ID NO 1035
<211> LENGTH: 8
<212> TYPE: PRT
<213> ORGANISM: Mus musculus

<400> SEQUENCE: 1035

Ile Tyr Pro Gly Gly Gly Tyr Ala
1               5

<210> SEQ ID NO 1036
<211> LENGTH: 11
<212> TYPE: PRT
<213> ORGANISM: Mus musculus

<400> SEQUENCE: 1036

Lys Ala Gly Gln Asn Val Gly Thr Asn Val Ala
1               5                   10

<210> SEQ ID NO 1037
<211> LENGTH: 11
<212> TYPE: PRT
<213> ORGANISM: Mus musculus

<400> SEQUENCE: 1037

Lys Ala Ser Gln Asn Val Gly Ile Asn Val Ala
1               5                   10

<210> SEQ ID NO 1038
<211> LENGTH: 11
<212> TYPE: PRT
<213> ORGANISM: Mus musculus

<400> SEQUENCE: 1038

Lys Ala Ser Gln Asn Val Gly Thr Asn Val Ala
1               5                   10

<210> SEQ ID NO 1039
<211> LENGTH: 11
<212> TYPE: PRT
<213> ORGANISM: Mus musculus

<400> SEQUENCE: 1039

Lys Ala Ser Gln Asn Val Gly Thr Asn Val Ala
1               5                   10
```

<210> SEQ ID NO 1040
<211> LENGTH: 11
<212> TYPE: PRT
<213> ORGANISM: Mus musculus

<400> SEQUENCE: 1040

Lys Ala Ser Gln Ser Val Gly Thr Asn Val Ala
1               5                   10

<210> SEQ ID NO 1041
<211> LENGTH: 31
<212> TYPE: PRT
<213> ORGANISM: Mus musculus

<400> SEQUENCE: 1041

Lys Ala Thr Phe Thr Ala Asp Thr Ser Ser Thr Thr Tyr Met Gln
1               5                   10                  15

Leu Ser Ser Leu Thr Ser Glu Asp Ser Ala Ile Tyr Phe Cys Thr
                20                  25                  30

<210> SEQ ID NO 1042
<211> LENGTH: 31
<212> TYPE: PRT
<213> ORGANISM: Mus musculus

<400> SEQUENCE: 1042

Lys Ala Thr Leu Thr Ala Asp Thr Phe Ser Ser Thr Ala Tyr Met Gln
1               5                   10                  15

Leu Ser Ser Leu Thr Ser Glu Asp Ser Ala Ile Tyr Tyr Cys Thr
                20                  25                  30

<210> SEQ ID NO 1043
<211> LENGTH: 31
<212> TYPE: PRT
<213> ORGANISM: Mus musculus

<400> SEQUENCE: 1043

Lys Ala Thr Leu Thr Ala Asp Thr Ser Ser Ser Thr Ala Asp Met Gln
1               5                   10                  15

Leu Ser Ser Leu Thr Ser Glu Asp Ser Ala Ile Tyr Tyr Cys Thr
                20                  25                  30

<210> SEQ ID NO 1044
<211> LENGTH: 31
<212> TYPE: PRT
<213> ORGANISM: Mus musculus

<400> SEQUENCE: 1044

Lys Ala Thr Leu Thr Ala Asp Thr Ser Ser Ser Thr Ala Tyr Met Asn
1               5                   10                  15

Leu Ser Ser Leu Thr Ser Glu Asp Ser Ala Ile Tyr Tyr Cys Thr
                20                  25                  30

<210> SEQ ID NO 1045
<211> LENGTH: 31
<212> TYPE: PRT
<213> ORGANISM: Mus musculus

<400> SEQUENCE: 1045

Lys Ala Thr Leu Thr Ala Asp Thr Ser Ser Ser Thr Ala Tyr Met Gln
1               5                   10                  15

Leu Ser Ser Leu Thr Ser Glu Asp Ser Ala Ile Tyr Tyr Cys Thr

<210> SEQ ID NO 1046
<211> LENGTH: 31
<212> TYPE: PRT
<213> ORGANISM: Mus musculus

<400> SEQUENCE: 1046

Lys Ala Thr Leu Thr Ala Asp Thr Ser Ser Thr Ala Tyr Met Gln
1               5                   10                  15

Leu Ser Ser Leu Thr Ser Glu Asp Ser Ala Ile Tyr Tyr Cys Val
            20                  25                  30

<210> SEQ ID NO 1047
<211> LENGTH: 31
<212> TYPE: PRT
<213> ORGANISM: Mus musculus

<400> SEQUENCE: 1047

Lys Ala Thr Leu Thr Ala Asp Thr Ser Ser Thr Ala Tyr Met Gln
1               5                   10                  15

Leu Ser Ser Leu Thr Ser Glu Gly Ser Ala Ile Tyr Tyr Cys Thr
            20                  25                  30

<210> SEQ ID NO 1048
<211> LENGTH: 31
<212> TYPE: PRT
<213> ORGANISM: Mus musculus

<400> SEQUENCE: 1048

Lys Ala Thr Leu Thr Ala Asp Thr Ser Ser Thr Ala Tyr Met Gln
1               5                   10                  15

Leu Ser Ser Leu Thr Ser Gly Asp Ser Ala Ile Tyr Tyr Cys Val
            20                  25                  30

<210> SEQ ID NO 1049
<211> LENGTH: 31
<212> TYPE: PRT
<213> ORGANISM: Mus musculus

<400> SEQUENCE: 1049

Lys Ala Thr Leu Thr Ala Asp Thr Ser Ser Thr Ala Tyr Met Ser
1               5                   10                  15

Leu Ser Ser Leu Thr Ser Glu Asp Ser Ala Ile Tyr Tyr Cys Thr
            20                  25                  30

<210> SEQ ID NO 1050
<211> LENGTH: 31
<212> TYPE: PRT
<213> ORGANISM: Mus musculus

<400> SEQUENCE: 1050

Lys Ala Thr Leu Thr Ala Gly Thr Ser Ser Thr Ala Tyr Met Gln
1               5                   10                  15

Leu Ser Ser Leu Thr Ser Glu Asp Ser Ala Ile Tyr Tyr Cys Val
            20                  25                  30

<210> SEQ ID NO 1051
<211> LENGTH: 36
<212> TYPE: PRT
<213> ORGANISM: Mus musculus

<400> SEQUENCE: 1051

```
Lys Leu Ala Ser Gly Val Pro Ala Arg Phe Ser Gly Ser Gly Ser Gly
1               5                   10                  15

Thr Ser Tyr Ser Leu Ser Ile Ser Ser Met Glu Thr Glu Asp Ala Ala
                20                  25                  30

Thr Tyr Tyr Cys
            35

<210> SEQ ID NO 1052
<211> LENGTH: 36
<212> TYPE: PRT
<213> ORGANISM: Mus musculus

<400> SEQUENCE: 1052

Lys Leu Ala Ser Gly Val Pro Ala Arg Phe Ser Gly Ser Gly Ser Gly
1               5                   10                  15

Thr Ser Tyr Ser Leu Thr Ile Ser Ser Met Glu Ala Glu Asp Ala Ala
                20                  25                  30

Thr Tyr Tyr Cys
            35

<210> SEQ ID NO 1053
<211> LENGTH: 36
<212> TYPE: PRT
<213> ORGANISM: Mus musculus

<400> SEQUENCE: 1053

Lys Leu Asp Pro Gly Ile Pro Asp Arg Phe Ser Gly Ser Gly Ser Glu
1               5                   10                  15

Thr Asp Phe Thr Leu Lys Ile Ser Arg Val Glu Ala Glu Asp Leu Gly
                20                  25                  30

Val Tyr Tyr Cys
            35

<210> SEQ ID NO 1054
<211> LENGTH: 36
<212> TYPE: PRT
<213> ORGANISM: Mus musculus

<400> SEQUENCE: 1054

Lys Leu Asp Ser Gly Val Pro Asp Gly Phe Thr Gly Ser Gly Ser Gly
1               5                   10                  15

Thr Asp Phe Thr Leu Lys Ile Ser Arg Val Glu Ala Glu Asp Leu Gly
                20                  25                  30

Val Tyr Tyr Cys
            35

<210> SEQ ID NO 1055
<211> LENGTH: 36
<212> TYPE: PRT
<213> ORGANISM: Mus musculus

<400> SEQUENCE: 1055

Lys Leu Asp Ser Gly Val Pro Asp Arg Phe Thr Gly Ser Gly Ser Gly
1               5                   10                  15

Thr Asp Phe Thr Leu Lys Ile Asn Arg Val Glu Ala Glu Asp Leu Gly
                20                  25                  30

Val Tyr Tyr Cys
            35
```

-continued

<210> SEQ ID NO 1056
<211> LENGTH: 36
<212> TYPE: PRT
<213> ORGANISM: Mus musculus

<400> SEQUENCE: 1056

Lys Leu Asp Ser Gly Val Pro Asp Arg Phe Thr Gly Ser Gly Ser Gly
1               5                   10                  15

Thr Asp Phe Thr Leu Lys Ile Ser Arg Val Glu Ala Glu Asp Leu Gly
            20                  25                  30

Val Tyr Tyr Cys
        35

<210> SEQ ID NO 1057
<211> LENGTH: 6
<212> TYPE: PRT
<213> ORGANISM: Mus musculus

<400> SEQUENCE: 1057

Lys Asn Ser Tyr Ser Tyr
1               5

<210> SEQ ID NO 1058
<211> LENGTH: 9
<212> TYPE: PRT
<213> ORGANISM: Mus musculus

<400> SEQUENCE: 1058

Lys Gln Ala Tyr Asp Val Pro Trp Thr
1               5

<210> SEQ ID NO 1059
<211> LENGTH: 6
<212> TYPE: PRT
<213> ORGANISM: Mus musculus

<400> SEQUENCE: 1059

Lys Ser Ile Ser Lys Tyr
1               5

<210> SEQ ID NO 1060
<211> LENGTH: 11
<212> TYPE: PRT
<213> ORGANISM: Mus musculus

<400> SEQUENCE: 1060

Lys Ser Leu Leu His Ser Asn Gly Asn Thr Tyr
1               5                   10

<210> SEQ ID NO 1061
<211> LENGTH: 11
<212> TYPE: PRT
<213> ORGANISM: Mus musculus

<400> SEQUENCE: 1061

Lys Ser Leu Leu Tyr Lys Asp Gly Lys Thr Tyr
1               5                   10

<210> SEQ ID NO 1062
<211> LENGTH: 3
<212> TYPE: PRT
<213> ORGANISM: Mus musculus

<400> SEQUENCE: 1062

Lys Val Ser
1

<210> SEQ ID NO 1063
<211> LENGTH: 3
<212> TYPE: PRT
<213> ORGANISM: Mus musculus

<400> SEQUENCE: 1063

Leu Ala Ser
1

<210> SEQ ID NO 1064
<211> LENGTH: 17
<212> TYPE: PRT
<213> ORGANISM: Mus musculus

<400> SEQUENCE: 1064

Leu Ala Trp Tyr Gln Glu Lys Pro Gly Lys Thr Asn Lys Leu Leu Ile
1               5                   10                  15

Tyr

<210> SEQ ID NO 1065
<211> LENGTH: 17
<212> TYPE: PRT
<213> ORGANISM: Mus musculus

<400> SEQUENCE: 1065

Leu Ala Trp Tyr Gln Gln Lys Pro Gly Asn Ala Pro Arg Leu Leu Ile
1               5                   10                  15

Ser

<210> SEQ ID NO 1066
<211> LENGTH: 17
<212> TYPE: PRT
<213> ORGANISM: Mus musculus

<400> SEQUENCE: 1066

Leu Ala Trp Tyr Gln Gln Lys Pro Gly Gln Ser Pro Lys Leu Leu Ile
1               5                   10                  15

Tyr

<210> SEQ ID NO 1067
<211> LENGTH: 17
<212> TYPE: PRT
<213> ORGANISM: Mus musculus

<400> SEQUENCE: 1067

Leu Ala Trp Tyr Gln Gln Lys Pro Gly Gln Ser Pro Lys Leu Leu Val
1               5                   10                  15

Tyr

<210> SEQ ID NO 1068
<211> LENGTH: 17
<212> TYPE: PRT
<213> ORGANISM: Mus musculus

<400> SEQUENCE: 1068

Leu Ala Trp Tyr Gln Gln Lys Gln Gly Lys Ser Pro Gln Leu Leu Ile
1               5                   10                  15

Tyr

```
<210> SEQ ID NO 1069
<211> LENGTH: 17
<212> TYPE: PRT
<213> ORGANISM: Mus musculus

<400> SEQUENCE: 1069

Leu Ala Trp Tyr Gln Gln Lys Gln Gly Lys Ser Pro Gln Leu Leu Val
1               5                   10                  15

Tyr

<210> SEQ ID NO 1070
<211> LENGTH: 17
<212> TYPE: PRT
<213> ORGANISM: Mus musculus

<400> SEQUENCE: 1070

Leu Glu Trp Phe Gln Gln Lys Gln Gly Lys Ser Pro Gln Leu Leu Val
1               5                   10                  15

Tyr

<210> SEQ ID NO 1071
<211> LENGTH: 17
<212> TYPE: PRT
<213> ORGANISM: Mus musculus

<400> SEQUENCE: 1071

Leu Glu Trp Tyr Leu Gln Lys Pro Gly Gln Ser Pro Lys Leu Leu Ile
1               5                   10                  15

Tyr

<210> SEQ ID NO 1072
<211> LENGTH: 17
<212> TYPE: PRT
<213> ORGANISM: Mus musculus

<400> SEQUENCE: 1072

Leu Glu Trp Tyr Gln Gln Lys Gln Gly Lys Ser Pro Gln Leu Leu Val
1               5                   10                  15

Tyr

<210> SEQ ID NO 1073
<211> LENGTH: 17
<212> TYPE: PRT
<213> ORGANISM: Mus musculus

<400> SEQUENCE: 1073

Leu Glu Trp Tyr Gln Gln Lys Gln Gly Lys Ser Pro Gln Leu Leu Val
1               5                   10                  15

Tyr

<210> SEQ ID NO 1074
<211> LENGTH: 17
<212> TYPE: PRT
<213> ORGANISM: Mus musculus

<400> SEQUENCE: 1074

Leu Gly Trp Ile Lys Gln Arg Pro Gly His Gly Leu Glu Trp Ile Gly
1               5                   10                  15

Asp
```

```
<210> SEQ ID NO 1075
<211> LENGTH: 17
<212> TYPE: PRT
<213> ORGANISM: Mus musculus

<400> SEQUENCE: 1075

Leu Gly Trp Val Lys Gln Arg Pro Gly His Gly Leu Glu Trp Ile Gly
1               5                   10                  15

Asp

<210> SEQ ID NO 1076
<211> LENGTH: 17
<212> TYPE: PRT
<213> ORGANISM: Mus musculus

<400> SEQUENCE: 1076

Leu His Trp Tyr Leu Gln Lys Pro Gly Gln Ser Pro Lys Leu Leu Ile
1               5                   10                  15

Tyr

<210> SEQ ID NO 1077
<211> LENGTH: 17
<212> TYPE: PRT
<213> ORGANISM: Mus musculus

<400> SEQUENCE: 1077

Leu His Trp Tyr Gln Gln Lys Pro Gly Ser Ser Pro Lys Leu Trp Ile
1               5                   10                  15

Tyr

<210> SEQ ID NO 1078
<211> LENGTH: 17
<212> TYPE: PRT
<213> ORGANISM: Mus musculus

<400> SEQUENCE: 1078

Leu His Trp Tyr Gln Gln Lys Ser Glu Thr Ser Pro Lys Pro Trp Ile
1               5                   10                  15

Tyr

<210> SEQ ID NO 1079
<211> LENGTH: 17
<212> TYPE: PRT
<213> ORGANISM: Mus musculus

<400> SEQUENCE: 1079

Leu His Trp Tyr Gln Gln Lys Ser His Glu Ser Pro Arg Leu Leu Ile
1               5                   10                  15

Lys

<210> SEQ ID NO 1080
<211> LENGTH: 17
<212> TYPE: PRT
<213> ORGANISM: Mus musculus

<400> SEQUENCE: 1080

Leu Lys Trp Tyr Leu Gln Lys Pro Gly Gln Ser Pro Lys Leu Leu Ile
1               5                   10                  15

Tyr

<210> SEQ ID NO 1081
```

```
<211> LENGTH: 3
<212> TYPE: PRT
<213> ORGANISM: Mus musculus

<400> SEQUENCE: 1081

Leu Met Ser
1

<210> SEQ ID NO 1082
<211> LENGTH: 17
<212> TYPE: PRT
<213> ORGANISM: Mus musculus

<400> SEQUENCE: 1082

Leu Asn Cys Phe Leu Gln Arg Pro Gly Gln Ser Pro Gln Leu Leu Ile
1               5                   10                  15

Tyr

<210> SEQ ID NO 1083
<211> LENGTH: 17
<212> TYPE: PRT
<213> ORGANISM: Mus musculus

<400> SEQUENCE: 1083

Leu Asn Trp Leu Leu Gln Arg Pro Gly Gln Ser Pro Lys Arg Leu Ile
1               5                   10                  15

Tyr

<210> SEQ ID NO 1084
<211> LENGTH: 17
<212> TYPE: PRT
<213> ORGANISM: Mus musculus

<400> SEQUENCE: 1084

Leu Asn Trp Leu Gln Gln Glu Pro Asp Gly Thr Ile Lys Arg Leu Ile
1               5                   10                  15

Ser

<210> SEQ ID NO 1085
<211> LENGTH: 17
<212> TYPE: PRT
<213> ORGANISM: Mus musculus

<400> SEQUENCE: 1085

Leu Asn Trp Leu Gln Gln Glu Pro Asp Gly Thr Ile Lys Arg Leu Ile
1               5                   10                  15

Tyr

<210> SEQ ID NO 1086
<211> LENGTH: 17
<212> TYPE: PRT
<213> ORGANISM: Mus musculus

<400> SEQUENCE: 1086

Leu Asn Trp Leu Gln Gln Arg Pro Gly Gln Ala Pro Lys His Leu Met
1               5                   10                  15

Tyr

<210> SEQ ID NO 1087
<211> LENGTH: 17
<212> TYPE: PRT
```

<400> SEQUENCE: 1087

Leu Asn Trp Tyr Leu Gln Lys Pro Gly Gln Ser Pro Gln Leu Leu Ile
1               5                   10                  15

Tyr

<210> SEQ ID NO 1088
<211> LENGTH: 17
<212> TYPE: PRT
<213> ORGANISM: Mus musculus

<400> SEQUENCE: 1088

Leu Asn Trp Tyr Gln Gln Lys Pro Asp Gly Thr Val Lys Leu Leu Ile
1               5                   10                  15

Tyr

<210> SEQ ID NO 1089
<211> LENGTH: 17
<212> TYPE: PRT
<213> ORGANISM: Mus musculus

<400> SEQUENCE: 1089

Leu Asn Trp Tyr Gln Gln Lys Ser Asp Gly Thr Val Lys Leu Leu Ile
1               5                   10                  15

Tyr

<210> SEQ ID NO 1090
<211> LENGTH: 17
<212> TYPE: PRT
<213> ORGANISM: Mus musculus

<400> SEQUENCE: 1090

Leu Asn Trp Tyr Gln Gln Arg Pro Asp Gly Thr Val Lys Leu Leu Ile
1               5                   10                  15

Tyr

<210> SEQ ID NO 1091
<211> LENGTH: 16
<212> TYPE: PRT
<213> ORGANISM: Mus musculus

<400> SEQUENCE: 1091

Leu Asn Tyr Gln Gln Lys Pro Asp Gly Thr Val Lys Leu Leu Ile Tyr
1               5                   10                  15

<210> SEQ ID NO 1092
<211> LENGTH: 10
<212> TYPE: PRT
<213> ORGANISM: Mus musculus

<400> SEQUENCE: 1092

Leu Gln Gly Thr Tyr Tyr Pro Thr Trp Thr
1               5                   10

<210> SEQ ID NO 1093
<211> LENGTH: 9
<212> TYPE: PRT
<213> ORGANISM: Mus musculus

<400> SEQUENCE: 1093

Leu Gln His Trp Asn Tyr Pro Tyr Thr
1               5

<210> SEQ ID NO 1094
<211> LENGTH: 9
<212> TYPE: PRT
<213> ORGANISM: Mus musculus

<400> SEQUENCE: 1094

Leu Gln Ser Asp Asn Met Pro Leu Thr
1               5

<210> SEQ ID NO 1095
<211> LENGTH: 9
<212> TYPE: PRT
<213> ORGANISM: Mus musculus

<400> SEQUENCE: 1095

Leu Gln Ser Asp Asn Met Pro Tyr Thr
1               5

<210> SEQ ID NO 1096
<211> LENGTH: 9
<212> TYPE: PRT
<213> ORGANISM: Mus musculus

<400> SEQUENCE: 1096

Leu Gln Val Thr His Val Pro Phe Ala
1               5

<210> SEQ ID NO 1097
<211> LENGTH: 9
<212> TYPE: PRT
<213> ORGANISM: Mus musculus

<400> SEQUENCE: 1097

Leu Gln Tyr Ala Ser Ser Pro Phe Thr
1               5

<210> SEQ ID NO 1098
<211> LENGTH: 9
<212> TYPE: PRT
<213> ORGANISM: Mus musculus

<400> SEQUENCE: 1098

Leu Gln Tyr Ala Ser Ser Pro His Thr
1               5

<210> SEQ ID NO 1099
<211> LENGTH: 9
<212> TYPE: PRT
<213> ORGANISM: Mus musculus

<400> SEQUENCE: 1099

Leu Gln Tyr Ala Ser Ser Pro Arg Thr
1               5

<210> SEQ ID NO 1100
<211> LENGTH: 9
<212> TYPE: PRT
<213> ORGANISM: Mus musculus

<400> SEQUENCE: 1100

Leu Gln Tyr Ala Ser Ser Pro Trp Thr
1               5

```
<210> SEQ ID NO 1101
<211> LENGTH: 9
<212> TYPE: PRT
<213> ORGANISM: Mus musculus

<400> SEQUENCE: 1101

Leu Gln Tyr Ala Ser Ser Pro Tyr Thr
1               5

<210> SEQ ID NO 1102
<211> LENGTH: 9
<212> TYPE: PRT
<213> ORGANISM: Mus musculus

<400> SEQUENCE: 1102

Leu Gln Tyr Ala Ser Tyr Pro Arg Thr
1               5

<210> SEQ ID NO 1103
<211> LENGTH: 9
<212> TYPE: PRT
<213> ORGANISM: Mus musculus

<400> SEQUENCE: 1103

Leu Gln Tyr Ala Ser Tyr Pro Tyr Thr
1               5

<210> SEQ ID NO 1104
<211> LENGTH: 9
<212> TYPE: PRT
<213> ORGANISM: Mus musculus

<400> SEQUENCE: 1104

Leu Gln Tyr Ala Thr Phe Pro Tyr Thr
1               5

<210> SEQ ID NO 1105
<211> LENGTH: 9
<212> TYPE: PRT
<213> ORGANISM: Mus musculus

<400> SEQUENCE: 1105

Leu Gln Tyr Asp Glu Phe Pro Trp Thr
1               5

<210> SEQ ID NO 1106
<211> LENGTH: 9
<212> TYPE: PRT
<213> ORGANISM: Mus musculus

<400> SEQUENCE: 1106

Leu Gln Tyr Asp Glu Phe Pro Tyr Thr
1               5

<210> SEQ ID NO 1107
<211> LENGTH: 9
<212> TYPE: PRT
<213> ORGANISM: Mus musculus

<400> SEQUENCE: 1107

Leu Gln Tyr Ile Ser Tyr Pro Arg Thr
1               5

<210> SEQ ID NO 1108
<211> LENGTH: 17
```

```
<212> TYPE: PRT
<213> ORGANISM: Mus musculus

<400> SEQUENCE: 1108

Leu Arg Trp Tyr Leu Gln Lys Pro Gly Gln Ser Pro Lys Leu Leu Ile
1               5                   10                  15

Tyr

<210> SEQ ID NO 1109
<211> LENGTH: 17
<212> TYPE: PRT
<213> ORGANISM: Mus musculus

<400> SEQUENCE: 1109

Leu Ser Trp Phe Gln Gln Lys Pro Gly Lys Ser Pro Lys Thr Leu Ile
1               5                   10                  15

Tyr

<210> SEQ ID NO 1110
<211> LENGTH: 17
<212> TYPE: PRT
<213> ORGANISM: Mus musculus

<400> SEQUENCE: 1110

Leu Ser Trp Phe Gln Gln Lys Pro Gly Lys Ser Pro Gln Thr Leu Ile
1               5                   10                  15

Tyr

<210> SEQ ID NO 1111
<211> LENGTH: 17
<212> TYPE: PRT
<213> ORGANISM: Mus musculus

<400> SEQUENCE: 1111

Leu Ser Trp Leu Gln Gln Lys Pro Asp Gly Thr Ile Lys Arg Leu Ile
1               5                   10                  15

Tyr

<210> SEQ ID NO 1112
<211> LENGTH: 17
<212> TYPE: PRT
<213> ORGANISM: Mus musculus

<400> SEQUENCE: 1112

Leu Ser Trp Leu Gln Gln Lys Pro Asp Gly Thr Ile Lys Arg Leu Thr
1               5                   10                  15

Tyr

<210> SEQ ID NO 1113
<211> LENGTH: 17
<212> TYPE: PRT
<213> ORGANISM: Mus musculus

<400> SEQUENCE: 1113

Leu Ser Trp Tyr Gln Gln Lys Pro Asp Gly Thr Ile Lys Leu Leu Ile
1               5                   10                  15

Tyr

<210> SEQ ID NO 1114
<211> LENGTH: 12
<212> TYPE: PRT
```

```
<213> ORGANISM: Mus musculus

<400> SEQUENCE: 1114

Leu Thr Phe Gly Ala Gly Thr Lys Leu Glu Ile Lys
1               5                   10

<210> SEQ ID NO 1115
<211> LENGTH: 3
<212> TYPE: PRT
<213> ORGANISM: Mus musculus

<400> SEQUENCE: 1115

Leu Thr Pro
1

<210> SEQ ID NO 1116
<211> LENGTH: 3
<212> TYPE: PRT
<213> ORGANISM: Mus musculus

<400> SEQUENCE: 1116

Leu Val Ser
1

<210> SEQ ID NO 1117
<211> LENGTH: 17
<212> TYPE: PRT
<213> ORGANISM: Mus musculus

<400> SEQUENCE: 1117

Leu Val Trp Tyr Gln Gln Lys Gln Gly Lys Ser Pro His Leu Leu Val
1               5                   10                  15

Tyr

<210> SEQ ID NO 1118
<211> LENGTH: 37
<212> TYPE: PRT
<213> ORGANISM: Mus musculus

<400> SEQUENCE: 1118

Leu Tyr Asn Gln Lys Phe Gly Lys Ala Thr Met Thr Val Asp Lys Ser
1               5                   10                  15

Ser Ser Thr Ala Tyr Leu Glu Leu Ala Arg Leu Thr Ser Asp Asp Ser
                20                  25                  30

Ala Ile Tyr Tyr Cys
                35

<210> SEQ ID NO 1119
<211> LENGTH: 38
<212> TYPE: PRT
<213> ORGANISM: Mus musculus

<400> SEQUENCE: 1119

Leu Tyr Asn Gln Lys Phe Lys Gly Lys Ala Thr Met Thr Val Asp Lys
1               5                   10                  15

Ser Ser Ser Thr Ala Tyr Leu Glu Leu Ala Arg Leu Thr Ser Asp Asp
                20                  25                  30

Ser Ala Ile Tyr Tyr Cys
                35

<210> SEQ ID NO 1120
<211> LENGTH: 38
```

<212> TYPE: PRT
<213> ORGANISM: Mus musculus

<400> SEQUENCE: 1120

Leu Tyr Asn Gln Lys Phe Lys Gly Lys Ala Thr Met Thr Val Asp Lys
1               5                   10                  15

Ser Ser Ser Thr Ala Tyr Leu Glu Leu Ala Arg Leu Thr Ser Glu Asp
            20                  25                  30

Ser Ala Ile Tyr Tyr Cys
        35

<210> SEQ ID NO 1121
<211> LENGTH: 17
<212> TYPE: PRT
<213> ORGANISM: Mus musculus

<400> SEQUENCE: 1121

Leu Tyr Trp Phe Leu Gln Arg Pro Gly Gln Ser Pro Gln Leu Leu Ile
1               5                   10                  15

Tyr

<210> SEQ ID NO 1122
<211> LENGTH: 3
<212> TYPE: PRT
<213> ORGANISM: Mus musculus

<400> SEQUENCE: 1122

Met Ala Ser
1

<210> SEQ ID NO 1123
<211> LENGTH: 17
<212> TYPE: PRT
<213> ORGANISM: Mus musculus

<400> SEQUENCE: 1123

Met His Trp Val Lys Gln Arg His Gly Gln Gly Leu Glu Trp Ile Gly
1               5                   10                  15

Asn

<210> SEQ ID NO 1124
<211> LENGTH: 17
<212> TYPE: PRT
<213> ORGANISM: Mus musculus

<400> SEQUENCE: 1124

Met His Trp Val Lys Gln Arg Pro Glu Gln Gly Leu Glu Trp Ile Gly
1               5                   10                  15

Trp

<210> SEQ ID NO 1125
<211> LENGTH: 17
<212> TYPE: PRT
<213> ORGANISM: Mus musculus

<400> SEQUENCE: 1125

Met His Trp Val Lys Gln Arg Pro Gly Gln Asp Leu Glu Trp Ile Gly
1               5                   10                  15

Tyr

<210> SEQ ID NO 1126

```
<211> LENGTH: 17
<212> TYPE: PRT
<213> ORGANISM: Mus musculus

<400> SEQUENCE: 1126

Met His Trp Val Lys Gln Ser His Ala Lys Ser Leu Glu Trp Ile Gly
1               5                   10                  15

Val

<210> SEQ ID NO 1127
<211> LENGTH: 17
<212> TYPE: PRT
<213> ORGANISM: Mus musculus

<400> SEQUENCE: 1127

Met His Trp Val Arg Gln Ser His Ala Lys Asn Leu Glu Trp Ile Gly
1               5                   10                  15

Val

<210> SEQ ID NO 1128
<211> LENGTH: 17
<212> TYPE: PRT
<213> ORGANISM: Mus musculus

<400> SEQUENCE: 1128

Met His Trp Val Arg Gln Ser His Ala Lys Ser Leu Glu Trp Ile Gly
1               5                   10                  15

Val

<210> SEQ ID NO 1129
<211> LENGTH: 17
<212> TYPE: PRT
<213> ORGANISM: Mus musculus

<400> SEQUENCE: 1129

Met His Trp Tyr Gln Gln Lys Pro Gly Gln Pro Pro Lys Leu Leu Ile
1               5                   10                  15

Tyr

<210> SEQ ID NO 1130
<211> LENGTH: 17
<212> TYPE: PRT
<213> ORGANISM: Mus musculus

<400> SEQUENCE: 1130

Met His Trp Tyr Gln Gln Lys Pro Gly Thr Ser Pro Lys Arg Trp Ile
1               5                   10                  15

Tyr

<210> SEQ ID NO 1131
<211> LENGTH: 17
<212> TYPE: PRT
<213> ORGANISM: Mus musculus

<400> SEQUENCE: 1131

Met His Trp Tyr Gln Gln Lys Ser Gly Thr Ser Pro Lys Arg Trp Ile
1               5                   10                  15

Tyr

<210> SEQ ID NO 1132
<211> LENGTH: 26
```

```
<212> TYPE: PRT
<213> ORGANISM: Mus musculus

<400> SEQUENCE: 1132

Met Leu Val Met Thr Gln Thr Pro Leu Ser Leu Pro Val Ser Leu Gly
1               5                   10                  15

Asp Gln Ala Ser Ile Ser Cys Arg Ser Ser
            20                  25

<210> SEQ ID NO 1133
<211> LENGTH: 17
<212> TYPE: PRT
<213> ORGANISM: Mus musculus

<400> SEQUENCE: 1133

Met Asn Trp Phe Gln Lys Lys Pro Gly Gln Pro Pro Lys Leu Leu Ile
1               5                   10                  15

Tyr

<210> SEQ ID NO 1134
<211> LENGTH: 17
<212> TYPE: PRT
<213> ORGANISM: Mus musculus

<400> SEQUENCE: 1134

Met Asn Trp Tyr Gln Gln Lys Pro Gly Glu Pro Pro Lys Leu Leu Ile
1               5                   10                  15

Ser

<210> SEQ ID NO 1135
<211> LENGTH: 17
<212> TYPE: PRT
<213> ORGANISM: Mus musculus

<400> SEQUENCE: 1135

Met Asn Trp Tyr Gln Gln Lys Pro Gly Gln Pro Pro Lys Leu Leu Ile
1               5                   10                  15

Tyr

<210> SEQ ID NO 1136
<211> LENGTH: 9
<212> TYPE: PRT
<213> ORGANISM: Mus musculus

<400> SEQUENCE: 1136

Met Gln His Leu Glu Tyr Pro Tyr Thr
1               5

<210> SEQ ID NO 1137
<211> LENGTH: 17
<212> TYPE: PRT
<213> ORGANISM: Mus musculus

<400> SEQUENCE: 1137

Met Gln Trp Val Arg Gln Ser His Ala Lys Ser Leu Glu Trp Ile Gly
1               5                   10                  15

Val

<210> SEQ ID NO 1138
<211> LENGTH: 17
<212> TYPE: PRT
<213> ORGANISM: Mus musculus
```

<400> SEQUENCE: 1138

Met Arg Trp Val Lys Gln Ser His Ala Lys Ser Leu Glu Trp Ile Gly
1               5                   10                  15

Val

<210> SEQ ID NO 1139
<211> LENGTH: 17
<212> TYPE: PRT
<213> ORGANISM: Mus musculus
<220> FEATURE:
<221> NAME/KEY: misc_feature
<222> LOCATION: (10)..(10)
<223> OTHER INFORMATION: Xaa can be any naturally occurring amino acid

<400> SEQUENCE: 1139

Met Arg Trp Val Lys Gln Ser Pro Ala Xaa Ser Leu Glu Trp Ile Gly
1               5                   10                  15

Val

<210> SEQ ID NO 1140
<211> LENGTH: 17
<212> TYPE: PRT
<213> ORGANISM: Mus musculus

<400> SEQUENCE: 1140

Met Tyr Trp Tyr Gln Gln Lys Pro Gly Ser Ser Pro Arg Leu Leu Ile
1               5                   10                  15

Tyr

<210> SEQ ID NO 1141
<211> LENGTH: 17
<212> TYPE: PRT
<213> ORGANISM: Mus musculus

<400> SEQUENCE: 1141

Met Tyr Trp Tyr Gln Gln Lys Pro Arg Ser Ser Pro Lys Pro Trp Ile
1               5                   10                  15

Tyr

<210> SEQ ID NO 1142
<211> LENGTH: 3
<212> TYPE: PRT
<213> ORGANISM: Mus musculus

<400> SEQUENCE: 1142

Asn Ala Asn
1

<210> SEQ ID NO 1143
<211> LENGTH: 36
<212> TYPE: PRT
<213> ORGANISM: Mus musculus

<400> SEQUENCE: 1143

Asn Leu Ala Asp Gly Val Pro Ser Arg Phe Ser Gly Ser Gly Ser Gly
1               5                   10                  15

Thr Gln Tyr Ser Leu Lys Ile Asn Ser Leu Gln Ser Glu Asp Phe Gly
                20                  25                  30

Ser Tyr Tyr Cys
            35

```
<210> SEQ ID NO 1144
<211> LENGTH: 36
<212> TYPE: PRT
<213> ORGANISM: Mus musculus

<400> SEQUENCE: 1144

Asn Leu Ala Ser Gly Val Pro Ala Arg Phe Ser Gly Ser Gly Ser Gly
1               5                   10                  15

Thr Ser Tyr Ser Leu Thr Ile Ser Ser Met Glu Ala Glu Asp Ala Ala
            20                  25                  30

Thr Tyr Tyr Cys
        35

<210> SEQ ID NO 1145
<211> LENGTH: 36
<212> TYPE: PRT
<213> ORGANISM: Mus musculus

<400> SEQUENCE: 1145

Asn Leu Ala Ser Gly Val Pro Asp Arg Phe Ser Gly Ser Gly Ser Gly
1               5                   10                  15

Thr Ala Phe Thr Leu Arg Ile Ser Arg Val Glu Ala Glu Asp Val Gly
            20                  25                  30

Val Tyr Tyr Cys
        35

<210> SEQ ID NO 1146
<211> LENGTH: 36
<212> TYPE: PRT
<213> ORGANISM: Mus musculus

<400> SEQUENCE: 1146

Asn Leu Ala Ser Gly Val Pro Val Arg Phe Ser Gly Ser Gly Ser Gly
1               5                   10                  15

Thr Ser Tyr Ser Leu Thr Ile Ser Arg Met Glu Ala Glu Asp Ala Ala
            20                  25                  30

Thr Tyr Tyr Cys
        35

<210> SEQ ID NO 1147
<211> LENGTH: 36
<212> TYPE: PRT
<213> ORGANISM: Mus musculus

<400> SEQUENCE: 1147

Asn Leu Ala Ser Gly Val Pro Val Arg Phe Ser Gly Ser Gly Ser Gly
1               5                   10                  15

Thr Ser Tyr Ser Leu Thr Ile Ser Ser Met Glu Ala Glu Asp Ala Ala
            20                  25                  30

Thr Tyr Tyr Cys
        35

<210> SEQ ID NO 1148
<211> LENGTH: 36
<212> TYPE: PRT
<213> ORGANISM: Mus musculus

<400> SEQUENCE: 1148

Asn Leu Glu Ser Gly Ile Pro Ala Arg Phe Ser Gly Ser Gly Ser Gly
1               5                   10                  15
```

-continued

Thr Asp Phe Thr Leu Asn Ile His Pro Val Glu Glu Glu Asp Ala Ala
              20                  25                  30

Thr Tyr Tyr Cys
        35

<210> SEQ ID NO 1149
<211> LENGTH: 36
<212> TYPE: PRT
<213> ORGANISM: Mus musculus

<400> SEQUENCE: 1149

Asn Leu Glu Ser Gly Ile Pro Ala Arg Phe Ser Gly Ser Gly Ser Arg
1               5                   10                  15

Thr Gly Phe Thr Leu Thr Ile Asn Pro Val Glu Ala Asp Asp Val Ala
              20                  25                  30

Thr Tyr Tyr Cys
        35

<210> SEQ ID NO 1150
<211> LENGTH: 36
<212> TYPE: PRT
<213> ORGANISM: Mus musculus

<400> SEQUENCE: 1150

Asn Leu Glu Ser Gly Val Pro Ala Arg Phe Ser Gly Ser Gly Ser Arg
1               5                   10                  15

Thr Asp Phe Thr Leu Thr Ile Asp Pro Val Glu Ala Asp Asp Ala Ala
              20                  25                  30

Thr Tyr Tyr Cys
        35

<210> SEQ ID NO 1151
<211> LENGTH: 36
<212> TYPE: PRT
<213> ORGANISM: Mus musculus

<400> SEQUENCE: 1151

Asn Leu Gln Ser Gly Val Pro Ser Arg Phe Thr Gly Ser Gly Ser Gly
1               5                   10                  15

Thr Asp Tyr Ser Leu Thr Ile Ser Asn Leu Glu Gln Glu Asp Ile Ala
              20                  25                  30

Thr Tyr Phe Cys
        35

<210> SEQ ID NO 1152
<211> LENGTH: 36
<212> TYPE: PRT
<213> ORGANISM: Mus musculus

<400> SEQUENCE: 1152

Asn Gln Gly Ser Gly Val Pro Ala Arg Phe Ser Gly Ser Gly Ser Gly
1               5                   10                  15

Thr Asp Phe Ser Leu Asn Ile His Pro Met Glu Glu Asp Asp Thr Ala
              20                  25                  30

Met Tyr Phe Cys
        35

<210> SEQ ID NO 1153
<211> LENGTH: 36
<212> TYPE: PRT
<213> ORGANISM: Mus musculus

```
<400> SEQUENCE: 1153

Asn Arg Phe Ser Gly Val Leu Asp Arg Phe Ser Gly Ser Gly Ser Gly
1               5                   10                  15

Thr Asp Phe Thr Leu Lys Ile Ser Arg Val Glu Ala Glu Asp Leu Gly
            20                  25                  30

Val Tyr Phe Cys
        35

<210> SEQ ID NO 1154
<211> LENGTH: 36
<212> TYPE: PRT
<213> ORGANISM: Mus musculus

<400> SEQUENCE: 1154

Asn Arg Phe Ser Gly Val Pro Asp Arg Phe Ser Gly Ser Gly Ser Gly
1               5                   10                  15

Thr Asp Phe Thr Leu Lys Ile Ser Lys Val Glu Ala Glu Asp Leu Gly
            20                  25                  30

Val Tyr Tyr Cys
        35

<210> SEQ ID NO 1155
<211> LENGTH: 36
<212> TYPE: PRT
<213> ORGANISM: Mus musculus

<400> SEQUENCE: 1155

Asn Arg Phe Ser Gly Val Pro Asp Arg Phe Ser Gly Ser Gly Ser Gly
1               5                   10                  15

Thr Asp Phe Thr Leu Lys Ile Ser Arg Val Asp Ala Glu Asp Leu Gly
            20                  25                  30

Val Tyr Phe Cys
        35

<210> SEQ ID NO 1156
<211> LENGTH: 36
<212> TYPE: PRT
<213> ORGANISM: Mus musculus

<400> SEQUENCE: 1156

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Leu Gly
            20                  25                  30

Ile Tyr Tyr Cys
        35

<210> SEQ ID NO 1157
<211> LENGTH: 36
<212> TYPE: PRT
<213> ORGANISM: Mus musculus

<400> SEQUENCE: 1157

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Leu Gly
            20                  25                  30

Val Tyr Phe Cys
        35
```

<210> SEQ ID NO 1158
<211> LENGTH: 36
<212> TYPE: PRT
<213> ORGANISM: Mus musculus

<400> SEQUENCE: 1158

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Leu Gly
            20                  25                  30

Val Tyr Tyr Cys
            35

<210> SEQ ID NO 1159
<211> LENGTH: 36
<212> TYPE: PRT
<213> ORGANISM: Mus musculus

<400> SEQUENCE: 1159

Asn Arg Phe Ser Gly Val Pro Asp Arg Phe Ser Val Ser Gly Ser Gly
1               5                   10                  15

Thr Asp Phe Thr Leu Lys Ile Ser Arg Val Glu Ala Glu Asp Leu Gly
            20                  25                  30

Val Tyr Phe Cys
            35

<210> SEQ ID NO 1160
<211> LENGTH: 36
<212> TYPE: PRT
<213> ORGANISM: Mus musculus

<400> SEQUENCE: 1160

Asn Arg Phe Ser Gly Val Pro Asp Arg Phe Thr Gly Ser Gly Ser Gly
1               5                   10                  15

Thr Asp Phe Thr Leu Lys Ile Ser Arg Val Glu Ala Glu Asp Leu Gly
            20                  25                  30

Val Tyr His Cys
            35

<210> SEQ ID NO 1161
<211> LENGTH: 36
<212> TYPE: PRT
<213> ORGANISM: Mus musculus

<400> SEQUENCE: 1161

Asn Arg His Thr Gly Val Pro Asp Arg Phe Thr Gly Ser Gly Ser Gly
1               5                   10                  15

Ala Asp Phe Thr Leu Thr Ile Thr Asn Val Gln Ser Glu Asp Leu Ala
            20                  25                  30

Asp Tyr Phe Cys
            35

<210> SEQ ID NO 1162
<211> LENGTH: 36
<212> TYPE: PRT
<213> ORGANISM: Mus musculus

<400> SEQUENCE: 1162

Asn Arg Tyr Thr Gly Val Pro Asp Arg Phe Thr Gly Ser Gly Ser Ala
1               5                   10                  15

-continued

Thr Asp Phe Thr Leu Thr Ile Ser Ser Val Gln Ala Glu Asp Leu Ala
            20                  25                  30

Asp Tyr His Cys
        35

<210> SEQ ID NO 1163
<211> LENGTH: 36
<212> TYPE: PRT
<213> ORGANISM: Mus musculus

<400> SEQUENCE: 1163

Asn Arg Tyr Thr Gly Val Pro Asp Arg Phe Thr Gly Ser Gly Ser Ala
1               5                   10                  15

Thr Asp Phe Thr Leu Thr Ile Ser Ser Val Gln Ala Glu Asp Leu Ala
            20                  25                  30

Asp Tyr Arg Cys
        35

<210> SEQ ID NO 1164
<211> LENGTH: 36
<212> TYPE: PRT
<213> ORGANISM: Mus musculus

<400> SEQUENCE: 1164

Asn Arg Tyr Thr Gly Val Pro Asp Arg Phe Thr Gly Ser Gly Tyr Gly
1               5                   10                  15

Thr Asp Phe Thr Phe Thr Ile Ser Thr Val Gln Ala Glu Asp Leu Ala
            20                  25                  30

Val Tyr Phe Cys
        35

<210> SEQ ID NO 1165
<211> LENGTH: 12
<212> TYPE: PRT
<213> ORGANISM: Mus musculus

<400> SEQUENCE: 1165

Asn Val Ile Thr Thr Ala Thr Thr Trp Phe Ala Tyr
1               5                   10

<210> SEQ ID NO 1166
<211> LENGTH: 38
<212> TYPE: PRT
<213> ORGANISM: Mus musculus

<400> SEQUENCE: 1166

Asn Tyr Asp Glu Lys Phe Lys Ser Lys Gly Thr Leu Thr Val Asp Thr
1               5                   10                  15

Ser Ser Ser Thr Ala Tyr Met His Leu Ser Ser Leu Ala Ser Glu Asp
            20                  25                  30

Ser Ala Val Tyr Tyr Cys
        35

<210> SEQ ID NO 1167
<211> LENGTH: 38
<212> TYPE: PRT
<213> ORGANISM: Mus musculus

<400> SEQUENCE: 1167

Asn Tyr Asp Glu Lys Phe Lys Ser Lys Gly Thr Leu Thr Val Asp Thr
1               5                   10                  15

Ser Ser Ser Thr Ala Tyr Met His Leu Ser Ser Leu Thr Ser Glu Asp
            20                  25                  30

Ser Ala Val Tyr Cys Cys
            35

<210> SEQ ID NO 1168
<211> LENGTH: 38
<212> TYPE: PRT
<213> ORGANISM: Mus musculus

<400> SEQUENCE: 1168

Asn Tyr Asn Glu Lys Phe Glu Gly Lys Ala Thr Leu Thr Ala Asp Thr
1               5                   10                  15

Ser Ser Ser Thr Ala Tyr Met Gln Leu Ser Ser Leu Thr Ser Glu Asp
            20                  25                  30

Ser Ala Ile Tyr Tyr Cys
            35

<210> SEQ ID NO 1169
<211> LENGTH: 38
<212> TYPE: PRT
<213> ORGANISM: Mus musculus

<400> SEQUENCE: 1169

Asn Tyr Asn Glu Lys Phe Glu Gly Lys Ala Thr Leu Thr Ala Asp Thr
1               5                   10                  15

Ser Ser Ser Thr Ala Tyr Met Gln Leu Ser Ser Leu Thr Ser Glu Gly
            20                  25                  30

Ser Ala Ile Tyr Tyr Cys
            35

<210> SEQ ID NO 1170
<211> LENGTH: 37
<212> TYPE: PRT
<213> ORGANISM: Mus musculus

<400> SEQUENCE: 1170

Asn Tyr Asn Glu Lys Phe Gly Lys Ala Thr Leu Thr Ala Asp Thr Ser
1               5                   10                  15

Ser Thr Ala Tyr Met Gln Leu Ser Ser Leu Thr Ser Glu Asp Ser
            20                  25                  30

Ala Val Tyr Phe Cys
            35

<210> SEQ ID NO 1171
<211> LENGTH: 38
<212> TYPE: PRT
<213> ORGANISM: Mus musculus

<400> SEQUENCE: 1171

Asn Tyr Asn Glu Lys Phe Lys Gly Lys Ala Thr Leu Thr Ala Asp Thr
1               5                   10                  15

Phe Ser Ser Thr Ala Tyr Met Gln Leu Ser Ser Leu Thr Ser Glu Asp
            20                  25                  30

Ser Ala Ile Tyr Tyr Cys
            35

<210> SEQ ID NO 1172
<211> LENGTH: 38
<212> TYPE: PRT

<213> ORGANISM: Mus musculus

<400> SEQUENCE: 1172

Asn Tyr Asn Glu Lys Phe Lys Gly Lys Ala Thr Leu Thr Ala Asp Thr
1               5                   10                  15

Ser Pro Ser Thr Ala Tyr Met Gln Leu Ser Ser Leu Thr Ser Glu Asp
            20                  25                  30

Ser Ala Val Tyr Phe Cys
            35

<210> SEQ ID NO 1173
<211> LENGTH: 38
<212> TYPE: PRT
<213> ORGANISM: Mus musculus

<400> SEQUENCE: 1173

Asn Tyr Asn Glu Lys Phe Lys Gly Lys Ala Thr Leu Thr Ala Asp Thr
1               5                   10                  15

Ser Ser Ser Thr Ala Asp Met Gln Leu Ser Ser Leu Thr Ser Glu Asp
            20                  25                  30

Ser Ala Ile Tyr Tyr Cys
            35

<210> SEQ ID NO 1174
<211> LENGTH: 38
<212> TYPE: PRT
<213> ORGANISM: Mus musculus

<400> SEQUENCE: 1174

Asn Tyr Asn Glu Lys Phe Lys Gly Lys Ala Thr Leu Thr Ala Asp Thr
1               5                   10                  15

Ser Ser Ser Thr Ala Tyr Met Asn Leu Ser Ser Leu Thr Ser Glu Asp
            20                  25                  30

Ser Ala Ile Tyr Tyr Cys
            35

<210> SEQ ID NO 1175
<211> LENGTH: 38
<212> TYPE: PRT
<213> ORGANISM: Mus musculus

<400> SEQUENCE: 1175

Asn Tyr Asn Glu Lys Phe Lys Gly Lys Ala Thr Leu Thr Ala Asp Thr
1               5                   10                  15

Ser Ser Ser Thr Ala Tyr Met Asn Leu Ser Ser Leu Thr Ser Gly Asp
            20                  25                  30

Ser Ala Ile Tyr Tyr Cys
            35

<210> SEQ ID NO 1176
<211> LENGTH: 38
<212> TYPE: PRT
<213> ORGANISM: Mus musculus

<400> SEQUENCE: 1176

Asn Tyr Asn Glu Lys Phe Lys Gly Lys Ala Thr Leu Thr Ala Asp Thr
1               5                   10                  15

Ser Ser Ser Thr Ala Tyr Met Gln Leu Asn Ser Leu Thr Ser Glu Asp
            20                  25                  30

Ser Ala Val Tyr Phe Cys

<210> SEQ ID NO 1177
<211> LENGTH: 38
<212> TYPE: PRT
<213> ORGANISM: Mus musculus

<400> SEQUENCE: 1177

Asn Tyr Asn Glu Lys Phe Lys Gly Lys Ala Thr Leu Thr Ala Asp Thr
1               5                   10                  15

Ser Ser Ser Thr Ala Tyr Met Gln Leu Ser Ser Leu Thr Ser Glu Asp
            20                  25                  30

Ser Ala Ile Tyr Tyr Cys
        35

<210> SEQ ID NO 1178
<211> LENGTH: 38
<212> TYPE: PRT
<213> ORGANISM: Mus musculus

<400> SEQUENCE: 1178

Asn Tyr Asn Glu Lys Phe Lys Gly Lys Ala Thr Leu Thr Ala Asp Thr
1               5                   10                  15

Ser Ser Ser Thr Ala Tyr Met Gln Leu Ser Ser Leu Thr Ser Glu Asp
            20                  25                  30

Ser Ala Val Tyr Phe Cys
        35

<210> SEQ ID NO 1179
<211> LENGTH: 38
<212> TYPE: PRT
<213> ORGANISM: Mus musculus

<400> SEQUENCE: 1179

Asn Tyr Asn Glu Lys Phe Lys Gly Lys Ala Thr Leu Thr Ala Asp Thr
1               5                   10                  15

Ser Ser Ser Thr Ala Tyr Met Gln Leu Ser Ser Leu Thr Ser Glu Gly
            20                  25                  30

Ser Ala Ile Tyr Tyr Cys
        35

<210> SEQ ID NO 1180
<211> LENGTH: 38
<212> TYPE: PRT
<213> ORGANISM: Mus musculus

<400> SEQUENCE: 1180

Asn Tyr Asn Glu Lys Phe Lys Gly Lys Ala Thr Leu Thr Ala Asp Thr
1               5                   10                  15

Ser Ser Ser Thr Ala Tyr Met Ser Leu Ser Ser Leu Thr Ser Glu Asp
            20                  25                  30

Ser Ala Ile Tyr Tyr Cys
        35

<210> SEQ ID NO 1181
<211> LENGTH: 38
<212> TYPE: PRT
<213> ORGANISM: Mus musculus

<400> SEQUENCE: 1181

Asn Tyr Asn Glu Lys Phe Lys Gly Lys Ala Thr Leu Thr Ala Asp Thr

-continued

```
                1               5                  10                 15
Ser Ser Ser Thr Thr Tyr Met Gln Leu Ser Ser Leu Thr Ser Glu Asp
                        20                 25                 30

Ser Ala Ile Tyr Tyr Cys
                35

<210> SEQ ID NO 1182
<211> LENGTH: 37
<212> TYPE: PRT
<213> ORGANISM: Mus musculus

<400> SEQUENCE: 1182

Asn Tyr Asn Glu Lys Phe Lys Lys Ala Thr Leu Thr Ala Asp Thr Ser
1               5                  10                 15

Ser Ser Thr Ala Tyr Met Gln Leu Ser Ser Leu Thr Ser Glu Asp Ser
                        20                 25                 30

Ala Val Tyr Phe Cys
                35

<210> SEQ ID NO 1183
<211> LENGTH: 37
<212> TYPE: PRT
<213> ORGANISM: Mus musculus

<400> SEQUENCE: 1183

Asn Tyr Asn Glu Lys Phe Lys Lys Ala Thr Leu Thr Ala Asp Thr Ser
1               5                  10                 15

Ser Val Thr Ala Tyr Met Gln Leu Ser Ser Leu Thr Ser Glu Asp Ser
                        20                 25                 30

Ala Val Tyr Phe Cys
                35

<210> SEQ ID NO 1184
<211> LENGTH: 38
<212> TYPE: PRT
<213> ORGANISM: Mus musculus

<400> SEQUENCE: 1184

Asn Tyr Asn Glu Lys Phe Thr Gly Lys Ala Thr Leu Thr Ala Asp Thr
1               5                  10                 15

Ser Ser Ser Thr Ala Tyr Met Gln Leu Ser Ser Leu Thr Ser Glu Asp
                        20                 25                 30

Ser Ala Ile Tyr Tyr Cys
                35

<210> SEQ ID NO 1185
<211> LENGTH: 37
<212> TYPE: PRT
<213> ORGANISM: Mus musculus

<400> SEQUENCE: 1185

Asn Tyr Asn Glu Asn Phe Gly Lys Ala Thr Phe Thr Ala Asp Thr Ser
1               5                  10                 15

Ser Asn Thr Thr Tyr Met Gln Leu Ser Ser Leu Thr Ser Glu Asp Ser
                        20                 25                 30

Ala Val Tyr Tyr Cys
                35

<210> SEQ ID NO 1186
<211> LENGTH: 38
```

```
<212> TYPE: PRT
<213> ORGANISM: Mus musculus

<400> SEQUENCE: 1186

Asn Tyr Asn Glu Asn Phe Lys Gly Lys Ala Thr Phe Thr Ala Asp Thr
1               5                   10                  15

Ser Ser Asn Thr Thr Tyr Ile Gln Leu Ser Ser Leu Ser Ser Glu Asp
            20                  25                  30

Ser Ala Val Tyr Tyr Cys
            35

<210> SEQ ID NO 1187
<211> LENGTH: 38
<212> TYPE: PRT
<213> ORGANISM: Mus musculus

<400> SEQUENCE: 1187

Asn Tyr Asn Glu Asn Phe Lys Gly Lys Ala Thr Phe Thr Ala Asp Thr
1               5                   10                  15

Ser Ser Asn Thr Thr Tyr Met Leu Leu Ser Ser Leu Ser Ser Glu Asp
            20                  25                  30

Ser Ala Val Tyr Tyr Cys
            35

<210> SEQ ID NO 1188
<211> LENGTH: 38
<212> TYPE: PRT
<213> ORGANISM: Mus musculus

<400> SEQUENCE: 1188

Asn Tyr Asn Glu Asn Phe Lys Gly Lys Ala Thr Phe Thr Ala Asp Thr
1               5                   10                  15

Ser Ser Asn Thr Thr Tyr Met Gln Leu Ser Ser Leu Thr Ser Glu Asp
            20                  25                  30

Ser Ala Val Tyr Tyr Cys
            35

<210> SEQ ID NO 1189
<211> LENGTH: 38
<212> TYPE: PRT
<213> ORGANISM: Mus musculus

<400> SEQUENCE: 1189

Asn Tyr Asn Glu Asn Phe Lys Gly Lys Ala Thr Phe Thr Ala Asp Thr
1               5                   10                  15

Ser Ser Ser Thr Thr Tyr Met Gln Leu Ser Ser Leu Thr Ser Glu Asp
            20                  25                  30

Ser Ala Ile Tyr Phe Cys
            35

<210> SEQ ID NO 1190
<211> LENGTH: 37
<212> TYPE: PRT
<213> ORGANISM: Mus musculus

<400> SEQUENCE: 1190

Asn Tyr Asn Gln Lys Phe Gly Lys Ala Thr Met Thr Val Asp Lys Ser
1               5                   10                  15

Ser Ser Thr Ala Tyr Met Glu Leu Ala Arg Leu Thr Ser Glu Asp Ser
            20                  25                  30
```

```
Ala Ile Tyr Tyr Cys
        35

<210> SEQ ID NO 1191
<211> LENGTH: 25
<212> TYPE: PRT
<213> ORGANISM: Mus musculus

<400> SEQUENCE: 1191

Pro Gly Pro Thr Gln Gln Pro Gly Ser Glu Leu Val Arg Pro Gly Ala
1               5                   10                  15

Ser Val Lys Leu Ser Cys Lys Ala Ser
            20                  25

<210> SEQ ID NO 1192
<211> LENGTH: 25
<212> TYPE: PRT
<213> ORGANISM: Mus musculus

<400> SEQUENCE: 1192

Pro Ile Gln Leu Gln Gln Ser Gly Ala Glu Leu Val Arg Pro Gly Ala
1               5                   10                  15

Ser Val Lys Leu Ser Cys Lys Ala Ser
            20                  25

<210> SEQ ID NO 1193
<211> LENGTH: 25
<212> TYPE: PRT
<213> ORGANISM: Mus musculus

<400> SEQUENCE: 1193

Gln Ala Tyr Leu Gln Gln Ser Gly Ala Glu Leu Val Arg Pro Gly Thr
1               5                   10                  15

Ser Val Lys Ile Ser Cys Lys Ala Ser
            20                  25

<210> SEQ ID NO 1194
<211> LENGTH: 25
<212> TYPE: PRT
<213> ORGANISM: Mus musculus

<400> SEQUENCE: 1194

Gln Ala Tyr Leu Gln Gln Ser Gly Ala Glu Leu Val Arg Pro Gly Thr
1               5                   10                  15

Ser Val Lys Met Ser Cys Lys Ala Ala
            20                  25

<210> SEQ ID NO 1195
<211> LENGTH: 25
<212> TYPE: PRT
<213> ORGANISM: Mus musculus

<400> SEQUENCE: 1195

Gln Ala Tyr Leu Gln Gln Ser Gly Ala Glu Leu Val Arg Pro Gly Val
1               5                   10                  15

Ser Leu Lys Ile Ser Cys Lys Gly Ser
            20                  25

<210> SEQ ID NO 1196
<211> LENGTH: 25
<212> TYPE: PRT
<213> ORGANISM: Mus musculus
```

<400> SEQUENCE: 1196

Gln Ala Tyr Leu Gln Gln Ser Gly Ala Glu Leu Val Arg Pro Gly Val
1               5                   10                  15

Ser Val Lys Ile Ser Cys Lys Gly Ser
            20                  25

<210> SEQ ID NO 1197
<211> LENGTH: 25
<212> TYPE: PRT
<213> ORGANISM: Mus musculus

<400> SEQUENCE: 1197

Gln Ala Tyr Leu Gln Gln Ser Gly Ala Glu Leu Val Arg Ser Gly Ala
1               5                   10                  15

Ser Val Lys Leu Ser Cys Thr Ala Ser
            20                  25

<210> SEQ ID NO 1198
<211> LENGTH: 6
<212> TYPE: PRT
<213> ORGANISM: Mus musculus

<400> SEQUENCE: 1198

Gln Asp Ile Gly Leu Asn
1               5

<210> SEQ ID NO 1199
<211> LENGTH: 6
<212> TYPE: PRT
<213> ORGANISM: Mus musculus

<400> SEQUENCE: 1199

Gln Asp Ile Gly Ser Ser
1               5

<210> SEQ ID NO 1200
<211> LENGTH: 6
<212> TYPE: PRT
<213> ORGANISM: Mus musculus

<400> SEQUENCE: 1200

Gln Asp Ile Asn Asn Phe
1               5

<210> SEQ ID NO 1201
<211> LENGTH: 6
<212> TYPE: PRT
<213> ORGANISM: Mus musculus

<400> SEQUENCE: 1201

Gln Asp Ile Asn Arg Tyr
1               5

<210> SEQ ID NO 1202
<211> LENGTH: 6
<212> TYPE: PRT
<213> ORGANISM: Mus musculus

<400> SEQUENCE: 1202

Gln Asp Ile Arg Asn Tyr
1               5

<210> SEQ ID NO 1203

```
<211> LENGTH: 6
<212> TYPE: PRT
<213> ORGANISM: Mus musculus

<400> SEQUENCE: 1203

Gln Asp Ile Ser Asn Tyr
1               5

<210> SEQ ID NO 1204
<211> LENGTH: 6
<212> TYPE: PRT
<213> ORGANISM: Mus musculus

<400> SEQUENCE: 1204

Gln Asp Val Gly Thr Ala
1               5

<210> SEQ ID NO 1205
<211> LENGTH: 6
<212> TYPE: PRT
<213> ORGANISM: Mus musculus

<400> SEQUENCE: 1205

Gln Asp Val Ile Thr Ala
1               5

<210> SEQ ID NO 1206
<211> LENGTH: 6
<212> TYPE: PRT
<213> ORGANISM: Mus musculus

<400> SEQUENCE: 1206

Gln Asp Val Asn Thr Ala
1               5

<210> SEQ ID NO 1207
<211> LENGTH: 8
<212> TYPE: PRT
<213> ORGANISM: Mus musculus

<400> SEQUENCE: 1207

Gln Asp Val Asn Thr Ala Val Ala
1               5

<210> SEQ ID NO 1208
<211> LENGTH: 6
<212> TYPE: PRT
<213> ORGANISM: Mus musculus

<400> SEQUENCE: 1208

Gln Asp Val Arg Thr Ala
1               5

<210> SEQ ID NO 1209
<211> LENGTH: 6
<212> TYPE: PRT
<213> ORGANISM: Mus musculus

<400> SEQUENCE: 1209

Gln Asp Val Ser Thr Ala
1               5

<210> SEQ ID NO 1210
<211> LENGTH: 6
<212> TYPE: PRT
```

```
<213> ORGANISM: Mus musculus

<400> SEQUENCE: 1210

Gln Glu Ile Ser Gly Tyr
1               5

<210> SEQ ID NO 1211
<211> LENGTH: 6
<212> TYPE: PRT
<213> ORGANISM: Mus musculus

<400> SEQUENCE: 1211

Gln Gly Ile Ser Asn Tyr
1               5

<210> SEQ ID NO 1212
<211> LENGTH: 9
<212> TYPE: PRT
<213> ORGANISM: Mus musculus

<400> SEQUENCE: 1212

Gln His Phe Trp Gly Thr Pro Pro Thr
1               5

<210> SEQ ID NO 1213
<211> LENGTH: 9
<212> TYPE: PRT
<213> ORGANISM: Mus musculus

<400> SEQUENCE: 1213

Gln His Phe Trp Gly Thr Pro Trp Thr
1               5

<210> SEQ ID NO 1214
<211> LENGTH: 9
<212> TYPE: PRT
<213> ORGANISM: Mus musculus

<400> SEQUENCE: 1214

Gln His His Tyr Gly Ile Pro Tyr Thr
1               5

<210> SEQ ID NO 1215
<211> LENGTH: 9
<212> TYPE: PRT
<213> ORGANISM: Mus musculus

<400> SEQUENCE: 1215

Gln His His Tyr Gly Ser Pro Trp Thr
1               5

<210> SEQ ID NO 1216
<211> LENGTH: 9
<212> TYPE: PRT
<213> ORGANISM: Mus musculus

<400> SEQUENCE: 1216

Gln His His Tyr Gly Ser Pro Tyr Thr
1               5

<210> SEQ ID NO 1217
<211> LENGTH: 9
<212> TYPE: PRT
<213> ORGANISM: Mus musculus
```

<400> SEQUENCE: 1217

Gln His His Tyr Gly Thr Pro Trp Thr
1               5

<210> SEQ ID NO 1218
<211> LENGTH: 25
<212> TYPE: PRT
<213> ORGANISM: Mus musculus

<400> SEQUENCE: 1218

Gln Ile Gln Leu Gln Gln Pro Gly Ala Glu Leu Ala Lys Pro Gly Ala
1               5                   10                  15

Ser Val Lys Met Ser Cys Lys Ala Ser
            20                  25

<210> SEQ ID NO 1219
<211> LENGTH: 25
<212> TYPE: PRT
<213> ORGANISM: Mus musculus

<400> SEQUENCE: 1219

Gln Ile Gln Leu Gln Gln Pro Gly Ala Glu Leu Val Lys Pro Gly Ala
1               5                   10                  15

Ser Val Lys Leu Pro Cys Lys Ala Ser
            20                  25

<210> SEQ ID NO 1220
<211> LENGTH: 25
<212> TYPE: PRT
<213> ORGANISM: Mus musculus

<400> SEQUENCE: 1220

Gln Ile Gln Leu Gln Pro Gly Ala Glu Leu Val Arg Pro Gly Thr
1               5                   10                  15

Ser Val Lys Ile Ser Cys Lys Ala Ser
            20                  25

<210> SEQ ID NO 1221
<211> LENGTH: 25
<212> TYPE: PRT
<213> ORGANISM: Mus musculus

<400> SEQUENCE: 1221

Gln Ile Gln Leu Gln Gln Pro Gly Ala Glu Leu Val Arg Pro Gly Thr
1               5                   10                  15

Ser Val Lys Met Ser Cys Lys Ala Ala
            20                  25

<210> SEQ ID NO 1222
<211> LENGTH: 114
<212> TYPE: PRT
<213> ORGANISM: Mus musculus

<400> SEQUENCE: 1222

Gln Ile Gln Leu Gln Gln Pro Gly Ala Glu Leu Val Arg Pro Gly Thr
1               5                   10                  15

Ser Val Lys Met Ser Cys Lys Ala Ala Gly Tyr Thr Phe Thr Lys Tyr
            20                  25                  30

Trp Ile Gly Trp Val Lys Gln Arg Pro Gly His Gly Leu Glu Trp Ile
        35                  40                  45

Gly Asp Ile His Pro Gly Gly Gly Tyr Ile Asn Tyr Asn Glu Lys Phe

```
                50             55              60
Thr Gly Lys Ala Thr Leu Thr Ala Gly Thr Ser Ser Thr Ala Tyr
 65                  70                  75                  80

Met Gln Leu Ser Ser Leu Thr Ser Glu Asp Ser Ala Ile Tyr Tyr Cys
                 85                  90                  95

Val Ser Arg Asn Phe Ala Asn Trp Gly Gln Gly Thr Leu Val Thr Val
            100                 105                 110

Ser Ala

<210> SEQ ID NO 1223
<211> LENGTH: 25
<212> TYPE: PRT
<213> ORGANISM: Mus musculus

<400> SEQUENCE: 1223

Gln Ile Gln Leu Gln Gln Pro Gly Ala Glu Leu Val Arg Pro Gly Val
 1               5                  10                  15

Ser Leu Lys Ile Ser Cys Lys Gly Ser
            20                  25

<210> SEQ ID NO 1224
<211> LENGTH: 25
<212> TYPE: PRT
<213> ORGANISM: Mus musculus

<400> SEQUENCE: 1224

Gln Ile Gln Leu Gln Gln Ser Gly Ala Asp Leu Met Lys Pro Gly Ala
 1               5                  10                  15

Ser Val Lys Ile Ser Cys Lys Ala Ser
            20                  25

<210> SEQ ID NO 1225
<211> LENGTH: 25
<212> TYPE: PRT
<213> ORGANISM: Mus musculus

<400> SEQUENCE: 1225

Gln Ile Gln Leu Gln Gln Ser Gly Ala Glu Leu Ala Lys Pro Gly Ala
 1               5                  10                  15

Ser Val Lys Met Ser Cys Lys Ala Ser
            20                  25

<210> SEQ ID NO 1226
<211> LENGTH: 25
<212> TYPE: PRT
<213> ORGANISM: Mus musculus

<400> SEQUENCE: 1226

Gln Ile Gln Leu Gln Gln Ser Gly Ala Glu Leu Val Arg Pro Gly Thr
 1               5                  10                  15

Ser Leu Lys Met Ser Cys Lys Ala Ala
            20                  25

<210> SEQ ID NO 1227
<211> LENGTH: 25
<212> TYPE: PRT
<213> ORGANISM: Mus musculus

<400> SEQUENCE: 1227

Gln Ile Gln Leu Gln Gln Ser Gly Ala Glu Leu Val Arg Pro Gly Thr
 1               5                  10                  15
```

```
Ser Val Lys Ile Ser Cys Lys Ala Ser
            20              25

<210> SEQ ID NO 1228
<211> LENGTH: 25
<212> TYPE: PRT
<213> ORGANISM: Mus musculus

<400> SEQUENCE: 1228

Gln Ile Gln Leu Gln Gln Ser Gly Ala Glu Leu Val Arg Pro Gly Thr
1               5                   10                  15

Ser Val Lys Met Ser Cys Lys Ala Ala
            20              25

<210> SEQ ID NO 1229
<211> LENGTH: 114
<212> TYPE: PRT
<213> ORGANISM: Mus musculus

<400> SEQUENCE: 1229

Gln Ile Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Ser Asn Tyr
            20                  25                  30

Trp Ile Gly Trp Val Lys Gln Arg Pro Gly His Gly Leu Glu Trp Ile
        35                  40                  45

Gly Asp Ile His Pro Gly Gly Gly Tyr Ile Asn Tyr Asn Glu Lys Phe
    50                  55                  60

Thr Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Ile Tyr Tyr Cys
                85                  90                  95

Val Ser Arg Asn Phe Ala Asn Trp Gly Gln Gly Thr Leu Val Thr Val
            100                 105                 110

Ser Ala

<210> SEQ ID NO 1230
<211> LENGTH: 114
<212> TYPE: PRT
<213> ORGANISM: Mus musculus

<400> SEQUENCE: 1230

Gln Ile Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Lys Tyr
            20                  25                  30

Trp Ile Gly Trp Val Lys Gln Arg Ser Gly His Gly Leu Glu Trp Ile
        35                  40                  45

Gly Asp Ile His Pro Gly Gly Tyr Ile Asn Tyr Asn Glu Lys Phe
    50                  55                  60

Thr Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Ile Tyr Tyr Cys
                85                  90                  95

Val Ser Arg Asn Phe Ala Asn Trp Gly Gln Gly Thr Leu Val Thr Val
            100                 105                 110

Ser Ala
```

<210> SEQ ID NO 1231
<211> LENGTH: 114
<212> TYPE: PRT
<213> ORGANISM: Mus musculus

<400> SEQUENCE: 1231

Gln Ile Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn Tyr
                20                  25                  30

Trp Ile Gly Trp Val Lys Gln Arg Pro Gly His Gly Leu Glu Trp Ile
            35                  40                  45

Gly Asp Phe Tyr Pro Gly Gly Asp Tyr Ile Asn Tyr Asn Glu Lys Phe
        50                  55                  60

Lys Gly Lys Ala Thr Leu Thr Ala Asp Thr Ser Ser Thr Ala Tyr
65                  70                  75                  80

Met Gln Leu Ser Ser Leu Thr Ser Glu Asp Ser Ala Ile Tyr Tyr Cys
                85                  90                  95

Thr Ser Arg Asn Phe Ala Tyr Trp Gly Gln Gly Thr Pro Val Thr Val
                100                 105                 110

Ser Ser

<210> SEQ ID NO 1232
<211> LENGTH: 114
<212> TYPE: PRT
<213> ORGANISM: Mus musculus

<400> SEQUENCE: 1232

Gln Ile Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn Tyr
                20                  25                  30

Trp Ile Gly Trp Val Lys Gln Arg Pro Gly His Gly Leu Glu Trp Ile
            35                  40                  45

Gly Asp Ile His Pro Gly Gly Asp Tyr Ser Asn Tyr Asn Glu Lys Phe
        50                  55                  60

Lys Gly Lys Ala Thr Leu Thr Ala Asp Thr Ser Ser Ser Thr Ala Tyr
65                  70                  75                  80

Met Asn Leu Ser Ser Leu Thr Ser Glu Asp Ser Ala Ile Tyr Tyr Cys
                85                  90                  95

Thr Ser Arg Asn Phe Ala Tyr Trp Gly Gln Gly Thr Leu Val Thr Val
                100                 105                 110

Ser Ser

<210> SEQ ID NO 1233
<211> LENGTH: 114
<212> TYPE: PRT
<213> ORGANISM: Mus musculus

<400> SEQUENCE: 1233

Gln Ile Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn Tyr
                20                  25                  30

Trp Ile Gly Trp Val Lys Gln Arg Pro Gly His Gly Leu Glu Trp Ile
            35                  40                  45

Gly Asp Ile His Pro Gly Gly Asp Tyr Ser Asn Tyr Asn Glu Lys Phe
            50                  55                  60

Lys Gly Lys Ala Thr Leu Thr Ala Asp Thr Ser Ser Thr Ala Tyr
65                  70                  75                  80

Met Ser Leu Ser Ser Leu Thr Ser Glu Asp Ser Ala Ile Tyr Tyr Cys
                85                  90                  95

Thr Ser Arg Asn Phe Ala Tyr Trp Gly Gln Gly Thr Leu Val Thr Val
                100                 105                 110

Ser Ala

<210> SEQ ID NO 1234
<211> LENGTH: 114
<212> TYPE: PRT
<213> ORGANISM: Mus musculus

<400> SEQUENCE: 1234

Gln Ile Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn Tyr
                20                  25                  30

Trp Ile Gly Trp Val Lys Gln Arg Pro Gly His Gly Leu Glu Trp Ile
            35                  40                  45

Gly Asp Ile His Pro Gly Gly Gly Tyr Thr Asn Tyr Asn Glu Lys Phe
        50                  55                  60

Lys Gly Lys Ala Thr Leu Thr Ala Asp Thr Ser Ser Thr Ala Asp
65                  70                  75                  80

Met Gln Leu Ser Ser Leu Thr Ser Glu Asp Ser Ala Ile Tyr Tyr Cys
                85                  90                  95

Thr Ser Arg Asn Phe Ala Tyr Trp Gly Gln Gly Thr Leu Val Thr Val
                100                 105                 110

Ser Ala

<210> SEQ ID NO 1235
<211> LENGTH: 114
<212> TYPE: PRT
<213> ORGANISM: Mus musculus

<400> SEQUENCE: 1235

Gln Ile Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn Tyr
                20                  25                  30

Trp Ile Gly Trp Val Lys Gln Arg Pro Gly His Gly Leu Glu Trp Ile
            35                  40                  45

Gly Asp Ile His Pro Gly Gly Gly Tyr Thr Asn Tyr Asn Glu Lys Phe
        50                  55                  60

Lys Gly Lys Ala Thr Leu Thr Ala Asp Thr Ser Ser Thr Ala Tyr
65                  70                  75                  80

Met Gln Leu Ser Ser Leu Thr Ser Glu Asp Ser Ala Ile Tyr Tyr Cys
                85                  90                  95

Thr Ser Arg Asn Phe Ala Tyr Trp Gly Gln Gly Thr Leu Val Thr Val
                100                 105                 110

Ser Ala

<210> SEQ ID NO 1236

```
<211> LENGTH: 114
<212> TYPE: PRT
<213> ORGANISM: Mus musculus

<400> SEQUENCE: 1236

Gln Ile Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn Tyr
            20                  25                  30

Trp Ile Gly Trp Val Lys Gln Arg Pro Gly His Gly Leu Glu Trp Ile
        35                  40                  45

Gly Asp Ile His Pro Gly Gly Gly Tyr Thr Asn Tyr Asn Glu Lys Phe
    50                  55                  60

Lys Gly Lys Ala Thr Leu Thr Ala Asp Thr Ser Ser Thr Ala Tyr
65                  70                  75                  80

Met Gln Leu Ser Ser Leu Thr Ser Glu Asp Ser Ala Ile Tyr Tyr Cys
                85                  90                  95

Thr Ser Arg Asn Phe Ala Tyr Trp Gly Gln Gly Thr Pro Val Thr Val
            100                 105                 110

Ser Ser

<210> SEQ ID NO 1237
<211> LENGTH: 114
<212> TYPE: PRT
<213> ORGANISM: Mus musculus

<400> SEQUENCE: 1237

Gln Ile Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn Tyr
            20                  25                  30

Trp Ile Gly Trp Val Lys Gln Arg Pro Gly His Gly Leu Glu Trp Ile
        35                  40                  45

Gly Asp Ile His Pro Gly Gly Ser Tyr Thr Asn Tyr Asn Glu Asn Phe
    50                  55                  60

Lys Gly Lys Ala Thr Phe Thr Ala Asp Thr Ser Ser Ser Thr Thr Tyr
65                  70                  75                  80

Met Gln Leu Ser Ser Leu Thr Ser Glu Asp Ser Ala Ile Tyr Phe Cys
                85                  90                  95

Thr Ser Arg Asn Phe Ala Lys Trp Gly Gln Gly Thr Pro Val Thr Val
            100                 105                 110

Ser Ser

<210> SEQ ID NO 1238
<211> LENGTH: 114
<212> TYPE: PRT
<213> ORGANISM: Mus musculus

<400> SEQUENCE: 1238

Gln Ile Gln Leu Gln Gln Ser Gly Ala Glu Leu Val Arg Pro Gly Thr
1               5                   10                  15

Ser Val Lys Met Ser Cys Lys Ala Ala Gly Tyr Thr Ser Thr Asn Tyr
            20                  25                  30

Trp Ile Gly Trp Val Lys Gln Arg Pro Gly His Gly Leu Glu Trp Ile
        35                  40                  45

Gly Asp Ile His Pro Gly Gly Asp Tyr Ser Asn Tyr Asn Glu Lys Phe
    50                  55                  60
```

```
Lys Gly Lys Ala Thr Leu Thr Ala Asp Thr Ser Ser Thr Ala Tyr
 65                  70                  75                  80

Met Asn Leu Ser Ser Leu Thr Ser Glu Asp Ser Ala Ile Tyr Tyr Cys
                 85                  90                  95

Thr Ser Arg Asn Phe Ala Tyr Trp Gly Gln Gly Thr Leu Val Thr Val
            100                 105                 110

Ser Ala

<210> SEQ ID NO 1239
<211> LENGTH: 25
<212> TYPE: PRT
<213> ORGANISM: Mus musculus

<400> SEQUENCE: 1239

Gln Ile Gln Leu Gln Gln Ser Gly Ala Glu Leu Val Arg Pro Gly Val
 1               5                  10                  15

Ser Leu Lys Ile Ser Cys Lys Gly Ser
            20                  25

<210> SEQ ID NO 1240
<211> LENGTH: 25
<212> TYPE: PRT
<213> ORGANISM: Mus musculus

<400> SEQUENCE: 1240

Gln Ile Gln Leu Gln Gln Ser Gly Ala Glu Leu Val Arg Pro Gly Val
 1               5                  10                  15

Ser Val Lys Ile Ser Cys Lys Gly Ser
            20                  25

<210> SEQ ID NO 1241
<211> LENGTH: 25
<212> TYPE: PRT
<213> ORGANISM: Mus musculus

<400> SEQUENCE: 1241

Gln Ile Gln Leu Gln Gln Ser Gly Ala Glu Met Val Arg Pro Gly Val
 1               5                  10                  15

Ser Val Lys Ile Ser Cys Lys Gly Ser
            20                  25

<210> SEQ ID NO 1242
<211> LENGTH: 9
<212> TYPE: PRT
<213> ORGANISM: Mus musculus

<400> SEQUENCE: 1242

Gln Asn Gly His Ser Phe Pro Arg Thr
 1               5

<210> SEQ ID NO 1243
<211> LENGTH: 6
<212> TYPE: PRT
<213> ORGANISM: Mus musculus

<400> SEQUENCE: 1243

Gln Asn Val Gly Ile Asn
 1               5

<210> SEQ ID NO 1244
<211> LENGTH: 6
```

<212> TYPE: PRT
<213> ORGANISM: Mus musculus

<400> SEQUENCE: 1244

Gln Asn Val Gly Ser Asn
1               5

<210> SEQ ID NO 1245
<211> LENGTH: 6
<212> TYPE: PRT
<213> ORGANISM: Mus musculus

<400> SEQUENCE: 1245

Gln Asn Val Gly Thr Asn
1               5

<210> SEQ ID NO 1246
<211> LENGTH: 8
<212> TYPE: PRT
<213> ORGANISM: Mus musculus

<400> SEQUENCE: 1246

Gln Asn Val Gly Thr Asn Val Ala
1               5

<210> SEQ ID NO 1247
<211> LENGTH: 6
<212> TYPE: PRT
<213> ORGANISM: Mus musculus

<400> SEQUENCE: 1247

Gln Asn Val Arg Thr Ala
1               5

<210> SEQ ID NO 1248
<211> LENGTH: 9
<212> TYPE: PRT
<213> ORGANISM: Mus musculus

<400> SEQUENCE: 1248

Gln Gln Ala Tyr Trp Ser Pro Tyr Thr
1               5

<210> SEQ ID NO 1249
<211> LENGTH: 9
<212> TYPE: PRT
<213> ORGANISM: Mus musculus

<400> SEQUENCE: 1249

Gln Gln Asp Tyr Arg Ser Pro Tyr Thr
1               5

<210> SEQ ID NO 1250
<211> LENGTH: 9
<212> TYPE: PRT
<213> ORGANISM: Mus musculus

<400> SEQUENCE: 1250

Gln Gln Asp Tyr Ser Ser Pro Pro Thr
1               5

<210> SEQ ID NO 1251
<211> LENGTH: 9
<212> TYPE: PRT
<213> ORGANISM: Mus musculus

<400> SEQUENCE: 1251

Gln Gln Asp Tyr Ser Ser Pro Trp Thr
1               5

<210> SEQ ID NO 1252
<211> LENGTH: 9
<212> TYPE: PRT
<213> ORGANISM: Mus musculus

<400> SEQUENCE: 1252

Gln Gln Gly His Thr Leu Pro Pro Thr
1               5

<210> SEQ ID NO 1253
<211> LENGTH: 9
<212> TYPE: PRT
<213> ORGANISM: Mus musculus

<400> SEQUENCE: 1253

Gln Gln Gly Asn Thr Leu Pro Pro Thr
1               5

<210> SEQ ID NO 1254
<211> LENGTH: 9
<212> TYPE: PRT
<213> ORGANISM: Mus musculus

<400> SEQUENCE: 1254

Gln Gln Gly Asn Thr Leu Pro Arg Thr
1               5

<210> SEQ ID NO 1255
<211> LENGTH: 9
<212> TYPE: PRT
<213> ORGANISM: Mus musculus

<400> SEQUENCE: 1255

Gln Gln Gly Asn Thr Leu Pro Trp Thr
1               5

<210> SEQ ID NO 1256
<211> LENGTH: 9
<212> TYPE: PRT
<213> ORGANISM: Mus musculus

<400> SEQUENCE: 1256

Gln Gln His Phe Asn Ser Pro Tyr Thr
1               5

<210> SEQ ID NO 1257
<211> LENGTH: 9
<212> TYPE: PRT
<213> ORGANISM: Mus musculus

<400> SEQUENCE: 1257

Gln Gln His Asn Glu Tyr Pro Trp Thr
1               5

<210> SEQ ID NO 1258
<211> LENGTH: 9
<212> TYPE: PRT
<213> ORGANISM: Mus musculus

<400> SEQUENCE: 1258

```
Gln Gln His Tyr Ser Ser Pro Trp Thr
1               5

<210> SEQ ID NO 1259
<211> LENGTH: 9
<212> TYPE: PRT
<213> ORGANISM: Mus musculus

<400> SEQUENCE: 1259

Gln Gln His Tyr Ser Thr His Val His
1               5

<210> SEQ ID NO 1260
<211> LENGTH: 9
<212> TYPE: PRT
<213> ORGANISM: Mus musculus

<400> SEQUENCE: 1260

Gln Gln His Tyr Ser Thr Pro Phe Thr
1               5

<210> SEQ ID NO 1261
<211> LENGTH: 9
<212> TYPE: PRT
<213> ORGANISM: Mus musculus

<400> SEQUENCE: 1261

Gln Gln His Tyr Ser Thr Pro Pro Thr
1               5

<210> SEQ ID NO 1262
<211> LENGTH: 10
<212> TYPE: PRT
<213> ORGANISM: Mus musculus

<400> SEQUENCE: 1262

Gln Gln His Tyr Ser Thr Pro Pro Trp Thr
1               5                   10

<210> SEQ ID NO 1263
<211> LENGTH: 9
<212> TYPE: PRT
<213> ORGANISM: Mus musculus

<400> SEQUENCE: 1263

Gln Gln His Tyr Ser Thr Pro Arg Thr
1               5

<210> SEQ ID NO 1264
<211> LENGTH: 9
<212> TYPE: PRT
<213> ORGANISM: Mus musculus

<400> SEQUENCE: 1264

Gln Gln His Tyr Ser Thr Pro Trp Thr
1               5

<210> SEQ ID NO 1265
<211> LENGTH: 9
<212> TYPE: PRT
<213> ORGANISM: Mus musculus

<400> SEQUENCE: 1265

Gln Gln His Tyr Ser Thr Pro Tyr Thr
```

```
1               5

<210> SEQ ID NO 1266
<211> LENGTH: 9
<212> TYPE: PRT
<213> ORGANISM: Mus musculus

<400> SEQUENCE: 1266

Gln Gln Asn Asn Glu Asp Pro Tyr Thr
1               5

<210> SEQ ID NO 1267
<211> LENGTH: 9
<212> TYPE: PRT
<213> ORGANISM: Mus musculus

<400> SEQUENCE: 1267

Gln Gln Ser Lys Glu Val Pro Tyr Thr
1               5

<210> SEQ ID NO 1268
<211> LENGTH: 9
<212> TYPE: PRT
<213> ORGANISM: Mus musculus

<400> SEQUENCE: 1268

Gln Gln Ser Asn Glu Asp Pro Leu Thr
1               5

<210> SEQ ID NO 1269
<211> LENGTH: 9
<212> TYPE: PRT
<213> ORGANISM: Mus musculus

<400> SEQUENCE: 1269

Gln Gln Ser Asn Glu Asp Pro Arg Thr
1               5

<210> SEQ ID NO 1270
<211> LENGTH: 9
<212> TYPE: PRT
<213> ORGANISM: Mus musculus

<400> SEQUENCE: 1270

Gln Gln Ser Asn Glu Asp Pro Tyr Thr
1               5

<210> SEQ ID NO 1271
<211> LENGTH: 9
<212> TYPE: PRT
<213> ORGANISM: Mus musculus

<400> SEQUENCE: 1271

Gln Gln Ser Asn Ser Leu Pro Pro Thr
1               5

<210> SEQ ID NO 1272
<211> LENGTH: 9
<212> TYPE: PRT
<213> ORGANISM: Mus musculus

<400> SEQUENCE: 1272

Gln Gln Ser Asn Thr Leu Pro Pro Thr
1               5
```

<210> SEQ ID NO 1273
<211> LENGTH: 9
<212> TYPE: PRT
<213> ORGANISM: Mus musculus

<400> SEQUENCE: 1273

Gln Gln Val Tyr Thr Leu Pro Trp Thr
1               5

<210> SEQ ID NO 1274
<211> LENGTH: 9
<212> TYPE: PRT
<213> ORGANISM: Mus musculus

<400> SEQUENCE: 1274

Gln Gln Trp Ser Ser Asn Pro Pro Thr
1               5

<210> SEQ ID NO 1275
<211> LENGTH: 10
<212> TYPE: PRT
<213> ORGANISM: Mus musculus

<400> SEQUENCE: 1275

Gln Gln Trp Ser Ser Asn Pro Pro Tyr Thr
1               5                   10

<210> SEQ ID NO 1276
<211> LENGTH: 9
<212> TYPE: PRT
<213> ORGANISM: Mus musculus

<400> SEQUENCE: 1276

Gln Gln Trp Ser Ser Asn Pro Tyr Thr
1               5

<210> SEQ ID NO 1277
<211> LENGTH: 9
<212> TYPE: PRT
<213> ORGANISM: Mus musculus

<400> SEQUENCE: 1277

Gln Gln Trp Ser Ser Tyr Pro Leu Thr
1               5

<210> SEQ ID NO 1278
<211> LENGTH: 9
<212> TYPE: PRT
<213> ORGANISM: Mus musculus

<400> SEQUENCE: 1278

Gln Gln Trp Ser Ser Tyr Pro Tyr Thr
1               5

<210> SEQ ID NO 1279
<211> LENGTH: 9
<212> TYPE: PRT
<213> ORGANISM: Mus musculus

<400> SEQUENCE: 1279

Gln Gln Trp Thr Ser Asn Pro Pro Thr
1               5

<210> SEQ ID NO 1280

```
<211> LENGTH: 9
<212> TYPE: PRT
<213> ORGANISM: Mus musculus

<400> SEQUENCE: 1280

Gln Gln Tyr Asp Ser Tyr Pro Tyr Thr
1               5

<210> SEQ ID NO 1281
<211> LENGTH: 9
<212> TYPE: PRT
<213> ORGANISM: Mus musculus

<400> SEQUENCE: 1281

Gln Gln Tyr Asn Asn His Pro Tyr Thr
1               5

<210> SEQ ID NO 1282
<211> LENGTH: 9
<212> TYPE: PRT
<213> ORGANISM: Mus musculus

<400> SEQUENCE: 1282

Gln Gln Tyr Asn Asn Ser Pro Leu Thr
1               5

<210> SEQ ID NO 1283
<211> LENGTH: 9
<212> TYPE: PRT
<213> ORGANISM: Mus musculus

<400> SEQUENCE: 1283

Gln Gln Tyr Asn Asn Tyr Pro Leu Thr
1               5

<210> SEQ ID NO 1284
<211> LENGTH: 9
<212> TYPE: PRT
<213> ORGANISM: Mus musculus

<400> SEQUENCE: 1284

Gln Gln Tyr Asn Asn Tyr Pro Trp Thr
1               5

<210> SEQ ID NO 1285
<211> LENGTH: 9
<212> TYPE: PRT
<213> ORGANISM: Mus musculus

<400> SEQUENCE: 1285

Gln Gln Tyr Asn Arg Tyr Pro Tyr Thr
1               5

<210> SEQ ID NO 1286
<211> LENGTH: 9
<212> TYPE: PRT
<213> ORGANISM: Mus musculus

<400> SEQUENCE: 1286

Gln Gln Tyr Asn Ser Tyr Pro Arg Thr
1               5

<210> SEQ ID NO 1287
<211> LENGTH: 9
<212> TYPE: PRT
```

<213> ORGANISM: Mus musculus

<400> SEQUENCE: 1287

Gln Gln Tyr Asn Thr Tyr Pro Tyr Thr
1               5

<210> SEQ ID NO 1288
<211> LENGTH: 9
<212> TYPE: PRT
<213> ORGANISM: Mus musculus

<400> SEQUENCE: 1288

Gln Gln Tyr Asn Thr Tyr Pro Tyr Thr
1               5

<210> SEQ ID NO 1289
<211> LENGTH: 9
<212> TYPE: PRT
<213> ORGANISM: Mus musculus

<400> SEQUENCE: 1289

Gln Gln Tyr Ser Lys Leu Pro Trp Thr
1               5

<210> SEQ ID NO 1290
<211> LENGTH: 9
<212> TYPE: PRT
<213> ORGANISM: Mus musculus

<400> SEQUENCE: 1290

Gln Gln Tyr Ser Asn Tyr Leu Thr Phe
1               5

<210> SEQ ID NO 1291
<211> LENGTH: 9
<212> TYPE: PRT
<213> ORGANISM: Mus musculus

<400> SEQUENCE: 1291

Gln Gln Tyr Ser Ser Tyr Pro Leu Thr
1               5

<210> SEQ ID NO 1292
<211> LENGTH: 9
<212> TYPE: PRT
<213> ORGANISM: Mus musculus

<400> SEQUENCE: 1292

Gln Gln Tyr Trp Ser Thr Pro Pro Thr
1               5

<210> SEQ ID NO 1293
<211> LENGTH: 7
<212> TYPE: PRT
<213> ORGANISM: Mus musculus

<400> SEQUENCE: 1293

Gln Gln Tyr Tyr Ser Tyr Pro
1               5

<210> SEQ ID NO 1294
<211> LENGTH: 9
<212> TYPE: PRT
<213> ORGANISM: Mus musculus

```
<400> SEQUENCE: 1294

Gln Gln Tyr Tyr Ser Tyr Pro Trp Thr
1               5

<210> SEQ ID NO 1295
<211> LENGTH: 8
<212> TYPE: PRT
<213> ORGANISM: Mus musculus

<400> SEQUENCE: 1295

Gln Gln Tyr Tyr Ser Tyr Arg Thr
1               5

<210> SEQ ID NO 1296
<211> LENGTH: 6
<212> TYPE: PRT
<213> ORGANISM: Mus musculus

<400> SEQUENCE: 1296

Gln Ser Ile Ser Asp Tyr
1               5

<210> SEQ ID NO 1297
<211> LENGTH: 36
<212> TYPE: PRT
<213> ORGANISM: Mus musculus

<400> SEQUENCE: 1297

Gln Ser Ile Ser Gly Ile Pro Ser Arg Phe Ser Gly Ser Gly Ser Gly
1               5                   10                  15

Ser Asp Phe Thr Leu Ser Ile Asn Ser Val Glu Pro Glu Asp Val Gly
            20                  25                  30

Val Tyr Tyr Cys
        35

<210> SEQ ID NO 1298
<211> LENGTH: 11
<212> TYPE: PRT
<213> ORGANISM: Mus musculus

<400> SEQUENCE: 1298

Gln Ser Ile Val His Asn Asn Gly Asn Thr Tyr
1               5                   10

<210> SEQ ID NO 1299
<211> LENGTH: 11
<212> TYPE: PRT
<213> ORGANISM: Mus musculus

<400> SEQUENCE: 1299

Gln Ser Ile Val His Ser Asn Gly Asn Thr Tyr
1               5                   10

<210> SEQ ID NO 1300
<211> LENGTH: 11
<212> TYPE: PRT
<213> ORGANISM: Mus musculus

<400> SEQUENCE: 1300

Gln Ser Leu Glu Asn Ser Asn Gly Asn Thr Tyr
1               5                   10

<210> SEQ ID NO 1301
```

<211> LENGTH: 11
<212> TYPE: PRT
<213> ORGANISM: Mus musculus

<400> SEQUENCE: 1301

Gln Ser Leu Leu Asp Ser Asp Gly Lys Thr Tyr
1               5                   10

<210> SEQ ID NO 1302
<211> LENGTH: 12
<212> TYPE: PRT
<213> ORGANISM: Mus musculus

<400> SEQUENCE: 1302

Gln Ser Leu Leu Asn Ser Ser Asn Gln Lys Asn Tyr
1               5                   10

<210> SEQ ID NO 1303
<211> LENGTH: 11
<212> TYPE: PRT
<213> ORGANISM: Mus musculus

<400> SEQUENCE: 1303

Gln Ser Leu Leu Tyr Ser Asn Gly Lys Thr Tyr
1               5                   10

<210> SEQ ID NO 1304
<211> LENGTH: 12
<212> TYPE: PRT
<213> ORGANISM: Mus musculus

<400> SEQUENCE: 1304

Gln Ser Leu Leu Tyr Ser Ser Asn Gln Lys Asn Tyr
1               5                   10

<210> SEQ ID NO 1305
<211> LENGTH: 11
<212> TYPE: PRT
<213> ORGANISM: Mus musculus

<400> SEQUENCE: 1305

Gln Ser Leu Val His Asn Asn Gly Asn Thr Tyr
1               5                   10

<210> SEQ ID NO 1306
<211> LENGTH: 11
<212> TYPE: PRT
<213> ORGANISM: Mus musculus

<400> SEQUENCE: 1306

Gln Ser Leu Val His Ser Asn Gly Asn Thr Tyr
1               5                   10

<210> SEQ ID NO 1307
<211> LENGTH: 11
<212> TYPE: PRT
<213> ORGANISM: Mus musculus

<400> SEQUENCE: 1307

Gln Ser Leu Val His Ser Tyr Gly Asn Thr Tyr
1               5                   10

<210> SEQ ID NO 1308
<211> LENGTH: 10
<212> TYPE: PRT

<213> ORGANISM: Mus musculus

<400> SEQUENCE: 1308

Gln Ser Val Asp Tyr Asp Gly Asp Ser Tyr
1               5                   10

<210> SEQ ID NO 1309
<211> LENGTH: 6
<212> TYPE: PRT
<213> ORGANISM: Mus musculus

<400> SEQUENCE: 1309

Gln Ser Val Asn Asn Asp
1               5

<210> SEQ ID NO 1310
<211> LENGTH: 6
<212> TYPE: PRT
<213> ORGANISM: Mus musculus

<400> SEQUENCE: 1310

Gln Ser Val Ser Asn Asp
1               5

<210> SEQ ID NO 1311
<211> LENGTH: 11
<212> TYPE: PRT
<213> ORGANISM: Mus musculus

<400> SEQUENCE: 1311

Gln Thr Leu Leu His Ser Asp Gly Asn Thr Tyr
1               5                   10

<210> SEQ ID NO 1312
<211> LENGTH: 25
<212> TYPE: PRT
<213> ORGANISM: Mus musculus

<400> SEQUENCE: 1312

Gln Val Gln Leu Lys Gln Ser Gly Ala Asp Leu Met Lys Pro Gly Ala
1               5                   10                  15

Ser Val Lys Ile Ser Cys Lys Ala Ser
            20                  25

<210> SEQ ID NO 1313
<211> LENGTH: 24
<212> TYPE: PRT
<213> ORGANISM: Mus musculus

<400> SEQUENCE: 1313

Gln Val Gln Leu Gln Pro Gly Ala Glu Leu Val Arg Pro Gly Thr Ser
1               5                   10                  15

Val Lys Ile Ser Cys Lys Ala Ser
            20

<210> SEQ ID NO 1314
<211> LENGTH: 25
<212> TYPE: PRT
<213> ORGANISM: Mus musculus

<400> SEQUENCE: 1314

Gln Val Gln Leu Gln Gln Pro Gly Ala Glu Leu Val Arg Pro Gly Thr
1               5                   10                  15

Ser Val Lys Ile Ser Cys Lys Ala Ser
            20                  25

<210> SEQ ID NO 1315
<211> LENGTH: 25
<212> TYPE: PRT
<213> ORGANISM: Mus musculus

<400> SEQUENCE: 1315

Gln Val Gln Leu Gln Gln Pro Gly Ala Glu Leu Val Arg Pro Gly Thr
1               5                   10                  15

Ser Val Lys Met Ser Cys Lys Ala Ala
            20                  25

<210> SEQ ID NO 1316
<211> LENGTH: 114
<212> TYPE: PRT
<213> ORGANISM: Mus musculus

<400> SEQUENCE: 1316

Gln Val Gln Leu Gln Gln Pro Gly Ala Glu Leu Val Arg Pro Gly Thr
1               5                   10                  15

Ser Val Lys Met Ser Cys Lys Ala Ala Gly Tyr Thr Phe Ser Asn Tyr
            20                  25                  30

Trp Ile Gly Trp Val Lys Gln Arg Pro Gly His Gly Leu Glu Trp Ile
        35                  40                  45

Gly Asp Ile His Pro Gly Gly Gly Tyr Ile Asn Tyr Asn Glu Lys Phe
    50                  55                  60

Thr Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Ile Tyr Tyr Cys
                85                  90                  95

Val Ser Arg Asn Phe Ala Asn Trp Gly Gln Gly Thr Leu Val Thr Val
            100                 105                 110

Ser Ala

<210> SEQ ID NO 1317
<211> LENGTH: 114
<212> TYPE: PRT
<213> ORGANISM: Mus musculus

<400> SEQUENCE: 1317

Gln Val Gln Leu Gln Gln Pro Gly Ala Glu Leu Val Arg Pro Gly Thr
1               5                   10                  15

Ser Val Lys Met Ser Cys Lys Ala Ala Gly Tyr Thr Phe Ser Asn Tyr
            20                  25                  30

Trp Ile Gly Trp Val Lys Gln Arg Pro Gly His Gly Leu Glu Trp Ile
        35                  40                  45

Gly Asp Ile His Pro Gly Gly Gly Tyr Ile Asn Tyr Asn Glu Lys Phe
    50                  55                  60

Thr Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Ile Tyr Tyr Cys
                85                  90                  95

Val Ser Arg Asn Phe Ala Asn Trp Gly Gln Gly Thr Pro Val Thr Val
            100                 105                 110

Ser Ser

<210> SEQ ID NO 1318
<211> LENGTH: 114
<212> TYPE: PRT
<213> ORGANISM: Mus musculus

<400> SEQUENCE: 1318

Gln Val Gln Leu Gln Gln Pro Gly Ala Glu Leu Val Arg Pro Gly Thr
1               5                   10                  15

Ser Val Lys Met Ser Cys Lys Ala Ala Gly Tyr Thr Phe Thr Asn Tyr
            20                  25                  30

Trp Ile Gly Trp Val Lys Gln Arg Pro Gly His Gly Leu Glu Trp Ile
        35                  40                  45

Gly Asp Ile His Pro Gly Gly Asp Tyr Ser Asn Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Asn Leu Ser Ser Leu Thr Ser Glu Asp Ser Ala Ile Tyr Tyr Cys
                85                  90                  95

Thr Ser Arg Asn Phe Ala Tyr Trp Gly Gln Gly Thr Leu Val Thr Val
            100                 105                 110

Ser Ala

<210> SEQ ID NO 1319
<211> LENGTH: 25
<212> TYPE: PRT
<213> ORGANISM: Mus musculus

<400> SEQUENCE: 1319

Gln Val Gln Leu Gln Gln Pro Gly Ala Glu Leu Val Arg Pro Gly Val
1               5                   10                  15

Ser Leu Lys Ile Ser Cys Lys Gly Ser
            20                  25

<210> SEQ ID NO 1320
<211> LENGTH: 25
<212> TYPE: PRT
<213> ORGANISM: Mus musculus

<400> SEQUENCE: 1320

Gln Val Gln Leu Gln Gln Pro Gly Ala Glu Met Ala Lys Pro Gly Ala
1               5                   10                  15

Ser Val Lys Met Ser Cys Lys Ala Ser
            20                  25

<210> SEQ ID NO 1321
<211> LENGTH: 25
<212> TYPE: PRT
<213> ORGANISM: Mus musculus

<400> SEQUENCE: 1321

Gln Val Gln Leu Gln Gln Ser Gly Ala Asp Leu Met Lys Pro Gly Ala
1               5                   10                  15

Ser Val Lys Met Ser Cys Arg Ala Ser
            20                  25

<210> SEQ ID NO 1322
<211> LENGTH: 25
<212> TYPE: PRT
<213> ORGANISM: Mus musculus

```
<400> SEQUENCE: 1322

Gln Val Gln Leu Gln Gln Ser Gly Ala Glu Leu Val Arg Pro Gly Ala
1               5                   10                  15

Ser Val Lys Ile Ser Cys Lys Ala Ser
            20                  25

<210> SEQ ID NO 1323
<211> LENGTH: 25
<212> TYPE: PRT
<213> ORGANISM: Mus musculus

<400> SEQUENCE: 1323

Gln Val Gln Leu Gln Gln Ser Gly Ala Glu Leu Val Arg Pro Gly Ile
1               5                   10                  15

Ser Val Lys Ile Ser Cys Lys Gly Ser
            20                  25

<210> SEQ ID NO 1324
<211> LENGTH: 25
<212> TYPE: PRT
<213> ORGANISM: Mus musculus

<400> SEQUENCE: 1324

Gln Val Gln Leu Gln Gln Ser Gly Ala Glu Leu Val Arg Pro Gly Thr
1               5                   10                  15

Ser Leu Lys Met Ser Cys Lys Ala Ala
            20                  25

<210> SEQ ID NO 1325
<211> LENGTH: 25
<212> TYPE: PRT
<213> ORGANISM: Mus musculus

<400> SEQUENCE: 1325

Gln Val Gln Leu Gln Gln Ser Gly Ala Glu Leu Val Arg Pro Gly Thr
1               5                   10                  15

Ser Val Lys Ile Ser Cys Lys Ala Ser
            20                  25

<210> SEQ ID NO 1326
<211> LENGTH: 25
<212> TYPE: PRT
<213> ORGANISM: Mus musculus

<400> SEQUENCE: 1326

Gln Val Gln Leu Gln Gln Ser Gly Ala Glu Leu Val Arg Pro Gly Thr
1               5                   10                  15

Ser Val Lys Met Ser Cys Lys Ala Ala
            20                  25

<210> SEQ ID NO 1327
<211> LENGTH: 114
<212> TYPE: PRT
<213> ORGANISM: Mus musculus

<400> SEQUENCE: 1327

Gln Val Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Ser Asn Tyr
            20                  25                  30

Trp Ile Gly Trp Val Lys Gln Arg Pro Gly His Gly Leu Glu Trp Ile
```

-continued

```
                35                  40                  45
Gly Asp Ile His Pro Gly Gly Tyr Ile Asn Tyr Asn Glu Lys Phe
        50                  55                  60
Thr Gly Lys Ala Thr Leu Thr Ala Asp Thr Ser Ser Thr Ala Tyr
 65                  70                  75                  80
Met Gln Leu Ser Ser Leu Thr Ser Glu Asp Ser Ala Ile Tyr Tyr Cys
                85                  90                  95
Val Ser Arg Asn Phe Ala Asn Trp Gly Gln Gly Thr Leu Val Thr Val
                100                 105                 110
Ser Ala

<210> SEQ ID NO 1328
<211> LENGTH: 114
<212> TYPE: PRT
<213> ORGANISM: Mus musculus

<400> SEQUENCE: 1328

Gln Val Gln Leu Gln Gln Ser Gly Ala Glu Leu Val Arg Pro Gly Thr
 1               5                  10                  15
Ser Val Lys Met Ser Cys Lys Ala Ala Gly Tyr Thr Phe Ser Asn Tyr
                20                  25                  30
Trp Ile Gly Trp Val Lys Gln Arg Pro Gly Arg Gly Leu Glu Trp Ile
                35                  40                  45
Gly Asp Ile His Pro Gly Gly Tyr Ile Asn Tyr Asn Glu Lys Phe
        50                  55                  60
Thr Gly Lys Ala Thr Leu Thr Ala Asp Thr Ser Ser Thr Ala Tyr
 65                  70                  75                  80
Met Gln Leu Ser Ser Leu Thr Ser Gly Asp Ser Ala Ile Tyr Tyr Cys
                85                  90                  95
Val Ser Arg Asn Phe Ala Asn Trp Gly Gln Gly Thr Leu Val Thr Val
                100                 105                 110
Ser Ala

<210> SEQ ID NO 1329
<211> LENGTH: 114
<212> TYPE: PRT
<213> ORGANISM: Mus musculus

<400> SEQUENCE: 1329

Gln Val Gln Leu Gln Gln Ser Gly Ala Glu Leu Val Arg Pro Gly Thr
 1               5                  10                  15
Ser Val Lys Met Ser Cys Lys Ala Ala Gly Tyr Thr Phe Thr Asn Tyr
                20                  25                  30
Trp Ile Gly Trp Ile Lys Gln Arg Pro Gly His Gly Leu Glu Trp Ile
                35                  40                  45
Gly Asp Ile His Pro Gly Gly Asp Tyr Thr Asn Tyr Asn Glu Lys Phe
        50                  55                  60
Lys Gly Lys Ala Thr Leu Thr Ala Asp Thr Phe Ser Ser Thr Ala Tyr
 65                  70                  75                  80
Met Gln Leu Ser Ser Leu Thr Ser Glu Asp Ser Ala Ile Tyr Tyr Cys
                85                  90                  95
Thr Gly Arg Asn Phe Ala Tyr Trp Gly Gln Gly Thr Leu Val Thr Val
                100                 105                 110
Ser Ser
```

```
<210> SEQ ID NO 1330
<211> LENGTH: 114
<212> TYPE: PRT
<213> ORGANISM: Mus musculus

<400> SEQUENCE: 1330

Gln Val Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn Tyr
            20                  25                  30

Trp Ile Gly Trp Val Lys Gln Arg Pro Gly His Asp Leu Glu Trp Ile
        35                  40                  45

Gly Asp Ile His Pro Gly Gly Asp Tyr Ser Asn Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Asn Leu Ser Ser Leu Thr Ser Glu Asp Ser Ala Ile Tyr Tyr Cys
                85                  90                  95

Thr Ser Arg Asn Phe Ala Tyr Trp Gly Gln Gly Thr Leu Val Thr Val
            100                 105                 110

Ser Ala

<210> SEQ ID NO 1331
<211> LENGTH: 114
<212> TYPE: PRT
<213> ORGANISM: Mus musculus

<400> SEQUENCE: 1331

Gln Val Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn Tyr
            20                  25                  30

Trp Ile Gly Trp Val Lys Gln Arg Pro Gly His Gly Leu Glu Trp Ile
        35                  40                  45

Gly Asp Phe Tyr Pro Gly Gly Asp Tyr Ile Asn Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Ile Tyr Tyr Cys
                85                  90                  95

Thr Ser Arg Asn Phe Ala Tyr Trp Gly Gln Gly Thr Leu Val Thr Val
            100                 105                 110

Ser Ala

<210> SEQ ID NO 1332
<211> LENGTH: 114
<212> TYPE: PRT
<213> ORGANISM: Mus musculus

<400> SEQUENCE: 1332

Gln Val Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn Tyr
            20                  25                  30

Trp Ile Gly Trp Val Lys Gln Arg Pro Gly His Gly Leu Glu Trp Ile
        35                  40                  45

Gly Asp Ile His Pro Gly Gly Asp Tyr Ser Asn Tyr Asn Glu Lys Phe
```

```
                      50                  55                  60
Lys Gly Lys Ala Thr Leu Thr Ala Asp Thr Ser Ser Thr Ala Tyr
 65                  70                  75                  80

Met Asn Leu Ser Ser Leu Thr Ser Glu Asp Ser Ala Ile Tyr Tyr Cys
                     85                  90                  95

Thr Ser Arg Asn Phe Ala Tyr Trp Gly Gln Gly Thr Pro Val Thr Val
                100                 105                 110

Ser Ser

<210> SEQ ID NO 1333
<211> LENGTH: 114
<212> TYPE: PRT
<213> ORGANISM: Mus musculus

<400> SEQUENCE: 1333

Gln Val Gln Leu Gln Gln Ser Gly Ala Glu Leu Val Arg Pro Gly Thr
  1               5                  10                  15

Ser Val Lys Met Ser Cys Lys Ala Ala Gly Tyr Thr Phe Thr Asn Tyr
                 20                  25                  30

Trp Ile Gly Trp Val Lys Gln Arg Pro Gly His Gly Leu Glu Trp Ile
             35                  40                  45

Gly Asp Ile His Pro Gly Gly Asp Tyr Ser Asn Tyr Asn Glu Lys Phe
         50                  55                  60

Lys Gly Lys Ala Thr Leu Thr Ala Asp Thr Ser Ser Ser Thr Ala Tyr
 65                  70                  75                  80

Met Asn Leu Ser Ser Leu Thr Ser Glu Asp Ser Ala Ile Tyr Tyr Cys
                     85                  90                  95

Thr Ser Arg Asn Phe Ala Tyr Trp Gly Gln Gly Thr Leu Val Thr Val
                100                 105                 110

Ser Ala

<210> SEQ ID NO 1334
<211> LENGTH: 114
<212> TYPE: PRT
<213> ORGANISM: Mus musculus

<400> SEQUENCE: 1334

Gln Val Gln Leu Gln Gln Ser Gly Ala Glu Leu Val Arg Pro Gly Thr
  1               5                  10                  15

Ser Val Lys Met Ser Cys Lys Ala Ala Gly Tyr Thr Phe Thr Asn Tyr
                 20                  25                  30

Trp Ile Gly Trp Val Lys Gln Arg Pro Gly His Gly Leu Glu Trp Ile
             35                  40                  45

Gly Asp Ile His Pro Gly Gly Tyr Ile Asp Tyr Asn Glu Lys Phe
         50                  55                  60

Thr Gly Lys Ala Thr Leu Thr Ala Asp Thr Ser Ser Ser Thr Ala Tyr
 65                  70                  75                  80

Met Gln Leu Ser Ser Leu Thr Ser Glu Asp Ser Ala Ile Tyr Tyr Cys
                     85                  90                  95

Val Ser Arg Asn Phe Ala Lys Trp Gly Gln Gly Thr Leu Val Thr Val
                100                 105                 110

Ser Ala

<210> SEQ ID NO 1335
<211> LENGTH: 114
<212> TYPE: PRT
```

<213> ORGANISM: Mus musculus

<400> SEQUENCE: 1335

Gln Val Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn Tyr
            20                  25                  30

Trp Ile Gly Trp Val Lys Gln Arg Pro Gly His Gly Leu Glu Trp Ile
        35                  40                  45

Gly Asp Ile His Pro Gly Gly Tyr Thr Asn Tyr Asn Glu Lys Phe
    50                  55                  60

Lys Gly Lys Ala Thr Leu Thr Ala Asp Thr Ser Ser Thr Ala Tyr
65                  70                  75                  80

Met Gln Leu Ser Ser Leu Thr Ser Glu Asp Ser Ala Ile Tyr Tyr Cys
            85                  90                  95

Thr Ser Arg Asn Phe Ala Tyr Trp Gly Gln Gly Thr Leu Val Thr Val
            100                 105                 110

Ser Ala

<210> SEQ ID NO 1336
<211> LENGTH: 25
<212> TYPE: PRT
<213> ORGANISM: Mus musculus

<400> SEQUENCE: 1336

Gln Val Gln Leu Gln Gln Ser Gly Ala Glu Leu Val Arg Pro Gly Thr
1               5                   10                  15

Ser Val Arg Met Ser Cys Lys Ala Ala
            20                  25

<210> SEQ ID NO 1337
<211> LENGTH: 25
<212> TYPE: PRT
<213> ORGANISM: Mus musculus

<400> SEQUENCE: 1337

Gln Val Gln Leu Gln Gln Ser Gly Ala Glu Leu Val Arg Pro Gly Val
1               5                   10                  15

Ser Leu Lys Ile Ser Cys Lys Gly Ser
            20                  25

<210> SEQ ID NO 1338
<211> LENGTH: 25
<212> TYPE: PRT
<213> ORGANISM: Mus musculus

<400> SEQUENCE: 1338

Gln Val Gln Leu Gln Gln Ser Gly Ala Glu Leu Val Arg Pro Gly Val
1               5                   10                  15

Ser Val Lys Ile Ser Cys Lys Gly Ser
            20                  25

<210> SEQ ID NO 1339
<211> LENGTH: 25
<212> TYPE: PRT
<213> ORGANISM: Mus musculus

<400> SEQUENCE: 1339

Gln Val Gln Leu Gln Gln Ser Gly Ala Glu Leu Val Arg Ser Gly Ala
1               5                   10                  15

```
Ser Val Lys Leu Ser Cys Thr Ala Ser
            20                  25

<210> SEQ ID NO 1340
<211> LENGTH: 25
<212> TYPE: PRT
<213> ORGANISM: Mus musculus

<400> SEQUENCE: 1340

Gln Val Gln Leu Gln Gln Ser Gly Ala Glu Val Ala Lys Pro Gly Ala
1               5                   10                  15

Ser Val Lys Met Ser Cys Lys Ala Ser
            20                  25

<210> SEQ ID NO 1341
<211> LENGTH: 25
<212> TYPE: PRT
<213> ORGANISM: Mus musculus

<400> SEQUENCE: 1341

Gln Val Gln Leu Gln Gln Ser Gly Ala Gly Leu Val Arg Pro Gly Val
1               5                   10                  15

Ser Leu Lys Ile Ser Cys Lys Gly Ser
            20                  25

<210> SEQ ID NO 1342
<211> LENGTH: 25
<212> TYPE: PRT
<213> ORGANISM: Mus musculus

<400> SEQUENCE: 1342

Gln Val Gln Leu Gln Gln Ser Gly Ser Glu Leu Val Arg Pro Gly Ala
1               5                   10                  15

Ser Val Lys Leu Ser Cys Lys Ala Ser
            20                  25

<210> SEQ ID NO 1343
<211> LENGTH: 25
<212> TYPE: PRT
<213> ORGANISM: Mus musculus

<400> SEQUENCE: 1343

Gln Val Gln Met Lys Gln Ser Gly Ala Glu Leu Ala Lys Pro Gly Ala
1               5                   10                  15

Ser Val Lys Met Ser Cys Lys Ala Ser
            20                  25

<210> SEQ ID NO 1344
<211> LENGTH: 3
<212> TYPE: PRT
<213> ORGANISM: Mus musculus

<400> SEQUENCE: 1344

Gln Val Ser
1

<210> SEQ ID NO 1345
<211> LENGTH: 3
<212> TYPE: PRT
<213> ORGANISM: Mus musculus

<400> SEQUENCE: 1345
```

Arg Ala Asn
1

<210> SEQ ID NO 1346
<211> LENGTH: 3
<212> TYPE: PRT
<213> ORGANISM: Mus musculus

<400> SEQUENCE: 1346

Arg Ala Ser
1

<210> SEQ ID NO 1347
<211> LENGTH: 26
<212> TYPE: PRT
<213> ORGANISM: Mus musculus

<400> SEQUENCE: 1347

Arg Cys Pro Asp Asp Pro Ser Pro Ser Ser Leu Ser Ala Ser Leu Gly
1               5                   10                  15

Glu Arg Val Ser Leu Thr Cys Arg Ala Ser
            20                  25

<210> SEQ ID NO 1348
<211> LENGTH: 26
<212> TYPE: PRT
<213> ORGANISM: Mus musculus

<400> SEQUENCE: 1348

Arg Cys Gln Met Asn Gln Ser Pro Ser Ser Leu Ser Ala Ser Leu Gly
1               5                   10                  15

Glu Arg Val Ser Leu Thr Cys Arg Ala Ser
            20                  25

<210> SEQ ID NO 1349
<211> LENGTH: 26
<212> TYPE: PRT
<213> ORGANISM: Mus musculus

<400> SEQUENCE: 1349

Arg His Cys Glu Ser Gln Ser His Lys Phe Met Ser Thr Ser Ile Gly
1               5                   10                  15

Asp Arg Val Ser Ile Thr Cys Lys Ala Ser
            20                  25

<210> SEQ ID NO 1350
<211> LENGTH: 36
<212> TYPE: PRT
<213> ORGANISM: Mus musculus

<400> SEQUENCE: 1350

Arg Leu His Ser Gly Val Pro Ser Arg Phe Ser Gly Ser Glu Ser Gly
1               5                   10                  15

Thr Asp Tyr Ser Leu Thr Ile Ser Asn Leu Glu Gln Glu Asp Ile Ala
            20                  25                  30

Thr Tyr Phe Cys
        35

<210> SEQ ID NO 1351
<211> LENGTH: 36
<212> TYPE: PRT
<213> ORGANISM: Mus musculus

<400> SEQUENCE: 1351

Arg Leu His Ser Gly Val Pro Ser Arg Phe Ser Gly Ser Gly Ser Gly
1               5                   10                  15

Thr Asp Phe Ser Leu Thr Ile Ser Asn Leu Glu Gln Glu Asp Ile Ala
                20                  25                  30

Thr Tyr Phe Cys
        35

<210> SEQ ID NO 1352
<211> LENGTH: 36
<212> TYPE: PRT
<213> ORGANISM: Mus musculus

<400> SEQUENCE: 1352

Arg Leu His Ser Gly Val Pro Ser Arg Phe Ser Gly Ser Gly Ser Gly
1               5                   10                  15

Thr Asp Tyr Ser Leu Thr Ile Ser Asn Leu Glu Gln Glu Asp Phe Ala
                20                  25                  30

Asn Tyr Phe Cys
        35

<210> SEQ ID NO 1353
<211> LENGTH: 36
<212> TYPE: PRT
<213> ORGANISM: Mus musculus

<400> SEQUENCE: 1353

Arg Leu His Ser Gly Val Pro Ser Arg Phe Ser Gly Ser Gly Ser Gly
1               5                   10                  15

Thr Asp Tyr Ser Leu Thr Ile Ser Asn Leu Glu Gln Glu Asp Ile Ala
                20                  25                  30

Thr Tyr Phe Cys
        35

<210> SEQ ID NO 1354
<211> LENGTH: 36
<212> TYPE: PRT
<213> ORGANISM: Mus musculus

<400> SEQUENCE: 1354

Arg Leu His Ser Gly Val Ser Arg Phe Ser Gly Ser Gly Ser Gly
1               5                   10                  15

Thr Asp Tyr Ser Leu Thr Ile Ser Asn Leu Glu Gln Glu Asp Phe Ala
                20                  25                  30

Thr Tyr Phe Cys
        35

<210> SEQ ID NO 1355
<211> LENGTH: 36
<212> TYPE: PRT
<213> ORGANISM: Mus musculus

<400> SEQUENCE: 1355

Arg Leu Gln Ser Gly Val Pro Ser Arg Phe Thr Gly Ser Gly Ser Gly
1               5                   10                  15

Thr Asp Tyr Ser Leu Thr Ile Ser Asn Leu Glu Gln Glu Asp Ile Ala
                20                  25                  30

Thr Tyr Phe Cys
        35

<210> SEQ ID NO 1356
<211> LENGTH: 36
<212> TYPE: PRT
<213> ORGANISM: Mus musculus

<400> SEQUENCE: 1356

Arg Leu Val Asp Gly Val Pro Ser Arg Phe Ser Gly Ser Gly Ser Gly
1               5                   10                  15

Gln His Tyr Ser Leu Thr Ile Ser Gly Leu Glu Tyr Glu Asp Leu Gly
            20                  25                  30

Ile Tyr Tyr Cys
        35

<210> SEQ ID NO 1357
<211> LENGTH: 36
<212> TYPE: PRT
<213> ORGANISM: Mus musculus

<400> SEQUENCE: 1357

Arg Leu Val Asp Gly Val Pro Ser Arg Phe Ser Gly Ser Gly Ser Gly
1               5                   10                  15

Gln Asn Tyr Ser Leu Thr Ile Ser Leu Glu Tyr Glu Asp Met Gly
            20                  25                  30

Ile Tyr Tyr Cys
        35

<210> SEQ ID NO 1358
<211> LENGTH: 36
<212> TYPE: PRT
<213> ORGANISM: Mus musculus

<400> SEQUENCE: 1358

Arg Leu Tyr Ser Gly Val Pro Ser Arg Phe Ser Gly Ser Gly Ser Gly
1               5                   10                  15

Ala Asp Tyr Ser Leu Thr Ile Ser Asn Leu Glu Gln Glu Asp Ile Ala
            20                  25                  30

Thr Tyr Phe Cys
        35

<210> SEQ ID NO 1359
<211> LENGTH: 36
<212> TYPE: PRT
<213> ORGANISM: Mus musculus

<400> SEQUENCE: 1359

Arg Leu Tyr Ser Gly Val Pro Ser Arg Phe Ser Gly Ser Gly Ser Gly
1               5                   10                  15

Thr Asp Tyr Ser Leu Thr Ile Ser Asn Leu Glu Gln Glu Asp Ile Ala
            20                  25                  30

Thr Tyr Phe Cys
        35

<210> SEQ ID NO 1360
<211> LENGTH: 3
<212> TYPE: PRT
<213> ORGANISM: Mus musculus

<400> SEQUENCE: 1360

Arg Met Ser
1

```
<210> SEQ ID NO 1361
<211> LENGTH: 3
<212> TYPE: PRT
<213> ORGANISM: Mus musculus

<400> SEQUENCE: 1361

Arg Val Ser
1

<210> SEQ ID NO 1362
<211> LENGTH: 8
<212> TYPE: PRT
<213> ORGANISM: Mus musculus

<400> SEQUENCE: 1362

Ser Ala Ser Tyr Arg Tyr Ser Gly
1               5

<210> SEQ ID NO 1363
<211> LENGTH: 8
<212> TYPE: PRT
<213> ORGANISM: Mus musculus

<400> SEQUENCE: 1363

Ser Ala Ser Tyr Arg Tyr Ser Gly
1               5

<210> SEQ ID NO 1364
<211> LENGTH: 10
<212> TYPE: PRT
<213> ORGANISM: Mus musculus

<400> SEQUENCE: 1364

Ser Gly Gly Gly Thr Lys Leu Glu Ile Lys
1               5                   10

<210> SEQ ID NO 1365
<211> LENGTH: 3
<212> TYPE: PRT
<213> ORGANISM: Mus musculus

<400> SEQUENCE: 1365

Ser Gly Ser
1

<210> SEQ ID NO 1366
<211> LENGTH: 36
<212> TYPE: PRT
<213> ORGANISM: Mus musculus

<400> SEQUENCE: 1366

Ser Leu Asp Ser Gly Val Pro Lys Arg Phe Ser Gly Ser Arg Ser Gly
1               5                   10                  15

Ser Asp Tyr Ser Leu Thr Ile Ser Ser Leu Glu Ser Glu Asp Phe Val
            20                  25                  30

Asp Tyr Tyr Cys
        35

<210> SEQ ID NO 1367
<211> LENGTH: 36
<212> TYPE: PRT
<213> ORGANISM: Mus musculus

<400> SEQUENCE: 1367
```

```
Ser Leu Glu Thr Gly Val Pro Ser Arg Phe Ser Gly Ser Gly Ser Gly
1               5                   10                  15

Lys Asp Tyr Thr Leu Ser Ile Thr Ser Leu Gln Thr Glu Asp Val Ala
                20                  25                  30

Thr Tyr Tyr Cys
        35

<210> SEQ ID NO 1368
<211> LENGTH: 36
<212> TYPE: PRT
<213> ORGANISM: Mus musculus

<400> SEQUENCE: 1368

Ser Leu His Ser Gly Val Pro Ser Arg Phe Ser Gly Ser Gly Ser Gly
1               5                   10                  15

Thr Asp Tyr Ser Leu Thr Ile Ser Asn Leu Glu Pro Glu Asp Ile Ala
                20                  25                  30

Thr Tyr Tyr Cys
        35

<210> SEQ ID NO 1369
<211> LENGTH: 9
<212> TYPE: PRT
<213> ORGANISM: Mus musculus

<400> SEQUENCE: 1369

Ser Gln Ser Thr His Val Pro His Thr
1               5

<210> SEQ ID NO 1370
<211> LENGTH: 9
<212> TYPE: PRT
<213> ORGANISM: Mus musculus

<400> SEQUENCE: 1370

Ser Gln Ser Thr His Val Pro Leu Thr
1               5

<210> SEQ ID NO 1371
<211> LENGTH: 9
<212> TYPE: PRT
<213> ORGANISM: Mus musculus

<400> SEQUENCE: 1371

Ser Gln Ser Thr His Val Pro Pro Thr
1               5

<210> SEQ ID NO 1372
<211> LENGTH: 9
<212> TYPE: PRT
<213> ORGANISM: Mus musculus

<400> SEQUENCE: 1372

Ser Gln Ser Thr His Val Pro Arg Thr
1               5

<210> SEQ ID NO 1373
<211> LENGTH: 8
<212> TYPE: PRT
<213> ORGANISM: Mus musculus

<400> SEQUENCE: 1373
```

Ser Gln Ser Thr His Val Pro Thr
1               5

<210> SEQ ID NO 1374
<211> LENGTH: 9
<212> TYPE: PRT
<213> ORGANISM: Mus musculus

<400> SEQUENCE: 1374

Ser Gln Ser Thr His Val Pro Trp Thr
1               5

<210> SEQ ID NO 1375
<211> LENGTH: 9
<212> TYPE: PRT
<213> ORGANISM: Mus musculus

<400> SEQUENCE: 1375

Ser Gln Ser Thr His Val Pro Tyr Thr
1               5

<210> SEQ ID NO 1376
<211> LENGTH: 8
<212> TYPE: PRT
<213> ORGANISM: Mus musculus

<400> SEQUENCE: 1376

Ser Gln Ser Thr His Val Tyr Thr
1               5

<210> SEQ ID NO 1377
<211> LENGTH: 6
<212> TYPE: PRT
<213> ORGANISM: Mus musculus

<400> SEQUENCE: 1377

Ser Arg Asn Phe Ala Lys
1               5

<210> SEQ ID NO 1378
<211> LENGTH: 6
<212> TYPE: PRT
<213> ORGANISM: Mus musculus

<400> SEQUENCE: 1378

Ser Arg Asn Phe Ala Asn
1               5

<210> SEQ ID NO 1379
<211> LENGTH: 6
<212> TYPE: PRT
<213> ORGANISM: Mus musculus

<400> SEQUENCE: 1379

Ser Arg Asn Phe Ala Tyr
1               5

<210> SEQ ID NO 1380
<211> LENGTH: 5
<212> TYPE: PRT
<213> ORGANISM: Mus musculus

<400> SEQUENCE: 1380

Ser Arg Val Thr Tyr
1               5

<210> SEQ ID NO 1381
<211> LENGTH: 5
<212> TYPE: PRT
<213> ORGANISM: Mus musculus

<400> SEQUENCE: 1381

Ser Ser Ile Gly Tyr
1               5

<210> SEQ ID NO 1382
<211> LENGTH: 7
<212> TYPE: PRT
<213> ORGANISM: Mus musculus

<400> SEQUENCE: 1382

Ser Ser Ile Ser Ser Ser Asn
1               5

<210> SEQ ID NO 1383
<211> LENGTH: 5
<212> TYPE: PRT
<213> ORGANISM: Mus musculus

<400> SEQUENCE: 1383

Ser Ser Val Ile Tyr
1               5

<210> SEQ ID NO 1384
<211> LENGTH: 7
<212> TYPE: PRT
<213> ORGANISM: Mus musculus

<400> SEQUENCE: 1384

Ser Ser Val Ser Ser Ser Tyr
1               5

<210> SEQ ID NO 1385
<211> LENGTH: 5
<212> TYPE: PRT
<213> ORGANISM: Mus musculus

<400> SEQUENCE: 1385

Ser Ser Val Ser Tyr
1               5

<210> SEQ ID NO 1386
<211> LENGTH: 3
<212> TYPE: PRT
<213> ORGANISM: Mus musculus

<400> SEQUENCE: 1386

Ser Thr Ser
1

<210> SEQ ID NO 1387
<211> LENGTH: 37
<212> TYPE: PRT
<213> ORGANISM: Mus musculus

<400> SEQUENCE: 1387

Ser Tyr Asn Gln Lys Phe Gly Lys Ala Thr Met Thr Val Asp Lys Ser
1               5                   10                  15

Ser Ser Thr Ala Tyr Met Glu Leu Ala Arg Leu Thr Ser Glu Asp Ser

-continued

```
                20                  25                  30

Ala Ile Tyr Tyr Cys
        35

<210> SEQ ID NO 1388
<211> LENGTH: 38
<212> TYPE: PRT
<213> ORGANISM: Mus musculus

<400> SEQUENCE: 1388

Ser Tyr Asn Gln Lys Phe Lys Gly Lys Ala Thr Met Thr Val Asp Lys
1               5                   10                  15

Ser Ser Ser Thr Ala Tyr Met Glu Leu Ala Arg Leu Thr Pro Glu Asp
            20                  25                  30

Ser Ala Ile Tyr Tyr Cys
        35

<210> SEQ ID NO 1389
<211> LENGTH: 38
<212> TYPE: PRT
<213> ORGANISM: Mus musculus

<400> SEQUENCE: 1389

Ser Tyr Asn Gln Lys Phe Lys Gly Lys Ala Thr Met Thr Val Asp Lys
1               5                   10                  15

Ser Ser Ser Thr Ala Tyr Met Glu Leu Ala Arg Leu Thr Ser Glu Asp
            20                  25                  30

Ser Ala Ile Tyr Tyr Cys
        35

<210> SEQ ID NO 1390
<211> LENGTH: 38
<212> TYPE: PRT
<213> ORGANISM: Mus musculus

<400> SEQUENCE: 1390

Ser Tyr Asn Gln Lys Phe Lys Gly Lys Ala Thr Met Thr Val Asp Lys
1               5                   10                  15

Ser Ser Ser Thr Ala Tyr Met Glu Leu Ala Arg Leu Thr Ser Glu Asp
            20                  25                  30

Ser Ala Thr Tyr Tyr Cys
        35

<210> SEQ ID NO 1391
<211> LENGTH: 6
<212> TYPE: PRT
<213> ORGANISM: Mus musculus

<400> SEQUENCE: 1391

Thr Asp Ile Asp Asp Asp
1               5

<210> SEQ ID NO 1392
<211> LENGTH: 17
<212> TYPE: PRT
<213> ORGANISM: Mus musculus

<400> SEQUENCE: 1392

Thr Glu Trp Ile Lys Gln Arg Pro Gly His Gly Leu Glu Trp Ile Gly
1               5                   10                  15

Glu
```

<210> SEQ ID NO 1393
<211> LENGTH: 11
<212> TYPE: PRT
<213> ORGANISM: Mus musculus

<400> SEQUENCE: 1393

Thr Phe Gly Gly Gly Thr Lys Leu Glu Ile Lys
1               5                   10

<210> SEQ ID NO 1394
<211> LENGTH: 11
<212> TYPE: PRT
<213> ORGANISM: Mus musculus

<400> SEQUENCE: 1394

Thr Phe Gly Gly Gly Thr Lys Leu Glu Met Lys
1               5                   10

<210> SEQ ID NO 1395
<211> LENGTH: 7
<212> TYPE: PRT
<213> ORGANISM: Mus musculus

<400> SEQUENCE: 1395

Thr Gly Arg Asn Phe Ala Tyr
1               5

<210> SEQ ID NO 1396
<211> LENGTH: 36
<212> TYPE: PRT
<213> ORGANISM: Mus musculus

<400> SEQUENCE: 1396

Thr Leu Ala Glu Gly Val Pro Ser Arg Phe Ser Gly Ile Gly Ser Gly
1               5                   10                  15
Thr Gln Phe Ser Leu Lys Ile Asn Ser Leu Gln Pro Glu Asp Phe Gly
            20                  25                  30
Thr Tyr Tyr Cys
        35

<210> SEQ ID NO 1397
<211> LENGTH: 36
<212> TYPE: PRT
<213> ORGANISM: Mus musculus

<400> SEQUENCE: 1397

Thr Leu Ala Glu Gly Val Pro Ser Arg Phe Ser Gly Ser Gly Ser Gly
1               5                   10                  15
Thr His Phe Ser Leu Lys Ile Asn Ser Leu Gln Pro Glu Asp Phe Gly
            20                  25                  30
Asn Tyr Tyr Cys
        35

<210> SEQ ID NO 1398
<211> LENGTH: 36
<212> TYPE: PRT
<213> ORGANISM: Mus musculus

<400> SEQUENCE: 1398

Thr Leu Ala Glu Gly Val Pro Ser Arg Phe Ser Gly Ser Gly Ser Gly
1               5                   10                  15

Thr Gln Phe Ser Leu Lys Ile Asn Ser Leu Gln Pro Glu Asp Phe Gly
            20                  25                  30

Ser Tyr Tyr Cys
        35

<210> SEQ ID NO 1399
<211> LENGTH: 36
<212> TYPE: PRT
<213> ORGANISM: Mus musculus

<400> SEQUENCE: 1399

Thr Leu Ala Glu Gly Val Pro Ser Arg Phe Ser Gly Ser Gly Ser Gly
1               5                   10                  15

Thr Gln Phe Ser Leu Lys Ile Asn Ser Leu Gln Pro Glu Asp Phe Gly
            20                  25                  30

Thr Tyr Tyr Cys
        35

<210> SEQ ID NO 1400
<211> LENGTH: 36
<212> TYPE: PRT
<213> ORGANISM: Mus musculus

<400> SEQUENCE: 1400

Thr Leu Ala Glu Gly Val Pro Ser Arg Phe Ser Gly Ser Gly Ser Gly
1               5                   10                  15

Thr Gln Phe Ser Leu Arg Ile Asn Ser Leu Gln Pro Glu Asp Phe Gly
            20                  25                  30

Thr Tyr Tyr Cys
        35

<210> SEQ ID NO 1401
<211> LENGTH: 36
<212> TYPE: PRT
<213> ORGANISM: Mus musculus

<400> SEQUENCE: 1401

Thr Leu Ala Glu Gly Val Pro Ser Arg Phe Ser Val Ser Gly Ser Gly
1               5                   10                  15

Thr Gln Phe Ser Leu Lys Ile Asn Ser Leu Gln Pro Glu Asp Phe Gly
            20                  25                  30

Ser Tyr Tyr Cys
        35

<210> SEQ ID NO 1402
<211> LENGTH: 36
<212> TYPE: PRT
<213> ORGANISM: Mus musculus

<400> SEQUENCE: 1402

Thr Leu Asp Ser Gly Val Pro Lys Arg Phe Ser Gly Ser Arg Ser Gly
1               5                   10                  15

Ser Asp Tyr Ser Leu Thr Ile Ser Ser Leu Glu Ser Glu Asp Phe Ala
            20                  25                  30

Asp Tyr Tyr Cys
        35

<210> SEQ ID NO 1403
<211> LENGTH: 36
<212> TYPE: PRT
<213> ORGANISM: Mus musculus

```
<400> SEQUENCE: 1403

Thr Leu Glu Asp Gly Val Pro Ser Arg Phe Ser Gly Ser Gly Ser Gly
1               5                   10                  15

Thr Gln Phe Ser Met Lys Ile Asn Asn Met Gln Pro Glu Asp Thr Ala
            20                  25                  30

Thr Tyr Phe Cys
        35

<210> SEQ ID NO 1404
<211> LENGTH: 36
<212> TYPE: PRT
<213> ORGANISM: Mus musculus

<400> SEQUENCE: 1404

Thr Leu Gly Glu Gly Val Pro Ser Arg Phe Ser Gly Ser Gly Ser Gly
1               5                   10                  15

Thr Gln Phe Tyr Leu Lys Ile Asn Ser Leu Gln Pro Glu Asp Phe Gly
            20                  25                  30

Ser Tyr Tyr Cys
        35

<210> SEQ ID NO 1405
<211> LENGTH: 36
<212> TYPE: PRT
<213> ORGANISM: Mus musculus

<400> SEQUENCE: 1405

Thr Leu Gln Ser Gly Ile Pro Ser Arg Phe Ser Gly Ser Gly Ser Gly
1               5                   10                  15

Thr Asp Phe Thr Leu Thr Ile Ser Ser Leu Glu Pro Glu Asp Phe Ala
            20                  25                  30

Met Tyr Tyr Cys
        35

<210> SEQ ID NO 1406
<211> LENGTH: 36
<212> TYPE: PRT
<213> ORGANISM: Mus musculus

<400> SEQUENCE: 1406

Thr Leu Arg Pro Gly Val Pro Ser Arg Phe Ser Ser Ser Gly Tyr Gly
1               5                   10                  15

Thr Asp Phe Val Phe Thr Ile Glu Asn Thr Leu Ser Glu Asp Val Ala
            20                  25                  30

Asp Tyr Tyr Cys
        35

<210> SEQ ID NO 1407
<211> LENGTH: 36
<212> TYPE: PRT
<213> ORGANISM: Mus musculus

<400> SEQUENCE: 1407

Thr Leu Thr Ser Gly Val Pro Ala Arg Phe Ser Gly Ser Gly Ser Gly
1               5                   10                  15

Thr Ser Tyr Ser Leu Thr Ile Ser Gly Met Glu Ala Glu Asp Ala Ala
            20                  25                  30

Thr Tyr Tyr Cys
        35
```

```
<210> SEQ ID NO 1408
<211> LENGTH: 36
<212> TYPE: PRT
<213> ORGANISM: Mus musculus

<400> SEQUENCE: 1408

Thr Leu Val Glu Gly Val Pro Ser Arg Phe Ser Gly Ser Gly Ser Gly
1               5                   10                  15

Thr Gln Phe Ser Leu Lys Ile Asn Ser Leu Gln Pro Glu Asp Phe Gly
            20                  25                  30

Ser Tyr Tyr Cys
        35

<210> SEQ ID NO 1409
<211> LENGTH: 36
<212> TYPE: PRT
<213> ORGANISM: Mus musculus

<400> SEQUENCE: 1409

Thr Arg Ala Ser Gly Val Ser Asn Arg Phe Ser Gly Ser Gly Ser Gly
1               5                   10                  15

Thr Asp Phe Thr Leu Glu Ile Ser Arg Val Lys Ala Glu Asp Val Gly
            20                  25                  30

Val Tyr Tyr Cys
        35

<210> SEQ ID NO 1410
<211> LENGTH: 36
<212> TYPE: PRT
<213> ORGANISM: Mus musculus

<400> SEQUENCE: 1410

Thr Arg Glu Ser Gly Val Pro Asp Arg Phe Ile Gly Ser Gly Ser Gly
1               5                   10                  15

Thr Asp Phe Thr Leu Thr Ile Ser Ser Val Gln Ala Glu Asp Leu Ala
            20                  25                  30

Asp Tyr Phe Cys
        35

<210> SEQ ID NO 1411
<211> LENGTH: 36
<212> TYPE: PRT
<213> ORGANISM: Mus musculus

<400> SEQUENCE: 1411

Thr Arg Glu Ser Gly Val Pro Asp Arg Phe Thr Gly Ser Gly Ser Gly
1               5                   10                  15

Thr Asp Phe Thr Leu Thr Ile Ser Ser Val Lys Ala Glu Asp Leu Ala
            20                  25                  30

Val Tyr Tyr Cys
        35

<210> SEQ ID NO 1412
<211> LENGTH: 36
<212> TYPE: PRT
<213> ORGANISM: Mus musculus

<400> SEQUENCE: 1412

Thr Arg His Thr Gly Val Pro Asp Arg Phe Thr Gly Ser Gly Ser Gly
1               5                   10                  15
```

```
Thr Asp Phe Thr Leu Thr Ile Ser Ile Val Gln Ser Glu Asp Leu Ala
            20                  25                  30

Asp Tyr Phe Cys
        35

<210> SEQ ID NO 1413
<211> LENGTH: 36
<212> TYPE: PRT
<213> ORGANISM: Mus musculus

<400> SEQUENCE: 1413

Thr Arg His Thr Gly Val Pro Ser Gly Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 1414
<211> LENGTH: 36
<212> TYPE: PRT
<213> ORGANISM: Mus musculus

<400> SEQUENCE: 1414

Thr Arg His Thr Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 1415
<211> LENGTH: 15
<212> TYPE: PRT
<213> ORGANISM: Mus musculus

<400> SEQUENCE: 1415

Thr Arg Gln Asn Tyr Tyr Gly Ser Ser His Trp Tyr Phe Asp Val
1               5                   10                  15

<210> SEQ ID NO 1416
<211> LENGTH: 14
<212> TYPE: PRT
<213> ORGANISM: Mus musculus

<400> SEQUENCE: 1416

Thr Arg Ser Gly Val Glu Gly Leu Leu His Trp Tyr Phe Asp
1               5                   10

<210> SEQ ID NO 1417
<211> LENGTH: 12
<212> TYPE: PRT
<213> ORGANISM: Mus musculus

<400> SEQUENCE: 1417

Thr Arg Trp Ile Thr Thr Asp His Tyr Phe Asp Tyr
1               5                   10

<210> SEQ ID NO 1418
<211> LENGTH: 7
<212> TYPE: PRT
<213> ORGANISM: Mus musculus
```

<400> SEQUENCE: 1418

Thr Ser Arg Asn Phe Ala Lys
1               5

<210> SEQ ID NO 1419
<211> LENGTH: 7
<212> TYPE: PRT
<213> ORGANISM: Mus musculus

<400> SEQUENCE: 1419

Thr Ser Arg Asn Phe Ala Tyr
1               5

<210> SEQ ID NO 1420
<211> LENGTH: 14
<212> TYPE: PRT
<213> ORGANISM: Mus musculus

<400> SEQUENCE: 1420

Thr Val Phe Trp Tyr Gly Asn Asn Tyr Ala Gly Phe Ala Tyr
1               5                   10

<210> SEQ ID NO 1421
<211> LENGTH: 17
<212> TYPE: PRT
<213> ORGANISM: Mus musculus

<400> SEQUENCE: 1421

Val Ala Trp Tyr His Gln Lys Pro Gly Gln Ser Pro Lys Ala Leu Ile
1               5                   10                  15

Tyr

<210> SEQ ID NO 1422
<211> LENGTH: 17
<212> TYPE: PRT
<213> ORGANISM: Mus musculus

<400> SEQUENCE: 1422

Val Ala Trp Tyr Gln His Lys Pro Gly Gln Ser Pro Lys Leu Leu Ile
1               5                   10                  15

Tyr

<210> SEQ ID NO 1423
<211> LENGTH: 17
<212> TYPE: PRT
<213> ORGANISM: Mus musculus

<400> SEQUENCE: 1423

Val Ala Trp Tyr Gln Gln Glu Pro Gly Gln Ser Pro Lys Ala Leu Ile
1               5                   10                  15

Tyr

<210> SEQ ID NO 1424
<211> LENGTH: 17
<212> TYPE: PRT
<213> ORGANISM: Mus musculus

<400> SEQUENCE: 1424

Val Ala Trp Tyr Gln Gln Lys Pro Gly Gln Ala Pro Arg Leu Leu Ile
1               5                   10                  15

Tyr

<210> SEQ ID NO 1425
<211> LENGTH: 17
<212> TYPE: PRT
<213> ORGANISM: Mus musculus

<400> SEQUENCE: 1425

Val Ala Trp Tyr Gln Gln Lys Pro Gly Gln Ser Pro Lys Ala Leu Ile
1               5                   10                  15

Tyr

<210> SEQ ID NO 1426
<211> LENGTH: 17
<212> TYPE: PRT
<213> ORGANISM: Mus musculus

<400> SEQUENCE: 1426

Val Ala Trp Tyr Gln Gln Lys Pro Gly Gln Ser Pro Lys Leu Leu Ile
1               5                   10                  15

His

<210> SEQ ID NO 1427
<211> LENGTH: 17
<212> TYPE: PRT
<213> ORGANISM: Mus musculus

<400> SEQUENCE: 1427

Val Ala Trp Tyr Gln Gln Lys Pro Gly Gln Ser Pro Lys Leu Leu Ile
1               5                   10                  15

Tyr

<210> SEQ ID NO 1428
<211> LENGTH: 17
<212> TYPE: PRT
<213> ORGANISM: Mus musculus

<400> SEQUENCE: 1428

Val Ala Trp Tyr Gln Gln Lys Pro Gly Gln Ser Pro Lys Leu Pro Ile
1               5                   10                  15

Tyr

<210> SEQ ID NO 1429
<211> LENGTH: 17
<212> TYPE: PRT
<213> ORGANISM: Mus musculus

<400> SEQUENCE: 1429

Val Ala Trp Tyr Gln Gln Lys Pro Gly Gln Ser Pro Lys Pro Leu Ile
1               5                   10                  15

Tyr

<210> SEQ ID NO 1430
<211> LENGTH: 16
<212> TYPE: PRT
<213> ORGANISM: Mus musculus

<400> SEQUENCE: 1430

Val Ala Tyr Gln Gln Lys Pro Gly Gln Ser Pro Lys Ala Leu Ile Tyr
1               5                   10                  15

<210> SEQ ID NO 1431

```
<211> LENGTH: 16
<212> TYPE: PRT
<213> ORGANISM: Mus musculus

<400> SEQUENCE: 1431

Val Ala Tyr Gln Gln Lys Pro Gly Gln Ser Pro Lys Ala Leu Ile Tyr
1               5                   10                  15

<210> SEQ ID NO 1432
<211> LENGTH: 16
<212> TYPE: PRT
<213> ORGANISM: Mus musculus

<400> SEQUENCE: 1432

Val Ala Tyr Gln Gln Lys Pro Gly Gln Ser Pro Lys Pro Leu Ile Tyr
1               5                   10                  15

<210> SEQ ID NO 1433
<211> LENGTH: 17
<212> TYPE: PRT
<213> ORGANISM: Mus musculus

<400> SEQUENCE: 1433

Val Glu Trp Tyr Gln Gln Lys Gln Gly Lys Ser Pro Gln Leu Leu Val
1               5                   10                  15

Tyr

<210> SEQ ID NO 1434
<211> LENGTH: 12
<212> TYPE: PRT
<213> ORGANISM: Mus musculus

<400> SEQUENCE: 1434

Val His Val Arg Arg Gly Asp Gln Ala Gly Asn Gln
1               5                   10

<210> SEQ ID NO 1435
<211> LENGTH: 17
<212> TYPE: PRT
<213> ORGANISM: Mus musculus

<400> SEQUENCE: 1435

Val Leu Trp Tyr Gln Gln Lys Pro Gly Gln Ser Pro Lys Leu Leu Ile
1               5                   10                  15

Tyr

<210> SEQ ID NO 1436
<211> LENGTH: 17
<212> TYPE: PRT
<213> ORGANISM: Mus musculus

<400> SEQUENCE: 1436

Val Asn Trp Tyr Gln Gln Lys Pro Asp Gly Thr Val Lys Leu Leu Ile
1               5                   10                  15

Tyr

<210> SEQ ID NO 1437
<211> LENGTH: 31
<212> TYPE: PRT
<213> ORGANISM: Mus musculus

<400> SEQUENCE: 1437

Val Pro Asp Arg Phe Ala Gly Ser Gly Ser Gly Thr Asp Phe Thr Leu
```

```
                1               5                  10                 15
        Thr Ile Ser Asn Val Gln Ser Glu Asp Leu Ala Glu Tyr Phe Cys
                    20                  25                  30

<210> SEQ ID NO 1438
<211> LENGTH: 31
<212> TYPE: PRT
<213> ORGANISM: Mus musculus

<400> SEQUENCE: 1438

Val Pro Asp Arg Phe Thr Gly Ser Gly Ser Gly Thr Asp Phe Thr Leu
1               5                   10                  15

Thr Ile Asn Asn Val Gln Ser Glu Asp Leu Ala Glu Tyr Phe Cys
                    20                  25                  30

<210> SEQ ID NO 1439
<211> LENGTH: 31
<212> TYPE: PRT
<213> ORGANISM: Mus musculus

<400> SEQUENCE: 1439

Val Pro Asp Arg Phe Thr Gly Ser Gly Ser Gly Thr Asp Phe Thr Leu
1               5                   10                  15

Thr Ile Ser Asn Val Gln Ser Glu Asp Leu Ala Glu Tyr Phe Cys
                    20                  25                  30

<210> SEQ ID NO 1440
<211> LENGTH: 31
<212> TYPE: PRT
<213> ORGANISM: Mus musculus

<400> SEQUENCE: 1440

Val Pro Asp Arg Phe Thr Gly Ser Gly Ser Gly Thr Asp Phe Thr Leu
1               5                   10                  15

Thr Ile Ser Asn Val Gln Ser Glu Asp Leu Ala Glu Tyr Phe Cys
                    20                  25                  30

<210> SEQ ID NO 1441
<211> LENGTH: 10
<212> TYPE: PRT
<213> ORGANISM: Mus musculus

<400> SEQUENCE: 1441

Val Arg Arg Gly Asp Gln Ala Gly Asn Glu
1               5                   10

<210> SEQ ID NO 1442
<211> LENGTH: 8
<212> TYPE: PRT
<213> ORGANISM: Mus musculus

<400> SEQUENCE: 1442

Val Arg Ser Pro Ile Leu Asp Tyr
1               5

<210> SEQ ID NO 1443
<211> LENGTH: 7
<212> TYPE: PRT
<213> ORGANISM: Mus musculus

<400> SEQUENCE: 1443

Val Arg Val Thr Pro Ala Ser
1               5
```

<210> SEQ ID NO 1444
<211> LENGTH: 7
<212> TYPE: PRT
<213> ORGANISM: Mus musculus

<400> SEQUENCE: 1444

Val Ser Arg Asn Phe Ala Lys
1               5

<210> SEQ ID NO 1445
<211> LENGTH: 7
<212> TYPE: PRT
<213> ORGANISM: Mus musculus

<400> SEQUENCE: 1445

Val Ser Arg Asn Phe Ala Asn
1               5

<210> SEQ ID NO 1446
<211> LENGTH: 17
<212> TYPE: PRT
<213> ORGANISM: Mus musculus

<400> SEQUENCE: 1446

Val Ser Trp Tyr Gln Gln Lys Pro Glu Gln Ser Pro Lys Leu Leu Ile
1               5                   10                  15

Tyr

<210> SEQ ID NO 1447
<211> LENGTH: 17
<212> TYPE: PRT
<213> ORGANISM: Mus musculus

<400> SEQUENCE: 1447

Val Val Trp Tyr Gln Gln Lys Pro Gly Gln Ser Pro Lys Leu Leu Ile
1               5                   10                  15

Tyr

<210> SEQ ID NO 1448
<211> LENGTH: 12
<212> TYPE: PRT
<213> ORGANISM: Mus musculus

<400> SEQUENCE: 1448

Val Trp Gly Ala Gly Thr Thr Val Thr Val Ser Ser
1               5                   10

<210> SEQ ID NO 1449
<211> LENGTH: 17
<212> TYPE: PRT
<213> ORGANISM: Mus musculus
<220> FEATURE:
<221> NAME/KEY: misc_feature
<222> LOCATION: (2)..(2)
<223> OTHER INFORMATION: Xaa can be any naturally occurring amino acid

<400> SEQUENCE: 1449

Val Xaa Trp Tyr Gln Gln Lys Pro Gly Gln Ser Pro Lys Ala Leu Ile
1               5                   10                  15

Tyr

<210> SEQ ID NO 1450

```
<211> LENGTH: 3
<212> TYPE: PRT
<213> ORGANISM: Mus musculus

<400> SEQUENCE: 1450

Trp Ala Ser
1

<210> SEQ ID NO 1451
<211> LENGTH: 11
<212> TYPE: PRT
<213> ORGANISM: Mus musculus

<400> SEQUENCE: 1451

Trp Gly Gln Gly Ala Thr Val Thr Val Ser Ser
1               5                   10

<210> SEQ ID NO 1452
<211> LENGTH: 11
<212> TYPE: PRT
<213> ORGANISM: Mus musculus

<400> SEQUENCE: 1452

Trp Gly Gln Gly Thr Thr Leu Thr Val Ser Ala
1               5                   10

<210> SEQ ID NO 1453
<211> LENGTH: 9
<212> TYPE: PRT
<213> ORGANISM: Mus musculus

<400> SEQUENCE: 1453

Trp Gly Gln Gly Thr Thr Val Ser Ala
1               5

<210> SEQ ID NO 1454
<211> LENGTH: 11
<212> TYPE: PRT
<213> ORGANISM: Mus musculus

<400> SEQUENCE: 1454

Trp Gly Arg Gly Thr Ser Leu Thr Val Ser Ser
1               5                   10

<210> SEQ ID NO 1455
<211> LENGTH: 11
<212> TYPE: PRT
<213> ORGANISM: Mus musculus

<400> SEQUENCE: 1455

Trp Gly Arg Gly Thr Thr Leu Thr Val Ser Ser
1               5                   10

<210> SEQ ID NO 1456
<211> LENGTH: 17
<212> TYPE: PRT
<213> ORGANISM: Mus musculus

<400> SEQUENCE: 1456

Trp Ile Gly Trp Ile Lys Gln Arg Pro Gly His Gly Leu Glu Trp Ile
1               5                   10                  15

Gly

<210> SEQ ID NO 1457
```

-continued

<210> SEQ ID NO 1457
<211> LENGTH: 17
<212> TYPE: PRT
<213> ORGANISM: Mus musculus

<400> SEQUENCE: 1457

Trp Ile Gly Trp Val Lys Gln Arg Pro Gly His Asp Leu Glu Trp Ile
1               5                   10                  15

Gly

<210> SEQ ID NO 1458
<211> LENGTH: 17
<212> TYPE: PRT
<213> ORGANISM: Mus musculus

<400> SEQUENCE: 1458

Trp Ile Gly Trp Val Lys Gln Arg Pro Gly His Gly Leu Glu Trp Ile
1               5                   10                  15

Gly

<210> SEQ ID NO 1459
<211> LENGTH: 17
<212> TYPE: PRT
<213> ORGANISM: Mus musculus

<400> SEQUENCE: 1459

Trp Ile Gly Trp Val Lys Gln Arg Pro Gly Arg Gly Leu Glu Trp Ile
1               5                   10                  15

Gly

<210> SEQ ID NO 1460
<211> LENGTH: 17
<212> TYPE: PRT
<213> ORGANISM: Mus musculus

<400> SEQUENCE: 1460

Trp Ile Gly Trp Val Lys Gln Arg Ser Gly His Gly Leu Glu Trp Ile
1               5                   10                  15

Gly

<210> SEQ ID NO 1461
<211> LENGTH: 9
<212> TYPE: PRT
<213> ORGANISM: Mus musculus

<400> SEQUENCE: 1461

Trp Gln Gly Ala His Phe Pro Trp Thr
1               5

<210> SEQ ID NO 1462
<211> LENGTH: 8
<212> TYPE: PRT
<213> ORGANISM: Mus musculus

<400> SEQUENCE: 1462

Trp Gln Gly Thr Phe Ser Ser His
1               5

<210> SEQ ID NO 1463
<211> LENGTH: 9
<212> TYPE: PRT
<213> ORGANISM: Mus musculus

<400> SEQUENCE: 1463

Trp Gln Gly Thr His Phe Pro Gln Thr
1               5

<210> SEQ ID NO 1464
<211> LENGTH: 9
<212> TYPE: PRT
<213> ORGANISM: Mus musculus

<400> SEQUENCE: 1464

Trp Gln Gly Thr His Phe Pro Arg Thr
1               5

<210> SEQ ID NO 1465
<211> LENGTH: 9
<212> TYPE: PRT
<213> ORGANISM: Mus musculus

<400> SEQUENCE: 1465

Trp Gln Gly Thr His Phe Pro Trp Thr
1               5

<210> SEQ ID NO 1466
<211> LENGTH: 8
<212> TYPE: PRT
<213> ORGANISM: Mus musculus

<400> SEQUENCE: 1466

Trp Gln Gly Thr His Phe Arg Thr
1               5

<210> SEQ ID NO 1467
<211> LENGTH: 12
<212> TYPE: PRT
<213> ORGANISM: Mus musculus

<400> SEQUENCE: 1467

Trp Thr Phe Gly Gly Gly Thr Lys Leu Glu Ile Lys
1               5                   10

<210> SEQ ID NO 1468
<211> LENGTH: 12
<212> TYPE: PRT
<213> ORGANISM: Mus musculus

<400> SEQUENCE: 1468

Trp Thr Phe Gly Gly Gly Thr Lys Leu Glu Met Lys
1               5                   10

<210> SEQ ID NO 1469
<211> LENGTH: 12
<212> TYPE: PRT
<213> ORGANISM: Mus musculus

<400> SEQUENCE: 1469

Trp Thr Phe Gly Arg Gly Thr Lys Leu Glu Ile Lys
1               5                   10

<210> SEQ ID NO 1470
<211> LENGTH: 15
<212> TYPE: PRT
<213> ORGANISM: Mus musculus

<400> SEQUENCE: 1470

Trp Tyr Gln Gln Lys Pro Gly Gln Ala Pro Arg Leu Leu Ile Tyr

-continued

```
1               5                   10                  15

<210> SEQ ID NO 1471
<211> LENGTH: 15
<212> TYPE: PRT
<213> ORGANISM: Mus musculus

<400> SEQUENCE: 1471

Trp Tyr Gln Gln Lys Pro Gly Gln Ser Pro Lys Ala Leu Ile Tyr
1               5                   10                  15

<210> SEQ ID NO 1472
<211> LENGTH: 15
<212> TYPE: PRT
<213> ORGANISM: Mus musculus

<400> SEQUENCE: 1472

Trp Tyr Gln Gln Lys Pro Gly Gln Ser Pro Lys Ala Leu Ile Tyr
1               5                   10                  15

<210> SEQ ID NO 1473
<211> LENGTH: 15
<212> TYPE: PRT
<213> ORGANISM: Mus musculus

<400> SEQUENCE: 1473

Trp Tyr Gln Gln Lys Pro Gly Gln Ser Pro Lys Pro Leu Ile Tyr
1               5                   10                  15

<210> SEQ ID NO 1474
<211> LENGTH: 11
<212> TYPE: PRT
<213> ORGANISM: Mus musculus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 1474

Xaa Gly Arg Gly Thr Xaa Leu Thr Val Ser Ser
1               5                   10

<210> SEQ ID NO 1475
<211> LENGTH: 9
<212> TYPE: PRT
<213> ORGANISM: Mus musculus
<220> FEATURE:
<221> NAME/KEY: misc_feature
<222> LOCATION: (1)..(1)
<223> OTHER INFORMATION: Xaa can be any naturally occurring amino acid

<400> SEQUENCE: 1475

Xaa Gln Tyr Asn Ser Tyr Pro Tyr Thr
1               5

<210> SEQ ID NO 1476
<211> LENGTH: 3
<212> TYPE: PRT
<213> ORGANISM: Mus musculus

<400> SEQUENCE: 1476

Tyr Ala Ser
1
```

```
<210> SEQ ID NO 1477
<211> LENGTH: 36
<212> TYPE: PRT
<213> ORGANISM: Mus musculus

<400> SEQUENCE: 1477

Tyr Arg Tyr Gly Gly Val Pro Asp Arg Phe Thr Gly Ser Gly Ser Gly
1               5                   10                  15

Thr Asp Phe Thr Leu Thr Ile Ser Asn Val Gln Ser Glu Asp Leu Ala
            20                  25                  30

Glu Tyr Phe Cys
        35

<210> SEQ ID NO 1478
<211> LENGTH: 36
<212> TYPE: PRT
<213> ORGANISM: Mus musculus

<400> SEQUENCE: 1478

Tyr Arg Tyr Asn Gly Val Pro Asp Arg Phe Thr Gly Ser Gly Ser Gly
1               5                   10                  15

Thr Asp Phe Thr Leu Thr Ile Ser Asn Val Gln Ser Glu Asp Leu Ala
            20                  25                  30

Glu Tyr Phe Cys
        35

<210> SEQ ID NO 1479
<211> LENGTH: 36
<212> TYPE: PRT
<213> ORGANISM: Mus musculus

<400> SEQUENCE: 1479

Tyr Arg Tyr Ser Gly Val Pro Asp Arg Phe Thr Gly Ser Gly Ser Gly
1               5                   10                  15

Thr Asp Phe Thr Leu Lys Ile Ser Arg Val Glu Ala Glu Asp Leu Gly
            20                  25                  30

Val Tyr Phe Cys
        35

<210> SEQ ID NO 1480
<211> LENGTH: 36
<212> TYPE: PRT
<213> ORGANISM: Mus musculus

<400> SEQUENCE: 1480

Tyr Arg Tyr Ser Gly Val Pro Asp Arg Phe Thr Gly Ser Gly Ser Gly
1               5                   10                  15

Thr Asp Phe Thr Leu Thr Ile Asn Asn Val Gln Ser Glu Asp Leu Ala
            20                  25                  30

Glu Tyr Phe Cys
        35

<210> SEQ ID NO 1481
<211> LENGTH: 36
<212> TYPE: PRT
<213> ORGANISM: Mus musculus

<400> SEQUENCE: 1481

Tyr Arg Tyr Ser Gly Val Pro Asp Arg Phe Thr Gly Ser Gly Ser Gly
1               5                   10                  15
```

-continued

Thr Asp Phe Thr Leu Thr Ile Asn Ser Val Gln Ser Glu Asp Leu Ala
            20                  25                  30

Asp Tyr Phe Cys
        35

<210> SEQ ID NO 1482
<211> LENGTH: 36
<212> TYPE: PRT
<213> ORGANISM: Mus musculus

<400> SEQUENCE: 1482

Tyr Arg Tyr Ser Gly Val Pro Asp Arg Phe Thr Gly Ser Gly Ser Gly
1               5                   10                  15

Thr Asp Phe Thr Leu Thr Ile Ser Asn Val Gln Ser Glu Asp Leu Ala
            20                  25                  30

Asp Tyr Phe Cys
        35

<210> SEQ ID NO 1483
<211> LENGTH: 36
<212> TYPE: PRT
<213> ORGANISM: Mus musculus

<400> SEQUENCE: 1483

Tyr Arg Tyr Ser Gly Val Pro Asp Arg Phe Thr Gly Ser Gly Ser Gly
1               5                   10                  15

Thr Asp Phe Thr Leu Thr Ile Ser Asn Val Gln Ser Glu Asp Leu Ala
            20                  25                  30

Glu Tyr Phe Cys
        35

<210> SEQ ID NO 1484
<211> LENGTH: 36
<212> TYPE: PRT
<213> ORGANISM: Mus musculus

<400> SEQUENCE: 1484

Tyr Arg Tyr Ser Gly Val Pro Asp Arg Phe Thr Gly Ser Gly Ser Gly
1               5                   10                  15

Thr Asp Phe Thr Leu Thr Ile Ser Asn Val Gln Ser Glu Asp Leu Ala
            20                  25                  30

Glu Tyr Phe Cys
        35

<210> SEQ ID NO 1485
<211> LENGTH: 36
<212> TYPE: PRT
<213> ORGANISM: Mus musculus

<400> SEQUENCE: 1485

Tyr Arg Tyr Ser Gly Val Pro Asp Arg Phe Thr Gly Ser Gly Ser Gly
1               5                   10                  15

Thr Asp Phe Thr Leu Thr Ile Ser Asn Val Gln Ser Glu Asp Leu Ala
            20                  25                  30

Glu Tyr Leu Cys
        35

<210> SEQ ID NO 1486
<211> LENGTH: 36
<212> TYPE: PRT

<213> ORGANISM: Mus musculus

<400> SEQUENCE: 1486

Tyr Arg Tyr Ser Gly Val Pro Asp Arg Phe Thr Gly Ser Gly Ser Gly
1               5                   10                  15

Thr Asp Phe Thr Leu Thr Ile Ser Asn Val Gln Ser Glu Asp Leu Thr
            20                  25                  30

Glu Tyr Phe Cys
        35

<210> SEQ ID NO 1487
<211> LENGTH: 36
<212> TYPE: PRT
<213> ORGANISM: Mus musculus

<400> SEQUENCE: 1487

Tyr Arg Tyr Ser Gly Val Pro Asp Arg Phe Thr Gly Ser Gly Ser Gly
1               5                   10                  15

Thr Gly Phe Thr Leu Thr Ile Ser Asn Val Gln Ser Glu Asp Leu Ala
            20                  25                  30

Glu Tyr Phe Cys
        35

<210> SEQ ID NO 1488
<211> LENGTH: 36
<212> TYPE: PRT
<213> ORGANISM: Mus musculus

<400> SEQUENCE: 1488

Tyr Arg Tyr Ser Gly Val Pro Asp Arg Ile Thr Gly Arg Gly Ser Gly
1               5                   10                  15

Thr Asp Phe Thr Leu Thr Ile Ser Asn Val Gln Ser Glu Asp Leu Ala
            20                  25                  30

Asp Tyr Phe Cys
        35

<210> SEQ ID NO 1489
<211> LENGTH: 36
<212> TYPE: PRT
<213> ORGANISM: Mus musculus

<400> SEQUENCE: 1489

Tyr Arg Tyr Ser Gly Val Pro Asp Arg Leu Thr Gly Ser Gly Ser Gly
1               5                   10                  15

Thr Asp Phe Thr Leu Thr Ile Ser Asn Val Gln Ser Glu Asp Leu Ala
            20                  25                  30

Glu Tyr Phe Cys
        35

<210> SEQ ID NO 1490
<211> LENGTH: 36
<212> TYPE: PRT
<213> ORGANISM: Mus musculus

<400> SEQUENCE: 1490

Tyr Arg Tyr Ser Gly Val Pro Gly Arg Phe Thr Gly Ser Gly Ser Gly
1               5                   10                  15

Thr Asp Phe Thr Leu Thr Ile Ser Asn Val Gln Ser Glu Asp Leu Ala
            20                  25                  30

Glu Tyr Phe Cys

<210> SEQ ID NO 1491
<211> LENGTH: 36
<212> TYPE: PRT
<213> ORGANISM: Mus musculus

<400> SEQUENCE: 1491

Tyr Arg Tyr Thr Gly Val Pro Asp Arg Phe Thr Gly Ser Gly Ser Gly
1               5                   10                  15

Thr Asp Phe Thr Phe Thr Ile Ser Ser Val Gln Ala Glu Asp Leu Ala
            20                  25                  30

Val Tyr Tyr Cys
            35

<210> SEQ ID NO 1492
<211> LENGTH: 36
<212> TYPE: PRT
<213> ORGANISM: Mus musculus

<400> SEQUENCE: 1492

Tyr Arg Tyr Thr Gly Val Pro Asp Arg Phe Thr Gly Ser Gly Ser Arg
1               5                   10                  15

Thr Asp Phe Thr Phe Thr Ile Ser Ser Val Gln Ala Glu Asp Leu Ala
            20                  25                  30

Val Tyr Tyr Cys
            35

<210> SEQ ID NO 1493
<211> LENGTH: 12
<212> TYPE: PRT
<213> ORGANISM: Mus musculus

<400> SEQUENCE: 1493

Tyr Thr Phe Gly Gly Gly Thr Lys Leu Glu Ile Lys
1               5                   10

<210> SEQ ID NO 1494
<211> LENGTH: 12
<212> TYPE: PRT
<213> ORGANISM: Mus musculus

<400> SEQUENCE: 1494

Tyr Thr Phe Gly Gly Gly Thr Lys Leu Glu Met Lys
1               5                   10

<210> SEQ ID NO 1495
<211> LENGTH: 3
<212> TYPE: PRT
<213> ORGANISM: Mus musculus

<400> SEQUENCE: 1495

Tyr Thr Ser
1

<210> SEQ ID NO 1496
<211> LENGTH: 12
<212> TYPE: PRT
<213> ORGANISM: Mus musculus

<400> SEQUENCE: 1496

Tyr Trp Gly Gln Gly Thr Leu Val Thr Ala Leu Ser
1               5                   10

-continued

<210> SEQ ID NO 1497
<211> LENGTH: 20
<212> TYPE: DNA
<213> ORGANISM: Artificial Sequence
<220> FEATURE:
<223> OTHER INFORMATION: sequencing primer

<400> SEQUENCE: 1497
acgcctgcga agtcacccat                                                    20

<210> SEQ ID NO 1498
<211> LENGTH: 31
<212> TYPE: DNA
<213> ORGANISM: Artificial Sequence
<220> FEATURE:
<223> OTHER INFORMATION: sequencing primer

<400> SEQUENCE: 1498
agaaacacaa agtctacgcc tgcgaagtca c                                       31

<210> SEQ ID NO 1499
<211> LENGTH: 24
<212> TYPE: DNA
<213> ORGANISM: Artificial Sequence
<220> FEATURE:
<223> OTHER INFORMATION: sequencing primer

<400> SEQUENCE: 1499
agcggataac aatttcacac agga                                               24

<210> SEQ ID NO 1500
<211> LENGTH: 20
<212> TYPE: DNA
<213> ORGANISM: Artificial Sequence
<220> FEATURE:
<223> OTHER INFORMATION: sequencing primer

<400> SEQUENCE: 1500
cggataacaa tttcacacag                                                    20

<210> SEQ ID NO 1501
<211> LENGTH: 118
<212> TYPE: PRT
<213> ORGANISM: Mus musculus

<400> SEQUENCE: 1501

Asp Val Lys Leu Val Glu Ser Gly Gly Leu Val Lys Pro Gly Gly Ser
1               5                   10                  15

Leu Lys Leu Ser Cys Ala Ala Ser Gly Phe Thr Phe Ser Ser Tyr Ala
            20                  25                  30

Met Ser Trp Val Arg Gln Thr Pro Glu Lys Arg Leu Glu Trp Val Ala
        35                  40                  45

Ser Ile Ser Ser Gly Gly Ser Thr Tyr Tyr Pro Asp Ser Val Lys Gly
    50                  55                  60

Arg Phe Thr Ile Ser Arg Asp Asn Ala Arg Asn Ile Leu Tyr Leu Gln
65                  70                  75                  80

Met Ser Ser Leu Arg Ser Glu Asp Thr Ala Met Tyr Tyr Cys Ala Arg
                85                  90                  95

```
Gly Glu Ile Trp Gly Lys Ala Trp Phe Ala Tyr Trp Gly Gln Gly Thr
            100             105                 110
Leu Val Thr Val Ser Ala
        115
```